US012492238B2

(12) United States Patent
Lipovsek et al.

(10) Patent No.: US 12,492,238 B2
(45) **Date of Patent: *Dec. 9, 2025**

(54) GLYPICAN-3-BINDING FIBRONECTIN BASED SCAFFOLD MOLECULES

(71) Applicant: Bristol-Myers Squibb Company, Princeton, NJ (US)

(72) Inventors: Dasa Lipovsek, Pepperell, MA (US); Joseph Toth, Waltham, MA (US); Ginger C. Rakestraw, Somerville, MA (US); Irvith M. Carvajal, Brighton, MA (US); Stanley Richard Krystek, Jr., Ringoes, NJ (US); Steven R. O'Neil, Wayland, MA (US); Guodong Chen, East Brunswick, NJ (US); Richard Y. Huang, Bridgewater, NJ (US); Bryan C. Barnhart, Vancouver (CA); John Thomas Loffredo, Yardley, PA (US); Christina Terragni, Wilmington, MA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 88 days.

This patent is subject to a terminal disclaimer.

(21) Appl. No.: 17/985,012

(22) Filed: Nov. 10, 2022

(65) Prior Publication Data

US 2023/0312686 A1 Oct. 5, 2023

Related U.S. Application Data

(60) Division of application No. 16/751,788, filed on Jan. 24, 2020, now Pat. No. 11,524,992, which is a continuation of application No. 15/760,449, filed as application No. PCT/US2016/053185 on Sep. 22, 2016, now Pat. No. 10,584,160.

(60) Provisional application No. 62/222,633, filed on Sep. 23, 2015.

(51) Int. Cl.

| | |
|---|---|
| ***C07K 14/00*** | (2006.01) |
| ***A61K 47/60*** | (2017.01) |
| ***A61K 47/64*** | (2017.01) |
| ***C07K 14/78*** | (2006.01) |
| ***G01N 33/68*** | (2006.01) |
| *A61K 38/00* | (2006.01) |

(52) U.S. Cl.

CPC .............. *C07K 14/78* (2013.01); *A61K 47/60* (2017.08); *A61K 47/64* (2017.08); *A61K 47/6435* (2017.08); *G01N 33/6872* (2013.01); *A61K 38/00* (2013.01)

(58) Field of Classification Search

CPC ........................... C07K 14/78; C07K 2319/30; C07K 14/4725; A61K 47/60; A61K 47/64; A61K 47/6435; A61K 38/00; G01N 33/6872; A61P 35/00

See application file for complete search history.

(56) References Cited

U.S. PATENT DOCUMENTS

| | | | |
|---|---|---|---|
| 7,115,396 | B2 | 10/2006 | Lipovsek et al. |
| 9,260,492 | B2 | 2/2016 | Matschiner |
| 10,584,160 | B2 | 3/2020 | Lipovsek et al. |
| 11,524,992 | B2 | 12/2022 | Lipovsek et al. |
| 2008/0015339 | A1* | 1/2008 | Lipovsek ........... C12N 15/1037 530/395 |
| 2012/0094909 | A1 | 4/2012 | Camphausen et al. |
| 2019/0077844 | A1 | 3/2019 | Lipovsek et al. |
| 2020/0262893 | A1 | 8/2020 | Lipovsek et al. |

FOREIGN PATENT DOCUMENTS

| | | | | |
|---|---|---|---|---|
| WO | 98/56915 | A2 | 12/1998 | |
| WO | 0232925 | A2 | 4/2002 | |
| WO | WO-2009073115 | A1 * | 6/2009 | ....... A61K 39/39558 |
| WO | 2009133208 | A1 | 11/2009 | |
| WO | 2009142773 | A2 | 11/2009 | |
| WO | 2011/103105 | A1 | 8/2011 | |
| WO | 2011130324 | A1 | 10/2011 | |
| WO | 2012016245 | A2 | 2/2012 | |
| WO | 2012/065978 | A1 | 5/2012 | |
| WO | 2012/073992 | A1 | 6/2012 | |
| WO | WO-2014043344 | A1 * | 3/2014 | ............. A61K 38/17 |
| WO | 2014/159087 | A1 | 10/2014 | |
| WO | 2015/023879 | A1 | 2/2015 | |
| WO | 2015143156 | A1 | 9/2015 | |

OTHER PUBLICATIONS

DATABASE Geneseq "Human 10Fn3 domain derived peptide li-38 SEQ: 174," XP002765485, retrieved from EBI accession No. GSP:BBL29072 Database accession No. BBL29072 (Sep. 25, 2014) 1 page.

Extended European Search Report, European Application No. 20168319, dated Sep. 25, 2020, 4 pages.

International Preliminary Report on Patentability, PCT/US2016/053185, dated Mar. 27, 2018, 8 pages.

International Search Report and Written Opinion, PCT/US2016/053185, dated Feb. 13, 2017, 13 pages.

Lipovsek, D: "Adnectins: engineered target-binding protein therapeutics," Protein Engineering, Design and Selection, Oxford Journal, London, GB, vol. 24(No. 1-2) Issue S11: 3-9 (2011).

Peters, C. et al., "Antibody-drug conjugates as novel anti-cancer chemotherapeutics," Bioscience Reports, vol. 35 (4):e00225-e00225 (2015).

(Continued)

*Primary Examiner* — Jeanette M Lieb

(74) *Attorney, Agent, or Firm* — Nelson Mullins Riley & Scarborough LLP; Jane E. Remillard, Esq.; Jeanne DiGiorgio, Esq.

(57) ABSTRACT

Provided herein are polypeptides which include tenth fibronectin type III domains ($^{10}$Fn3) that bind to glypican-3. Also provided are fusion molecules comprising a $^{10}$Fn3 domain that bind to glypican-3 for use in diagnostic and therapeutic applications. Glypican-3 $^{10}$Fn3 drug conjugates are also provided.

6 Claims, 36 Drawing Sheets

Specification includes a Sequence Listing.

(56) References Cited

OTHER PUBLICATIONS

U.S. Appl. No. 16/751,788, filed Jan. 24, 2020, Dasa Lipovsek, U.S. Pat. No. 11,524,992.
U.S. Appl. No. 15/760,449, filed Mar. 15, 2018, Dasa Lipovsek, U.S. Pat. No. 10,584,160.

* cited by examiner

| | | AB | | BC | | CD | | DE | | EF | | FG | |
|---|---|---|---|---|---|---|---|---|---|---|---|---|---|
| SEQ ID NO:3 | VSDVPRDLEVVA | (X)u | LLISW | (X)v | YRITY | (X)w | FTV | (X)x | ATISGL | (X)y | YTITVYA | (X)z | ISINYRT |
| WT | VSDVPRDLEVVA | TPTS | LLISW | DAPAVTVR | YRITY | GETGGNSPVQ | FTV | PGSKST | ATISGL | KPGV | YTITVYA | VTGRGDSPASSK | ISINYRT |
| 4578F03 | VSDVPRDLEVVA | TPTS | LLISW | HPPHPNIVS | YHIYY | GETGGNSPVQ | FTV | EGSKST | AKISGL | KPGV | YTITVYA | VAPEIEKYYQ | IWINYRT |
| 4578H08 | VSDVPRDLEVVA | TPTS | LLISW | SGYDYGDS | YRITY | GETGGNSPVQ | FTV | PDGSNT | ATISGL | KPGV | YTITVYA | VEAYGKGYTRYT | ISINYRT |
| 4578G06 | VSDVPRDLEVVA | TPTS | LLISW | FPDRYV | YYITY | GETGGNSPVQ | FTV | EGHKQT | AYISGL | KPGV | YTITVYA | AYISGL | ISINYRT |
| 4606F06 | VSDVPRDLEVVA | TPTS | LLISW | NSGHSGQY | YRITY | GETGGNSPVQ | FTV | PRYGYT | ATISGL | KPGV | YTITVYA | VAHSEASAP | ISINYRT |
| 5273C01 | VSDVPRDLEVVA | TPTS | LLISW | SDPYEEER | YRITY | GETGGNSPVQ | FTV | PAFHTT | ATISGL | KPGV | YTITVYA | VTYKHKYAYYYP | ISINYRT |
| 5273D01 | VSDVPRDLEVVA | TPTS | LLISW | EPSYKDDR | YRITY | GETGGNSPVQ | FTV | PSFHQT | ATISGL | KPGV | YTITVYA | VTYEPDEYYFYY | ISINYRT |
| 5274E01 | VSDVPRDLEVVA | TPTS | LLISW | SGDYHPHR | YRITY | GETGGNSPVQ | FTV | PGEHET | ATISGL | KPGV | YTITVYA | VTYDGEKADKYP | ISINYRT |
| | | | | | | | | | | | | | |
| 5561A01 | VSDVPRDLEVVA | TPTS | LLISW | SGDYHPHR | YRITY | GETGGNSPVQ | FTV | PGEHET | ATISGL | KPGV | YTITVYA | VTYDGEKADKYP | ISINYRT |
| 6077F02 | VSDVPRDLEVVA | TPTS | LLISW | SDDYHAHR | YRITY | GETGGNSPVQ | FTV | PGEHVT | ATISGL | KPGV | YTITVYA | VTYDGEKAATDW | ISINYRT |
| | | | | | | | | | | | | | |
| 6093A01 | VSDVPRDLEVVA | TPTS | LLISW | DAPAVTVR | YRITY | GETGGNSPVQ | FTV | PGSKST | ATISGL | KPGV | YTITVYA | VTGRGESPASSK | ISINYRT |

FIG. 1

Direct Conjugate, DAR2

| | ADX_6077_F02-961(DAR1) | ADX_6912_G02-961(DAR2) |
|---|---|---|
| EC50 | 0.6645 | 0.5371 |

| | ADX_6077_F02-961(DAR1) | ADX_6912_G02-961(DAR2) |
|---|---|---|
| EC50 | 0.3857 | 0.5727 |

| | ADX_6077_F02-961(DAR1) | ADX_6912_G02-961(DAR2) |
|---|---|---|
| EC50 | 0.3366 | 0.3695 |

| | ADX_6093_A01-961(DAR1) -Control | ADX_6093_A01-961(DAR2) -Control |
|---|---|---|
| EC50 | 170.9 | 140.1 |

| | ADX_6077_F02-961(DAR1) | ADX_6912_G02-961(DAR2) |
|---|---|---|
| EC50 | 5.504 | 2.462 |

| | ADX_6093_A01-961(DAR1) -Control | ADX_6093_A01-961(DAR2) -Control |
|---|---|---|
| EC50 | 74.22 | 31.71 |

| | ADX_6077_F02.SS13-6 | ADX_6093_A01.SS13-16 | ADX_6561_A01.SS13-4 |
| --- | --- | --- | --- |
| EC50 | 0.5267 | 74.21 | 33.74 |

| | ADX_6077_F02.SS13-6 | ADX_6093_A01.SS13-16 | ADX_6561_A01.SS13-4 |
|---|---|---|---|
| EC50 | 0.4429 | 169.0 | 22.75 |

| Treatments (n=3) | T/C | TR D29 | TGI |
|---|---|---|---|
| **DAR1 GPC3-AdxDC** | 62 | 27 | 80 |
| **DAR2 GPC3-AdxDC** | 74 | 0 | 92 |

| Treatments (n=3) | T/C | TR D29 | TGI |
|---|---|---|---|
| **DAR1 GPC3-AdxDC** | 62 | 27 | 80 |
| **DAR2 GPC3-AdxDC** | 74 | 0 | 92 |

| Treatments (n=3) | T/C | TR D29 | TGI |
|---|---|---|---|
| DAR1 GPC3-AdxDC | 62 | 27 | 80 |
| DAR2 GPC3-AdxDC | 74 | 0 | 92 |

| Treatments (n=3) | T/C | TR D29 | TGI |
|---|---|---|---|
| DAR1 GPC3-AdxDC | 62 | 27 | 80 |
| DAR2 GPC3-AdxDC | 74 | 0 | 92 |

| Treatments | T/C | TR (D29) | TGI |
|---|---|---|---|
| DAR2 GPC3_AdxDC | 88 | 31 | 110 |

| Treatments | T/C | TR (D29) | TGI |
|---|---|---|---|
| DAR2 GPC3_AdxDC | 88 | 31 | 110 |

| Treatments (n=3) | T/C | TR (D29) | TGI |
|---|---|---|---|
| DAR2 GPC3-AdxDC | 82 | 17 | 103 |

| Treatments (n=3) | T/C | TR (D29) | TGI |
|---|---|---|---|
| DAR2 GPC3_AdxDC | 82 | 17 | 103 |

TOTAL:105 PEPTIDES,87.4% COVERAGE, 2.66 REDUNDANCY
87% SEQUENCE COVERAGE
HDX: 1m, 10m, 4HR IN DUPLICATE (24HDXs, 2600 PEPTIDE SIGNALS)

Mice Dosed with [$^3$H]GPC3 Adx DC at 0.015 μmol/kg

Non-Binding Control
Mice Dosed with $[^3H]$RGE AdxDC at 0.22 µmol/kg

10nM (79G)

| wt | D | A | P | A | V | T | V |
|---|---|---|---|---|---|---|---|
| par | S | D | D | Y | H | A | H |
| # | 23 | 24 | 25 | 26 | 27 | 28 | 29 |
| * | 0.29 | 0.04 | 0.11 | 0.30 | 0.15 | 0.18 | 0.10 |
| P | 1.57 | 0.08 | 0.05 | 0.02 | 0.13 | 1.34 | 0.34 |
| G | 0.89 | 0.12 | 0.14 | 0.01 | 0.84 | 1.40 | 0.59 |
| A | 1.20 | 0.09 | 0.46 | 0.04 | 0.68 | 1.00 | 1.22 |
| C | 1.27 | 0.14 | 0.28 | 0.07 | 0.54 | 0.89 | 1.48 |
| S | 1.00 | 0.33 | 0.40 | 0.02 | 1.10 | 1.46 | 1.35 |
| T | 1.51 | 0.16 | 0.15 | 0.01 | 1.28 | 1.27 | 1.48 |
| V | 1.15 | 0.11 | 0.16 | 0.02 | 0.17 | 1.44 | 0.52 |
| L | 1.62 | 0.07 | 0.19 | 0.09 | 0.66 | 1.41 | 1.58 |
| I | 1.21 | 0.10 | 0.12 | 0.07 | 0.38 | 1.62 | 0.84 |
| M | 1.39 | 0.07 | 0.24 | 0.14 | 0.65 | 1.67 | 1.82 |
| K | 1.23 | 0.03 | 0.12 | 0.02 | 0.45 | 1.01 | 1.16 |
| R | 1.53 | 0.04 | 0.15 | 0.02 | 0.37 | 1.07 | 1.18 |
| H | 1.28 | 0.15 | 0.60 | 0.18 | 1.00 | 1.60 | 1.00 |
| F | 1.60 | 0.06 | 0.30 | 0.66 | 0.94 | 2.25 | 1.78 |
| Y | 1.60 | 0.06 | 0.32 | 1.00 | 0.91 | 2.08 | 1.68 |
| W | 1.95 | 0.07 | 0.48 | 0.62 | 0.82 | 3.01 | 2.30 |
| N | 1.14 | 0.44 | 0.45 | 0.02 | 1.14 | 1.54 | 1.44 |
| D | 1.35 | 1.00 | 1.00 | 0.01 | 0.99 | 1.77 | 1.40 |
| E | 1.34 | 0.39 | 0.55 | 0.01 | 0.75 | 1.79 | 1.67 |
| Q | 1.26 | 0.17 | 0.27 | 0.04 | 0.67 | 1.43 | 1.36 |

FIG. 24A

1nM (79G)

| wt | D | A | P | A | V | T | V |
|---|---|---|---|---|---|---|---|
| par | S | D | D | Y | H | A | H |
| # | 23 | 24 | 25 | 26 | 27 | 28 | 29 |
| * | 0.35 | 0.08 | 0.12 | 0.32 | 0.20 | 0.26 | 0.16 |
| P | 1.68 | 0.08 | 0.06 | 0.03 | 0.17 | 1.45 | 0.39 |
| G | 0.87 | 0.13 | 0.14 | 0.02 | 0.85 | 1.50 | 0.58 |
| A | 1.27 | 0.10 | 0.44 | 0.04 | 0.66 | 1.00 | 1.29 |
| C | 1.37 | 0.18 | 0.29 | 0.10 | 0.57 | 1.09 | 1.59 |
| S | 1.00 | 0.33 | 0.39 | 0.03 | 1.16 | 1.59 | 1.42 |
| T | 1.67 | 0.16 | 0.15 | 0.02 | 1.34 | 1.41 | 1.59 |
| V | 1.20 | 0.13 | 0.16 | 0.03 | 0.17 | 1.53 | 0.51 |
| L | 1.74 | 0.08 | 0.19 | 0.09 | 0.67 | 1.53 | 1.70 |
| I | 1.27 | 0.11 | 0.11 | 0.07 | 0.35 | 1.69 | 0.86 |
| M | 1.48 | 0.08 | 0.25 | 0.13 | 0.62 | 1.79 | 1.94 |
| K | 1.26 | 0.04 | 0.12 | 0.02 | 0.43 | 1.04 | 1.19 |
| R | 1.61 | 0.03 | 0.15 | 0.03 | 0.36 | 1.11 | 1.31 |
| H | 1.36 | 0.16 | 0.55 | 0.17 | 1.00 | 1.68 | 1.00 |
| F | 1.85 | 0.07 | 0.30 | 0.64 | 0.98 | 2.65 | 1.94 |
| Y | 1.75 | 0.08 | 0.31 | 1.00 | 0.96 | 2.30 | 1.84 |
| W | 2.08 | 0.08 | 0.46 | 0.61 | 0.85 | 3.93 | 2.53 |
| N | 1.20 | 0.42 | 0.44 | 0.02 | 1.14 | 1.64 | 1.52 |
| D | 1.38 | 1.00 | 1.00 | 0.01 | 1.02 | 1.91 | 1.49 |
| E | 1.37 | 0.41 | 0.52 | 0.02 | 0.72 | 1.93 | 1.86 |
| Q | 1.31 | 0.16 | 0.24 | 0.04 | 0.75 | 1.51 | 1.51 |

FIG. 24B

10nM (79A)

| wt | D | A | P | A | V | T | V |
|---|---|---|---|---|---|---|---|
| par | S | D | D | Y | H | A | H |
| # | 23 | 24 | 25 | 26 | 27 | 28 | 29 |
| * | 0.24 | 0.05 | 0.08 | 0.29 | 0.15 | 0.22 | 0.11 |
| P | 1.71 | 0.03 | 0.02 | 0.02 | 0.12 | 1.37 | 0.28 |
| G | 0.72 | 0.05 | 0.04 | 0.02 | 0.62 | 1.18 | 0.26 |
| A | 1.16 | 0.05 | 0.16 | 0.02 | 0.45 | 1.00 | 1.06 |
| C | 1.23 | 0.11 | 0.15 | 0.07 | 0.28 | 0.76 | 1.26 |
| S | 1.00 | 0.10 | 0.15 | 0.02 | 0.99 | 1.33 | 1.07 |
| T | 1.50 | 0.04 | 0.04 | 0.02 | 1.21 | 1.26 | 1.45 |
| V | 1.06 | 0.05 | 0.04 | 0.02 | 0.07 | 1.48 | 0.30 |
| L | 1.62 | 0.04 | 0.05 | 0.03 | 0.33 | 1.28 | 1.17 |
| I | 1.13 | 0.05 | 0.04 | 0.03 | 0.13 | 1.67 | 0.53 |
| M | 1.37 | 0.04 | 0.06 | 0.04 | 0.33 | 1.62 | 1.57 |
| K | 1.18 | 0.02 | 0.04 | 0.02 | 0.21 | 1.01 | 0.90 |
| R | 1.52 | 0.02 | 0.04 | 0.02 | 0.18 | 1.06 | 0.90 |
| H | 1.24 | 0.06 | 0.31 | 0.06 | 1.00 | 1.45 | 1.00 |
| F | 1.68 | 0.05 | 0.09 | 0.48 | 0.73 | 1.79 | 1.48 |
| Y | 1.74 | 0.05 | 0.09 | 1.00 | 0.63 | 1.74 | 1.38 |
| W | 2.27 | 0.04 | 0.22 | 0.35 | 0.48 | 2.15 | 1.85 |
| N | 0.98 | 0.15 | 0.21 | 0.02 | 0.98 | 1.36 | 1.41 |
| D | 1.29 | 1.00 | 1.00 | 0.02 | 0.68 | 1.53 | 1.05 |
| E | 1.18 | 0.17 | 0.27 | 0.02 | 0.38 | 1.72 | 1.27 |
| Q | 1.18 | 0.06 | 0.09 | 0.03 | 0.42 | 1.52 | 1.16 |

FIG. 25A

1nM (79A)

| wt | D | A | P | A | V | T | V |
|---|---|---|---|---|---|---|---|
| par | S | D | D | Y | H | A | H |
| # | 23 | 24 | 25 | 26 | 27 | 28 | 29 |
| * | 0.38 | 0.12 | 0.13 | 0.31 | 0.17 | 0.24 | 0.15 |
| P | 1.79 | 0.04 | 0.05 | 0.03 | 0.17 | 1.46 | 0.34 |
| G | 0.73 | 0.07 | 0.07 | 0.02 | 0.63 | 1.25 | 0.28 |
| A | 1.19 | 0.06 | 0.17 | 0.04 | 0.49 | 1.00 | 1.09 |
| C | 1.32 | 0.22 | 0.24 | 0.13 | 0.36 | 0.95 | 1.35 |
| S | 1.00 | 0.10 | 0.17 | 0.04 | 1.09 | 1.42 | 1.11 |
| T | 1.59 | 0.06 | 0.06 | 0.03 | 1.25 | 1.29 | 1.53 |
| V | 1.12 | 0.09 | 0.06 | 0.03 | 0.07 | 1.59 | 0.31 |
| L | 1.74 | 0.06 | 0.07 | 0.05 | 0.34 | 1.35 | 1.22 |
| I | 1.19 | 0.10 | 0.06 | 0.03 | 0.15 | 1.77 | 0.55 |
| M | 1.39 | 0.05 | 0.08 | 0.05 | 0.34 | 1.66 | 1.62 |
| K | 1.25 | 0.04 | 0.06 | 0.04 | 0.25 | 1.03 | 0.97 |
| R | 1.60 | 0.04 | 0.05 | 0.03 | 0.19 | 1.12 | 0.95 |
| H | 1.29 | 0.07 | 0.32 | 0.07 | 1.00 | 1.50 | 1.00 |
| F | 1.80 | 0.09 | 0.13 | 0.51 | 0.73 | 1.89 | 1.57 |
| Y | 1.89 | 0.09 | 0.13 | 1.00 | 0.62 | 1.79 | 1.42 |
| W | 2.41 | 0.10 | 0.24 | 0.32 | 0.54 | 2.36 | 2.03 |
| N | 1.01 | 0.17 | 0.21 | 0.03 | 1.04 | 1.46 | 1.36 |
| D | 1.35 | 1.00 | 1.00 | 0.03 | 0.74 | 1.63 | 1.13 |
| E | 1.25 | 0.22 | 0.29 | 0.03 | 0.38 | 1.83 | 1.34 |
| Q | 1.16 | 0.07 | 0.10 | 0.04 | 0.44 | 1.49 | 1.26 |

FIG. 25B

10nM (79G)

| wt | G | S | K | S |
|---|---|---|---|---|
| par | — | E | H | V |
| # | 52 | 53 | 54 | 55 |
| * | 0.09 | 0.07 | 0.06 | 0.51 |
| P | 0.01 | 0.35 | 0.02 | 0.40 |
| G | 1.00 | 0.03 | 0.01 | 0.34 |
| A | 0.07 | 0.39 | 0.01 | 0.52 |
| C | 0.04 | 0.08 | 0.10 | 0.52 |
| S | 0.02 | 0.02 | 0.01 | 0.48 |
| T | 0.02 | 0.01 | 0.01 | 1.13 |
| V | 0.02 | 0.04 | 0.01 | 1.00 |
| L | 0.02 | 0.03 | 0.03 | 0.87 |
| I | 0.02 | 0.02 | 0.03 | 1.94 |
| M | 0.01 | 0.03 | 0.15 | 0.56 |
| K | 0.01 | 0.01 | 0.01 | 0.31 |
| R | 0.02 | 0.01 | 0.01 | 0.16 |
| H | 0.01 | 0.02 | 1.00 | 0.55 |
| F | 0.02 | 0.26 | 0.07 | 0.94 |
| Y | 0.02 | 0.03 | 0.05 | 1.10 |
| W | 0.03 | 0.10 | 0.03 | 1.12 |
| N | 0.01 | 0.01 | 0.02 | 0.73 |
| D | 0.02 | 0.10 | 0.01 | 0.74 |
| E | 0.01 | 1.00 | 0.01 | 0.62 |
| Q | 0.02 | 0.12 | 0.03 | 0.42 |

FIG. 26A

1nM (79G)

| wt | G | S | K | S |
|---|---|---|---|---|
| par | — | E | H | V |
| # | 52 | 53 | 54 | 55 |
| * | 0.12 | 0.10 | 0.08 | 0.63 |
| P | 0.02 | 0.36 | 0.03 | 0.39 |
| G | 1.00 | 0.04 | 0.02 | 0.33 |
| A | 0.08 | 0.39 | 0.01 | 0.52 |
| C | 0.08 | 0.15 | 0.13 | 0.54 |
| S | 0.03 | 0.02 | 0.01 | 0.46 |
| T | 0.03 | 0.02 | 0.02 | 1.19 |
| V | 0.03 | 0.05 | 0.02 | 1.00 |
| L | 0.03 | 0.05 | 0.04 | 0.90 |
| I | 0.03 | 0.04 | 0.04 | 2.17 |
| M | 0.03 | 0.04 | 0.14 | 0.58 |
| K | 0.02 | 0.02 | 0.02 | 0.29 |
| R | 0.03 | 0.02 | 0.02 | 0.16 |
| H | 0.02 | 0.03 | 1.00 | 0.54 |
| F | 0.04 | 0.28 | 0.08 | 0.97 |
| Y | 0.03 | 0.04 | 0.06 | 1.15 |
| W | 0.05 | 0.12 | 0.04 | 1.16 |
| N | 0.02 | 0.02 | 0.02 | 0.73 |
| D | 0.04 | 0.10 | 0.02 | 0.75 |
| E | 0.02 | 1.00 | 0.01 | 0.62 |
| Q | 0.03 | 0.12 | 0.04 | 0.43 |

FIG. 26B

10nM (79A)

| wt | G | S | K | S |
|---|---|---|---|---|
| par | — | E | H | V |
| # | 52 | 53 | 54 | 55 |
| * | 0.19 | 0.10 | 0.11 | 0.79 |
| P | 0.02 | 0.07 | 0.03 | 0.13 |
| G | 1.00 | 0.03 | 0.02 | 0.12 |
| A | 0.03 | 0.18 | 0.02 | 0.23 |
| C | 0.10 | 0.13 | 0.07 | 0.25 |
| S | 0.03 | 0.03 | 0.02 | 0.20 |
| T | 0.03 | 0.02 | 0.02 | 0.99 |
| V | 0.03 | 0.05 | 0.02 | 1.00 |
| L | 0.04 | 0.05 | 0.03 | 0.75 |
| I | 0.04 | 0.06 | 0.03 | 2.29 |
| M | 0.03 | 0.04 | 0.03 | 0.42 |
| K | 0.02 | 0.03 | 0.02 | 0.15 |
| R | 0.03 | 0.03 | 0.02 | 0.05 |
| H | 0.03 | 0.02 | 1.00 | 0.31 |
| F | 0.04 | 0.08 | 0.03 | 0.90 |
| Y | 0.04 | 0.04 | 0.04 | 1.22 |
| W | 0.05 | 0.06 | 0.04 | 1.12 |
| N | 0.03 | 0.02 | 0.03 | 0.47 |
| D | 0.04 | 0.05 | 0.02 | 0.55 |
| E | 0.03 | 1.00 | 0.02 | 0.38 |
| Q | 0.04 | 0.05 | 0.03 | 0.20 |

FIG. 27A

1nM (79A)

| wt | G | S | K | S |
|---|---|---|---|---|
| par | — | E | H | V |
| # | 52 | 53 | 54 | 55 |
| * | 0.29 | 0.20 | 0.14 | 1.19 |
| P | 0.04 | 0.10 | 0.09 | 0.14 |
| G | 1.00 | 0.05 | 0.04 | 0.13 |
| A | 0.05 | 0.20 | 0.03 | 0.24 |
| C | 0.19 | 0.29 | 0.13 | 0.29 |
| S | 0.05 | 0.04 | 0.03 | 0.20 |
| T | 0.07 | 0.05 | 0.03 | 1.03 |
| V | 0.07 | 0.11 | 0.04 | 1.00 |
| L | 0.08 | 0.11 | 0.06 | 0.77 |
| I | 0.08 | 0.12 | 0.05 | 2.51 |
| M | 0.09 | 0.07 | 0.06 | 0.41 |
| K | 0.05 | 0.04 | 0.03 | 0.16 |
| R | 0.06 | 0.06 | 0.04 | 0.06 |
| H | 0.06 | 0.04 | 1.00 | 0.31 |
| F | 0.09 | 0.14 | 0.06 | 0.92 |
| Y | 0.08 | 0.09 | 0.06 | 1.27 |
| W | 0.12 | 0.10 | 0.07 | 1.17 |
| N | 0.05 | 0.04 | 0.05 | 0.48 |
| D | 0.07 | 0.07 | 0.04 | 0.55 |
| E | 0.06 | 1.00 | 0.03 | 0.37 |
| Q | 0.09 | 0.08 | 0.05 | 0.20 |

FIG. 27B

10nM (79G)

| wt | G | R | G | D | S | P | A | S | S | K | P |
|---|---|---|---|---|---|---|---|---|---|---|---|
| par | Y | D | — | E | K | A | — | T | D | W | S |
| # | 77 | 78 | 79 | 80 | 81 | 82 | 83 | 84 | 85 | 86 | 87 |
| * | 0.09 | 0.22 | 0.05 | 0.96 | 0.75 | 0.11 | 0.25 | 0.31 | 0.32 | 0.61 | 0.75 |
| P | 0.01 | 0.28 | 0.10 | 0.19 | 0.24 | 0.78 | 0.35 | 0.65 | 0.33 | 0.02 | 0.26 |
| G | 0.01 | 0.34 | 1.00 | 1.45 | 0.89 | 0.88 | 1.39 | 0.69 | 0.44 | 0.41 | 1.38 |
| A | 0.02 | 0.53 | 0.43 | 1.57 | 1.12 | 1.00 | 1.00 | 0.86 | 0.69 | 0.09 | 1.49 |
| C | 0.03 | 0.54 | 0.83 | 1.72 | 1.12 | 0.75 | 1.49 | 1.14 | 0.46 | 0.22 | 1.49 |
| S | 0.03 | 0.61 | 0.71 | 1.66 | 1.38 | 1.27 | 1.58 | 0.92 | 0.83 | 0.22 | 1.00 |
| T | 0.01 | 0.73 | 0.68 | 1.71 | 1.34 | 0.88 | 1.59 | 1.00 | 0.60 | 0.10 | 1.55 |
| V | 0.01 | 0.57 | 0.46 | 1.86 | 1.30 | 1.22 | 1.53 | 1.45 | 0.69 | 0.02 | 1.56 |
| L | 0.02 | 0.57 | 0.77 | 1.86 | 1.19 | 1.01 | 1.31 | 1.45 | 0.42 | 0.05 | 1.58 |
| I | 0.01 | 0.59 | 0.48 | 1.96 | 1.19 | 1.49 | 1.39 | 1.36 | 0.64 | 0.02 | 1.53 |
| M | 0.01 | 0.65 | 0.74 | 1.90 | 1.11 | 0.99 | 1.49 | 1.23 | 0.62 | 0.05 | 1.63 |
| K | 0.01 | 0.70 | 0.64 | 1.47 | 1.00 | 2.09 | 1.75 | 1.06 | 0.85 | 0.08 | 1.79 |
| R | 0.01 | 0.72 | 0.70 | 2.09 | 1.62 | 1.97 | 1.57 | 1.20 | 0.38 | 0.14 | 1.86 |
| H | 0.03 | 0.54 | 0.64 | 2.01 | 1.43 | 0.85 | 1.62 | 0.87 | 0.49 | 0.28 | 1.59 |
| F | 0.72 | 0.71 | 0.67 | 2.36 | 1.43 | 1.82 | 1.60 | 1.10 | 0.43 | 0.60 | 1.48 |
| Y | 1.00 | 0.71 | 0.69 | 2.51 | 1.41 | 1.16 | 1.59 | 1.36 | 0.37 | 1.32 | 1.63 |
| W | 0.96 | 0.68 | 0.76 | 3.04 | 1.40 | 1.19 | 1.65 | 0.92 | 0.40 | 1.00 | 1.76 |
| N | 0.01 | 0.98 | 0.73 | 1.85 | 1.25 | 0.76 | 1.40 | 1.12 | 0.95 | 0.12 | 1.37 |
| D | 0.00 | 1.00 | 0.49 | 1.40 | 0.81 | 0.27 | 1.26 | 0.68 | 1.00 | 0.12 | 1.15 |
| E | 0.01 | 0.52 | 0.63 | 1.00 | 0.85 | 0.11 | 1.36 | 0.73 | 0.85 | 0.04 | 1.16 |
| Q | 0.00 | 0.54 | 0.68 | 1.63 | 1.11 | 0.78 | 1.60 | 1.12 | 0.78 | 0.05 | 1.47 |

FIG. 28

1nM (79G)

| wt | G | R | G | D | S | P | A | S | S | K | P |
|---|---|---|---|---|---|---|---|---|---|---|---|
| par | Y | D | — | E | K | A | — | T | D | W | S |
| # | 77 | 78 | 79 | 80 | 81 | 82 | 83 | 84 | 85 | 86 | 87 |
| * | 0.11 | 0.22 | 0.05 | 1.09 | 0.83 | 0.15 | 0.28 | 0.34 | 0.33 | 0.76 | 0.81 |
| P | 0.01 | 0.25 | 0.10 | 0.18 | 0.22 | 0.84 | 0.38 | 0.65 | 0.31 | 0.02 | 0.27 |
| G | 0.01 | 0.32 | 1.00 | 1.54 | 0.89 | 0.87 | 1.42 | 0.69 | 0.44 | 0.40 | 1.43 |
| A | 0.03 | 0.51 | 0.41 | 1.68 | 1.19 | 1.00 | 1.00 | 0.87 | 0.70 | 0.09 | 1.63 |
| C | 0.05 | 0.56 | 0.91 | 1.93 | 1.28 | 0.78 | 1.58 | 1.19 | 0.49 | 0.23 | 1.63 |
| S | 0.03 | 0.58 | 0.71 | 1.79 | 1.44 | 1.30 | 1.71 | 0.92 | 0.84 | 0.21 | 1.00 |
| T | 0.02 | 0.71 | 0.66 | 1.84 | 1.33 | 0.93 | 1.69 | 1.00 | 0.58 | 0.10 | 1.65 |
| V | 0.02 | 0.56 | 0.45 | 2.10 | 1.34 | 1.21 | 1.57 | 1.52 | 0.70 | 0.02 | 1.69 |
| L | 0.02 | 0.53 | 0.76 | 2.02 | 1.22 | 1.05 | 1.35 | 1.51 | 0.42 | 0.05 | 1.68 |
| I | 0.01 | 0.52 | 0.45 | 2.14 | 1.29 | 1.57 | 1.41 | 1.43 | 0.62 | 0.02 | 1.69 |
| M | 0.01 | 0.66 | 0.74 | 2.03 | 1.23 | 1.04 | 1.47 | 1.28 | 0.56 | 0.04 | 1.73 |
| K | 0.02 | 0.69 | 0.65 | 1.65 | 1.00 | 2.30 | 1.84 | 1.10 | 0.85 | 0.08 | 1.96 |
| R | 0.01 | 0.68 | 0.69 | 2.34 | 1.73 | 2.15 | 1.64 | 1.22 | 0.37 | 0.14 | 2.02 |
| H | 0.03 | 0.54 | 0.65 | 2.19 | 1.46 | 0.84 | 1.71 | 0.86 | 0.50 | 0.27 | 1.70 |
| F | 0.70 | 0.70 | 0.67 | 2.64 | 1.46 | 1.93 | 1.67 | 1.16 | 0.45 | 0.59 | 1.62 |
| Y | 1.00 | 0.69 | 0.68 | 2.95 | 1.40 | 1.21 | 1.72 | 1.39 | 0.41 | 1.41 | 1.72 |
| W | 0.91 | 0.62 | 0.77 | 3.72 | 1.48 | 1.26 | 1.71 | 0.89 | 0.39 | 1.00 | 1.87 |
| N | 0.01 | 0.93 | 0.74 | 2.06 | 1.40 | 0.71 | 1.50 | 1.19 | 1.00 | 0.11 | 1.47 |
| D | 0.01 | 1.00 | 0.49 | 1.52 | 0.79 | 0.24 | 1.30 | 0.64 | 1.00 | 0.12 | 1.29 |
| E | 0.01 | 0.51 | 0.68 | 1.00 | 0.87 | 0.12 | 1.36 | 0.74 | 0.91 | 0.04 | 1.17 |
| Q | 0.01 | 0.49 | 0.68 | 1.80 | 1.22 | 0.80 | 1.67 | 1.18 | 0.77 | 0.06 | 1.53 |

FIG. 29

10nM (79A)

| wt | G | R | G | D | S | P | A | S | S | K | P |
|---|---|---|---|---|---|---|---|---|---|---|---|
| par | Y | D | A | E | K | A | — | T | D | W | S |
| # | 77 | 78 | 79 | 80 | 81 | 82 | 83 | 84 | 85 | 86 | 87 |
| * | 0.14 | 0.34 | 0.11 | 0.73 | 0.93 | 0.12 | 0.38 | 0.19 | 0.18 | 0.76 | 0.73 |
| P | 0.00 | 0.26 | 0.24 | 0.92 | 0.14 | 0.48 | 0.12 | 0.12 | 0.06 | 0.03 | 0.09 |
| G | 0.01 | 0.20 | 2.31 | 2.86 | 0.94 | 0.48 | 1.07 | 0.11 | 0.12 | 0.10 | 1.22 |
| A | 0.04 | 1.03 | 1.00 | 1.66 | 0.88 | 1.00 | 1.00 | 0.26 | 0.49 | 0.02 | 1.50 |
| C | 0.06 | 0.94 | 1.91 | 2.40 | 1.05 | 0.71 | 1.68 | 0.57 | 0.24 | 0.09 | 1.55 |
| S | 0.03 | 0.89 | 1.65 | 1.67 | 1.02 | 1.12 | 1.85 | 0.34 | 0.59 | 0.05 | 1.00 |
| T | 0.02 | 1.02 | 1.57 | 1.56 | 1.30 | 1.33 | 1.75 | 1.00 | 0.24 | 0.03 | 1.57 |
| V | 0.02 | 1.36 | 1.06 | 2.17 | 1.37 | 1.34 | 1.83 | 1.49 | 0.44 | 0.02 | 1.65 |
| L | 0.03 | 1.16 | 1.78 | 1.95 | 1.02 | 1.51 | 1.33 | 0.94 | 0.18 | 0.03 | 1.64 |
| I | 0.01 | 1.47 | 1.11 | 2.22 | 1.32 | 1.85 | 1.60 | 1.35 | 0.37 | 0.03 | 1.76 |
| M | 0.03 | 1.38 | 1.72 | 2.18 | 1.04 | 0.91 | 1.58 | 0.75 | 0.33 | 0.03 | 1.73 |
| K | 0.01 | 1.68 | 1.48 | 1.90 | 1.00 | 2.52 | 1.74 | 0.32 | 0.50 | 0.03 | 1.81 |
| R | 0.04 | 1.56 | 1.62 | 2.52 | 1.64 | 2.89 | 2.00 | 0.29 | 0.16 | 0.05 | 1.96 |
| H | 0.02 | 1.16 | 1.47 | 2.61 | 1.29 | 0.81 | 1.80 | 0.23 | 0.22 | 0.04 | 1.47 |
| F | 0.72 | 1.83 | 1.56 | 3.04 | 1.04 | 2.42 | 1.83 | 0.35 | 0.10 | 0.16 | 1.76 |
| Y | 1.00 | 1.76 | 1.61 | 3.30 | 1.06 | 1.79 | 1.74 | 0.66 | 0.18 | 0.99 | 1.78 |
| W | 1.34 | 1.42 | 1.75 | 3.78 | 0.99 | 1.89 | 1.43 | 0.17 | 0.11 | 1.00 | 1.85 |
| N | 0.02 | 1.09 | 1.68 | 2.21 | 0.92 | 0.62 | 1.51 | 0.73 | 0.69 | 0.02 | 1.18 |
| D | 0.02 | 1.00 | 1.12 | 1.65 | 0.42 | 0.38 | 1.02 | 0.31 | 1.00 | 0.02 | 1.01 |
| E | 0.01 | 1.13 | 1.46 | 1.00 | 0.68 | 0.13 | 1.37 | 0.34 | 0.74 | 0.03 | 1.02 |
| Q | 0.01 | 1.20 | 1.58 | 1.85 | 1.21 | 0.61 | 1.93 | 0.56 | 0.54 | 0.02 | 1.55 |

FIG. 30

1nM (79A)

| wt | G | R | G | D | S | P | A | S | S | K | P |
|---|---|---|---|---|---|---|---|---|---|---|---|
| par | Y | D | A | E | K | A | — | T | D | W | S |
| # | 77 | 78 | 79 | 80 | 81 | 82 | 83 | 84 | 85 | 86 | 87 |
| * | 0.15 | 0.32 | 0.12 | 0.80 | 1.07 | 0.27 | 0.25 | 0.24 | 0.25 | 0.69 | 0.96 |
| P | 0.02 | 0.27 | 0.25 | 0.95 | 0.17 | 0.54 | 0.18 | 0.14 | 0.07 | 0.04 | 0.11 |
| G | 0.02 | 0.20 | 2.46 | 3.08 | 0.96 | 0.48 | 1.09 | 0.14 | 0.14 | 0.11 | 1.26 |
| A | 0.04 | 1.02 | 1.00 | 1.63 | 0.80 | 1.00 | 1.00 | 0.26 | 0.53 | 0.02 | 1.59 |
| C | 0.13 | 0.97 | 2.23 | 2.74 | 1.28 | 0.90 | 1.74 | 0.62 | 0.32 | 0.16 | 1.63 |
| S | 0.03 | 0.84 | 1.74 | 1.81 | 1.05 | 1.14 | 1.87 | 0.31 | 0.62 | 0.06 | 1.00 |
| T | 0.02 | 0.99 | 1.63 | 1.66 | 1.35 | 1.37 | 1.85 | 1.00 | 0.28 | 0.03 | 1.66 |
| V | 0.03 | 1.37 | 1.11 | 2.36 | 1.40 | 1.36 | 1.87 | 1.54 | 0.47 | 0.03 | 1.79 |
| L | 0.03 | 1.13 | 1.88 | 1.99 | 1.04 | 1.59 | 1.36 | 0.98 | 0.21 | 0.05 | 1.74 |
| I | 0.03 | 1.43 | 1.11 | 2.34 | 1.40 | 1.97 | 1.63 | 1.44 | 0.43 | 0.03 | 1.93 |
| M | 0.04 | 1.42 | 1.81 | 2.25 | 1.08 | 0.91 | 1.57 | 0.77 | 0.33 | 0.04 | 1.75 |
| K | 0.03 | 1.62 | 1.60 | 2.03 | 1.00 | 2.75 | 1.89 | 0.39 | 0.56 | 0.05 | 1.90 |
| R | 0.04 | 1.56 | 1.70 | 2.77 | 1.76 | 3.18 | 1.96 | 0.28 | 0.19 | 0.07 | 2.00 |
| H | 0.03 | 1.11 | 1.61 | 2.60 | 1.35 | 0.76 | 1.93 | 0.22 | 0.20 | 0.05 | 1.47 |
| F | 0.68 | 1.77 | 1.64 | 3.42 | 1.06 | 2.66 | 1.84 | 0.35 | 0.20 | 0.16 | 1.85 |
| Y | 1.00 | 1.67 | 1.67 | 3.54 | 1.11 | 1.92 | 1.73 | 0.65 | 0.22 | 1.02 | 1.89 |
| W | 1.30 | 1.42 | 1.89 | 4.17 | 1.00 | 2.06 | 1.47 | 0.22 | 0.18 | 1.00 | 1.96 |
| N | 0.02 | 1.07 | 1.82 | 2.41 | 0.93 | 0.54 | 1.64 | 0.71 | 0.64 | 0.04 | 1.22 |
| D | 0.02 | 1.00 | 1.21 | 1.76 | 0.42 | 0.34 | 0.98 | 0.35 | 1.00 | 0.02 | 1.13 |
| E | 0.02 | 1.18 | 1.68 | 1.00 | 0.73 | 0.17 | 1.40 | 0.35 | 0.78 | 0.04 | 1.14 |
| Q | 0.03 | 1.22 | 1.66 | 1.92 | 1.16 | 0.63 | 1.87 | 0.51 | 0.56 | 0.04 | 1.72 |

FIG. 31

GLYPICAN-3-BINDING FIBRONECTIN BASED SCAFFOLD MOLECULES

CROSS-REFERENCE TO RELATED APPLICATIONS

This application is a divisional of U.S. patent application Ser. No. 16/751,788, filed on Jan. 24, 2020, (now U.S. Pat. No. 11,524,992), which is a continuation of U.S. application Ser. No. 15/760,449, filed on Mar. 15, 2018 (now U.S. Pat. No. 10,584,160), which is a 35 U.S.C. 371 national stage filing of International Application No. PCT/US2016/053185, filed Sep. 22, 2016, and which claims priority to U.S. Provisional Application No. 62/222,633, filed Sep. 23, 2015. The contents of the aforementioned applications are hereby incorporated by reference.

REFERENCE TO SEQUENCE LISTING

The instant application contains a Sequence Listing which has been submitted electronically in xml format and is hereby incorporated by reference in its entirety. Said xml copy, created on Jun. 9, 2023, is named MXI-546US-CNDV_Sequence_Listing.xml and is 769,113 bytes in size.

BACKGROUND

Glypican-3 is an oncofetal antigen that belongs to the glypican family of glycosyl-phosphatidylinositol-anchored heparin sulfate proteoglycans. Glypicans regulate the activity of several growth factors including Wnts, Hedgehogs, bone morphogenic proteins and fibroblast growth factors (FGFs) (Filmus et al. FEBS J. 2013, 280:2471-2476). Glypicans are characterized by a covalent linkage to complex polysaccharide chains called heparinsulphate glycosaminoglycans. Glypicans are involved in cell signaling at the cellular-extracellular matrix interface. (Sasisekharan et al., Nature Reviews|Cancer, Volume 2 (2002). To date, six distinct members of the human glypican family have been identified. Cell membrane-bound glypican-3 is composed of two subunits, linked by one or more disulfide bonds.

Glypican-3 is expressed in fetal liver and placenta during development and is down-regulated or silenced in normal adult tissues. Mutations and depletions in the glypican-3 gene are responsible for the Simpson-Golabi-Behmel or Simpson dysmorphia syndrome in humans. Glypican-3 is expressed in various cancers and, in particular, hepatocellular carcinoma ("HCC"), melanoma, Wilm's tumor, and hepatoblastoma. (Jakubovic and Jothy; Ex. Mol. Path. 82:184-189 (2007); Nakatsura and Nishimura, Biodrugs 19(2):71-77 (2005). The cell surface form of Glypican-3 is highly expressed in HCC (>50%) and in other cancers including squamous lung cancer (approximately 25%).

Glypican-3 promotes tumor growth in vitro and in vivo by stimulating canonical Wnt signaling which induces the cytosolic accumulation and nuclear translocation of the transcription factor β-catenin (Filmus, supra). It has been shown that GPC3 can form a complex with several Wnts (Capurro et al., Cancer Res., 2005, 65:6245-6254), and Frizzleds, the signaling receptor for Wnts (Filmus, et al., Genome Biol., 2008, 9:224).

HCC is the third leading cause of cancer-related deaths worldwide. Each year, HCC accounts for about 1 million deaths. (Nakatsura and Nishimura, Biodrugs 19(2):71-77 (2005).) Hepatitis B virus, hepatitis C virus, and chronic heavy alcohol use leading to cirrhosis of the liver remain the most common causes of HCC. Its incidence has increased dramatically in the United States because of the spread of hepatitis C virus infection and is expected to increase for the next 2 decades. HCC is treated primarily by liver transplantation or tumor resection. Patient prognosis is dependent on both the underlying liver function and the stage at which the tumor is diagnosed. (Parikh and Hyman, Am J. Med. 120 (3):194-202 (2007).) Effective HCC treatment strategies are needed.

SUMMARY

Provided herein are polypeptides containing fibronectin based scaffolds (FBS) that bind to human glypican-3 and conjugates of these polypeptides that are suitable as therapeutic and diagnostic agents.

In one aspect, provided is a polypeptide comprising an FBS which specifically binds to human glypican-3 (GPC3). In some embodiments, the anti-GPC3 FBS is conjugated to therapeutic or diagnostic agent.

In another aspect, provided are methods of treating cancer in a human subject by administering to the subject a therapeutically effective amount of a polypeptide comprising an anti-GPC3 FBS or an anti-GPC3 FBS-drug conjugate. In some embodiments, the cancer over-expresses glypican-3 relative to non-cancerous cells. In some embodiments, the cancer is liver cancer (e.g., hepatocelluar carncinoma, hepatoblastoma), melanoma, Wilm's tumor or lung cancer (e.g., squamous lung cancer).

In another aspect, provided are methods of detecting GPC3 in vitro and in vivo, comprising contacting a cell with a polypeptide comprising an anti-GPC3 FBS under conditions to allow binding of the anti-GPC3 FBS to GPC3, and detecting complexes comprising the anti-GPC3 FBS and GPC3. In some embodiments, the anti-GPC3 FBS is linked to a detectable label (e.g., FITC).

Also provided are compositions, including pharmaceutical and diagnostic compositions, comprising the anti-GPC3 FBS polypeptides and/or anti-GPC3 FBS drug conjugates.

Also provided are nucleic acid molecules encoding the anti-GPC3 FBS, as well as expression vectors comprising such nucleic acids and host cells comprising such expression vectors. Also provided are kits comprising the anti-GPC3 FBS polypeptides and anti-GPC3 FBS conjugates and instructions for use.

Other features and advantages of the instant invention will be apparent from the following detailed description and examples which should not be construed as limiting.

BRIEF DESCRIPTION OF THE FIGURES

FIG. 1 depicts the amino acid sequences of representative anti-GPC3 adnectin polypeptides. 4578F03 (SEQ ID NO: 9), 4578H08 (SEQ ID NO: 18), 4578B06 (SEQ ID NO: 35), 4606F06 (SEQ ID NO: 48), 5273C01 (SEQ ID NO: 61), 5273D01 (SEQ ID NO: 74), 5274E01 (SEQ ID NO: 87), 6561A01 (SEQ ID NO: 87), 6077F02 (SEQ ID NO: 102), 6093A01 (SEQ ID NO: 463).

FIGS. 24A and 24B show heat maps of the BC loop of GPC3_AdxDC DG (amino acids 15-21 of SEQ ID NO: 98) obtained by positional scanning using 10 nM (FIG. 24A) or 1 nM (FIG. 24B) human glypican-3-biotin. The sequence of the wt BC loop is set forth in amino acids 15-21 of SEQ ID NO: 1.

FIGS. 25A and 25B show heat maps of the BC loop of GPC3_AdxDC DA (amino acids 15-21 of SEQ ID NO: 98) obtained by positional scanning using 10 nM (FIG. 25A) or 1 nM (FIG. 25B) human glypican-3-biotin. The sequence of the wt BC loop is set forth in amino acids 15-21 of SEQ ID NO: 1.

FIGS. 26A and 26B show heat maps of the DE loop of GPC3_AdxDC DG obtained by positional scanning using 10 nM (FIG. 26A) or 1 nM (FIG. 26B) human glypican-3-biotin. The sequence of the wt DE loop is set forth in amino acids 52-55 SEQ ID NO: 1.

FIGS. 27A and 27B show heat maps of the DE loop of GPC3_AdxDC DA obtained by positional scanning using 10 nM (FIG. 27A) or 1 nM (FIG. 27B) human glypican-3-biotin. The sequence of the wt DE loop is set forth in amino acids 52-55 of SEQ ID NO: 1.

FIG. 28 shows heat maps of the FG loop of GPC3_AdxDC DG (amino acids 69-79 of SEQ ID NO: 98) obtained by positional scanning using 10 nM human glypican-3-biotin. The sequence of the wt FG loop is set forth in amino acids 77-87 SEQ ID NO: 1.

FIG. 29 shows heat maps of the FG loop of GPC3_AdxDC DG (amino acids 69-79 of SEQ ID NO: 98) obtained by positional scanning using 1 nM human glypican-3-biotin. The sequence of the wt FG loop is set forth in amino acids 77-87 SEQ ID NO: 1.

FIG. 30 shows heat maps of the FG loop of GPC3_AdxDC DA (amino acids 69-79 of SEQ ID NO: 98) obtained by positional scanning using 10 nM human glypican-3-biotin. The sequence of the wt FG loop is set forth in amino acids 77-87 SEQ ID NO: 1.

FIG. 31 shows heat maps of the FG loop of GPC3_AdxDC DA (amino acids 69-79 of SEQ ID NO: 98) obtained by positional scanning using 1 nM human glypican-3-biotin. The sequence of the wt FG loop is set forth in amino acids 77-87 SEQ ID NO: 1.

DETAILED DESCRIPTION

Definitions

Figure 2A:
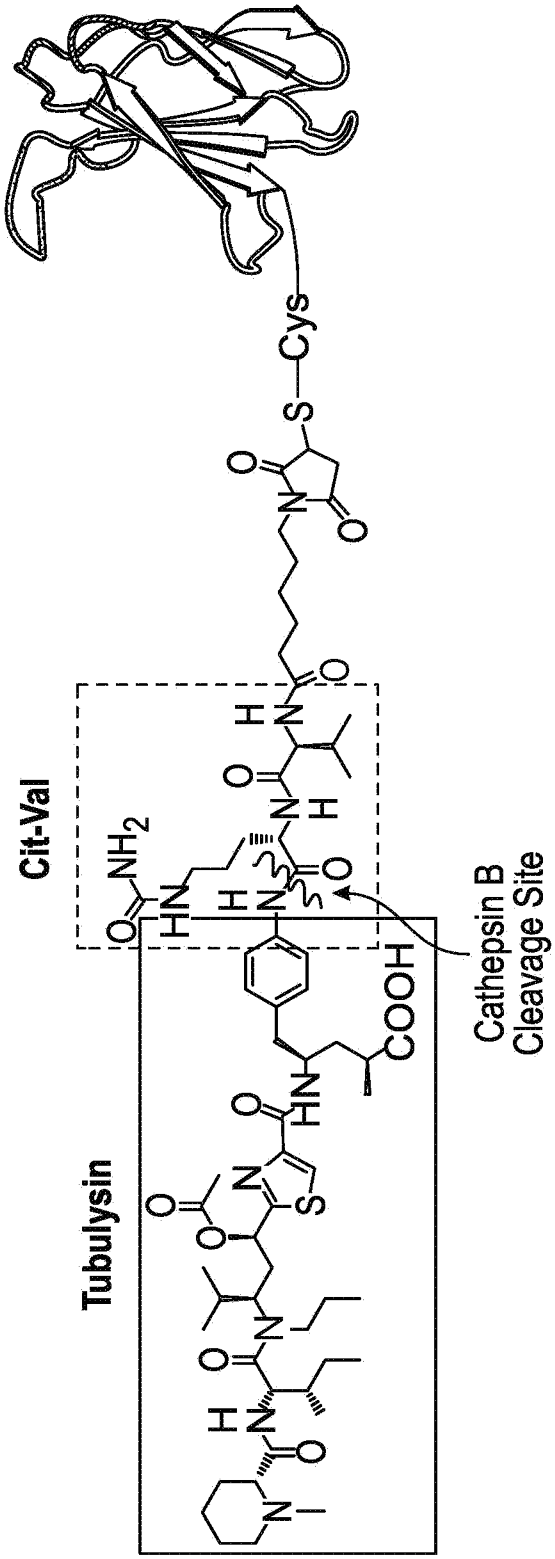
FIGS. 2A and 2B are schematics depicting the structure of the DAR1 and DAR2 tubulysin analog-GPC3 Adnectin drug conjugates.

Unless defined otherwise, all technical and scientific terms used herein have the same meaning as commonly understood by the skilled artisan. Although any methods and compositions similar or equivalent to those described herein can be used in practice or testing of the present invention, the preferred methods and compositions are described herein.

The terms "glypican-3, "glypican proteoglycan 3," "GPC3," "OTTHUMP00000062492," "GTR2-2," "SGB," "DGSX," "SDYS," "SGBS," "OCI-5," and "SGBS1" are used interchangeably, and include variants, isoforms and species homologs of human glypican-3. The complete amino acid sequence of an exemplary human glypican-3 has Genbank/NCBI accession number NM_004484 (SEQ ID NO: 344).

An "amino acid residue" is the remaining portion of an amino acid after a water molecule has been lost (an H+ from the nitrogenous side and an OH− from the carboxylic side) in the formation of a peptide bond.

By "polypeptide" is meant any sequence of two or more amino acids, regardless of length, post-translation modification, or function. Polypeptides can include natural amino acids and non-natural amino acids such as those described in U.S. Pat. No. 6,559,126, incorporated herein by reference. Polypeptides can also be modified in any of a variety of standard chemical ways (e.g., an amino acid can be modified with a protecting group; the carboxy-terminal amino acid can be made into a terminal amide group; the amino-terminal residue can be modified with groups to, e.g., enhance lipophilicity; or the polypeptide can be chemically glycosylated or otherwise modified to increase stability or in vivo half-life). Polypeptide modifications can include the attachment of another structure such as a cyclic compound or other molecule to the polypeptide and can also include polypeptides that contain one or more amino acids in an altered configuration (i.e., R or S; or, L or D).

An "isolated" polypeptide is one that has been identified and separated and/or recovered from a component of its natural environment. Contaminant components of its natural environment are materials that would interfere with diagnostic or therapeutic uses for the polypeptide, and may include enzymes, hormones, and other proteinaceous or nonproteinaceous solutes. In certain embodiments, the polypeptide will be purified (1) to greater than 95% by weight of polypeptide as determined by the Lowry method, and most preferably more than 99% by weight, (2) to a degree sufficient to obtain at least residues of N-terminal or internal amino acid sequence by use of a spinning cup sequenator, or (3) to homogeneity by SDS-PAGE under reducing or nonreducing condition using Coomassie blue or, preferably, silver stain.

As used herein, a "$^{10}$Fn3 domain" or "$^{10}$Fn3 moiety" or "$^{10}$Fn3 molecule" refers to wild-type $^{10}$Fn3 and biologically active variants thereof, e.g., biologically active variants that specifically bind to a target, such as a target protein. A wild-type human $^{10}$Fn3 domain may comprise the amino acid sequence set forth in SEQ ID NO: 1. Biologically active variants of a wild-type human $^{10}$Fn3 domain include $^{10}$Fn3 domains that comprise at least, at most or about 1, 2, 3, 4, 5, 6, 7, 8, 9, 10, 11, 12, 13, 14, 15, 16, 17, 18, 19, 20, 21, 22, 23, 24, 25, 30, 35, 40 or 45 amino acid changes, i.e., substitutions, additions or deletions, relative to a $^{10}$Fn3 domain comprising SEQ ID NOs: 1.

An "Adnectin" or "Adx" or "adnectin" or "adx" refers to a human $^{10}$Fn3 molecule that has been modified (relative to the wild-type sequence) to bind specifically to a target.

A "GPC3 Adnectin" or "anti-GPC3 Adnectin" is an Adnectin that binds specifically to GPC3, e.g., with a $K_D$ of 1 μM or less.

A "region" of a $^{10}$Fn3 domain (or moiety or molecule) as used herein refers to either a loop (AB, BC, CD, DE, EF and FG), a β-strand (A, B, C, D, E, F and G), the N-terminus (corresponding to amino acid residues 1-7 of SEQ ID NO: 1), or the C-terminus (corresponding to amino acid residues 93-94 of SEQ ID NO: 1).

A "north pole loop" of a $^{10}$Fn3 domain (or moiety) refers to any one of the BC, DE and FG loops of a $^{10}$Fn3 domain.

A "south pole loop" of a $^{10}$Fn3 domain (or moiety) refers to any one of the AB, CD and EF loops of a $^{10}$Fn3 domain.

A "scaffold region" refers to any non-loop region of a human $^{10}$Fn3 domain. The scaffold region includes the A, B, C, D, E, F and G β-strands as well as the N-terminal region (amino acids corresponding to residues 1-7 of SEQ ID NO: 1) and the C-terminal region (amino acids corresponding to residues 93-94 of SEQ ID NO: 1).

"Percent (%) amino acid sequence identity" herein is defined as the percentage of amino acid residues in a candidate sequence that are identical with the amino acid residues in a selected sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST$^{SM}$, BLAST$^{SM}$-2, ALIGN, ALIGN-2 or Megalign (DNASTAR®) software. Those skilled in the art can determine appropriate parameters for measuring alignment, including any algorithms needed to achieve maximal alignment over the full-length of the sequences being compared.

For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y where X is the number of amino acid residues scored as identical matches by a sequence alignment program, such as BLAST$^{SM}$, BLAST$^{SM}$-2, ALIGN, ALIGN-2 or Megalign (DNASTAR®), in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

As used herein, the term "Adnectin binding site" refers to the site or portion of a protein (e.g., GPC3) that interacts or binds to a particular Adnectin. Adnectin binding sites can be formed from contiguous amino acids or noncontiguous amino acids juxtaposed by tertiary folding of a protein. Adnectin binding sites formed by contiguous amino acids are typically retained on exposure to denaturing solvents, whereas Adnectin binding sites formed by tertiary folding are typically lost on treatment of denaturing solvents.

An Adnectin binding site for an anti-GPC3 Adnectin described herein may be determined by application of standard techniques typically used for epitope mapping of antibodies including, but not limited to protease mapping and mutational analysis.

As used herein, an amino acid residue in a polypeptide is considered to "contribute to binding" a target if (1) any of the non-hydrogen atoms of the residue's side chain or main chain is found to be within five angstroms of any atom of the binding target based on an experimentally determined three-dimensional structure of the complex, and/or (2) mutation of the residue to its equivalent in wild-type $^{10}$Fn3 (e.g., SEQ ID NO: 1), to alanine, or to a residue having a similarly sized or smaller side chain than the residue in question, leads to a measured increase of the equilibrium dissociation constant to the target (e.g., an increase in the $k_{on}$).

The terms "specifically binds," "specific binding," "selective binding, and "selectively binds," as used interchangeably herein in the context of FBS binding to GPC3 refers to an FBS that exhibits affinity for GPC3, but does not significantly bind (e.g., less than about 10% binding) to a different polypeptides as measured by a technique available in the art such as, but not limited to, Scatchard analysis and/or competitive binding assays (e.g., competition ELISA, BIACORE assay). The term is also applicable where e.g., a binding domain of an FBS described herein is specific for GPC3 from one or more species (e.g., human, rodent, primate), but does not does not cross-react with other glypicans (e.g., glypican-1, glypican-2, glypican-5, glypican-6).

The term "preferentially binds" as used herein in the context of Adnectins binding to GPC3 refers to the situation in which an Adnectin described herein binds GPC3 at least about 20% greater than it binds a different polypeptide as measured by a technique available in the art such as, but not limited to, Scatchard analysis and/or competitive binding assays (e.g., competition ELISA, BIACORE assay).

The term "$K_D$," as used herein, e.g., in the context of Adnectins binding to GPC3, is intended to refer to the dissociation equilibrium constant of a particular Adnectin-protein (e.g., GPC3) interaction or the affinity of an Adnectin for a protein (e.g., GPC3), as measured using a surface plasmon resonance assay or a cell binding assay. A "desired $K_D$," as used herein, refers to a $K_D$ of an Adnectin that is sufficient for the purposes contemplated. For example, a desired $K_D$ may refer to the $K_D$ of an Adnectin required to elicit a functional effect in an in vitro assay, e.g., a cell-based luciferase assay.

The term "$k_a$", as used herein in the context of Adnectins binding to a protein, is intended to refer to the association rate constant for the association of an Adnectin into the Adnectin/protein complex.

The term "$k_d$", as used herein in the context of Adnectins binding to a protein, is intended to refer to the dissociation rate constant for the dissociation of an Adnectin from the Adnectin/protein complex.

The term "$IC_{50}$", as used herein in the context of Adnectins, refers to the concentration of an Adnectin that inhibits a response, either in an in vitro or an in vivo assay, to a level that is 50% of the maximal inhibitory response, i.e., halfway between the maximal inhibitory response and the untreated response.

The term "glypican activity" or "glypican-3" activity as used herein refers to one or more of growth-regulatory or morphogenetic activities associated with activation of cell signaling by GPC3, for example, activation of Wnt signaling. For example, GPC3 may modulate tumor cell growth by complex formation with Wnt and/or Frizzeled proteins. GPC3 may also activate signaling pathways and tumor cell growth by interacting with FGF. GPC3 activity can be determined using art-recognized methods, such as those described herein. The phrases "glypican-3 activity" or "antagonize glypican-3 activity" or "antagonize glypican-3" are used interchangeably to refer to the ability of the anti-GPC3 FBS and anti-GPC3 drug conjugates provided herein to neutralize or antagonize an activity of GPC3 in vivo or in vitro. The terms "inhibit" or "neutralize" as used herein with respect to an activity of an anti-GPC3 FBS means the ability to substantially antagonize, prohibit, prevent, restrain, slow, disrupt, eliminate, stop, reduce or reverse e.g., progression or severity of that which is being inhibited including, but not limited to, a biological activity or property, a disease or a condition (e.g., tumor cell growth). The inhibition or neutralization is preferably at least about 10%, 20%, 30%, 40%, 50%, 60%, 70%, 80%, 90%, 95% or higher.

As used herein, the term "linked" refers to the association of two or more molecules. The linkage can be covalent or non-covalent. The linkage may be between a polypeptide and a chemical moiety or another polypeptide moiety. The linkage also can be genetic (i.e., recombinantly fused). Such linkages can be achieved using a wide variety of art recognized techniques, such as chemical conjugation and recombinant protein production.

The term "PK" is an acronym for "pharmacokinetic" and encompasses properties of a compound including, by way of example, absorption, distribution, metabolism, and elimination by a subject. A "PK modulation protein" or "PK moiety" as used herein refers to any protein, peptide, or moiety that affects the pharmacokinetic properties of a biologically active molecule when fused to or administered together with the biologically active molecule. Examples of a PK modulation protein or PK moiety include PEG, human serum albumin (HSA) binders (as disclosed in U.S. Publication Nos. 2005/0287153 and 2007/0003549, PCT Publication Nos. WO 2009/083804 and WO 2009/133208), human serum albumin and variants thereof, transferrin and variants thereof, Fc or Fc fragments and variants thereof, and sugars (e.g., sialic acid).

The serum or plasma "half-life" of a polypeptide can generally be defined as the time taken for the serum concentration of the polypeptide to be reduced by 50%, in vivo, for example due to degradation of the polypeptide and/or clearance or sequestration of the polypeptide by natural mechanisms. The half-life can be determined in any manner known per se, such as by pharmacokinetic analysis. Suitable techniques will be clear to the person skilled in the art, and may, for example, generally involve the steps of administering a suitable dose of a polypeptide to a primate; collecting blood samples or other samples from said primate at regular intervals; determining the level or concentration of the polypeptide in said blood sample; and calculating, from (a plot of) the data thus obtained, the time until the level or concentration of the polypeptide has been reduced by 50% compared to the initial level upon dosing. Methods for determining half-life may be found, for example, in Kenneth et al., *Chemical Stability of Pharmaceuticals: A Handbook for Pharmacists* (1986); Peters et al., *Pharmacokinete Analysis: A Practical Approach* (1996); and Gibaldi, M. et al., *Pharmacokinetics*, Second Rev. Edition, Marcel Dekker (1982).

Serum half-life can be expressed using parameters such as the $t_{1/2}$-alpha, $t_{1/2}$-beta and the area under the curve (AUC). An "increase in half-life" refers to an increase in any one of these parameters, any two of these parameters, or in all three these parameters. In certain embodiments, an increase in half-life refers to an increase in the $t_{1/2}$-beta and/or HL_Lambda_z, either with or without an increase in the $t_{1/2}$-alpha and/or the AUC or both.

The term "detectable" refers to the ability to detect a signal over the background signal. The term "detectable signal" is a signal derived from non-invasive imaging techniques such as, but not limited to, positron emission tomography (PET). The detectable signal is detectable and distinguishable from other background signals that may be generated from the subject. In other words, there is a measurable and statistically significant difference (e.g., a statistically significant difference is enough of a difference to distinguish among the detectable signal and the background, such as about 0.1%, 1%, 3%, 5%, 10%, 15%, 20%, 25%, 30%, or 40% or more difference between the detectable signal and the background) between the detectable signal and the background. Standards and/or calibration curves can be used to determine the relative intensity of the detectable signal and/or the background.

A "detectably effective amount" of a composition comprising an imaging agent described herein is defined as an amount sufficient to yield an acceptable image using equipment that is available for clinical use. A detectably effective amount of an imaging agent provided herein may be administered in more than one injection. The detectably effective amount can vary according to factors such as the degree of susceptibility of the individual, the age, sex, and weight of the individual, idiosyncratic responses of the individual, and the like. Detectably effective amounts of imaging compositions can also vary according to instrument and methodologies used. Optimization of such factors is well within the level of skill in the art. In certain embodiments, a GPC3 imaging agent, e.g., those described herein, provides a differentiation factor (i.e., specific signal to background signal) of 2 or more, e.g., 3, 4, 5 or more.

The terms "individual," "subject," and "patient," used interchangeably herein, refer to an animal, preferably a mammal (including a nonprimate and a primate), e.g., a human.

A "cancer" refers a broad group of various diseases characterized by the uncontrolled growth of abnormal cells in the body. Unregulated cell division and growth divide and grow results in the formation of malignant tumors that invade neighboring tissues and may also metastasize to distant parts of the body through the lymphatic system or bloodstream.

"Treatment" or "therapy" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication, condition or biochemical indicia associated with a disease.

"Administration" or "administering," as used herein in the context of anti-GPC3 Adnectins, refers to introducing a GPC3 Adnectin or GPC3 Adnectin-based probe or a labeled probe (also referred to as the "imaging agent") described herein into a subject. Any route of administration is suitable, such as intravenous, oral, topical, subcutaneous, peritoneal, intra-arterial, inhalation, vaginal, rectal, nasal, introduction into the cerebrospinal fluid, or instillation into body compartments can be used.

The terms "co-administration" or the like, as used herein, are meant to encompass administration of the selected pharmaceutical agents to a single patient, and are intended to include regimens in which the agents are administered by the same or different route of administration or at the same or different time.

The term "therapeutically effective amount" refers to at least the minimal dose, but less than a toxic dose, of an agent which is necessary to impart a therapeutic benefit to a subject.

As used herein, an "effective amount" refers to at least an amount effective, at dosages and for periods of time necessary, to achieve the desired result.

As used herein, a "sufficient amount" refers to an amount sufficient to achieve the desired result.

The term "sample" can refer to a tissue sample, cell sample, a fluid sample, and the like. The sample may be taken from a subject. The tissue sample can include hair (including roots), buccal swabs, blood, saliva, semen, muscle, or from any internal organs. The fluid may be, but is not limited to, urine, blood, ascites, pleural fluid, spinal fluid, and the like. The body tissue can include, but is not limited to, skin, muscle, endometrial, uterine, and cervical tissue.

Overview

Provided herein are novel fibronectin based scaffold polypeptides which bind to human glypican-3. Such polypeptides can be coupled to other therapeutic and diagnostic agents and are useful, for example, in targeting therapeutic and diagnostic agents to cells and tissues expressing glypican-3 (e.g., cancer cells over-expressing glypican-3).

I. Anti-GPC3 Fibronectin Based Scaffolds

As used herein, a "fibronectin based scaffold" or "FBS" protein or moiety refers to proteins or moieties that are based on a fibronectin type III ("Fn3") repeat and can be modified to bind specifically to given targets, e.g., target proteins. Fn3 is a small (about 10 kDa) domain that has the structure of an immunoglobulin (Ig) fold (i.e., an Ig-like β-sandwich structure, consisting of seven β-strands and six loops). Fibronectin has 18 Fn3 repeats, and while the sequence homology between the repeats is low, they all share a high similarity in tertiary structure. Fn3 domains are also present in many proteins other than fibronectin, such as adhesion molecules, cell surface molecules, e.g., cytokine receptors, and carbohydrate binding domains. For reviews see Bork et al., *Proc. Natl. Acad. Sci. USA,* 89(19):8990-8994 (1992); Bork et al., *J. Mol. Biol.,* 242(4):309-320 (1994); Campbell et al., *Structure,* 2(5):333-337 (1994); Harpez et al., *J. Mol. Biol.,* 238(4):528-539 (1994)). The term "FBS" protein or moiety is intended to include scaffolds based on Fn3 domains from these other proteins (i.e., non fibronectin molecules).

An Fn3 domain is small, monomeric, soluble, and stable. It lacks disulfide bonds and, therefore, is stable under reducing conditions. Fn3 domains comprise, in order from N-terminus to C-terminus, a beta or beta-like strand, A; a loop, AB; a beta or beta-like strand, B; a loop, BC; a beta or beta-like strand, C; a loop, CD; a beta or beta-like strand, D; a loop, DE; a beta or beta-like strand, E; a loop, EF; a beta or beta-like strand, F; a loop, FG; and a beta or beta-like strand, G. The seven antiparallel β-strands are arranged as two beta sheets that form a stable core, while creating two "faces" composed of the loops that connect the beta or beta-like strands. Loops AB, CD, and EF are located at one face ("the south pole") and loops BC, DE, and FG are located on the opposing face ("the north pole").

The loops in Fn3 molecules are structurally similar to complementary determining regions (CDRs) of antibodies, and when altered, may be involved in binding of the Fn3 molecule to a target, e.g., a target protein. Other regions of Fn3 molecules, such as the beta or beta-like strands and N-terminal or C-terminal regions, when altered, may also be involved in binding to a target. Any or all of loops AB, BC, CD, DE, EF and FG may participate in binding to a target. Any of the beta or beta-like strands may be involved in binding to a target. Fn3 domains may also bind to a target through one or more loops and one or more beta or beta-like strands. Binding may also require the N-terminal or C-terminal regions.

An anti-GPC3 FBS may be based on the tenth fibronectin type III domain, i.e., the tenth module of human Fn3 ($^{10}$Fn3) in which one or more solvent accessible loops have been randomized or mutated. The amino acid sequence of a wild-type human $^{10}$Fn3 moiety is as follows:

VSDVPRDLEVVAATPTSLLISWDAPAVTVRYYRITY-GETGGNSPVQEFTVPGSKSTATIS-GLKPGVDYTITVYAVTGRGDSPASSKPISINYRT (SEQ ID No. 1)

The AB, CD and EF loops are underlined; the BC, FG, and DE loops are emphasized in bold; the β-strands are located between or adjacent to each of the loop regions; and the N-terminal region is shown in italics). The last two amino acid residues of SEQ ID NO: 1 are a portion of a C-terminal region. The core $^{10}$Fn3 domain begins with amino acid 9 ("E") and ends with amino acid 94 ("T") and corresponds to an 86 amino acid polypeptide. The core wild-type human $^{10}$Fn3 domain is set forth in SEQ ID NO: 2. Both variant and wild-type $^{10}$Fn3 proteins are characterized by the same structure, namely seven beta-strand domain sequences designated A through G and six loop regions (AB loop, BC loop, CD loop, DE loop, EF loop, and FG loop) which connect the seven beta-strand domain sequences. The beta strands positioned closest to the N- and C-termini may adopt a beta-like conformation in solution. In SEQ ID NO: 1, the AB loop corresponds to residues 14-17, the BC loop corresponds to residues 23-31, the CD loop corresponds to residues 37-47, the DE loop corresponds to residues 51-56, the EF loop corresponds to residues 63-67, and the FG loop corresponds to residues 76-87.

Accordingly, in certain embodiments, the anti-GPC3 FBS moiety (e.g., anti-GPC3 Adnectin) comprises a $^{10}$Fn3 domain that is defined generally by the following degenerate sequence:

VSDVPRDLEVVAA$(X)_u$LLIWS$(X)_v$YRITY$(X)_w$FTV$(X)_x$ATISGL$(X)_y$YTITVYA$(X)_z$ISINYRT (SEQ ID No. 3), or by a sequence lacking 1, 2, 3, 4, 5, 6 or 7 N-terminal amino acids, respectively.

or by a sequence lacking 1, 2, 3, 4, 5, 6 or 7 N-terminal amino acids, respectively.

In SEQ ID NO: 3, the AB loop is represented by $(X)_u$, the BC loop is represented by $(X)_v$, the CD loop is represented by $(X)_w$, the DE loop is represented by $(X)_x$, the EF loop is represented by $(X)_y$ and the FG loop is represented by $X_z$. X represents any amino acid and the subscript following the X represents an integer of the number of amino acids. In particular, u, v, w, x, y and z may each independently be anywhere from 2-20, 2-15, 2-10, 2-8, 5-20, 5-15, 5-10, 5-8, 6-20, 6-15, 6-10, 6-8, 2-7, 5-7, or 6-7 amino acids. The sequences of the beta strands (underlined in SEQ ID NO: 3) may have anywhere from 0 to 10, from 0 to 8, from 0 to 6, from 0 to 5, from 0 to 4, from 0 to 3, from 0 to 2, or from 0 to 1 substitutions, deletions or additions across all 7 scaffold regions relative to the corresponding amino acids shown in SEQ ID NO: 3. In some embodiments, the sequences of the beta strands may have anywhere from 0 to 10, from 0 to 8, from 0 to 6, from 0 to 5, from 0 to 4, from 0 to 3, from 0 to 2, or from 0 to 1 substitutions, e.g., conservative substitutions, across all 7 scaffold regions relative to the corresponding amino acids shown in SEQ ID NO: 3.

It should be understood that not every residue within a loop region needs to be modified or altered in order to achieve a $^{10}$Fn3 binding domain having strong affinity for a desired target. Additionally, insertions and deletions in the loop regions may also be made while still producing high affinity anti-GPC3 $^{10}$Fn3 binding domains. By "altered" is meant one or more amino acid sequence alterations relative to a template sequence (i.e., the corresponding wild-type human fibronectin domain) and includes amino acid additions, deletions, substitutions or a combination thereof.

In some embodiments, the anti-GPC3 FBS moiety comprises a $^{10}$Fn3 domain wherein the non-loop regions comprise an amino acid sequence that is at least 80, 85, 90, 95, 98, or 100% identical to the non-loop regions of SEQ ID NO: 1, and wherein at least one loop selected from AB, BC, CD, DE, EF and FG is altered.

In some embodiments, one or more loops selected from AB, BC, CD, DE, EF and FG may be extended or shortened in length relative to the corresponding loop in wild-type human $^{10}$Fn3. In any given polypeptide, one or more loops may be extended in length, one or more loops may be reduced in length, or combinations thereof. In some embodiments, the length of a given loop may be extended by 2-25, 2-20, 2-15, 2-10, 2-5, 5-25, 5-20, 5-15, 5-10, 10-25, 10-20, or 10-15 amino acids. In some embodiments, the length of a given loop may be reduced by 1-15, 1-11, 1-10, 1-5, 1-3, 1-2, 2-10, or 2-5 amino acids. In particular, the FG loop of $^{10}$Fn3 is 13 residues long, whereas the corresponding loop in antibody heavy chains ranges from 4-28 residues. Therefore, in some embodiments, the length of the FG loop of $^{10}$Fn3 may be altered in length as well as in sequence to obtain the greatest possible flexibility and target affinity in polypeptides relying on the FG for target binding.

In certain embodiments, the anti-GPC3 FBS moiety comprises a tenth fibronectin type III ($^{10}$Fn3) domain, wherein the $^{10}$Fn3 domain comprises a loop, AB; a loop, BC; a loop, CD; a loop, DE; a loop EF; and a loop FG; and has at least one loop selected from loop BC, DE, and FG with an altered amino acid sequence relative to the sequence of the corresponding loop of the human $^{10}$Fn3 domain. In some embodiments, the anti-GPC3 Adnectin described herein comprise a $^{10}$Fn3 domain comprising an amino acid sequence at least 80%, 85%, 90%, 95%, 98%, 99% or 100% identical to the non-loop regions of SEQ ID NO: 1 or 2, wherein at least one loop selected from BC, DE, and FG is altered. In certain embodiments, the BC and FG loops are altered, in certain embodiments, the BC and DE loops are altered, in certain embodiments, the DE and FG loops are altered, and in certain embodiments, the BC, DE, and FG loops are altered, i.e., the $^{10}$Fn3 domains comprise non-naturally occurring loops. In certain embodiments, the AB, CD and/or the EF loops are altered. In some embodiments, one or more specific scaffold alterations are combined with one or more loop alterations.

In some embodiments, the non-ligand binding sequences of the anti-GPC3 $^{10}$Fn3 may be altered provided that the $^{10}$Fn3 retains ligand binding function and/or structural stability. In some embodiments, the non-loop region of a $^{10}$Fn3 domain may be modified by one or more conservative substitutions. As many as 5%, 10%, 20% or even 30% or more of the amino acids in the $^{10}$Fn3, domain may be altered by a conservative substitution without substantially altering the affinity of the $^{10}$Fn3 for a ligand. In certain embodiments, the non-loop regions, e.g., the β-strands may comprise anywhere from 0-15, 0-10, 0-8, 0-6, 0-5, 0-4, 0-3, 1-15, 1-10, 1-8, 1-6, 1-5, 1-4, 1-3, 2-15, 2-10, 2-8, 2-6, 2-5, 2-4, 5-15, or 5-10 conservative amino acid substitutions. In exemplary embodiments, the scaffold modification may reduce the binding affinity of the $^{10}$Fn3 binder for a ligand by less than 100-fold, 50-fold, 25-fold, 10-fold, 5-fold, or 2-fold. It may be that such changes may alter the immunogenicity of the $^{10}$Fn3 in vivo, and where the immunogenicity is decreased, such changes may be desirable. As used herein, "conservative substitutions" are residues that are physically or functionally similar to the corresponding reference residues. That is, a conservative substitution and its reference residue have similar size, shape, electric charge, chemical properties including the ability to form covalent or hydrogen bonds, or the like. Exemplary conservative substitutions include those fulfilling the criteria defined for an accepted point mutation in Dayhoff et al., Atlas of Protein Sequence and Structure, 5:345-352 (1978 and Supp.). Examples of conservative substitutions include substitutions within the following groups: (a) valine, glycine; (b) glycine, alanine; (c) valine, isoleucine, leucine; (d) aspartic acid, glutamic acid; (e) asparagine, glutamine; (f) serine, threonine; (g) lysine, arginine, methionine; and (h) phenylalanine, tyrosine.

In some embodiments, one or more of Asp 7, Glu 9, and Asp 23 is replaced by another amino acid, such as, for example, a non-negatively charged amino acid residue (e.g., Asn, Lys, etc.). A variety of additional alterations in the $^{10}$Fn3 scaffold that are either beneficial or neutral have been disclosed. See, for example, Baton et al., Protein Eng., 15(12):1015-1020 (December 2002); Koide et al., Biochemistry, 40(34):10326-10333 (Aug. 28, 2001).

In other embodiments, the hydrophobic core amino acid residues (bolded residues in SEQ ID NO: 3 above) are fixed, and any substitutions, conservative substitutions, deletions or additions occur at residues other than the hydrophobic core amino acid residues in the $^{10}$Fn3 scaffold. Thus, in some embodiments, the hydrophobic core residues of the polypeptides provided herein have not been modified relative to the wild-type human $^{10}$Fn3 domain (e.g., SEQ ID NO: 1).

A $^{10}$Fn3 molecule may comprise the flexible linker between the 10th and 11th repeat of the Fn3 domain, i.e., EIDKPSQ (SEQ ID NO: 369). The wild type $^{10}$Fn3 polypeptide with EIDKPSQ (SEQ ID NO: 369) at its C-terminus is represented by
VSDVPRDLEVVAATPTSLLISWDAPAVTBRYYRITY-
GETGGNSPVOEFTVPGSKSTATIS-
GLKPGVDYTITVYAVGRGRDSPASSKPIS-
INYRTEIDKPSO (SEQ ID No. 4)

In some embodiments, one or more residues of the integrin-binding motif "arginine-glycine-aspartic acid" (RGD) (amino acids 78-80 of SEQ ID NO: 1) may be substituted so as to disrupt integrin binding. In some embodiments, the FG loop of the polypeptides provided herein does not contain an RGD integrin binding site. In one embodiment, the RGD sequence is replaced by a polar amino acid-neutral amino acid-acidic amino acid sequence (in the N-terminal to C-terminal direction). In certain embodiments, the RGD sequence is replaced with SGE or RGE.

A. Exemplary anti-GPC3 Adnectins

In some embodiments, the BC loop of the anti-GPC3 FBS (e.g., an Adnectin that binds specifically to human GPC3) comprises an amino acid sequence set forth in SEQ ID NOs: 6, 19, 32, 45, 58, 71, 84 or 99, wherein, optionally, the BC loop comprises 1, 2 or 3 amino acid substitutions, deletions or insertions relative to the BC loop of SEQ ID NOs: 6, 19, 32, 45, 58, 71, 84 or 99.

In some embodiments, the DE loop of the anti-GPC3 FBS comprises an amino acid sequence set forth in SEQ ID NOs: 7, 20, 33, 46, 59, 72, 85 or 100, wherein, optionally, the DE loop comprises 1, 2 or 3 amino acid substitutions, deletions or insertions relative to the DE loop of SEQ ID NOs: 7, 20, 33, 46, 59, 72, 85 or 100.

In some embodiments, the FG loop of the anti-GPC3 FBS comprises an amino acid sequence set forth in SEQ ID NOs: 8, 21, 34, 47, 60, 73, 86, 101, 129, 156, 183, 210, 237, 264, 291 or 318, wherein, optionally, the FG loop comprises 1, 2 or 3 amino acid substitutions, deletions or insertions relative to the FG loop of SEQ ID NOs: 8, 21, 34, 47, 60, 73, 86, 101, 129, 156, 183, 210, 237, 264, 291 or 318.

In some embodiments, the BC loop of the anti-GPC3 Adnectin (i.e., an Adnectin that binds specifically to human GPC3) comprises an amino acid sequence set forth in SEQ ID NOs: 6, 19, 32, 45, 58, 71, 84 or 99, wherein, optionally, the BC loop comprises 1, 2 or 3 amino acid substitutions, deletions or insertions relative to the BC loop of SEQ ID NOs: 6, 19, 32, 45, 58, 71, 84 or 99; the DE loop of the anti-GPC3 Adnectin comprises an amino acid sequence set forth in SEQ ID NOs: 7, 20, 33, 46, 59, 72, 85 or 100, wherein, optionally, the DE loop comprises 1, 2 or 3 amino acid substitutions, deletions or insertions relative to the DE loop of SEQ ID NOs: 7, 20, 33, 46, 59, 72, 85 or 100; and the FG loop of the anti-GPC3 FBS comprises an amino acid sequence set forth in SEQ ID NOs: 8, 21, 34, 47, 60, 73, 86, 101, 129, 156, 183, 210, 237, 264, 291 or 318, wherein, optionally, the FG loop comprises 1, 2 or 3 amino acid substitutions, deletions or insertions relative to the FG loop of SEQ ID NOs: 8, 21, 34, 47, 60, 73, 86, 101, 129, 156, 183, 210, 237, 264, 291 or 318.

In some embodiments, the anti-GPC3 FBS comprises a BC loop comprising an amino acid sequence set forth in SEQ ID NOs: 6, 19, 32, 45, 58, 71, 84 or 99; a DE loop comprising amino acid sequence set forth in SEQ ID NOs: 7, 20, 33, 46, 59, 72, 85 or 100; and an FG loop comprising an amino acid sequence set forth in SEQ ID NOs: 8, 21, 34, 47, 60, 73, 86, 101, 129, 156, 183, 210, 237, 264, 291 or 318.

In some embodiments, the anti-GPC3 FBS comprises the BC, DE, and FG loops as set forth in SEQ ID NOs: 6, 19, 32, 45, 58, 71, 84 or 99; 7, 20, 33, 46, 59, 72, 85 or 100; and 8, 21, 34, 47, 60, 73, 86, 101, 129, 156, 183, 210, 237, 264, 291 or 318, respectively, and has amino acid substitutions in the BC, DE, and FG loops which allow the FBS to maintain binding to GPC3.

In some embodiments, the anti-GPC3 FBS comprises the amino acid sequence set forth in SEQ ID NO: 3, wherein BC, DE and FG loops as represented by $(X)_v$, $(X)_x$, and $(X)_z$, respectively, have amino acid sequences at least 75%, 80%, 85%, 90%, 95%, 97%, 98%, or 99% identical to the BC, DE or FG loop sequences set forth in SEQ ID NOs: 6, 7 and 8, respectively.

In some embodiments, the anti-GPC3 Adnectin comprises the amino acid sequence set forth in SEQ ID NO: 3, wherein the BC, DE, and FG loops comprise the amino acid sequences set forth in SEQ ID NOs: 6, 7 and 8, respectively, wherein the BC loop has 0, 1, 2, 3, 4, 5, or 6 amino acid substitutions, such as conservative amino acid substitutions, and the DE loop has 0, 1, 2 or 3 amino acid substitutions, such as a conservative amino acid substitution, and the FG loop has 0, 1, 2, 3, 4, 5, 6, 7, or 8 amino acid substitutions, such as conservative amino acid substitutions.

In certain embodiments, an anti-GPC3 Adnectin (e.g., an anti-FBS moiety comprising a human $^{10}$Fn3) comprises the sequence set forth in SEQ ID NO: 3, wherein BC, DE and FG loops as represented by $(X)_v$, $(X)_x$, and $(X)_z$, respectively, comprise BC, DE, and FG loops having the amino acid sequences of SEQ ID NOs: 6, 7 and 8, respectively.

In certain embodiments, an anti-GPC3 Adnectin comprises the sequence set forth in SEQ ID NO: 3, wherein BC, DE and FG loops as represented by $(X)_v$, $(X)_x$, and $(X)_z$, respectively, have amino acid sequences at least 75%, 80%, 85%, 90%, 95%, 97%, 98%, or 99% identical to the BC, DE or FG loop sequences set forth in SEQ ID NOs: 19, 20 and 21, respectively.

In some embodiments, the anti-GPC3 Adnectin comprises the amino acid sequence set forth in SEQ ID NO: 3, wherein the BC, DE, and FG loops comprise the amino acid sequences set forth in SEQ ID NOs: 19, 20 and 21, respectively, wherein the BC loop has 0, 1, 2, 3, 4, 5, or 6 amino acid substitutions, such as conservative amino acid substitutions, and the DE loop has 0, 1, 2 or 3 amino acid substitutions, such as a conservative amino acid substitution, and the FG loop has 0, 1, 2, 3, 4, 5, 6, 7, or 8 amino acid substitutions, such as conservative amino acid substitutions.

In certain embodiments, an anti-GPC3 Adnectin comprises the sequence set forth in SEQ ID NO: 3, wherein BC, DE and FG loops as represented by $(X)_y$, $(X)_x$, and $(X)_z$, respectively, comprise BC, DE, and FG loops having the amino acid sequences of SEQ ID NOs: 19, 20 and 21, respectively.

In certain embodiments, an anti-GPC3 Adnectin comprises the sequence set forth in SEQ ID NO: 3, wherein BC, DE and FG loops as represented by $(X)_y$, $(X)_x$, and $(X)_z$, respectively, have amino acid sequences at least 75%, 80%, 85%, 90%, 95%, 97%, 98%, or 99% identical to the BC, DE or FG loop sequences set forth in SEQ ID NOs: 32, 33 and 34, respectively.

In some embodiments, the anti-GPC3 Adnectin comprises the amino acid sequence set forth in SEQ ID NO: 3, wherein the BC, DE, and FG loops comprise the amino acid sequences set forth in SEQ ID NOs: 32, 33 and 34, respectively, wherein the BC loop has 0, 1, 2, 3, 4, 5, or 6 amino acid substitutions, such as conservative amino acid substitutions, and the DE loop has 0, 1, 2 or 3 amino acid substitutions, such as a conservative amino acid substitution, and the FG loop has 0, 1, 2, 3, 4, 5, 6, 7, or 8 amino acid substitutions, such as conservative amino acid substitutions.

In certain embodiments, an anti-GPC3 Adnectin comprises the sequence set forth in SEQ ID NO: 3, wherein BC, DE and FG loops as represented by $(X)_y$, $(X)_x$, and $(X)_z$, respectively, comprise BC, DE, and FG loops having the amino acid sequences of SEQ ID NOs: 32, 33 and 34, respectively.

In certain embodiments, an anti-GPC3 Adnectin comprises the sequence set forth in SEQ ID NO: 3, wherein BC, DE and FG loops as represented by $(X)_y$, $(X)_x$, and $(X)_z$, respectively, have amino acid sequences at least 75%, 80%, 85%, 90%, 95%, 97%, 98%, or 99% identical to the BC, DE or FG loop sequences set forth in SEQ ID NOs: 45, 46 and 47, respectively.

In some embodiments, the anti-GPC3 Adnectin comprises the amino acid sequence set forth in SEQ ID NO: 3, wherein the BC, DE, and FG loops comprise the amino acid sequences set forth in SEQ ID NOs: 45, 46 and 47, respectively, wherein the BC loop has 0, 1, 2, 3, 4, 5, or 6 amino acid substitutions, such as conservative amino acid substitutions, and the DE loop has 0, 1, 2 or 3 amino acid substitutions, such as a conservative amino acid substitution, and the FG loop has 0, 1, 2, 3, 4, 5, 6, 7, or 8 amino acid substitutions, such as conservative amino acid substitutions.

In certain embodiments, an anti-GPC3 Adnectin comprises the sequence set forth in SEQ ID NO: 3, wherein BC, DE and FG loops as represented by $(X)_y$, $(X)_x$, and $(X)_z$, respectively, comprise BC, DE, and FG loops having the amino acid sequences of SEQ ID NOs: 45, 46 and 47, respectively.

In certain embodiments, an anti-GPC3 Adnectin comprises the sequence set forth in SEQ ID NO: 3, wherein BC, DE and FG loops as represented by $(X)_y$, $(X)_x$, and $(X)_z$, respectively, have amino acid sequences at least 75%, 80%, 85%, 90%, 95%, 97%, 98%, or 99% identical to the BC, DE or FG loop sequences set forth in SEQ ID NOs: 58, 59 and 60, respectively.

In some embodiments, the anti-GPC3 Adnectin comprises the amino acid sequence set forth in SEQ ID NO: 3, wherein the BC, DE, and FG loops comprise the amino acid sequences set forth in SEQ ID NOs: 58, 59 and 60, respectively, wherein the BC loop has 0, 1, 2, 3, 4, 5, or 6 amino acid substitutions, such as conservative amino acid substitutions, and the DE loop has 0, 1, 2 or 3 amino acid substitutions, such as a conservative amino acid substitution, and the FG loop has 0, 1, 2, 3, 4, 5, 6, 7, or 8 amino acid substitutions, such as conservative amino acid substitutions.

In certain embodiments, an anti-GPC3 Adnectin comprises the sequence set forth in SEQ ID NO: 3, wherein BC, DE and FG loops as represented by $(X)_y$, $(X)_x$, and $(X)_z$, respectively, comprise BC, DE, and FG loops having the amino acid sequences of SEQ ID NOs: 58, 59 and 60, respectively.

In certain embodiments, an anti-GPC3 Adnectin comprises the sequence set forth in SEQ ID NO: 3, wherein BC, DE and FG loops as represented by $(X)_y$, $(X)_x$, and $(X)_z$, respectively, have amino acid sequences at least 75%, 80%, 85%, 90%, 95%, 97%, 98%, or 99% identical to the BC, DE or FG loop sequences set forth in SEQ ID NOs: 71, 72 and 73, respectively.

In some embodiments, the anti-GPC3 Adnectin comprises the amino acid sequence set forth in SEQ ID NO: 3, wherein the BC, DE, and FG loops comprise the amino acid sequences set forth in SEQ ID NOs: 71, 72 and 73, respectively, wherein the BC loop has 0, 1, 2, 3, 4, 5, or 6 amino acid substitutions, such as conservative amino acid substitutions, and the DE loop has 0, 1, 2 or 3 amino acid substitutions, such as a conservative amino acid substitution, and the FG loop has 0, 1, 2, 3, 4, 5, 6, 7, or 8 amino acid substitutions, such as conservative amino acid substitutions.

In certain embodiments, an anti-GPC3 Adnectin comprises the sequence set forth in SEQ ID NO: 3, wherein BC, DE and FG loops as represented by $(X)_y$, $(X)_x$, and $(X)_z$, respectively, comprise BC, DE, and FG loops having the amino acid sequences of SEQ ID NOs: 71, 72 and 73, respectively.

In certain embodiments, an anti-GPC3 Adnectin comprises the sequence set forth in SEQ ID NO: 3, wherein BC, DE and FG loops as represented by $(X)_y$, $(X)_x$, and $(X)_z$, respectively, have amino acid sequences at least 75%, 80%, 85%, 90%, 95%, 97%, 98%, or 99% identical to the BC, DE or FG loop sequences set forth in SEQ ID NOs: 84, 85 and 86, respectively.

In some embodiments, the anti-GPC3 Adnectin comprises the amino acid sequence set forth in SEQ ID NO: 3, wherein the BC, DE, and FG loops comprise the amino acid sequences set forth in SEQ ID NOs: 84, 85 and 86, respectively, wherein the BC loop has 0, 1, 2, 3, 4, 5, or 6 amino acid substitutions, such as conservative amino acid substitutions, and the DE loop has 0, 1, 2 or 3 amino acid substitutions, such as a conservative amino acid substitution, and the FG loop has 0, 1, 2, 3, 4, 5, 6, 7, or 8 amino acid substitutions, such as conservative amino acid substitutions.

In certain embodiments, an anti-GPC3 Adnectin comprises the sequence set forth in SEQ ID NO: 3, wherein BC, DE and FG loops as represented by $(X)_y$, $(X)_x$, and $(X)_z$, respectively, comprise BC, DE, and FG loops having the amino acid sequences of SEQ ID NOs: 84, 85 and 86, respectively.

In certain embodiments, an anti-GPC3 Adnectin comprises the sequence set forth in SEQ ID NO: 3, wherein BC, DE and FG loops as represented by $(X)_y$, $(X)_x$, and $(X)_z$, respectively, have amino acid sequences at least 75%, 80%, 85%, 90%, 95%, 97%, 98%, or 99% identical to the BC, DE or FG loop sequences set forth in SEQ ID NOs: 99, 100 and 101, respectively.

In some embodiments, the anti-GPC3 Adnectin comprises the amino acid sequence set forth in SEQ ID NO: 3, wherein the BC, DE, and FG loops comprise the amino acid sequences set forth in SEQ ID NOs: 99, 100 and 101, respectively, wherein the BC loop has 0, 1, 2, 3, 4, 5, or 6 amino acid substitutions, such as conservative amino acid substitutions, and the DE loop has 0, 1, 2 or 3 amino acid substitutions, such as a conservative amino acid substitution, and the FG loop has 0, 1, 2, 3, 4, 5, 6, 7, or 8 amino acid substitutions, such as conservative amino acid substitutions.

In certain embodiments, an anti-GPC3 Adnectin comprises the sequence set forth in SEQ ID NO: 3, wherein BC, DE and FG loops as represented by $(X)_y$, $(X)_x$, and $(X)_z$, respectively, comprise BC, DE, and FG loops having the amino acid sequences of SEQ ID NOs: 99, 100 and 101, respectively.

In some embodiments, the anti-GPC3 Adnectin comprises the amino acid sequence set forth in SEQ ID NO: 3, wherein the BC, DE, and FG loops comprise the amino acid sequences set forth in SEQ ID NOs: 99, 100 and 129, respectively, wherein the BC loop has 0, 1, 2, 3, 4, 5, or 6 amino acid substitutions, such as conservative amino acid substitutions, and the DE loop has 0, 1, 2 or 3 amino acid substitutions, such as a conservative amino acid substitution.

In certain embodiments, an anti-GPC3 Adnectin comprises the sequence set forth in SEQ ID NO: 3, wherein BC, DE and FG loops as represented by $(X)_y$, $(X)_x$, and $(X)_z$, respectively, comprise BC, DE, and FG loops having the amino acid sequences of SEQ ID NOs: SEQ ID NOs: 99, 100 and 129, respectively.

In some embodiments, the anti-GPC3 Adnectin comprises the amino acid sequence set forth in SEQ ID NO: 3, wherein the BC, DE, and FG loops comprise the amino acid sequences set forth in SEQ ID NOs: 99, 100 and 156, respectively, wherein the BC loop has 0, 1, 2, 3, 4, 5, or 6 amino acid substitutions, such as conservative amino acid substitutions, and the DE loop has 0, 1, 2 or 3 amino acid substitutions, such as a conservative amino acid substitution.

In certain embodiments, an anti-GPC3 Adnectin comprises the sequence set forth in SEQ ID NO: 3, wherein BC, DE and FG loops as represented by $(X)_y$, $(X)_x$, and $(X)_z$, respectively, comprise BC, DE, and FG loops having the amino acid sequences of SEQ ID NOs: SEQ ID NOs: 99, 100 and 156, respectively.

In some embodiments, the anti-GPC3 Adnectin comprises the amino acid sequence set forth in SEQ ID NO: 3, wherein the BC, DE, and FG loops comprise the amino acid sequences set forth in SEQ ID NOs: 99, 100 and 183, respectively, wherein the BC loop has 0, 1, 2, 3, 4, 5, or 6 amino acid substitutions, such as conservative amino acid substitutions, and the DE loop has 0, 1, 2 or 3 amino acid substitutions, such as a conservative amino acid substitution.

In certain embodiments, an anti-GPC3 Adnectin comprises the sequence set forth in SEQ ID NO: 3, wherein BC, DE and FG loops as represented by $(X)_y$, $(X)_x$, and $(X)_z$, respectively, comprise BC, DE, and FG loops having the amino acid sequences of SEQ ID NOs: SEQ ID NOs: 99, 100 and 183, respectively.

In some embodiments, the anti-GPC3 Adnectin comprises the amino acid sequence set forth in SEQ ID NO: 3, wherein the BC, DE, and FG loops comprise the amino acid sequences set forth in SEQ ID NOs: 99, 100 and 210, respectively, wherein the BC loop has 0, 1, 2, 3, 4, 5, or 6 amino acid substitutions, such as conservative amino acid substitutions, and the DE loop has 0, 1, 2 or 3 amino acid substitutions, such as a conservative amino acid substitution.

In certain embodiments, an anti-GPC3 Adnectin comprises the sequence set forth in SEQ ID NO: 3, wherein BC, DE and FG loops as represented by $(X)_y$, $(X)_x$, and $(X)_z$, respectively, comprise BC, DE, and FG loops having the amino acid sequences of SEQ ID NOs: SEQ ID NOs: 99, 100 and 210, respectively.

In some embodiments, the anti-GPC3 Adnectin comprises the amino acid sequence set forth in SEQ ID NO: 3, wherein the BC, DE, and FG loops comprise the amino acid sequences set forth in SEQ ID NOs: 99, 100 and 237, respectively, wherein the BC loop has 0, 1, 2, 3, 4, 5, or 6 amino acid substitutions, such as conservative amino acid substitutions, and the DE loop has 0, 1, 2 or 3 amino acid substitutions, such as a conservative amino acid substitution.

In certain embodiments, an anti-GPC3 Adnectin comprises the sequence set forth in SEQ ID NO: 3, wherein BC, DE and FG loops as represented by $(X)_y$, $(X)_x$, and $(X)_z$, respectively, comprise BC, DE, and FG loops having the amino acid sequences of SEQ ID NOs: SEQ ID NOs: 99, 100 and 237, respectively.

In some embodiments, the anti-GPC3 Adnectin comprises the amino acid sequence set forth in SEQ ID NO: 3, wherein the BC, DE, and FG loops comprise the amino acid sequences set forth in SEQ ID NOs: 99, 100 and 264, respectively, wherein the BC loop has 0, 1, 2, 3, 4, 5, or 6 amino acid substitutions, such as conservative amino acid substitutions, and the DE loop has 0, 1, 2 or 3 amino acid substitutions, such as a conservative amino acid substitution.

In certain embodiments, an anti-GPC3 Adnectin comprises the sequence set forth in SEQ ID NO: 3, wherein BC, DE and FG loops as represented by $(X)_y$, $(X)_x$, and $(X)_z$, respectively, comprise BC, DE, and FG loops having the amino acid sequences of SEQ ID NOs: SEQ ID NOs: 99, 100 and 264, respectively.

In some embodiments, the anti-GPC3 Adnectin comprises the amino acid sequence set forth in SEQ ID NO: 3, wherein the BC, DE, and FG loops comprise the amino acid sequences set forth in SEQ ID NOs: 99, 100 and 291, respectively, wherein the BC loop has 0, 1, 2, 3, 4, 5, or 6 amino acid substitutions, such as conservative amino acid substitutions, and the DE loop has 0, 1, 2 or 3 amino acid substitutions, such as a conservative amino acid substitution.

In certain embodiments, an anti-GPC3 Adnectin comprises the sequence set forth in SEQ ID NO: 3, wherein BC, DE and FG loops as represented by $(X)_y$, $(X)_x$, and $(X)_z$, respectively, comprise BC, DE, and FG loops having the amino acid sequences of SEQ ID NOs: SEQ ID NOs: 99, 100 and 291, respectively.

In some embodiments, the anti-GPC3 Adnectin comprises the amino acid sequence set forth in SEQ ID NO: 3, wherein the BC, DE, and FG loops comprise the amino acid sequences set forth in SEQ ID NOs: 99, 100 and 318, respectively, wherein the BC loop has 0, 1, 2, 3, 4, 5, or 6 amino acid substitutions, such as conservative amino acid substitutions, and the DE loop has 0, 1, 2 or 3 amino acid substitutions, such as a conservative amino acid substitution.

In certain embodiments, an anti-GPC3 Adnectin comprises the sequence set forth in SEQ ID NO: 3, wherein BC, DE and FG loops as represented by $(X)_y$, $(X)_x$, and $(X)_z$, respectively, comprise BC, DE, and FG loops having the amino acid sequences of SEQ ID NOs: SEQ ID NOs: 99, 100 and 318, respectively.

The scaffold regions of such anti-GPC3 Adnectins may comprise anywhere from 0 to 20, from 0 to 15, from 0 to 10, from 0 to 8, from 0 to 6, from 0 to 5, from 0 to 4, from 0 to 3, from 0 to 2, or from 0 to 1 substitutions, conservative substitutions, deletions or additions relative to the scaffold amino acids residues of SEQ ID NO: 3. Such scaffold modifications may be made, so long as the anti-GPC3 Adnectin is capable of binding GPC3 with a desired $K_D$.

In certain embodiments, the anti-GPC3 Adnectin comprises an amino acid sequence at least 70%, 75%, 80%, 85%, 90%, 95%, 98%, 99%, or 100% identical to that of an anti-GPC3 Adnectin disclosed herein and having, e.g., any one of SEQ ID NOs: 5, 18, 31, 44, 57, 70, 83 and 98.

In certain embodiments, the anti-GPC3 Adnectin comprises an amino acid sequence at least 70%, 75%, 80%, 85%, 90%, 95%, 98%, 99%, or 100% identical to any one of SEQ ID NOs: 5, 9-18, 22-31, 35-44, 48-57, 61-70, 74-83, 87-98, 102-128, 130-155, 157-182, 184-209, 211-236, 238-263, 265-290, 292-317 and 319-343.

In certain embodiments, the anti-GPC3 Adnectins described herein comprise an amino acid sequence at least 80%, 85%, 90%, 95%, 98%, 99% or 100% identical to the non-BC, DE, and FG loop regions of SEQ ID NOs: 3, 5, 18, 31, 44, 57, 70, 83 or 98.

In certain embodiments, the anti-GPC3 Adnectin comprises BC, DE, and FG loops as set forth in SEQ ID NOs: 6, 7, and 8, respectively; and an amino acid sequence at least 80%, 85%, 90%, 95%, 98%, 99% or 100% identical to the non-BC, DE, and FG loop regions of SEQ ID NOs: 3, 5, 18, 31, 44, 57, 70, 83 or 98.

In certain embodiments, the anti-GPC3 Adnectin comprises BC, DE, and FG loops as set forth in SEQ ID NOs: 19, 20 and 21, respectively; and an amino acid sequence at least 80%, 85%, 90%, 95%, 98%, 99% or 100% identical to the non-BC, DE, and FG loop regions of SEQ ID NOs: 3, 5, 18, 31, 44, 57, 70, 83 or 98.

In certain embodiments, the anti-GPC3 Adnectin comprises BC, DE, and FG loops as set forth in SEQ ID NOs: 32, 33 and 34, respectively; and an amino acid sequence at least 80%, 85%, 90%, 95%, 98%, 99% or 100% identical to the non-BC, DE, and FG loop regions of SEQ ID NOs: 3, 5, 18, 31, 44, 57, 70, 83 or 98.

In certain embodiments, the anti-GPC3 Adnectin comprises BC, DE, and FG loops as set forth in SEQ ID NOs: 45, 46 and 47, respectively; and an amino acid sequence at least 80%, 85%, 90%, 95%, 98%, 99% or 100% identical to the non-BC, DE, and FG loop regions of SEQ ID NOs: 3, 5, 18, 31, 44, 57, 70, 83 or 98.

In certain embodiments, the anti-GPC3 Adnectin comprises BC, DE, and FG loops as set forth in SEQ ID NOs: 58, 59 and 60, respectively and an amino acid sequence at least 80%, 85%, 90%, 95%, 98%, 99% or 100% identical to the non-BC, DE, and FG loop regions of SEQ ID NOs: 3, 5, 18, 31, 44, 57, 70, 83 or 98.

In certain embodiments, the anti-GPC3 Adnectin comprises BC, DE, and FG loops as set forth in SEQ ID NOs: 71, 72 and 73, respectively and an amino acid sequence at least 80%, 85%, 90%, 95%, 98%, 99% or 100% identical to the non-BC, DE, and FG loop regions of SEQ ID NOs: 3, 5, 18, 31, 44, 57, 70, 83 or 98.

In certain embodiments, the anti-GPC3 Adnectin comprises BC, DE, and FG loops as set forth in SEQ ID NOs: 84, 85 and 86, respectively and an amino acid sequence at least 80%, 85%, 90%, 95%, 98%, 99% or 100% identical to the non-BC, DE, and FG loop regions of SEQ ID NOs: 3, 5, 18, 31, 44, 57, 70, 83 or 98.

In certain embodiments, the anti-GPC3 Adnectin comprises BC, DE, and FG loops as set forth in SEQ ID NOs: 99, 100 and 101, respectively and an amino acid sequence at least 80%, 85%, 90%, 95%, 98%, 99% or 100% identical to the non-BC, DE, and FG loop regions of SEQ ID NOs: 3, 5, 18, 31, 44, 57, 70, 83 or 98.

In certain embodiments, the anti-GPC3 Adnectin comprises BC, DE, and FG loops as set forth in SEQ ID NOs: 99, 100 and 129, respectively and an amino acid sequence at least 80%, 85%, 90%, 95%, 98%, 99% or 100% identical to the non-BC, DE, and FG loop regions of SEQ ID NOs: 3, 5, 18, 31, 44, 57, 70, 83 or 98.

In certain embodiments, the anti-GPC3 Adnectin comprises BC, DE, and FG loops as set forth in SEQ ID NOs: 99, 100 and 129, respectively and an amino acid sequence at least 80%, 85%, 90%, 95%, 98%, 99% or 100% identical to the non-BC, DE, and FG loop regions of SEQ ID NOs: 3, 5, 18, 31, 44, 57, 70, 83 or 98.

In certain embodiments, the anti-GPC3 Adnectin comprises BC, DE, and FG loops as set forth in SEQ ID NOs: 99, 100 and 156, respectively and an amino acid sequence at least 80%, 85%, 90%, 95%, 98%, 99% or 100% identical to the non-BC, DE, and FG loop regions of SEQ ID NOs: 3, 5, 18, 31, 44, 57, 70, 83 or 98.

In certain embodiments, the anti-GPC3 Adnectin comprises BC, DE, and FG loops as set forth in SEQ ID NOs: 99, 100 and 183, respectively and an amino acid sequence at least 80%, 85%, 90%, 95%, 98%, 99% or 100% identical to the non-BC, DE, and FG loop regions of SEQ ID NOs: 3, 5, 18, 31, 44, 57, 70, 83 or 98.

In certain embodiments, the anti-GPC3 Adnectin comprises BC, DE, and FG loops as set forth in SEQ ID NOs: 99, 100 and 210, respectively and an amino acid sequence at least 80%, 85%, 90%, 95%, 98%, 99% or 100% identical to the non-BC, DE, and FG loop regions of SEQ ID NOs: 3, 5, 18, 31, 44, 57, 70, 83 or 98.

In certain embodiments, the anti-GPC3 Adnectin comprises BC, DE, and FG loops as set forth in SEQ ID NOs: 99, 100 and 237, respectively and an amino acid sequence at least 80%, 85%, 90%, 95%, 98%, 99% or 100% identical to the non-BC, DE, and FG loop regions of SEQ ID NOs: 3, 5, 18, 31, 44, 57, 70, 83 or 98.

In certain embodiments, the anti-GPC3 Adnectin comprises BC, DE, and FG loops as set forth in SEQ ID NOs: 99, 100 and 264, respectively and an amino acid sequence at least 80%, 85%, 90%, 95%, 98%, 99% or 100% identical to the non-BC, DE, and FG loop regions of SEQ ID NOs: 3, 5, 18, 31, 44, 57, 70, 83 or 98.

In certain embodiments, the anti-GPC3 Adnectin comprises BC, DE, and FG loops as set forth in SEQ ID NOs: 99, 100 and 291, respectively and an amino acid sequence at least 80%, 85%, 90%, 95%, 98%, 99% or 100% identical to the non-BC, DE, and FG loop regions of SEQ ID NOs: 3, 5, 18, 31, 44, 57, 70, 83 or 98.

In certain embodiments, the anti-GPC3 Adnectin comprises BC, DE, and FG loops as set forth in SEQ ID NOs: 99, 100 and 318, respectively and an amino acid sequence at least 80%, 85%, 90%, 95%, 98%, 99% or 100% identical to the non-BC, DE, and FG loop regions of SEQ ID NOs: 3, 5, 18, 31, 44, 57, 70, 83 or 98.

In some embodiments, the anti-GPC3 Adnectin comprises an amino acid sequence selected from the group consisting of 5, 18, 31, 44, 57, 70, 83, 98, 128, 155, 182, 209, 209, 236, 263, 290 and 317.

In some embodiments, anti-GPC3 Adnectin further comprises a C-terminal moiety selected from the group consisting of $P_mX_n$, $P_mCX_n$ and $P_mCX_{n1}CX_{n2}$, wherein X is any amino acid and m, n, n1 and n2 are independently 0 or an integer of 1, 2, 3, 4, 5 or more.

In some embodiments, the anti-GPC3 Adnectin comprises an amino acid sequence selected from the group consisting of 5, 9-18, 22-31, 35-44, 48-57, 61-70, 74-83, 87-98, 102-128, 130-155, 157-182, 184-209, 211-236, 238-263, 265-290, 292-317 and 319-343.

In certain embodiments, anti-GPC3 Adnectin comprises an amino acid sequence selected from the group consisting of SEQ ID NOs: 98, 102-128, 129-155, 157-182, 184-209, 211-236, 238-263, 265-290, 292-317 and 319-343, optionally with one or more histidines (e.g., 6×His) at the C-terminus.

In certain embodiments, the anti-GPC3 Adnectin comprises an amino acid sequence selected from the group consisting of SEQ ID NOs: 102-127. In certain embodiments, the anti-GPC3 Adnectin comprises SEQ ID NOs: 114-118. In other embodiments, the anti-GPC3 Adnectin comprises SEQ ID NOs: 123-127.

Provided herein are polypeptides that bind specifically to human GPC3 with a KD of $10^{-7}$ or less, wherein the polypeptides comprise a $^{10}$Fn3 domain comprising the BC, DE and FG loops of ADX_6077_A01, i.e., SEQ ID NOs: 99, 100 and 101. Provided herein are polypeptides that bind specifically to human GPC3 with a KD of $10^{-7}$ or less, wherein the polypeptides comprise a $^{10}$Fn3 domain comprising a BC loop comprising SEQ ID NO: 99, a DE loop comprising SEQ ID NO: 100 and an FG loop comprising SEQ ID NO: 101. Also provided are polypeptides that bind specifically to human GPC3 with a KD of $10^{-7}$ or less, wherein the polypeptides comprise a $^{10}$Fn3 domain comprising a BC loop comprising SEQ ID NO: 99, a DE loop comprising SEQ ID NO: 100 and an FG loop comprising SEQ ID NO: 101, wherein one of the two amino acid residues DG in the FG loop is substituted with another amino acid. Also provided are polypeptides that bind specifically to human GPC3 with a KD of $10^{-7}$ or less, wherein the polypeptides comprise a $^{10}$Fn3 domain comprising a BC loop comprising SEQ ID NO: 99, a DE loop comprising SEQ ID NO: 100 and an FG loop comprising SEQ ID NO: 101, wherein amino acid residue D of DG in the FG loop (i.e., D78; the numbering is relative to that in SEQ ID NO: 102) is substituted with another amino acid, e.g., E, S, A, and G. Also provided are polypeptides that bind specifically to human GPC3 with a KD of $10^{-7}$ or less, wherein the polypeptides comprise a $^{10}$Fn3 domain comprising a BC loop comprising SEQ ID NO: 99, a DE loop comprising SEQ ID NO: 100 and an FG loop comprising SEQ ID NO: 101, wherein amino acid residue G of DG in the FG loop (i.e., D79) is substituted with another amino acid residue, e.g., S, A, L or V. Also provided are polypeptides that bind specifically to human GPC3 with a KD of $10^{-7}$ or less, wherein the polypeptides comprise a $^{10}$Fn3 domain comprising a BC loop comprising SEQ ID NO: 99, a DE loop comprising SEQ ID NO: 100 and an FG loop comprising SEQ ID NO: 101, 129, 156, 183, 210, 237, 264, 291 or 318. Any of the polypeptides described in this paragraph may comprise a cysteine residue linked directly or indirectly to the C-terminal end of the polypeptide and/or may comprise one of the following amino acid residues or sequences linked directly or indirectly to the C-terminal end of the polypeptide: P, PC, PCHHHHHH (SEQ ID NO: 395), PCPPPPPC (SEQ ID NO: 416) or PCPPPPPCHHHHHH (SEQ ID NO: 424).

Also provided are polypeptides that bind specifically to human GPC3 with a KD of $10^{-7}$ or less, wherein the polypeptides comprise a $^{10}$Fn3 domain comprising the ADX_6077_A01 core sequence, i.e., SEQ ID NO: 98, or an amino acid sequence that is at least 90%, 95%, 97%, 98%, or 99% identical thereto or that differs therefrom in 1-10, 1-5, 1-3, 1-2 or 1 amino acid substitution (e.g., conservative amino acid substitutions), deletions or additions. Also provided are polypeptides that bind specifically to human GPC3 with a KD of $10^{-7}$ or less, wherein the polypeptides comprise a $^{10}$Fn3 domain comprising the ADX_6077_A01 core sequence, i.e., SEQ ID NO: 98, or an amino acid sequence that is at least 90%, 95%, 97%, 98%, or 99% identical thereto or that differs therefrom in 1-10, 1-5, 1-3, 1-2 or 1 amino acid substitution (e.g., conservative amino acid substitutions), deletions or additions, and the $^{10}$Fn3 domain comprises a BC loop comprising SEQ ID NO: 99, a DE loop comprising SEQ ID NO: 100 and an FG loop comprising SEQ ID NO: 101, or which differs therefrom in one amino acid of DG. Also provided are polypeptides that bind specifically to human GPC3 with a KD of $10^{-7}$ or less, wherein the polypeptides comprise a $^{10}$Fn3 domain comprising SEQ ID NO: 98, or an amino acid sequence that is at least 90%, 95%, 97%, 98%, or 99% identical thereto or that differs therefrom in 1-10, 1-5, 1-3, 1-2 or 1 amino acid substitution (e.g., conservative amino acid substitutions), deletions or additions, and the $^{10}$Fn3 domain comprises a BC loop comprising SEQ ID NO: 99, a DE loop comprising SEQ ID NO: 100 and an FG loop comprising SEQ ID NO: 101, 129, 156, 183, 210, 237, 264, 291 or 318. Also provided are polypeptides that bind specifically to human GPC3 with a KD of $10^{-7}$ or less, wherein the polypeptides comprise a $^{10}$Fn3 domain comprising the ADX_6077_A01 core sequence, i.e., SEQ ID NO: 98, or an amino acid sequence that is at least 90%, 95%, 97%, 98%, or 99% identical thereto or that differs therefrom in 1-10, 1-5, 1-3, 1-2 or 1 amino acid substitution (e.g., conservative amino acid substitutions), deletions or additions, and further comprises a cysteine residue linked directly or indirectly to the C-terminal end of the polypeptide. Also provided are polypeptides that bind specifically to human GPC3 with a KD of $10^{-7}$ or less, wherein the polypeptides comprise a $^{10}$Fn3 domain comprising the ADX_6077_A01 core sequence, i.e., SEQ ID NO: 98, or an amino acid sequence that is at least 90%, 95%, 97%, 98%, or 99% identical thereto or that differs therefrom in 1-10, 1-5, 1-3, 1-2 or 1 amino acid substitution (e.g., conservative amino acid substitutions), deletions or additions, and further comprises one of the following amino acid residues or sequences linked directly or indirectly to the C-terminal end of the polypeptide: P, PC, PCHHHHHH (SEQ ID NO: 395), PCPPPPPC (SEQ ID NO: 416) or PCPPPPPCHHHHHH (SEQ ID NO: 424).

Provided herein are polypeptides comprising the amino acid sequence of ADX_6077_A01 or ADX_6912_G02 (with or without an N-terminal methionine) and with or without a 6×His tail.

Also provided herein are $^{10}$Fn3 proteins that bind specifically to human GPC3 with a KD of 10 or less, and comprise the BC, DE and FG loops of ADX_6077_A01, i.e., SEQ ID NOs: 99, 100 and 101. Provided herein are $^{10}$Fn3 proteins that bind specifically to human GPC3 with a KD of 10 or less, and comprise a BC loop comprising SEQ ID NO: 99, a DE loop comprising SEQ ID NO: 100 and an FG loop comprising SEQ ID NO: 101. Also provided are $^{10}$Fn3 proteins that bind specifically to human GPC3 with a KD of 10 or less, and comprise a BC loop comprising SEQ ID NO: 99, a DE loop comprising SEQ ID NO: 100 and an FG loop comprising SEQ ID NO: 101, wherein one of the two amino acid residues DG in the FG loop is substituted with another amino acid. Also provided are $^{10}$Fn3 proteins that bind specifically to human GPC3 with a KD of $10^{-7}$ or less, and comprise a BC loop comprising SEQ ID NO: 99, a DE loop comprising SEQ ID NO: 100 and an FG loop comprising SEQ ID NO: 101, wherein amino acid residue D of DG in the FG loop (i.e., D78; the numbering is relative to that in SEQ ID NO: 102) is substituted with another amino acid, e.g., E, S, A, and G. Also provided are $^{10}$Fn3 proteins that bind specifically to human GPC3 with a KD of $10^{-7}$ or less, and comprise a BC loop comprising SEQ ID NO: 99, a DE loop comprising SEQ ID NO: 100 and an FG loop comprising SEQ ID NO: 101, wherein amino acid residue G of DG in the FG loop (i.e., D79) is substituted with another amino acid residue, e.g., S, A, L or V. Also provided are $^{10}$Fn3 proteins that bind specifically to human GPC3 with a KD of $10^{-7}$ or less, and comprise a BC loop comprising SEQ ID NO: 99, a DE loop comprising SEQ ID NO: 100 and an FG loop comprising SEQ ID NO: 101, 129, 156, 183, 210, 237, 264, 291 or 318. Any of the $^{10}$Fn3 proteins described in this paragraph may comprise a cysteine residue linked directly or indirectly to its C-terminus and/or may comprise one of the following amino acid residues or sequences linked directly or indirectly to the C-terminus: P, PC, PCHHHHHH (SEQ ID NO: 395), PCPPPPPC (SEQ ID NO: 416) or PCPPPPPCHHHHHH (SEQ ID NO: 424).

Also provided are $^{10}$Fn3 proteins that bind specifically to human GPC3 with a KD of $10^{-7}$ or less, and comprise the ADX_6077_A01 core sequence, i.e., SEQ ID NO: 98, or an amino acid sequence that is at least 90%, 95%, 97%, 98%, or 99% identical thereto or that differs therefrom in 1-10, 1-5, 1-3, 1-2 or 1 amino acid substitution (e.g., conservative amino acid substitutions), deletions or additions. Also provided are $^{10}$Fn3 proteins that bind specifically to human GPC3 with a KD of $10^{-7}$ or less, and comprise the ADX_6077_A01 core sequence, i.e., SEQ ID NO: 98, or an amino acid sequence that is at least 90%, 95%, 97%, 98%, or 99% identical thereto or that differs therefrom in 1-10, 1-5, 1-3, 1-2 or 1 amino acid substitution (e.g., conservative amino acid substitutions), deletions or additions, and comprise a BC loop comprising SEQ ID NO: 99, a DE loop comprising SEQ ID NO: 100 and an FG loop comprising SEQ ID NO: 101, or which differs therefrom in one amino acid of DG. Also provided are $^{10}$Fn3 proteins that bind specifically to human GPC3 with a KD of $10^{-7}$ or less, and comprise SEQ ID NO: 98, or an amino acid sequence that is at least 90%, 95%, 97%, 98%, or 99% identical thereto or that differs therefrom in 1-10, 1-5, 1-3, 1-2 or 1 amino acid substitution (e.g., conservative amino acid substitutions), deletions or additions, and comprise a BC loop comprising SEQ ID NO: 99, a DE loop comprising SEQ ID NO: 100 and an FG loop comprising SEQ ID NO: 101, 129, 156, 183, 210, 237, 264, 291 or 318. Also provided are $^{10}$Fn3 proteins that bind specifically to human GPC3 with a KD of 10 or less, and comprise a $^{10}$Fn3 domain comprising the ADX_6077_A01 core sequence, i.e., SEQ ID NO: 98, or an amino acid sequence that is at least 90%, 95%, 97%, 98%, or 99% identical thereto or that differs therefrom in 1-10, 1-5, 1-3, 1-2 or 1 amino acid substitution (e.g., conservative amino acid substitutions), deletions or additions, and further comprises a cysteine residue linked directly or indirectly to its C-terminus. Also provided are $^{10}$Fn3 proteins that bind specifically to human GPC3 with a KD of $10^{-7}$ or less, and comprise a $^{10}$Fn3 domain comprising the ADX_6077_A01 core sequence, i.e., SEQ ID NO: 98, or an amino acid sequence that is at least 90%, 95%, 97%, 98%, or 99% identical thereto or that differs therefrom in 1-10, 1-5, 1-3, 1-2 or 1 amino acid substitution (e.g., conservative amino acid substitutions), deletions or additions, and further comprises one of the following amino acid residues or sequences linked directly or indirectly to its C-terminus: P, PC, PCHHHHHH (SEQ ID NO: 395), PCPPPPPC (SEQ ID NO: 416) or PCPPPPPCHHHHHH (SEQ ID NO: 424).

Provided herein are $^{10}$Fn3 proteins comprising the amino acid sequence of ADX_6077_A01 or ADX_6912_G02 (with or without an N-terminal methionine) and with or without a 6×His tail.

Also provided are drug conjugates comprising one of the polypeptides or $^{10}$Fn3 proteins described in the above paragraphs, conjugated to a drug moiety, such as a tubulysin analog.

Further provided are $^{10}$Fn3 proteins or polypeptides comprising $^{10}$Fn3 domains comprising at their C-terminus a sequence comprising one or more cysteines, wherein at least one cysteine is conjugated to a tubulysin analog described herein. For example, $^{10}$Fn3 proteins or polypeptides comprising $^{10}$Fn3 domains may be linked to a peptide comprising the amino acid sequence PmCn, wherein m and n are independent an integer of 1 or more and wherein one or more cysteines is conjugated to a tubulysin analog described herein.

In certain embodiments, BC, DE and/or FG loop amino acid sequences of any one of the anti-GPC3 Adnectins (e.g., SEQ ID NOs: 5, 9-18, 22-31, 35-44, 48-57, 61-70, 74-83, 87-98, 102-128, 130-155, 157-182, 184-209, 211-236, 238-263, 265-290, 292-317 and 319-343) described herein are grafted into non-$^{10}$Fn3 domain protein scaffolds. For instance, one or more loop amino acid sequences is exchanged for or inserted into one or more CDR loops of an antibody heavy or light chain or fragment thereof. In other embodiments, the protein domain into which one or more amino acid loop sequences are exchanged or inserted includes, but is not limited to, consensus Fn3 domains (Centocor, US), ankyrin repeat proteins (Molecular Partners AG, Zurich Switzerland), domain antibodies (Domantis, Ltd, Cambridge, MA), single domain camelid nanobodies (Ablynx, Belgium), lipocalins (e.g., anticalins; Pieris Proteolab AG, Freising, Germany), Avimers (Amgen, CA), affibodies (Affibody AG, Sweden), ubiquitin (e.g., affilins; Scil Proteins GmbH, Halle, Germany), protein epitope mimetics (Polyphor Ltd, Allschwil, Switzerland), helical bundle scaffolds (e.g. alphabodies, Complix, Belgium), Fyn SH3 domains (Covagen AG, Switzerland), or atrimers (Anaphor, Inc., CA).

B. Cross-Competing Anti-GPC3 Adnectins

Also provided are Adnectins that compete (e.g., cross-compete) for binding to human GPC3 with the particular anti-GPC3 Adnectins described herein. Such competing Adnectins can be identified based on their ability to competitively inhibit binding to GPC3 of Adnectins described herein in standard GPC3 binding assays. For example, standard ELISA assays can be used in which a recombinant GPC3 protein is immobilized on the plate, one of the Adnectins is fluorescently labeled and the ability of non-labeled Adnectins to compete off the binding of the labeled Adnectin is evaluated.

In certain embodiments, a competitive ELISA format can be performed to determine whether two anti-GPC3 Adnectins bind overlapping Adnectin binding sites on GPC3. In one format, Adnectin #1 is coated on a plate, which is then blocked and washed. To this plate is added either GPC3 alone, or GPC3 pre-incubated with a saturating concentration of Adnectin #2. After a suitable incubation period, the plate is washed and probed with a polyclonal anti-GPC3 antibody, such as a biotinylated anti-GPC3 polyclonal antibody, followed by detection with streptavidin-HRP conjugate and standard tetramethylbenzidine development procedures. If the OD signal is the same with or without preincubation with Adnectin #2, then the two Adnectins bind independently of one another, and their Adnectin binding sites do not overlap. If, however, the OD signal for wells that received GPC3/Adnectin #2 mixtures is lower than for those that received GPC3 alone, then binding of Adnectin #2 is confirmed to block binding of Adnectin #1 to GPC3.

Alternatively, a similar experiment is conducted by surface plasmon resonance (SPR, e.g., BIAcore). Adnectin #1 is immobilized on an SPR chip surface, followed by injections of either GPC3 alone or GPC3 pre-incubated with a saturating concentration of Adnectin #2. If the binding signal for GPC3/Adnectin #2 mixtures is the same or higher than that of GPC3 alone, then the two Adnectins bind independently of one another, and their Adnectin binding sites do not overlap. If, however, the binding signal for GPC3/Adnectin #2 mixtures is lower than the binding signal for GPC3 alone, then binding of Adnectin #2 is confirmed to block binding of Adnectin #1 to GPC3. A feature of these experiments is the use of saturating concentrations of Adnectin #2. If GPC3 is not saturated with Adnectin #2, then the conclusions above do not hold. Similar experiments can be used to determine if any two GPC3 binding proteins bind to overlapping Adnectin binding sites.

Both assays exemplified above may also be performed in the reverse order where Adnectin #2 is immobilized and GPC3—Adnectin #1 are added to the plate. Alternatively, Adnectin #1 and/or #2 can be replaced with a monoclonal antibody and/or soluble receptor-Fc fusion protein.

In another embodiment, competition can be determined using a HTRF sandwich assay.

Candidate competing anti-GPC3 Adnectins can inhibit the binding of an anti-GPC3 Adnectin described herein to GPC3 by at least 50%, at least 55%, at least 60%, at least 65%, at least 70%, at least 75%, at least 80%, at least 85%, at least 90%, at least 95%, at least 97%, at least 98%, or at least 99% and/or their binding is inhibited by at least 50%, at least 55%, at least 60%, at least 65%, at least 70%, at least 75%, at least 80%, at least 85%, at least 90%, at least 95%, at least 97%, at least 98%, or at least 99%. The % competition can be determined using the methods described above.

In some embodiments, molecules that compete with the anti-GPC3 Adnectins described herein need not be an Adnectin, but can be any type of molecule that binds to GPC3, such as, but not limited to, an antibody, a small molecule, a peptide, and the like.

In certain embodiments, an Adnectin binds to the same Adnectin binding site on GPC3 as a particular anti-GPC3 Adnectin described herein. Standard mapping techniques, such as protease mapping, mutational analysis, HDX-MS, x-ray crystallography and 2-dimensional nuclear magnetic resonance, can be used to determine whether an Adnectin binds to the same Adnectin binding site as a reference Adnectin (see, e.g., *Epitope Mapping Protocols in Methods in Molecular Biology*, Vol. 66, G. E. Morris, Ed. (1996)).

In some embodiments, anti-GPC3 Adnectins provided herein bind to a discontinuous Adnectin binding site on human GPC3. In some embodiments, an anti-GPC3 FBS binds a region of, e.g., 10-20 amino acid residues, within human GPC3 (SEQ ID NO:344) which comprises SEQ ID NO: 345. In some embodiments, an anti-GPC3 Adnectin binds a region of, e.g., 10-20 amino acid residues, within human GPC3 (SEQ ID NO: 344) which comprises SEQ ID NO: 346. In other embodiments, an anti-GPC3 FBS binds two regions of, e.g., 10-20 amino acid residues, each within human GPC3 (SEQ ID NO: 344), one comprising SEQ ID NO: 345 and the other region comprising SEQ ID NO: 346, respectively.

C. N-Terminal and C-Terminal Modified Anti-GPC3 Adnectins

In some embodiments, the amino acid sequences of the N-terminal and/or C-terminal regions of an Adnectin are modified by deletion, substitution or insertion relative to the amino acid sequences of the corresponding regions of $^{10}$Fn3 domains comprising, e.g., SEQ ID NO: 1.

In certain embodiments, the amino acid sequence of the first 1, 2, 3, 4, 5, 6, 7, 8 or 9 residues of Adnectins, e.g., having sequences starting with "VSD", as in, e.g., SEQ ID NO: 1, may be modified or deleted in the polypeptides provided herein. In exemplary embodiments, the amino acids corresponding to amino acids 1-7, 8 or 9 of Adnectins having sequences starting with "VSD", as in, e.g., SEQ ID NO: 1 are replaced with an alternative N-terminal region having from 1-20, 1-15, 1-10, 1-8, 1-5, 1-4, 1-3, 1-2, or 1 amino acids in length.

Exemplary alternative N-terminal regions that can be added to GPC3 Adnectin core sequences or those starting with "VSD" include (represented by the single letter amino acid code) M, MG, G, MGVSDVPRD (SEQ ID NO: 351) and GVSDVPRD (SEQ ID NO: 352). Other suitable alternative N-terminal regions include, for example, $X_n$SDVPRDL (SEQ ID NO: 353), $X_n$DVPRDL (SEQ ID NO: 354), $X_n$VPRDL (SEQ ID NO: 355), $X_n$PRDL (SEQ ID NO: 356), $X_n$RDL (SEQ ID NO: 357), $X_n$DL (SEQ ID NO: 358), or $X_n$L, wherein n=0, 1 or 2 amino acids, wherein when n=1, X is Met or Gly, and when n=2, X is Met-Gly. When a Met-Gly sequence is added to the N-terminus of a $^{10}$Fn3 domain, the M will usually be cleaved off, leaving a G at the N-terminus. In other embodiments, the alternative N-terminal region comprises the amino acid sequence MASTSG (SEQ ID NO: 359). In certain embodiments, the N-terminal extension consists of an amino acid sequence selected from the group consisting of: M, MG, and G.

In some embodiments, an alternative C-terminal region having from 1-20, 1-15, 1-10, 1-8, 1-5, 1-4, 1-3, 1-2, or 1 amino acids in length can be added to the C-terminal region of GPC3 Adnectins ending in "RT", as, e.g., in SEQ ID NO: 1. Examples of alternative C-terminal region sequences include, for example, polypeptides comprising, consisting essentially of, or consisting of, EIEK (SEQ ID NO: 360), EGSGC (SEQ ID NO: 361), EIEKPCQ (SEQ ID NO: 362), EIEKPSQ (SEQ ID NO: 363), EIEKP (SEQ ID NO: 364), EIEKPS (SEQ ID NO: 365), EIEKPC (SEQ ID NO: 366), EIDK (SEQ ID NO: 367), EIDKPCQ (SEQ ID NO: 368) or EIDKPSQ (SEQ ID NO: 369). In certain embodiments, the C-terminal region consists of EIDKPCQ (SEQ ID NO: 368). In certain embodiments, $^{10}$Fn3 domain is linked to a C-terminal extension sequence that comprises E and D residues, and may be between 8 and 50, 10 and 30, 10 and 20, 5 and 10, and 2 and 4 amino acids in length. In some embodiments, tail sequences include ED-based linkers in which the sequence comprises tandem repeats of ED. In exemplary embodiments, the tail sequence comprises 2-10, 2-7, 2-5, 3-10, 3-7, 3-5, 3, 4 or 5 ED repeats. In certain embodiments, the ED-based tail sequences may also include additional amino acid residues, such as, for example: EI, EID, ES, EC, EGS, and EGC. Such sequences are based, in part, on known Adnectin tail sequences, such as EIDKPSQ (SEQ ID NO: 369), in which residues D and K have been removed. In some embodiments, the ED-based tail comprises an E, I or E1 residues before the ED repeats.

In certain embodiments, the N- or C-terminal extension sequences are linked to the $^{10}$Fn3 domain with known linker sequences (e.g., SEQ ID NOs:426-451 in Table 13). In some embodiments, sequences may be placed at the C-terminus of the $^{10}$Fn3 domain to facilitate attachment of a pharmacokinetic moiety. For example, a cysteine containing linker such as GSGC may be added to the C-terminus to facilitate site directed PEGylation on the cysteine residue.

In certain embodiments, an alternative C-terminal moiety, which can be linked to the C-terminal amino acids RT (i.e., amino acid 94, e.g., as in SEQ ID NO: 1) of GPC3 Adnectins comprises the amino acids $P_mX_n$, wherein P is proline, X is any amino acid, m is an integer that is at least 1 and n is 0 or an integer that is at least 1. In some embodiments, m may be 1, 2, 3 or more. For example, m may be 1-3 or m may be 1-2. “n” may be 0, 1, 2, 3 or more, e.g., n may be 1-3 or 1-2.

The $P_mX_n$ moiety may be linked directly to the C-terminal amino acid of a $^{10}$Fn3 moiety, e.g., to its 94$^{th}$ amino acid (based on amino acid numbering of SEQ ID NO: 1). The $P_mX_n$ moiety may be linked via a peptide bond to the 94$^{th}$ amino acid of a $^{10}$Fn3 moiety. A single proline residue at the end of SEQ ID NO: 1 is referred to as “95Pro” or “Pro95” or “P95” or “95P”.

In certain embodiments, n is not 0, and may be, e.g., 1, 2, 3, 4, 5, 6, 7, 8, 9, 10 or more. For example, n may be from 0-10, 0-5, 0-3, 1-10, 1-5, 1-3 or 1-2. However, more than 10 amino acids may be linked to the proline. For example, in a tandem FBS moiety or a FBS moiety fused to another polypeptide, the C-terminal amino acid of the FBS moiety may be linked to one or more prolines, and the last proline is linked to the second FBS moiety or to the heterologous moiety. Therefore, in certain embodiments, n may be an integer ranging from 0-100, 0-200, 0-300, 0-400, 0-500 or more.

In certain embodiments, $P_mX_n$ linked to the C-terminus of a GPC3 Adnectin comprises a cysteine. For example, the first amino acid after the proline may be a cysteine, and the cysteine may be the last amino acid in the molecule or the cysteine may be followed by one or more amino acids. The presence of a cysteine permits the conjugation of heterologous moieties to the FBS moiety, e.g., chemical moieties, e.g., PEG. Exemplary $P_mX_n$ moieties comprising a cysteine include: $P_mCX_n$, wherein C is a cysteine, each X is independently any amino acid, m is an integer that is at least 1 and n is 0 or an integer that is at least 1. In some embodiments, m may be 1, 2, 3 or more. For example, m may be 1-3 or m may be 1-2. “n” may be 0, 1, 2, 3 or more, e.g., n may be 1-3 or 1-2. Other exemplary $P_mX_n$ moieties include two cysteines, for example, $PmCXn_1CXn_2$, wherein each X is independently any amino acid, $n_1$ and $n_2$ are independently 0 or an integer that is at least 1. For example, $n_1$ may be 1, 2, 3, 4 or 5 and $n_2$ may be 1, 2, 3, 4 or 5. Exemplary PmXn moieties include those listed in Table 1.

TABLE 1

| Exemplary PmXn moieties | | |
|---|---|---|
| Moieties with 1 proline | Moieties with 2 or more prolines | Moieties with 2 cysteines |
| P | PP | PCC |
| PI | PPI | PCGC (SEQ ID NO: 412) |
| PC | PPC | PCPC (SEQ ID NO: 413) |
| PID | PPID (SEQ ID NO: 396) | PCGSGC (SEQ ID NO: 414) |
| PIE | PPIE (SEQ ID NO: 397) | PCPPPC (SEQ ID NO: 415) |
| PIDK (SEQ ID NO: 382) | PPIDK (SEQ ID NO: 398) | PCPPPPPC (SEQ ID NO: 416) |
| PIEK (SEQ ID NO: 383) | PPIEK (SEQ ID NO: 399) | PCGSGSGC (SEQ ID NO: 417) |
| PIDKP (SEQ ID NO: 384) | PPIDKP (SEQ ID NO: 400) | PCHHHHHC (SEQ ID NO: 418) |
| PIEKP (SEQ ID NO: 385) | PPIEKP (SEQ ID NO: 401) | PCCHHHHHH (SEQ ID NO: 419) |
| PIDKPS (SEQ ID NO: 386) | PPIDKPS (SEQ ID NO: 402) | PCGCHHHHHH (SEQ ID NO: 420) |
| PIEKPS (SEQ ID NO: 387) | PPIEKPS (SEQ ID NO: 403) | PCPCHHHHHH (SEQ ID NO: 421) |
| PIDKPC (SEQ ID NO: 388) | PPIDKPC (SEQ ID NO: 404) | PCGSGCHHHHHH (SEQ ID NO: 422) |
| PIEKPC (SEQ ID NO: 389) | PPIEKPC (SEQ ID NO: 405) | PCPPPCHHHHHH (SEQ ID NO: 423) |
| PIDKPSQ (SEQ ID NO: 390) | PPIDKPSQ (SEQ ID NO: 406) | PCPPPPPCHHHHHH (SEQ ID NO: 424) |
| PIEKPSQ (SEQ ID NO: 391) | PPIEKPSQ (SEQ ID NO: 407) | PCGSGSGCHHHHHH (SEQ ID NO: 425) |
| PIDKPCQ (SEQ ID NO: 392) | PPIDKPCQ (SEQ ID NO: 408) | |
| PIEKPCQ (SEQ ID NO: 393) | PPIEKPCQ (SEQ ID NO: 409) | |
| PHHHHHH (SEQ ID NO: 394) | PPHHHHHH (SEQ ID NO: 410) | |
| PCHHHHHH (SEQ ID NO: 395) | PPCHHHHHH (SEQ ID NO: 411) | |

In certain embodiments, for example, the PmXn moiety is selected from the group consisting of PC, PPC and PCC. In another embodiment, the PmXn moiety is $PmCXn_1CXn_2$. In certain embodiments, $PmCXn_1CXn_2$ is selected from the group consisting of PCPPPC (SEQ ID NO: 415) and PCPPPPPC (SEQ ID NO: 416).

Any of the C-terminal modifications described herein may be applied to GPC3 Adnectins.

Any of the PmXn moieties, e.g., those shown in Table 1 may be followed by a histidine tail, e.g., 6×His tag, or other tag. This does not exclude that a histidine tail may be included in PmXn.

In certain embodiments, the fibronectin based scaffold proteins comprise a $^{10}$Fn3 domain having both an alternative N-terminal region sequence and an alternative C-terminal region sequence, and optionally a 6× his tail.

II. Multivalent Polypeptides

In certain embodiments, a protein comprises GPC3 FBS and at least one other FBS. A multivalent FBS may comprise 2, 3 or more FBS, that are covalently associated. In exemplary embodiments, the FBS moiety is a bispecific or dimeric protein comprising two $^{10}$Fn3 domains.

The FBS moieties, e.g., $^{10}$Fn3 domains, in a multivalent protein may be connected by a polypeptide linker. Exemplary polypeptide linkers include polypeptides having from 1-20, 1-15, 1-10, 1-8, 1-5, 1-4, 1-3, or 1-2 amino acids. Suitable linkers for joining the $^{10}$Fn3 domains are those which allow the separate domains to fold independently of each other forming a three dimensional structure that permits high affinity binding to a target molecule. Specific examples of suitable linkers include glycine-serine based linkers, glycine-proline based linkers, proline-alanine based linkers as well as any other linkers described herein. In some embodiments, the linker is a glycine-proline based linker. These linkers comprise glycine and proline residues and may be between 3 and 30, 10 and 30, and 3 and 20 amino acids in length. Examples of such linkers include GPG, GPGPGPG (SEQ ID NO: 436) and GPGPGPGPGPG (SEQ ID NO: 437). In some embodiments, the linker is a proline-alanine based linker. These linkers comprise proline and alanine residues and may be between 3 and 30, 10 and 30, 3 and 20 and 6 and 18 amino acids in length. Examples of such linkers include PAPAPA (SEQ ID NO: 438), PAPAPAPAPAPA (SEQ ID NO: 439) and PAPAPAPAPAPAPAPAPA (SEQ ID NO: 440). In some embodiments, the linker is a glycine-serine based linker. These linkers comprise glycine and serine residues and may be between 8 and 50, 10 and 30, and 10 and 20 amino acids in length. Examples of such linkers may contain, for example, $(GS)_{5-10}$ (SEQ ID NO: 464), $(G_4S)_{2-5}$ (SEQ ID NO: 465), and $(G_4S)_2G$ (SEQ ID NO: 466). Examples of such linkers include SEQ ID NOs: 427-439. In exemplary embodiments, the linker does not contain any Asp-Lys (DK) pairs.

III. Pharmacokinetic Moieties

For therapeutic purposes, the anti-GPC3 Adnectins described herein may be linked directly or indirectly to a pharmacokinetic (PK) moiety. Improved pharmacokinetics may be assessed according to the perceived therapeutic need. Often it is desirable to increase bioavailability and/or increase the time between doses, possibly by increasing the time that a protein remains available in the serum after dosing. In some instances, it is desirable to improve the continuity of the serum concentration of the protein over time (e.g., decrease the difference in serum concentration of the protein shortly after administration and shortly before the next administration). The anti-GPC3 Adnectin may be attached to a moiety that reduces the clearance rate of the polypeptide in a mammal (e.g., mouse, rat, or human) by greater than two-fold, greater than three-fold, greater than four-fold or greater than five-fold relative to the unmodified anti-GPC3 Adnectin. Other measures of improved pharmacokinetics may include serum half-life, which is often divided into an alpha phase and a beta phase. Either or both phases may be improved significantly by addition of an appropriate moiety. For example, the PK moiety may increase the serum half-life of the polypeptide by more than 5, 10, 20, 30, 40, 50, 60, 70, 80, 90, 100, 120, 150, 200, 400, 600, 800, 1000% or more relative to the Fn3 domain alone.

Moieties that slow clearance of a protein from the blood, herein referred to as "PK moieties", include polyoxyalkylene moieties (e.g., polyethylene glycol), sugars (e.g., sialic acid), and well-tolerated protein moieties (e.g., Fc and fragments and variants thereof, transferrin, or serum albumin) The anti-GPC3 Adnectin may also be fused to albumin or a fragment (portion) or variant of albumin as described in U.S. Publication No. 2007/0048282, or may be fused to one or more serum albumin binding Adnectin, as described herein.

Other PK moieties that can be used in the invention include those described in Kontermann et al., (*Current Opinion in Biotechnology* 2011; 22:868-76), herein incorporated by reference. Such PK moieties include, but are not limited to, human serum albumin fusions, human serum albumin conjugates, human serum albumin binders (e.g., Adnectin PKE, AlbudAb, ABD), XTEN fusions, PAS fusions (i.e., recombinant PEG mimetics based on the three amino acids proline, alanine, and serine), carbohydrate conjugates (e.g., hydroxyethyl starch (HES)), glycosylation, polysialic acid conjugates, and fatty acid conjugates.

In some embodiments the invention provides an anti-GPC3 Adnectin fused to a PK moiety that is a polymeric sugar. In some embodiments, the PK moiety is a polyethylene glycol moiety or an Fc region. In some embodiments the PK moiety is a serum albumin binding protein such as those described in U.S. Publication Nos. 2007/0178082 and 2007/0269422. In some embodiments the PK moiety is human serum albumin. In some embodiments, the PK moiety is transferrin.

In some embodiments, the PK moiety is linked to the anti-GPC3 Adnectin via a polypeptide linker. Exemplary polypeptide linkers include polypeptides having from 1-20, 1-15, 1-10, 1-8, 1-5, 1-4, 1-3, or 1-2 amino acids. Suitable linkers for joining the Fn3 domains are those which allow the separate domains to fold independently of each other forming a three dimensional structure that permits high affinity binding to a target molecule. In exemplary embodiments, the linker does not contain any Asp-Lys (DK) pairs. A list of suitable linkers is provided in Table 14 (e.g., SEQ ID NOs: 426-451).

In some embodiments, an anti-GPC3 Adnectin is linked, for example, to an anti-HSA Adnectin via a polypeptide linker having a protease site that is cleavable by a protease in the blood or target tissue. Such embodiments can be used to release an anti-GPC3 Adnectin for better delivery or therapeutic properties or more efficient production.

Additional linkers or spacers, may be introduced at the N-terminus or C-terminus of a Fn3 domain between the Fn3 domain and the polypeptide linker.

Polyethylene Glycol

In some embodiments, the anti-GPC3 Adnectin comprises polyethylene glycol (PEG). PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented by the formula: $X—O(CH_2CH_2O)_{n-1}CH_2CH_2OH$, where n is 20 to 2300 and X is H or a terminal modification, e.g., a $C_{1-4}$ alkyl. PEG can contain further chemical groups which are necessary for binding reactions, which result from the chemical synthesis of the molecule; or which act as a spacer for optimal distance of parts of the molecule. In addition, such a PEG can consist of one or more PEG side-chains which are linked together. PEGs with more than one PEG chain are called multiarmed or branched PEGs. Branched PEGs are described in, for example, European Published Application No. 473084A and U.S. Pat. No. 5,932,462.

Immunoglobulin Fc Domain (and Fragments)

In certain embodiments, the anti-GPC3 Adnectin is fused to an immunoglobulin Fc domain, or a fragment or variant thereof. As used herein, a "functional Fc region" is an Fc domain or fragment thereof which retains the ability to bind FcRn. In some embodiments, a functional Fc region binds to FcRn, bud does not possess effector function. The ability of the Fc region or fragment thereof to bind to FcRn can be determined by standard binding assays known in the art. In other embodiments, the Fc region or fragment thereof binds to FcRn and possesses at least one "effector function" of a native Fc region. Exemplary "effector functions" include C1q binding; complement dependent cytotoxicity (CDC); Fc receptor binding; antibody-dependent cell-mediated cytotoxicity (ADCC); phagocytosis; down regulation of cell surface receptors (e.g., B cell receptor; BCR), etc. Such effector functions generally require the Fc region to be combined with a binding domain (e.g., an anti-GPC3 Adnectin) and can be assessed using various assays known in the art for evaluating such antibody effector functions.

A "native sequence Fc region" comprises an amino acid sequence identical to the amino acid sequence of an Fc region found in nature. A "variant Fc region" comprises an amino acid sequence which differs from that of a native sequence Fc region by virtue of at least one amino acid modification. Preferably, the variant Fc region has at least one amino acid substitution compared to a native sequence Fc region or to the Fc region of a parent polypeptide, e.g., from about one to about ten amino acid substitutions, and preferably from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably at least about 90% sequence identity therewith, more preferably at least about 95% sequence identity therewith.

In an exemplary embodiment, the Fc domain is derived from an IgG1 subclass, however, other subclasses (e.g., IgG2, IgG3, and IgG4) may also be used. Shown below is the sequence of a human IgG1 immunoglobulin Fc domain

```
                                        (SEQ ID NO: 463)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPGK
```

The core hinge sequence is underlined, and the CH2 and CH3 regions are in regular text. It should be understood that the C-terminal lysine is optional. Allotypes and mutants of this sequence may also be used. As is known in the art, mutants can be designed to modulate a variety of properties of the Fc, e.g., ADCC, CDC or half-life.

In certain embodiments, the Fc region used in the anti-GPC3 Adnectin fusion comprises a CH1 region. In certain embodiments, the Fc region used in the anti-GPC3 Adnectin fusion comprises CH2 and CH3 regions. In certain embodiments, the Fc region used in the anti-GPC3 Adnectin fusion comprises a CH2, CH3, and hinge region.

In certain embodiments, the "hinge" region comprises the core hinge residues spanning positions 1-16 of SEQ ID NO: 463 (DKTHTCPPCPAPELLG; SEQ ID NO: 464) of the IgG1 Fc region. In certain embodiments, the anti-GPC3 Adnectin-Fc fusion adopts a multimeric structure (e.g., dimer) owing, in part, to the cysteine residues at positions 6 and 9 of SEQ ID NO: within the hinge region.

IV. Vectors and Polynucleotides

Also provided herein are nucleic acids encoding the anti-GPC3 Andectins described herein. As appreciated by those skilled in the art, because of third base degeneracy, almost every amino acid can be represented by more than one triplet codon in a coding nucleotide sequence. In addition, minor base pair changes may result in a conservative substitution in the amino acid sequence encoded but are not expected to substantially alter the biological activity of the gene product. Therefore, a nucleic acid sequence encoding a protein described herein may be modified slightly in sequence and yet still encode its respective gene product. Certain exemplary nucleic acids encoding the anti-GPC3 Adnectins and their fusions described herein include nucleic acids having the sequences set forth in SEQ ID NOs: 452-462.

Nucleic acids encoding any of the various proteins comprising an anti-GPC3 Adnectin disclosed herein may be synthesized chemically, enzymatically or recombinantly. Codon usage may be selected so as to improve expression in a cell. Such codon usage will depend on the cell type selected. Specialized codon usage patterns have been developed for *E. coli* and other bacteria, as well as mammalian cells, plant cells, yeast cells and insect cells. See for example: Mayfield et al., *Proc. Natl. Acad. Sci. USA,* 100 (2):438-442 (Jan. 21, 2003); Sinclair et al., *Protein Expr. Purif.,* 26(1):96-105 (October 2002); Connell, N. D., *Curr. Opin. Biotechnol.,* 12(5):446-449 (October 2001); Makrides et al., *Microbiol. Rev.,* 60(3):512-538 (September 1996); and Sharp et al., *Yeast,* 7(7):657-678 (October 1991).

General techniques for nucleic acid manipulation are described for example in Sambrook et al., *Molecular Cloning: A Laboratory Manual, Second Edition*, Vols. 1-3, Cold Spring Harbor Laboratory Press (1989), or Ausubel, F. et al., *Current Protocols in Molecular Biology*, Green Publishing and Wiley-Interscience, New York (1987) and periodic updates, herein incorporated by reference. The DNA encoding the polypeptide is operably linked to suitable transcriptional or translational regulatory elements derived from mammalian, viral, or insect genes. Such regulatory elements include a transcriptional promoter, an optional operator sequence to control transcription, a sequence encoding suitable mRNA ribosomal binding sites, and sequences that control the termination of transcription and translation. The ability to replicate in a host, usually conferred by an origin of replication, and a selection gene to facilitate recognition of transformants are additionally incorporated.

The proteins described herein may be produced recombinantly not only directly, but also as a polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells that do not recognize and process a native signal sequence, the signal sequence is substituted by a prokaryotic signal sequence selected, for example, from the group of the alkaline phosphatase, penicillinase, 1pp, or heat-stable enterotoxin II leaders. For yeast secretion the native signal sequence may be substituted by, e.g., the yeast invertase leader, a factor leader (including *Saccharomyces* and *Kluyveromyces* alpha-factor leaders), or acid phosphatase leader, the *C. albicans* glucoamylase leader, or the signal described in PCT Publication No. WO 90/13646. In mammalian cell expression, mammalian signal sequences as well as viral secretory leaders, for example, the herpes simplex gD signal, are available. The DNA for such precursor regions may be ligated in reading frame to DNA encoding the protein.

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

A suitable selection gene for use in yeast is the trp1 gene present in the yeast plasmid YRp7 (Stinchcomb et al., *Nature,* 282:39 (1979)). The trp1 gene provides a selection marker for a mutant strain of yeast lacking the ability to grow in tryptophan, for example, ATCC® No. 44076 or PEP4-1. Jones, *Genetics,* 85:12 (1977). The presence of the trp1 lesion in the yeast host cell genome then provides an effective environment for detecting transformation by growth in the absence of tryptophan. Similarly, Leu2-deficient yeast strains (ATCC® 20,622 or 38,626) are complemented by known plasmids bearing the Leu2 gene.

Expression and cloning vectors usually contain a promoter that is recognized by the host organism and is operably linked to the nucleic acid encoding the protein. Promoters suitable for use with prokaryotic hosts include the phoA promoter, beta-lactamase and lactose promoter systems, alkaline phosphatase, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the protein.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT (SEQ ID NO: 465) region where N may be any nucleotide. At the 3' end of most eukaryotic genes is an AATAAA (SEQ ID NO: 466) sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP Patent Publication No. 73,657 and PCT Publication Nos. WO 2011/124718 and WO 2012/059486. Yeast enhancers also are advantageously used with yeast promoters.

Transcription from vectors in mammalian host cells can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the ACTIN® promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., *Nature,* 297:598-601 (1982) on expression of human β-interferon cDNA in mouse cells under the control of a thymidine kinase promoter from herpes simplex virus. Alternatively, the rous sarcoma virus long terminal repeat can be used as the promoter.

Transcription of a DNA encoding a protein by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, *Nature,* 297:17-18 (1982) on enhancing elements for activation of eukaryotic promoters. The enhancer may be spliced into the vector at a position 5' or 3' to the polypeptide-encoding sequence, but is preferably located at a site 5' from the promoter.

Expression vectors used in eukaryotic host cells (e.g., yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the polypeptide. One useful transcription termination component is the bovine growth hormone polyadenylation region. See WO 94/11026 and the expression vector disclosed therein.

The recombinant DNA can also include any type of protein tag sequence that may be useful for purifying the proteins. Examples of protein tags include but are not limited to a histidine tag, a FLAG® tag, a myc tag, an HA tag, or a GST tag. Appropriate cloning and expression vectors for use with bacterial, fungal, yeast, and mammalian cellular hosts can be found in *Cloning Vectors: A Laboratory Manual*, Elsevier, New York (1985), the relevant disclosure of which is hereby incorporated by reference.

The expression construct may be introduced into the host cell using a method appropriate to the host cell, as will be apparent to one of skill in the art. A variety of methods for introducing nucleic acids into host cells are known in the art, including, but not limited to, electroporation; transfection employing calcium chloride, rubidium chloride, calcium phosphate, DEAE-dextran, or other substances; microprojectile bombardment; lipofection; and infection (where the vector is an infectious agent).

Suitable host cells include prokaryotes, yeast, mammalian cells, or bacterial cells. Suitable bacteria include gram negative or gram positive organisms, for example, *E. coli* or *Bacillus* spp. Yeast, preferably from the *Saccharomyces* species, such as *S. cerevisiae*, may also be used for production of polypeptides. Various mammalian or insect cell culture systems can also be employed to express recombinant proteins. Baculovirus systems for production of heterologous proteins in insect cells are reviewed by Luckow et al. (*Bio/Technology,* 6:47 (1988)). Examples of suitable mammalian host cell lines include endothelial cells, COS-7 monkey kidney cells, CV-1, L cells, C127, 3T3, Chinese hamster ovary (CHO), human embryonic kidney cells, HeLa, 293, 293T, and BHK cell lines. Purified proteins are prepared by culturing suitable host/vector systems to express the recombinant proteins. The FBS protein is then purified from culture media or cell extracts.

V. Protein Production

Host cells are transformed with the herein-described expression or cloning vectors for protein production and cultured in conventional nutrient media modified as appropriate for inducing promoters, selecting transformants, or amplifying the genes encoding the desired sequences.

The host cells used to produce the proteins may be cultured in a variety of media. Commercially available media such as Ham's F10 (Sigma), Minimal Essential Medium ((MEM), (Sigma)), RPMI-1640 (Sigma), and Dulbecco's Modified Eagle's Medium ((DMEM), (Sigma)) are suitable for culturing the host cells. In addition, any of the media described in Ham et al., *Meth. Enzymol.,* 58:44 (1979), Barnes et al., *Anal. Biochem.,* 102:255 (1980), U.S. Pat. Nos. 4,767,704; 4,657,866; 4,927,762; 4,560,655; or 5,122,469; PCT Publication Nos. WO 90/03430; WO 87/00195; or U.S. Pat. No. RE30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as Gentamycin drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Proteins disclosed herein can also be produced using cell-free translation systems. For such purposes the nucleic acids encoding the protein must be modified to allow in vitro transcription to produce mRNA and to allow cell-free translation of the mRNA in the particular cell-free system being utilized (eukaryotic such as a mammalian or yeast cell-free translation system or prokaryotic such as a bacterial cell-free translation system).

Proteins can also be produced by chemical synthesis (e.g., by the methods described in *Solid Phase Peptide Synthesis*, Second Edition, The Pierce Chemical Co., Rockford, IL (1984)). Modifications to the protein can also be produced by chemical synthesis.

The proteins disclosed herein can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, gel filtration, gel permeation chromatography, affinity chromatography, electrophoresis, countercurrent distribution or any combinations of these. After purification, proteins may be exchanged into different buffers and/or concentrated by any of a variety of methods known to the art, including, but not limited to, filtration and dialysis.

The purified protein is preferably at least 85% pure, more preferably at least 95% pure, and most preferably at least 98% or 99% pure. Regardless of the exact numerical value of the purity, the protein is sufficiently pure for use as a pharmaceutical product.

One method for expressing Adnectins in *E. coli* is as follows. A nucleic acid encoding an Adnectin is cloned into the PET9d vector upstream of a HIS6tag and are transformed into *E. coli* BL21 DE3 plysS cells and inoculated in 5 ml LB medium containing 50 μg/mL kanamycin in a 24-well format and grown at 37° C. overnight. Fresh 5 ml LB medium (50 μg/mL kanamycin) cultures are prepared for inducible expression by aspiration of 200 μl from the overnight culture and dispensing it into the appropriate well. The cultures are grown at 37° C. until $A_{600}$ 0.6-0.9. After induction with 1 mM isopropyl-β-thiogalactoside (IPTG), the culture is expressed for 6 hours at 30° C. and harvested by centrifugation for 10 minutes at 2750 g at 4° C.

Cell pellets (in 24-well format) are lysed by resuspension in 450W of Lysis buffer (50 mM $NaH_2PO_4$, 0.5 M NaCl, 1× Complete™ Protease Inhibitor Cocktail-EDTA free (Roche), 1 mM PMSF, 10 mM CHAPS, 40 mM imidazole, 1 mg/ml lysozyme, 30 μg/ml DNAse, 2 μg/ml aprotonin, pH 8.0) and shaken at room temperature for 1-3 hours. Lysates are cleared and re-racked into a 96-well format by transfer into a 96-well Whatman GF/D Unifilter fitted with a 96-well, 1.2 ml catch plate and filtered by positive pressure. The cleared lysates are transferred to a 96-well Nickel or Cobalt-Chelating Plate that had been equilibrated with equilibration buffer (50 mM $NaH_2PO_4$, 0.5 M NaCl, 40 mM imidazole, pH 8.0) and are incubated for 5 min Unbound material is removed by positive pressure. The resin is washed twice with 0.3 ml/well with Wash buffer #1 (50 mM $NaH_2PO_4$, 0.5 M NaCl, 5 mM CHAPS, 40 mM imidazole, pH 8.0). Each wash is removed by positive pressure. Prior to elution, each well is washed with 50 μl Elution buffer (PBS+20 mM EDTA), incubated for 5 min, and this wash is discarded by positive pressure. Protein is eluted by applying an additional 100 μl of Elution buffer to each well. After a 30 minute incubation at room temperature, the plate(s) are centrifuged for 5 minutes at 200 g and eluted protein collected in 96-well catch plates containing 5 μl of 0.5 M $MgCl_2$ added to the bottom of elution catch plate prior to elution. Eluted protein is quantified using a total protein assay with wild-type $^{10}$Fn3 domain as the protein standard.

A method for midscale expression and purification of insoluble Adnectins is as follows. An nucleic acid endcoding an Adnectin(s) followed by the HIS6tag, is cloned into a pET9d (EMD Bioscience, San Diego, CA) vector and are expressed in *E. coli* HMS174 cells. Twenty ml of an inoculum culture (generated from a single plated colony) is used to inoculate 1 liter of LB medium containing 50 μg/ml carbenicillin and 34 μg/ml chloramphenicol. The culture is grown at 37° C. until $A_{600}$ 0.6-1.0. After induction with 1 mM isopropyl-β-thiogalactoside (IPTG) the culture is grown for 4 hours at 30° C. and is harvested by centrifugation for 30 minutes at >10,000 g at 4° C. Cell pellets are frozen at −80° C. The cell pellet is resuspended in 25 ml of lysis buffer (20 mM aH2PO$_4$, 0.5 M NaCl, 1× Complete Protease Inhibitor Cocktail-EDTA free (Roche), ImM PMSF, pH 7.4) using an ULTRA-TURRAX® homogenizer (IKA works) on ice. Cell lysis is achieved by high pressure homogenization (>18,000 psi) using a Model M-1 10S MICROFLUIDIZER® (Microfluidics). The insoluble fraction is separated by centrifugation for 30 minutes at 23,300 g at 4° C. The insoluble pellet recovered from centrifugation of the lysate is washed with 20 mM sodium phosphate/500 mM NaCl, pH7.4. The pellet is resolubilized in 6.0M guanidine hydrochloride in 20 mM sodium phosphate/500M NaCl pH 7.4 with sonication followed by incubation at 37 degrees for 1-2 hours. The resolubilized pellet is filtered to 0.45 μm and loaded onto a Histrap column equilibrated with the 20 mM sodium phosphate/500 M NaCl/6.0 M guanidine pH 7.4 buffer. After loading, the column is washed for an additional 25 CV with the same buffer. Bound protein is eluted with 50 mM Imidazole in 20 mM sodium phosphate/500 mM NaCl/6.0 M guan-HCl pH7.4. The purified protein is refolded by dialysis against 50 mM sodium acetate/150 mM NaCl pH 4.5.

A method for midscale expression and purification of soluble Adnectins is as follows. A nucleic acid encoding an Adnectin(s), followed by the HIS6tag, is cloned into a pET9d (EMD Bioscience, San Diego, CA) vector and expressed in *E. coli* HMS174 cells. Twenty ml of an inoculum culture (generated from a single plated colony) is used to inoculate 1 liter of LB medium containing 50 μg/ml carbenicillin and 34 μg/ml chloramphenicol. The culture is grown at 37° C. until $A_{600}$ 0.6-1.0. After induction with 1 mM isopropyl-β-thiogalactoside (IPTG), the culture is grown for 4 hours at 30° C. and harvested by centrifugation for 30 minutes at >10,000 g at 4° C. Cell pellets are frozen at −80° C. The cell pellet is resuspended in 25 ml of lysis buffer (20 mM $NaH_2PO_4$, 0.5 M NaCl, 1× Complete Protease Inhibitor Cocktail-EDTA free (Roche), ImM PMSF, pH 7.4) using an ULTRA-TURRAX® homogenizer (IKA works) on ice. Cell lysis is achieved by high pressure homogenization (>18,000 psi) using a Model M-1 10S MICROFLUIDIZER® (Microfluidics). The soluble fraction is separated by centrifugation for 30 minutes at 23,300 g at 4° C. The supernatant is clarified via 0.45 μm filter. The clarified lysate is loaded onto a Histrap column (GE) pre-equilibrated with the 20 mM sodium phosphate/500M NaCl pH 7.4. The column is then washed with 25 column volumes of the same buffer, followed by 20 column volumes of 20 mM sodium phosphate/500 M NaCl/25 mM Imidazole, pH 7.4 and then 35 column volumes of 20 mM sodium phosphate/500 M NaCl/40 mM Imidazole, pH 7.4. Protein is eluted with 15 column volumes of 20 mM sodium phosphate/500 M NaCl/500 mM Imidazole, pH 7.4, fractions are pooled based on absorbance at $A_2$so and dialyzed against 1λPBS, 50 mM Tris, 150 mM NaCl; pH 8.5 or 50 mM NaOAc; 150 mM NaCl; pH4.5. Any precipitate is removed by filtering at 0.22 μm.

VI. Biophysical and Biochemical Characterization

Binding of the anti-GPC3 Adnectins described herein may be assessed in terms of equilibrium constants (e.g., dissociation, $K_D$) and in terms of kinetic constants (e.g., on-rate constant, $k_{on}$ and off-rate constant, $k_{off}$). An Adnectin will generally bind to a target molecule with a $K_D$ of less than 1 μM, 500 nM, 100 nM, 10 nM, 1 nM, 500 pM, 200 pM, or 100 pM, although higher $K_D$ values may be tolerated where the $k_{off}$ is sufficiently low or the $k_{on}$, is sufficiently high.

In Vitro Assays for Binding Affinity

Exemplary assays for determining the binding affinity of an anti-GPC3 Adnectin includes, but is not limited to, solution phase methods such as the kinetic exclusion assay (KinExA) (Blake et al., *JBC* 1996; 271:27677-85; Drake et al., *Anal Biochem* 2004; 328:35-43), surface plasmon resonance (SPR) with the Biacore system (Uppsala, Sweden) (Welford et al., *Opt. Quant. Elect* 1991; 23:1; Morton and Myszka, *Methods in Enzymology* 1998; 295:268) and homogeneous time resolved fluorescence (HTRF) assays (Newton et al., *J Biomol Screen* 2008; 13:674-82; Patel et al., *Assay Drug Dev Technol* 2008; 6:55-68).

In certain embodiments, biomolecular interactions can be monitored in real time with the Biacore system, which uses SPR to detect changes in the resonance angle of light at the surface of a thin gold film on a glass support due to changes in the refractive index of the surface up to 300 nm away. Biacore analysis generates association rate constants, dissociation rate constants, equilibrium dissociation constants, and affinity constants. Binding affinity is obtained by assessing the association and dissociation rate constants using a Biacore surface plasmon resonance system (Biacore, Inc.).

A biosensor chip is activated for covalent coupling of the target. The target is then diluted and injected over the chip to obtain a signal in response units of immobilized material. Since the signal in resonance units (RU) is proportional to the mass of immobilized material, this represents a range of immobilized target densities on the matrix. Association and dissociation data are fit simultaneously in a global analysis to solve the net rate expression for a 1:1 bimolecular interaction, yielding best fit values for $k_{on}$, $k_{off}$ and $R_{max}$ (maximal response at saturation). Equilibrium dissociation constants for binding, $K_D$'s are calculated from SPR measurements as $k_{off}/k_{on}$.

In some embodiments, the anti-GPC3 Adnectins described herein exhibit a $K_D$ in the SPR affinity assay described in Example 2 of 1 μM or less, 500 nM or less, 400 nM or less, 300 nM or less, 200 nM or less, 150 nM or less, 100 nM or less, 90 nM or less, 80 nM or less, 70 nM or less, 60 nM or less, 50 nM or less, 40 nM or less, 30 nM or less, 20 nM or less, 15 nM or less, 10 nM or less, 5 nM or less, or 1 nM or less.

In some embodiments, the anti-GPC3 Adnectin does not substantially bind to related proteins, for example, the anti-GPC3 Adnectin does not substantially bind to Glypican-1, Glypican-2, Glypican-4 or Glypican-6.

It should be understood that the assays described herein above are exemplary, and that any method known in the art for determining the binding affinity between proteins (e.g., fluorescence based-transfer (FRET), enzyme-linked immunosorbent assay, and competitive binding assays (e.g., radioimmunoassays) can be used to assess the binding affinities of the anti-GPC3 Adnectins described herein.

Cell Assays for Binding

In some embodiments, the anti-GPC3 Adnectin and conjugates thereof is internalized into a cell expressing Glypican-3. Standard assays to evaluate polypeptide internalization are known in the art, including, for example, a HumZap internalization assay. To assess binding to tumor cells, e.g. Hep-3b or Hep-G2 (ATCC Deposit No. HB-8064 and HB-8065, respectively), cells can be obtained from publicly available sources, such as the American Type Culture Collection, and used in standard assays, such as flow cytometric analysis.

VII. Drug Conjugates

Also provided are polypeptides comprising a FBS domain, e.g., an Adnectin, conjugated to a therapeutic agent or drug moiety. In an Adnectin-drug conjugate (AdxDC), the FBS moiety (e.g., anti-GPC3 Adnectin) is conjugated to a drug moiety, with the Adnectin functioning as a targeting agent for directing the AdxDC to a target cell expressing GPC3, such as a cancer cell. Once there, the drug is released, either inside the target cell or in its vicinity, to act as a therapeutic agent. For a review on the mechanism of action and use of drug conjugates as used with antibodies, e.g., in cancer therapy, see Schrama et al., *Nature Rev. Drug Disc.*, 5:147 (2006).

Suitable drug moieties for use in drug conjugates include cytoxins or radiotoxins. A cytotoxin or cytotoxic agent includes any agent that is detrimental to (e.g., kills) cells, including, antimetabolites, alkylating agents, DNA minor groove binders, DNA intercalators, DNA crosslinkers, histone deacetylase inhibitors, nuclear export inhibitors, proteasome inhibitors, topoisomerase I or II inhibitors, heat shock protein inhibitors, tyrosine kinase inhibitors, antibiotics, and anti-mitotic agents.

Examples of suitable agents include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). Other preferred examples of therapeutic cytotoxins that can be conjugated to an anti-GPC3 Adnectin of the invention include duocarmycins, calicheamicins, maytansines and auristatins, and derivatives thereof.

The Adnectin drug conjugates can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, *pseudomonas* exotoxin, or diphtheria toxin; a protein such as tumor necrosis factor or interferon-.gamma; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

An anti-GPC3 Adnectin can be conjugated to a therapeutic agent using linker technology available in the art. Examples of linker types that have been used to conjugate a cytotoxin to an Adnectin include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D). Examples of cytotoxins are described, for example, in U.S. Pat. Nos. 6,989,452, 7,087,600, and 7,129,261, and in PCT Application Nos. PCT/US02/17210, PCT/US2005/017804, PCT/US06/37793, PCT/US06/060050, PCT/US2006/060711, WO/2006/110476, and in U.S. Patent Application No. 60/891,028, all of which are incorporated herein by reference in their entirety.

In certain embodiments, the anti-GPC3 Adnecin and therapeutic agent preferably are conjugated via a cleavable linker such as a peptidyl, disulfide, or hydrazone linker. More preferably, the linker is a peptidyl linker which may comprise Val-Cit, Ala-Val, Val-Ala-Val, Lys-Lys, Pro-Val-Gly-Val-Val (SEQ ID NO: 467), Ala-Asn-Val, Val-Leu-Lys, Ala-Ala-Asn, Cit-Cit, Val-Lys, Lys, Cit, Ser, or Glu. The FBS-DCs can be prepared according to methods similar to those described in U.S. Pat. Nos. 7,087,600; 6,989,452; and 7,129,261; PCT Publication Nos. WO 02/096910; WO 07/038658; WO 07/051081; WO 07/059404; WO 08/083312; and WO 08/103693; U.S. Patent Publication Nos. 2006/0024317; 2006/0004081; and 2006/0247295; the disclosures of which are incorporated herein by reference.

A linker can itself be linked, e.g., covalently linked, e.g., using maleimide chemistry, to a cysteine of a PmXn moiety on the anti-GPC3 Adnectin, wherein at least one X is a cysteine. For example, a linker can be covalently linked to an anti-GPC3 Adnectin-PmXn, wherein at least one X is a cysteine. For example, a linker can be linked to an anti-GPC3 Adnectin-PmCn, wherein P is a proline, C is a cysteine, and m and n are integers that are at least 1, e.g., 1-3. Ligation to a cysteine can be performed as known in the art using maleimide chemistry (e.g., Imperiali, B. et al., *Protein Engineering: Nucleic Acids and Molecular Biology*, Vol. 22, pp. 65-96, Gross, H. J., ed. (2009)). For attaching a linker to a cysteine on an anti-GPC3FBS, the linker may, e.g., comprise a maleinimido moiety, which moiety then reacts with the cysteine to form a covalent bond. In certain embodiments, the amino acids surrounding the cysteine are optimized to facilitate the chemical reaction. For example, a cysteine may be surrounded by negatively charged amino acid for a faster reaction relative to a cysteine that is surrounded by a stretch of positively charged amino acids (EP 1074563). Linkage of a drug moiety to a cysteine on an anti-GPC3 Adnectin is a site specific linkage.

For cancer treatment, the drug preferably is a cytotoxic drug that causes death of the targeted cancer cell. Cytotoxic drugs that can be used in anti-GPC3 FBS-DCs include, e.g., the following types of compounds and their analogs and derivatives:

(a) enediynes such as calicheamicin (see, e.g., Lee et al., *J. Am. Chem. Soc.* 1987, 109, 3464 and 3466) and uncialamycin (see, e.g., Davies et al., WO 2007/038868 A2 (2007); Chowdari et al., U.S. Pat. No. 8,709,431 B2 (2012); and Nicolaou et al., WO 2015/023879 A1 (2015));

(b) tubulysins (see, e.g., Domling et al., U.S. Pat. No. 7,778,814 B2 (2010); Cheng et al., U.S. Pat. No. 8,394,922 B2 (2013); and Cong et al., U.S. Pat. No. 8,980,824 B2 (2015));

(c) DNA alkylators such as analogs of CC-1065 and duocarmycin (see, e.g., Boger, U.S. Pat. No. 6,5458,530 B1 (2003); Sufi et al., U.S. Pat. No. 8,461,117 B2 (2013); and Zhang et al., U.S. Pat. No. 8,852,599 B2 (2014));

(d) epothilones (see, e.g., Vite et al., US 2007/0275904 A1 (2007) and U.S. RE42930 E (2011));

(e) auristatins (see, e.g., Senter et al., U.S. Pat. No. 6,844,869 B2 (2005) and Doronina et al., U.S. Pat. No. 7,498,298 B2 (2009));

(f) pyrrolobezodiazepine (PBD) dimers (see, e.g., Howard et al., US 2013/0059800 A1(2013); US 2013/0028919 A1 (2013); and WO 2013/041606 A1 (2013)); and (g) maytansinoids such as DM1 and DM4 (see, e.g., Chari et al., U.S. Pat. No. 5,208,020 (1993) and Amphlett et al., U.S. Pat. No. 7,374,762 B2 (2008)).

The foregoing drug moiety references, in addition to disclosing the drug moieties proper, also disclose linkers that can be used in making drug-linker compounds suitable for conjugating them. Particularly pertinent disclosures relating to the preparation of drug-linker compounds are found in Chowdari et al., U.S. Pat. No. 8,709,431 B2 (2012); Cheng et al., U.S. Pat. No. 8,394,922 B2 (2013); Cong et al., U.S. Pat. No. 8,980,824 B2 (2015); Sufi et al., U.S. Pat. No. 8,461,117 B2 (2013); and Zhang et al., U.S. Pat. No. 8,852,599.

Preferably, the drug moiety is a DNA alkylator, tubulysin, auristatin, pyrrolobenzodiazepine, enediyne, or maytansinoid compound, such as:

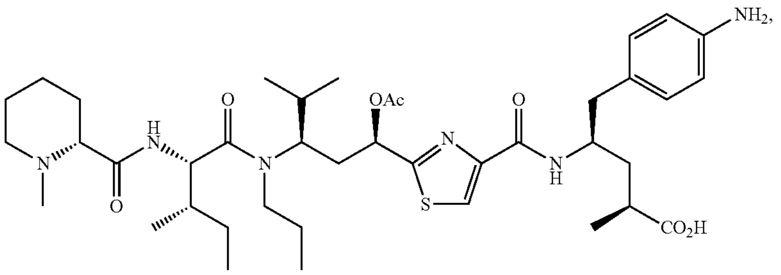

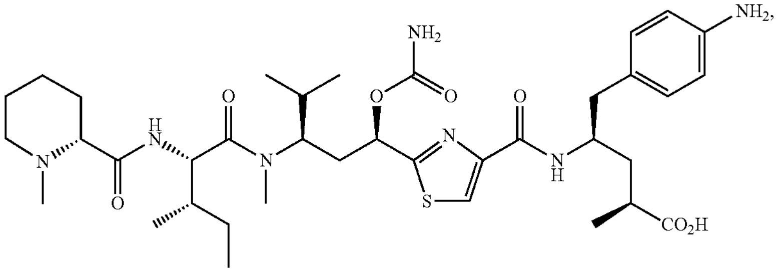

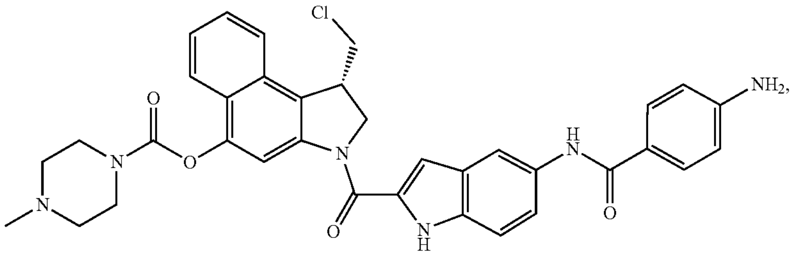

-continued

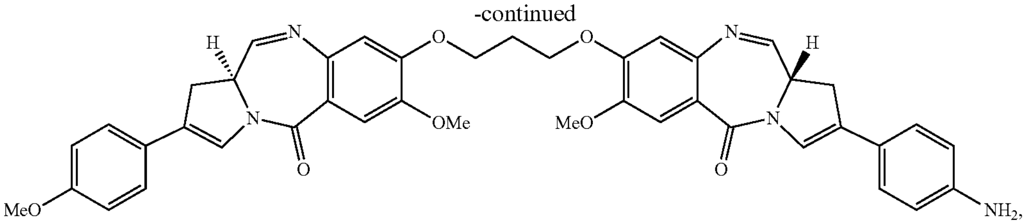

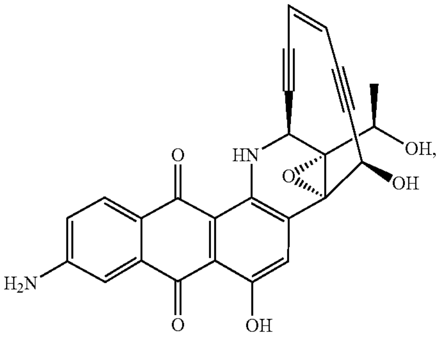

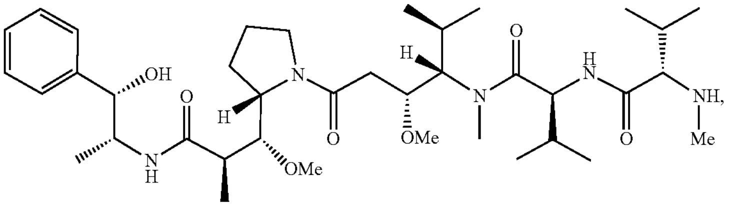

or

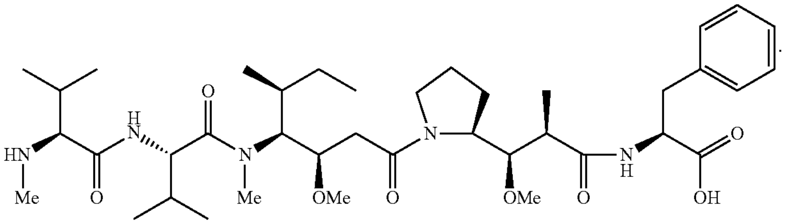

The functional group at which conjugation is effected is the amine (—$NH_2$) group in the case of the first five drugs above and the methyl amine (—NHMe) group in the case of the last two drugs.

To conjugate a drug to an adnectin, a linker group is needed. The drug is combined with the linker to form a drug-linker compound, which is then conjugated to the adnectin. A drug-linker compound can be represented by formula (I)

(I)

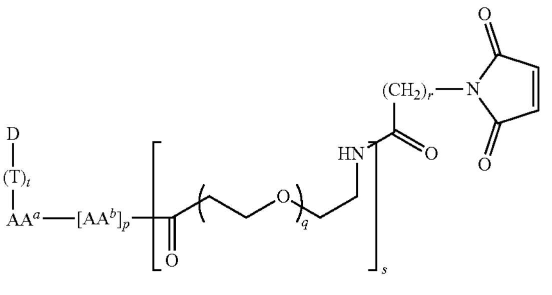

wherein

D is a drug;

T is a self-immolating group;

t is 0 or 1;

$AA^a$ and each $AA^b$ are independently selected from the group consisting of alanine, β-alanine, γ-aminobutyric acid, arginine, asparagine, aspartic acid, γ-carboxyglutamic acid, citrulline, cysteine, glutamic acid, glutamine, glycine, histidine, isoleucine, leucine, lysine, methionine, norleucine, norvaline, ornithine, phenylalanine, proline, serine, threonine, tryptophan, tyrosine, and valine;

p is 1, 2, 3, or 4;

q is 2, 3, 4, 5, 6, 7, 8, 9, or 10;

r is 1, 2, 3, 4, or 5; and s is 0 or 1.

In formula II, $-AA^a-[AA^b]_p-$ represents a polypeptide whose length is determined by the value of p (dipeptide if p is 1, tetrapeptide if p is 3, etc.). $AA^a$ is at the carboxy terminus of the polypeptide and its carboxyl group forms a peptide (amide) bond with an amine nitrogen of drug D (or self-immolating group T, if present). Conversely, the last $AA^b$ is at the amino terminus of the polypeptide and its α-amino group forms a peptide bond with

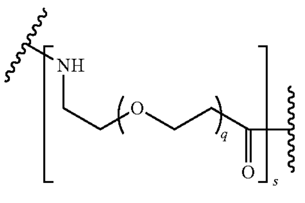
or
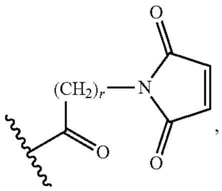
, depending on whether s is 1 or 0, respectively. Preferred polypeptides -$AA^a$-$[AA^b]_p$- are Val-Cit, Val-Lys, Lys-Val-Ala, Asp-Val-Ala, Val-Ala, Lys-Val-Cit, Ala-Val-Cit, Val-Gly, Val-Gln, and Asp-Val-Cit, written in the conventional N-to-C direction, as in $H_2N$-Val-Cit-$CO_2H$). More preferably, the polypeptide is Val-Cit, Val-Lys, or Val-Ala. Preferably, a polypeptide -$AA^a$-$[AA^b]_p$- is cleavable by an enzyme found inside the target (cancer) cell, for example a cathepsin and especially cathepsin B.

If the subscript s is 1, drug-linker (I) contains a poly (ethylene glycol) (PEG) group, which can advantageously improve the solubility of drug-linker (I), facilitating conjugation to the adnectin—a step that is performed in aqueous media. Also, a PEG group can serve as a spacer between the adnectin and the peptide -$AA^a$-$[AA^b]_p$-, so that the bulk of the adnectin does not sterically interfere with action of a peptide-cleaving enzyme.

As indicated by the subscript t equals 0 or 1, a self-immolating group T is optionally present. A self-immolating group is one such that cleavage from $AA^a$ or $AA^b$, as the case may be, initiates a reaction sequence resulting in the self-immolating group disbonding itself from drug D and freeing the latter to exert its therapeutic function. When present, the self-immolating group T preferably is a p-aminobenzyl oxycarbonyl (PABC) group, whose structure is shown below, with an asterisk (*) denoting the end of the PABC bonded to an amine nitrogen of drug D and a wavy line (~~~~) denoting the end bonded to the polypeptide

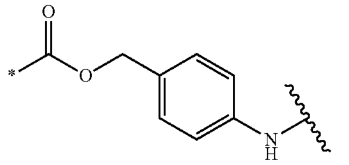 [SMILES: *Nc1ccc(COC(*)=O)cc1]

Another self-immolating group that can be used is a substituted thiazole, as disclosed in Feng, U.S. Pat. No. 7,375,078 B2 (2008).

The maleimide group in formula (I) serves as a reactive functional group for attachment to the adnectin via a Michael addition reaction by a sulfhydryl group on the adnectin, as shown below:

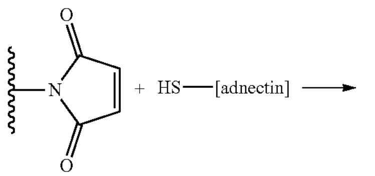

-continued

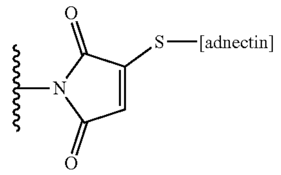
.

Alternatively, an ε-amino group in the side chain of a lysine residue of the adnectin can be reacted with 2-iminothiolane to introduce a free thiol (—SH) group. The thiol group can react with the maleimide group in drug-linker (I) to effect conjugation:

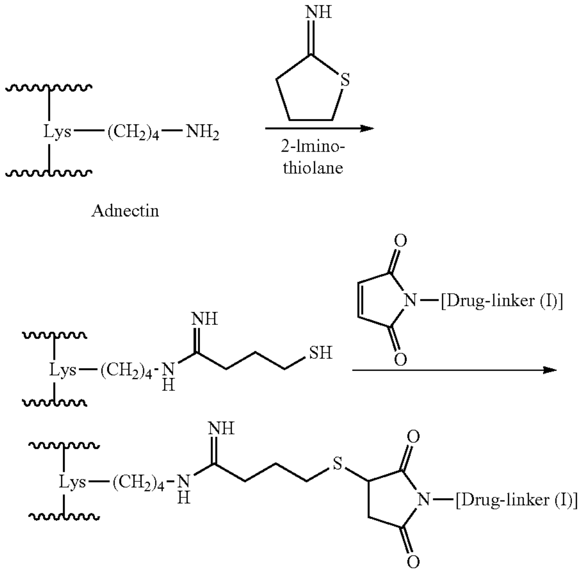

Adnectin Conjugate

Conjugation by this latter method is sometimes referred to as "random conjugation," as the number and position of the lysine residues modified by the iminothiolane is difficult to predict.

In certain embodiments, the therapeutic agent in an FBS drug conjugate, e.g., AdxDC, is tubulysin or tubulysin analog. Tubulysins belong to a group of naturally occurring antimitotic polypeptides and depsipeptides that includes the phomopsins, the dolastatins, and the cryptophycins (Hamel et al., Curr. Med. Chem.—Anti-Cancer Agents, 2002, 2:19-53). The tubulysins prevent the assembly of the tubulins into microtubules, causing the affected cells to accumulate in the G2/M phase and undergo apoptosis (Khalil et al., ChemBioChem 2006, 7:678-683).

In addition to the naturally occurring tubulysins, synthetic tubulysin analogs with potent cytotoxic activity which are suitable for use in the FBS scaffold drug conjugate, e.g., AdxDC, provided herein have been described, for example, in U.S. Pat. Nos. 8,394,922 and 8,980,824 (incorporated by reference herein).

In some embodiments, therapeutic agent in the AdxDC is a synthetic tubulysin analog and has a structure represented by formula (II):

(II)

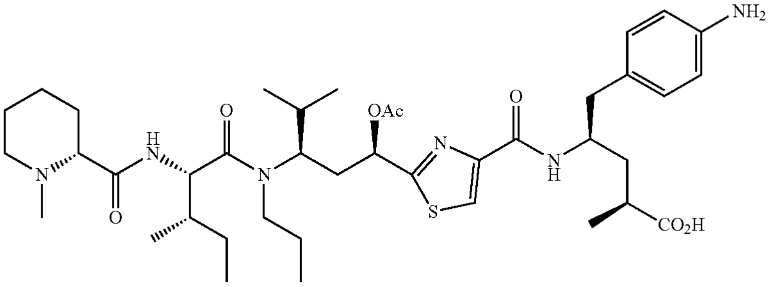

To conjugate a drug moiety, e.g., having formula II, to an FBS scaffold, e.g., an anti-GPC3 FBS scaffold, a linker moiety is used which has a structure represented by formula (III):

(III)

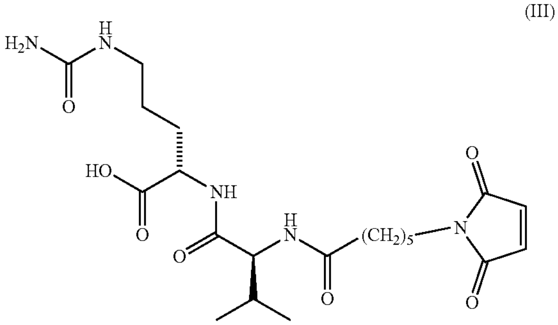

This linker moiety comprises a valine-citrulline (Val-Cit, recited in the conventional N-to-C direction) dipeptide, which is designed to be cleaved by the intracellular enzyme cathepsin B after the AdxDC has reached a target cancer cell and has been internalized by it, thus releasing the therapeutic agent to exert its cytotoxic effect (Dubowchik et al., Biorg. Med. Chem Lett., 1998, 8:3341-3346; Dubowchik et al., Biorg. Med. Chem Lett., 1998, 8:3347-3352; Dubowchik et al., Bioconjugate Chem., 2002, 13:855-869).

Drug (II) and linker (III) are coupled to produce a drug-linker compound having a structure represented by formula (IV), which is then conjugated to the adnectin. The preparation of drug-linker (IV) is described in Cheng et al., U.S. Pat. No. 8,394,922 B2 (2013) (see, e.g., FIG. 20*b* and Example 22), the disclosure of which is incorporated herein. Those skilled in the art will appreciate that, in the instance of drug-linker (IV), neither of a optional self-immolating group or a PEG group are present, but that such groups can be incorporated if desired.

In the preparation of an AdxDC conjugate, a therapeutic agent-linker compound having a structure represented by formula (IV) is prepared, which is then conjugated to the FBS scaffold.

(IV)

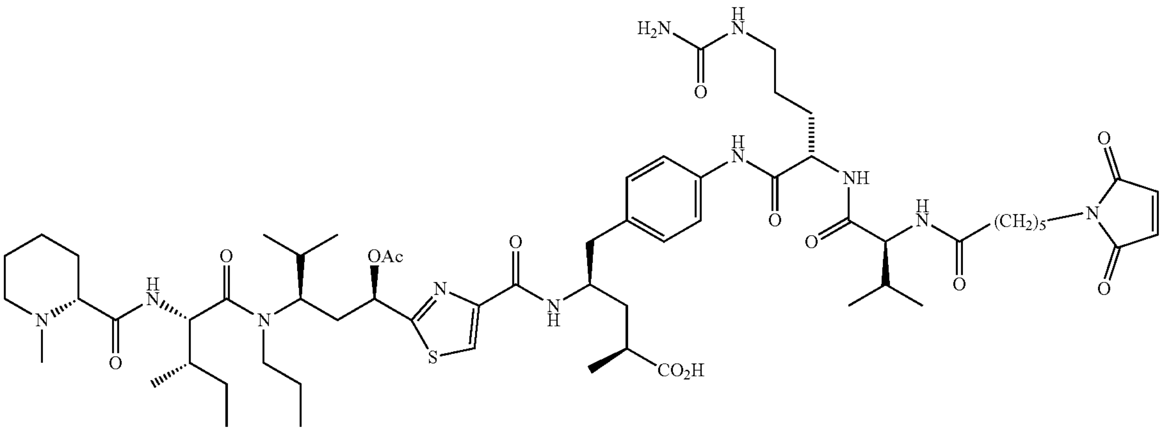

In some embodiments, the FBS-drug conjugate has a structure represented by formula (V).

(V)

(I)

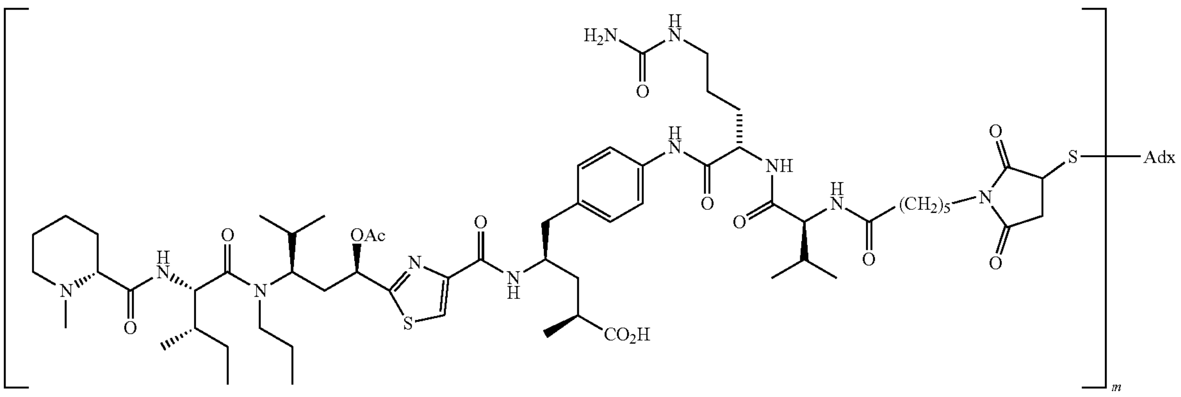

wherein m is 1, 2, 3, 4 or more. In certain embodiments, m is 1. In other embodiments, m is 2.

In one embodiment, a thiol group in the side chain of a C-terminal cysteine residue of the anti-GPC3 Adnectin (Adx) is reacted with the maleimide group in compound (V) to effect conjugation:

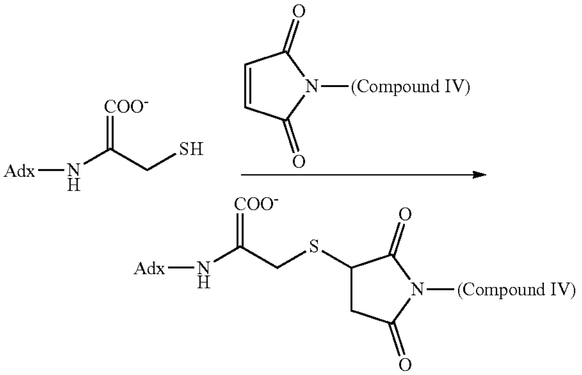

AdxDC DAR1

Figure 2B:
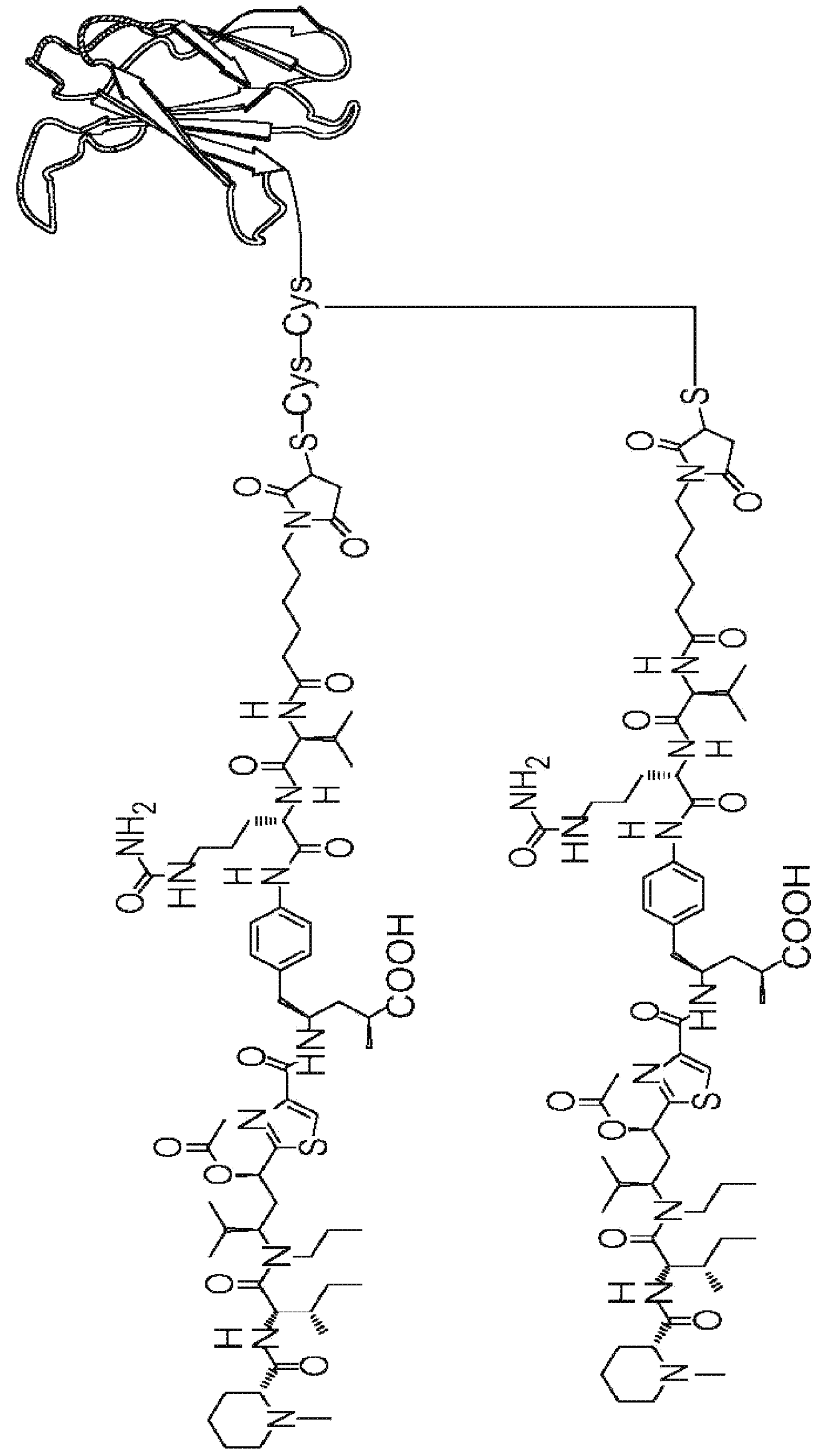
Figure 3A:
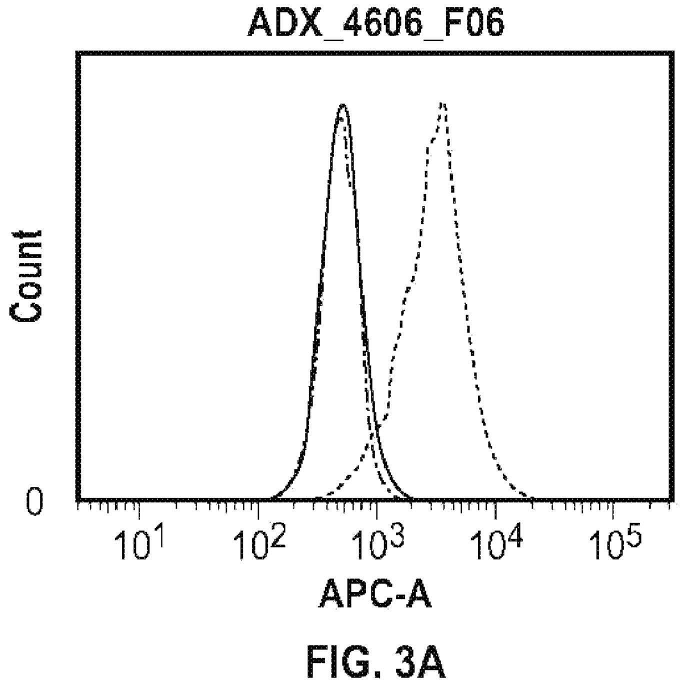
FIGS. 3A-3D show flow cytometry results of anti-GPC3 Adnectins binding to human Glypican-3 positive cells.
Figure 3B:
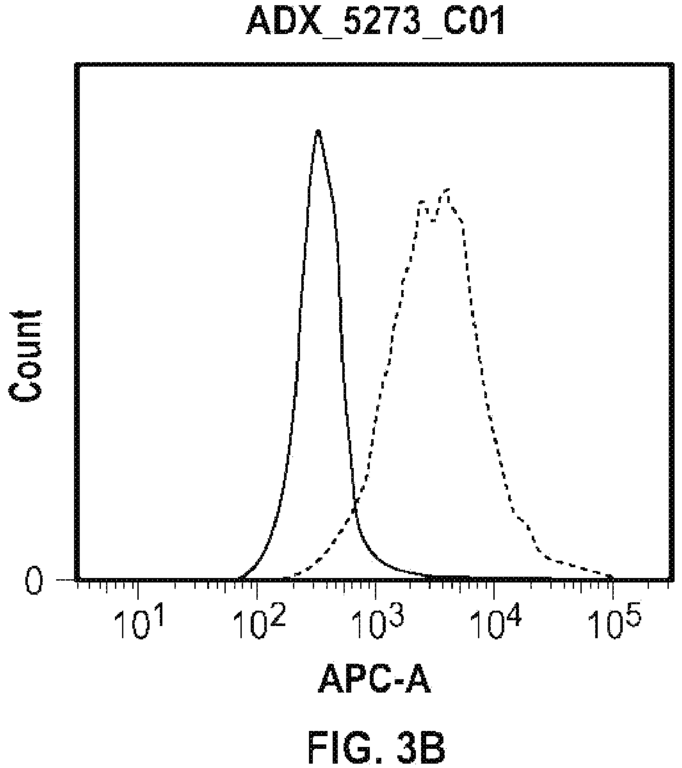
Figure 3C:
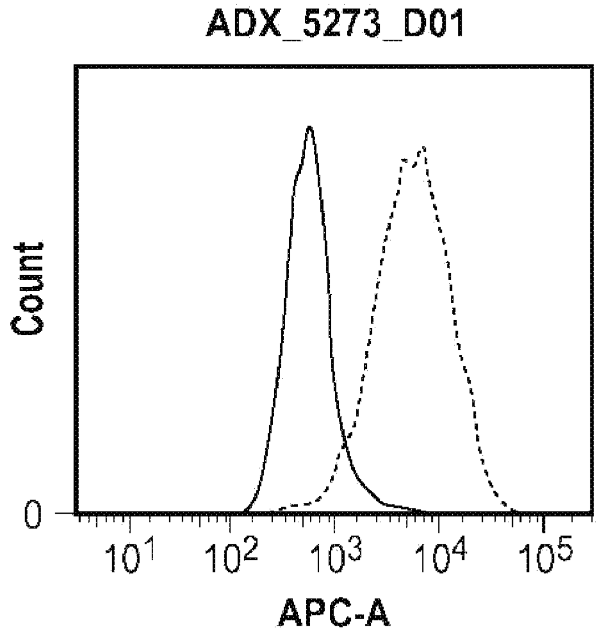
Figure 3D:
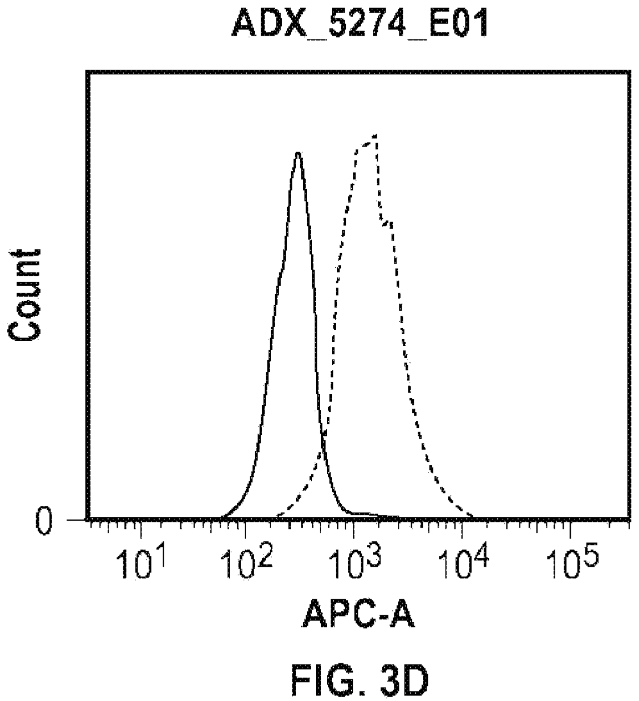
Figure 4A:
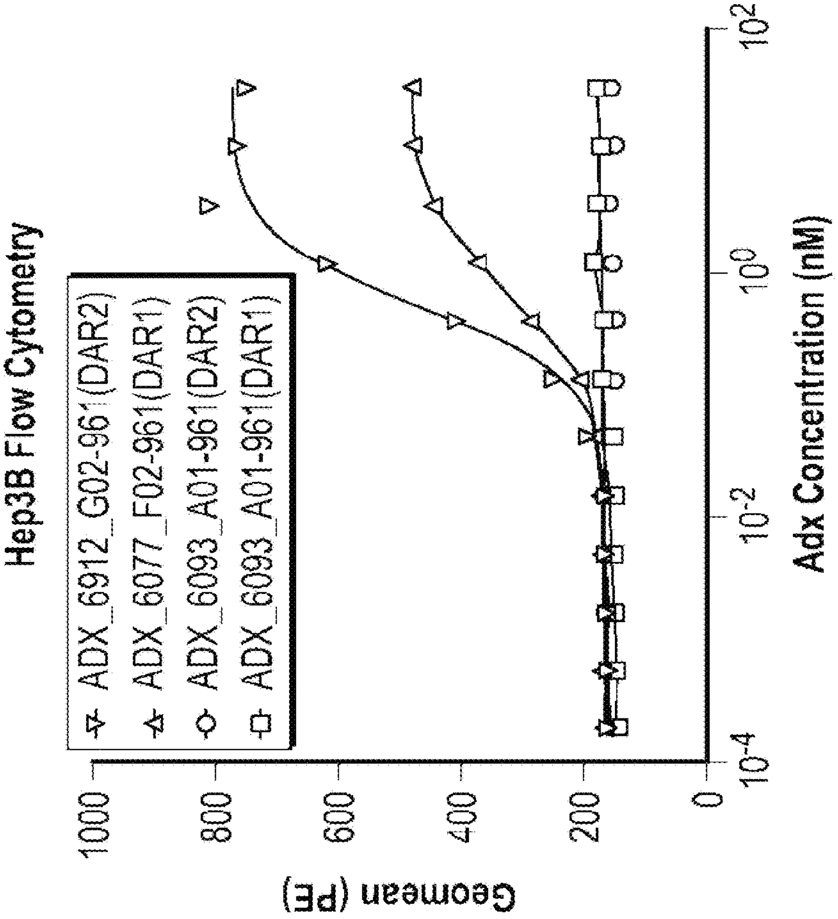
FIGS. 4A and 4B show flow cytometry results of anti-GPC3 AdxDC DAR1 and DAR2 binding to human Hep3B and H446 cells.
Figure 4B:
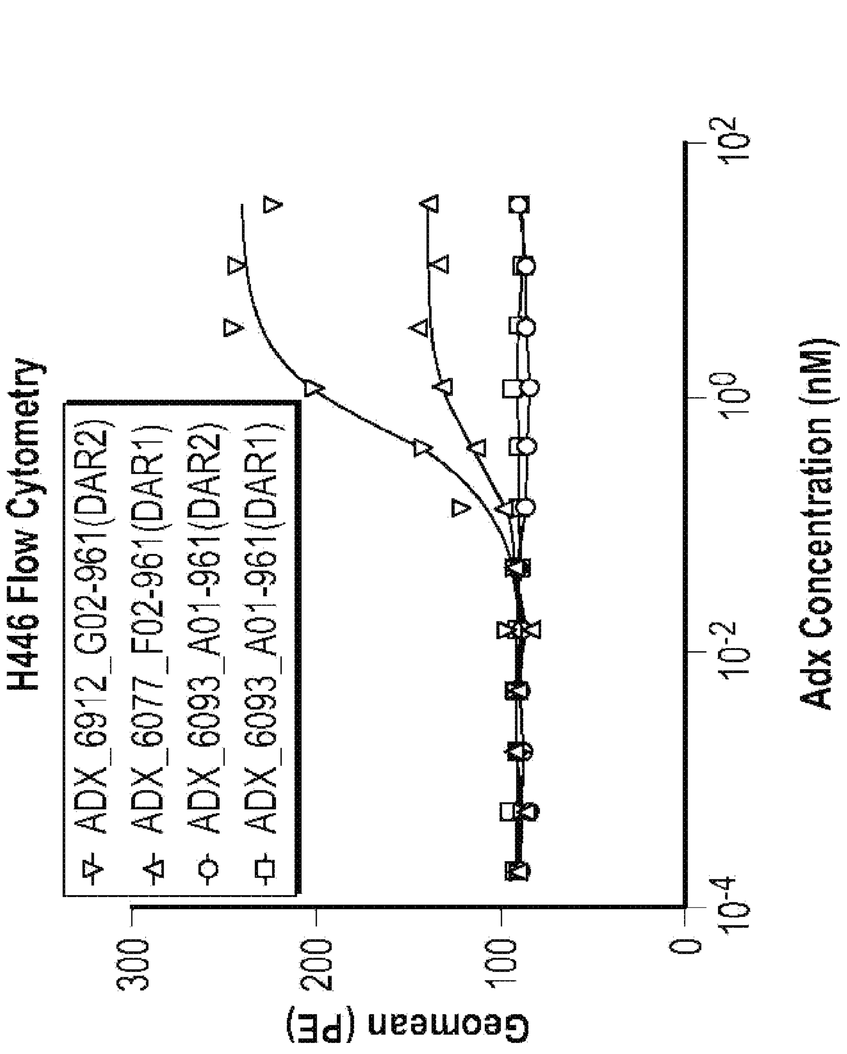
Figure 5A:
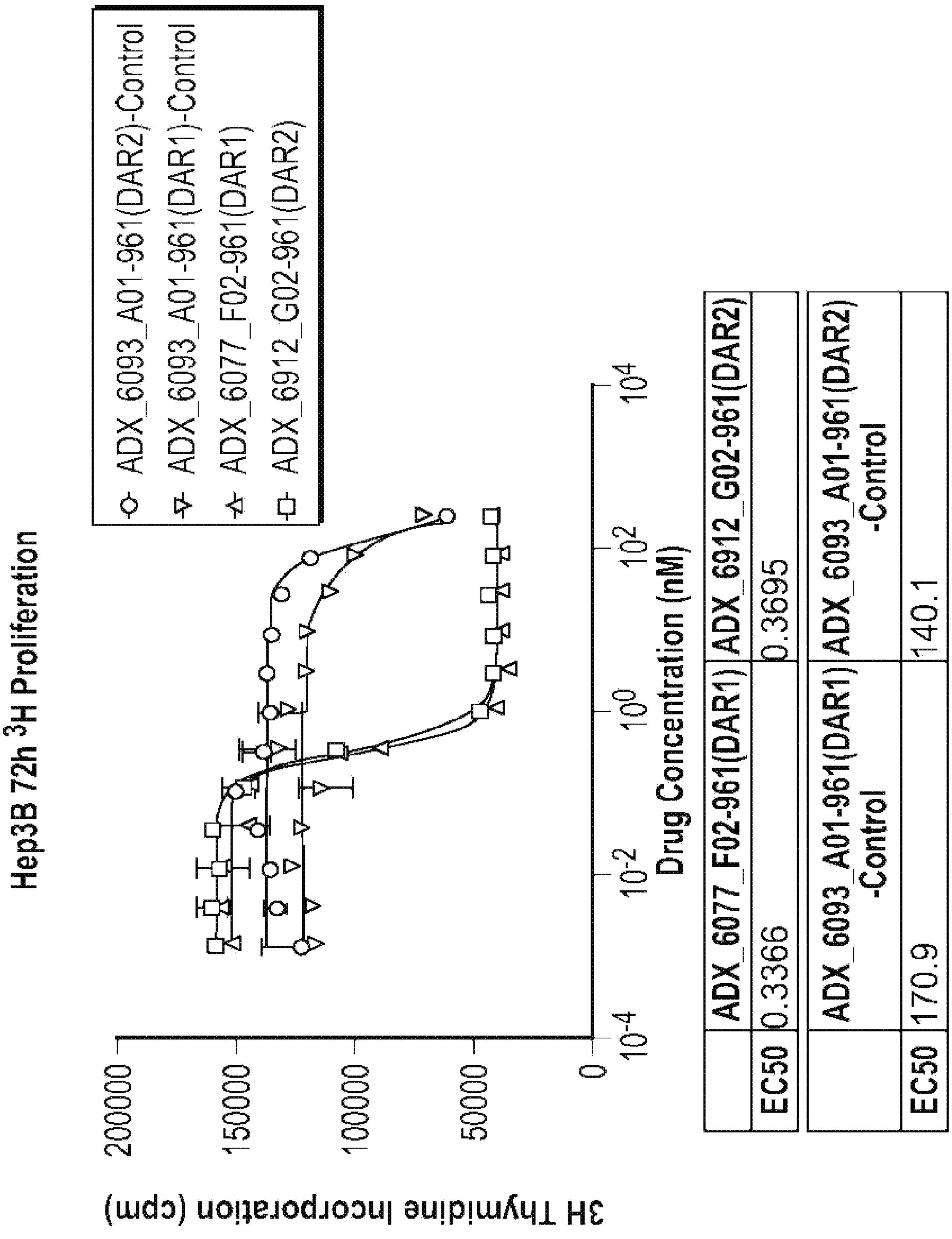
FIGS. 5A and 5B show cell growth inhibition of Hep3B and H446 cells by anti-GPC3 AdxDC DAR1 and DAR2.
Figure 5B:
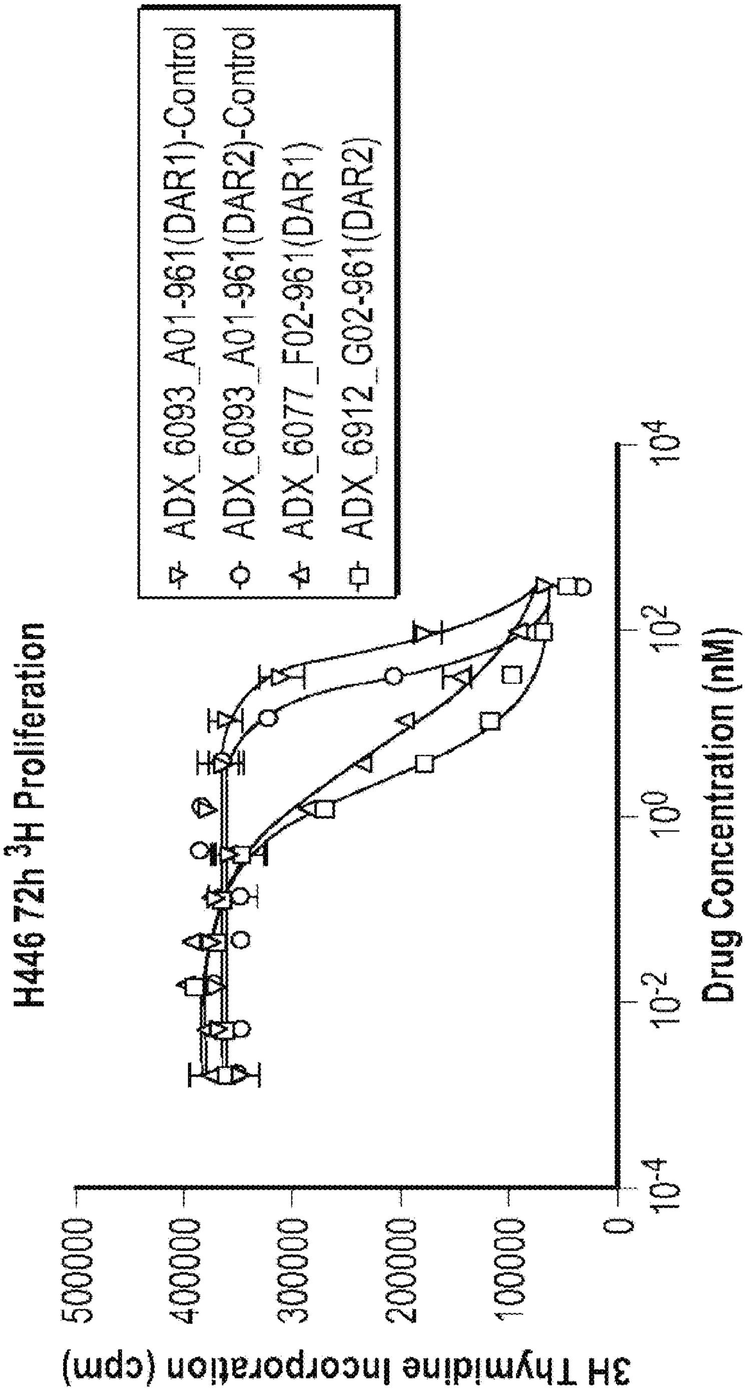
Figure 6A:
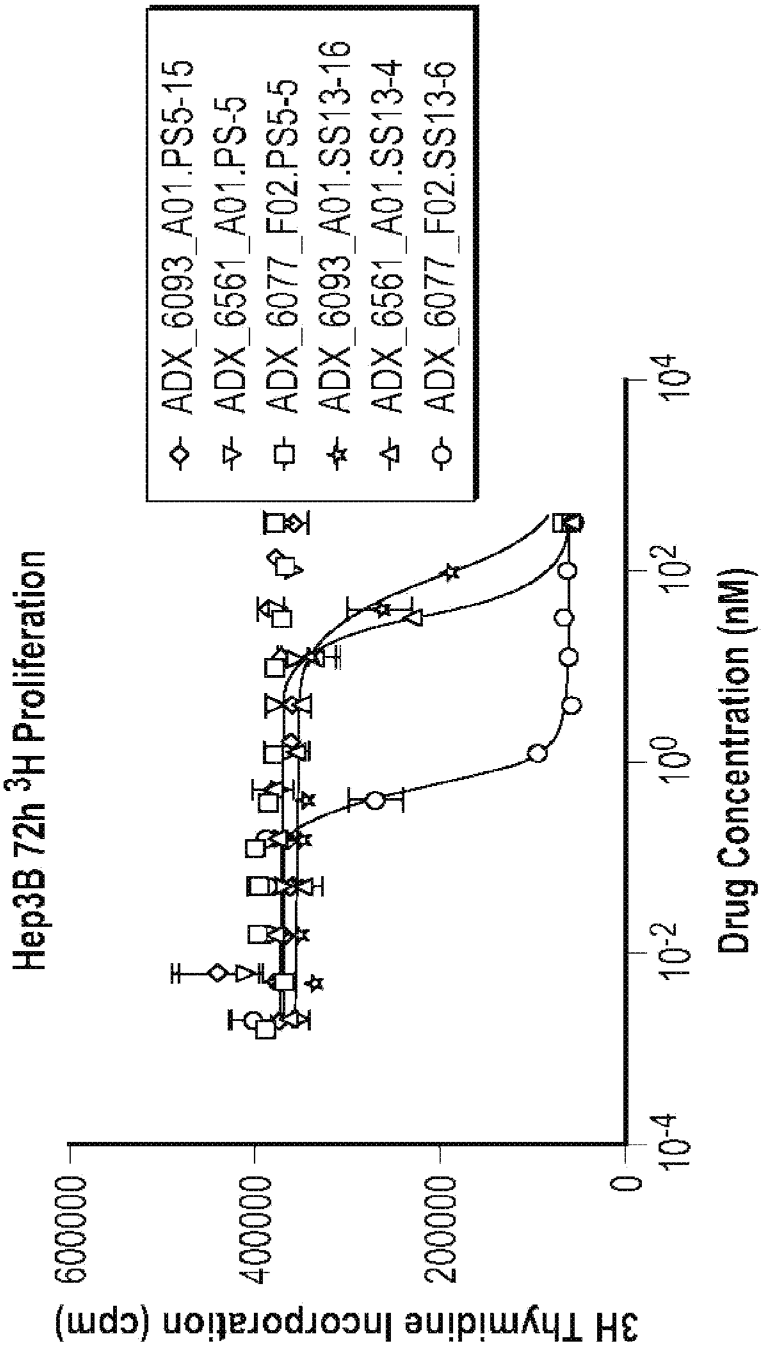
FIGS. 6A and 6B show cell growth inhibition of Hep3B and HepG2 cells by anti-GPC3 AdxDC DAR1 and DAR2.
Figure 6B:
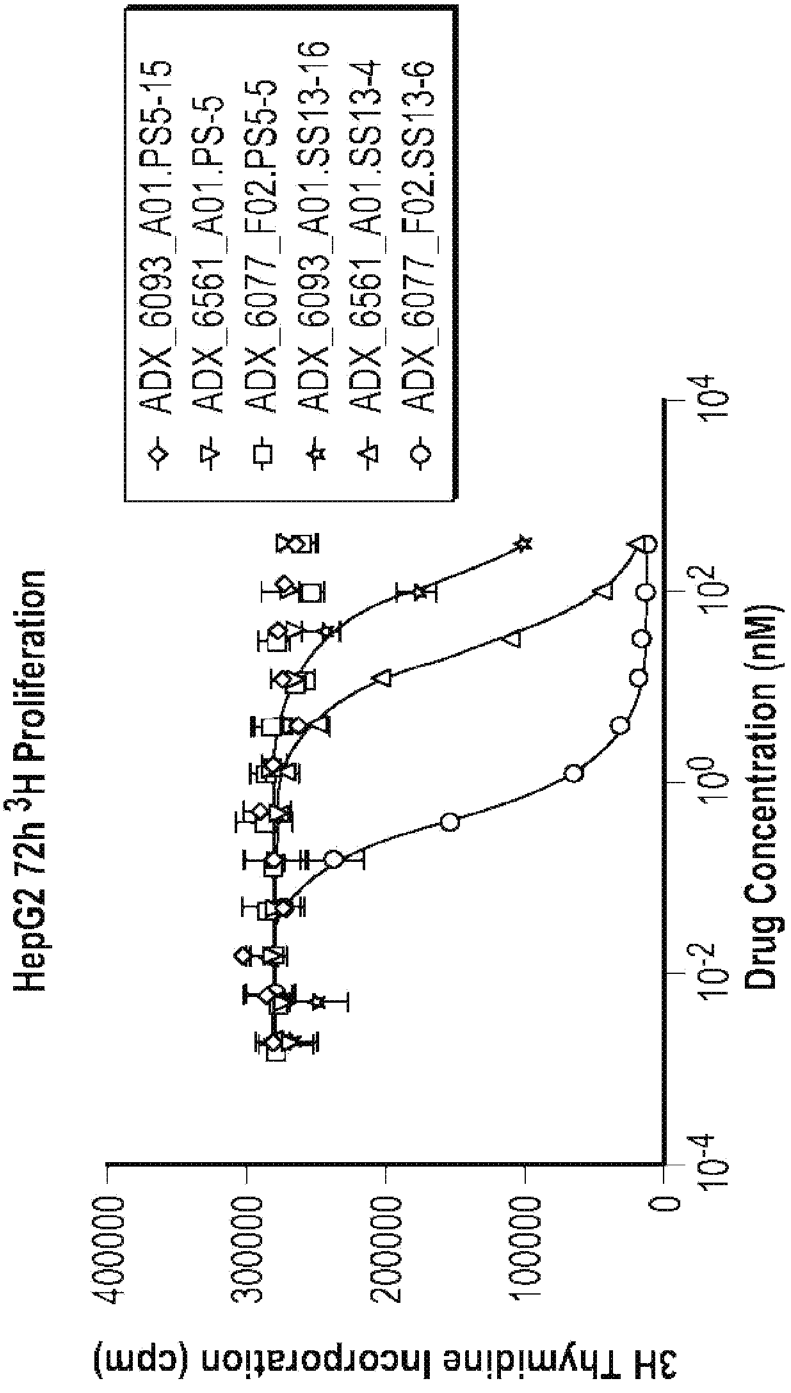

In another embodiment, the thiol groups of two cysteines located at the C-terminus of the anti-GPC3 Adnectin (Adx) is reacted with the maleimide group in compound (IV) to effect conjugation of two drug molecules per Adnectin (e.g., DAR2, FIG. 2).

In some embodiments, the anti-GPC3Adx in the conjugate has an amino acid sequence as described above in Section IA which has been modified to contain a C-terminal tail comprising a cysteine. In some embodiments, the anti-GPC3Adx comprises a core amino acid sequence selected from the group consisting of SEQ ID NOs: 5, 9-10, 18, 22-23, 31, 35-3644, 48-49, 57, 61-62, 70, 74-75, 83, 87-88, 98, 102-105, 128, 130-132, 155, 157-159, 180, 184-186, 20-, 211-213, 236, 238-240, 263, 265-267, 290, 292-294, 317 and 319-321, which is modified to contain a C-terminal moiety comprising a cysteine.

In some embodiments, the anti-GPC3Adx has been modified to contain a C-terminal moiety consisting $P_mCX_n$ or $P_mCX_{n1}CX_{n2}$, as defined herein. In certain embodiments, the C-terminal moiety consists of PC, PCC or any one of the C-terminal sequences described herein, e.g., amino acid sequences set forth in SEQ ID NOs: 409-423. In certain embodiments, the C-terminal moiety consists of PC or PCPPPPPC (SEQ ID NO: 416).

In certain embodiments, the modified anti-GPC3 Adx comprises a C-terminal moiety consisting of $P_mCX_n$, and is selected from the group consisting of SEQ ID NOs: 11-14, 24-27, 37-40, 50-53, 63-66, 76-79, 89-93, 106-118, 133-145, 160-172, 187-199, 214-226, 241-253, 268-280, 295-307, and 322-334.

In certain embodiments, the modified anti-GPC3 Adx comprises a C-terminal moiety consisting of $P_mCX_{n1}CX_{n2}$, and is selected from the group consisting of SEQ ID NOs: 15-17, 28-30, 41-43, 54-57, 67-70, 80-83, 94-97, 119-127, 146-154, 173-181, 200-208, 227-235, 254-262, 281-289, 308-316, and 335-343.

In particular embodiments, the anti-GPC3 Adx for use in the drug conjugate is any one of SEQ ID NOs: 114-118; 123-127; 141-145; 150-154; 168-172; 177-181; 195-199; 204-208; 222-226; 231-235; 249-253; 258-262; 276-280; 285-289; 303-307; 312-316; 330-334; and 339-343.

Anti-GPC3 Adnectins described herein also can be conjugated to a radioactive isotope to generate cytotoxic radiopharmaceuticals. Examples of radioactive isotopes that can be conjugated to antibodies for use diagnostically or therapeutically include, but are not limited to, iodine$^{131}$, indium$^{111}$, yttrium$^{90}$ and lutetium$^{177}$. Methods for preparing radioconjugates are established in the art.

VIII. Pharmaceutical Compositions

Also provided are pharmaceutically acceptable compositions comprising the anti-GPC3 Adnectins and conjugates described herein, wherein the composition is essentially endotoxin and/or pyrogen free.

Methods well known in the art for making formulations are found, for example, in “Remington: The Science and Practice of Pharmacy” (20th ed., ed. A. R. Gennaro A R., 2000, Lippincott Williams & Wilkins, Philadelphia, Pa.). Formulations for parenteral administration may, for example, contain excipients, sterile water, saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, liposomes) may be used to control the biodistribution of the compounds. Other potentially useful parenteral delivery systems include ethylene-vinyl acetate copolymer particles, osmotic pumps, implantable infusion systems, and liposomes. The concentration of the compound in the formulation varies depending upon a number of factors, including the dosage of the drug to be administered, and the route of administration.

Therapeutic formulations comprising proteins are prepared for storage by mixing the described proteins having the desired degree of purity with optional physiologically acceptable carriers, excipients or stabilizers (Osol, A., ed., *Remington's Pharmaceutical Sciences,* 16th Edition (1980)), in the form of aqueous solutions, lyophilized or other dried formulations. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyidimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as Tween, PLURONIC® or polyethylene glycol (PEG).

The polypeptide may be optionally administered as a pharmaceutically acceptable salt, such as non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include zinc, iron, and the like. In one example, the polypeptide is formulated in the presence of sodium acetate to increase thermal stability.

The formulations herein may also contain more than one active compounds as necessary for the particular indication being treated, preferably those with complementary activities that do not adversely affect each other. Such molecules are suitably present in combination in amounts that are effective for the purpose intended.

The proteins may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Osol, A., ed., *Remington's Pharmaceutical Sciences,* 16th Edition (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the proteins described herein, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT® (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

For therapeutic applications, the proteins are administered to a subject, in a pharmaceutically acceptable dosage form. They can be administered intravenously as a bolus or by continuous in over a period of time, by intramuscular, subcutaneous, intra-articular, intrasynovial, intrathecal, oral, topical, or inhalation routes. The protein may also be administered by intratumoral, peritumoral, intralesional, or perilesional routes, to exert local as well as systemic therapeutic effects. Suitable pharmaceutically acceptable carriers, diluents, and excipients are well known and can be determined by those of skill in the art as the clinical situation warrants. Examples of suitable carriers, diluents and/or excipients include: (1) Dulbecco's phosphate buffered saline, pH about 7.4, containing about 1 mg/ml to 25 mg/ml human serum albumin, (2) 0.9% saline (0.9% w/v NaCl), and (3) 5% (w/v) dextrose. The methods of the present invention can be practiced in vitro, in vivo, or ex vivo.

Administration of proteins, and one or more additional therapeutic agents, whether co-administered or administered sequentially, may occur as described above for therapeutic applications. Suitable pharmaceutically acceptable carriers, diluents, and excipients for co-administration will be understood by the skilled artisan to depend on the identity of the particular therapeutic agent being co-administered.

When present in an aqueous dosage form, rather than being lyophilized, the protein typically will be formulated at a concentration of about 0.1 mg/ml to 100 mg/ml, although wide variation outside of these ranges is permitted. For the treatment of disease, the appropriate dosage of proteins will depend on the type of disease to be treated, the severity and course of the disease, whether the proteins are administered for preventive or therapeutic purposes, the course of previous therapy, the patient's clinical history and response to the fusion, and the discretion of the attending physician. The protein is suitably administered to the patient at one time or over a series of treatments.

A therapeutically effective dose refers to a dose that produces the therapeutic effects for which it is administered. The exact dose will depend on the disorder to be treated, and may be ascertained by one skilled in the art using known techniques. Preferred dosages can range from about 10 mg/square meter to about 2000 mg/square meter, more preferably from about 50 mg/square meter to about 1000 mg/square meter. In some embodiments, the anti-GPC3Adnectin or anti-GPC3 AdxDC is administered at about 0.01 μg/kg to about 50 mg/kg per day, 0.01 mg/kg to about 30 mg/kg per day, or 0.1 mg/kg to about 20 mg/kg per day.

The anti-GPC3Adnectin or anti-GPC3 AdxDC may be given daily (e.g., once, twice, three times, or four times daily) or less frequently (e.g., once every other day, once or twice weekly, once every two weeks, once every three weeks or monthly). In addition, as is known in the art, adjustments for age as well as the body weight, general health, sex, diet, time of administration, drug interaction, and the severity of the disease may be necessary, and will be ascertainable with routine experimentation by those skilled in the art.

IX. Therapeutic Methods

The anti-GPC3 Adnectins and drug conjugates thereof described herein are suitable for use in the treatment of a cancers having tumor cells expressing GPC3, e.g., high levels of GPC3, e.g., relative to healthy tissues. In some embodiments, the cancer is selected from the group consisting of liver cancer (e.g., hepatocellular carcinoma (HCC) or hepatoblastoma), melanoma, sarcoma, lung cancer (e.g., squamous lung cancer) and Wilm's tumor. Additionally, the GPC3 Adnectins described herein are suitable for use in treating refractory or recurrent malignancies.

As used herein, the term "subject" is intended to include human and non-human animals. Preferred subjects include human patients having disorders mediated by GPC3 activity or undesirable cells expressing high levels of GPC3. When anti-GPC3 Adnectins or drug conjugates thereof are administered together with another agent, the two can be administered in either order or simultaneously.

For example, the anti-GPC3 Adnectins, multispecific or bispecific molecules and the drug conjugates thereof can be used to elicit in vivo or in vitro one or more of the following biological activities: to inhibit the growth of and/or kill a cell expressing GPC3; to mediate phagocytosis or ADCC of a cell expressing GPC3 in the presence of human effector cells, or to potentially modulate GPC3 activity, e.g., by blocking a GPC3 ligand from binding to GPC3.

In certain embodiments, the anti-GPC3 Adnectins or anti-GPC3 AdxDC described herein are combined with an immunogenic agent, for example, a preparation of cancerous cells, purified tumor antigens (including recombinant proteins, peptides, and carbohydrate molecules), antigen-presenting cells such as dendritic cells bearing tumor-associated antigens, and cells transfected with genes encoding immune stimulating cytokines (He et ah, 2004). Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF. GPC3 blockade may also be effectively combined with standard cancer treatments, including chemotherapeutic regimes, radiation, surgery, hormone deprivation and angiogenesis inhibitors, as well as another immunotherapeutic agent (e.g., an anti-PD-1, anti-CTLA-4, and anti-LAG-3 Adnectins or antibodies).

Provided herein are methods of combination therapy in which an anti-GPC3 Adnectin and/or or anti-GPC3 AdxDC is administered (simultaneously or successively) with one or more additional agents, e g, small molecule drugs, antibodies or antigen binding portions thereof, that are effective in stimulating immune responses to thereby enhance, stimulate or upregulate immune responses in a subject.

Generally, an anti-GPC3 Adnectin or or anti-GPC3 AdxDC, e.g., described herein, can be combined with an immuno-oncology agent, e.g., (i) an agonist of a stimulatory (e.g., co-stimulatory) molecule (e.g., receptor or ligand) and/or (ii) an antagonist of an inhibitory signal or molecule (e.g., receptor or ligand) on immune cells, such as T cells, both of which result in amplifying immune responses, such as antigen-specific T cell responses. In certain aspects, an immuno-oncology agent is (i) an agonist of a stimulatory (including a co-stimulatory) molecule (e.g., receptor or ligand) or (ii) an antagonist of an inhibitory (including a co-inhibitory) molecule (e.g., receptor or ligand) on cells involved in innate immunity, e.g., NK cells, and wherein the immuno-oncology agent enhances innate immunity Such immuno-oncology agents are often referred to as immune checkpoint regulators, e.g., immune checkpoint inhibitor or immune checkpoint stimulator.

In certain embodiments, a anti-GPC3 Adnectin or anti-GPC3 AdxDC is administered with an agent that targets a stimulatory or inhibitory molecule that is a member of the immunoglobulin super family (IgSF). For example, anti-GPC3 Adnectins and or anti-GPC3 AdxDCs, e.g., described herein, may be administered to a subject with an agent that targets a member of the IgSF family to increase an immune response. For example, a anti-GPC3 Adnectin or anti-GPC3 AdxDC may be administered with an agent that targets (or binds specifically to) a member of the B7 family of membrane-bound ligands that includes B7-1, B7-2, B7-H1 (PD-L1), B7-DC (PD-L2), B7-H2 (ICOS-L), B7-H3, B7-H4, B7-H5 (VISTA), and B7-H6 or a co-stimulatory or co-inhibitory receptor binding specifically to a B7 family member.

An anti-GPC3 Adnectin or anti-GPC3 AdxDC may also be administered with an agent that targets a member of the TNF and TNFR family of molecules (ligands or receptors), such as CD40 and CD40L, OX-40, GITR, GITRL, OX-40L, CD70, CD27L, CD30, CD30L, 4-1BBL, CD137, TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDA1, EDA2, TNFR1, Lymphotoxin α/TNFβ, TNFR2, TNFα, LTβR, Lymphotoxin α1β2, FAS, FASL, RELT, DR6, TROY, and NGFR (see, e.g., Tansey (2009) Drug Discovery Today 00:1).

T cell responses can be stimulated by administering one or more of the following agents:

(1) An antagonist (inhibitor or blocking agent) of a protein that inhibits T cell activation (e.g., immune checkpoint inhibitors), such as CTLA-4, PD-1, PD-L1, PD-L2, and LAG-3, as described above, and any of the following proteins: TIM-3, Galectin 9, CEACAM-1, BTLA, CD69, Galectin-1, TIGIT, CD113, GPR56, VISTA, B7-H3, B7-H4, 2B4, CD48, GARP, PD1H, LAIR1, TIM-1, and TIM-4; and/or (2) An agonist of a protein that stimulates T cell activation, such as B7-1, B7-2, CD28, 4-1BB (CD137), 4-1BBL, ICOS, ICOS-L, OX40, OX40L, GITR, GITRL, CD70, CD27, CD40, DR3 and CD28H.

Exemplary agents that modulate one of the above proteins and may be combined with anti-GPC3 Adnectins and/or or anti-GPC3 AdxDCs, e.g., those described herein, for treating cancer, include: Yervoy™ (ipilimumab) or Tremelimumab (to CTLA-4), galiximab (to B7.1), BMS-936558 (to PD-1), MK-3475 (to PD-1), AMP224 (to B7DC), BMS-936559 (to B7-H1), MPDL3280A (to B7-H1), MEDI-570 (to ICOS), AMG557 (to B7H2), MGA271 (to B7H3), IMP321 (to LAG-3), BMS-663513 (to CD137), PF-05082566 (to CD137), CDX-1127 (to CD27), anti-OX40 (Providence Health Services), huMAbOX40L (to OX40L), Atacicept (to TACI), CP-870893 (to CD40), Lucatumumab (to CD40), Dacetuzumab (to CD40), Muromonab-CD3 (to CD3), Ipilumumab (to CTLA-4) and/or MK4166.

Anti-GPC3 Adnectins or anti-GPC3 AdxDC may also be administered with pidilizumab (CT-011), although its specificity for PD-1 binding has been questioned.

Other molecules that can be combined with anti-GPC3 Adnectins or anti-GPC3 AdxDCs for the treatment of cancer include antagonists of inhibitory receptors on NK cells or agonists of activating receptors on NK cells. For example, anti-GITR agonist antibodies can be combined with antagonists of KIR (e.g., lirilumab).

T cell activation is also regulated by soluble cytokines, and anti GPC3 Adnectins or or anti-GPC3 AdxDCs may be administered to a subject, e.g., having cancer, with antagonists of cytokines that inhibit T cell activation or agonists of cytokines that stimulate T cell activation.

In certain embodiments, anti-GPC3 Adnectins or or anti-GPC3 AdxDCs can be used in combination with (i) antagonists (or inhibitors or blocking agents) of proteins of the IgSF family or B7 family or the TNF family that inhibit T cell activation or antagonists of cytokines that inhibit T cell activation (e.g., IL-6, IL-10, TGF-ß, VEGF; "immunosuppressive cytokines") and/or (ii) agonists of stimulatory receptors of the IgSF family, B7 family or the TNF family or of cytokines that stimulate T cell activation, for stimulating an immune response, e.g., for treating proliferative diseases, such as cancer.

Yet other agents for combination therapies include agents that inhibit or deplete macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

Anti-GPC3 Adnectins or anti-GPC3 AdxDCs may also be administered with agents that inhibit TGF-β signaling.

Additional agents that may be combined with an anti-GPC3 Adnectin and or anti-GPC3 AdxDCs include agents that enhance tumor antigen presentation, e.g., dendritic cell vaccines, GM-CSF secreting cellular vaccines, CpG oligonucleotides, and imiquimod, or therapies that enhance the immunogenicity of tumor cells (e.g., anthracyclines).

Yet other therapies that may be combined with an anti-GPC3 Adnectin or anti-GPC3 AdxDC include therapies that deplete or block Treg cells, e.g., an agent that specifically binds to CD25.

Another therapy that may be combined with an anti-GPC3 Adnectin or anti-GPC3 AdxDC is a therapy that inhibits a metabolic enzyme such as indoleamine dioxigenase (IDO), dioxigenase, arginase, or nitric oxide synthetase.

Another class of agents that may be used with a anti-GPC3 Adnectin or or anti-GPC3 AdxDC includes agents that inhibit the formation of adenosine or inhibit the adenosine A2A receptor.

Other therapies that may be combined with a anti-GPC3 Adnectin or or anti-GPC3 AdxDC for treating cancer include therapies that reverse/prevent T cell anergy or exhaustion and therapies that trigger an innate immune activation and/or inflammation at a tumor site.

An anti-GPC3 Adnectin or anti-GPC3 AdxDC may be combined with more than one immuno-oncology agent, and may be, e.g., combined with a combinatorial approach that targets multiple elements of the immune pathway, such as one or more of the following: a therapy that enhances tumor antigen presentation (e.g., dendritic cell vaccine, GM-CSF secreting cellular vaccines, CpG oligonucleotides, imiquimod); a therapy that inhibits negative immune regulation e.g., by inhibiting CTLA-4 and/or PD1/PD-L1/PD-L2 pathway and/or depleting or blocking Tregs or other immune suppressing cells; a therapy that stimulates positive immune regulation, e.g., with agonists that stimulate the CD-137, OX-40, and/or GITR pathway and/or stimulate T cell effector function; a therapy that increases systemically the frequency of anti-tumor T cells; a therapy that depletes or inhibits Tregs, such as Tregs in the tumor, e.g., using an antagonist of CD25 (e.g., daclizumab) or by ex vivo anti-CD25 bead depletion; a therapy that impacts the function of suppressor myeloid cells in the tumor; a therapy that enhances immunogenicity of tumor cells (e.g., anthracyclines); adoptive T cell or NK cell transfer including genetically modified cells, e.g., cells modified by chimeric antigen receptors (CAR-T therapy); a therapy that inhibits a metabolic enzyme such as indoleamine dioxigenase (IDO), dioxigenase, arginase, or nitric oxide synthetase; a therapy that reverses/prevents T cell anergy or exhaustion; a therapy that triggers an innate immune activation and/or inflammation at a tumor site; administration of immune stimulatory cytokines; or blocking of immuno repressive cytokines.

Anti-GPC3 Adnectins and or anti-GPC3 AdxDCs described herein can be used together with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell anergy or exhaustion) and agents that trigger innate immune activation and/or inflammation at tumor sites.

Provided herein is the use of any anti-GPC3 Adnectin described herein for the preparation of a medicament for for treating subjects afflicted with cancer. The disclosure provides medical uses of any anti-GPC3 Adnectin described herein corresponding to all the embodiments of the methods of treatment employing an anti-GPC3 Adnectin described herein.

X. Detectable Labels

The anti-GPC3 Adnectins described herein also are useful in a variety of diagnostic and imaging applications. In certain embodiments, an anti-GPC3 Adnectin is labeled with a moiety that is detectable in vivo and such labeled Adnectins may be used as in vivo imaging agents, e.g., for whole body imaging. For example, in one embodiment, a method for detecting a GPC3 positive tumor in a subject comprises administering to the subject an anti-GPC3 Adnectin linked to a detectable label, and following an appropriate time, detecting the label in the subject.

An anti-GPC3 Adnectin imaging agent may be used to diagnose a disorder or disease associated with increased levels of GPC3, for example, a cancer in which a tumor selectively overexpresses GPC3. In a similar manner, an anti-GPC3 Adnectin can be used to monitor GPC3 levels in a subject, e.g., a subject that is being treated to reduce GPC3 levels and/or GPC3 positive cells (e.g., tumor cells). The anti-GPC3 Adnectins may be used with or without modification, and may be labeled by covalent or non-covalent attachment of a detectable moiety.

Detectable labels can be any of the various types used currently in the field of in vitro diagnostics, including particulate labels including metal sols such as colloidal gold, isotopes such as $I^{125}$ or $Tc^{99}$ presented for instance with a peptidic chelating agent of the $N_2S_2$, $N_3S$ or $N_4$ type, chromophores including fluorescent markers, biotin, luminescent markers, phosphorescent markers and the like, as well as enzyme labels that convert a given substrate to a detectable marker, and polynucleotide tags that are revealed following amplification such as by polymerase chain reaction. A biotinylated anti-GPC3 FBS would then be detectable by avidin or streptavidin binding. Suitable enzyme labels include horseradish peroxidase, alkaline phosphatase and the like. For instance, the label can be the enzyme alkaline phosphatase, detected by measuring the presence or formation of chemiluminescence following conversion of 1,2 dioxetane substrates such as adamantyl methoxy phosphoryloxy phenyl dioxetane (AMPPD), disodium 3-(4-(methoxyspiro{1,2-dioxetane-3,2'-(5'-chloro)tricyclo{3.3.1.1 3,7}decan}-4-yl) phenyl phosphate (CSPD), as well as CDP and CDP-STAR® or other luminescent substrates well-known to those in the art, for example the chelates of suitable lanthanides such as Terbium(III) and Europium(III).

Detectable moieties that may be used include radioactive agents, such as: radioactive heavy metals such as iron chelates, radioactive chelates of gadolinium or manganese, positron emitters of oxygen, nitrogen, iron, carbon, or gallium, $^{18}F$ $^{60}Cu$, $^{61}Cu$, $^{62}Cu$, $^{64}Cu$, $^{124}I$, $^{86}Y$, $^{89}Zr$, $^{66}Ga$, $^{67}Ga$, $^{68}Ga$, $^{44}Sc$, $^{47}SC$, $^{11}C$, $^{111}In$, $^{114m}In$, $^{114}In$, $^{125}I$, $^{124}I$, $^{131}I$, $^{123}I$, $^{131}I$, $^{123}I$, $^{32}Cl$, $^{33}Cl$, $^{34}Cl$, $^{74}Br$, $^{75}Br$, $^{76}Br$, $^{77}Br$, $^{78}Br$, $^{89}Zr$, $^{186}Re$, $^{188}Re$, $^{86}Y$, $^{90}Y$, $^{177}Lu$, $^{99}Tc$, $^{212}Bi$, $^{213}Bi$, $^{212}Pb$, $^{225}Ac$, or $^{153}Sm$.

The detection means is determined by the chosen label. Appearance of the label or its reaction products can be achieved using the naked eye, in the case where the label is particulate and accumulates at appropriate levels, or using instruments such as a spectrophotometer, a luminometer, a fluorometer, and the like, all in accordance with standard practice.

A detectable moiety may be linked to a cysteine according to methods known in the art. When the detectable moiety is a radioactive agent, e.g., those described further herein, the detectable moiety is linked to an FBS through a chelating agent that is reactive with cysteines, such as a maleimide containing chelating agent, such as maleimide-NODAGA or maleimide-DBCO. Maleimide-NODAGA or maleimide-DBCO can be reacted with a cysteine on the C-terminus of an FBS (e.g., through the PmXn moiety, wherein at least one X is a cysteine), to yield FBS-NODAGA or FBS-DBCO, respectively. Any one of the following chelating agents may be used provided that it comprises, or can be modified to comprise, a reactive moiety that reacts with cysteines: DFO, DOTA and its derivatives (CB-DO2A, 3p-C-DEPA, TCMC, Oxo-DO3A), TE2A, CB-TE2A, CB-TE1A1P, CB-TE2P, MM-TE2A, DM-TE2A, diamsar and derivatives, NODASA, NODAGA, NOTA, NETA, TACN-TM, DTPA, 1B4M-DTPA, CHX-A"-DTPA, TRAP (PRP9), NOPO, AAZTA and derivatives (DATA), $H_2$dedpa, $H_4$octapa, $H_2$azapa, $H_5$decapa, $H_6$phospa, HBED, SHBED, BPCA, CP256, PCTA, HEHA, PEPA, EDTA, TETA, and TRITA based chelating agents, and close analogs and derivatives thereof.

In certain embodiments, an FBS is labeled with a PET tracer and used as an in vivo imaging agent. For example, an FBS may be labeled with the PET tracer $^{64}Cu$. $^{64}Cu$ may be linked to an FBS with a C-terminal cysteine with a chelating agent, such as maleimide-NODAGA.

Other art-recognized methods for labelling polypeptides with radionuclides such as $^{64}Cu$ and $^{18}F$ for synthesizing the anti-GPC3 Adnectin-based imaging agents described herein may also be used. See, e.g., US2014/0271467; Gill et al., *Nature Protocols* 2011; 6:1718-25; Berndt et al. *Nuclear Medicine and Biology* 2007; 34:5-15, Inkster et al., *Bioorganic & Medicinal Chemistry Letters* 2013; 23:3920-6, the contents of which are herein incorporated by reference in their entirety.

In certain embodiments, a GPC3 imaging agent comprises a PEG molecule (e.g., 5 KDa PEG, 6KDa PEG, 7KDa PEG, 8KDa PEG, 9KDa PEG, or 10KDa PEG) to increase the blood PK of the imaging agent by small increments to enhance the imaging contrast or increase avidity of the anti-GPC3 Adnectin based imaging agent.

XI. Detection of GPC3

In Vivo Detection Methods

In certain embodiments, the labeled anti-GPC3 Adnectins can be used to image GPC3-positive cells or tissues, e.g., GPC3 expressing tumors. For example, the labeled anti-GPC3 Adnectin is administered to a subject in an amount sufficient to uptake the labeled Adnectin into the tissue of interest (e.g., the GPC3-expressing tumor). The subject is then imaged using an imaging system such as PET for an amount of time appropriate for the particular radionuclide being used. The labeled anti-GPC3 Adnectin-bound GPC3-expressing cells or tissues, e.g., GPC3-expressing tumors, are then detected by the imaging system.

PET imaging with a GPC3 imaging agent may be used to qualitatively or quantitatively detect GPC3. A GPC3 imaging agent may be used as a biomarker, and the presence or absence of a GPC3 positive signal in a subject may be indicative that, e.g., the subject would be responsive to a given therapy, e.g., a cancer therapy, or that the subject is responding or not to a therapy.

In certain embodiments, the progression or regression of disease (e.g., tumor) can be imaged as a function of time or treatment. For instance, the size of the tumor can be monitored in a subject undergoing cancer therapy (e.g., chemotherapy, radiotherapy) and the extent of regression of the tumor can be monitored in real-time based on detection of the labeled anti-GPC3 Adnectin.

The amount effective to result in uptake of the imaging agent (e.g., $^{18}F$-Adnectin imaging agent, $^{64}Cu$-Adnectin imaging agent) into the cells or tissue of interest (e.g., tumors) may depend upon a variety of factors, including for example, the age, body weight, general health, sex, and diet of the host; the time of administration; the route of administration; the rate of excretion of the specific probe employed; the duration of the treatment; the existence of other drugs used in combination or coincidental with the specific composition employed; and other factors.

In certain embodiments, imaging of tissues expressing GPC3 is effected before, during, and after administration of the labeled anti-GPC3 Adnectin.

In certain embodiments, the anti-GPC3 Adnectins described herein are useful for PET imaging of lungs, heart, kidneys, liver, and skin, and other organs, or tumors associated with these organs which express GPC3.

In certain embodiments, the anti-GPC3 imaging agents provide a contrast of at least 50%, 75%, 2, 3, 4, 5 or more. The Examples show that all anti-GPC3 Adnectins that were used provided a PET contrast of 2 or more, and that the affinity of the Adnectins was not important.

When used for imaging (e.g., PET) with short half-life radionuclides (e.g., 18F), the radiolabeled anti-GPC3 Adnectins are preferably administered intravenously. Other routes of administration are also suitable and depend on the half-life of the radionuclides used.

In certain embodiments, the anti-GPC3 imaging agents described herein are used to detect GPC3 positive cells in a subject by administering to the subject an anti-GPC3 imaging agent disclosed herein, and detecting the imaging agent, the detected imaging agent defining the location of the GPC3 positive cells in the subject. In certain embodiments, the imaging agent is detected by positron emission tomography.

In certain embodiments, the anti-GPC3 imaging agents described herein are used to detect GPC3 expressing tumors in a subject by administering to the subject an anti-GPC3 imaging agent disclosed herein, and detecting the imaging agent, the detected imaging agent defining the location of the tumor in the subject. In certain embodiments, the imaging agent is detected by positron emission tomography.

In certain embodiments, an image of an anti-GPC3 imaging agent described herein is obtained by administering the imaging agent to a subject and imaging in vivo the distribution of the imaging agent by positron emission tomography.

Accordingly, provided herein are methods of obtaining a quantitative image of tissues or cells expressing GPC3, the method comprising contacting the cells or tissue with an anti-GPC3 imaging agent described herein and detecting or quantifying the tissue expressing GPC3 using positron emission tomography.

Also provided herein are methods of detecting a GPC3-expressing tumor comprising administering an imaging-effective amount of an anti-GPC3 imaging agent described herein to a subject having a GPC3-expressing tumor, and detecting the radioactive emissions of said imaging agent in the tumor using positron emission tomography, wherein the radioactive emissions are detected in the tumor.

Also provided herein are methods of diagnosing the presence of a GPC3-expressing tumor in a subject, the method comprising administering to a subject in need thereof an anti-GPC3 imaging agent described herein; and obtaining an radio-image of at least a portion of the subject to detect the presence or absence of the imaging agent;

wherein the presence and location of the imaging agent above background is indicative of the presence and location of the disease.

Also provided herein are methods of monitoring the progress of an anti-tumor therapy against GPC3-expressing tumors in a subject, the method comprising administering to a subject in need thereof an anti-GPC3 imaging agent described herein at a first time point and obtaining an image of at least a portion of the subject to determine the size of the tumor;

administering an anti-tumor therapy to the subject;

administering to the subject the imaging agent at one or more subsequent time points and obtaining an image of at least a portion of the subject at each time point;

wherein the dimension and location of the tumor at each time point is indicative of the progress of the disease.

In Vitro Detection Methods

In addition to detecting GPC3 in vivo, anti-PDL1 Adnectins, such as those described herein, may be used for detecting a target molecule in a sample. A method may comprise contacting the sample with an anti-GPC3 Adnectins described herein, wherein said contacting is carried out under conditions that allow anti-GPC3 Adnectin-target complex formation; and detecting said complex, thereby detecting said target in said sample. Detection may be carried out using any art-recognized technique, such as, e.g., radiography, immunological assay, fluorescence detection, mass spectroscopy, or surface plasmon resonance. The sample may be from a human or other mammal. For diagnostic purposes, appropriate agents are detectable labels that include radioisotopes, for whole body imaging, and radioisotopes, enzymes, fluorescent labels and other suitable antibody tags for sample testing.

The detectable labels can be any of the various types used currently in the field of in vitro diagnostics, including particulate labels including metal sols such as colloidal gold, isotopes such as $I^{125}$ or $Tc^{99}$ presented for instance with a peptidic chelating agent of the $N_2S_2$, $N_3S$ or $N_4$ type, chromophores including fluorescent markers, biotin, luminescent markers, phosphorescent markers and the like, as well as enzyme labels that convert a given substrate to a detectable marker, and polynucleotide tags that are revealed following amplification such as by polymerase chain reaction. A biotinylated FBS would then be detectable by avidin or streptavidin binding. Suitable enzyme labels include horseradish peroxidase, alkaline phosphatase and the like. For instance, the label can be the enzyme alkaline phosphatase, detected by measuring the presence or formation of chemiluminescence following conversion of 1,2 dioxetane substrates such as adamantyl methoxy phosphoryloxy phenyl dioxetane (AMPPD), disodium 3-(4-(methoxyspiro {1,2-dioxetane-3,2'-(5'-chloro)tricyclo {3.3.1.1 3,7}decan}-4-yl) phenyl phosphate (CSPD), as well as CDP and CDP-Star® or other luminescent substrates well-known to those in the art, for example the chelates of suitable lanthanides such as Terbium(III) and Europium(III). Other labels include those set forth above in the imaging section. The detection means is determined by the chosen label. Appearance of the label or its reaction products can be achieved using the naked eye, in the case where the label is particulate and accumulates at appropriate levels, or using instruments such as a spectrophotometer, a luminometer, a fluorimeter, and the like, all in accordance with standard practice.

XII. Kits and Articles of Manufacture

The anti-GPC3 Adnectins and drug conjugates thereof described herein can be provided in a kit, a packaged combination of reagents in predetermined amounts with instructions for use in the therapeutic or diagnostic methods described herein.

For example, in certain embodiments, an article of manufacture containing materials useful for the treatment or prevention of the disorders or conditions described herein, or for use in the methods of detection described herein, are provided. The article of manufacture comprises a container and a label. Suitable containers include, for example, bottles, vials, syringes, and test tubes. The containers may be formed from a variety of materials such as glass or plastic. The container may hold a composition described herein for in vivo imaging, and may have a sterile access port (for example the container may be an intravenous solution bag or a vial having a stopper pierceable by a hypodermic injection needle). The active agent in the composition is an anti-GPC3 Adnectin or anti-GPC3 AdxDC described herein. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

EXEMPLARY EMBODIMENTS

1. A polypeptide comprising a fibronectin based scaffold (FBS) comprising BC, DE and FG loops, wherein one or more of the loops are altered relative to the corresponding loop of the wild-type FBS domain, and wherein the polypeptide binds specifically to human glypican-3 (GPC3) with a $K_D$ or 1 μM or less.
2. The polypeptide of embodiment 1, wherein the FBS is a fibronectin type III (Fn3) domain.
3. The polypeptide of embodiment 2, wherein the Fn3 domain is a human tenth fibronectin type III ($^{10}$Fn3) domain.
4. The polypeptide of any one of the preceding embodiments, wherein the BC loop comprises an amino acid sequence selected from the group consisting of
   (a) SEQ ID NOs: 6, 19, 32, 45, 58, 71, 84 or 99; and
   (b) a BC loop with 1, 2 or 3 amino acid substitutions, insertions or deletions relative to the BC loop of SEQ ID NOs: 6, 19, 32, 45, 58, 71, 84 or 99
5. The polypeptide of any one of the preceding embodiments, wherein the DE loop comprises an amino acid sequence selected from the group consisting of
   (a) SEQ ID NOs: 7, 20, 33, 46, 59, 72, 85 or 100; and
   (b) a DE loop with 1, 2 or 3 amino acid substitutions, insertions or deletions relative to the DE loop of SEQ ID NOs: 7, 20, 33, 46, 59, 72, 85 or 100.
6. The polypeptide of any one of the preceding embodiments, wherein the FG loop comprises an amino acid sequence selected from the group consisting of
   (a) SEQ ID NOs: 8, 21, 34, 47, 60, 73, 86, 101, 129, 156, 183, 210, 237, 264, 291 or 318, and
   (b) an FG loop with 1, 2 or 3 amino acid substitutions, insertions or deletions relative to the FG loop of SEQ ID NOs: 8, 21, 34, 47, 60, 73, 86, 101, 129, 156, 183, 210, 237, 264, 291 or 318.
7. The polypeptide of any one of the preceding embodiments, wherein the BC loop comprises and amino acid sequence selected from the group consisting of SEQ ID NOs: 6, 19, 32, 45, 58, 71, 84 or 99; the DE loop comprises an amino acid sequences selected from the group consisting of SEQ ID NOs: 7, 20, 33, 46, 59, 72, 85 and 100; and the FG loop comprises an amino acid sequence selected from the group consisting of SEQ ID NOs: 8, 21, 34, 47, 60, 73, 86, 101, 129, 156, 183, 210, 237, 264, 291 and 318, respectively, and wherein, optionally, the BC, DE and/or FG loop comprises 1, 2 or 3 amino acid substitutions.
8. The polypeptide of any one of the preceding embodiments, wherein
   (a) the BC, DE and FG loops comprise SEQ ID NOs: 6, 7 and 8, respectively;
   (b) at least one of the BC, DE and FG loops comprises 1, 2 or 3 amino acid substitutions relative to the respective BC, DE and FG loops of SEQ ID NOs: 6, 7 and 8;
   (c) the BC, DE and FG loops comprise SEQ ID NOs: 19, 20 and 21, respectively;
   (d) at least one of the BC, DE and FG loops comprises 1, 2 or 3 amino acid substitutions relative to the respective BC, DE and FG loops of SEQ ID NOs: 19, 20 and 22;
   (e) the BC, DE and FG loops comprise SEQ ID NOs: 32, 33 and 34, respectively;
   (f) at least one of the BC, DE and FG loops comprises 1, 2 or 3 amino acid substitutions relative to the respective BC, DE and FG loops of SEQ ID NOs: 32, 33 and 34;
   (g) the BC, DE and FG loops comprise SEQ ID NOs: 45, 46 and 47, respectively;
   (h) at least one of the BC, DE and FG loops comprises 1, 2 or 3 amino acid substitutions relative to the respective BC, DE and FG loops of SEQ ID NOs: 45, 46 and 47;
   (i) the BC, DE and FG loops comprise SEQ ID NOs: 58, 59 and 60, respectively;
   (j) at least one of the BC, DE and FG loops comprises 1, 2 or 3 amino acid substitutions relative to the respective BC, DE and FG loops of SEQ ID NOs: 58, 59 and 60;
   (k) the BC, DE and FG loops comprise SEQ ID NOs: 71, 72 and 73, respectively;
   (l) at least one of the BC, DE and FG loops comprises 1, 2 or 3 amino acid substitutions relative to the respective BC, DE and FG loops of SEQ ID NOs: 71, 72 and 73;
   (m) the BC, DE and FG loops comprise SEQ ID NOs: 84, 85 and 86, respectively;
   (n) at least one of the BC, DE and FG loops comprises 1, 2 or 3 amino acid substitutions relative to the respective BC, DE and FG loops of SEQ ID NOs: 84, 85 and 86;
   (o) the BC, DE and FG loops comprise SEQ ID NOs: 99, 100 and 101, respectively;
   (p) at least one of the BC, DE and FG loops comprises 1, 2 or 3 amino acid substitutions relative to the respective BC, DE and FG loops of SEQ ID NOs: 99, 100 and 101.
9. The polypeptide of any one of the preceding embodiments, wherein the FBS comprises the amino acid sequence set forth in SEQ ID NO: 3, wherein BC, DE and FG loops as represented by $(X)_v$, $(X)_z$, and $(X)_z$, respectively, and
   (a) comprise amino acid sequences at least 75%, 80%, 85%, 90%, 95%, 97%, 98%, or 99% identical to the BC, DE or FG loop sequences set forth in SEQ ID NOs: 6, 7 and 8, respectively;
   (b) comprise BC, DE, and FG loops having the amino acid sequences of SEQ ID NOs: 6, 7 and 8, respectively;
   (c) comprise amino acid sequences at least 75%, 80%, 85%, 90%, 95%, 97%, 98%, or 99% identical to the BC, DE or FG loop sequences set forth in SEQ ID NOs: 19, 20 and 21, respectively;

(d) comprise BC, DE, and FG loops having the amino acid sequences of SEQ ID NOs: 19, 20 and 21, respectively;

(e) comprise amino acid sequences at least 75%, 80%, 85%, 90%, 95%, 97%, 98%, or 99% identical to the BC, DE or FG loop sequences set forth in SEQ ID NOs: 32, 33 and 34, respectively;

(f) comprise BC, DE, and FG loops having the amino acid sequences of SEQ ID NOs:32, 33 and 34;

(g) comprise amino acid sequences at least 75%, 80%, 85%, 90%, 95%, 97%, 98%, or 99% identical to the BC, DE or FG loop sequences set forth in SEQ ID NOs: 45, 46 and 47, respectively;

(h) comprise BC, DE, and FG loops having the amino acid sequences of SEQ ID NOs: 45, 46 and 47;

(i) comprise amino acid sequences at least 75%, 80%, 85%, 90%, 95%, 97%, 98%, or 99% identical to the BC, DE or FG loop sequences set forth in SEQ ID NOs: 58, 59 and 60, respectively;

(j) comprise BC, DE, and FG loops having the amino acid sequences of SEQ ID NOs: 58, 59 and 60;

(k) comprise amino acid sequences at least 75%, 80%, 85%, 90%, 95%, 97%, 98%, or 99% identical to the BC, DE or FG loop sequences set forth in SEQ ID NOs: 71, 72 and 73, respectively;

(l) comprise BC, DE, and FG loops having the amino acid sequences of SEQ ID NOs: 71, 72 and 73;

(m) comprise amino acid sequences at least 75%, 80%, 85%, 90%, 95%, 97%, 98%, or 99% identical to the BC, DE or FG loop sequences set forth in SEQ ID NOs: 84, 85 and 86, respectively;

(n) comprise BC, DE, and FG loops having the amino acid sequences of SEQ ID NOs: 84, 85 and 86;

(o) comprise amino acid sequences at least 75%, 80%, 85%, 90%, 95%, 97%, 98%, or 99% identical to the BC, DE or FG loop sequences set forth in SEQ ID NOs: 99, 100 and 101, respectively;

(p) comprise BC, DE, and FG loops having the amino acid sequences of SEQ ID NOs: 99, 100 and 101;

(q) comprise BC, DE, and FG loops having the amino acid sequences of SEQ ID NOs: 99, 100 and 129;

(r) comprise BC, DE, and FG loops having the amino acid sequences of SEQ ID NOs: 99, 100 and 156;

(s) comprise BC, DE, and FG loops having the amino acid sequences of SEQ ID NOs: 99, 100 and 183;

(t) comprise BC, DE, and FG loops having the amino acid sequences of SEQ ID NOs: 99, 100 and 210;

(u) comprise BC, DE, and FG loops having the amino acid sequences of SEQ ID NOs: 99, 100 and 237;

(v) comprise BC, DE, and FG loops having the amino acid sequences of SEQ ID NOs: 99, 100 and 264;

(w) comprise BC, DE, and FG loops having the amino acid sequences of SEQ ID NOs: 99, 100 and 264; or (x) comprise BC, DE, and FG loops having the amino acid sequences of SEQ ID NOs: 99, 100 and 318.

10. The polypeptide of any one of the preceding embodiments, wherein the FBS comprises an amino acid sequence at least 80%, 85%, 90%, 95%, 98%, 99% or 100% identical to the non-BC, DE, and FG loop regions of SEQ ID NOs: 3, 5, 18, 31, 44, 57, 70, 83 and 98.

11. The polypeptide of any one of the preceding embodiments, wherein the FBS comprises an amino acid sequence at least 80%, 85%, 90%, 95%, 98%, 99% or 100% identical to any one of SEQ ID NOs: 5, 18, 31, 44, 57, 70, 83 and 98.

12. The polypeptide of any one of the preceding embodiments, wherein the FBS comprises an amino acid sequence at least 90%, 95%, 98%, 99% or 100% to the amino acid sequence of any one of SEQ ID NOs 5, 9-18, 22-31, 35-44, 48-57, 61-70, 74-83, 87-98, 102-128, 130-155, 157-182, 184-209, 211-236, 238-263, 265-290, 292-317 or 319-343.

13. The polypeptide of any one of the preceding embodiments, wherein the FBS comprises an amino acid that is at least 95% identical to the amino acid sequence of SEQ ID NOs: 98, 102-128, 129-155, 157-182, 184-209, 211-236, 238-263, 265-290, 292-317 and 319-343.

14. The polypeptide any one of the preceding embodiments, wherein the FBS comprises an amino acid sequence selected from the group consisting of SEQ ID NOs: 5, 18, 31, 44, 57, 70, 83, 98, 128, 155, 182, 209, 209, 236, 263, 290 and 317.

15. The polypeptide any one of the preceding embodiments, wherein the FBS comprises an amino acid sequence selected from the group consisting of SEQ ID NOs: 5, 9-18, 22-31, 35-44, 48-57, 61-70, 74-83, 87-98, 102-128, 130-155, 157-182, 184-209, 211-236, 238-263, 265-290, 292-317 and 319-343.

16. The polypeptide of anyone of the preceding embodiments, wherein the FBS comprises an amino acid sequence selected from the group consisting of SEQ ID NOs: 98, 102-128, 129-155, 157-182, 184-209, 211-236, 238-263, 265-290, 292-317 and 319-343.

17. The polypeptide of any one of the preceding embodiments, wherein the FBS competes with an FBS comprising the amino acid sequence of SEQ ID NO: 98 for binding with glypican-3.

18. The polypeptide of any one of the preceding embodiments, wherein the FBS binds to a region of 10-20 amino acid residues within glypican-3 which comprise HQVSFF (SEQ ID NO:209).

19. The polypeptide of any one of the preceding embodiments, wherein the FBS binds to a region of 10-20 amino acid residues within glypican-3 which comprise EQLLQSASM (SEQ ID NO:210).

20. The polypeptide of any one of the preceding embodiments, wherein the FBS binds to a discontinuous Adnectin site within glypican-3 comprising HQVSFF (SEQ ID NO:209) and EQLLQSASM (SEQ ID NO:210).

21. The polypeptide of any one of the preceding embodiments, further comprising a heterologous protein.

22. The polypeptide of any one of the preceding embodiments, further comprising one or more pharmacokinetic (PK) moieties selected from the group consisting of polyethylene glycol, sialic acid, Fc, Fc fragment, transferrin, serum albumin, a serum albumin binding protein, and a serum immunoglobulin binding protein.

23. The polypeptide of any one of the preceding embodiments, wherein the C-terminus of the FBS is linked to a moiety consisting of the amino acid sequence $P_mX_n$, wherein P is proline, X is any amino acid, m is an integer that is at least 1 and n is 0 or an integer that is at least 1.

24. The polypeptide of embodiment 23, wherein m is 1 or 2, and n is an integer from 1-10.

25. The polypeptide of embodiment 23 or 24, wherein moiety comprises cysteine.

26. The polypeptide of embodiment 25, wherein the moiety consists of the amino acid sequence $P_mCX_n$, wherein C is a cysteine, each X is independently any amino acid.
27. The polypeptide of embodiment 25, wherein the moiety consists of the amino acid sequence $PmCXn_1CXn_2$, wherein each X is independently any amino acid, $n_1$ and $n_2$ are independently 0 or an integer that is at least 1.
28. The polypeptide of embodiment 28, wherein $n_1$ and $n_2$ are independently an integer from 1-5.
29. The polypeptide of embodiment 23, wherein the moiety is selected from the group consisting of PI, PC, PID, PIE, PIDK (SEQ ID NO: 382), PIEK (SEQ ID NO: 383), PIDKP (SEQ ID NO: 384), PIEKP (SEQ ID NO: 385), PIDKPS (SEQ ID NO: 386), PIEKPS (SEQ ID NO: 387), PIDKPC (SEQ ID NO: 388), PIEKPC (SEQ ID NO: 389), PIDKPSQ (SEQ ID NO: 390), PIEKPSQ (SEQ ID NO: 391), PIDKPCQ (SEQ ID NO: 392), PIEKPCQ (SEQ ID NO: 393), PHHHHHH (SEQ ID NO: 394) and PCHHHHHH (SEQ ID NO: 395).
30. The polypeptide of embodiment 26, wherein the moiety is PC or PPC.
31. The polypeptide of embodiment 27, wherein the moiety is selected from the group consisting of PCGC (SEQ ID NO: 412), PCPC (SEQ ID NO: 413), PCGSGC (SEQ ID NO: 414), PCPPPC (SEQ ID NO: 415), PCPPPPPC(SEQ ID NO: 416), PCGSGSGC (SEQ ID NO: 417), PCHHHHHC (SEQ ID NO: 418), PCCHHHHHH (SEQ ID NO: 419), PCGCHHHHHH (SEQ ID NO: 420), PCPCHHHHHH (SEQ ID NO: 421), PCGSGCHHHHHH (SEQ ID NO: 422), PCPPPCHHHHHH (SEQ ID NO: 423), PCPPPP-PHHHHHH (SEQ ID NO: 424) and PCGSGSGCH-HHHHH (SEQ ID NO: 425).
32. The polypeptide of embodiment 31, wherein the moiety is PCPPPPPC (SEQ ID NO: 416).
33. The polypeptide of any one of embodiments 25-32, wherein the cysteine in the C-terminal moiety is conjugated to a heterologous moiety.
34. The polypeptide of embodiment 33, wherein the heterologous moiety is a detectable moiety.
35. The polypeptide of embodiment 33, wherein the heterologous moiety is a drug moiety, and the FBS and drug moiety form a FBS-drug conjugate.
36. An FBS-drug conjugate comprising the FBS moiety of any one of embodiments 1-31, wherein the drug moiety is conjugated to the FBS moiety by a linker.
37. The FBS-drug conjugate of embodiment 36, wherein the linker is a hydrazones, thioether, ester, disulfide or peptide-containing linker.
38. The FBS-drug conjugate of embodiment 37, wherein the linker is a peptidyl linker.
39. The FBS-drug conjugate of embodiment 38, wherein the peptidyl linker is Val-Cit, Ala-Val, Val-Ala-Val, Lys-Lys, Pro-Val-Gly-Val-Val (SEQ ID NO: 467), Ala-Asn-Val, Val-Leu-Lys, Ala-Ala-Asn, Cit-Cit, Val-Lys, Lys, Cit, Ser, or Glu.
40. The FBS-drug conjugate of any one of embodiments 36-39, wherein the drug moiety is a cytotoxic drug.
41. The FBS-drug conjugate of embodiment 40, wherein the cytotoxic drug selected from the group consisting of:
(a) enediynes such as calicheamicin and uncialamycin;
(b) tubulysins;
(c) DNA alkylators such as analogs of CC-1065 and duocarmycin;
(d) epothilones;
(e) auristatins;
(f) pyrrolobezodiazepine (PBD) dimers;
(g) maytansinoids such as DM1 and DM4
and analogs and derivatives thereof.
42. The FBS-drug conjugate of embodiment 41, wherein the drug moiety is:

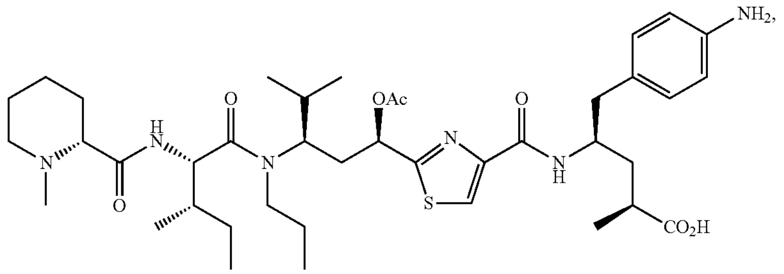

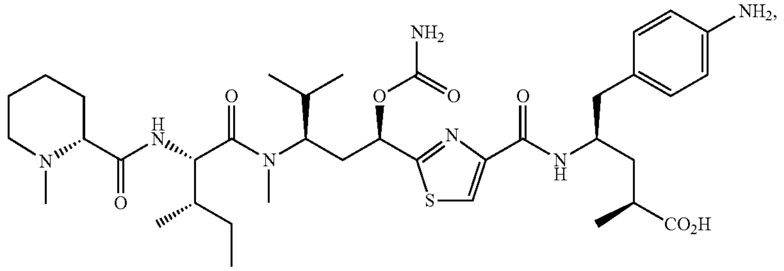

-continued
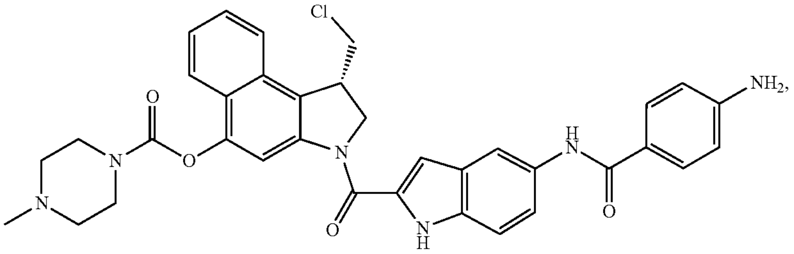
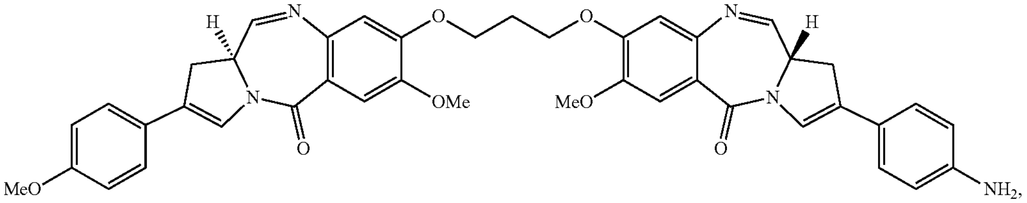
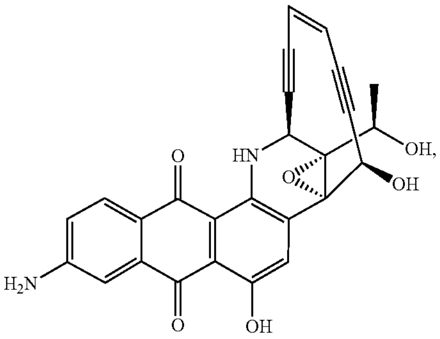
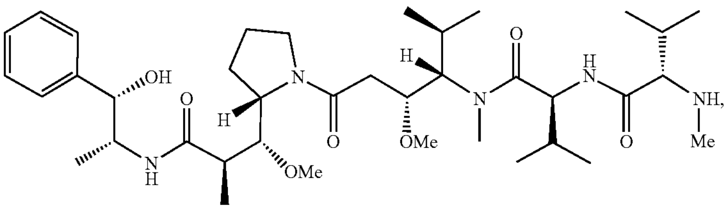
or
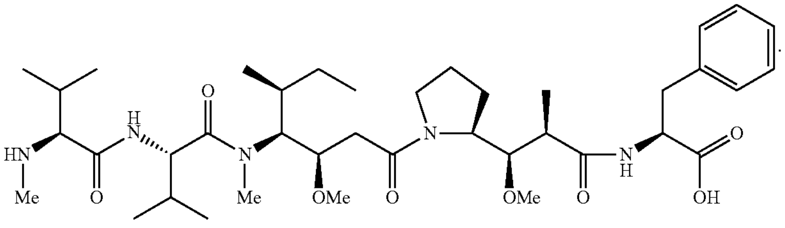

43. The FBS-drug conjugate of any one of embodiments 36-41, wherein the drug moiety is a synthetic tubulysin analog having the structure of formula (II):

(II)

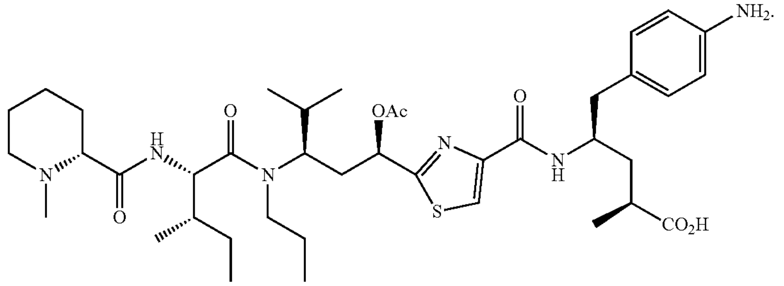

44. The FBS-drug conjugate of any one of embodiments 36-43, wherein the FBS and drug moiety are conjugated with a linker moiety having the structure of formula (III):

(III)

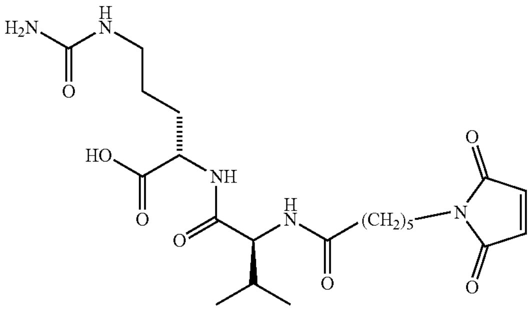

45. The FBS-drug conjugate of embodiment 44, wherein the drug-moiety-linker has the structure of formula (IV):

(IV)

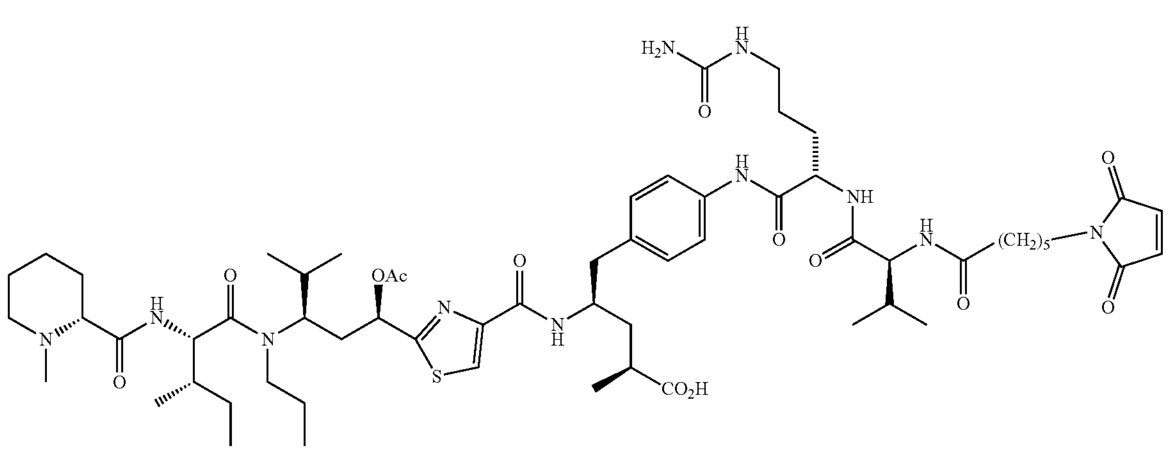

wherein the maleimide group is reacted with a sulfhydryl group of a cysteine of the FBS, thereby forming a thioether bond between the drug-moiety-linker and the FBS.

46. The FBS-drug conjugate of any one of embodiments 36-45, wherein the FBS moiety comprises a C-terminal moiety comprising a cysteine.

47. The FBS-drug conjugate of embodiment 46, wherein the C-terminal moiety consists of the amino acid sequence $P_mCX_n$, wherein C is a cysteine, each X is independently any amino acid, m is an integer that is at least 1 and n is 0 or an integer that is at least 1.

48. The FBS-drug conjugate of embodiment 47, wherein m is 1 or 2, and n is an integer from 1-10.

49. The FBS-drug conjugate of embodiment 46, wherein the moiety consists of the amino acid sequence $PmCXn_1CXn_2$, wherein each X is independently any amino acid, $n_1$ and $n_2$ are independently 0 or an integer that is at least 1.

50. The FBS-drug conjugate of embodiment 49, wherein $n_1$ and $n_2$ are independently an integer from 1-5.

51. The FBS-drug conjugate of embodiment 47, wherein the C-terminal moiety is PC or PPC.

52. The FBS-drug conjugate of embodiment 49, wherein the moiety is selected from the group consisting of PCGC (SEQ ID NO: 412), PCPC (SEQ ID NO: 413), PCGSGC (SEQ ID NO: 414), PCPPPC (SEQ ID NO: 415), PCPPPPPC(SEQ ID NO: 416), PCGSGSGC (SEQ ID NO: 417), PCHHHHHC (SEQ ID NO: 418), PCCHHHHHH (SEQ ID NO: 419), PCGCHHHHHH (SEQ ID NO: 420), PCPCHHHHHH (SEQ ID NO: 421), PCGSGCHHHHHH (SEQ ID NO: 422), PCPPPCHHHHHH (SEQ ID NO: 423), PCPPPP-PHHHHHH (SEQ ID NO: 424) and PCGSGSGCH-HHHHH (SEQ ID NO: 425).

53. The FBS-drug conjugate of embodiment 52, wherein the moiety is PCPPPPPC (SEQ ID NO: 16).

54. An FBS-drug conjugate, having a structure represented by formula (I)

(I)

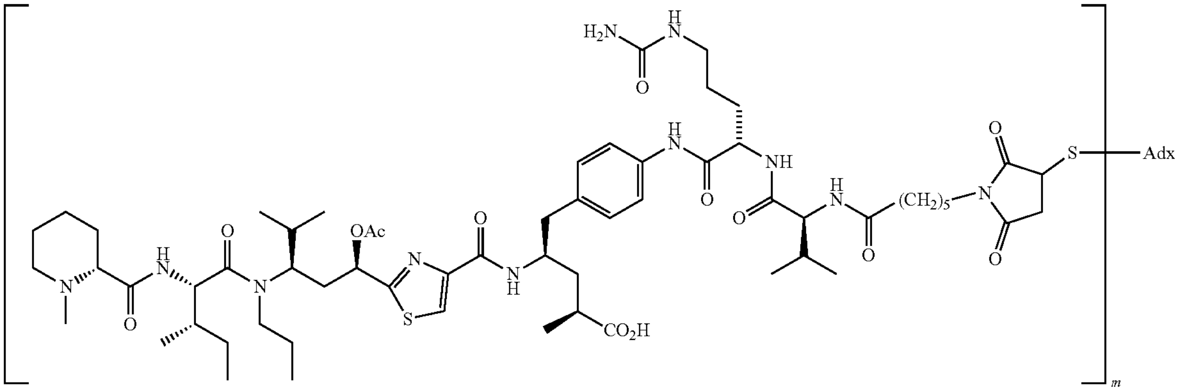

wherein m is 1, 2, 3 or 4 and Adx is an Adnectin that binds specifically to human GPC3 with a $K_D$ or 1 μM or less, and wherein the sulfur atom that is linked to "Adx" is a sulfur atom of a sulfhydryl group of a cysteine of the Adnectin.

55. The FBS-drug conjugate of embodiment 54, wherein Adx is a human $^{10}$Fn3 domain wherein, (a) the BC, DE and FG loops comprise SEQ ID NOs: 6, 7 and 8, respectively;

(b) the BC, DE and FG loops comprise SEQ ID NOs: 19, 20 and 21, respectively;

(c) the BC, DE and FG loops comprise SEQ ID NOs: 32, 33 and 34, respectively;

(d) the BC, DE and FG loops comprise SEQ ID NOs: 45, 46 and 47, respectively;

(e) the BC, DE and FG loops comprise SEQ ID NOs: 58, 59 and 60, respectively;

(f) the BC, DE and FG loops comprise SEQ ID NOs: 71, 72 and 73, respectively;

(g) the BC, DE and FG loops comprise SEQ ID NOs: 84, 85 and 86, respectively;

(h) the BC, DE and FG loops comprise SEQ ID NOs: 99, 100 and 101, respectively;

(i) the BC, DE and FG loops comprise SEQ ID NOs: 99, 100 and 129, respectively;

(j) the BC, DE and FG loops comprise SEQ ID NOs: 99, 100 and 156, respectively;

(k) the BC, DE and FG loops comprise SEQ ID NOs: 99, 100 and 183, respectively;

(l) the BC, DE and FG loops comprise SEQ ID NOs: 99, 100 and 210, respectively;

(m) the BC, DE and FG loops comprise SEQ ID NOs: 99, 100 and 237, respectively;

(n) the BC, DE and FG loops comprise SEQ ID NOs: 99, 100 and 264, respectively;

(o) the BC, DE and FG loops comprise SEQ ID NOs: 99, 100 and 264, respectively; or (p) the BC, DE and FG loops comprise SEQ ID NOs: 99, 100 and 318, respectively, and, the $^{10}$Fn3 domain comprises a C-terminal moiety consisting of the amino acid sequence $P_mCX_n$, or $P_mCX_{n1}CX_{n2}$, wherein each X is independently any amino acid, $n_1$ and $n_2$ are independently 0 or an integer that is at least 1.

56. The FBS-drug conjugate of embodiment 55, wherein the C-terminal moiety is PC or PPC, PCGC (SEQ ID NO: 412), PCPC (SEQ ID NO: 413), PCGSGC (SEQ ID NO: 414), PCPPPC (SEQ ID NO: 415), PCPPPPPC (SEQ ID NO: 416), PCGSGSGC (SEQ ID NO: 417), PCHHHHHC (SEQ ID NO: 418), PCCHHHHHH (SEQ ID NO: 419), PCGCHHHHHH (SEQ ID NO: 420), PCPCHHHHHH (SEQ ID NO: 421), PCGSGCHHHHHH (SEQ ID NO: 422), PCPPPCH-HHHHH (SEQ ID NO: 423), PCPPPPPHHHHHH (SEQ ID NO: 424) or PCGSGSGCHHHHHH (SEQ ID NO: 425).

57. The FBS-drug conjugate of embodiment 52, wherein the moiety is PC or PCPPPPPC (SEQ ID NO: 16).

58. The FBS-drug conjugate of embodiment 54, wherein Adx comprises an amino acid sequence selected from the group consisting of SEQ ID NOs: 12-17, 24-30, 38-43, 51-56, 64-69, 77-82, 90-97, 110-127, 137-154, 164-181, 191-208, 218-235, 245-262, 272-289, 299-316 and 326-343.

59. The FBS-drug conjugate of embodiment 54, wherein Adx comprises an amino acid sequence selected from the group consisting of SEQ ID NOs: 110-127, 137-154, 164-181, 191-208, 218-235, 245-262, 272-289, 299-316 and 326-343.

60. The FBS-conjugate of embodiment 54, wherein Adx comprises an amino acid sequence selected from the group consisting of SEQ ID NOs: 110-127.

61. A pharmaceutical composition comprising a polypeptide of any one of embodiments 1-35, and a pharmaceutically acceptable carrier.

62. A pharmaceutical composition comprising an FBS-drug conjugate of any one of embodiments 36-60.

63. The composition of embodiment 61 or 62, wherein the composition is essentially endotoxin-free.

64. An isolated nucleic acid molecule encoding the polypeptide of any one of embodiments 1-35.
65. An expression vector comprising a nucleotide sequence encoding the polypeptide of any one of embodiments 1-35.
66. A cell comprising a nucleic acid encoding the polypeptide of any one of embodiments 1-35.
67. A method of producing the polypeptide of any one of embodiments 1-35, comprising culturing the cell of embodiment 66 under conditions suitable for expressing the polypeptide, and purifying the polypeptide.
68. A method of attenuating or inhibiting a glypican-3 disease or disorder in a subject comprising administering to the subject an effective amount of the pharmaceutical composition of embodiment 61 or 62.
69. The method of embodiment 68, wherein the glypican-3 disease or disorder is cancer.
70. The method of embodiment 69, wherein the cancer is hepatocellular carcinoma, melanoma, Wilm's tumor, hepatoblastoma ovarian cancer or squamous lung cancer.
71. A kit comprising the polypeptide, FBS-drug conjugate or pharmaceutical composition of any one of embodiments 1-62, and instructions for use.
72. A method of detecting or measuring glypican-3 in a sample comprising contacting the sample with the polypeptide of any one of embodiments 1-35, and detecting or measuring binding of the FBS to glypican-3.
73. An FBS-drug conjugate, having a structure represented by formula (I)

(I)

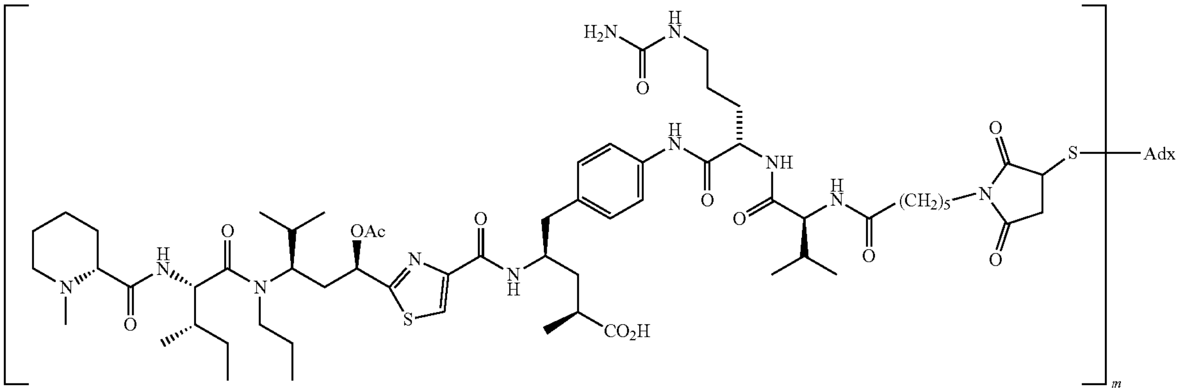

wherein m is 1 and Adx is an Adnectin comprising the amino acid sequence of any one of SEQ ID NO: 110-117 and 272-289; and wherein the sulfur atom that is linked to "Adx" is a sulfur atom of a sulfhydryl group of the C-terminal cysteine of the Adnectin.
74. An FBS-drug conjugate, having a structure represented by formula (I)

(I)

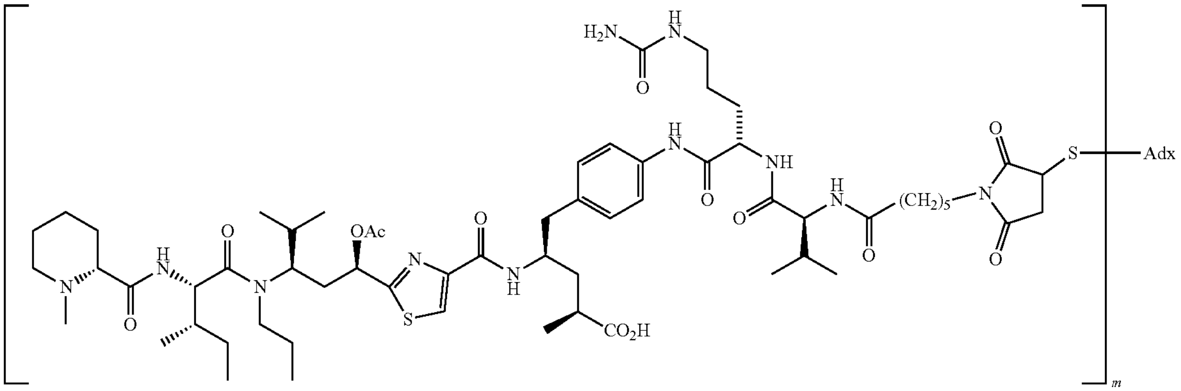

wherein m is 2 and Adx is an Adnectin comprising the amino acid sequence of SEQ ID NO: 119-126 and 281-288; and wherein the sulfur atom that is linked to "Adx" is a sulfur atom of a sulfhydryl group of each of the two C-terminal cysteines of the Adnectin.

75. An FBS-drug conjugate, having a structure represented by formula (VI)

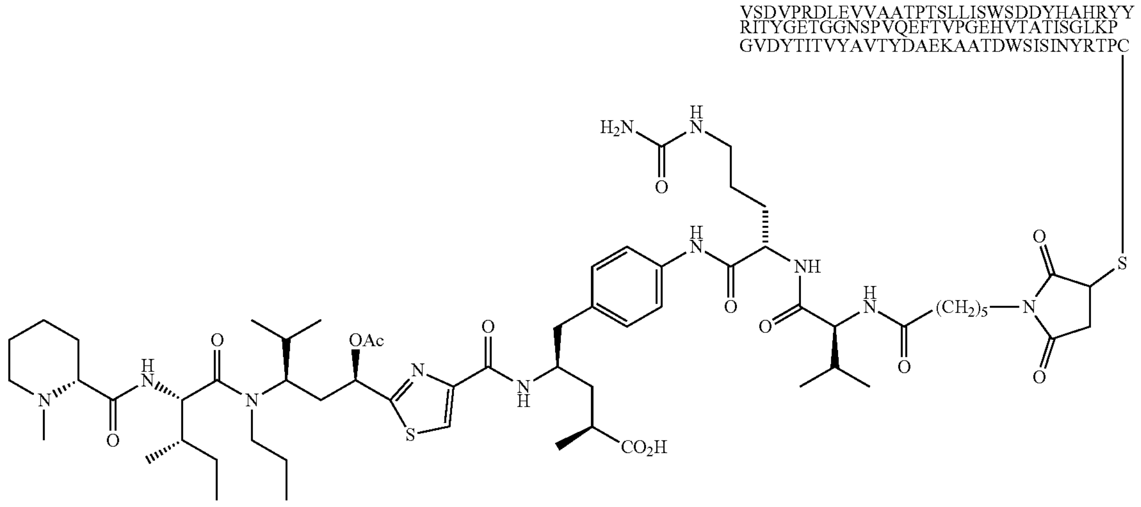

wherein the sulfur atom linked to the cysteine is the sulfur atom of the sulfhydryl group of the cysteine.

76. An FBS-drug conjugate, having a structure represented by formula (VII):

(VII)

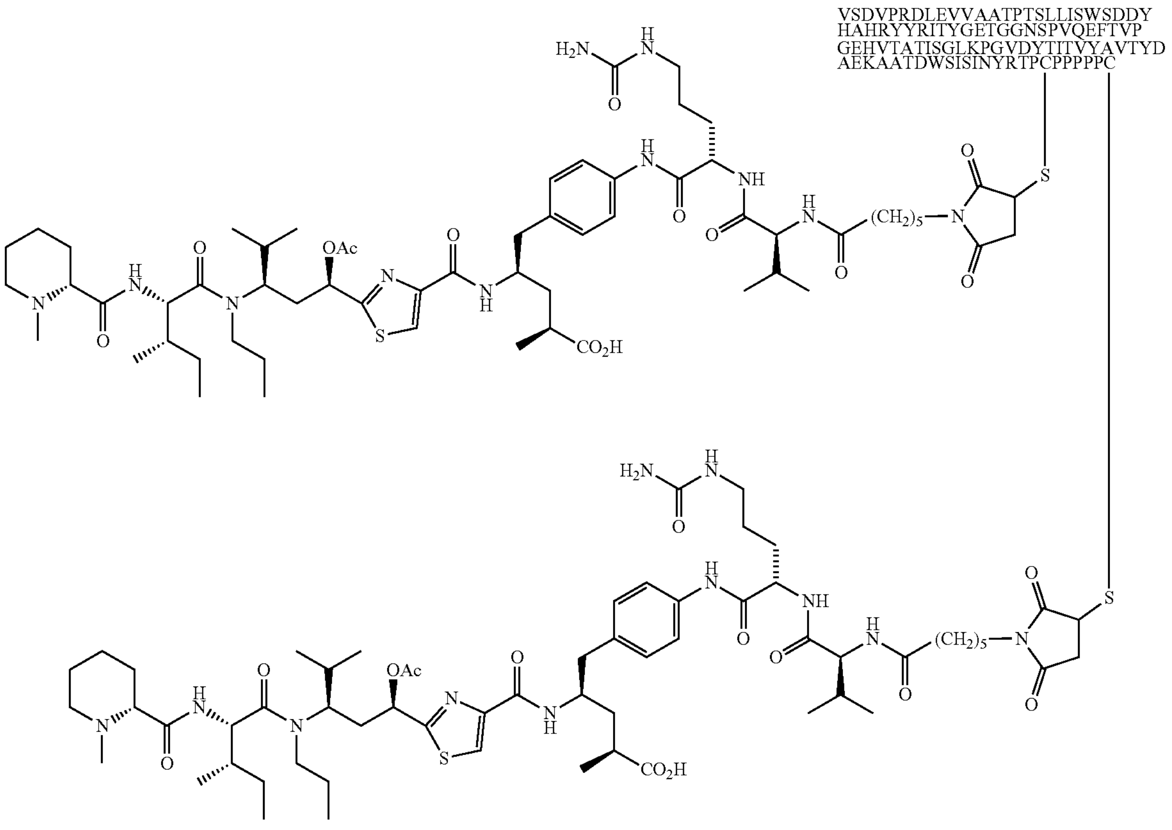

wherein the sulfur atom linked to the cysteines is the sulfur atom of the sulfhydryl group of the cysteines.

INCORPORATION BY REFERENCE

The contents of all figures and all references, Genbank sequences, websites, patents and published patent applications cited throughout this application are expressly incorporated herein by reference to the same extent as if there were written in this document in full or in part. The content of PCT/US2015/021466 is specifically incorporated by reference herein.

The invention is now described by reference to the following examples, which are illustrative only, and are not intended to limit the present invention. While the invention has been described in detail and with reference to specific embodiments thereof, it will be apparent to one of skill in the art that various changes and modifications can be made thereto without departing from the spirit and scope thereof.

EXAMPLES

Example 1: Selection, Expression and Purification of Anti-Glypican-3 Binding Adnectins Glypican-3 (GPC3) binding Adnectins were isolated from an Adnectin library screened with a Glypican-3 protein, or were affinity matured by PROfusion from clones identified in the library. For a detailed description of the RNA-protein technology and fibronectin-based scaffold protein library screening methods see Szostak et al., U.S. Pat. Nos. 6,258,558; 6,261,804; 6,214,553; 6,281,344; 6,207,446; 6,518,018; PCT Publication Nos. WO 00/34784; WO 01/64942; WO 02/032925; and Roberts et al., *Proc Natl. Acad. Sci.,* 94:12297-12302 (1997), herein incorporated by reference.

The amino acid and nucleotide sequences of 7 adnectins with good binding and biophysical properties are provided below:

ADX_4578_F03

(SEQ ID NO: 10)

MGVSDVPRDLEVVAATPTSLLISWHPPHPNIVSYHIYYGETGGNSPVQEF

TVEGSKSTAKISGLKPGVDYTITVYAVAPEIEKYYQIWINYRTEGSGS*

(SEQ ID NO: 452)

ATGGGAGTTTCTGATGTGCCGCGCGACTTGGAAGTGGTTGCCGCCACCCC

CACCAGCCTGCTGATCTCTTGGCATCCGCCGCATCCGAACATCGTTTCTT

ACCATATCTACTACGGCGAAACAGGAGGCAATAGCCCTGTCCAGGAGTTC

ACTGTGGAAGGTTCTAAATCTACTGCTAAAATCAGCGGCCTTAAACCTGG

CGTTGATTATACCATCACTGTGTACGCTGTTGCTCCGGAAATCGAAAAAT

ACTACCAGATTTGGATTAATTACCGCACAGAAGGCAGCGGTTCCTAA

ADX_4578_H08

(SEQ ID NO: 23)

MGVSDVPRDLEVVAATPTSLLISWSGYDYGDSYYRITYGETGGNSPVQEF

TVPDGSNTATISGLKPGVDYTITVYAVEAYGKGYTRYTPISINYRTEIDK

PSQ*

(SEQ ID NO: 452)

ATGGGAGTTTCTGATGTGCCGCGCGACCTGGAAGTGGTTGCTGCCACCCC

CACCAGCCTGCTGATCAGCTGGTCTGGTTACGACTACGGTGACTCTTATT

-continued

ACCGCATCACTTACGGCGAAACAGGAGGCAATAGCCCTGTCCAGGAGTTC

ACTGTGCCTGACGGTTCTAACACAGCTACCATCAGCGGCCTTAAACCTGG

CGTTGATTATACCATCACTGTGTATGCTGTCGAAGCTTACGGTAAAGGTT

ACACTCGTTACACTCCAATTTCCATTAATTACCGCACAGAAATTGACAAA

CCATCCCAGTAA

ADX_4578_B06

(SEQ ID NO: 36)

MGVSDVPRDLEVVAATPTSLLISWFPDRYVYYITYGETGGNSPVQEFTVE

GHKQTAYISGLKPGVDYTITVYAIYYYPDDFQGYPQPISINYRTEGSGS*

(SEQ ID NO: 454)

ATGGGAGTTTCTGATGTGCCGCGCGACTTGGAAGTGGTTGCCGCCACCCC

CACCAGCCTGCTGATCTCTTGGTTCCCGGACCGTTACGTTTACTACATCA

CTTACGGCGAAACAGGAGGCAATAGCCCTGTCCAGGAGTTCACTGTGGAA

GGTCATAAACAGACTGCTTACATCAGCGGCCTTAAACCTGGCGTTGATTA

TACCATCACTGTGTACGCTATCTACTACTACCCGGACGACTTCCAGGGTT

ACCCGCAGCCGATTTCTATTAATTACCGCACAGAAGGCAGCGGTTCCTAA

ADX_4606_F06

(SEQ ID NO: 49)

MGVSDVPRDLEVVAATPTSLLISWNSGHSGQYYRITYGETGGNSPVQEFT

VPRYGYTATISGLKPGVDYTITVYAVAHSEASAPISINYRTEIDKPSQ*

(SEQ ID NO: 455)

ATGGGAGTTTCTGATGTGCCGCGCGACCTGGAAGTGGTTGCTGCCACCCC

CACCAGCCTGCTGATCAGCTGGAACTCTGGTCATTCTGGTCAGTATTACC

GCATCACTTACGGCGAAACAGGAGGCAATAGCCCTGTCCAGGAGTTCACT

GTGCCTCGTTACGGTTACACAGCTACCATCAGCGGCCTTAAACCTGGCGT

TGATTATACCATCACTGTGTATGCTGTCGCTCATTCTGAAGCTTCTGCTC

CAATTTCCATTAATTACCGCACAGAAATTGACAAACCATCCCAGTAA

ADX_5273_C01

(SEQ ID NO: 62)

MGVSDVPRDLEVVAATPTSLLISWSDPYEEERYYRITYGETGGNSPVQEF

TVPAFHTTATISGLKPGVDYTITVYAVTYKHKYAYYYPPISINYRTEIDK

PSQ*

(SEQ ID NO: 456)

ATGGGAGTTTCTGATGTGCCGCGCGACCTGGAAGTGGTTGCTGCCACCCC

CACCAGCCTGCTGATCAGCTGGTCTGACCCGTACGAAGAAGAACGATATT

ACCGCATCACTTACGGCGAAACAGGAGGCAATAGCCCTGTCCAGGAGTTC

ACTGTGCCTGCTTTCCATACTACAGCTACCATCAGCGGCCTTAAACCTGG

CGTTGATTATACCATCACTGTGTATGCTGTCACTTACAAACATAAATACG

CTTACTACTACCCGCCAATTTCCATTAATTACCGCACAGAAATTGACAAA

CCATCCCAGTAA

-continued

ADX_5273_D01

(SEQ ID NO: 75)

```
MGVSDVPRDLEVVAATPTSLLISWEPSYKDDRYYRITYGETGGNSPVQEF
TVPSFHQTATISGLKPGVDYTITVYAVTYEPDEYYFYYPISINYRTEIDK
PSQ*
```

(SEQ ID NO: 457)

```
ATGGGAGTTTCTGATGTGCCGCGCGACCTGGAAGTGGTTGCTGCCACCCC
CACCAGCCTGCTGATCAGCTGGGAACCGTCTTACAAAGACGACCGATATT
ACCGCATCACTTACGGCGAAACAGGAGGCAATAGCCCTGTCCAGGAGTTC
ACTGTGCCTTCTTTCCATCAGACAGCTACCATCAGCGGCCTTAAACCTGG
CGTTGATTATACCATCACTGTGTATGCTGTCACTTACGAACCGGACGAAT
ACTACTTCTACTACCCAATTTCCATTAATTACCGCACAGAAATTGACAAA
CCATCCCAGTAA
```

ADX_5274_

(SEQ ID NO: 88)

```
MGVSDVPRDLEVVAATPTSLLISWSGDYHPHRYYRITYGETGGNSPVQEF
TVPGEHETATISGLKPGVDYTITVYAVTYDGEKADKYPPISINYRTEIDK
PSQ*
```

(SEQ ID NO: 458)

```
ATGGGAGTTTCTGATGTGCCGCGCGACCTGGAAGTGGTTGCTGCCACCCC
CACCAGCCTGCTGATCAGCTGGTCTGGTGACTACCATCCGCATCGATATT
ACCGCATCACTTACGGCGAAACAGGAGGCAATAGCCCTGTCCAGGAGTTC
ACTGTGCCTGGTGAACATGAAACAGCTACCATCAGCGGCCTTAAACCTGG
CGTTGATTATACCATCACTGTGTATGCTGTCACTTACGACGGTGAAAAAG
CTGACAAATACCCGCCAATTTCCATTAATTACCGCACAGAAATTGACAAA
CCATCCCAGTAA
```

The binding characteristics of the 7 GPC3 binding Adnectins were determined via ELISA using recombinant GPC3 and flow cytometry, using the GPC3 positive CHO cell line and the HepG2 human tumor cell line. For the flow cytometry experiments, CHO-Kl or CHO-Glypican-3 cells or HepG2 tumor cell line were treated with Versene and resuspended in FACS Buffer (PBS 2.5% FBS). Adnectins diluted in FACS buffer were incubated with cells for 1 hour at 4° C. After 1 wash in FACS buffer the cells were incubated with an anti-His antibody at 2 ug/ml and incubated for 1 hour at 4° C. After 2 washes in FACS Buffer the cells were resuspended in FIX Buffer (2.5% formaldehyde in PBS). Analysis was done with the BB Biosciences FACS Canto.

The results of the ELISA experiments are shown in Table 3, and exemplary flow cytometry results are shown in FIG. 3A-D. The aggregation score of the Adnectins, as determined by Size Exclusion Chromatograph (SEC) is also provided in the Table 2. None of these Adnectins aggregated significantly.

TABLE 2

ELISA and SEC scores of human GPC3 binding Adnectins

| Clone | ELISA OD | SEC score |
|---|---|---|
| ADX_4578_F03 | 0.60 | 2 |
| ADX_4578_H08 | 1.02 | 2 |
| ADX_4578_B06 | 0.17 | 3 |
| ADX_4606_F06 | 1.73 | 3 |
| ADX_5273_C01 | 1.35 | 3 |
| ADX_5273_D01 | 2.1 | 2 |
| ADX_5274_E01 | 2.37 | 1 |

The C-terminus of ADX_5274_E01 was modified by inclusion of a C-terminal cysteine and a 6×His tail, to produce Adnectin ADX_6561_A01:

(SEQ ID NO: 94)

```
MGVSDVPRDLEVVAATPTSLLISWSGDYHPHRYYRITYGETGGNSPVQEF
TVPGEHETATISGLKPGVDYTITVYAVTYDGEKADKYPPISINYRTPCHH
HHHH
```

The nucleic acid encoding ADX_6561_A01 was diversified by introducing a small fraction of substitutions at each nucleotide position that encoded an amino acid residue in loop BC, DE or FG. The resulting library of Adnectin sequences related to ADX_6561_A01 was then subjected to in vitro selection by PROfusion (mRNA display) for binding to human GPC3 under high stringency conditions. The clones enriched after selection was completed were sequenced, expressed in HTPP format, and further analyzed.

The selection identified Adnectin ADX_6077_F02 as binding to human GPC3 with high affinity. The amino acid sequence of ADX_6077_F02, and the nucleotide sequence encoding it are as follows:

(SEQ ID NO: 118; the BC, DE and FG loops are shown in bold)

MGVSDVPRDLEVVAATPTSLLISWSDDYHAHRYYRITYGETGGNSPVQEF
TVPGEHVTATISGLKPGVDYTITVYAVTYDGEKAATDWSISINYRTPCHH
HHHH (SEQ ID NO: 459)

```
ATGGGAGTTTCTGATGTGCCGCGCGACCTGGAAGTGGTTGCTGCCACCCC
CACCAGCCTGCTGATCAGCTGGTCTGATGACTACCATGCGCATCGATATT
ACCGCATCACTTACGGCGAAACAGGAGGCAATAGCCCTGTCCAGGAGTTC
ACTGTGCCTGGTGAACATGTGACAGCTACCATCAGCGGCCTTAAACCTGG
CGTTGATTATACCATCACTGTGTATGCTGTCACTTACGACGGTGAAAAGG
CTGCCACAGATTGGTCAATTTCCATTAATTACCGCACACCGTGCCACCAT
CACCACCACCACTGA
```

Binding of the anti-GPC3 Adnectin to other glypican molecules was tested, and the results, indicate that ADX_6077_F02 binds specifically to human GPC3, and does not cross-react to the other human glypicans GPC1, GPC2, GPC5 and GPC6.

Example 2: Adnectins with C-Terminal Cysteines for Conjugation of a Drug Moiety For preparing Adnectins linked to a drug moiety, the Adnectins were modified at their C-terminus to comprise one of the following C-terminal amino acid sequences: NYRTPC (SEQ ID NO: 466; for forming DAR1 Adnectins, i.e., Adnectins with a single cysteine in the linker, for linking to a single drug moiety); NYRTPCC (SEQ ID NO: 467; for forming DAR2 Adnectins, i.e., Adnectins with two cysteines in the linker, for linking to two drug moieties, one per cysteine); NYRTPCHHHHHH (SEQ ID NO: 468; for forming DAR1 Adnectins with a 6×His tail) and NYRTPCPPPPPCHHHHHH (SEQ NO: 469; for forming DAR2 Adnectins with a 6×His tail).

To prevent dislufide-linked dimers of the uncongugated Adnectins containing one or more Cysteine residues, the cysteine residue(s) of the Adnectins were carboxymethylated as follows: An Adnectin solution was treated with a reducing agent (5 mM DTT or 5 mM TCEP) and incubated for 30 minutes at room temperature. Ioodoaceamide (500 mM, Sigma P/N A3221-10VL) was added to a final concentration of 50 mM. Samples were incubated for 1 hour in the dark at room temperature. Samples were then dialyzed to PBS or Sodium Acetate buffer.

Example 3: Production of GPC3-Adnectin Drug Conjugates (GPC3-AdxDC)

Production of Adnectins, e.g., GPC3 Adnectins: A nucleic acid encoding an Adnectin, e.g., (SEQ ID NO: 459), which encodes a protein having the amino acid sequence

```
(SEQ ID NO: 118; ADX_6077_F02)
MGVSDVPRDLEVVAATPTSLLISWSDDYHAHRYYRITYGETGGNSPVQE

FTVPGEHVTATISGLKPGVDYTITVYAVTYDGEKAATDWSISINYRTPC

HHHHHH,
```

was cloned into a pET9d (EMD Biosciences, San Diego, CA) vector and expressed in *E. coli* BL21 DE3 pLys-S cells. Twenty nil of an inoculum culture (generated from a single plated colony) was used to inoculate 1 liter of Magic Media *E. coli* expression medium (Invitrogen, Catalog K6803A/B) containing 50 ug/ml Kanamycin in a 2.5 Liter Ultra Yield flask (Thomson Instruments Co. P/N 931136-B). The culture was grown at 37° C. for 6 hours, followed by 20° C. for 18 hours with shaking at 225 RPM. After the incubation period, the culture was harvested by centrifugation for 30 minutes at ≥10,000 g at 4° C. Cell pellets were frozen at −80° C. The cell pellet was thawed and resuspended in 25 mL of lysis buffer (20 mM Sodium Phosphate, 500 mM Sodium Chloride, 5 mM Dithiothreitol, 1× Complete™ Protease Inhibitor Cocktail-EDTA free (Roche) using an Ultra-Turrax homgenizer (IKA-Works) on ice. Cell lysis was achieved by high pressure homogenization (≥18,000 psi) using a Model M-110P Microfluidizer (Microfluidics). The insoluble fraction was separated by centrifugation for 30 minutes at 23,300 g at 4° C. and discarded. The soluble fraction was filtered with a 0.2 micron vacuum filter. The filtered supernatant was loaded onto a Histrap column (GE Healthcare P/N 17-5248-02) equilibrated with 20 mM Sodium Phosphate/500 mM Sodium chloride pH 7.4+5 mM DTT buffer. After loading, the column was washed with 10 CV equilibration buffer, followed by 10 CV of 40 mM Imidazole in equilibration buffer, followed by 10 CV 2.0M Sodium Chloride in PBS. Bound protein was eluted with 500 mM Imidazole in 20 mM Sodium Phosphate/500 mM Sodium Chloride pH 7.4+5 mM DTT. The eluate from the HisTrap column was buffer exchanged to 50 mM Sodium Acetate/10 mM Sodium Chloride pH 5.5 using G25 gel filtration chromatography. The sample was then applied to a cation exchange chromatography column (SP HP, GE Healthcare 17-1152-01). Bound protein was eluted in a gradient of increasing sodium chloride concentration in 50 mM Sodium Acetate pH 5.5 buffer. Fractions were pooled for conjugation with tubulsyin.

Production of Tubulysin analog-Linker: A tubulysin analog-linker compound having the structure of formula (IV) was produced as described in U.S. Pat. No. 8,394,922 (hereby incorporated by reference).

(IV)

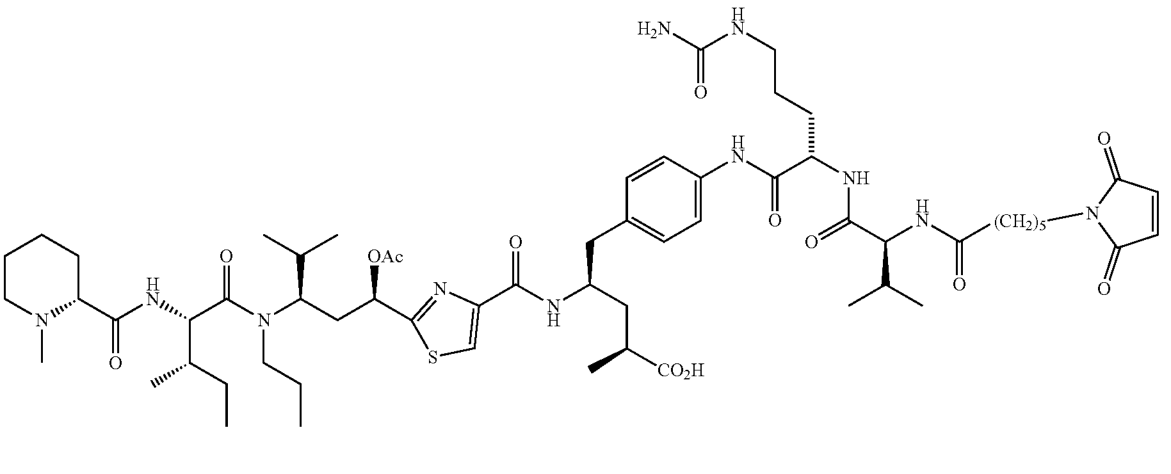

Adnectin-Drug Conjugation: Conjugation of a tubulysin analog-linker to Adnectins comprising a C terminal cysteine was conducted as follows:

A sample of the adnectin to be conjugated to the tubulysin analog was treated with 5 mM TCEP and incubated at room temperature for approximately 1 h. TCEP was removed using a G25 gel filtration column (GE Healthcare) equilibrated with 50 mM NaOAc/10 mM NaCl pH 5.5. The tubulysin analog was dissolved in 100% DMSO and added to a final concentration of 5× molar and the reaction was incubated for 2 hours at RT followed by overnight at 4° C.

To remove unreacted tubulsyin analog, the reaction mixture was re-applied to the SP cation exchange column as described above.

Adnectins, e.g., GPC3 Adnectins, containing two cysteine residues near the C-terminus were conjugated to two molecules of tubulysin analog using the same methodology described above to generate DAR2 (Drug-Adnectin Ratio 2) Adnectins.

Protein concentration was determined using a Nanodrop 8000 spectrophotometer (Thermo Scientific). The molecular weight of conjugated and unconjugated Adnectin was determined by LC-mass spectrometry using an Agilent Technologies 6540 UHD Accurate Mass Q-ToF LC-MS equipped with a Zorbax C8 RRHD column.

Using these techniques of expressing, purifying, conjugating and alkylating Adnectins, the Adnectins and Adnectin-drug conjugates listed in Table 3 were prepared.

TABLE 3

Control and Anti-Glypican-3 Binding Adnectins

| ADX ID | C-term elements | Modifications | Protein sequence |
|---|---|---|---|
| ADX_6561_A01 | Cys, $His_6$ | | MGVSDVPRDLEVVAATPTSLLISWSGDYH PHRYYRITYGETGGNSPVQEFTVPGEHETA TISGLKPGVDYTITVYAVTYDGEKADKYPP ISINYRTPCHHHHHH* (SEQ ID NO: 94) |
| ADX_6077_F02<br>ADX_6077_F02<br>ADX_6077_F02 | Cys, $His_6$<br>Cys, $His_6$<br>Cys, $His_6$ | none<br>alkylated<br>Drug/linker DAR1 | MGVSDVPRDLEVVAATPTSLLISWSDDYH AHRYYRITYGETGGNSPVQEFTVPGEHVT ATISGLKPGVDYTITVYAVTYDGEKAATD WSISINYRTPCHHHHHH* (SEQ ID NO: 11) |
| ADX_6077_F02 | Cys | none | GVSDVPRDLEVVAATPTSLLISWSDDYHA HRYYRITYGETGGNSPVQEFTVPGEHVTAT ISGLKPGVDYTITVYAVTYDGEKAATDWSI SINYRTP* (SEQ ID NO: 104) |
| ADX_6912_G02<br>ADX_6912_G02<br>ADX_6912_G02 | 2Cys, $His_6$<br>2Cys, $His_6$<br>2Cys, $His_6$ | none<br>alkylated (2x)<br>Drug/linker (2x) DAR2 | MGVSDVPRDLEVVAATPTSLLISWSDDYH AHRYYRITYGETGGNSPVQEFTVPGEHVT ATISGLKPGVDYTITVYAVTYDGEKAATD WSISINYRTPCPPPPPCHHHHHH* (SEQ ID NO: 127) |
| ADX_6912_G02 | 2Cys | None | MGVSDVPRDLEVVAATPTSLLISWSDDYH AHRYYRITYGETGGNSPVQEFTVPGEHVT ATISGLKPGVDYTITVYAVTYDGEKAATD WSISINYRTPCPPPPPC* (SEQ ID NO: 126) |
| ADX_6093_A01<br>ADX_6093_A01<br>ADX_6093_A01 | Cys, $His_6$<br>Cys, $His_6$<br>C-term $His_6$ | none<br>alkylated<br>Drug/linker DAR1 | MGVSDVPRDLEVVAATPTSLLISWDAPAV TVRYYRITYGETGGNSPVQEFTVPGSKSTA TISGLKPGVDYTITVYAVTGRGESPASSKPI SINYRTPCHHHHHH* (SEQ ID NO: 348) |
| ADX_6093_A01 | Cys | none | GVSDVPRDLEVVAATPTSLLISWDAPAVT VRYYRITYGETGGNSPVQEFTVPGSKSTAT ISGLKPGVDYTITVYAVTGRGESPASSKPISI NYRTPC* (SEQ ID NO: 349) |
| | 2Cys, $His_6$<br>2Cys, $His_6$<br>2Cys, $His_6$ | none<br>alkylated (2x)<br>Drug/linker (2x) DAR2 | MGVSDVPRDLEVVAATPTSLLISWDAPAV TVRYYRITYGETGGNSPVQEFTVPGSKSTA TISGLKPGVDYTITVYAVTGRGESPASSKPI SINYRTPCPPPPPCHHHHHH* (SEQ ID NO: 350) |

Example 4: In Vitro Characterization of Anti-GPC3 Adnectins and GPC3-AdxDCs

Size exclusion chromatography: Standard size exclusion chromatography (SEC) was performed on candidate Adnectins resulting from the midscale process. SEC of midscaled material was performed using a Superdex 200 10/30 or on a Superdex 75 10/30 column (GE Healthcare) on an Agilent 1100 or 1200 HPLC system with UV detection at A214 nm and A280 nm and with fluorescence detection (excitation 280 nm, emission 350 nm). A buffer of 100 mM sodium sulfate/100 mM sodium phosphate/150 mM sodium chloride, pH 6.8 was used at the appropriate flow rate for the SEC column employed. Gel filtration standards (Bio-Rad Laboratories, Hercules, CA) were used for molecular weight calibration.

Thermostability: Thermal Scanning Fluorescence (TSF) analysis of HTPP Adnectins was performed to screen them by relative thermal stability. Samples were normalized to 0.2 mg/ml in PBS. 1 μl of Sypro orange dye diluted 1:40 with PBS was added to 25 μl of each sample and the plate was sealed with a clear 96 well microplate adhesive seal. Samples were scanned using a BioRad RT-PCR machine by ramping the temperature from 25° C.-95° C., at a rate of 2 degrees per minute. The data was analyzed using BioRad CFX manager 2.0 software. The values obtained by TSF have been shown to correlate well with Tm values obtained by DSC over a melting range of 40° C. to 70° C. This is considered the acceptable working range for this technique. A result of ND ("No data") is obtained when the slope of the transition curve is too small to allow its derivative peak (the rate of change in fluorescence with time) to be distinguished from noise. An "ND" result cannot be interpreted as an indication of thermostability. Differential Scanning calorimetry (DSC) analyses of dialyzed HTPP'd and midscaled Adnectins were performed to determine their respective $T_m$'s. A 0.5 mg/ml solution was scanned in a VP-Capillary Differential Scanning calorimeter (GE Microcal) by ramping the temperature from 15° C. to 110° C., at a rate of 1 degree per minute under 70 p.s.i pressure. The data was analyzed vs. a control run of the appropriate buffer using a best fit using Origin Software (OriginLab Corp).

SPR Affinity Measurements: Surface plasmon resonance (SPR) was performed to calculate off-rates (10 and binding affinities of α-GPC3 adnectins and tubulysin-conjugated AdxDCs using a Biacore T100 instrument (GE Healthcare). Recombinant human (aa 1-559) and murine (aa 25-557) glypican-3 proteins (R&D Systems) were diluted to 10 μg/ml in 10 mM sodium acetate pH 4.5 and individually immobilized onto active flow cells of a CM5 biosensor following the manufacturer's amine coupling protocol (GE Healthcare), targeting ~1000RU immobilization density of each protein per flow cell. SPR experiments were conducted at 37° C. using HBS-P+ (10 mM HEPES, 150 mM NaCl, 0.05% (v/v) Surfactant P20, pH 7.4) running buffer (GE Healthcare). For affinity measurements, a concentration series of 200-1.56 nM α-GPC3 adnectins and AdxDCs were prepared in running buffer and injected at 30 μl/min across the human and murine GPC3 biosensor flow cells. For off-rate measurements, single 200 nM adnectin/AdxDC concentrations were injected using identical conditions. One 30s injection of 10 mM glycine pH 1.7 was used to remove bound adnectin and regenerate the GPC3 surfaces between assay cycles.

Rate constants $k_a$ ($k_{on}$) and $k_d$ ($k_{off}$) were derived from reference-subtracted sensorgrams fit to a 1:1 binding model in Biacore T100 Evaluation Software v2.0.4 (GE Healthcare). The affinity constant, $K_D$ was calculated from the ratio of rate constants $k_d/k_a$.

Cell Binding Assay: The binding of GPC3 adnectins to huGPC3 positive cells Huh7 was evaluated by flow cytometry essentially as follows. Huh7 carcinoma cells grown in DMEM media with 10% FBS. Cells were harvested using Versene, an EDTA cell dissociation solution from Lonza, Cat. #17-711E. Tumor cells (1E5 cells/reaction) were suspended in FACS buffer (PBS, 1% BSA, 0.05% Na Azide) and mixed with a serial dilution of AdxDC for one hour on ice. Cells were washed three times with FACS buffer, and bound AdxDC was detected with an in house anti-scaffold monoclonal Ab and PE-conjugated Antibody from (RnD Systems), cat #NL007, and read on a flow cytometer. Data analysis was done using FlowJo Software, and EC50 of 50% of maximum binding was determined using PRISM™ software, version 5.0 (GraphPad Software, La Jolla, CA, USA).

Cell Growth Inhibition Assay: A $^3$H thymidine assay, where the inhibition of incorporation of $^3$H thymidine indicates inhibition of proliferation of the tested cell line, was used to assess the dose-dependent inhibitory effect of the AdxDC on the proliferation of Hep3B, Huh7 and HepG2 cells. The human tumor cell lines were obtained from the American Type Culture Collection (ATCC), P.O. Box 1549, Manassas, VA 20108, USA, and cultured according to instructions from ATCC. Cells were seeded at $1.25\times10^4$ cells/well in 96-well plates, and 1:3 serial dilutions of GPC3 AdxDC were added to the wells. Plates were allowed to incubate for 72 h. The plates were pulsed with 1.0 μCi of $^3$H-thymidine per well for the last 24 hours of the total incubation period, harvested, and read on a Top Count Scintillation Counter (Packard Instruments, Meriden, CT). The $EC_{50}$ values—the Adnectin drug conjugate concentration at which 50% of maximum cell proliferation inhibition was achieved—were determined using PRISM™ software, version 4.0 (GraphPad Software, La Jolla, CA, USA).

A summary of the in vitro properties of DAR1 and DAR2 forms of the AdxDC conjugate is summarized in Table 4.

TABLE 4

In vitro characterization of GPC3-Tubulysin AdxDC

| | Non-binding control | Glypican-3-binding |
|---|---|---|
| Adnectin ID | ADX_6093_A01 | ADX_6077_F02 |
| Conjugate | DAR1<br>DAR2 | DAR1<br>DAR2 |
| % monomer | 100% | 100% |
| DSC $T_m$ (PBS) | 86° C. | 89° C., 93° C. |
| SPR $K_D$ (37° C.) | No binding | 12 nM (hu)<br>11 nM (mu) |
| SPR $k_{off}$ (37° C.) | No binding | $9.8\times10^{-4}\ s^{-1}$ (hu)<br>$7.7\times10^{-4}\ s^{-1}$ (mu) |
| Adnectin cell-binding $EC_{50}$ | No binding up to ~200 nM[alk] | 5 nM (hu; Huh7)[alk] |
| AdxDC cell-killing $IC_{50}$ | No effect up to ~25 nM | 0.2 nM (hu; Huh7, HepG2) |

[alk]measured for alkylated (capped Adnectin); all other measurements for DAR1 AdxDC (no PEG)

Example 5: Cell Binding of GPC3-AdxDC to Human Hep3B and H446 Tumor Cells

GPC3 AdxDC were evaluated by flow cytometry for binding to human Hep3B hepatocellular carcinoma cells grown in MEM with 10% FBS, and H446 small cell lung carcinoma cells grown in RPMI with 10% FBS. Cells were harvested using Cellstripper, a non-enzymatic cell dissociation solution from Mediatch (Corning: Manassas, VA 20109), Cat. #25-056-CL. Tumor cells (25,000/reaction) were suspended in FACS buffer (PBS+5% FBS+0.01% $NaN_3$) and mixed with a serial dilution of AdxDC for 1 hour on ice. Cells were washed three times with FACS buffer, and bound AdxDC was detected with His Tag PE-conjugated Antibody from R&D System, cat #IC050P, and read on a flow cytometer. Data analysis was done using FlowJo Software, and EC50 of 50% of maximum binding was determined using PRISM™ software, version 5.0 (GraphPad Software, La Jolla, CA, USA).

The results, which are shown in FIG. 4A-D, show that ADX_6077_F02 AdxDC DAR1 and DAR2 bind to both types of human tumor cells.

Example 6: GPC3 AdxDC Inhibit Cell Growth of Hep3B, H446 and HepG2 Tumor Cells

This Example shows that GPC3 AdxDC DAR1 and DAR2 inhibit cell proliferation of Hep3B (Glypican3 high) HCC cells, H446 (Glypican3 low) SCLC Cells and HepG2 tumor cells. Thymidine incorporation assays were conducted as described above. The results, which are shown in FIGS. 5A-B and 6A-B show that GPC3 AdxDC DAR1 and DAR2 inhibit cell growth of the three different cell lines, but that the control AdxDC adnectin conjugate does not inhibit growth of these cells.

Example 7: Cell Surface Binding Assay Time Course for GPC3-AdxDC

To ensure maximum target engagement prior to internalization studies, binding of ADX_6077_F02 DAR1 (i.e., with a "PC" terminus, but not conjugated) to GPC-3 positive cells Hep3B was determined using the following binding assay: AF-488 fluorescently labeled adnectin ADX_6077_F02 and negative control (NBC) ADX_6093_A01 were used in Hep3B cell binding assay. For binding analysis, Hep3B cells were plated into a 384 well plate, incubated for 16 h to allow cells to adhere and then the cells were fixed with 2% formaldehyde. ADX_6077_F02 and ADX_6093_A01 at 100 nM were added into the cell plate and incubated at room temperature for 7 time points: 0 minute, 10 minutes, 15 minutes, 20 minutes, 60 minutes, 120 minutes and 180 minutes. After binding, the cells were washed with phosphate-buffered saline (PBS) twice and total cell fluorescence intensity per cell was then measured using high content analysis.

The results, indicate that ADX_6077_F02 demonstrated fast association onto cell surfaces. Two hours was found to be sufficient to reach a greater than 95% binding plateau using 100 nM of the Adnectin.

Example 8: Kinetic Internalization of GPC3-AdxDC

To quantify anti-glypican 3 adnectin induced internalization, a high-content Alexa quenching assay was applied. Hep3B and H446 cells were seeded in 384 well plates and incubated for 16 hours at 37° C. AF-488 fluorescently labeled ADX_6077_F02 DAR1 at 100 nM were then added into the cell plates and incubated at 37° C. for the indicated time prior to fixation and quenching. Internalized Adnectin was measured as increased fluorescence above the unquenchable signal. Total fluorescence from "unquenched control" at each time point was monitored in parallel to be used as indicator of the amount of adnectin initially bound to the cells. The images of the cells were taken by Arrayscan to show the localization of the adnectin, and used for cell fluorescence intensity quantification.

Quantification studies confirmed high expression levels of the GPC3 receptor on Hep3B (approximately $1.1\times10^6$ active binding copies/cell) and lower levels on H446 cells (approximately $2.6\times10^5$ active binding copies/cell). Following fixation, total and intracellular FL were determined and used to measure internalization of the Adnectin molecules.

Figure 7A:
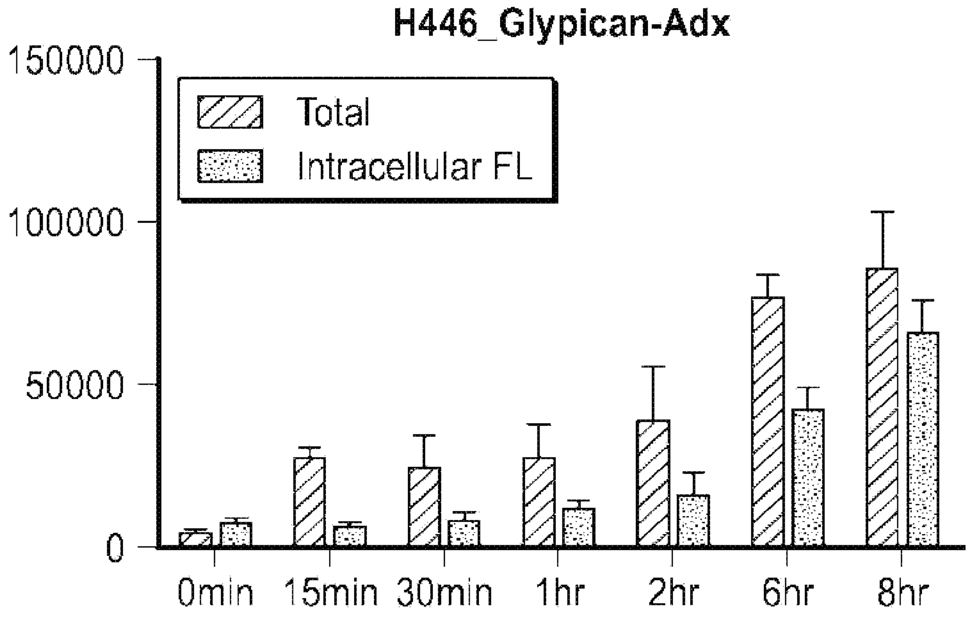
FIGS. 7A and 7B are bar graphs depicting the internalization rate of the anti-GPC3 adnectin, ADX_6077_F02, into H446 and HepB3 cells
Figure 7B:
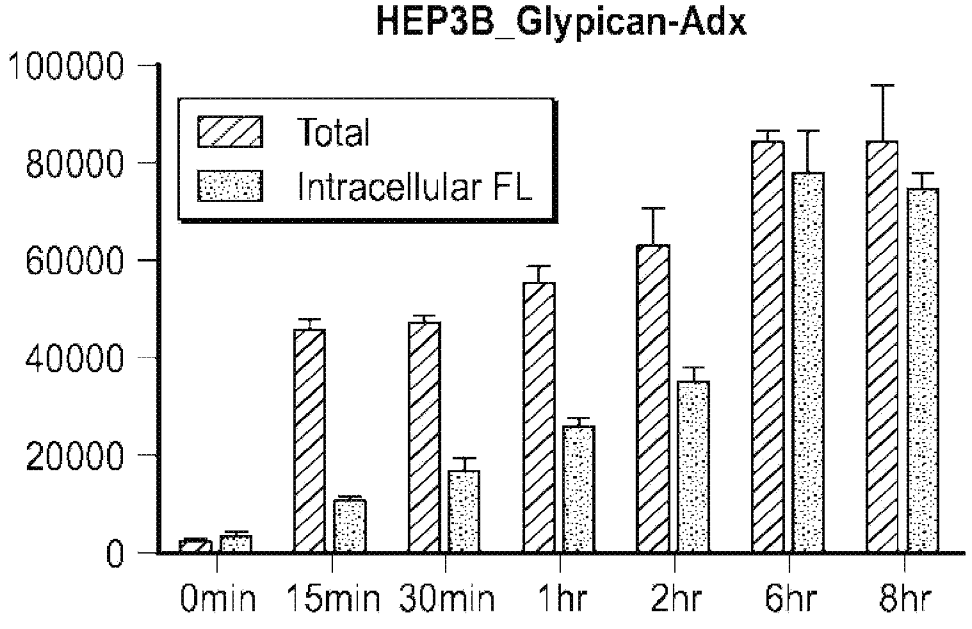
Figure 8A:
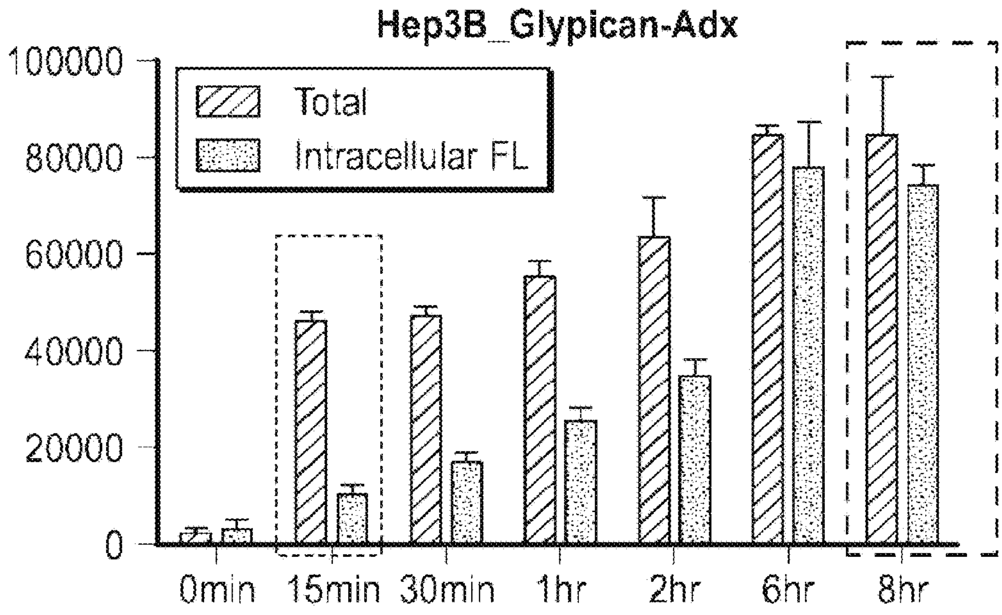
FIGS. 8A-8E depict the membrane and internalized AF488 labeled anti-GPC3 adnectin, ADX_6077_F02, at the 15 minute and 8 hour time points.
Figure 8B:
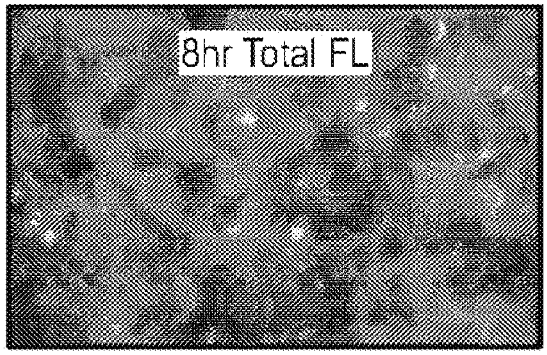
Figure 8C:
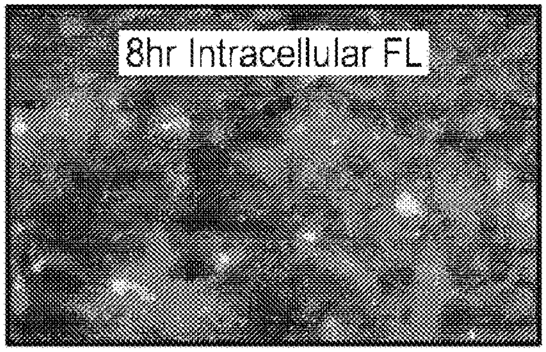
Figure 8D:
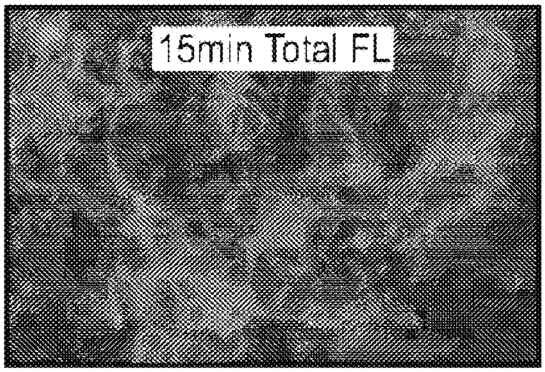
Figure 8E:
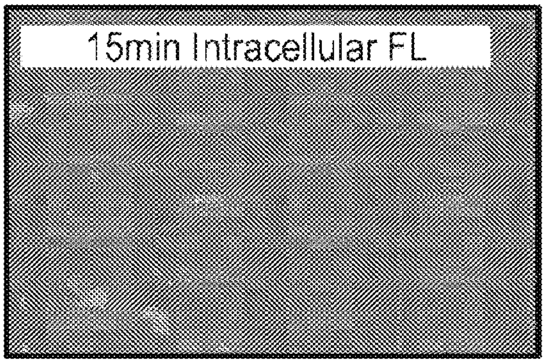

The results of these assays indicate that the anti-GPC3 adnectin is internalized by Hep3B and H446 cells (FIG. 7) at a medium-slow rate ($T_{1/2}$>1 hr) and reaches>90% internalization after 6 hours. As shown in FIG. 8, at the 15 minute time point, most of the anti-GPC3 adnectin is membrane associated, and by the 8 hour time point most of the GPC3-Adectin signal is inside of the cells.

Example 9: In Vivo Pharmacokinetics of GPC3-AdxDC

The systemic exposure profile of anti-GPC3 AdxDC (DAR1) was determined in mice. Female NOD/SCID mice (13 weeks of age) were dosed intravenously with a single dose of high (240 nmol/kg) and low (24 nmol/kg) doses of GPC3-binding and non-binding-control AdxDCs (GPC3 DAR1 AdxDC and RGE AdxDC, respectively) as per the experimental design below. The indicated blood time points were serial tail vein collections using CPD anticoagulant (Citrate-phosphate-dextrose solution, Sigma C7165). Plasma obtained from these blood samples were aliquoted and stored at −80 C until ready for analysis.

TABLE 5

Dosing Schedule for Xenograft Model

| Group | N | Test Article | Dose (nmol/kg) |
|---|---|---|---|
| 1 Low dose | 3 | Glypican3 binding AdxDC | 24 |
| 1 High Dose | 3 | | 240 |

Timepoints: 5 - 20-40 min, 1 - 1.5 - 2 - 3 - 4 - 6 - 8-24 h

AdxDC plasma levels where analyzed using Mesoscale (MSD) ligand binding assays with two different formats. MSD assays for total levels of conjugated and unconjugated Adnectin assays used for capture an in house generated anti-His monoclonal antibody (at 4 ug/ml), and for detection a pooled in-house generated rabbit anti-scaffold polyclonal at 1:10000 dilution followed by a goat anti-rabbit sulfo-tagged antibody (at 1 ug/ml). MSD assays for intact conjugated Adnectin used for capture an in-house generated anti-His monoclonal antibody (at 4 ug/ml), and for detection an in-house generated sulfotagged mouse anti-tubulysin antibody (at 1 ug/ml).

Figure 9:
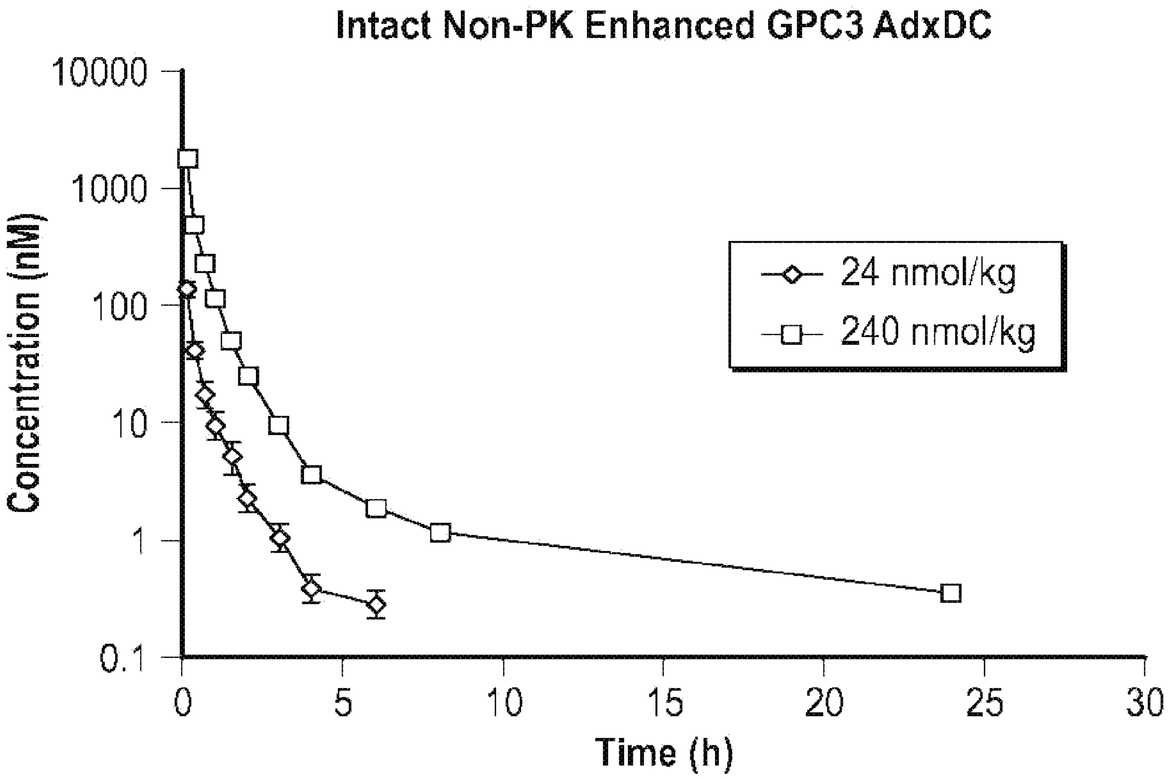
FIG. 9 is a graph depicting the exposure profile of the tubulysin analog-anti-GPC3 adnectin drug conjugate in mice.

The results of this assay, which are summarized in Table 6 (Non compartmental Phoenix WinNonlin analysis, NCA model) and FIG. 9 (Anti-tubulysin MSD assay), further indicate that the AdxDC has a short exposure profile in mice.

TABLE 6

Pharmacokinetics Parameter Summary of GPC3 AdxDC

NCA

| dose | species | HL_Lambda_z (h) | Cl_obs (mL/h/kg) | Vss_obs (mL/kg) | AUCall (h*nmol/L) | AUCINF_obs (h*nmol/L) | AUC_% Extrap_obs (%) | MRTINF_obs (h) | Cmax (nmol/L) |
|---|---|---|---|---|---|---|---|---|---|
| high | total | 0.74 | 288 | 136 | 835 | 836 | 0.11 | 0.47 | 2124 |
| | intact | 0.80 | 353 | 249 | 740 | 740 | 0.06 | 0.71 | 1870 |
| low | total | 0.59 | 344 | 192 | 69 | 70 | 1.12 | 0.56 | 165 |
| | intact | 0.63 | 445 | 233 | 58 | 59 | 0.48 | 0.52 | 145 |

Example 10: Inhibition of Tumor Growth in Rodent Xenograft Models

The efficacy of unPEGylated GPC3-tubulysin drug conjugate was tested in CD1 mice and Fischer rats.

NOD-SCID and CD1 female mice (13 weeks old, from Charles River Laboratories, Wilmington, MA) and female Fischer rats (10 weeks of age, from Charles River laboratories, Wilmington, MA) were housed in a temperature-controlled room with a reversed 12 hour light/dark cycle. Water and standard chow food were available ad libitum Animals for safety studies were randomized and distributed between treatment groups to receive either control or test AdxDC based on body weight (about 20-25 g).

Figure 10A:
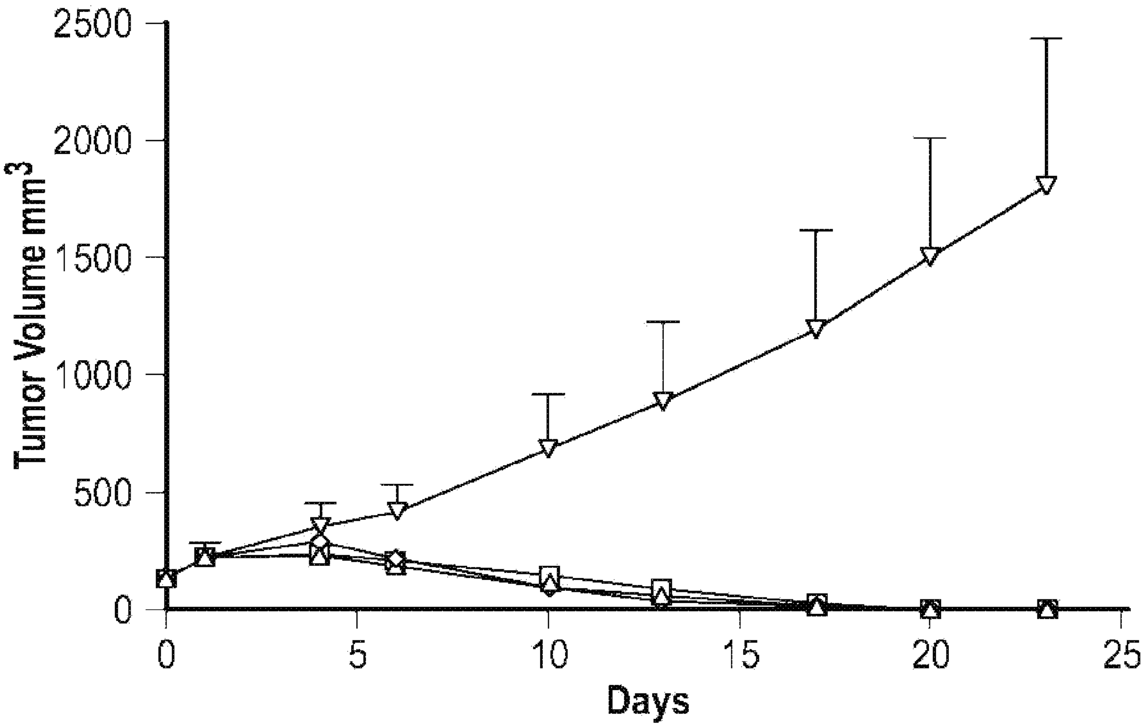
FIGS. 10A and 10B are graphs depicting the efficacy of anti-GPC3 adnectin drug conjugates in a HepG2 xenograft model, as measured by tumor volume shrinkage and percent body weight change.
Figure 10B:
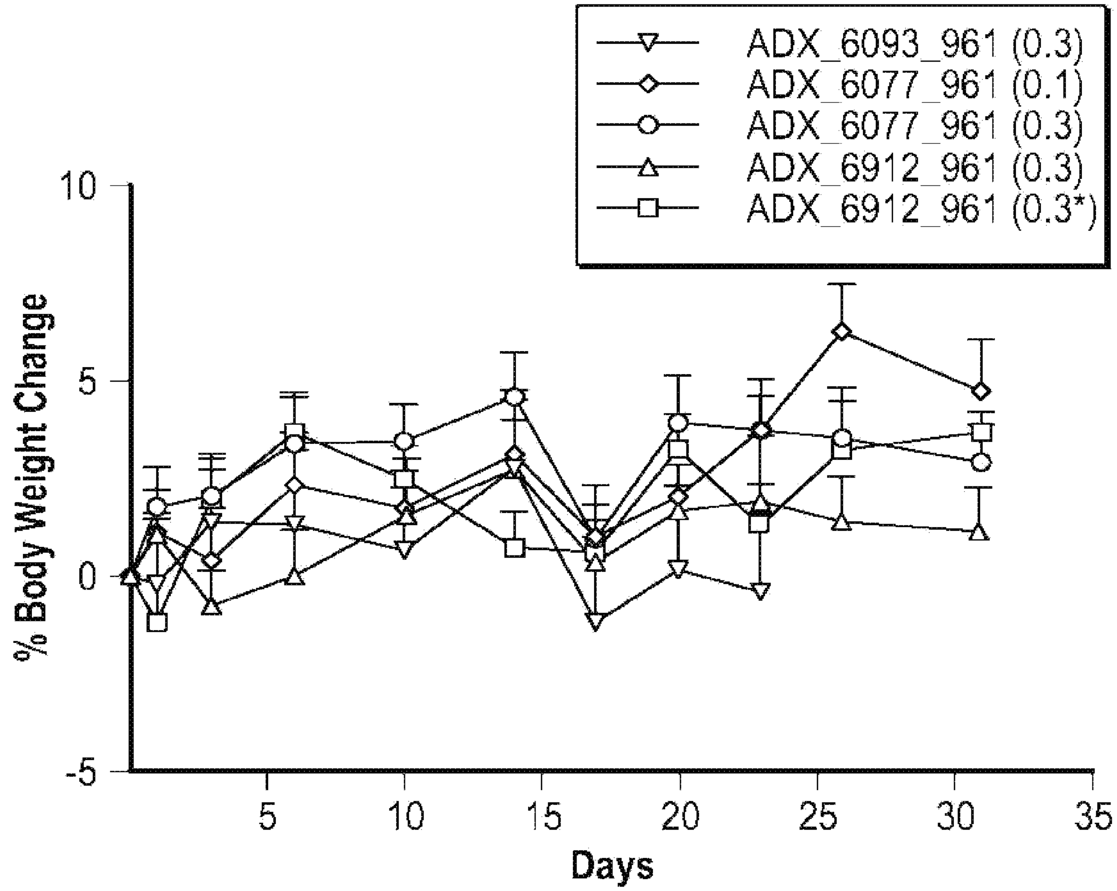
Figure 11A:
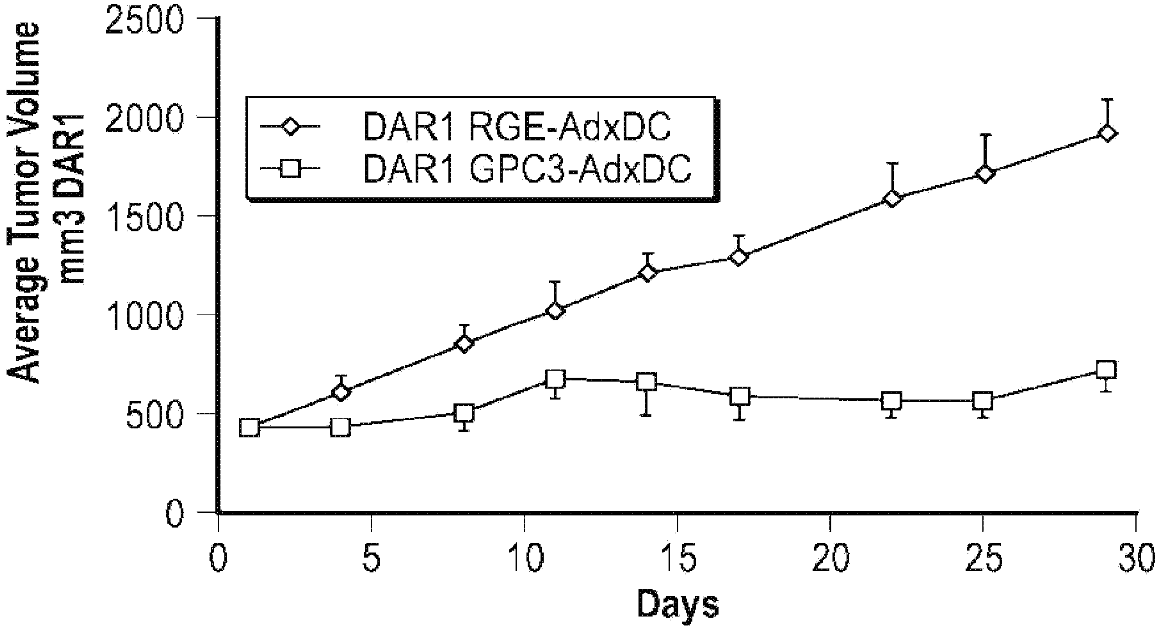
FIGS. 11A-11D are graphs depicting the efficacy of DAR1 and DAR2 in a HepG2 xenograft model ($TV_0$=380-480 $mm^3$), as measured by tumor volume shrinkage and percent body weight change.
Figure 11B:
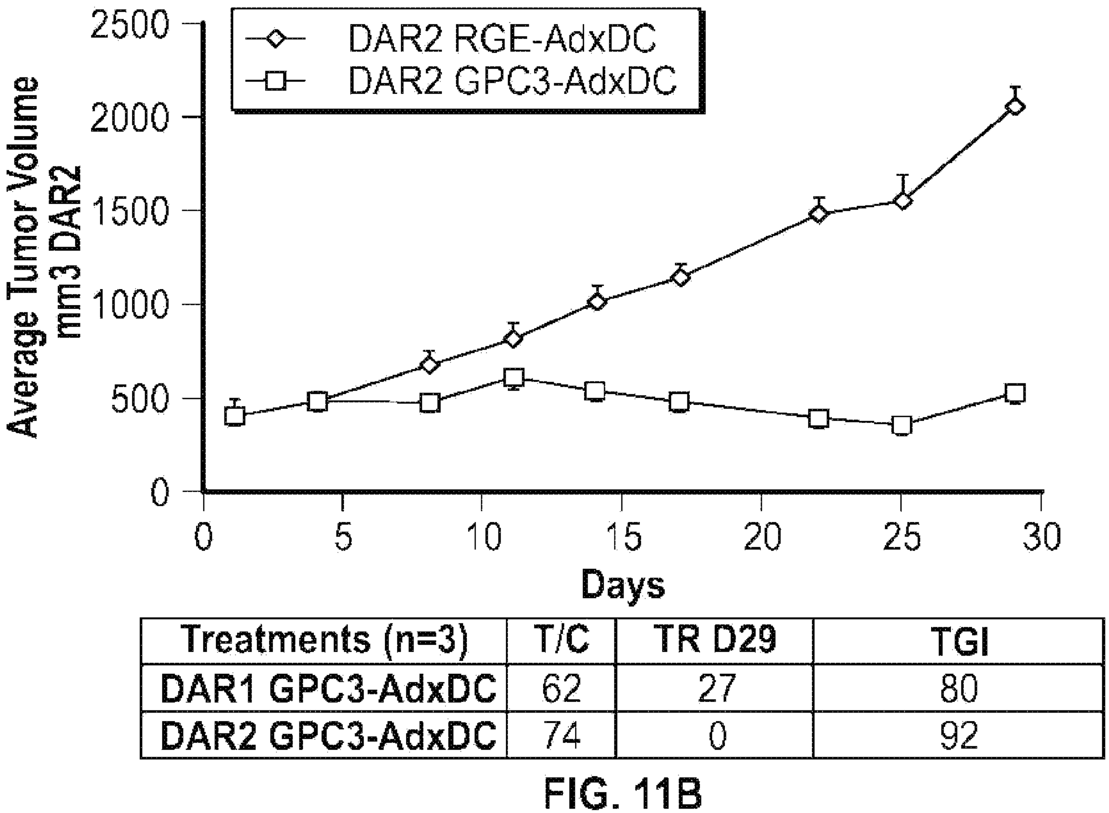
Figure 11C:
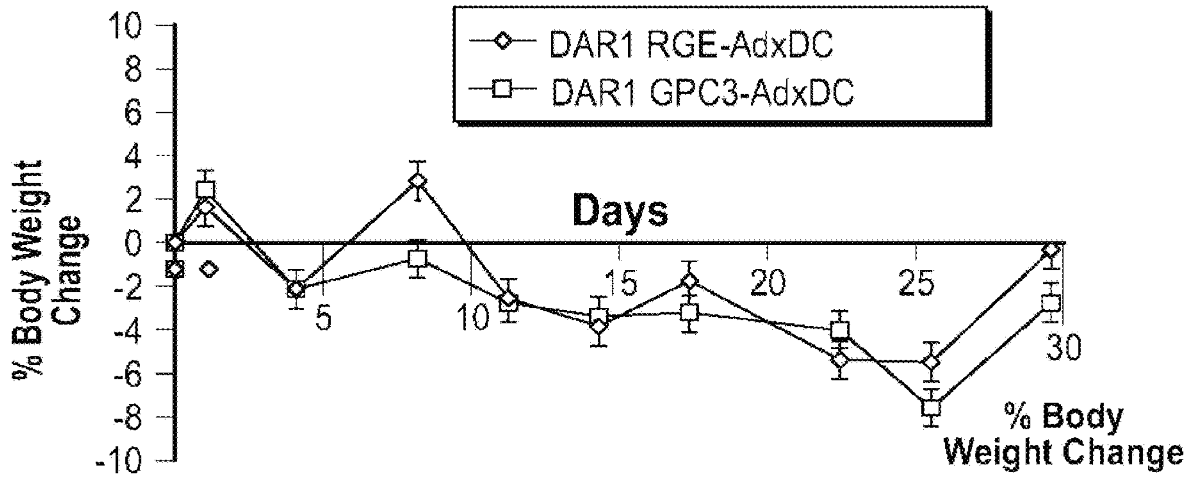
Figure 11D:
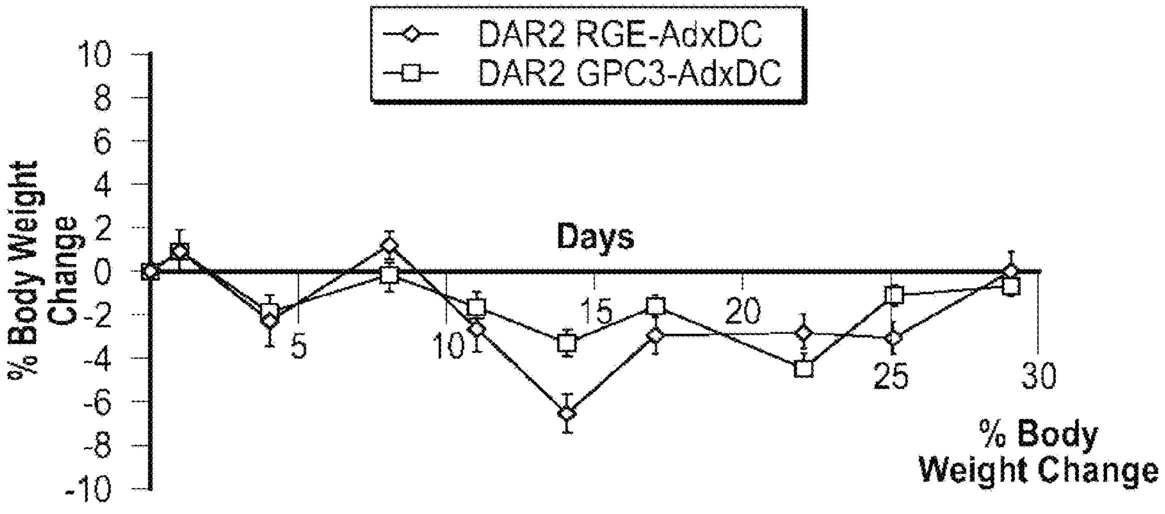

Hep3B, a human hepatocellular carcinoma, was maintained in culture using EMEM Cat #ATCC 30-2003 supplemented with 10% FBS (Thermo Cat #ATK-33398). For efficacy studies, xenografts were generated by subcutaneous implantation of 100 ul of Hep3B $5\times10^6$ cells (50% cellular suspension with Standard Phenol Red Matrigel, Corning Cat #354234) in the right flank of NOD-SCID mice. In order to demonstrate in vivo efficacy, the AdxDCs were administered by intravenous injection in either 50 mM NaOAc/150 mM NaCl/pH 5.5, or Phosphate-Buffered Saline (PBS). Controls were treated with a non-binding control AdxDC. Test animals (n=8 animals/group) were dosed intravenously every three days with a total of six doses, with varying dosages of the AdxDC. Body weight measurements were recorded pre-randomization, on randomization day, and two times a week during the treatment periods and at the end of the study. Tumor growth was monitored using digital caliper measurements twice a week. The results were assessed using student's t-test 2 tailed paired analysis. Representative study design and results using every three days dosing administration are represented in Table 7 and FIG. 10.

TABLE 7

| Dosing Schedule | | | | |
|---|---|---|---|---|
| AdxDC | DAR | Dose μmol/kg | Schedule | T/C (d 17) (%) |
| ADX_6093_A01-961 (non-binding control) | 1 | 0.3 | Every 3 days | |
| ADX_6077_F02-961 | 1 | 0.1 | Every 3 days | 96 |
| ADX_6077_F02-961 | 1 | 0.3 | Every 3 days | 95 |
| ADX_6912_G02-961 | 2 | 0.3 | Every 3 days | 96 |
| ADX_6912_G02-961 | 2 | 0.3 | Every 5 days | 96 |

Figure 12A:
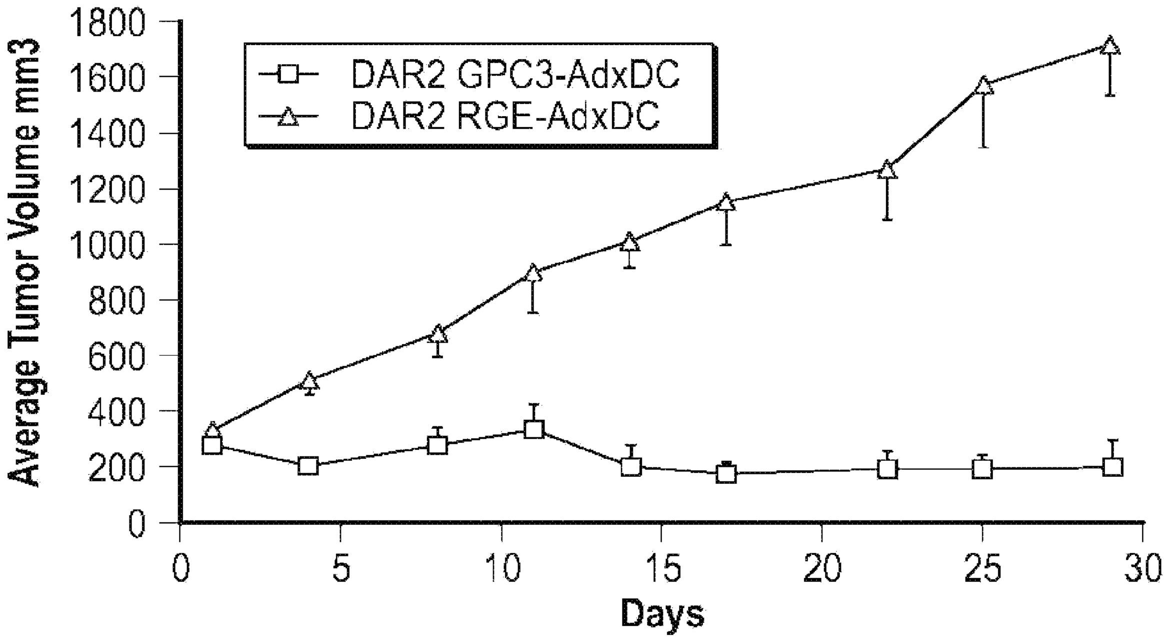
FIGS. 12A and 12B are graphs depicting the efficacy of DAR2 in a HepG2 xenograft model ($TV_0$=228-350 $mm^3$), as measured by tumor volume shrinkage and percent body weight change.
Figure 12B:
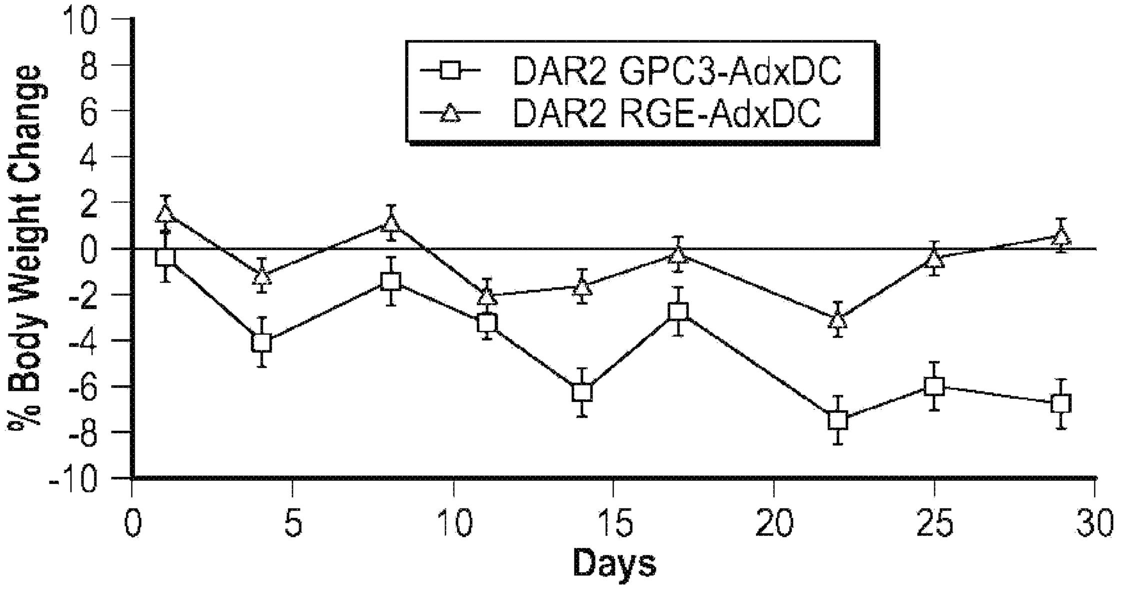
Figure 13A:
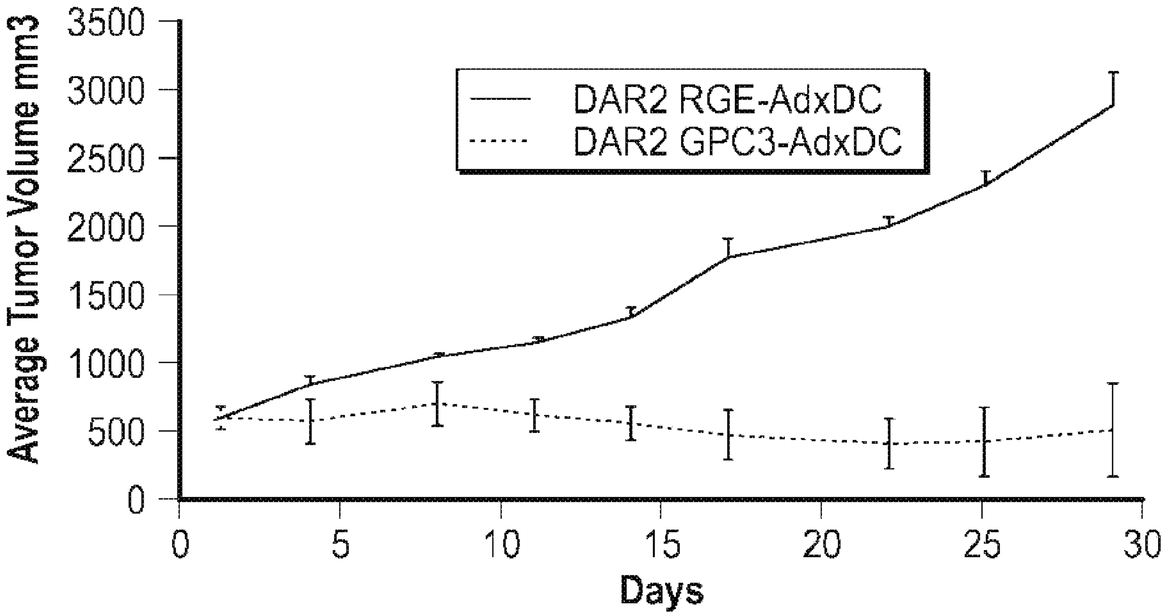
FIGS. 13A and 13B are graphs depicting the efficacy of DAR2 in a HepG2 xenograft model ($TV_0$=514-673 $mm^3$), as measured by tumor volume shrinkage and percent body weight change.
Figure 13B:
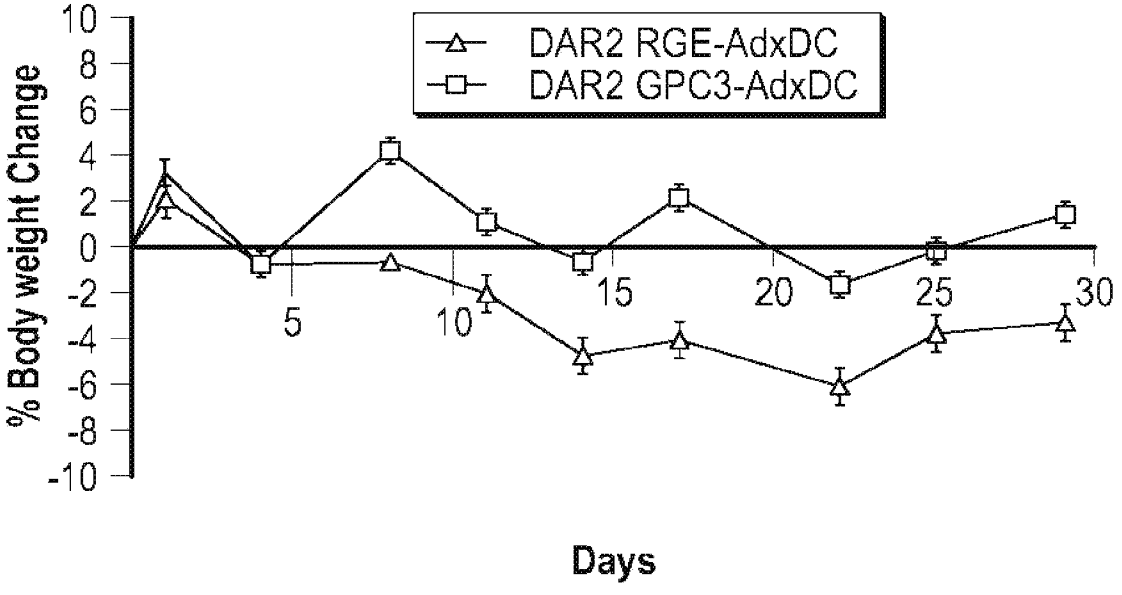

Weekly administration was evaluated in Hep3B xenografts. The results indicate that QW administration of ADX_6077_F02-961 DAR1 and DAR2 at 0.1 μmol/kg effectively inhibited HepG2 xenografts $TV_0$=380-480$^3$ (FIG. 11), $TV_0$=228-350 $mm^3$ (FIG. 12), and $TV_0$=514-673 $mm^3$ (FIG. 13).

In summary, weekly administration of GPC3 AdxDCs inhibits growth of HCC tumor xenografts, and DAR1 and DAR2 GPC3 AdxDCs demonstrated equivalent tumor growth inhibition, which was target-dependent. In addition, the prevention of tumor burden-induced weight loss was associated with the anti-tumor activity of the GPC3 AdxDCs.

In mice safety studies, CD1 mice treated intravenously every other day for a total of 9 doses at varying doses up to a highest dose of 0.5 umol/kg, 5× the efficacious dose (0.1 umol/kg) with both GPC3 and non-binding control AdxDCs. No MTD was identified in the CD1 mice safety studies. No kidney toxicity was observed for any group, at any dose or frequency. In CD1 mice, the half-life of the AdxDC was approximately 20 minutes (MSD assays as described above). No body weight loss was observed and all mice survived treatment to scheduled necroscopy. Serum chemistry and hematology were evaluated at intervals through the dosing period using Abaxis Veterinary Diagnostics instruments, VETSCAN VS2 and HM5, respectively. There were no significant differences observed in serum chemistry or hematology compared to baseline. Histopathology was evaluated via H&E staining of heart, liver, spleen and kidney tissues collected at the end of the study. No dose-limiting toxicities were observed in any of the evaluated tissues, and minimal/mild tubular epithelium neuropathy was observed in all groups.

In Fischer rat safety studies, the half life of the AdxDC was approximately 30 minutes (MSD assays as described above). Some dose dependent tolerability and skeletal muscle degeneration were observed at the most frequent administration (every other day) of doses of 0.36 umol/kg with no changes in bone marrow or liver histopathology or heart toxicity. These findings were not observed when the same rat studies were conducted using weekly administration of AdxDCs at the same dosage range.

Overall, excellent efficacy despite the short plasma half-life and low off-target toxicity, consistent with low systemic exposure, was observed in both rodent species.

Example 11: Mapping of Adnectin Binding Site on Human GPC3 Using HDX-MS

The Adnectin binding site on human GPC3 (amino acid sequence shown in FIG. 14) was evaluated using hydrogen-deuterium exchange mass spectrometry (HDX-MS). The hydrogen/deuterium exchange mass spectrometry (HDX-MS) method probes protein conformation and conformational dynamics in solution by monitoring the deuterium exchange rate and extent in the backbone amide hydrogens. The level of HDX depends on the solvent accessibility of backbone amide hydrogens and the conformation of the protein. The mass increase of the protein upon HDX can be precisely measured by MS. When this technique is paired with enzymatic digestion, structural features at the peptide level can be obtained, enabling differentiation of surface exposed peptides from those folded inside, or from those sequestered at the interface of a protein-protein complex. Typically, the deuterium labeling and subsequent quenching experiments are performed, followed by online pepsin digestion, peptide separation, and MS analysis.

Figure 14:
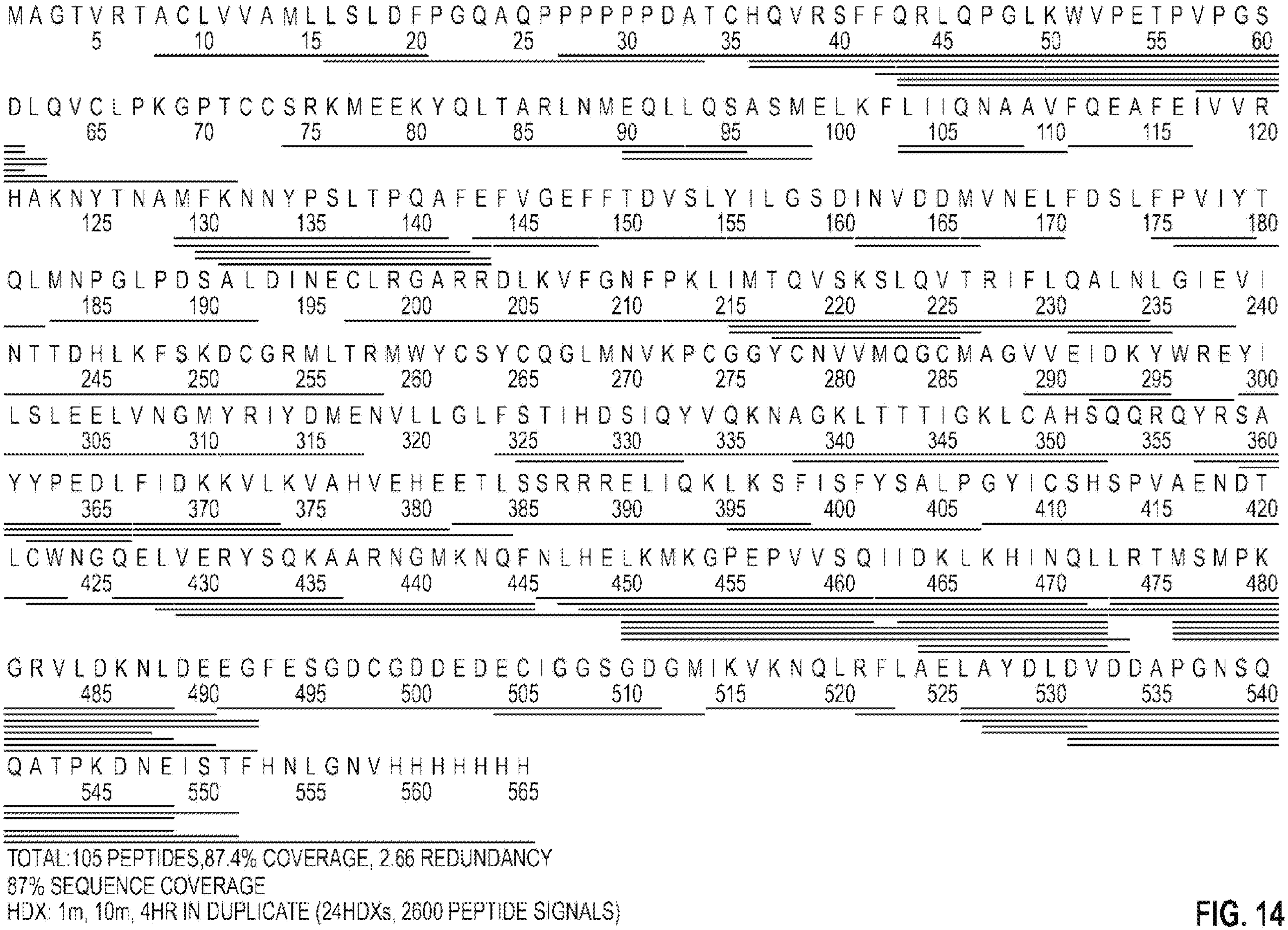
FIG. 14 depicts the common peptic peptides for human GPC3 (amino acids 1-559 of SEQ ID NO: 344, followed by 6× his) determined by mass spectrometry.

Prior to mapping the Adnectin binding site on human GPC3 recognized by ADX_6077_F02 by HDX-MS, non-deuteriated experiments were performed to generate a list of common peptic peptides for GPC3 samples, achieving a sequence coverage of 87.4% for GPC3 (FIG. 14). In this experiment, 10 mM phosphate buffer (pH 7.0) was used during the labeling step, followed by adding quenching buffer (200 mM phosphate buffer with 4M GdnC1 and 0.4M TCEP, pH 2.5, 1:1, v/v).

Figure 15:
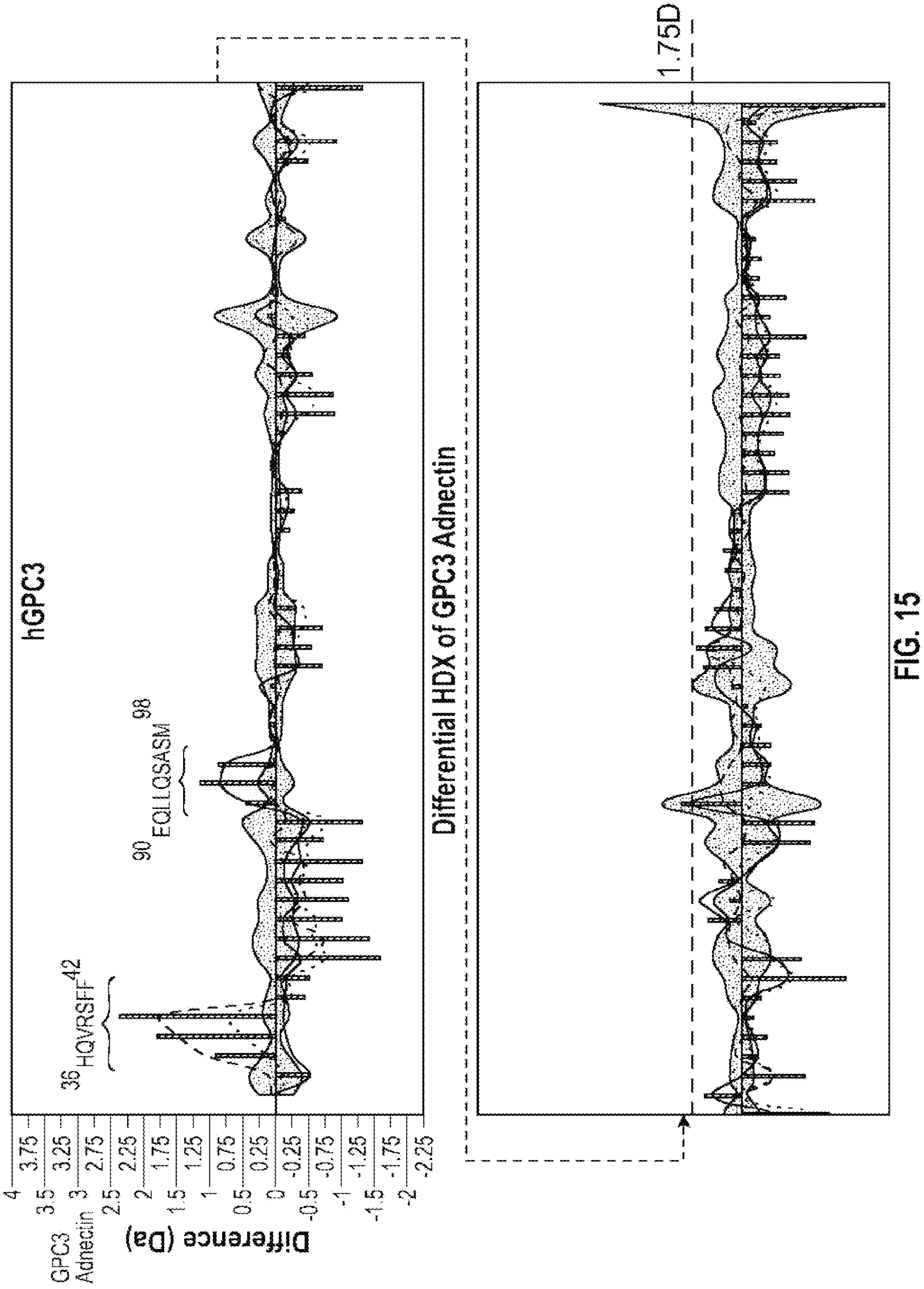
FIG. 15 is a graphic depiction of the ADX_6077_F02 adnectin binding site on human GPC3, as determined by HDX-MS.

For Adnectin binding site mapping experiments, 5 μL of each sample (GPC3 or GPC3 with ADX_6077_F02) was mixed with 55 μL HDX labeling buffer (10 mM phosphate buffer in D20, pD 7.0) to start the labeling reactions. The reactions were carried out for different periods of time: 1 min, 10 min, and 240 min. By the end of each labeling reaction period, the reaction was quenched by adding quenching buffer (1:1, v/v) and the quenched sample was injected into Waters HDX-MS system for analysis. The observed common peptic peptides were monitored for their deuterium uptake levels in the absence/presence of ADX_6077_F02 (FIGS. 14 and 15).

Experimental data obtained from HDX-MS measurements indicate that AADX_6077_F02 recognizes a discontinuous Adnectin binding site comprised of two peptide regions in human GPC3:

Region 1: HQVRSFF (amino acid residues 36-42 of GPC3); SEQ ID NO: 356

Region 2: EQLLQSASM (amino acid residues 90-98 of GPC3); SEQ ID NO: 346

Example 12: Generation of DG Variants

Analysis of the amino acid sequence of ADX_6077_F02 indicated that the DG in the FG loop of the molecule might be at low risk of aspartate isomerization.

(SEQ ID NO: 118)
MGVSDVPRDLEVVAATPTSLLISWSDDYHAHRYYRITYGETGGNSPVQEF

TVPGEHVTATISGLKPGVDYTITVYAVTYDGEKAATDWSISINYRTPCHH

HHHH

Eight variants of ADX_6077_F02 with mutations at the DG site were generated. The sequences of these mutants are summarized in Table 8.

TABLE 8

| ADX_6077_F02 Variants | | | |
|---|---|---|---|
| | C-term elements | Modification | Protein sequence |
| DG→EG mutant | Cys | alkylated | GVSDVPRDLEVVAATPTSLLISWSDDYHAH RYYRITYGETGGNSPVQEFTVPGEHVTATIS GLKPGVDYTITVYAVTY**EG**EKAATDWSISIN YRTPC* (SEQ ID NO: 143) |
| DG→SG mutant | Cys | alkylated | GVSDVPRDLEVVAATPTSLLISWSDDYHAH RYYRITYGETGGNSPVQEFTVPGEHVTATIS GLKPGVDYTITVYAVTY**SG**EKAATDWSISIN YRTPC* (SEQ ID NO: 169) |
| DG→AG mutant | Cys | alkylated | GVSDVPRDLEVVAATPTSLLISWSDDYHAH RYYRITYGETGGNSPVQEFTVPGEHVTATIS GLKPGVDYTITVYAVTY**AG**EKAATDWSISI NYRTPC* (SEQ ID NO: 197) |
| DG→GG mutant | Cys | alkylated | GVSDVPRDLEVVAATPTSLLISWSDDYHAH RYYRITYGETGGNSPVQEFTVPGEHVTATIS GLKPGVDYTITVYAVTY**GG**EKAATDWSISI NYRTPC* (SEQ ID NO: 224) |
| DG→DS mutant | Cys | alkylated | GVSDVPRDLEVVAATPTSLLISWSDDYHAH RYYRITYGETGGNSPVQEFTVPGEHVTATIS GLKPGVDYTITVYAVTY**DS**EKAATDWSISIN YRTPC* (SEQ ID NO: 251) |
| DG→DA mutant | Cys | alkylated | GVSDVPRDLEVVAATPTSLLISWSDDYHAH RYYRITYGETGGNSPVQEFTVPGEHVTATIS GLKPGVDYTITVYAVTY**DA**EKAATDWSISIN YRTPC* (SEQ ID NO: 278) |
| DG→DL mutant | Cys | alkylated | GVSDVPRDLEVVAATPTSLLISWSDDYHAH RYYRITYGETGGNSPVQEFTVPGEHVTATIS GLKPGVDYTITVYAVTY**DL**EKAATDWSISIN YRTPC* (SEQ ID NO: 305) |
| DG→DV mutant | Cys | alkylated | GVSDVPRDLEVVAATPTSLLISWSDDYHAH RYYRITYGETGGNSPVQEFTVPGEHVTATIS GLKPGVDYTITVYAVTY**DV**EKAATDWSISIN YRTPC* (SEQ ID NO: 332) |

Example 13: Biophysical Characterization of DG Variants

One-hundred to one-hundred-fifty milligrams of each of the eight mutants was made, purified and alkylated as previously above. Three to five milligrams of each of eight alkylated variants at 1-3 mg/mL were subjected to SEC, DSC, GPC3 binding (SPR 1 pt off-rates), MS and HIC. The results are summarized in Table 9.

TABLE 9

| Biophysical properties of ADX_6077_F02_DG Variants | | | | | |
|---|---|---|---|---|---|
| Mutant | Clone ID | huGPC3 $k_{off}$ (mut/par) | muGPC3 $k_{off}$ (mut/par) | mono % (SEC) | $T_m$ (DSC) |
| DG→EG | P1-055673 | 5.4 | 5.1 | 96% | 88° C. |
| DG→SG | P1-055668 | 5.2 | 4.8 | 96% | 85, 91° C. |
| DG→AG | P1-055669 | 5.9 | 5.5 | 96% | 85, 91° C. |
| DG→GG | P1-055670 | 14 | 12 | 96% | 84, 90° C. |
| DG→DS | P1-055667 | 3.5 | 3.3 | 96% | 84° C. |
| DG→DA | P1-055660 | 3.9 | 3.7 | 96% | 86, 98° C. |
| DG→DL | P1-055671 | 3.6 | 3.1 | 96% | 84° C. |
| DG→DV | P1-055672 | 7.9 | 7.0 | 96% | 84° C. |

Six of the eight DG mutants demonstrated a 3-5 fold increase in $k_{off}$ compared to the parental adnectin, and were monomeric and thermostable. The binding affinities of the alkylated GPC3 DG mutant adnectins for human and murine GPC3 were further evaluated by Biacore T100 using HBS-P+ running buffer with direct immobilization of human and mouse GPC3 proteins [Hu (Fc 2,3) and Mu (Fc 4) GPC3-His (R&D Systems)] with a 200-1.56 nM series injected for 180s association, 600s dissociation. The data fit a 1:1 binding model in BiaEvaluation software and is summarized in Table 10.

TABLE 10

| Binding Kinetics of DG Mutant Adnectins | | | | | | | | |
|---|---|---|---|---|---|---|---|---|
| | huGPC3 | | | | muGPC3 | | | |
| Description | ka (1/Ms) | kd (1/s) | KD (M) | Fold affinity (KD) difference vs alkylated parent | ka (1/Ms) | kd (1/s) | KD (M) | Fold affinity (KD) difference vs alkylated parent |
| ADX_6077_F02 alkylated | 9.53E+04 | 5.34E−04 | 5.60E−09 | 1.0 | 1.3E+05 | 4.9E−04 | 3.8E−09 | 1.0 |
| 6077_F02 DG−>DA | 7.22E+04 | 1.83E−03 | 2.54E−08 | 4.5 | 1.0E+05 | 1.7E−03 | 1.6E−08 | 4.3 |
| 6077_F02 DG−>DS | 7.16E+04 | 1.66E−03 | 2.33E−08 | 4.2 | 1.0E+05 | 1.5E−03 | 1.5E−08 | 3.9 |
| 6077_F02 DG−>SG | 9.40E+04 | 2.21E−03 | 2.35E−08 | 4.2 | 1.3E+05 | 2.0E−03 | 1.6E−08 | 4.1 |
| 6077_F02 DG−>AG | 1.03E+05 | 2.43E−03 | 2.37E−08 | 4.2 | 1.4E+05 | 2.1E−03 | 1.5E−08 | 4.0 |
| 6077_F02 DG−>DL | 7.26E+04 | 1.59E−03 | 2.19E−08 | 3.9 | 1.0E+05 | 1.5E−03 | 1.5E−08 | 3.8 |
| 6077_F02 DG−>DV | 7.10E+04 | 3.09E−03 | 4.35E−08 | 7.8 | 8.5E+04 | 2.5E−03 | 3.0E−08 | 7.8 |
| 6077_F02 DG−>EG | 7.63E+04 | 2.29E−03 | 3.00E−08 | 5.3 | 1.1E+05 | 2.1E−03 | 1.9E−08 | 5.1 |

Figure 16A:
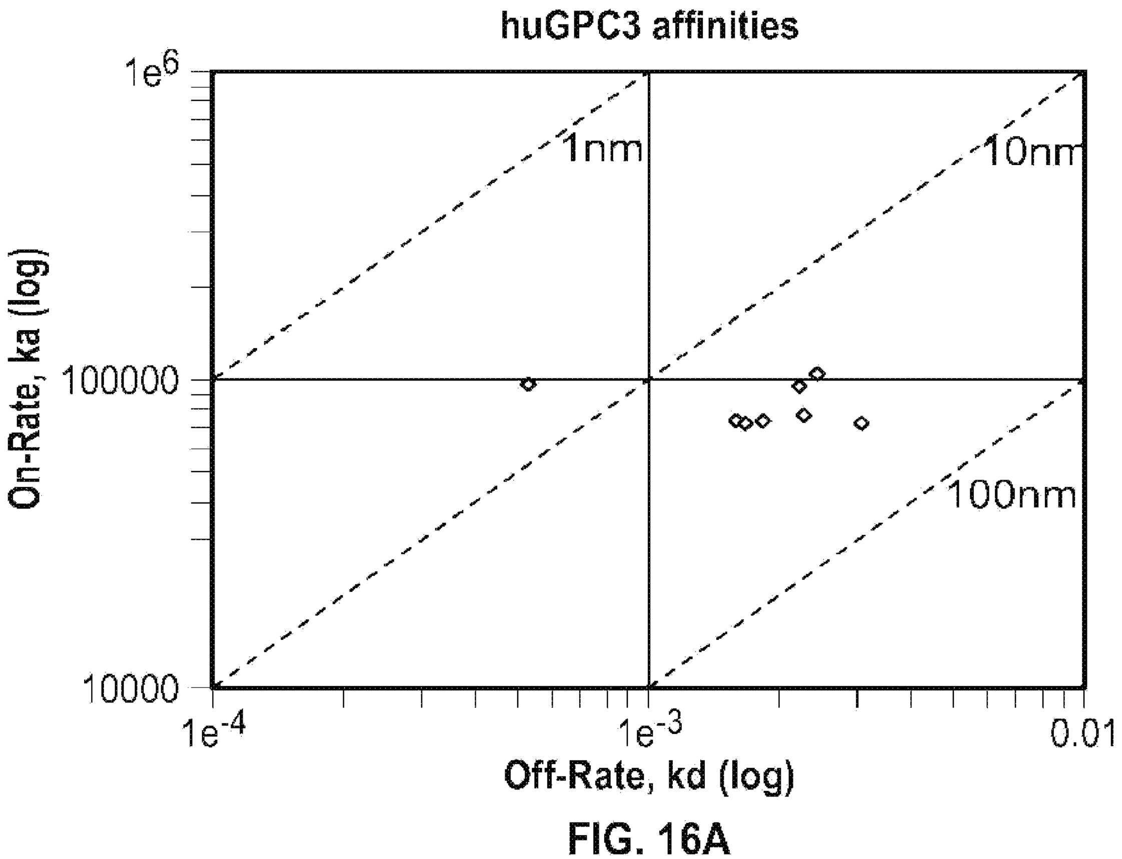
FIGS. 16A and 16B are graphic comparisons of the binding kinetics of anti-GPC3 DG mutants with the parent anti-GPC3 adnectin.
Figure 16B:
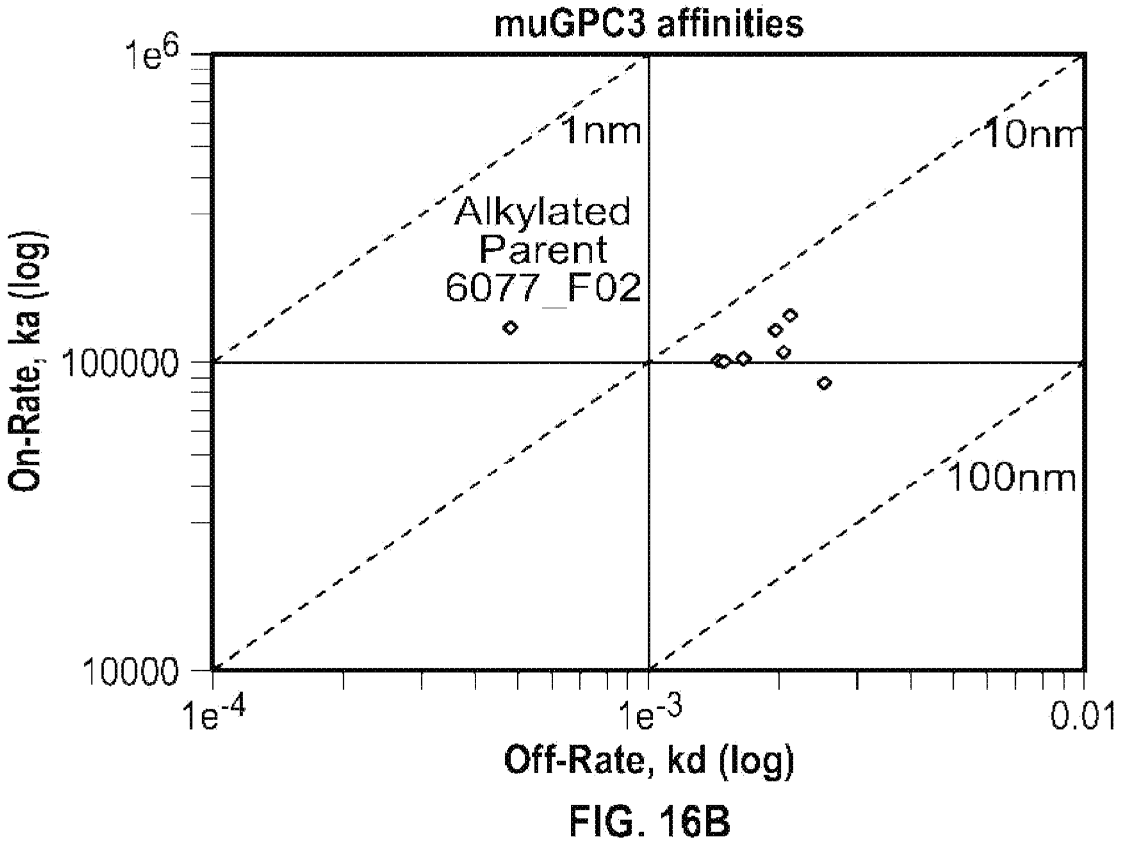

The data demonstrated that these GPC3 DG mutants have approximately 3-5 fold decreased affinity for human and murine GPC3 compared to parental ADX_6077_F02. The differences in affinities were driven by faster off-rates, whereas the on-rates were consistent with the parental adnectin (FIG. 16).

Example 14: Cell Binding and Immunogenicity Assessment of DG Variants

The binding of DG variants to huGPC3 in DG GPC3 AdxDCs mutants were evaluated by flow cytometry for binding to Huh7 carcinoma cells grown in DMEM media with 10% FBS. Cells were harvested using Versene, an EDTA cell dissociation solution from Lonza, Cat. #17-711E. Tumor cells (1E5 cells/reaction) were suspended in FACS buffer (PBS, 1% BSA, 0.05% Na Azide) and mixed with a serial dilution of AdxDC for one hour on ice. Cells were washed three times with FACS buffer, and bound AdxDC was detected with an in house anti-scaffold monoclonal Ab and PE-conjugated Antibody from (RnD Systems), cat #NL007, and read on a flow cytometer. Data analysis was done using FlowJo Software, and EC50 of 50% of maximum binding was determined using PRISM™ software, version 5.0 (GraphPad Software, La Jolla, CA, USA).

For anti-His detection of (non DG mutants), the same protocol was used, except in house generated APC-conjugated anti-His antibody was used.

The results, which are shown in Table 11, indicate that the mutants had similar EC50 values as that of the parent Adnectin.

The DG variants to huGPC3 were also assessed for their potential to elicit an immune response in humans using a human PBMC proliferation assay. PBMCs from 40 donor with HLA Class II haplotypes closely matching the world population frequencies were cultured in the presence of the DG variants or controls for 7 days. At the end of the assay, CFSE-labeled CD4+ T cells were analyzed by FACS for proliferation. The percentage of donors that showed proliferating CD4+ T cells were analyzed as a read-out for human immunogenicity risk. Assay results indicate that the DG to DA mutant (PI-055660) has a significantly lower risk for immunogenicity (IMG) (18% of donors responded positive) compared to the other DG mutants (36-54% positive responses) as summarized in Table 11.

TABLE 11

| Cell Binding Kinetics of DG Variants | | | |
|---|---|---|---|
| Mutant | Clone ID P1- | huGPC3 on cells $EC_{50}$ (mutant/parent) | IMG: % +ve responders |
| DG→EG | 055673 | 1.6 | 49% |
| DG→SG | 055668 | 1.1 | 41% |
| DG→AG | 055669 | 1.1 | 54% |
| DG→DS | 055667 | 1.4 | 36% |
| DG→DA | 055660 | 1.3 | 18% |
| DG→DL | 055671 | 1.7 | 54% |

A summary of the characteristics of the DA variant AdxDC DAR1 ("GPC3_AdxDC DA variant-DAR1" or "DA variant AdxDC DAR1") are set forth in Table 12:

TABLE 12

| Characteristics of the DA variant AdxDC DAR1 | |
|---|---|
| % monomer | 100% |
| DSC $T_m$ (PBS) | 79, 87° C. |
| SPR $K_d$ | 25 nM (hu, 37° C.)<br>23 nM (mu, 37° C.) |
| SPR $k_{off}$ | $2.1 \times 10^{-3}$ $s^{-1}$ (hu, 37° C.)<br>$9.5 \times 10^{-4}$ $s^{-1}$ (mu, 37° C.) |
| Cell-binding $EC_{50}$ (Huh7) | 2.2 nM * |
| Cell-killing $IC_{50}$ (Huh7) | 0.2 nM |

* Measured for unconjugated protein

Example 15: FITC Labeled and PEGylated Anti-GPC3 Adnectins

FITC Labeling: ADX_6077_F02 and non-binding control Adnectin were reduced with DTT or TCEP followed by G25 gel filtration chromatography or dialysis. Excess Fluorescein-5-maleimide reagent (Thermo Scientific) was then added and the mixture incubated at room temperature for approximately 2 hours followed by G25 gel filtration chromatography or extensive dialysis (3-4 buffer changes). The resulting degree of labeling was measured by absorbance following the manufacturer's instructions and/or by mass spectrometry. The binding affinities of FITC-labeled and PEGylated GPC3 for human and murine GPC3 was evaluated as described in the previous Examples, and the results are summarized in Table 13.

TABLE 13

Kinetics of Modified GPC3 Adnectins

| | huGPC3 | | | muGPC3 | | |
|---|---|---|---|---|---|---|
| Adnectin | ka (1/Ms) | kd (1/s) | KD (M) | ka (1/Ms) | kd (1/s) | KD (M) |
| ADX_6077_F02 alkylated | 8.90E+04 | 5.24E−04 | 5.88E−09 | 1.23E+05 | 4.53E−04 | 3.69E−09 |
| 6077_F02-FITC | 8.15E+04 | 4.98E−04 | 6.11E−09 | 1.12E+05 | 4.46E−04 | 3.97E−09 |
| RGE-FITC | | No binding | | | No binding | |
| 6077_F02.dPEG | 7.35E+04 | 6.02E−04 | 8.19E−09 | 1.03E+05 | 5.59E−04 | 5.43E−09 |
| 6077_F02.dPEG | 7.50E+04 | 6.07E−04 | 8.10E−09 | 1.06E+05 | 5.57E−04 | 5.26E−09 |
| 6077_F02-PEG3.4 | 7.18E+04 | 5.84E−04 | 8.14E−09 | 1.02E+05 | 5.23E−04 | 5.12E−09 |

The data demonstrated that both FITC-labeled and PEGylated anti-GPC3 adnectins retained binding affinity to both human and murine GPC3.

Example 16: Additional Characteristics of GPC3_AdxDC DA and DG Molecules

The GPC3_AdxDC DA variant-DAR1 was shown to be chemically and biophysically stable at pH 6.0, in accelerated-stability studies. In addition, its affinity for human GPC3 (by SPR) was unchanged after 4 weeks at 40° C.

Aspartate isomerization of the DA variant was about 4 fold lower than that of the parent DG molecule. The percent isomerization of D80 of the DG molecule, after incubation for 3 weeks at 40° C. at pH 6 or pH 7 was 3.6 and 2.4, respectively.

The GPC3_AdxDC (DG) shows a favorable toxicity profile under weekly dosing in CDF rats (Q7Dx4) (Table 14). No adverse responses were seen in hematology or serum chemistry profiles in CDF rats under weekly administration of GPC3 AdxDC (Q7Dx4).

TABLE 14

Toxicity profile of GPC3_AdxDC (DG)

| Treatment (umol/kg) | | Heart (degeneration) | Liver (↑ mitosis) | Skeletal Muscle (regeneration) | Kidney (↑ mitosis) |
|---|---|---|---|---|---|
| NBC* AdxDC | 0.28 | minimal | none | none | minimal |
| GPC3 AdxDC | 0.093 | none | none | none | none |
| | 0.28 | none | none | none | minimal |

*"NBC" refers to non-binding AdxDC (Adnectin Drug Conjugate)

Example 17: GPC3 Adnectin Drug Conjugates Bind Human GPC3 Xenograft Tissue In Vivo Human GPC3 high expression Hep3B xenograft tissue was incubated with FITC-conjugated GPC3-binding Adnectin DG molecule ("GPC3_AdxDC (DG)") DAR1 at a concentration of 0.04 μg/ml or with a non GPC3 binding Adnectin at 0.2 μg/ml. The results indicate that the GPC3_AdxDC (DG) molecule binds Hep3B xenograt tissue, whereas the non-binding Adnectin did not significantly bind.

Other tissues were also tested for binding, and the results indicate that there is some non-specific binding of GPC3_AdxDC (DG) to placenta. However, the molecule does not bind significantly to stomach, heart, kidney, liver, skin or tonsil tissue.

GPC3_AdxDC (DA) DAR1 shows similar but weaker binding in Xenograft Hep3B. Saturated binding was achieved at 0.2 μg/ml.

Example 18: GPC3_AdxDC (DA) is Highly Efficacious in Cell-Line—Derived Xenografts with High Expression of Glypican-3

Hep3B (hepatocellular carcinoma; 260,000 GPC3 molecules/cell) xenografts were used in NSG mice. GPC3_AdxDC (DA) DART or a non-binding control Adnectin were administered i.v. weekly, 3 times, at the doses indicated in Table 15.

TABLE 15

Dosage and tumor growth inhibition of Hep3B xenografts in NSG mice

| | Dose | | $TGI_{D26}$* |
|---|---|---|---|
| AdxDC | mpk | μmol/kg | (%) |
| GPC3_AdxDC (DA) | 1.4 | 0.12 | 109 |
| | 0.5 | 0.04 | 103 |
| | 0.1 | 0.01 | 62 |
| | 0.05 | 0.004 | 20 |
| Non-binding Adnectin (RGE; −ve control) | 1.4 | 0.12 | — |

$TGI_{D26}$*: Tumor Growth Inhibition at Day 26

Figure 17:
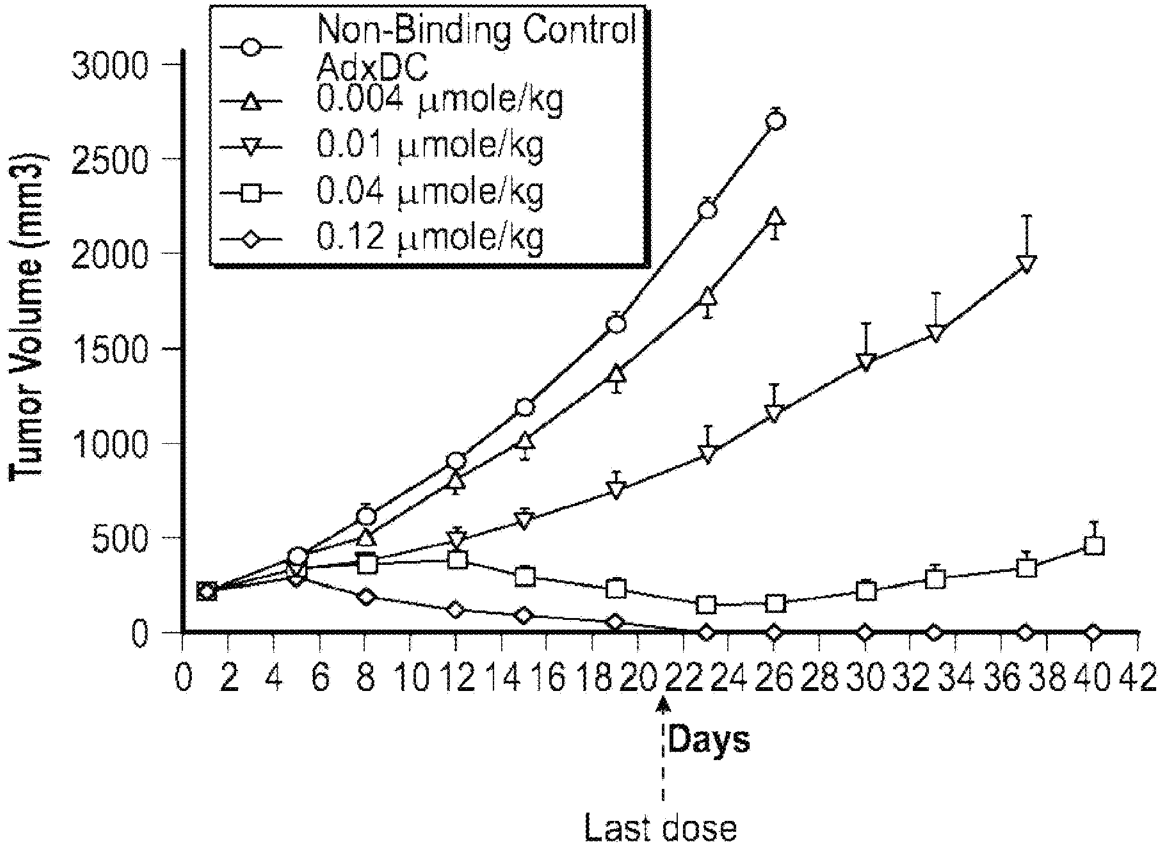
FIG. 17 shows tumor volume as a function of days after administration of various doses of GPC3_AdxDC DA or control non-binding AdxDC to NSG mice implanted with Hep3B tumor cells, showing that GPC3_AdxDC DA is efficacious in cell line derived xenografts with high expression of glypican-3.

The results, which are shown in Table 15 and FIG. 17, indicate that GPC3_AdxDC (DA) is effective in inhibiting Hep3B tumor growth in vivo.

A similar experiment was conducted with cell-line—derived xenografts with low expression of Glypican-3 (H446). H446 cells are small-cell lung carcinoma cells with about 40,000 human PC3 molecules/cell. The cells were injected into CB17 SCID mice.

TABLE 16

| Dosage and tumor growth inhibition of H446 cells in CB17 SCID mice | | | |
|---|---|---|---|
| | Dose (Q3Dx4) | | $TGI_{D21}$ |
| AdxDC | mpk | μmol/kg | (%) |
| GPC3-binding (BMT-279771) | 12 | 1.0 | |
| | 8 | 0.67 | 53 |
| | 4 | 0.33 | |
| | 2 | 0.17 | 16 |
| RGE (−ve control) | 1.4 | 0.12 | — |

Figure 18:
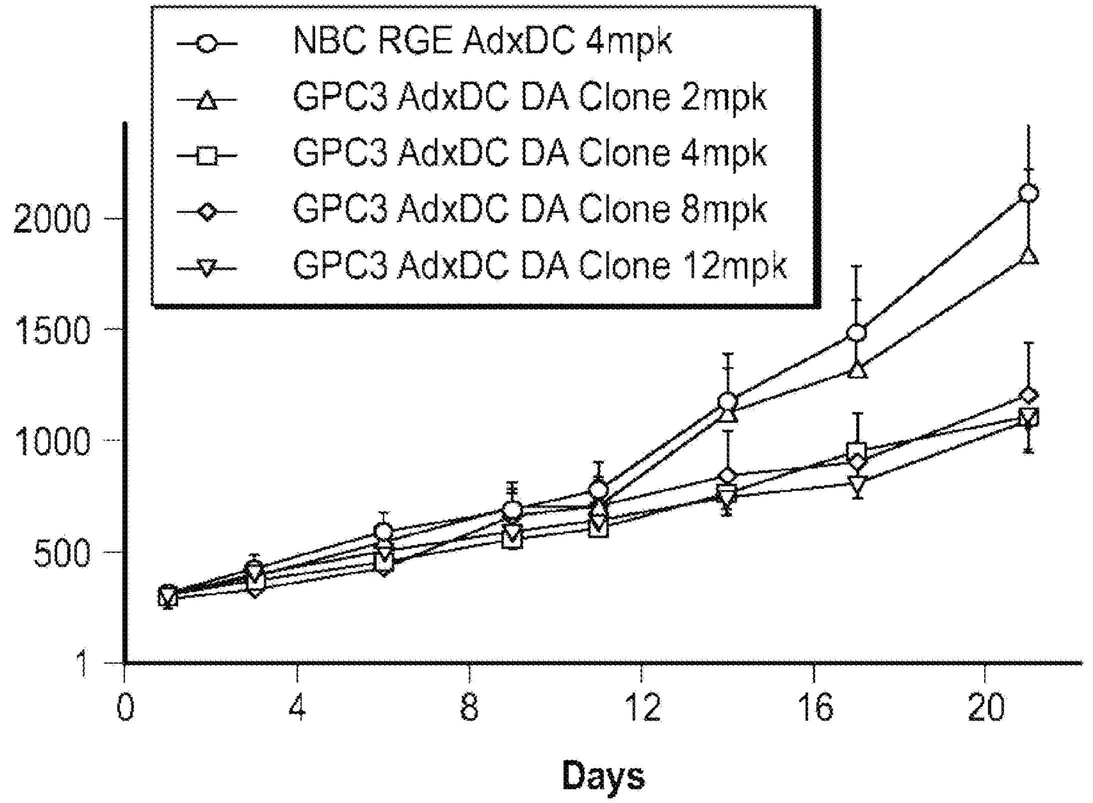
FIG. 18 shows tumor volume as a function of days after administration of various doses of GPC3_AdxDC DA or control non binding AdxDC to CB17 SCID mice implanted with H446 tumor cells, showing that GPC3_AdxDC DA slows growth of cell line derived xenografts with low expression of glypican-3.

The results, which are shown in Table 16 and FIG. 18, indicate that GPC3_AdxDC (DA) slows down the growth of these tumors.

Example 19: Preferential Uptake of GPC3_AdxDC to Hep3B Tumor Relative to Normal Tissues Mice were dosed with $^3H$ labeled GPC3_AdxDC at 0.015 or 0.22 mol/kg, and radioactivity was measured by Whole-Body Autoradiography (QWBA) after 0.17 hours, 1 hour, 5 hours and 168 hours.

Figure 19:
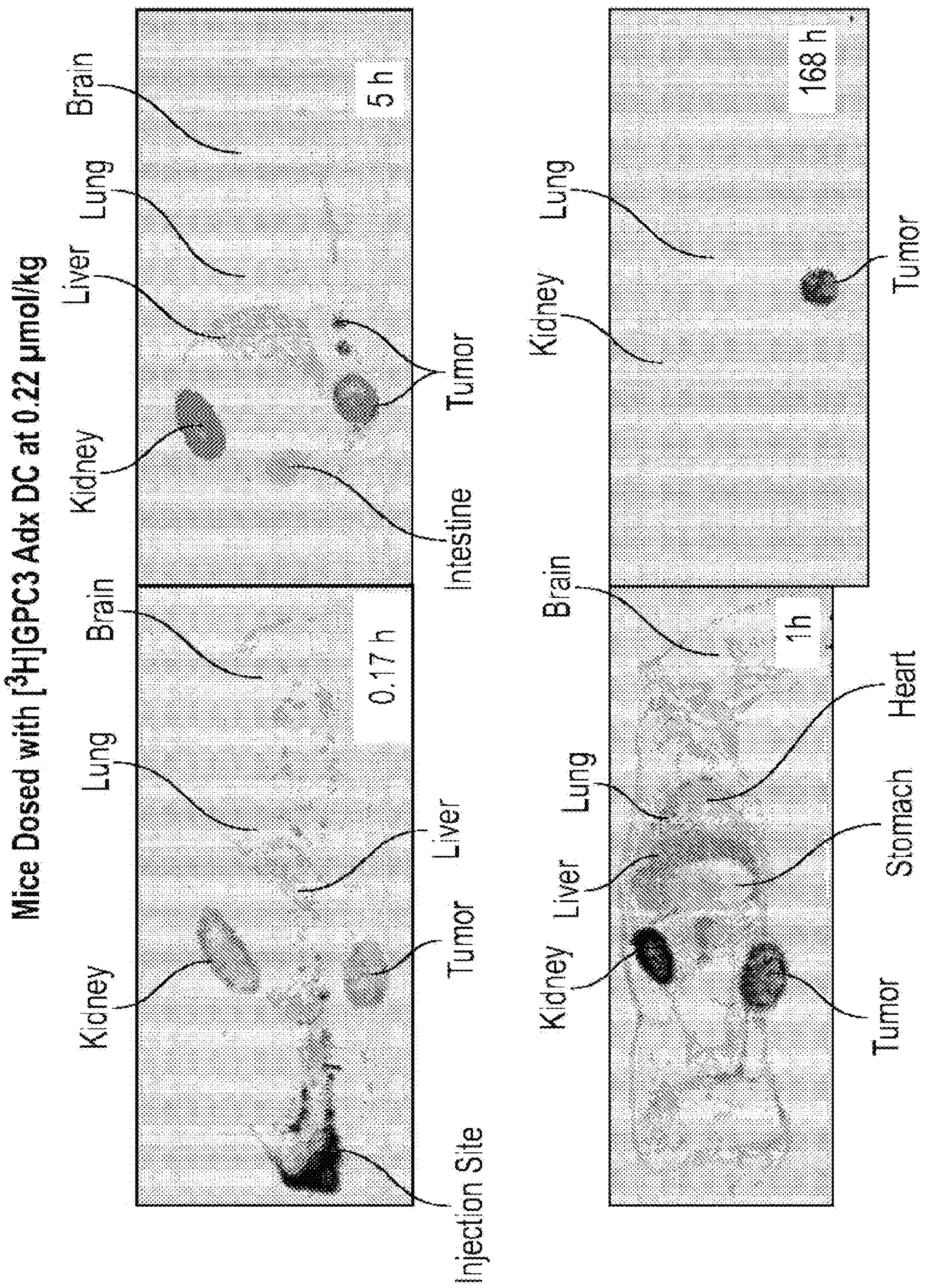
FIG. 19 shows Quantitative Whole-Body Autoradiography (QWBA) of mice tissues taken 0.17 hours, 1 hour, 5 hours and 168 hours after administration of 0.22 μM/kg of $^3$H GPC3_AdxDC to the mice, showing preferential uptake to Hep3B tumor relative to normal tissues.
Figure 20:
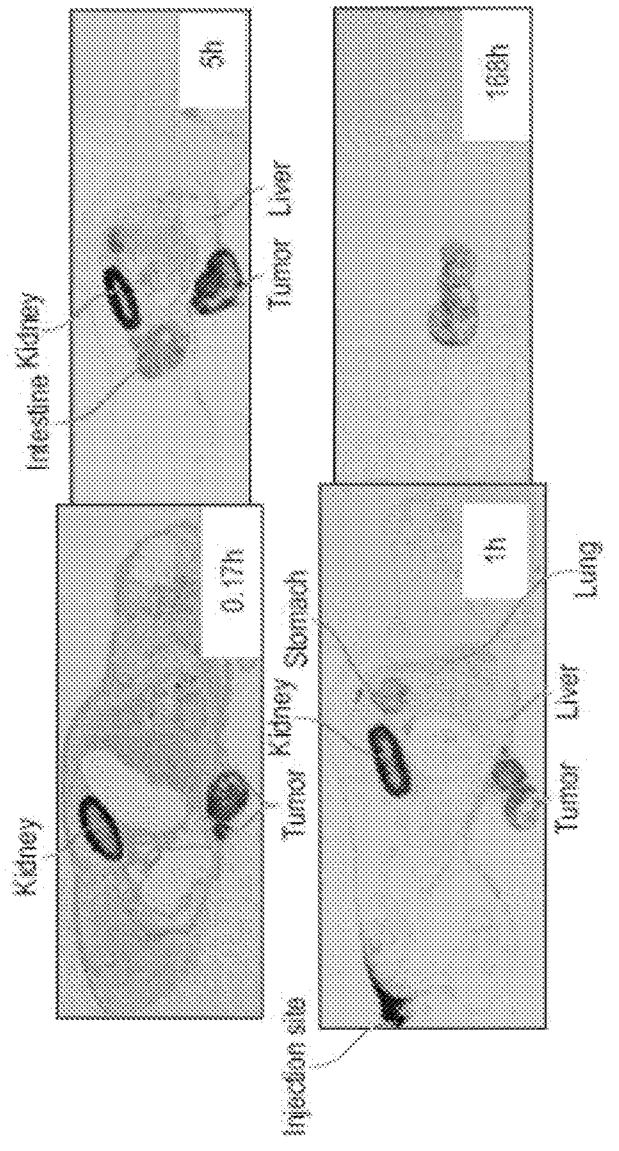
FIG. 20 shows QWBA of mice tissues taken 0.17 hours, 1 hour, 5 hours and 168 hours after administration of 0.015 μM/kg of $^3$H GPC3_AdxDC to the mice, showing preferential uptake to Hep3B tumor relative to normal tissues.

The results, which are shown in FIGS. 19 and 20, indicate the following:

- Rapid distribution to tumor and highly perfused tissues;
- High level radioactivity remained in the tumors 168 hours after dosing, with no, or low, radioactivity in other tissues;
- Significant radioactivity in kidney: about 30% of the radioactivity was excreted in the urine; and
- Similar patters of expression between high and low dose groups.

In a similar experiment, mice were dosed with $^3H$ labeled GPC3_AdxDC or non-binding AdxDC control at 0.22 μmol/kg, and radioactivity was measured by QWBA after 0.17 hours, 1 hour, 5 hours and 168 hours.

Figure 21:
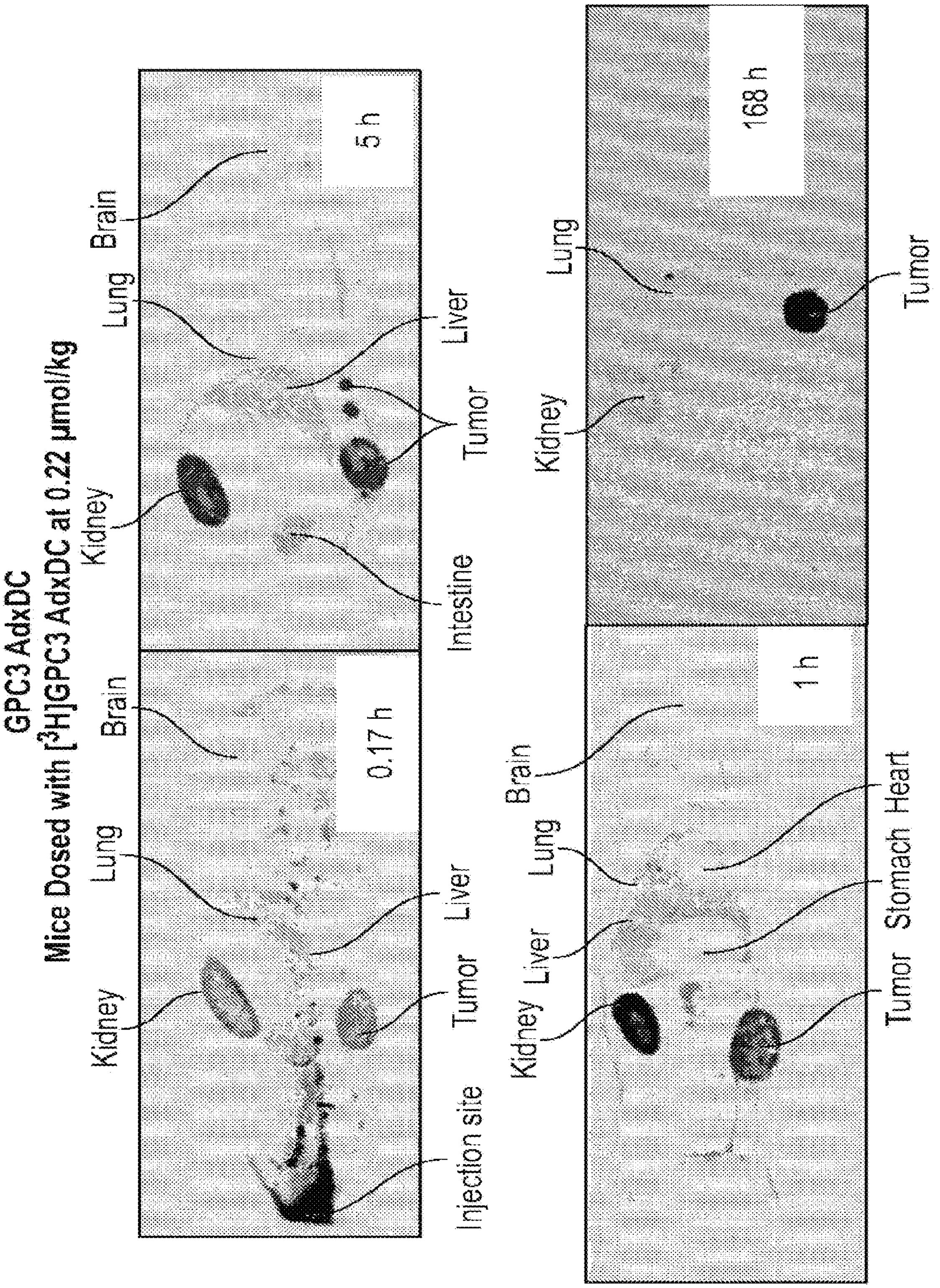
FIG. 21 shows QWBA of mice tissues taken 0.17 hours, 1 hour, 5 hours and 168 hours after administration of 0.22 μM/kg of 3H GPC3_AdxDC to the mice, showing a higher uptake to Hep3B tumor relative to that of non-binding control AdxDC.
Figure 22:
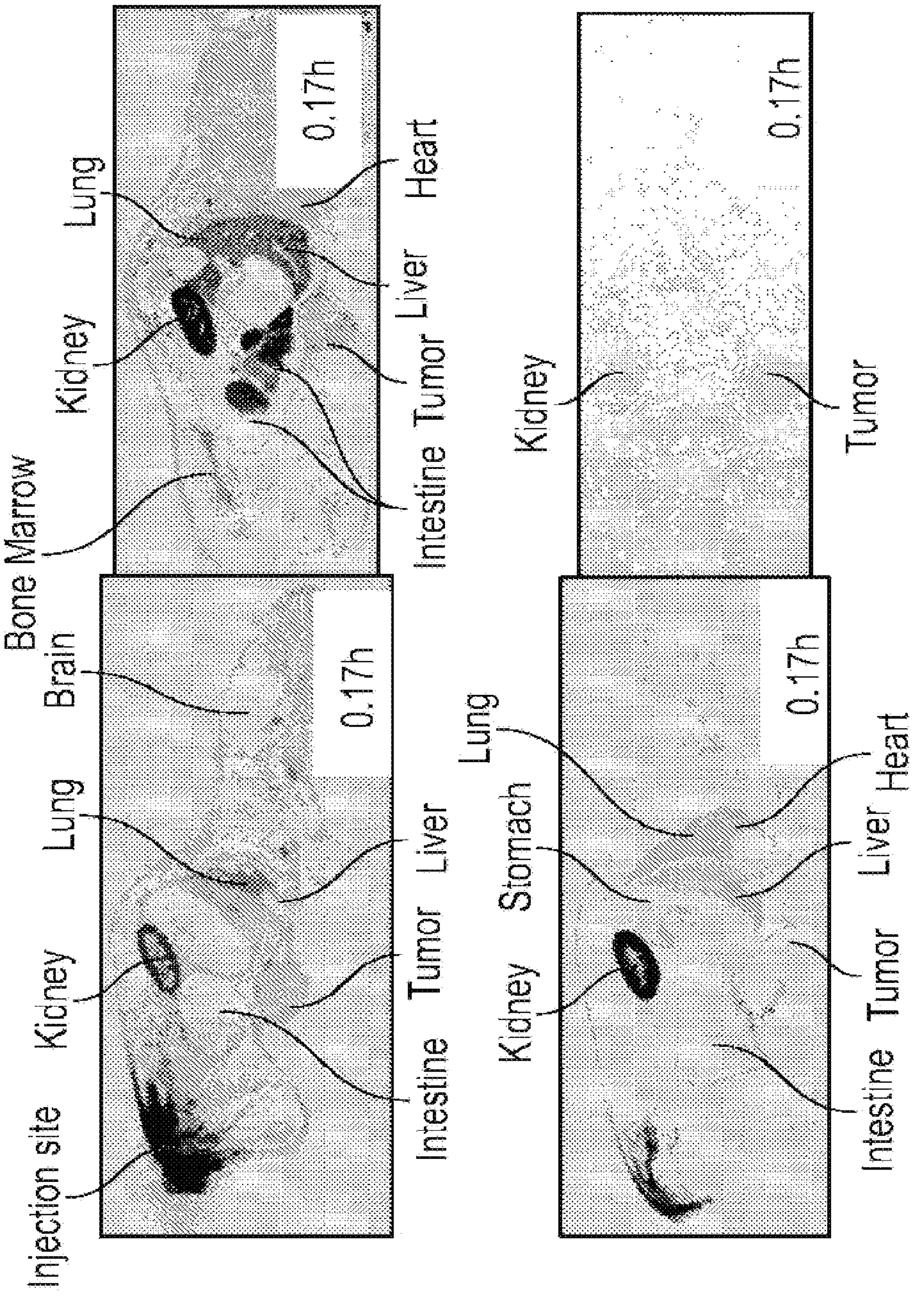
FIG. 22 shows QWBA of mice tissues taken 0.17 hours, 1 hour, 5 hours and 168 hours after administration of 0.22 μM/kg of $^3$H RGE_AdxDC (control, non GPC3-binding AdxDC) to the mice, showing a lower uptake to Hep3B tumor relative to that of GPC3_AdxDC.

The results, which are shown in FIGS. 21 and 22, indicate that there is a higher uptake to Hep3B Tumor with GPC3_AdxDC relative to the non-binding control (RGE AdxDC). The distribution profile in other tissues is comparable for the GPC3_AdxDC and the non-binding AdxDC control.

Figure 23:
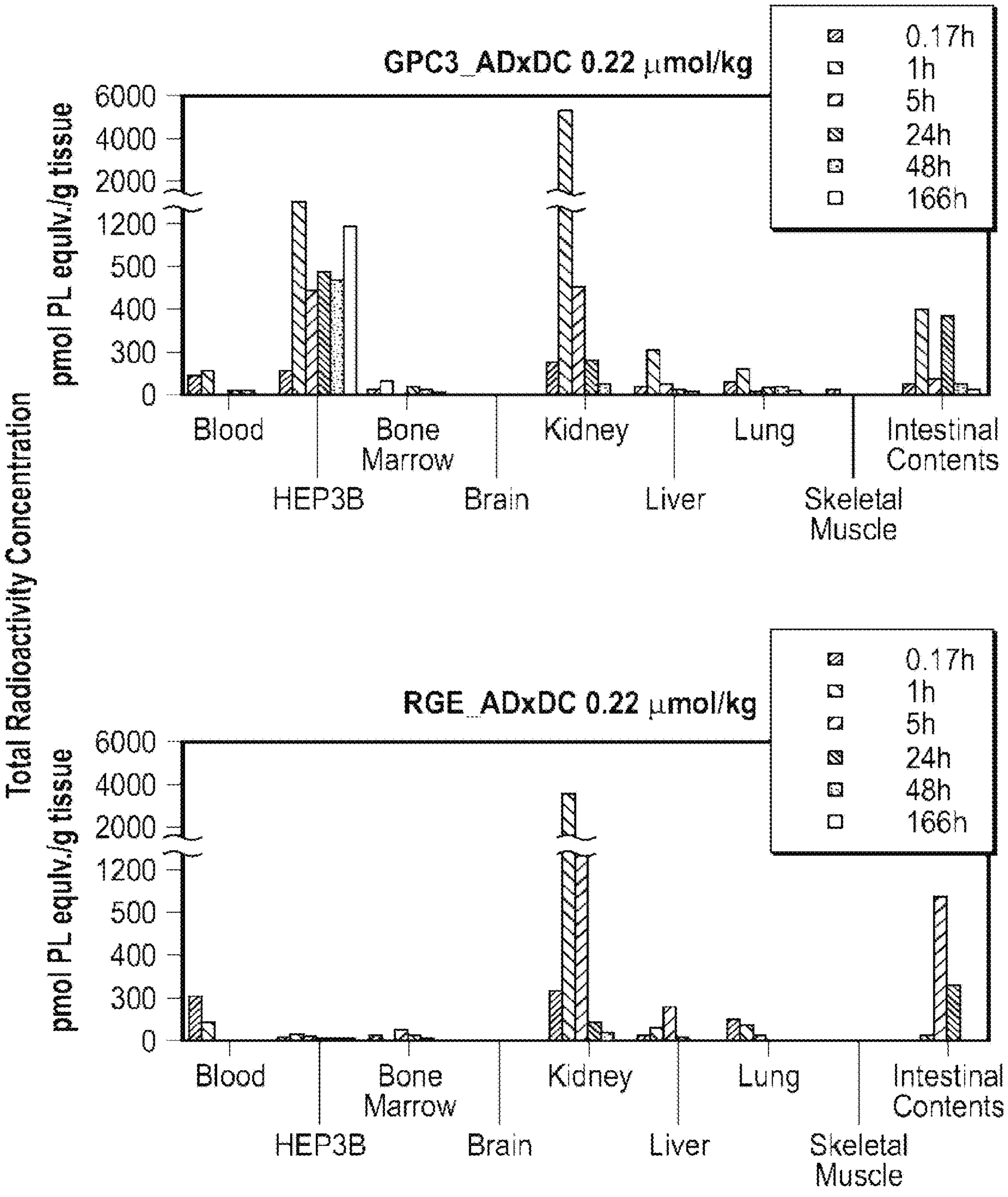
FIG. 23 shows the total radioactivity concentration in various mouse tissues at 0.17 hours, 1 hour, 5 hours, 24 hours, 48 hours and 168 hours after administration of $^3$H GPC3_AdxDC or non-binding AdxDC control ("RGE_ADxDC") administered to mice. The bars for each tissue are shown in the order set forth in the previous sentence.

The total radioactivity concentration of GPC3_AdxDC in tumor and tissues is represented in FIG. 23. The figure shows the presence of much higher level of GPC3_AdxDC in the tumors than in other tissues (except the kidney).

Example 20: Positional Scanning of Anti-GPC3 Adnectins

This Example describes positional scanning of 6077_F02 in which EIDKPSQ (SEQ ID NO: 369) was removed and PC was added, and wherein amino acid 79 (i.e., the "D" of "DG") is either G (as in original clone) or A.

The two proteins, different only at amino acid 79, were mixed during the library construction. Binding to human glypican-3-biotin was determined at 100 nM, 10 nM and 1 nM. For each batch, the 10 nM selection elution was compared to the flag elution and the 1 nM selection elution was also compared to the flag elution. This generated 4 heat maps for each loop: 10 nM when 79 is G; 1 nM when 79 is G; 10 nM when 79 is A and 1 nM when 79 is A.

For the FG loop, the three segments were combined together to show the full heat map. For position 79, on heat map was generated where it was normalized to the G, and one heat map where it was normalized to the A.

The results, in the form of heat maps, are shown in FIGS. 24-31. In the heat maps, a number>1 indicates a favorable substitution, however, any number>0.2 is also acceptable as a substitution The higher the number, the more favorable the substitution. For example, the heat maps indicate the following for the DG parent adnectin:

- In loop BC (i.e., sequence SDDYHAH (amino acids 15-21 of SEQ ID NO: 98)):
  - S23 may be substituted with any amino acid;
  - D24, is preferably not substituted with any other amino acid, although S and E may be acceptable.
  - Other acceptable substitutions may be derived from the heat maps, wherein any substitution having a number>0.2 is acceptable and a number>1 is preferable.

EQUIVALENTS

Those skilled in the art will recognize, or be able to ascertain using no more than routine experimentation, many equivalents of the specific embodiments of the invention described herein. Such equivalents are intended to be encompassed by the following claims.

TABLE 2

| SUMMARY OF SEQUENCES | | |
|---|---|---|
| SEQ ID | Description | SEQUENCE |
| 1 | Full length wild-type human $^{10}$Fn3 domain | VSDVPRDLEVVAATPTSLLISWDAPAVTVRYYRITYGETGGNSPVQEFTVPGSKSTATISGLKPGVDYTITVYAVTGRGDSPASSKPISINYRT |
| 2 | Core wild-type human $^{10}$Fn3 domain | EVVAATPTSLLISWDAPAVTVRYYRITYGETGGNSPVQEFTVPGSKSTATISGLKPGVDYTITVYAVTGRGDSPASSKPISINYRT |
| 3 | Human $^{10}$Fn3 domain six loop sequences generically defined | VSDVPRDLEVVAA$(X)_u$LLISW$(X)_v$YYRITY$(X)_w$FTV$(X)_x$ATISG$(X)_y$YTITVYAV$(X_z$ISINYRT |
| 4 | Wild-type human $^{10}$Fn3 domain C-terminal flexible linker | VSDVPRDLEVVAATPTSLLISWDAPAVTVRYYRITYGETGGNSPVQEFTVPGSKSTATISGLKPGVDYTITVYAVTGRGDSPASSKPISINYRT*EIDKPSQ* |
| 5 | ADX_4578_F03 Core | EVVAATPTSLLISW**HPPHPNIVS**YHIYYGETGGNSPVQEFTV**EGSKST**AKISGLKPGVDYTITVYA**VAPEIEKYYQ**IWINYRT |

TABLE 2-continued

SUMMARY OF SEQUENCES

| SEQ ID | Description | SEQUENCE |
|---|---|---|
| 6 | ADX_4578_F03 BC loop | HPPHPNIVS |
| 7 | ADX_4578_F03 DE loop | EGSKST |
| 8 | ADX_4578_F03 DE loop | VAPEIEKYYQ |
| 9 | ADX_45708_F03 full-length | VSDVPRDLEVVAATPTSLLISWHPPHPNIVSYHIYYGETGGNSPVQEFTVEGSKSTAKISGLKPGVDYTITVYAVAPEIEKYYQIWINYRT |
| 10 | ADX_4578_F03 full-length w/N-terminal leader and C-terminal tail | *MG*VSDVPRDLEVVAATPTSLLISWHPPHPNIVSYHIYYGETGGNSPVQEFTVEGSKSTAKISGLKPGVDYTITVYAVAPEIEKYYQIWINYRT*EGSGS* |
| 11 | ADX_4578_F03 full-length with C-terminal $P_mX_n$ | VSDVPRDLEVVAATPTSLLISWHPPHPNIVSYHIYYGETGGNSPVQEFTVEGSKSTAKISGLKPGVDYTITVYAVAPEIEKYYQIWINYRT$P_mX_n$ |
| 12 | ADX_4578_F03 full-length with C-terminal $P_mCX_n$ | VSDVPRDLEVVAATPTSLLISWHPPHPNIVSYHIYYGETGGNSPVQEFTVEGSKSTAKISGLKPGVDYTITVYAVAPEIEKYYQIWINYRT$P_mCX_n$ |
| 13 | ADX_4578_F03 full-length with C-terminal PmCXn (m = 1; n = 0) | VSDVPRDLEVVAATPTSLLISWHPPHPNIVSYHIYYGETGGNSPVQEFTVEGSKSTAKISGLKPGVDYTITVYAVAPEIEKYYQIWINYRTPC |
| 14 | ADX_4578_F03 full-length with C-terminal PmCXn (m = 1; n = 0) and $His_6$ tag | VSDVPRDLEVVAATPTSLLISWHPPHPNIVSYHIYYGETGGNSPVQEFTVEGSKSTAKISGLKPGVDYTITVYAVAPEIEKYYQIWINYRTPCHHHHHH |
| 15 | ADX_4578_F03 full-length with C-terminal $P_mCX_{n1}CX_{n2}$ | VSDVPRDLEVVAATPTSLLISWHPPHPNIVSYHIYYGETGGNSPVQEFTVEGSKSTAKISGLKPGVDYTITVYAVAPEIEKYYQIWINYRT$P_mCX_{n1}CX_{n2}$ |
| 16 | ADX_4578_F03 full-length with C-terminal $PmCX_{n1}CX_{n2}$ (m = 1, n1 = 5, n2 = 0) | VSDVPRDLEVVAATPTSLLISWHPPHPNIVSYHIYYGETGGNSPVQEFTVEGSKSTAKISGLKPGVDYTITVYAVAPEIEKYYQIWINYRTPCPPPPPC |
| 17 | ADX_4578_F03 full-length with C-terminal $PmCX_{n1}CX_{n2}$ (m = 1, n1 = 5, n2 = 0) and $His_6$ tag | VSDVPRDLEVVAATPTSLLISWHPPHPNIVSYHIYYGETGGNSPVQEFTVEGSKSTAKISGLKPGVDYTITVYAVAPEIEKYYQIWINYRTPCPPPPPCHHHHHH |
| 18 | ADX_4578_H08 core | ~~EVVAATPTSLLISW~~**~~HPPHPNIVS~~**~~YHIYYGETGGNSPVQEFTV~~**~~EGSKST~~**~~AKISGLKPGVDYTITVYA~~**~~VAPEIEKYYQ~~**~~IWINYRT~~<br>EVVAATPTSLLISW**SGYDYGDSY**YRITYGETGGNSPVQEFTV**PDGSNT**ATISGLKPGVDYTITVYAV**EAYGKGYTRYTP**ISINYRT |
| 19 | ADX_4578_H08 BC loop | SGYDYGDSY |
| 20 | ADX_4578_H08 DE loop | PDGNST |
| 21 | ADX_4578_H08 FG loop | VEAYGKGYTRYTP |
| 22 | ADX_4578_H08 full-length | VSDVPRDLEVVAATPTSLLISWSGYDYGDSYYRITYGETGGNSPVQEFTVPDGSNTATISGLKPGVDYTITVYAVEAYGKGYTRYTPISINYRT |
| 23 | ADX_4578_H08 full-length w/N-terminal leader and C-terminal tail | *MG*VSDVPRDLEVVAATPTSLLISWSGYDYGDSYYRITYGETGGNSPVQEFTVPDGSNTATISGLKPGVDYTITVYAVEAYGKGYTRYTPISINYRT*EIDKPSQ* |
| 24 | ADX_4578_H08 full-length with C-terminal PmXn | VSDVPRDLEVVAATPTSLLISWSGYDYGDSYYRITYGETGGNSPVQEFTVPDGSNTATISGLKPGVDYTITVYAVEAYGKGYTRYTPISINYRT$P_mX_n$ |

TABLE 2-continued

SUMMARY OF SEQUENCES

| SEQ ID | Description | SEQUENCE |
|---|---|---|
| 25 | ADX_4578_H08 full-length with C-terminal PmCXn | VSDVPRDLEVVAATPTSLLISWSGYDYGDSYYRITYGETGGNSPVQEFTVPDGSNTATISGLKPGVDYTITVYAVEAYGKGYTRYTPISINYRTP$_m$CX$_n$ |
| 26 | ADX_4578_H08 full-length with C-terminal PmCXn (m = 1; n = 0) | VSDVPRDLEVVAATPTSLLISWSGYDYGDSYYRITYGETGGNSPVQEFTVPDGSNTATISGLKPGVDYTITVYAVEAYGKGYTRYTPISINYRTPC |
| 27 | ADX_4578_H08 full-length with C-terminal PmCXn (m = 1; n = 0) and His$_6$ tag | VSDVPRDLEVVAATPTSLLISWSGYDYGDSYYRITYGETGGNSPVQEFTVPDGSNTATISGLKPGVDYTITVYAVEAYGKGYTRYTPISINYRTPCHHHHHH |
| 28 | ADX_4578_H08 full-length with C-terminal PmCX$_{n1}$CX$_{n2}$ | VSDVPRDLEVVAATPTSLLISWSGYDYGDSYYRITYGETGGNSPVQEFTVPDGSNTATISGLKPGVDYTITVYAVEAYGKGYTRYTPISINYRTP$_m$CX$_{n1}$CX$_{n2}$ |
| 29 | ADX_4578_H08 full-length with C-terminal PmCX$_{n1}$CX$_{n2}$ (m = 1, n1 = 5, n2 = 0) | VSDVPRDLEVVAATPTSLLISWSGYDYGDSYYRITYGETGGNSPVQEFTVPDGSNTATISGLKPGVDYTITVYAVEAYGKGYTRYTPISINYRTPCPPPPPC |
| 30 | ADX_4578_H08 full-length with C-terminal PmCX$_{n1}$CX$_{n2}$ (m = 1, n1 = 5, n2 = 0) and His$_6$ tag | VSDVPRDLEVVAATPTSLLISWSGYDYGDSYYRITYGETGGNSPVQEFTVPDGSNTATISGLKPGVDYTITVYAVEAYGKGYTRYTPISINYRTPCPPPPPCHHHHHH |
| 31 | ADX_4578_B06 core | EVVAATPTSLLISW**FPDRYV**YYITYGETGGNSPVQEFTV**EGHKQT**AYISGLKPGVDYTITVYA**AYISGL**ISINYRT |
| 32 | ADX_4578_B06 BC loop | FPDRYV |
| 33 | ADX_4578_B06 DE loop | EGHKQT |
| 34 | ADX_4578_B06 FG loop | AYISGL |
| 35 | ADX_4578_B06 full-length | VSDVPRDLEVVAATPTSLLISWFPDRYVYYITYGETGGNSPVQEFTVEGHKQTAYISGLKPGVDYTITVYAIYYYPDDFQGYPQPISINYRT |
| 36 | ADX_4578_B06 full-length w/N-terminal leader and C-terminal tail | *MG*VSDVPRDLEVVAATPTSLLISWFPDRYVYYITYGETGGNSPVQEFTVEGHKQTAYISGLKPGVDYTITVYAIYYYPDDFQGYPQPISINYRT*EGSGS* |
| 37 | ADX_4578_B06 full-length with C-terminal PmXn | VSDVPRDLEVVAATPTSLLISWFPDRYVYYITYGETGGNSPVQEFTVEGHKQTAYISGLKPGVDYTITVYAIYYYPDDFQGYPQPISINYRTP$_m$X$_n$ |
| 38 | ADX_4578_B06 full-length with C-terminal PmCXn | VSDVPRDLEVVAATPTSLLISWFPDRYVYYITYGETGGNSPVQEFTVEGHKQTAYISGLKPGVDYTITVYAIYYYPDDFQGYPQPISINYRTP$_m$CX$_n$ |
| 39 | ADX_4578_B06 full-length with C-terminal PmCXn (m = 1; n = 0) | VSDVPRDLEVVAATPTSLLISWFPDRYVYYITYGETGGNSPVQEFTVEGHKQTAYISGLKPGVDYTITVYAIYYYPDDFQGYPQPISINYRTPC |
| 40 | ADX_4578_B06 full-length with C-terminal PmCXn (m = 1; n = 0) and His$_6$ tag | VSDVPRDLEVVAATPTSLLISWFPDRYVYYITYGETGGNSPVQEFTVEGHKQTAYISGLKPGVDYTITVYAIYYYPDDFQGYPQPISINYRTPCHHHHHH |
| 41 | ADX_4578_B06 full-length with C-terminal PmCX$_{n1}$CX$_{n2}$ | VSDVPRDLEVVAATPTSLLISWFPDRYVYYITYGETGGNSPVQEFTVEGHKQTAYISGLKPGVDYTITVYAIYYYPDDFQGYPQPISINYRTP$_m$CX$_{n1}$CX$_{n2}$ |
| 42 | ADX_4578_B06 full-length with C-terminal PmCX$_{n1}$CX$_{n2}$ (m = 1, n1 = 5, n2 = 0) | VSDVPRDLEVVAATPTSLLISWFPDRYVYYITYGETGGNSPVQEFTVEGHKQTAYISGLKPGVDYTITVYAIYYYPDDFQGYPQPISINYRTPCPPPPPC |
| 43 | ADX_4578_B06 full-length with C-terminal PmCX$_{n1}$CX$_{n2}$ (m = 1, n1 = 5, n2 = 0) and His$_6$ tag | VSDVPRDLEVVAATPTSLLISWFPDRYVYYITYGETGGNSPVQEFTVEGHKQTAYISGLKPGVDYTITVYAIYYYPDDFQGYPQPISINYRTPCPPPPPCHHHHHH |

TABLE 2-continued

| SUMMARY OF SEQUENCES | | |
|---|---|---|
| SEQ ID | Description | SEQUENCE |
| 44 | ADX_4606_F06 core | EVVAATPTSLLISW**NSGHSGQY**YRITYGETGGNSPVQEFTV**PRYGYT**ATISGLKPGVDYTITVYA**VAHSEASAP**ISINYRT |
| 45 | ADX_4606_F06 BC loop | NSGHSGQY |
| 46 | ADX_4606_F06 DE loop | PRYGYT |
| 47 | ADX_4606_F06 FG loop | VAHSEASAP |
| 48 | ADX_4606_F06 full-length | VSDVPRDLEVVAATPTSLLISWNSGHSGQYYRITYGETGGNSPVQEFTVPRYGYTATISGLKPGVDYTITVYAVAHSEASAPISINYRT |
| 49 | ADX_4606_F06 full-length w/N-terminal leader and C-terminal tail | *MG*VSDVPRDLEVVAATPTSLLISWNSGHSGQYYRITYGETGGNSPVQEFTVPRYGYTATISGLKPGVDYTITVYAVAHSEASAPISINYRT*EIDKPSQ* |
| 50 | ADX_4606_F06 full-length with C-terminal PmXn | VSDVPRDLEVVAATPTSLLISWNSGHSGQYYRITYGETGGNSPVQEFTVPRYGYTATISGLKPGVDYTITVYAVAHSEASAPISINYRT$P_mX_n$ |
| 51 | ADX_4606_F06 full-length with C-terminal PmCXn | VSDVPRDLEVVAATPTSLLISWNSGHSGQYYRITYGETGGNSPVQEFTVPRYGYTATISGLKPGVDYTITVYAVAHSEASAPISINYRT$P_mCX_n$ |
| 52 | ADX_4606_F06 full-length with C-terminal PmCXn (m = 1; n = 0) | VSDVPRDLEVVAATPTSLLISWNSGHSGQYYRITYGETGGNSPVQEFTVPRYGYTATISGLKPGVDYTITVYAVAHSEASAPISINYRTPC |
| 53 | ADX_4606_F06 full-length with C-terminal PmCXn (m = 1; n = 0) and $His_6$ tag | VSDVPRDLEVVAATPTSLLISWNSGHSGQYYRITYGETGGNSPVQEFTVPRYGYTATISGLKPGVDYTITVYAVAHSEASAPISINYRTPCHHHHHH |
| 54 | ADX_4606_F06 full-length with C-terminal $PmCX_{n1}CX_{n2}$ | VSDVPRDLEVVAATPTSLLISWNSGHSGQYYRITYGETGGNSPVQEFTVPRYGYTATISGLKPGVDYTITVYAVAHSEASAPISINYRT$P_mCX_{n1}CX_{n2}$ |
| 55 | ADX_4606_F06 full-length with C-terminal $PmCX_{n1}CX_{n2}$ (m = 1, n1 = 5, n2 = 0) | VSDVPRDLEVVAATPTSLLISWNSGHSGQYYRITYGETGGNSPVQEFTVPRYGYTATISGLKPGVDYTITVYAVAHSEASAPISINYRTPCPPPPPC |
| 56 | ADX_4606_F06 full-length with C-terminal $PmCX_{n1}CX_{n2}$ (m = 1, n1 = 5, n2 = 0) and $His_6$ tag | VSDVPRDLEVVAATPTSLLISWNSGHSGQYYRITYGETGGNSPVQEFTVPRYGYTATISGLKPGVDYTITVYAVAHSEASAPISINYRTPCPPPPPCHHHHHH |
| 57 | ADX_5273_C01 core | EVVAATPTSLLISW**SDPYEEERY**YRITYGETGGNSPVQEFTV**PAFHTT**ATISGLKPGVDYTITVYA**VTYKHKYAYYYPP**ISINYRT |
| 58 | ADX_5273_C01 BC loop | SDPYEEERY |
| 59 | ADX_5273_C01 DE loop | PAFHTT |
| 60 | ADX_5273_C01 FG loop | VTYKHKYAYYYPP |
| 61 | ADX_5273_C01 full-length | VSDVPRDLEVVAATPTSLLISWSDPYEEERYYRITYGETGGNSPVQEFTVPAFHTTATISGLKPGVDYTITVYAVTYKHKYAYYYPPISINYRT |
| 62 | ADX_5273_C01 full-length w/N-terminal leader and C-terminal tail | *MG*VSDVPRDLEVVAATPTSLLISWSDPYEEERYYRITYGETGGNSPVQEFTVPAFHTTATISGLKPGVDYTITVYAVTYKHKYAYYYPPISINYRT*EIDKPSQ* |
| 63 | ADX_5273_C01 full-length with C-terminal PmXn | VSDVPRDLEVVAATPTSLLISWSDPYEEERYYRITYGETGGNSPVQEFTVPAFHTTATISGLKPGVDYTITVYAVTYKHKYAYYYPPISINYRT$P_mX_n$ |
| 64 | ADX_5273_C01 full-length with C-terminal PmCXn | VSDVPRDLEVVAATPTSLLISWSDPYEEERYYRITYGETGGNSPVQEFTVPAFHTTATISGLKPGVDYTITVYAVTYKHKYAYYYPPISINYRT$P_mCX_n$ |

TABLE 2-continued

SUMMARY OF SEQUENCES

| SEQ ID | Description | SEQUENCE |
|---|---|---|
| 65 | ADX_5273_C01 full-length with C-terminal PmCXn (m = 1; n = 0) | VSDVPRDLEVVAATPTSLLISWSDPYEEERYYRITYGETGGNSPVQEFTVPAFHTTATISGLKPGVDYTITVYAVTYKHKYAYYYPPISINYRTPC |
| 66 | ADX_5273_C01 full-length with C-terminal PmCXn (m = 1; n = 0) and $His_6$ tag | VSDVPRDLEVVAATPTSLLISWSDPYEEERYYRITYGETGGNSPVQEFTVPAFHTTATISGLKPGVDYTITVYAVTYKHKYAYYYPPISINYRTPCHHHHHH |
| 67 | ADX_5273_C01 full-length with C-terminal $PmCX_{n1}CX_{n2}$ | VSDVPRDLEVVAATPTSLLISWSDPYEEERYYRITYGETGGNSPVQEFTVPAFHTTATISGLKPGVDYTITVYAVTYKHKYAYYYPPISINYRTP$_m$CX$_{n1}$CX$_{n2}$ |
| 68 | ADX_5273_C01 full-length with C-terminal $PmCX_{n1}CX_{n2}$ (m = 1, n1 = 5, n2 = 0) | VSDVPRDLEVVAATPTSLLISWSDPYEEERYYRITYGETGGNSPVQEFTVPAFHTTATISGLKPGVDYTITVYAVTYKHKYAYYYPPISINYRTPCPPPPPC |
| 69 | ADX_5273_C01 full-length with C-terminal $PmCX_{n1}CX_{n2}$ (m = 1, n1 = 5, n2 = 0) and $His_6$ tag | VSDVPRDLEVVAATPTSLLISWSDPYEEERYYRITYGETGGNSPVQEFTVPAFHTTATISGLKPGVDYTITVYAVTYKHKYAYYYPPISINYRTPCPPPPPCHHHHHH |
| 70 | ADX_5273_D01 core | EVVAATPTSLLISW**EPSYKDDRY**YRITYGETGGNSPVQEFTV**PSFHQT**ATISGLKPGVDYTITVYA**VTYEPDEYYFYYP**ISINYRT |
| 71 | ADX_5273_D01 BC loop | EPSYKDDRY |
| 72 | ADX_5273_D01 DE loop | PSFHQT |
| 73 | ADX_5273_D01 FG loop | VTYEPDEYYFYYP |
| 74 | ADX_5273_D01 full-length | VSDVPRDLEVVAATPTSLLISWEPSYKDDRYYRITYGETGGNSPVQEFTVPSFHQTATISGLKPGVDYTITVYAVTYEPDEYYFYYPISINYRT |
| 75 | ADX_5273_D01 full-length w/N-terminal leader and C-terminal tail | *MG*VSDVPRDLEVVAATPTSLLISWEPSYKDDRYYRITYGETGGNSPVQEFTVPSFHQTATISGLKPGVDYTITVYAVTYEPDEYYFYYPISINYRT*EIDKPSQ* |
| 76 | ADX_5273_D01 full-length with C-terminal PmXn | VSDVPRDLEVVAATPTSLLISWEPSYKDDRYYRITYGETGGNSPVQEFTVPSFHQTATISGLKPGVDYTITVYAVTYEPDEYYFYYPISINYRTP$_m$X$_n$ |
| 77 | ADX_5273_D01 full-length with C-terminal PmCXn | VSDVPRDLEVVAATPTSLLISWEPSYKDDRYYRITYGETGGNSPVQEFTVPSFHQTATISGLKPGVDYTITVYAVTYEPDEYYFYYPISINYRTP$_m$CX$_n$ |
| 78 | ADX_5273_D01 full-length with C-terminal PmCXn (m = 1; n = 0) | VSDVPRDLEVVAATPTSLLISWEPSYKDDRYYRITYGETGGNSPVQEFTVPSFHQTATISGLKPGVDYTITVYAVTYEPDEYYFYYPISINYRTPC |
| 79 | ADX_5273_D01 full-length with C-terminal PmCXn (m = 1; n = 0) and $His_6$ tag | VSDVPRDLEVVAATPTSLLISWEPSYKDDRYYRITYGETGGNSPVQEFTVPSFHQTATISGLKPGVDYTITVYAVTYEPDEYYFYYPISINYRTPCHHHHHH |
| 80 | ADX_5273_D01 full-length with C-terminal $PmCX_{n1}CX_{n2}$ | VSDVPRDLEVVAATPTSLLISWEPSYKDDRYYRITYGETGGNSPVQEFTVPSFHQTATISGLKPGVDYTITVYAVTYEPDEYYFYYPISINYRTP$_m$CX$_{n1}$CX$_{n2}$ |
| 81 | ADX_5273_D01 full-length with C-terminal $PmCX_{n1}CX_{n2}$ (m = 1, n1 = 5, n2 = 0) | VSDVPRDLEVVAATPTSLLISWEPSYKDDRYYRITYGETGGNSPVQEFTVPSFHQTATISGLKPGVDYTITVYAVTYEPDEYYFYYPISINYRTPCPPPPPC |
| 82 | ADX_5273_D01 full-length with C-terminal $PmCX_{n1}CX_{n2}$ (m = 1, n1 = 5, n2 = 0) and $His_6$ tag | VSDVPRDLEVVAATPTSLLISWEPSYKDDRYYRITYGETGGNSPVQEFTVPSFHQTATISGLKPGVDYTITVYAVTYEPDEYYFYYPISINYRTPCPPPPPCHHHHHH |
| 83 | ADX_5274_E01 core | EVVAATPTSLLISW**SGDYHPHRY**YRITYGETGGNSPVQEFTV**PGEHET**AATISGLKPGVDYTITVYA**VTYDGEKADKYPP**ISINYRT |
| 84 | ADX_5274_E01 BC loop | SGDYHPHRY |

TABLE 2-continued

| SEQ ID | Description | SEQUENCE |
| --- | --- | --- |
| | SUMMARY OF SEQUENCES | |
| 85 | ADX_5274_E01 DE loop | PGEHET |
| 86 | ADX_5274_E01 FG loop | VTYDGEKADKYPP |
| 87 | ADX_5274_E01 full-length | VSDVPRDLEVVAATPTSLLISWSGDYHPHRYYRITYGETGGNSPVQEFTVPGEHETATISGLKPGVDYTITVYAVTYDGEKADKYPPISINYRT |
| 88 | ADX_5274 E01 full-length w/N-terminal leader and C-terminal tail | *MG*VSDVPRDLEVVAATPTSLLISWSGDYHPHRYYRITYGETGGNSPVQEFTVPGEHETATISGLKPGVDYTITVYAVTYDGEKADKYPPISINYRT*EIDKPSQ* |
| 89 | ADX_5274_E01 full-length w/C-terminal PmXn | VSDVPRDLEVVAATPTSLLISWSGDYHPHRYYRITYGETGGNSPVQEFTVPGEHETATISGLKPGVDYTITVYAVTYDGEKADKYPPISINYRT$P_mX_n$ |
| 90 | ADX_5274_E01 full-length with C-terminal $P_mCX_n$ | VSDVPRDLEVVAATPTSLLISWSGDYHPHRYYRITYGETGGNSPVQEFTVPGEHETATISGLKPGVDYTITVYAVTYDGEKADKYPPISINYRT$P_mCX_n$ |
| 91 | ADC_5274_E01 core with PmCXn C-terminal modification (m = 1; n = 0); aka ADX_6561_A01 core | EVVAATPTSLLISWSGDYHPHRYYRITYGETGGNSPVQEFTVPGEHETATISGLKPGVDYTITVYAVTYDGEKADKYPPISINYRT*PC* |
| 92 | ADX_5274_E01 full-length with C-terminal $P_mCX_n$ (m = 1; n = 0)] | VSDVPRDLEVVAATPTSLLISWSGDYHPHRYYRITYGETGGNSPVQEFTVPGEHETATISGLKPGVDYTITVYAVTYDGEKADKYPPISINYRT*PC* |
| 93 | ADX_5274_E01 full-length with C-terminal $P_mCX_n$ (m = 1; n = 0) and $His_6$ tag | VSDVPRDLEVVAATPTSLLISWSGDYHPHRYYRITYGETGGNSPVQEFTVPGEHETATISGLKPGVDYTITVYAVTYDGEKADKYPPISINYRT*PCHHHHHH* |
| 94 | ADX_5274_A01 full-length w/N-terminal leader, C-terminal $P_mCX_n$ (m = 1; n = 0) and $His_6$ tag | *MG*VSDVPRDLEVVAATPTSLLISWSGDYHPHRYYRITYGETGGNSPVQEFTVPGEHETATISGLKPGVDYTITVYAVTYDGEKADKYPPISINYRT*PCHHHHHH* |
| 95 | ADX_5274_E01 full-length with C-terminal $PmCXn_1CXn_2$ | VSDVPRDLEVVAATPTSLLISWSGDYHPHRYYRITYGETGGNSPVQEFTVPGEHETATISGLKPGVDYTITVYAVTYDGEKADKYPPISINYRT$P_mCX_{n1}CX_{n2}$ |
| 96 | ADX_5274_E01 full-length with C-terminal $PmCXn_1CXn_2$ (m = 1; n1 = 5; n2 = 0) | VSDVPRDLEVVAATPTSLLISWSGDYHPHRYYRITYGETGGNSPVQEFTVPGEHETATISGLKPGVDYTITVYAVTYDGEKADKYPPISINYRT*PCPPPPPC* |
| 97 | ADX_5274_E01 full-length with C-terminal $PmCXn_1CXn_2$ (m = 1; n1 = 5; n2 = 0) and $His_6$ tag | VSDVPRDLEVVAATPTSLLISWSGDYHPHRYYRITYGETGGNSPVQEFTVPGEHETATISGLKPGVDYTITVYAVTYDGEKADKYPPISINYRT*PCPPPPPCHHHHHH* |
| 98 | ADX_6077_A01 core | EVVAATPTSLLISW**SDDYHAHRY**YRITYGETGGNSPVQEFTV**PGEHVT**ATISGLKPGVDYTITVYA**VTYDGEKAATDWS**ISINYRT |
| 99 | ADX_6077_F02 BC loop | SDDYHAHRY |
| 100 | ADX_6077_F02 DE loop | PGEHVT |
| 101 | ADX_6077_F02 FG loop | VTYDGEKAATDWS |
| 102 | ADX_6077_F02 full-length | VSDVPRDLEVVAATPTSLLISWSDDYHAHRYYRITYGETGGNSPVQEFTVPGEHVTATISGLKPGVDYTITVYAVTYDGEKAATDWSISINYRT |
| 103 | ADX_6077_F02 full-length with C-terminal tail | VSDVPRDLEVVAATPTSLLISWSDDYHAHRYYRITYGETGGNSPVQEFTVPGEHVTATISGLKPGVDYTITVYAVTYDGEKAATDWSISINYRT*EIEKPCQ* |

TABLE 2-continued

SUMMARY OF SEQUENCES

| SEQ ID | Description | SEQUENCE |
|---|---|---|
| 104 | ADX_6077_F02 full-length with N-terminal leader (G) | GVSDVPRDLEVVAATPTSLLISWSDDYHAHRYYRITYGETGGNSP VQEFTVPGEHVTATISGLKPGVDYTITVYAVTYDGEKAATDWSIS INYRT |
| 105 | ADX_6077_F02 full-length with N-terminal leader (MG) | MGVSDVPRDLEVVAATPTSLLISWSDDYHAHRYYRITYGETGGNS PVQEFTVPGEHVTATISGLKPGVDYTITVYAVTYDGEKAATDWSI SINYRT |
| 106 | ADX_6077_F02 core with C-terminal PmXn | EVVAATPTSLLISWSDDYHAHRYYRITYGETGGNSPVQEFTVPGE HVTATISGLKPGVDYTITVYAVTYDGEKAATDWSISINYRTP$_m$X$_n$ |
| 107 | ADX_6077_F02 full-length with C-terminal PmXn | VSDVPRDLEVVAATPTSLLISWSDDYHAHRYYRITYGETGGNSPV QEFTVPGEHVTATISGLKPGVDYTITVYAVTYDGEKAATDWSISI NYRTP$_m$X$_n$ |
| 108 | ADX_6077_F02 full-length with N-terminal leader (G) and C-terminal PmXn | GVSDVPRDLEVVAATPTSLLISWSDDYHAHRYYRITYGETGGNSP VQEFTVPGEHVTATISGLKPGVDYTITVYAVTYDGEKAATDWSIS INYRTP$_m$X$_n$ |
| 109 | ADX_6077_F02 full-length with N-terminal leader (MG) and C-terminal PmXn | MGVSDVPRDLEVVAATPTSLLISWSDDYHAHRYYRITYGETGGNS PVQEFTVPGEHVTATISGLKPGVDYTITVYAVTYDGEKAATDWSI SINYRTP$_m$X$_n$ |
| 110 | ADX_6077_F02 core with C-terminal PmCXn | EVVAATPTSLLISWSDDYHAHRYYRITYGETGGNSPVQEFTVPGE HVTATISGLKPGVDYTITVYAVTYDGEKAATDWSISINYRTP$_m$CX$_n$ |
| 111 | ADX_6077_F02 full-length with C-terminal P$_m$CX$_n$ | VSDVPRDLEVVAATPTSLLISWSDDYHAHRYYRITYGETGGNSPV QEFTVPGEHVTATISGLKPGVDYTITVYAVTYDGEKAATDWSISI NYRTP$_m$CX$_n$ |
| 112 | ADX_6077_F02 full-length with N-terminal leader (G) and C-terminal P$_m$CX$_n$ | GVSDVPRDLEVVAATPTSLLISWSDDYHAHRYYRITYGETGGNSP VQEFTVPGEHVTATISGLKPGVDYTITVYAVTYDGEKAATDWSIS INYRTP$_m$CX$_n$ |
| 113 | ADX_6077_F02 full-length with N-terminal leader (MG) and C-terminal P$_m$CX$_n$ | MGVSDVPRDLEVVAATPTSLLISWSDDYHAHRYYRITYGETGGNS PVQEFTVPGEHVTATISGLKPGVDYTITVYAVTYDGEKAATDWSI SINYRTP$_m$CX$_n$ |
| 114 | ADX_6077_F02 core with C-terminal PmCXn (m = 1; n = 0) | EVVAATPTSLLISWSDDYHAHRYYRITYGETGGNSPVQEFTVPGE HVTATISGLKPGVDYTITVYAVTYDGEKAATDWSISINYRT*PC* |
| 115 | ADX_6077_F02 full-length with C-terminal PmCXn (m = 1; n = 0) | VSDVPRDLEVVAATPTSLLISWSDDYHAHRYYRITYGETGGNSPV QEFTVPGEHVTATISGLKPGVDYTITVYAVTYDGEKAATDWSISI NYRT*PC* |
| 116 | ADX_6007_F02 full-length w/N-terminal leader (G) and PmCXn C-terminal modification (m = 1; n = 0) | *G*VSDVPRDLEVVAATPTSLLISWSDDYHAHRYYRITYGETGGNSP VQEFTVPGEHVTATISGLKPGVDYTITVYAVTYDGEKAATDWSIS INYRT*PC* |
| 117 | ADX_6077_F02 full-length w/N-terminal eader (MG) and PmCXn C-terminal modification (m = 1; n = 0) | *MG*VSDVPRDLEVVAATPTSLLISWSDDYHAHRYYRITYGETGGNS PVQEFTVPGEHVTATISGLKPGVDYTITVYAVTYDGEKAATDWSI SINYRT*PC* |
| 118 | ADX_6077_F02 full-length w/PmCXn C-terminal modification (m = 1; n = 0) and His$_6$ tag | MGVSDVPRDLEVVAATPTSLLISWSDDYHAHRYYRITYGETGGNS PVQEFTVPGEHVTATISGLKPGVDYTITVYAVTYDGEKAATDWSI SINYRT*PCHHHHHH* |
| 119 | ADX_6077_F02 core with C-terminal PmCXn$_1$CXn$_2$ | EVVAATPTSLLISWSDDYHAHRYYRITYGETGGNSPVQEFTVPGE HVTATISGLKPGVDYTITVYAVTYDGEKAATDWSISINYRTP$_m$ CX$_{n1}$CX$_{n2}$ |
| 120 | ADX_6077_F02 full-length with C-terminal PmCXn$_1$CXn$_2$ | VSDVPRDLEVVAATPTSLLISWSDDYHAHRYYRITYGETGGNSPV QEFTVPGEHVTATISGLKPGVDYTITVYAVTYDGEKAATDWSISI NYRTP$_m$CX$_{n1}$CX$_{n2}$ |
| 121 | ADX_6077_F02 full-length with N-terminal leader (G), and C-terminal PmCXn$_1$CXn$_2$ | *G*VSDVPRDLEVVAATPTSLLISWSDDYHAHRYYRITYGETGGNSP VQEFTVPGEHVTATISGLKPGVDYTITVYAVTYDGEKAATDWSIS INYRTP$_m$CX$_{n1}$CX$_{n2}$ |

TABLE 2-continued

| SUMMARY OF SEQUENCES | | |
|---|---|---|
| SEQ ID | Description | SEQUENCE |
| 122 | ADX_6077_F02 full-length with N-terminal leader (MG), and C-terminal $PmCXn_1CXn_2$ | *MG*VSDVPRDLEVVAATPTSLLISWSDDYHAHRYYRITYGETGGNSPVQEFTVPGEHVTATISGLKPGVDYTITVYAVTYDGEKAATDWSISINYRT$P_mCX_{n1}CX_{n2}$ |
| 123 | ADX_6077_F02 core with C-terminal $PmCXn_1CXn_2$ (m = 1; n1 = 5; n2 = 0) | EVVAATPTSLLISWSDDYHAHRYYRITYGETGGNSPVQEFTVPGEHVTATISGLKPGVDYTITVYAVTYDGEKAATDWSISINYRT*PCPPPPPC* |
| 124 | ADX_6077_F02 full-length with C-terminal $PmCXn_1Xn_2$ (m = 1; n1 = 5, n2 = 0) | VSDVPRDLEVVAATPTSLLISWSDDYHAHRYYRITYGETGGNSPVQEFTVPGEHVTATISGLKPGVDYTITVYAVTYDGEKAATDWSISINYRT*PCPPPPPC* |
| 125 | ADX_6077_F02 full-length with N-terminal leader (G), and C-terminal $PmCXn_1CXn_2$ (m = 1; n1 = 5, n2 = 0) | GVSDVPRDLEVVAATPTSLLISWSDDYHAHRYYRITYGETGGNSPVQEFTVPGEHVTATISGLKPGVDYTITVYAVTYDGEKAATDWSISINYRT*PCPPPPPC* |
| 126 | ADX_6077_F02 full-length w/N-terminal leader (MG), and C-terminal $PmCXn_1CXn_2$ (m = 1; n1 = 5, n2 = 0) | *MG*VSDVPRDLEVVAATPTSLLISWSDDYHAHRYYRITYGETGGNSPVQEFTVPGEHVTATISGLKPGVDYTITVYAVTYDGEKAATDWSISINYRT*PCPPPPPC* |
| 127 | ADX_6077_F02 full-length w/C-terminal $PmCXn_1CXn_2$ (m = 1; n1 = 5, n2 = 0) and $His_6$ tag | MGVSDVPRDLEVVAATPTSLLISWSDDYHAHRYYRITYGETGGNSPVQEFTVPGEHVTATISGLKPGVDYTITVYAVTYDGEKAATDWSISINYRT*PCPPPPPCHHHHHH* |
| 128 | ADX_6077_F02 DG→EG mutant core | EVVAATPTSLLISWSDDYHAHRYYRITYGETGGNSPVQEFTVPGEHVTATISGLKPGVDYTITVYAVTYEGEKAATDWSISINYRT |
| 129 | ADX_6077_F02 DG→EG mutant FG loop | VTYEGEKAATDWS |
| 130 | ADX_6077_F02 DG→EG mutant full-length | VSDVPRDLEVVAATPTSLLISWSDDYHAHRYYRITYGETGGNSPVQEFTVPGEHVTATISGLKPGVDYTITVYAVTYEGEKAATDWSISINYRT |
| 131 | ADX_6077_F02 DG→EG mutant full-length with N-terminal leader (G) | GVSDVPRDLEVVAATPTSLLISWSDDYHAHRYYRITYGETGGNSPVQEFTVPGEHVTATISGLKPGVDYTITVYAVTYEGEKAATDWSISINYRT |
| 132 | ADX_6077_F02 DG→EG mutant full-length with N-terminal leader (MG) | MGVSDVPRDLEVVAATPTSLLISWSDDYHAHRYYRITYGETGGNSPVQEFTVPGEHVTATISGLKPGVDYTITVYAVTYEGEKAATDWSISINYRT |
| 133 | ADX_6077_F02 DG→EG mutant core with C-terminal PmXn | EVVAATPTSLLISWSDDYHAHRYYRITYGETGGNSPVQEFTVPGEHVTATISGLKPGVDYTITVYAVTYEGEKAATDWSISINYRT$P_mX_n$ |
| 134 | ADX_6077_F02 DG→EG mutant full-length with C-terminal PmXn | VSDVPRDLEVVAATPTSLLISWSDDYHAHRYYRITYGETGGNSPVQEFTVPGEHVTATISGLKPGVDYTITVYAVTYEGEKAATDWSISINYRT$P_mX_n$ |
| 135 | ADX_6077_F02 DG→EG mutant full-length with N-terminal leader (G) and C-terminal PmXn | GVSDVPRDLEVVAATPTSLLISWSDDYHAHRYYRITYGETGGNSPVQEFTVPGEHVTATISGLKPGVDYTITVYAVTYEGEKAATDWSISINYRT$P_mX_n$ |
| 136 | ADX_6077_F02 DG→EG mutant full-length with N-terminal leader (MG) and C-terminal PmXn | MGVSDVPRDLEVVAATPTSLLISWSDDYHAHRYYRITYGETGGNSPVQEFTVPGEHVTATISGLKPGVDYTITVYAVTYEGEKAATDWSISINYRT$P_mX_n$ |
| 137 | ADX_6077_F02 DG→EG mutant core with C-terminal $P_mCX_n$ | EVVAATPTSLLISWSDDYHAHRYYRITYGETGGNSPVQEFTVPGEHVTATISGLKPGVDYTITVYAVTYEGEKAATDWSISINYRT$P_mCX_n$ |
| 138 | ADX_6077_F02 DG→EG mutant full-length with C-terminal PmCXn | VSDVPRDLEVVAATPTSLLISWSDDYHAHRYYRITYGETGGNSPVQEFTVPGEHVTATISGLKPGVDYTITVYAVTYEGEKAATDWSISINYRT$P_mCX_n$ |
| 139 | ADX_6077_F02 DG→EG mutant full-length with N-terminal leader (G) and C-terminal $P_mCX_n$ | GVSDVPRDLEVVAATPTSLLISWSDDYHAHRYYRITYGETGGNSPVQEFTVPGEHVTATISGLKPGVDYTITVYAVTYEGEKAATDWSISINYRT$P_mCX_n$ |
| 140 | ADX_6077_F02 DG→EG mutant full-length with N-terminal leader (MG) and C-terminal $P_mCX_n$ | MGVSDVPRDLEVVAATPTSLLISWSDDYHAHRYYRITYGETGGNSPVQEFTVPGEHVTATISGLKPGVDYTITVYAVTYEGEKAATDWSISINYRT$P_mCX_n$ |

TABLE 2-continued

| SUMMARY OF SEQUENCES | | |
|---|---|---|
| SEQ ID | Description | SEQUENCE |
| 141 | ADX_6077_F02 DG→EG mutant core with C-terminal PmCXn (m = 1; n = 0) | EVVAATPTSLLISWSDDYHAHRYYRITYGETGGNSPVQEFTVPGEHVTATISGLKPGVDYTITVYAVTYEGEKAATDWSISINYRT*PC* |
| 142 | ADX_6077_F02 DG→EG mutant full-length with C-terminal PmCXn (m = 1; n = 0) | VSDVPRDLEVVAATPTSLLISWSDDYHAHRYYRITYGETGGNSPVQEFTVPGEHVTATISGLKPGVDYTITVYAVTYEGEKAATDWSISINYRT*PC* |
| 143 | ADX_6077_F02 DG→EG mutant full-length w/N-terminal leader (G) and PmCXn C-terminal modification (m = 1; n = 0) | GVSDVPRDLEVVAATPTSLLISWSDDYHAHRYYRITYGETGGNSPVQEFTVPGEHVTATISGLKPGVDYTITVYAVTYEGEKAATDWSISINYRT*PC* |
| 144 | ADX_6077_F02 DG→EG mutant full-length w/N-terminal eader (MG) and PmCXn C-terminal modification (m = 1; n = 0) | MGVSDVPRDLEVVAATPTSLLISWSDDYHAHRYYRITYGETGGNSPVQEFTVPGEHVTATISGLKPGVDYTITVYAVTYEGEKAATDWSISINYRT*PC* |
| 145 | ADX_6077_F02 DG→EG mutant full-length with C-terminal PmCXn (m = 1; n = 0) and $His_6$ tag | VSDVPRDLEVVAATPTSLLISWSDDYHAHRYYRITYGETGGNSPVQEFTVPGEHVTATISGLKPGVDYTITVYAVTYEGEKAATDWSISINYRT*PCHHHHHH* |
| 146 | ADX_6077_F02 DG→EG mutant core with C-terminal $PmCXn_1CXn_2$ | EVVAATPTSLLISWSDDYHAHRYYRITYGETGGNSPVQEFTVPGEHVTATISGLKPGVDYTITVYAVTYEGEKAATDWSISINYRT$P_mCX_{n1}CX_2$ |
| 147 | ADX_6077_F02 DG→EG mutant full-length with C-terminal $P_mCX_{n1}CX_2$ | VSDVPRDLEVVAATPTSLLISWSDDYHAHRYYRITYGETGGNSPVQEFTVPGEHVTATISGLKPGVDYTITVYAVTYEGEKAATDWSISINYRT$P_mCX_{n1}CX_2$ |
| 148 | ADX_6077_F02 DG→EG mutant full-length with N-terminal leader (G), and C-terminal $PmCXn_1CXn_2$ | GVSDVPRDLEVVAATPTSLLISWSDDYHAHRYYRITYGETGGNSPVQEFTVPGEHVTATISGLKPGVDYTITVYAVTYEGEKAATDWSISINYRT$P_mCX_{n1}CX_2$ |
| 149 | ADX_6077_F02 DG→EG mutant full-length with N-terminal leader (MG), and C-terminal $PmCXn_1CXn_2$ | MGVSDVPRDLEVVAATPTSLLISWSDDYHAHRYYRITYGETGGNSPVQEFTVPGEHVTATISGLKPGVDYTITVYAVTYEGEKAATDWSISINYRT$P_mCX_{n1}CX_2$ |
| 150 | ADX_6077_F02 DG→EG mutant core with C-terminal $PmCXn_1CXn_2$ (m = 1; n1 = 5; n2 = 0) | EVVAATPTSLLISWSDDYHAHRYYRITYGETGGNSPVQEFTVPGEHVTATISGLKPGVDYTITVYAVTYEGEKAATDWSISINYRT*PCPPPPPC* |
| 151 | ADX_6077_F02 DG→EG mutant full-length with C-terminal $P_mCX_{n1}CX_{n2}$ (m = 1; n1 = 5; n2 = 0) | VSDVPRDLEVVAATPTSLLISWSDDYHAHRYYRITYGETGGNSPVQEFTVPGEHVTATISGLKPGVDYTITVYAVTYEGEKAATDWSISINYRT*PCPPPPPC* |
| 152 | ADX_6077_F02 DG→EG mutant full-length with N-terminal leader (G), and C-terminal $PmCXn_1CXn_2$ (m = 1; n1 = 5, n2 = 0) | GVSDVPRDLEVVAATPTSLLISWSDDYHAHRYYRITYGETGGNSPVQEFTVPMGGEHVTATISGLKPGVDYTITVYAVTYEGEKAATDWSISINYRTP*CPPPPPC* |
| 153 | ADX_6077_F02 DG→EG mutant full-length with N-terminal leader (MG), and C-terminal $PmCXn_1CXn_2$ (m = 1; n1 = 5, n2 = 0) | MGVSDVPRDLEVVAATPTSLLISWSDDYHAHRYYRITYGETGGNSPVQEFTVPGEHVTATISGLKPGVDYTITVYAVTYEGEKAATDWSISINYRT*PCPPPPPC* |
| 154 | ADX_6077_F02 DG→EG mutant full-length with C-terminal $P_mCX_{n1}CX_{n2}$ (m = 1; n1 = 5; n2 = 0), and $His_6$ tag | VSDVPRDLEVVAATPTSLLISWSDDYHAHRYYRITYGETGGNSPVQEFTVPGEHVTATISGLKPGVDYTITVYAVTYEGEKAATDWSISINYRT*PCPPPPPCHHHHHH* |
| 155 | ADX_6077_F02 DG→SG mutant core | EVVAATPTSLLISWSDDYHAHRYYRITYGETGGNSPVQEFTVPGEHVTATISGLKPGVDYTITVYAVTYSGEKAATDWSISINYRT |
| 156 | ADX_6077_F02 DG→SG mutant FG loop | VTYSGEKAATDWS |
| 157 | ADX_6077_F02 DG→SG mutant full-length | VSDVPRDLEVVAATPTSLLISWSDDYHAHRYYRITYGETGGNSPVQEFTVPGEHVTATISGLKPGVDYTITVYAVTYSGEKAATDWSISINYRT |

TABLE 2-continued

SUMMARY OF SEQUENCES

| SEQ ID | Description | SEQUENCE |
|---|---|---|
| 158 | ADX_6077_F02 DG→SG mutant full-length with N-terminal leader (G) | GVSDVPRDLEVVAATPTSLLISWSDDYHAHRYYRITYGETGGNSPVQEFTVPGEHVTATISGLKPGVDYTITVYAVTYSGEKAATDWSISINYRT |
| 159 | ADX_6077_F02 DG→SG mutant full-length with N-terminal leader (MG) | MGVSDVPRDLEVVAATPTSLLISWSDDYHAHRYYRITYGETGGNSPVQEFTVPGEHVTATISGLKPGVDYTITVYAVTYSGEKAATDWSISINYRT |
| 160 | ADX_6077_F02 DG→SG mutant core with C-terminal PmXn | EVVAATPTSLLISWSDDYHAHRYYRITYGETGGNSPVQEFTVPGEHVTATISGLKPGVDYTITVYAVTYSGEKAATDWSISINYRT$P_mX_n$ |
| 161 | ADX_6077_F02 DG→SG mutant full-length with C-terminal PmXn | VSDVPRDLEVVAATPTSLLISWSDDYHAHRYYRITYGETGGNSPVQEFTVPGEHVTATISGLKPGVDYTITVYAVTYSGEKAATDWSISINYRT$P_mX_n$ |
| 162 | ADX_6077_F02 DG→SG mutant full-length with N-terminal leader (G) and C-terminal PmXn | GVSDVPRDLEVVAATPTSLLISWSDDYHAHRYYRITYGETGGNSPVQEFTVPGEHVTATISGLKPGVDYTITVYAVTYSGEKAATDWSISINYRT$P_mX_n$ |
| 163 | ADX_6077_F02 DG→SG mutant full-length with N-terminal leader (MG) and C-terminal PmXn | MGVSDVPRDLEVVAATPTSLLISWSDDYHAHRYYRITYGETGGNSPVQEFTVPGEHVTATISGLKPGVDYTITVYAVTYSGEKAATDWSISINYRT$P_mX_n$ |
| 164 | ADX_6077_F02 DG→SG mutant core with C-terminal $P_mCX_n$ | EVVAATPTSLLISWSDDYHAHRYYRITYGETGGNSPVQEFTVPGEHVTATISGLKPGVDYTITVYAVTYSGEKAATDWSISINYRT$P_mCX_n$ |
| 165 | ADX_6077_F02 DG→SG mutant full-length with C-terminal PmCXn | VSDVPRDLEVVAATPTSLLISWSDDYHAHRYYRITYGETGGNSPVQEFTVPGEHVTATISGLKPGVDYTITVYAVTYSGEKAATDWSISINYRT$P_mCX_n$ |
| 166 | ADX_6077_F02 DG→SG mutant full-length with N-terminal leader (G) and C-terminal $P_mCX_n$ | GVSDVPRDLEVVAATPTSLLISWSDDYHAHRYYRITYGETGGNSPVQEFTVPGEHVTATISGLKPGVDYTITVYAVTYSGEKAATDWSISINYRT$P_mCX_n$ |
| 167 | ADX_6077_F02 DG→SG full-length with N-terminal leader (MG) and C-terminal $P_mCX_n$ | MGVSDVPRDLEVVAATPTSLLISWSDDYHAHRYYRITYGETGGNSPVQEFTVPGEHVTATISGLKPGVDYTITVYAVTYSGEKAATDWSISINYRT$P_mCX_n$ |
| 168 | ADX_6077_F02 DG→SG mutant core with C-terminal PmCXn (m = 1; n = 0) | EVVAATPTSLLISWSDDYHAHRYYRITYGETGGNSPVQEFTVPGEHVTATISGLKPGVDYTITVYAVTYSGEKAATDWSISINYRTPC |
| 169 | ADX_6077_F02 DG→SG mutant full-length with C-terminal PmCXn (m = 1; n = 0) | VSDVPRDLEVVAATPTSLLISWSDDYHAHRYYRITYGETGGNSPVQEFTVPGEHVTATISGLKPGVDYTITVYAVTYSGEKAATDWSISINYRT*PC* |
| 170 | ADX_6077_F02 DG→SG mutant full-length w/N-terminal leader and PmCXn (m = 1; n = 0) | *GV*SDVPRDLEVVAATPTSLLISWSDDYHAHRYYRITYGETGGNSPVQEFTVPGEHVTATISGLKPGVDYTITVYAVTYSGEKAATDWSISINYRT*PC* |
| 171 | ADX_6077_F02 DG→SG mutant full-length w/N-terminal eader (MG) and PmCXn C-terminal modification (m = 1; n = 0) | *MGV*SDVPRDLEVVAATPTSLLISWSDDYHAHRYYRITYGETGGNSPVQEFTVPGEHVTATISGLKPGVDYTITVYAVTYSGEKAATDWSISINYRT*PC* |
| 172 | ADX_6077_F02 DG→SG mutant full-length with C-terminal PmCXn (m = 1; n = 0) and $His_6$ tag | VSDVPRDLEVVAATPTSLLISWSDDYHAHRYYRITYGETGGNSPVQEFTVPGEHVTATISGLKPGVDYTITVYAVTYSGEKAATDWSISINYRT*PCHHHHHH* |
| 173 | ADX_6077_F02 DG→SG mutant core with C-terminal $PmCXn_1CXn_2$ | EVVAATPTSLLISWSDDYHAHRYYRITYGETGGNSPVQEFTVPGEHVTATISGLKPGVDYTITVYAVTYSGEKAATDWSISINYRT$P_mCX_{n1}CX_2$ |
| 174 | ADX_6077_F02 DG→SG mutant full-length with C-terminal $P_mCX_{n1}CX_{n2}$ | VSDVPRDLEVVAATPTSLLISWSDDYHAHRYYRITYGETGGNSPVQEFTVPGEHVTATISGLKPGVDYTITVYAVTYSGEKAATDWSISINYRT$P_mCX_{n1}CX_2$ |
| 175 | ADX_6077_F02 DG→SG mutant full-length with N-terminal leader (G), and C-terminal $PmCXn_1CXn_2$ | GVSDVPRDLEVVAATPTSLLISWSDDYHAHRYYRITYGETGGNSPVQEFTVPGEHVTATISGLKPGVDYTITVYAVTYSGEKAATDWSISINYRT$P_mCX_{n1}CX_2$ |
| 176 | ADX_6077_F02 DG→SG mutant full-length with N-terminal leader (MG), and C-terminal $PmCXn_1CXn_2$ | MGVSDVPRDLEVVAATPTSLLISWSDDYHAHRYYRITYGETGGNSPVQEFTVPGEHVTATISGLKPGVDYTITVYAVTYSGEKAATDWSISINYRT$P_mCX_{n1}CX_2$ |

TABLE 2-continued

| SUMMARY OF SEQUENCES | | |
|---|---|---|
| SEQ ID | Description | SEQUENCE |
| 177 | ADX_6077_F02 DG→SG mutant core with C-terminal $PmCXn_1CXn_2$ (m = 1; n1 = 5; n2 = 0) | EVVAATPTSLLISWSDDYHAHRYYRITYGETGGNSPVQEFTVPGEHVTATISGLKPGVDYTITVYAVTYSGEKAATDWSISINYRTPCPPPPPC |
| 178 | ADX_6077_F02 DG→SG mutant full-length with C-terminal $P_mCX_{n1}CX_{n2}$ (m = 1; n1 = 5; n2 = 0) | VSDVPRDLEVVAATPTSLLISWSDDYHAHRYYRITYGETGGNSPVQEFTVPGEHVTATISGLKPGVDYTITVYAVTYSGEKAATDWSISINYRT*PCPPPPPC* |
| 179 | ADX_6077_F02 DG→SG mutant full-length with N-terminal leader (G), and C-terminal $PmCXn_1CXn_2$ (m = 1; n1 = 5, n2 = 0) | GVSDVPRDLEVVAATPTSLLISWSDDYHAHRYYRITYGETGGNSPVQEFTVPGEHVTATISGLKPGVDYTITVYAVTYSGEKAATDWSISINYRT*PCPPPPPC* |
| 180 | ADX_6077_F02 DG→SG mutant full-length with N-terminal leader (MG), and C-terminal $PmCXn_1CXn_2$ (m = 1; n1 = 5, n2 = 0) | MGVSDVPRDLEVVAATPTSLLISWSDDYHAHRYYRITYGETGGNSPVQEFTVPGEHVTATISGLKPGVDYTITVYAVTYSGEKAATDWSISINYRT*PCPPPPPC* |
| 181 | ADX_6077_F02 DG→SG mutant full-length with C-terminal $P_mCX_{n1}CX_{n2}$ (m = 1; n1 = 5; n2 = 0), and $His_6$ tag | VSDVPRDLEVVAATPTSLLISWSDDYHAHRYYRITYGETGGNSPVQEFTVPGEHVTATISGLKPGVDYTITVYAVTYSGEKAATDWSISINYRT*PCPPPPPCHHHHHH* |
| 182 | ADX_6077_F02 DG→AG mutant core | EVVAATPTSLLISWSDDYHAHRYYRITYGETGGNSPVQEFTVPGEHVTATISGLKPGVDYTITVYAVTYAGEKAATDWSISINYRT |
| 183 | ADX_6077_F02 DG→AG mutant FG loop | VTYAGEKAATDWS |
| 184 | ADX_6077_F02 DG→AG mutant full-length | VSDVPRDLEVVAATPTSLLISWSDDYHAHRYYRITYGETGGNSPVQEFTVPGEHVTATISGLKPGVDYTITVYAVTYAGEKAATDWSISINYRT |
| 185 | ADX_6077_F02 DG→AG mutant full-length with N-terminal leader (G) | GVSDVPRDLEVVAATPTSLLISWSDDYHAHRYYRITYGETGGNSPVQEFTVPGEHVTATISGLKPGVDYTITVYAVTYAGEKAATDWSISINYRT |
| 186 | ADX_6077_F02 DG→AG mutant full-length with N-terminal leader (MG) | MGVSDVPRDLEVVAATPTSLLISWSDDYHAHRYYRITYGETGGNSPVQEFTVPGEHVTATISGLKPGVDYTITVYAVTYAGEKAATDWSISINYRT |
| 187 | ADX_6077_F02 DG→AG mutant core with C-terminal PmXn | LEVVAATPTSLLISWSDDYHAHRYYRITYGETGGNSPVQEFTVPGEHVTATISGLKPGVDYTITVYAVTYAGEKAATDWSISINYRT$P_mX_n$ |
| 188 | ADX_6077_F02 DG→AG mutant full-length with C-terminal PmXn | VSDVPRDLEVVAATPTSLLISWSDDYHAHRYYRITYGETGGNSPVQEFTVPGEHVTATISGLKPGVDYTITVYAVTYAGEKAATDWSISINYRT$P_mX_n$ |
| 189 | ADX_6077_F02 DG→AG mutant full-length with N-terminal leader (G) and C-terminal PmXn | GVSDVPRDLEVVAATPTSLLISWSDDYHAHRYYRITYGETGGNSPVQEFTVPGEHVTATISGLKPGVDYTITVYAVTYAGEKAATDWSISINYRT$P_mX_n$ |
| 190 | ADX_6077_F02 DG→AG mutant full-length with N-terminal leader (MG) and C-terminal PmXn | MGVSDVPRDLEVVAATPTSLLISWSDDYHAHRYYRITYGETGGNSPVQEFTVPGEHVTATISGLKPGVDYTITVYAVTYAGEKAATDWSISINYRT$P_mX_n$ |
| 191 | ADX_6077_F02 DG→AG mutant core with C-terminal $P_mCX_n$ | EVVAATPTSLLISWSDDYHAHRYYRITYGETGGNSPVQEFTVPGEHVTATISGLKPGVDYTITVYAVTYAGEKAATDWSISINYRT$P_mCX_n$ |
| 192 | ADX_6077_F02 DG→AG mutant full-length with C-terminal PmCXn | VSDVPRDLEVVAATPTSLLISWSDDYHAHRYYRITYGETGGNSPVQEFTVPGEHVTATISGLKPGVDYTITVYAVTYAGEKAATDWSISINYRT$P_mCX_n$ |
| 193 | ADX_6077_F02 DG→AG mutant full-length with N-terminal leader (G) and C-terminal $P_mCX_n$ | GVSDVPRDLEVVAATPTSLLISWSDDYHAHRYYRITYGETGGNSPVQEFTVPGEHVTATISGLKPGVDYTITVYAVTYAGEKAATDWSISINYRT$P_mCX_n$ |
| 194 | ADX_6077_F02 DG→AG mutant full-length with N-terminal leader (MG) and C-terminal $P_mCX_n$ | MGVSDVPRDLEVVAATPTSLLISWSDDYHAHRYYRITYGETGGNSPVQEFTVPGEHVTATISGLKPGVDYTITVYAVTYAGEKAATDWSISINYRT$P_mCX_n$ |
| 195 | ADX_6077_F02 DG→AG mutant core with C-terminal PmCXn (m = 1; n = 0) | EVVAATPTSLLISWSDDYHAHRYYRITYGETGGNSPVQEFTVPGEHVTATISGLKPGVDYTITVYAVTYAGEKAATDWSISINYRT*PC* |

TABLE 2-continued

SUMMARY OF SEQUENCES

| SEQ ID | Description | SEQUENCE |
|---|---|---|
| 196 | ADX_6077_F02 DG→AG mutant full-length with C-terminal PmCXn (m = 1; n = 0) | VSDVPRDLEVVAATPTSLLISWSDDYHAHRYYRITYGETGGNSPVQEFTVPGEHVTATISGLKPGVDYTITVYAVTYAGEKAATDWSISINYRT*PC* |
| 197 | ADX_6077_F02 DG→AG mutant full-length w/N-terminal leader (G) and PmCXn C-terminal modification (m = 1; n = 0) | *G*VSDVPRDLEVVAATPTSLLISWSDDYHAHRYYRITYGETGGNSPVQEFTVPGEHVTATISGLKPGVDYTITVYAVTYAGEKAATDWSISINYRT*PC* |
| 198 | ADX_6077_F02 DG→AG mutant full-length w/N-terminal leader (MG) and PmCXn C-terminal modification (m = 1; n = 0) | *MG*VSDVPRDLEVVAATPTSLLISWSDDYHAHRYYRITYGETGGNSPVQEFTVPGEHVTATISGLKPGVDYTITVYAVTYAGEKAATDWSISINYRT*PC* |
| 199 | ADX_6077_F02 DG→AG mutant full-length with C-terminal PmCXn (m = 1; n = 0) and $His_6$ tag | VSDVPRDLEVVAATPTSLLISWSDDYHAHRYYRITYGETGGNSPVQEFTVPGEHVTATISGLKPGVDYTITVYAVTYAGEKAATDWSISINYRT*PCHHHHHH* |
| 200 | ADX_6077_F02 DG→AG mutant core with C-terminal $PmCXn_1CXn_2$ | EVVAATPTSLLISWSDDYHAHRYYRITYGETGGNSPVQEFTVPGEHVTATISGLKPGVDYTITVYAVTYAGEKAATDWSISINYRT$P_mCX_{n1}CX_2$ |
| 201 | ADX_6077_F02 DG→AG mutant full-length with C-terminal $P_mCXn_1CX_2$ | VSDVPRDLEVVAATPTSLLISWSDDYHAHRYYRITYGETGGNSPVQEFTVPGEHVTATISGLKPGVDYTITVYAVTYAGEKAATDWSISINYRT$P_mCX_{n1}CX_2$ |
| 202 | ADX_6077_F02 DG→AG mutant full-length with N-terminal leader (G), and C-terminal $PmCXn_1CXn_2$ | GVSDVPRDLEVVAATPTSLLISWSDDYHAHRYYRITYGETGGNSPVQEFTVPGEHVTATISGLKPGVDYTITVYAVTYAGEKAATDWSISINYRT$P_mCX_{n1}CX_2$ |
| 203 | ADX_6077_F02 DG→AG mutant full-length with N-terminal leader (MG), and C-terminal $PmCXn_1CXn_2$ | MGVSDVPRDLEVVAATPTSLLISWSDDYHAHRYYRITYGETGGNSPVQEFTVPGEHVTATISGLKPGVDYTITVYAVTYAGEKAATDWSISINYRT$P_mCX_{n1}CX_2$ |
| 204 | ADX_6077_F02 DG→AG mutant core with C-terminal $PmCXn_1CXn_2$ (m = 1; n1 = 5; n2 = 0) | EVVAATPTSLLISWSDDYHAHRYYRITYGETGGNSPVQEFTVPGEHVTATISGLKPGVDYTITVYAVTYAGEKAATDWSISINYRT*PCPPPPPC* |
| 205 | ADX_6077_F02 DG→AG mutant full-length with C-terminal $P_mCX_{n1}CX_{n2}$ (m = 1; n1 = 5; n2 = 0) | VSDVPRDLEVVAATPTSLLISWSDDYHAHRYYRITYGETGGNSPVQEFTVPGEHVTATISGLKPGVDYTITVYAVTYAGEKAATDWSISINYRT*PCPPPPPC* |
| 206 | ADX_6077_F02 DG→AG mutant full-length with N-terminal leader (G), and C-terminal $PmCXn_1CXn_2$ (m = 1; n1 = 5, n2 = 0) | GVSDVPRDLEVVAATPTSLLISWSDDYHAHRYYRITYGETGGNSPVQEFTVPGEHVTATISGLKPGVDYTITVYAVTYAGEKAATDWSISINYRT*PCPPPPPC* |
| 207 | ADX_6077_F02 DG→AG mutant full-length with N-terminal leader (MG), and C-terminal $PmCXn_1CXn_2$ (m = 1; n1 = 5, n2 = 0) | MGVSDVPRDLEVVAATPTSLLISWSDDYHAHRYYRITYGETGGNSPVQEFTVPGEHVTATISGLKPGVDYTITVYAVTYAGEKAATDWSISINYRT*PCPPPPPC* |
| 208 | ADX_6077_F02 AG→AG mutant full-length with C-terminal $P_mCX_{n1}CX_{n2}$ (m = 1; n1 = 5; n2 = 0), and $His_6$ tag | VSDVPRDLEVVAATPTSLLISWSDDYHAHRYYRITYGETGGNSPVQEFTVPGEHVTATISGLKPGVDYTITVYAVTYAGEKAATDWSISINYRT*PCPPPPPCHHHHHH* |
| 209 | ADX_6077 F02 DG→GG mutant core | EVVAATPTSLLISWSDDYHAHRYYRITYGETGGNSPVQEFTVPGEHVTATISGLKPGVDYTITVYAVTYGGEKAATDWSISINYRT |
| 210 | ADX_6077_F02 DG→GG mutant FG loop | TYGGEKAATDWS |
| 211 | ADX_6077_F02 DG→GG mutant full-length | VSDVPRDLEVVAATPTSLLISWSDDYHAHRYYRITYGETGGNSPVQEFTVPGEHVTATISGLKPGVDYTITVYAVTYGGEKAATDWSISINYRT |
| 212 | ADX_6077_F02 DG→GG mutant full-length with N-terminal leader (G) | GVSDVPRDLEVVAATPTSLLISWSDDYHAHRYYRITYGETGGNSPVQEFTVPGEHVTATISGLKPGVDYTITVYAVTYGGEKAATDWSISINYRT |

TABLE 2-continued

SUMMARY OF SEQUENCES

| SEQ ID | Description | SEQUENCE |
| --- | --- | --- |
| 213 | ADX_6077_F02 DG→GG mutant full-length with N-terminal leader (MG) | MGVSDVPRDLEVVAATPTSLLISWSDDYHAHRYYRITYGETGGNS PVQEFTVPGEHVTATISGLKPGVDYTITVYAVTYGGEKAATDWSI SINYRT |
| 214 | ADX_6077_F02 DG→GG mutant core with C-terminal PmXn | EVVAATPTSLLISWSDDYHAHRYYRITYGETGGNSPVQEFTVPGE HVTATISGLKPGVDYTITVYAVTYGGEKAATDWSISINYRTP$_m$X$_n$ |
| 215 | ADX_6077_F02 DG→GG mutant full-length with C-terminal PmXn | VSDVPRDLEVVAATPTSLLISWSDDYHAHRYYRITYGETGGNSPV QEFTVPGEHVTATISGLKPGVDYTITVYAVTYGGEKAATDWSISI NYRTP$_m$X$_n$ |
| 216 | ADX_6077_F02 DG→GG mutant full-length with N-terminal leader (G) and C-terminal PmXn | GVSDVPRDLEVVAATPTSLLISWSDDYHAHRYYRITYGETGGNSP VQEFTVPGEHVTATISGLKPGVDYTITVYAVTYGGEKAATDWSIS INYRTP$_m$X$_n$ |
| 217 | ADX_6077_F02 DG→GG mutant full-length with N-terminal leader (MG) and C-terminal PmXn | MGVSDVPRDLEVVAATPTSLLISWSDDYHAHRYYRITYGETGGNS PVQEFTVPGEHVTATISGLKPGVDYTITVYAVTYGGEKAATDWSI SINYRTP$_m$X$_n$ |
| 218 | ADX_6077_F02 DG→GG mutant core with C-terminal P$_m$CX$_n$ | EVVAATPTSLLISWSDDYHAHRYYRITYGETGGNSPVQEFTVPGE HVTATISGLKPGVDYTITVYAVTYGGEKAATDWSISINYRTP$_m$CX$_n$ |
| 219 | ADX_6077_F02 DG→GG mutant full-length with C-terminal PmCXn | VSDVPRDLEVVAATPTSLLISWSDDYHAHRYYRITYGETGGNSPV QEFTVPGEHVTATISGLKPGVDYTITVYAVTYGGEKAATDWSISI NYRTP$_m$CX$_n$ |
| 220 | ADX_6077_F02 DG→GG mutant full-length with N-terminal leader (G) and C-terminal P$_m$CX$_n$ | MVSDVPRDLEVVAATPTSLLISWSDDYHAHRYYRITYGETGGNSP VQEFTVPGEHVTATISGLKPGVDYTITVYAVTYGGEKAATDWSIS INYRTP$_m$CX$_n$ |
| 221 | ADX_6077_F02 DG→GG mutant full-length with N-terminal leader (MG) and C-terminal P$_m$CX$_n$ | MGVSDVPRDLEVVAATPTSLLISWSDDYHAHRYYRITYGETGGNS PVQEFTVPGEHVTATISGLKPGVDYTITVYAVTYGGEKAATDWSI SINYRTP$_m$CX$_n$ |
| 222 | ADX_6077_F02 DG→GG mutant core with C-terminal PmCXn (m = 1; n = 0) | EVVAATPTSLLISWSDDYHAHRYYRITYGETGGNSPVQEFTVPGE HVTATISGLKPGVDYTITVYAVTYGGEKAATDWSISINYRT*PC* |
| 223 | ADX_6077_F02 DG→GG mutant full-length with C-terminal PmCXn (m = 1; n = 0) | VSDVPRDLEVVAATPTSLLISWSDDYHAHRYYRITYGETGGNSPV QEFTVPGEHVTATISGLKPGVDYTITVYAVTYGGEKAATDWSISI NYRT*PC* |
| 224 | ADX_6077_F02 DG→GG mutant full-length with N-terminal leader (G) and C-terminal P$_m$CX$_n$ | GVSDVPRDLEVVAATPTSLLISWSDDYHAHRYYRITYGETGGNSP VQEFTVPGEHVTATISGLKPGVDYTITVYAVTYGGEKAATDWSIS INYRT*PC* |
| 225 | ADX_6077_F02 DG→GG mutant Full-length with N-terminal leader (MG) and C-terminal P$_m$CX$_n$ | MGVSDVPRDLEVVAATPTSLLISWSDDYHAHRYYRITYGETGGNS PVQEFTVPGEHVTATISGLKPGVDYTITVYAVTYGGEKAATDWSI SINYRT*PC* |
| 226 | ADX_6077_F02 DG→GG mutant full-length with C-terminal PmCXn (m = 1; n = 0) and His$_6$ tag | VSDVPRDLEVVAATPTSLLISWSDDYHAHRYYRITYGETGGNSPV QEFTVPGEHVTATISGLKPGVDYTITVYAVTYGGEKAATDWSISI NYRT*PCHHHHHH* |
| 227 | ADX_6077_F02 DG→GG mutant core with C-terminal PmCXn$_1$CXn$_2$ | EVVAATPTSLLISWSDDYHAHRYYRITYGETGGNSPVQEFTVPGE HVTATISGLKPGVDYTITVYAVTYGGEKAATDWSISINYRTP$_m$ CX$_{n1}$CX$_2$ |
| 228 | ADX_6077_F02 DG→GG mutant full-length with C-terminal P$_m$CX$_{n1}$CX$_2$ | VSDVPRDLEVVAATPTSLLISWSDDYHAHRYYRITYGETGGNSPV QEFTVPGEHVTATISGLKPGVDYTITVYAVTYGGEKAATDWSISI NYRTP$_m$CX$_{n1}$CX$_2$ |
| 229 | ADX_6077_F02 DG→GG mutant full-length with N-terminal leader (G), and C-terminal PmCXn$_1$CXn$_2$ | GVSDVPRDLEVVAATPTSLLISWSDDYHAHRYYRITYGETGGNSP VQEFTVPGEHVTATISGLKPGVDYTITVYAVTYGGEKAATDWSIS INYRTP$_m$CX$_{n1}$CX$_2$ |
| 230 | ADX_6077_F02 DG→GG mutant full-length with N-terminal leader (MG), and C-terminal PmCXn$_1$CXn$_2$ | MGVSDVPRDLEVVAATPTSLLISWSDDYHAHRYYRITYGETGGNS PVQEFTVPGEHVTATISGLKPGVDYTITVYAVTYGGEKAATDWSI SINYRTP$_m$CX$_{n1}$CX$_2$ |
| 231 | ADX_6077_F02 DG→GG mutant core with C-terminal PmCXn$_1$CXn$_2$ (m = 1; n1 = 5; n2 = 0) | EVVAATPTSLLISWSDDYHAHRYYRITYGETGGNSPVQEFTVPGE HVTATISGLKPGVDYTITVYAVTYGGEKAATDWSISINYRT*PCPP PPPC* |

TABLE 2-continued

| SUMMARY OF SEQUENCES | | |
|---|---|---|
| SEQ ID | Description | SEQUENCE |
| 232 | ADX_6077_F02 DG→GG mutant full-length with C-terminal $P_mCX_{n1}CX_{n2}$ (m = 1; n1 = 5; n2 = 0) | VSDVPRDLEVVAATPTSLLISWSDDYHAHRYYRITYGETGGNSPVQEFTVPGEHVTATISGLKPGVDYTITVYAVTYGGEKAATDWSISINYRT*PCPPPPPC* |
| 233 | ADX_6077_F02 DG→GG mutant full-length with N-terminal leader (G), and C-terminal $PmCXn_1CXn_2$ (m = 1; n1 = 5, n2 = 0) | GVSDVPRDLEVVAATPTSLLISWSDDYHAHRYYRITYGETGGNSPVQEFTVPGEHVTATISGLKPGVDYTITVYAVTYGGEKAATDWSISINYRT*PCPPPPPC* |
| 234 | ADX_6077_F02 DG→GG mutant full-length with N-terminal leader (MG), and C-terminal $PmCXn_1CXn_2$ (m = 1; n1 = 5, n2 = 0) | MGVSDVPRDLEVVAATPTSLLISWSDDYHAHRYYRITYGETGGNSPVQEFTVPGEHVTATISGLKPGVDYTITVYAVTYGGEKAATDWSISINYRT*PCPPPPPC* |
| 235 | ADX_6077_F02 DG→GG mutant full-length with C-terminal $P_mCX_{n1}CX_{n2}$ (m = 1; n1 = 5; n2 = 0), and $His_6$ tag | VSDVPRDLEVVAATPTSLLISWSDDYHAHRYYRITYGETGGNSPVQEFTVPGEHVTATISGLKPGVDYTITVYAVTYGGEKAATDWSISINYRT*PCPPPPPCHHHHHH* |
| 236 | ADX_6077_F02 DG→DS mutant core | EVVAATPTSLLISWSDDYHAHRYYRITYGETGGNSPVQEFTVPGEHVTATISGLKPGVDYTITVYAVTYDSEKAATDWSISINYRT |
| 237 | ADX_6077_F02 DG→DS mutant FG loop | VTYDSEKAATDWS |
| 238 | ADX_6077_F02 DG→DS mutant full-length | VSDVPRDLEVVAATPTSLLISWSDDYHAHRYYRITYGETGGNSPVQEFTVPGEHVTATISGLKPGVDYTITVYAVTYDSEKAATDWSISINYRT |
| 239 | ADX_6077_F02 DG→DS mutant full-length with N-terminal leader (G) | GVSDVPRDLEVVAATPTSLLISWSDDYHAHRYYRITYGETGGNSPVQEFTVPGEHVTATISGLKPGVDYTITVYAVTYDSEKAATDWSISINYRT |
| 240 | ADX_6077_F02 DG→DS mutant full-length with N-terminal leader (MG) | MGVSDVPRDLEVVAATPTSLLISWSDDYHAHRYYRITYGETGGNSPVQEFTVPGEHVTATISGLKPGVDYTITVYAVTYDSEKAATDWSISINYRT |
| 241 | ADX_6077_F02 DG→DS mutant core with C-terminal PmXn | EVVAATPTSLLISWSDDYHAHRYYRITYGETGGNSPVQEFTVPGEHVTATISGLKPGVDYTITVYAVTYDSEKAATDWSISINYRT$P_mX_n$ |
| 242 | ADX_6077_F02 DG→DS mutant full-length with C-terminal PmXn | VSDVPRDLEVVAATPTSLLISWSDDYHAHRYYRITYGETGGNSPVQEFTVPGEHVTATISGLKPGVDYTITVYAVTYDSEKAATDWSISINYRT$P_mX_n$ |
| 243 | ADX_6077_F02 DG→DS mutant full-length with N-terminal leader (G) and C-terminal PmXn | GVSDVPRDLEVVAATPTSLLISWSDDYHAHRYYRITYGETGGNSPVQEFTVPGEHVTATISGLKPGVDYTITVYAVTYDSEKAATDWSISINYRT$P_mX_n$ |
| 244 | ADX_6077_F02 DG→DS mutant full-length with N-terminal leader (MG) and C-terminal PmXn | MGVSDVPRDLEVVAATPTSLLISWSDDYHAHRYYRITYGETGGNSPVQEFTVPGEHVTATISGLKPGVDYTITVYAVTYDSEKAATDWSISINYRT$P_mX_n$ |
| 245 | ADX_6077_F02 DG→DS mutant core with C-terminal $P_mCX_n$ | EVVAATPTSLLISWSDDYHAHRYYRITYGETGGNSPVQEFTVPGEHVTATISGLKPGVDYTITVYAVTYDSEKAATDWSISINYRT$P_mCX_n$ |
| 246 | ADX_6077_F02 DG→DS mutant full-length with C-terminal PmCXn | VSDVPRDLEVVAATPTSLLISWSDDYHAHRYYRITYGETGGNSPVQEFTVPGEHVTATISGLKPGVDYTITVYAVTYDSEKAATDWSISINYRT$P_mCX_n$ |
| 247 | ADX_6077_F02 DG→DS mutant full-length with N-terminal leader (G) and C-terminal $P_mCX_n$ | GVSDVPRDLEVVAATPTSLLISWSDDYHAHRYYRITYGETGGNSPVQEFTVPGEHVTATISGLKPGVDYTITVYAVTYDSEKAATDWSISINYRT$P_mCX_n$ |
| 248 | ADX_6077_F02 DG→DS mutant full-length with N-terminal leader (MG) and C-terminal $P_mCX_n$ | MGVSDVPRDLEVVAATPTSLLISWSDDYHAHRYYRITYGETGGNSPVQEFTVPGEHVTATISGLKPGVDYTITVYAVTYDSEKAATDWSISINYRT$P_mCX_n$ |
| 249 | ADX_6077_F02 DG→DS mutant core with C-terminal PmCXn (m = 1; n = 0) | EVVAATPTSLLISWSDDYHAHRYYRITYGETGGNSPVQEFTVPGEHVTATISGLKPGVDYTITVYAVTYDSEKAATDWSISINYRT*PC* |
| 250 | ADX_6077_F02 DG→DS mutant full-length with C-terminal PmCXn (m = 1; n = 0) | VSDVPRDLEVVAATPTSLLISWSDDYHAHRYYRITYGETGGNSPVQEFTVPGEHVTATISGLKPGVDYTITVYAVTYDSEKAATDWSISINYRT*PC* |

TABLE 2-continued

SUMMARY OF SEQUENCES

| SEQ ID | Description | SEQUENCE |
|---|---|---|
| 251 | ADX_6077_F02 DG→DS mutant full-length w/ N-terminal leader (G) and PmCXn C-terminal modification (m = 1; n = 0) | GVSDVPRDLEVVAATPTSLLISWSDDYHAHRYYRITYGETGGNSPVQEFTVPGEHVTATISGLKPGVDYTITVYAVTYDSEKAATDWSISINYRT*PC* |
| 252 | ADX_6077_F02 DG→DS mutant full-length w/N-terminal eader (MG) and PmCXn C-terminal modification (m = 1; n = 0) | MGVSDVPRDLEVVAATPTSLLISWSDDYHAHRYYRITYGETGGNSPVQEFTVPGEHVTATISGLKPGVDYTITVYAVTYDSEKAATDWSISINYRT*PC* |
| 253 | ADX_6077_F02 DG→DS mutant full-length with C-terminal PmCXn (m = 1; n = 0) and $His_6$ tag | VSDVPRDLEVVAATPTSLLISWSDDYHAHRYYRITYGETGGNSPVQEFTVPGEHVTATISGLKPGVDYTITVYAVTYDSEKAATDWSISINYRT*PCHHHHHH* |
| 254 | ADX_6077_F02 DG→DS mutant core with C-terminal $PmCXn_1CXn_2$ | EVVAATPTSLLISWSDDYHAHRYYRITYGETGGNSPVQEFTVPGEHVTATISGLKPGVDYTITVYAVTYDSEKAATDWSISINYRT$P_mCX_{n1}CX_2$ |
| 255 | ADX_6077_F02 DG→DS mutant full-length with C-terminal $P_mCX_{n1}CX_2$ | VSDVPRDLEVVAATPTSLLISWSDDYHAHRYYRITYGETGGNSPVQEFTVPGEHVTATISGLKPGVDYTITVYAVTYDSEKAATDWSISINYRT$P_mCX_{n1}CX_2$ |
| 256 | ADX_6077_F02 DG→DS mutant full-length with N-terminal leader (G), and C-terminal $PmCXn_1CXn_2$ | GVSDVPRDLEVVAATPTSLLISWSDDYHAHRYYRITYGETGGNSPVQEFTVPGEHVTATISGLKPGVDYTITVYAVTYDSEKAATDWSISINYRT$P_mCX_{n1}CX_2$ |
| 257 | ADX_6077_F02 DG→DS mutant full-length with N-terminal leader (MG), and C-terminal $PmCXn_1CXn_2$ | MGVSDVPRDLEVVAATPTSLLISWSDDYHAHRYYRITYGETGGNSPVQEFTVPGEHVTATISGLKPGVDYTITVYAVTYDSEKAATDWSISINYRT$P_mCX_{n1}CX_2$ |
| 258 | ADX_6077_F02 DG→DS mutant core with C-terminal $PmCXn_1CXn_2$ (m = 1; n1 = 5; n2 = 0) | EVVAATPTSLLISWSDDYHAHRYYRITYGETGGNSPVQEFTVPGEHVTATISGLKPGVDYTITVYAVTYDSEKAATDWSISINYRT*PCPPPPPC* |
| 259 | ADX_6077_F02 DG→DS mutant full-length with C-terminal $P_mCX_{n1}CX_{n2}$ (m = 1; n1 = 5; n2 = 0) | VSDVPRDLEVVAATPTSLLISWSDDYHAHRYYRITYGETGGNSPVQEFTVPGEHVTATISGLKPGVDYTITVYAVTYDSEKAATDWSISINYRT*PCPPPPPC* |
| 260 | ADX_6077_F02 DG→DS mutant full-length with N-terminal leader (G), and C-terminal $PmCXn_1CXn_2$ (m = 1; n1 = 5, n2 = 0) | GVSDVPRDLEVVAATPTSLLISWSDDYHAHRYYRITYGETGGNSPVQEFTVPGEHVTATISGLKPGVDYTITVYAVTYDSEKAATDWSISINYRT*PCPPPPPC* |
| 261 | ADX_6077_F02 DG→DS mutant full-length with N-terminal leader (MG), and C-terminal $PmCXn_1CXn_2$ (m = 1; n1 = 5, n2 = 0) | MGVSDVPRDLEVVAATPTSLLISWSDDYHAHRYYRITYGETGGNSPVQEFTVPGEHVTATISGLKPGVDYTITVYAVTYDSEKAATDWSISINYRT*PCPPPPPC* |
| 262 | ADX_6077_F02 DG→DS mutant full-length with C-terminal $P_mCX_{n1}CX_{n2}$ (m = 1; n1 = 5; n2 = 0), and $His_6$ tag | VSDVPRDLEVVAATPTSLLISWSDDYHAHRYYRITYGETGGNSPVQEFTVPGEHVTATISGLKPGVDYTITVYAVTYDSEKAATDWSISINYRT*PCPPPPPCHHHHHH* |
| 263 | ADX_6077_F02 DG→DA mutant core | EVVAATPTSLLISWSDDYHAHRYYRITYGETGGNSPVQEFTVPGEHVTATISGLKPGVDYTITVYAVTYDAEKAATDWSISINYRT |
| 264 | ADX_6077 F02 DG→DA mutant FG loop | VTYDAEKAATDWS |
| 265 | ADX_6077_F02 DG→DA mutant full-length | VSDVPRDLEVVAATPTSLLISWSDDYHAHRYYRITYGETGGNSPVQEFTVPGEHVTATISGLKPGVDYTITVYAVTYDAEKAATDWSISINYRT |
| 266 | ADX_6077_F02 DG→DA mutant full-length with N-terminal leader (G) | GVSDVPRDLEVVAATPTSLLISWSDDYHAHRYYRITYGETGGNSPVQEFTVPGEHVTATISGLKPGVDYTITVYAVTYDAEKAATDWSISINYRT |
| 267 | ADX_6077_F02 DG→DA mutant full-length with N-terminal leader (MG) | MGVSDVPRDLEVVAATPTSLLISWSDDYHAHRYYRITYGETGGNSPVQEFTVPGEHVTATISGLKPGVDYTITVYAVTYDAEKAATDWSISINYRT |
| 268 | ADX_6077_F02 DG→DA mutant core with C-terminal PmXn | EVVAATPTSLLISWSDDYHAHRYYRITYGETGGNSPVQEFTVPGEHVTATISGLKPGVDYTITVYAVTYDAEKAATDWSISINYRT$P_mX_n$ |

TABLE 2-continued

SUMMARY OF SEQUENCES

| SEQ ID | Description | SEQUENCE |
|---|---|---|
| 269 | ADX_6077_F02 DG→DA mutant full-length with C-terminal PmXn | VSDVPRDLEVVAATPTSLLISWSDDYHAHRYYRITYGETGGNSPVQEFTVPGEHVTATISGLKPGVDYTITVYAVTYDAEKAATDWSISINYRTP$_m$X$_n$ |
| 270 | ADX_6077_F02 DG→DA mutant full-length with N-terminal leader (G) and C-terminal PmXn | GVSDVPRDLEVVAATPTSLLISWSDDYHAHRYYRITYGETGGNSPVQEFTVPGEHVTATISGLKPGVDYTITVYAVTYDAEKAATDWSISINYRTP$_m$X$_n$ |
| 271 | ADX_6077_F02 DG→DA mutant full-length with N-terminal leader (MG) and C-terminal PmXn | MGVSDVPRDLEVVAATPTSLLISWSDDYHAHRYYRITYGETGGNSPVQEFTVPGEHVTATISGLKPGVDYTITVYAVTYDAEKAATDWSISINYRTP$_m$X$_n$ |
| 272 | ADX_6077_F02 DG→DA mutant core with C-terminal P$_m$CX$_n$ | EVVAATPTSLLISWSDDYHAHRYYRITYGETGGNSPVQEFTVPGEHVTATISGLKPGVDYTITVYAVTYDAEKAATDWSISINYRTP$_m$CX$_n$ |
| 273 | ADX_6077_F02 DG→DA mutant full-length with C-terminal PmCXn | VSDVPRDLEVVAATPTSLLISWSDDYHAHRYYRITYGETGGNSPVQEFTVPGEHVTATISGLKPGVDYTITVYAVTYDAEKAATDWSISINYRTP$_m$CX$_n$ |
| 274 | ADX_6077_F02 DG→DA mutant full-length with N-terminal leader (G) and C-terminal P$_m$CX$_n$ | GVSDVPRDLEVVAATPTSLLISWSDDYHAHRYYRITYGETGGNSPVQEFTVPGEHVTATISGLKPGVDYTITVYAVTYDAEKAATDWSISINYRTP$_m$CX$_n$ |
| 275 | ADX_6077_F02 DG→DA mutant full-length with N-terminal leader (MG) and C-terminal P$_m$CX$_n$ | MGVSDVPRDLEVVAATPTSLLISWSDDYHAHRYYRITYGETGGNSPVQEFTVPGEHVTATISGLKPGVDYTITVYAVTYDAEKAATDWSISINYRTP$_m$CX$_n$ |
| 276 | ADX_6077_F02 DG→DA mutant core with C-terminal PmCXn (m = 1; n = 0) | EVVAATPTSLLISWSDDYHAHRYYRITYGETGGNSPVQEFTVPGEHVTATISGLKPGVDYTITVYAVTYDAEKAATDWSISINYRT*PC* |
| 277 | ADX_6077_F02 DG→DA mutant full-length with C-terminal PmCXn (m = 1; n = 0) | VSDVPRDLEVVAATPTSLLISWSDDYHAHRYYRITYGETGGNSPVQEFTVPGEHVTATISGLKPGVDYTITVYAVTYDAEKAATDWSISINYRT*PC* |
| 278 | ADX_6077_F02 DG→DA mutant full-length w/N-terminal leader and PmCXn C-terminal modification (m = 1; n = 0) | *G*VSDVPRDLEVVAATPTSLLISWSDDYHAHRYYRITYGETGGNSPVQEFTVPGEHVTATISGLKPGVDYTITVYAVTYDAEKAATDWSISINYRT*PC* |
| 279 | ADX_6077_F02 DG→DA mutant full-length w/N-terminal eader (MG) and PmCXn C-terminal modification (m = 1; n = 0) | *MG*VSDVPRDLEVVAATPTSLLISWSDDYHAHRYYRITYGETGGNSPVQEFTVPGEHVTATISGLKPGVDYTITVYAVTYDAEKAATDWSISINYRT*PC* |
| 280 | ADX_6077_F02 DG→DA mutant full-length with C-terminal PmCXn (m = 1; n = 0) and His$_6$ tag | VSDVPRDLEVVAATPTSLLISWSDDYHAHRYYRITYGETGGNSPVQEFTVPGEHVTATISGLKPGVDYTITVYAVTYDAEKAATDWSISINYRT*PCHHHHHH* |
| 281 | ADX_6077_F02 DG→DA mutant core with C-terminal PmCXn$_1$CXn$_2$ | EVVAATPTSLLISWSDDYHAHRYYRITYGETGGNSPVQEFTVPGEHVTATISGLKPGVDYTITVYAVTYDAEKAATDWSISINYRTP$_m$CX$_{n1}$CX$_2$ |
| 282 | ADX_6077_F02 DG→DA mutant full-length with C-terminal P$_m$CX$_{n1}$CX$_2$ | VSDVPRDLEVVAATPTSLLISWSDDYHAHRYYRITYGETGGNSPVQEFTVPGEHVTATISGLKPGVDYTITVYAVTYDAEKAATDWSISINYRTP$_m$CX$_{n1}$CX$_2$ |
| 283 | ADX_6077_F02 DG→DA mutant full-length with N-terminal leader (G), and C-terminal PmCXn$_1$CXn$_2$ | GVSDVPRDLEVVAATPTSLLISWSDDYHAHRYYRITYGETGGNSPVQEFTVPGEHVTATISGLKPGVDYTITVYAVTYDAEKAATDWSISINYRTP$_m$CX$_{n1}$CX$_2$ |
| 284 | ADX_6077_F02 DG→DA mutant full-length with N-terminal leader (MG), and C-terminal PmCXn$_1$CXn$_2$ | MGVSDVPRDLEVVAATPTSLLISWSDDYHAHRYYRITYGETGGNSPVQEFTVPGEHVTATISGLKPGVDYTITVYAVTYDAEKAATDWSISINYRTP$_m$CX$_{n1}$CX$_2$ |
| 285 | ADX_6077_F02 DG→DA mutant core with C-terminal PmCXn$_1$CXn$_2$ (m = 1; n1 = 5; n2 = 0) | EVVAATPTSLLISWSDDYHAHRYYRITYGETGGNSPVQEFTVPGEHVTATISGLKPGVDYTITVYAVTYDAEKAATDWSISINYRT*PCPPPPPC* |
| 286 | ADX_6077_F02 DG→DA mutant full-length with C-terminal P$_m$CX$_{n1}$CX$_{n2}$ (m = 1; n1 = 5; n2 = 0) | VSDVPRDLEVVAATPTSLLISWSDDYHAHRYYRITYGETGGNSPVQEFTVPGEHVTATISGLKPGVDYTITVYAVTYDAEKAATDWSISINYRT*PCPPPPPC* |

TABLE 2-continued

SUMMARY OF SEQUENCES

| SEQ ID | Description | SEQUENCE |
|---|---|---|
| 287 | ADX_6077_F02 DG→DA mutant full-length with N-terminal leader (G), and C-terminal $PmCXn_1CXn_2$ (m = 1; n1 = 5, n2 = 0) | GVSDVPRDLEVVAATPTSLLISWSDDYHAHRYYRITYGETGGNSPVQEFTVPGEHVTATISGLKPGVDYTITVYAVTYDAEKAATDWSISINYRT*PCPPPPPC* |
| 288 | ADX_6077_F02 DG→DA mutant full-length with N-terminal leader (MG), and C-terminal $PmCXn_1CXn_2$ (m = 1; n1 = 5, n2 = 0) | MGVSDVPRDLEVVAATPTSLLISWSDDYHAHRYYRITYGETGGNSPVQEFTVPGEHVTATISGLKPGVDYTITVYAVTYDAEKAATDWSISINYRT*PCPPPPPC* |
| 289 | ADX_6077_F02 DG→DA mutant full-length with C-terminal $P_mCX_{n1}CX_{n2}$ (m = 1; n1 = 5; n2 = 0), and $His_6$ tag | VSDVPRDLEVVAATPTSLLISWSDDYHAHRYYRITYGETGGNSPVQEFTVPGEHVTATISGLKPGVDYTITVYAVTYDAEKAATDWSISINYRT*PCPPPPPCHHHHHH* |
| 290 | ADX_6077_F02 DG→DL mutant core | EVVAATPTSLLISWSDDYHAHRYYRITYGETGGNSPVQEFTVPGEHVTATISGLKPGVDYTITVYAVTYDLEKAATDWSISINYRT |
| 291 | ADX_6077_F02 DG→DL mutant FG loop | VTYDLEKAATDWS |
| 292 | ADX_6077_F02 DG→DL mutant full-length | VSDVPRDLEVVAATPTSLLISWSDDYHAHRYYRITYGETGGNSPVQEFTVPGEHVTATISGLKPGVDYTITVYAVTYDLEKAATDWSISINYRT |
| 293 | ADX_6077_F02 DG→DL mutant full-length with N-terminal leader (G) | GVSDVPRDLEVVAATPTSLLISWSDDYHAHRYYRITYGETGGNSPVQEFTVPGEHVTATISGLKPGVDYTITVYAVTYDLEKAATDWSISINYRT |
| 294 | ADX_6077_F02 DG→DL mutant full-length with N-terminal leader (MG) | MGVSDVPRDLEVVAATPTSLLISWSDDYHAHRYYRITYGETGGNSPVQEFTVPGEHVTATISGLKPGVDYTITVYAVTYDLEKAATDWSISINYRT |
| 295 | ADX_6077_F02 DG→DL mutant core with C-terminal PmXn | EVVAATPTSLLISWSDDYHAHRYYRITYGETGGNSPVQEFTVPGEHVTATISGLKPGVDYTITVYAVTYDLEKAATDWSISINYRT$P_mX_n$ |
| 296 | ADX_6077_F02 DG→DL mutant full-length with C-terminal PmXn | VSDVPRDLEVVAATPTSLLISWSDDYHAHRYYRITYGETGGNSPVQEFTVPGEHVTATISGLKPGVDYTITVYAVTYDLEKAATDWSISINYRT$P_mX_n$ |
| 297 | ADX_6077_F02 DG→DL mutant full-length with N-terminal leader (G) and C-terminal PmXn | MVSDVPRDLEVVAATPTSLLISWSDDYHAHRYYRITYGETGGNSPVQEFTVPGEHVTATISGLKPGVDYTITVYAVTYDLEKAATDWSISINYRT$P_mX_n$ |
| 298 | ADX_6077_F02 DG→DL mutant full-length with N-terminal leader (MG) and C-terminal PmXn | MGVSDVPRDLEVVAATPTSLLISWSDDYHAHRYYRITYGETGGNSPVQEFTVPGEHVTATISGLKPGVDYTITVYAVTYDLEKAATDWSISINYRT$P_mX_n$ |
| 299 | ADX_6077_F02 DG→DL mutant core with C-terminal $P_mCX_n$ | EVVAATPTSLLISWSDDYHAHRYYRITYGETGGNSPVQEFTVPGEHVTATISGLKPGVDYTITVYAVTYDLEKAATDWSISINYRT$P_mCX_n$ |
| 300 | ADX_6077_F02 DG→DL mutant full-length with C-terminal PmCXn | VSDVPRDLEVVAATPTSLLISWSDDYHAHRYYRITYGETGGNSPVQEFTVPGEHVTATISGLKPGVDYTITVYAVTYDLEKAATDWSISINYRT$P_mCX_n$ |
| 301 | ADX_6077_F02 DG→DL mutant full-length with N-terminal leader (G) and C-terminal $P_mCX_n$ | MVSDVPRDLEVVAATPTSLLISWSDDYHAHRYYRITYGETGGNSPVQEFTVPGEHVTATISGLKPGVDYTITVYAVTYDLEKAATDWSISINYRT$P_mCX_n$ |
| 302 | ADX_6077_F02 DG→DL mutant full-length with N-terminal leader (MG) and C-terminal $P_mCX_n$ | MGVSDVPRDLEVVAATPTSLLISWSDDYHAHRYYRITYGETGGNSPVQEFTVPGEHVTATISGLKPGVDYTITVYAVTYDLEKAATDWSISINYRT$P_mCX_n$ |
| 303 | ADX_6077_F02 DG→DL mutant core with C-terminal PmCXn (m = 1; n = 0) | EVVAATPTSLLISWSDDYHAHRYYRITYGETGGNSPVQEFTVPGEHVTATISGLKPGVDYTITVYAVTYDLEKAATDWSISINYRT*PC* |
| 304 | ADX_6077_F02 DG→DL mutant full-length with C-terminal PmCXn (m = 1; n = 0) | VSDVPRDLEVVAATPTSLLISWSDDYHAHRYYRITYGETGGNSPVQEFTVPGEHVTATISGLKPGVDYTITVYAVTYDLEKAATDWSISINYRT*PC* |
| 305 | ADX_6077_F02 DG→DL mutant full-length w/N-terminal leader and PmCXn C-terminal modification (m = 1; n = 0) | *G*VSDVPRDLEVVAATPTSLLISWSDDYHAHRYYRITYGETGGNSPVQEFTVPGEHVTATISGLKPGVDYTITVYAVTYDLEKAATDWSISINYRT*PC* |

TABLE 2-continued

SUMMARY OF SEQUENCES

| SEQ ID | Description | SEQUENCE |
|---|---|---|
| 306 | ADX_6077_F02 DG→DL mutant full-length w/N-terminal eader (MG) and PmCXn C-terminal modification (m = 1; n = 0) | *MG*VSDVPRDLEVVAATPTSLLISWSDDYHAHRYYRITYGETGGNS PVQEFTVPGEHVTATISGLKPGVDYTITVYAVTYDLEKAATDWSI SINYRT*PC* |
| 307 | ADX_6077_F02 DG→DL mutant full-length with C-terminal PmCXn (m = 1; n = 0) and $His_6$ tag | VSDVPRDLEVVAATPTSLLISWSDDYHAHRYYRITYGETGGNSPV QEFTVPGEHVTATISGLKPGVDYTITVYAVTYDLEKAATDWSISI NYRT*PCHHHHHH* |
| 308 | ADX_6077_F02 DG→DL mutant core with C-terminal $PmCXn_1CXn_2$ | EVVAATPTSLLISWSDDYHAHRYYRITYGETGGNSPVQEFTVPGE HVTATISGLKPGVDYTITVYAVTYDLEKAATDWSISINYRT$P_m$ $CX_{n1}CX_2$ |
| 309 | ADX_6077_F02 DG→DL mutant full-length with C-terminal $P_mCX_{n1}CX_2$ | VSDVPRDLEVVAATPTSLLISWSDDYHAHRYYRITYGETGGNSPV QEFTVPGEHVTATISGLKPGVDYTITVYAVTYDLEKAATDWSISI NYRT$P_mCX_{n1}CX_2$ |
| 310 | ADX_6077_F02 DG→DL mutant full-length with N-terminal leader (G), and C-terminal $PmCXn_1CXn_2$ | GVSDVPRDLEVVAATPTSLLISWSDDYHAHRYYRITYGETGGNSP VQEFTVPGEHVTATISGLKPGVDYTITVYAVTYDLEKAATDWSIS INYRT$P_mCX_{n1}CX_2$ |
| 311 | ADX_6077_F02 DG→DL mutant full-length with N-terminal leader (MG), and C-terminal $PmCXn_1CXn_2$ | MGVSDVPRDLEVVAATPTSLLISWSDDYHAHRYYRITYGETGGNS PVQEFTVPGEHVTATISGLKPGVDYTITVYAVTYDLEKAATDWSI SINYRT$P_mCX_{n1}CX_2$ |
| 312 | ADX_6077_F02 DG→DL mutant core with C-terminal $PmCXn_1CXn_2$ (m = 1; n1 = 5; n2 = 0) | EVVAATPTSLLISWSDDYHAHRYYRITYGETGGNSPVQEFTVPGE HVTATISGLKPGVDYTITVYAVTYDLEKAATDWSISINYRT*PCPP PPPC* |
| 313 | ADX_6077_F02 DG→DL mutant full-length with C-terminal $P_mCX_{n1}CX_{n2}$ (m = 1; n1 = 5; n2 = 0) | VSDVPRDLEVVAATPTSLLISWSDDYHAHRYYRITYGETGGNSPV QEFTVPGEHVTATISGLKPGVDYTITVYAVTYDLEKAATDWSISI NYRT*PCPPPPPC* |
| 314 | ADX_6077_F02 DG→DL mutant full-length with N-terminal leader (G), and C-terminal $PmCXn_1CXn_2$ (m = 1; n1 = 5, n2 = 0) | GVSDVPRDLEVVAATPTSLLISWSDDYHAHRYYRITYGETGGNSP VQEFTVPGEHVTATISGLKPGVDYTITVYAVTYDLEKAATDWSIS INYRT*PCPPPPPC* |
| 315 | ADX_6077_F02 DG→DL mutant full-length with N-terminal leader (MG), and C-terminal $PmCXn_1CXn_2$ (m = 1; n1 = 5, n2 = 0) | MGVSDVPRDLEVVAATPTSLLISWSDDYHAHRYYRITYGETGGNS PVQEFTVPGEHVTATISGLKPGVDYTITVYAVTYDLEKAATDWSI SINYRT*PCPPPPPC* |
| 316 | ADX_6077_F02 DG→DL mutant full-length with C-terminal $P_mCX_{n1}CX_{n2}$ (m = 1; n1 = 5; n2 = 0), and $His_6$ tag | VSDVPRDLEVVAATPTSLLISWSDDYHAHRYYRITYGETGGNSPV QEFTVPGEHVTATISGLKPGVDYTITVYAVTYDLEKAATDWSISI NYRT*PCPPPPPCHHHHHH* |
| 317 | ADX_6077_F02 DG→DV mutant core | EVVAATPTSLLISWSDDYHAHRYYRITYGETGGNSPVQEFTVPGE HVTATISGLKPGVDYTITVYAVTYDVEKAATDWSISINYRT |
| 318 | ADX_6077_F02 DG→DV mutant FG loop | VTYDVEKAATDWS |
| 319 | ADX_6077_F02 DG→DV mutant full-length | VSDVPRDLEVVAATPTSLLISWSDDYHAHRYYRITYGETGGNSPV QEFTVPGEHVTATISGLKPGVDYTITVYAVTYDVEKAATDWSISI NYRT |
| 320 | ADX_6077_F02 DG→DV mutant full-length with N-terminal leader (G) | GVSDVPRDLEVVAATPTSLLISWSDDYHAHRYYRITYGETGGNSP VQEFTVPGEHVTATISGLKPGVDYTITVYAVTYDVEKAATDWSIS INYRT |
| 321 | ADX_6077_F02 DG→DV mutant full-length with N-terminal leader (MG) | MGVSDVPRDLEVVAATPTSLLISWSDDYHAHRYYRITYGETGGNS PVQEFTVPGEHVTATISGLKPGVDYTITVYAVTYDVEKAATDWSI SINYRT |
| 322 | ADX_6077_F02 DG→DV mutant core with C-terminal PmXn | EVVAATPTSLLISWSDDYHAHRYYRITYGETGGNSPVQEFTVPGE HVTATISGLKPGVDYTITVYAVTYDVEKAATDWSISINYRT$P_mX_n$ |
| 323 | ADX_6077_F02 DG→DV mutant full-length with C-terminal PmXn | VSDVPRDLEVVAATPTSLLISWSDDYHAHRYYRITYGETGGNSPV QEFTVPGEHVTATISGLKPGVDYTITVYAVTYDVEKAATDWSISI NYRT$P_mX_n$ |

TABLE 2-continued

| SUMMARY OF SEQUENCES | | |
|---|---|---|
| SEQ ID | Description | SEQUENCE |
| 324 | ADX_6077_F02 DG→DV mutant full-length with N-terminal leader (G) and C-terminal PmCXn | GVSDVPRDLEVVAATPTSLLISWSDDYHAHRYYRITYGETGGNSPVQEFTVPGEHVTATISGLKPGVDYTITVYAVTYDVEKAATDWSISINYRTP$_m$X$_n$ |
| 325 | ADX_6077_F02 DG→DV mutant full-length with N-terminal leader (MG) and C-terminal PmXn | MGVSDVPRDLEVVAATPTSLLISWSDDYHAHRYYRITYGETGGNSPVQEFTVPGEHVTATISGLKPGVDYTITVYAVTYDVEKAATDWSISINYRTP$_m$X$_n$ |
| 326 | ADX_6077_F02 DG→DV mutant core with C-terminal P$_m$CX$_n$ | EVVAATPTSLLISWSDDYHAHRYYRITYGETGGNSPVQEFTVPGEHVTATISGLKPGVDYTITVYAVTYDVEKAATDWSISINYRTP$_m$CX$_n$ |
| 327 | ADX_6077_F02 DG→DV mutant full-length with C-terminal PmCXn | VSDVPRDLEVVAATPTSLLISWSDDYHAHRYYRITYGETGGNSPVQEFTVPGEHVTATISGLKPGVDYTITVYAVTYDVEKAATDWSISINYRTP$_m$CX$_n$ |
| 328 | ADX_6077_F02 DG→DV mutant full-length with N-terminal leader (G) and C-terminal P$_m$CX$_n$ | GVSDVPRDLEVVAATPTSLLISWSDDYHAHRYYRITYGETGGNSPVQEFTVPGEHVTATISGLKPGVDYTITVYAVTYDVEKAATDWSISINYRTP$_m$CX$_n$ |
| 329 | ADX_6077_F02 DG→DV mutant full-length with N-terminal leader (MG) and C-terminal P$_m$CX$_n$ | MGVSDVPRDLEVVAATPTSLLISWSDDYHAHRYYRITYGETGGNSPVQEFTVPGEHVTATISGLKPGVDYTITVYAVTYDVEKAATDWSISINYRTP$_m$CX$_n$ |
| 330 | ADX_6077_F02 DG→DV mutant core with C-terminal PmCXn (m = 1; n = 0) | EVVAATPTSLLISWSDDYHAHRYYRITYGETGGNSPVQEFTVPGEHVTATISGLKPGVDYTITVYAVTYDVEKAATDWSISINYRT*PC* |
| 331 | ADX_6077_F02 DG→DV mutant full-length with C-terminal PmCXn (m = 1; n = 0) | VSDVPRDLEVVAATPTSLLISWSDDYHAHRYYRITYGETGGNSPVQEFTVPGEHVTATISGLKPGVDYTITVYAVTYDVEKAATDWSISINYRT*PC* |
| 332 | ADX_6077_F02 DG→DV mutant full-length w/N-terminal leader (G) and PmCXn C-terminal modification (m = 1; n = 0) | *G*VSDVPRDLEVVAATPTSLLISWSDDYHAHRYYRITYGETGGNSPVQEFTVPGEHVTATISGLKPGVDYTITVYAVTYDVEKAATDWSISINYRT*PC* |
| 333 | ADX_6077_F02 DG→DV mutant full-length w/N-terminal eader (MG) and PmCXn C-terminal modification (m = 1; n = 0) | *MG*VSDVPRDLEVVAATPTSLLISWSDDYHAHRYYRITYGETGGNSPVQEFTVPGEHVTATISGLKPGVDYTITVYAVTYDVEKAATDWSISINYRT*PC* |
| 334 | ADX_6077_F02 DG→DV mutant full-length with C-terminal PmCXn (m = 1; n = 0) and $His_6$ tag | VSDVPRDLEVVAATPTSLLISWSDDYHAHRYYRITYGETGGNSPVQEFTVPGEHVTATISGLKPGVDYTITVYAVTYDVEKAATDWSISINYRT*PCHHHHHH* |
| 335 | ADX_6077_F02 DG→DV mutant core with C-terminal PmCXn$_1$CXn$_2$ | EVVAATPTSLLISWSDDYHAHRYYRITYGETGGNSPVQEFTVPGEHVTATISGLKPGVDYTITVYAVTYDVEKAATDWSISINYRTP$_m$CX$_{n1}$CX$_2$ |
| 336 | ADX_6077_F02 DG→DV mutant full-length with C-terminal P$_m$CX$_{n1}$CX$_2$ | VSDVPRDLEVVAATPTSLLISWSDDYHAHRYYRITYGETGGNSPVQEFTVPGEHVTATISGLKPGVDYTITVYAVTYDVEKAATDWSISINYRTP$_m$CX$_{n1}$CX$_2$ |
| 337 | ADX_6077_F02 DG→DV mutant full-length with N-terminal leader (G), and C-terminal PmCXn$_1$CXn$_2$ | GVSDVPRDLEVVAATPTSLLISWSDDYHAHRYYRITYGETGGNSPVQEFTVPGEHVTATISGLKPGVDYTITVYAVTYDVEKAATDWSISINYRTP$_m$CX$_{n1}$CX$_2$ |
| 338 | ADX_6077_F02 DG→DV mutant full-length with N-terminal leader (MG), and C-terminal PmCXn$_1$CXn$_2$ | MGVSDVPRDLEVVAATPTSLLISWSDDYHAHRYYRITYGETGGNSPVQEFTVPGEHVTATISGLKPGVDYTITVYAVTYDVEKAATDWSISINYRTP$_m$CX$_{n1}$CX$_2$ |
| 339 | ADX_6077_F02 DG→DV mutant core with C-terminal PmCXn$_1$CXn$_2$ (m = 1; n1 = 5; n2 = 0) | EVVAATPTSLLISWSDDYHAHRYYRITYGETGGNSPVQEFTVPGEHVTATISGLKPGVDYTITVYAVTYDVEKAATDWSISINYRT*PCPPPPPC* |
| 340 | ADX_6077_F02 DG→DV mutant full-length with C-terminal P$_m$CX$_{n1}$CX$_{n2}$ (m = 1; n1 = 5; n2 = 0) | VSDVPRDLEVVAATPTSLLISWSDDYHAHRYYRITYGETGGNSPVQEFTVPGEHVTATISGLKPGVDYTITVYAVTYDVEKAATDWSISINYRT*PCPPPPPC* |
| 341 | ADX_6077_F02 DG→DV mutant full-length with N-terminal leader (G), and C-terminal PmCXn$_1$CXn$_2$ (m = 1; n1 = 5, n2 = 0) | GVSDVPRDLEVVAATPTSLLISWSDDYHAHRYYRITYGETGGNSPVQEFTVPGEHVTATISGLKPGVDYTITVYAVTYDVEKAATDWSISINYRT*PCPPPPPC* |

TABLE 2-continued

| SUMMARY OF SEQUENCES | | |
|---|---|---|
| SEQ ID | Description | SEQUENCE |
| 342 | ADX_6077_F02 DG→DV mutant full-length with N-terminal leader (MG), and C-terminal $PmCXn_1CXn_2$ (m = 1; n1 = 5, n2 = 0) | MGVSDVPRDLEVVAATPTSLLISWSDDYHAHRYYRITYGETGGNSPVQEFTVPGEHVTATISGLKPGVDYTITVYAVTYDVEKAATDWSISINYRT*PCPPPPPC* |
| 343 | ADX_6077_F02 DG→DV mutant full-length with C-terminal $P_mCX_{n1}CX_{n2}$ (m = 1; n1 = 5; n2 = 0), and $His_6$ tag | VSDVPRDLEVVAATPTSLLISWSDDYHAHRYYRITYGETGGNSPVQEFTVPGEHVTATISGLKPGVDYTITVYAVTYDVEKAATDWSISINYRT*PCPPPPPCHHHHHH* |
| 344 | Human GPC3 | MAGTVRTACLVVAMLLSLDFPGQAQPPPPPPDATCHQVRSFFQRLQPGLKWVPETPVPGSDLQVCLPKGPTCCSRKMEEKYQLTARLNMEQLLQSASMELKFLIIQNAAVFQEAFEIVVRHAKNYTNAMFKNNYPSLTPQAFEFVGEFFTDVSLYILGSDINVDDMVNELFDSLFPVIYTQLMNPGLPDSALDINECLRGARRDLKVFGNFPKLIMTQVSKSLQVTRIFLQALNLGIEVINTTDHLKFSKDCGRMLTRMWYCSYCQGLMMVKPCGGYCNVVMQGCMAGVVEIDKYWREYILSLEELVNGMYRIYDMENVLLGLFSTIHDSIQYVQKNAGKLTTTIGKLCAHSQQRQYRSAYYPEDLFIDKKVLKVAHVEHEETLSSRRRELIQKLKSFISFYSALPGYICSHSPVAENDTLCWNGQELVERYSQKAARNGMKNQFNLHELKMKGPEPVVSQIIDKLKHINQLLRTMSMPKGRVLDKNLDEEGFESGDCGDDEDECIGGSGDGMIKVKNQLRFLAELAYDLDVDDAPGNSQQATPKDNEISTFHNLGNVHSPLKLLTSMAISVVCFFFLVH |
| 345 | Human GPC3 Adnectin binding region 1 | HQVSFF |
| 346 | Human CPC3 Adnectin binding region 2 | EQLLQSASM |
| 347 | ADX_6093_A01 core (non-binding control) | sEVVAATPTSLLISW**DAPAVTVRY**YRITYGETGGNSPVQEFTV**PGSKST**ATISGLKPGVDYTITVYAV**TGRGESPASSKP**ISINYRT |
| 348 | ADX_6093_A01 full-length w/N-leader, PmCXn C-terminal modification (m = 1; n = 0), and His6 tag | *MG*VSDVPRDLEVVAATPTSLLISWDAPAVTVRYYRITYGETGGNSPVQEFTVPGSKSTATISGLKPGVDYTITVYAVTGRGESPASSKPISINYRT*PCHHHHHH* |
| 349 | ADX_6093_A01 full-length w/N-leader, PmCXn C-terminal modification (m = 1; n = 0) | *G*VSDVPRDLEVVAATPTSLLISWDAPAVTVRYYRITYGETGGNSPVQEFTVPGSKSTATISGLKPGVDYTITVYAVTGRGESPASSKPISINYRT*PC* |
| 350 | ADX_6093_A01 full-length w/N-leader, PmCXn C-terminal modification (m = 1; n = 7), and $His_6$ tag | *MG*VSDVPRDLEVVAATPTSLLISWDAPAVTVRYYRITYGETGGNSPVQEFTVPGSKSTATISGLKPGVDYTITVYAVTGRGESPASSKPISINYRT*PCPPPPPCHHHHHH* |
| 351 | N-terminal leader | MGVSDVPRD |
| 352 | N-terminal leader | GVSDVPRD |
| 353 | N-terminal leader | $X_n$SDVPRD |
| 354 | N-terminal leader | $X_n$DVPRD |
| 355 | N-terminal leader | $X_n$VPRD |
| 356 | N-terminal leader | $X_n$PRD |
| 357 | N-terminal leader | $X_n$RD |
| 358 | N-terminal leader | $X_n$D |
| 359 | N-terminal leader | MASTSG |
| 360 | C-terminal tail | EIEK |
| 361 | C-terminal tail | EGSGC |
| 362 | C-terminal tail | EIEKPCQ |
| 363 | C-terminal tail | EIEKPSQ |
| 364 | C-terminal tail | EIEKP |

TABLE 2-continued

| SUMMARY OF SEQUENCES | | |
|---|---|---|
| SEQ ID | Description | SEQUENCE |
| 365 | C-terminal tail | EIEKPS |
| 366 | C-terminal tail | EIEKPC |
| 367 | C-terminal tail | EIDK |
| 368 | C-terminal tail | EIDKPCQ |
| 369 | C-terminal tail | EIDKPSQ |
| 370 | 6X His tail | HHHHHH |
| 371 | C-terminal tail | EIEPKSS |
| 372 | C-terminal tail | EIDKPC |
| 373 | C-terminal tail | EIDKP |
| 374 | C-terminal tail | EIDKPS |
| 375 | C-terminal tail | EIDKPSQLE |
| 376 | C-terminal tail | EIEDEDEDEDED |
| 377 | C-terminal tail | EGSGS |
| 378 | C-terminal tail | EIDKPCQLE |
| 379 | C-terminal tail | EIDKPSQHHHHHH |
| 380 | C-terminal tail | GSGCHHHHHH |
| 381 | C-terminal tail | EGSGCHHHHHH |
| 382 | C-terminal tail | PIDK |
| 383 | C-terminal tail | PIEK |
| 384 | C-terminal tail | PIDKP |
| 385 | C-terminal tail | PIEKP |
| 386 | C-terminal tail | PIDKPS |
| 387 | C-terminal tail | PIEKPS |
| 388 | C-terminal tail | PIDKPC |
| 389 | C-terminal tail | PIEKPC |
| 390 | C-terminal tail | PIDKPSQ |
| 391 | C-terminal tail | PIEKPSQ |
| 392 | C-terminal tail | PIDKPCQ |
| 393 | C-terminal tail | PIEKPCQ |
| 394 | C-terminal tail | PHHHHHH |
| 395 | C-terminal tail | PCHHHHHH |
| 396 | C-terminal tail | PPID |
| 397 | C-terminal tail | PPIE |
| 398 | C-terminal tail | PPIDK |
| 399 | C-terminal tail | PPIEK |
| 400 | C-terminal tail | PPIDKP |
| 401 | C-terminal tail | PPIEKP |

TABLE 2-continued

SUMMARY OF SEQUENCES

| SEQ ID | Description | SEQUENCE |
|---|---|---|
| 402 | C-terminal tail | PPIDKPS |
| 403 | C-terminal tail | PPIEKPS |
| 404 | C-terminal tail | PPIDKPC |
| 405 | C-terminal tail | PPIEKPC |
| 406 | C-terminal tail | PPIDKPSQ |
| 407 | C-terminal tail | PPIEKPSQ |
| 408 | C-terminal tail | PPIDKPCQ |
| 409 | C-terminal tail | PPIEKPCQ |
| 410 | C-terminal tail | PPHHHHHH |
| 411 | C-terminal tail | PPCHHHHHH |
| 412 | C-terminal tail | PCGC |
| 413 | C-terminal tail | PCPC |
| 414 | C-terminal tail | PCGSGC |
| 415 | C-terminal tail | PCPPPC |
| 416 | C-terminal tail | PCPPPPPC |
| 417 | C-terminal tail | PCGSGSGC |
| 418 | C-terminal tail | PCCHHHHHH |
| 419 | C-terminal tail | PCHHHHHHC |
| 420 | C-terminal tail | PCGCHHHHHH |
| 421 | C-terminal tail | PCPCHHHHHH |
| 422 | C-terminal tail | PCGSGCHHHHHH |
| 423 | C-terminal tail | PCPPPCHHHHHH |
| 424 | C-terminal tail | PCPPPPPCHHHHHH |
| 425 | C-terminal tail | PCGSGSGCHHHHHH |
| 426 | Exemplary linker | (PSPEPPTPEP)$_n$ n = 1-10 |
| 427 | Exemplary linker | (EEEDE)$_n$E n = 1-10 |
| 428 | Linker | PSTPPTPSPSTPPTPSPS |
| 429 | Linker | GSGSGSGSGSGSGS |
| 430 | Linker | GGSGSGSGSGSGS |
| 431 | Linker | GGSGSGSGSGSGSGSG |
| 432 | Linker | GSEGSEGSEGSEGSE |
| 433 | Linker | GGSEGGSE |
| 434 | Linker | GSGSGSGS |
| 435 | Linker | GGGGSGGGGSGGGGSGGGGSGGGGSGGGGSGGGGS |
| 436 | Linker | GGGGSGGGGSGGGGSGGGGSGGGGS |
| 437 | Linker | GGGGSGGGGSGGGGSG |
| 438 | Linker | GPGPGPG |
| 439 | Linker | GPGPGPGPGPG |

TABLE 2-continued

| SUMMARY OF SEQUENCES | | |
|---|---|---|
| SEQ ID | Description | SEQUENCE |
| 440 | Linker | PAPAPA |
| 441 | Linker | PAPAPAPAPAPA |
| 442 | Linker | PAPAPAPAPAPAPAPAPA |
| 443 | Linker | PSPEPPTPEP |
| 444 | Linker | PSPEPPTPEPPSPEPPTPEP |
| 445 | Linker | PSPEPPTPEPPSPEPPTPEPPSPEPPTPEP |
| 446 | Linker | PSPEPPTPEPPSPEPPTPEPPSPEPPTPEPPSPEPPTPEP |
| 447 | Linker | EEEEDE |
| 448 | Linker | EEEEDEEEEDE |
| 449 | Linker | EEEEDEEEEDEEEEDEEEEDE |
| 450 | Linker | EEEEDEEEEDEEEEDEEEEDEEEEDEEEEDE |
| 451 | Linker | RGGEEKKKEKEKEEQEERETKTP |
| 452 | ADX_4578_F03 nucleotide sequence encoding (SEQ ID NO: 10) | ATGGGAGTTTCTGATGTGCCGCGCGACTTGGAAGTGGTTGCCGCC ACCCCCACCAGCCTGCTGATCTCTTGGCATCCGCCGCATCCGAAC ATCGTTTCTTACCATATCTACTACGGCGAAACAGGAGGCAATAGC CCTGTCCAGGAGTTCACTGTGGAAGGTTCTAAATCTACTGCTAAA ATCAGCGGCCTTAAACCTGGCGTTGATTATACCATCACTGTGTAC GCTGTTGCTCCGGAAATCGAAAAATACTACCAGATTTGGATTAAT TACCGCACAGAAGGCAGCGGTTCCTAA |
| 453 | ADX_4578_H08 | ATGGGAGTTTCTGATGTGCCGCGCGACCTGGAAGTGGTTGCTGCC ACCCCCACCAGCCTGCTGATCAGCTGGTCTGGTTACGACTACGGT GACTCTTATTACCGCATCACTTACGGCGAAACAGGAGGCAATAGC CCTGTCCAGGAGTTCACTGTGCCTGACGGTTCTAACACAGCTACC ATCAGCGGCCTTAAACCTGGCGTTGATTATACCATCACTGTGTAT GCTGTCGAAGCTTACGGTAAAGGTTACACTCGTTACACTCCAATT TCCATTAATTACCGCACAGAAATTGACAAACCATCCCAGTAA |
| 454 | ADX_4578 | ATGGGAGTTTCTGATGTGCCGCGCGACTTGGAAGTGGTTGCCGCC ACCCCCACCAGCCTGCTGATCTCTTGGTTCCCGGACCGTTACGTT TACTACATCACTTACGGCGAAACAGGAGGCAATAGCCCTGTCCAG GAGTTCACTGTGGAAGGTCATAAACAGACTGCTTACATCAGCGGC CTTAAACCTGGCGTTGATTATACCATCACTGTGTACGCTATCTAC TACTACCCGGACGACTTCCAGGGTTACCCGCAGCCGATTTCTATT AATTACCGCACAGAAGGCAGCGGTTCCTAA |
| 455 | ADX_4606_F06 | ATGGGAGTTTCTGATGTGCCGCGCGACCTGGAAGTGGTTGCTGCC ACCCCCACCAGCCTGCTGATCAGCTGGAACTCTGGTCATTCTGGT CAGTATTACCGCATCACTTACGGCGAAACAGGAGGCAATAGCCCT GTCCAGGAGTTCACTGTGCCTCGTTACGGTTACACAGCTACCATC AGCGGCCTTAAACCTGGCGTTGATTATACCATCACTGTGTATGCT GTCGCTCATTCTGAAGCTTCTGCTCCAATTTCCATTAATTACCGC ACAGAAATTGACAAACCATCCCAGTAA |
| 456 | ADX_5273_C01 | ATGGGAGTTTCTGATGTGCCGCGCGACCTGGAAGTGGTTGCTGCC ACCCCCACCAGCCTGCTGATCAGCTGGTCTGACCCGTACGAAGAA GAACGATATTACCGCATCACTTACGGCGAAACAGGAGGCAATAGC CCTGTCCAGGAGTTCACTGTGCCTGCTTTCCATACTACAGCTACC ATCAGCGGCCTTAAACCTGGCGTTGATTATACCATCACTGTGTAT GCTGTCACTTACAAACATAAATACGCTTACTACTACCCGCCAATT TCCATTAATTACCGCACAGAAATTGACAAACCATCCCAGTAA |
| 457 | ADX_5273_D01 | ATGGGAGTTTCTGATGTGCCGCGCGACCTGGAAGTGGTTGCTGCC ACCCCCACCAGCCTGCTGATCAGCTGGGAACCGTCTTACAAAGAC GACCGATATTACCGCATCACTTACGGCGAAACAGGAGGCAATAGC CCTGTCCAGGAGTTCACTGTGCCTTCTTTCCATCAGACAGCTACC ATCAGCGGCCTTAAACCTGGCGTTGATTATACCATCACTGTGTAT GCTGTCACTTACGAACCGGACGAATACTACTTCTACTACCCAATT TCCATTAATTACCGCACAGAAATTGACAAACCATCCCAGTAA |

TABLE 2-continued

SUMMARY OF SEQUENCES

| SEQ ID | Description | SEQUENCE |
|---|---|---|
| 458 | ADX_5274_E01 | ATGGGAGTTTCTGATGTGCCGCGCGACCTGGAAGTGGTTGCTGCC ACCCCCACCAGCCTGCTGATCAGCTGGTCTGGTGACTACCATCCG CATCGATATTACCGCATCACTTACGGCGAAACAGGAGGCAATAGC CCTGTCCAGGAGTTCACTGTGCCTGGTGAACATGAAACAGCTACC ATCAGCGGCCTTAAACCTGGCGTTGATTATACCATCACTGTGTAT GCTGTCACTTACGACGGTGAAAAAGCTGACAAATACCCGCCAATT TCCATTAATTACCGCACAGAAATTGACAAACCATCCCAGTAA |
| 459 | ADX_6077_F02 | ATGGGAGTTT CTGATGTGCC GCGCGACCTG GAAGTGGTTG CTGCCACCCC CACCAGCCTG CTGATCAGCT GGTCTGATGA CTACCATGCG CATCGATATT ACCGCATCAC TTACGGCGAA ACAGGAGGCA ATAGCCCTGT CCAGGAGTTC ACTGTGCCTG GTGAACATGT GACAGCTACC ATCAGCGGCC TTAAACCTGG CGTTGATTAT ACCATCACTG TGTATGCTGT CACTTACGAC GGTGAAAAGG CTGCCACAGA TTGGTCAATT TCCATTAATT ACCGCACACC GTGCCACCAT CACCACCACC ACTGA |
| 460 | ADX_6077_F02 w/o His-tag and including leader sequence | GGTGTT AGTGATGTTC CGCGTGATCT GGAAGTTGTT GCAGCAACCC CGACCAGCCT GCTGATTAGC TGGTCAGATG ATTATCATGC CCATCGTTAT TATCGCATTA CCTATGGTGA AACCGGTGGT AATAGTCCGG TTCAAGAATT CACCGTTCCG GGTGAACATG TTACCGCAAC CATTAGCGGT CTGAAACCGG GTGTTGATTA CACCATTACC GTTTATGCAG TTACCTACGA TGGTGAAAAA GCAGCAACCG ATTGGAGCAT TAGCATTAAC TATCGTACCC CGTGTTAA |
| 461 | ADX_6077_F02 w/leader sequence and PCPPPPPC | ATGAAAAAAATC TGGCTGGCAC TGGCAGGTCT GGTTCTGGCA TTTAGCGCTA GCGCCGGTGT TAGTGATGTT CCGCGTGATC TGGAAGTTGT TGCAGCAACC CCGACCAGCC TGCTGATTAG CTGGTCAGAT GATTATCATG CCCATCGTTA TTATCGCATT ACCTATGGTG AAACCGGTGG TAATAGTCCG GTTCAAGAAT TCACCGTTCC GGGTGAACAT GTTACCGCAA CCATTAGCGG TCTGAAACCG GGTGTTGATT ACACCATTAC CGTTTATGCA GTTACCTACG ATGGTGAAAA AGCAGCAACC GATTGGAGCA TTAGCATTAA CTATCGTACC CCGTGTCCGC CGCCACCGCC GTGTTGATAA |
| 462 | ADX_6077_F02 w/leader sequence and PCPPPPPCH6 | ATGGGAGTTT CTGATGTGCC GCGCGACCTG GAAGTGGTTG CTGCCACCCC CACCAGCCTG CTGATCAGCT GGTCTGATGA CTACCATGCG CATCGATATT ACCGCATCAC TTACGGCGAA ACAGGAGGCA ATAGCCCTGT CCAGGAGTTC ACTGTGCCTG GTGAACATGT GACAGCTACC ATCAGCGGCC TTAAACCTGG CGTTGATTAT ACCATCACTG TGTATGCTGT CACTTACGAC GGTGAAAAGG CTGCCACAGA TTGGTCAATT TCCATTAATT ACCGCACACC GTGCCCGCCG CCACCGCCGT GTCACCATCA CCACCACCAC TGA |
| 463 | ADX_6093_A01 full length | VSDVPRDLEVVAATPTSLLISWDAPAVTVRYYRITYGETGGNSPV QEFTVPGSKSTATISGLKPGVDYTITVYAVTGRGESPASSKPISI NYRT |
| 464 | linker | $(GS)_{5-10}$ |
| 465 | linker | $(G_4S)_{2-5}$ |
| 466 | linker | $(G_4S)_2G$ |
| 467 | linker | PVGVV |

SEQUENCE LISTING

Sequence total quantity: 467
SEQ ID NO: 1 moltype = AA length = 94
FEATURE Location/Qualifiers
REGION 1..94
note = misc_feature - Full length wild-type human 10Fn3 domain
source 1..94
mol_type = protein
organism = Homo sapiens -continued

```
SEQUENCE: 1
VSDVPRDLEV VAATPTSLLI SWDAPAVTVR YYRITYGETG GNSPVQEFTV PGSKSTATIS  60
GLKPGVDYTI TVYAVTGRGD SPASSKPISI NYRT                              94

SEQ ID NO: 2           moltype = AA  length = 86
FEATURE                Location/Qualifiers
REGION                 1..86
                       note = misc_feature - Core wild-type human 10Fn3 domain
source                 1..86
                       mol_type = protein
                       organism = Homo sapiens
SEQUENCE: 2
EVVAATPTSL LISWDAPAVT VRYYRITYGE TGGNSPVQEF TVPGSKSTAT ISGLKPGVDY  60
TITVYAVTGR GDSPASSKPI SINYRT                                       86

SEQ ID NO: 3           moltype = AA  length = 166
FEATURE                Location/Qualifiers
REGION                 1..166
                       note = misc_feature - Human 10Fn3 domain six loop sequences
                        generically defined
VARIANT                14..33
                       note = At least 2 and up to 20 Xaa may be present; if
                        present, Xaa can be any naturally occurring amino acid
VARIANT                39..58
                       note = At least 2 and up to 20 Xaa may be present; if
                        present, Xaa can be any naturally occurring amino acid
VARIANT                64..83
                       note = At least 2 and up to 20 Xaa may be present; if
                        present, Xaa can be any naturally occurring amino acid
VARIANT                87..106
                       note = At least 2 and up to 20 Xaa may be present; if
                        present, Xaa can be any naturally occurring amino acid
VARIANT                113..132
                       note = At least 2 and up to 20 Xaa may be present; if
                        present, Xaa can be any naturally occurring amino acid
VARIANT                140..159
                       note = At least 2 and up to 20 Xaa may be present; if
                        present, Xaa can be any naturally occurring amino acid
source                 1..166
                       mol_type = protein
                       organism = Homo sapiens
SEQUENCE: 3
VSDVPRDLEV VAAXXXXXXX XXXXXXXXXX XXXLLISWXX XXXXXXXXXX XXXXXXXXYR  60
ITYXXXXXXX XXXXXXXXXX XXXFTVXXXX XXXXXXXXXX XXXXXXATIS GLXXXXXXXX  120
XXXXXXXXXX XXYTITVYAX XXXXXXXXXX XXXXXXXXXI SINYRT                 166

SEQ ID NO: 4           moltype = AA  length = 101
FEATURE                Location/Qualifiers
REGION                 1..101
                       note = misc_feature - Wild-type human 10Fn3 domain
                        C-terminal flexible linker
source                 1..101
                       mol_type = protein
                       organism = Homo sapiens
SEQUENCE: 4
VSDVPRDLEV VAATPTSLLI SWDAPAVTVR YYRITYGETG GNSPVQEFTV PGSKSTATIS  60
GLKPGVDYTI TVYAVTGRGD SPASSKPISI NYRTEIDKPS Q                      101

SEQ ID NO: 5           moltype = AA  length = 83
FEATURE                Location/Qualifiers
REGION                 1..83
                       note = Synthetic: ADX_4578_F03, Core
source                 1..83
                       mol_type = protein
                       organism = synthetic construct
SEQUENCE: 5
EVVAATPTSL LISWHPPHPN IVSYHIYYGE TGGNSPVQEF TVEGSKSTAK ISGLKPGVDY  60
TITVYAVAPE IEKYYQIWIN YRT                                          83

SEQ ID NO: 6           moltype = AA  length = 9
FEATURE                Location/Qualifiers
REGION                 1..9
                       note = Synthetic: ADX_4578_F03, BC loop
source                 1..9
                       mol_type = protein
                       organism = synthetic construct
SEQUENCE: 6
HPPHPNIVS                                                          9
```

-continued

```
SEQ ID NO: 7            moltype = AA  length = 6
FEATURE                 Location/Qualifiers
REGION                  1..6
                        note = Synthetic: ADX_4578_F03, DE loop
source                  1..6
                        mol_type = protein
                        organism = synthetic construct
SEQUENCE: 7
EGSKST                                                             6

SEQ ID NO: 8            moltype = AA  length = 10
FEATURE                 Location/Qualifiers
REGION                  1..10
                        note = Synthetic: ADX_4578_F03, DE loop
source                  1..10
                        mol_type = protein
                        organism = synthetic construct
SEQUENCE: 8
VAPEIEKYYQ                                                         10

SEQ ID NO: 9            moltype = AA  length = 91
FEATURE                 Location/Qualifiers
REGION                  1..91
                        note = Synthetic: ADX_45708_F03, full-length
source                  1..91
                        mol_type = protein
                        organism = synthetic construct
SEQUENCE: 9
VSDVPRDLEV VAATPTSLLI SWHPPHPNIV SYHIYYGETG GNSPVQEFTV EGSKSTAKIS  60
GLKPGVDYTI TVYAVAPEIE KYYQIWINYR T                                 91

SEQ ID NO: 10           moltype = AA  length = 98
FEATURE                 Location/Qualifiers
REGION                  1..98
                        note = Synthetic: ADX_4578_F03, full-length w/N-terminal
                         leader and C-terminal tail
source                  1..98
                        mol_type = protein
                        organism = synthetic construct
SEQUENCE: 10
MGVSDVPRDL EVVAATPTSL LISWHPPHPN IVSYHIYYGE TGGNSPVQEF TVEGSKSTAK  60
ISGLKPGVDY TITVYAVAPE IEKYYQIWIN YRTEGSGS                          98

SEQ ID NO: 11           moltype = AA  length = 101
FEATURE                 Location/Qualifiers
REGION                  1..101
                        note = Synthetic: ADX_4578_F03, full-length with C-terminal
                         PmXn
VARIANT                 1..101
                        note = In the C-terminal PmXn, up to 5 proline and up to 5
                         Xaa may or may not be present
VARIANT                 97..101
                        note = Xaa can be any naturally occurring amino acid
source                  1..101
                        mol_type = protein
                        organism = synthetic construct
SEQUENCE: 11
VSDVPRDLEV VAATPTSLLI SWHPPHPNIV SYHIYYGETG GNSPVQEFTV EGSKSTAKIS  60
GLKPGVDYTI TVYAVAPEIE KYYQIWINYR TPPPPPXXXX X                      101

SEQ ID NO: 12           moltype = AA  length = 102
FEATURE                 Location/Qualifiers
REGION                  1..102
                        note = Synthetic: ADX_4578_F03, full-length with C-terminal
                         PmCXn
VARIANT                 1..102
                        note = In the C-terminal PmCXn, up to 5 proline and up to 5
                         Xaa may or may not be present
VARIANT                 98..102
                        note = Xaa can be any naturally occurring amino acid
source                  1..102
                        mol_type = protein
                        organism = synthetic construct
SEQUENCE: 12
VSDVPRDLEV VAATPTSLLI SWHPPHPNIV SYHIYYGETG GNSPVQEFTV EGSKSTAKIS  60
GLKPGVDYTI TVYAVAPEIE KYYQIWINYR TPPPPPCXXX XX                     102

SEQ ID NO: 13           moltype = AA  length = 93
FEATURE                 Location/Qualifiers
```

```
REGION                  1..93
                        note = Synthetic: ADX_4578_F03, full-length with C-terminal
                         PmCXn(m=1; n=0)
source                  1..93
                        mol_type = protein
                        organism = synthetic construct
SEQUENCE: 13
VSDVPRDLEV VAATPTSLLI SWHPPHPNIV SYHIYYGETG GNSPVQEFTV EGSKSTAKIS  60
GLKPGVDYTI TVYAVAPEIE KYYQIWINYR TPC                               93

SEQ ID NO: 14           moltype = AA  length = 99
FEATURE                 Location/Qualifiers
REGION                  1..99
                        note = Synthetic: ADX_4578_F03, full-length with C-terminal
                         PmCXn(m=1; n=0) and His6 tag
source                  1..99
                        mol_type = protein
                        organism = synthetic construct
SEQUENCE: 14
VSDVPRDLEV VAATPTSLLI SWHPPHPNIV SYHIYYGETG GNSPVQEFTV EGSKSTAKIS  60
GLKPGVDYTI TVYAVAPEIE KYYQIWINYR TPCHHHHHH                         99

SEQ ID NO: 15           moltype = AA  length = 108
FEATURE                 Location/Qualifiers
REGION                  1..108
                        note = Synthetic: ADX_4578_F03, full-length with C-terminal
                         PmCXn1CXn2
VARIANT                 1..108
                        note = In the C-terminal PmCXn1CXn2, up to 5 proline and up
                         to 5 Xaa (before and after the last Cys) may or may not be
                         present
VARIANT                 98..102
                        note = Xaa can be any naturally occurring amino acid
VARIANT                 104..108
                        note = Xaa can be any naturally occurring amino acid
source                  1..108
                        mol_type = protein
                        organism = synthetic construct
SEQUENCE: 15
VSDVPRDLEV VAATPTSLLI SWHPPHPNIV SYHIYYGETG GNSPVQEFTV EGSKSTAKIS  60
GLKPGVDYTI TVYAVAPEIE KYYQIWINYR TPPPPPCXXX XXCXXXXX               108

SEQ ID NO: 16           moltype = AA  length = 99
FEATURE                 Location/Qualifiers
REGION                  1..99
                        note = Synthetic: ADX_4578_F03, full-length with C-terminal
                         PmCXn1CXn2 (m=1, n1=5, n2=0)
source                  1..99
                        mol_type = protein
                        organism = synthetic construct
SEQUENCE: 16
VSDVPRDLEV VAATPTSLLI SWHPPHPNIV SYHIYYGETG GNSPVQEFTV EGSKSTAKIS  60
GLKPGVDYTI TVYAVAPEIE KYYQIWINYR TPCPPPPPC                         99

SEQ ID NO: 17           moltype = AA  length = 105
FEATURE                 Location/Qualifiers
REGION                  1..105
                        note = Synthetic: ADX_4578_F03, full-length with C-terminal
                         PmCXn1CXn2 (m=1, n1=5, n2=0) and His6 tag
source                  1..105
                        mol_type = protein
                        organism = synthetic construct
SEQUENCE: 17
VSDVPRDLEV VAATPTSLLI SWHPPHPNIV SYHIYYGETG GNSPVQEFTV EGSKSTAKIS  60
GLKPGVDYTI TVYAVAPEIE KYYQIWINYR TPCPPPPPCH HHHHH                  105

SEQ ID NO: 18           moltype = AA  length = 86
FEATURE                 Location/Qualifiers
REGION                  1..86
                        note = Synthetic: ADX_4578_H08, core
source                  1..86
                        mol_type = protein
                        organism = synthetic construct
SEQUENCE: 18
EVVAATPTSL LISWSGYDYG DSYYRITYGE TGGNSPVQEF TVPDGSNTAT ISGLKPGVDY  60
TITVYAVEAY GKGYTRYTPI SINYRT                                       86

SEQ ID NO: 19           moltype = AA  length = 9
FEATURE                 Location/Qualifiers
```

-continued

```
REGION                 1..9
                       note = Synthetic: ADX_4578_H08, BC loop
source                 1..9
                       mol_type = protein
                       organism = synthetic construct
SEQUENCE: 19
SGYDYGDSY                                                    9

SEQ ID NO: 20          moltype = AA  length = 6
FEATURE                Location/Qualifiers
REGION                 1..6
                       note = Synthetic: ADX_4578_H08, DE loop
source                 1..6
                       mol_type = protein
                       organism = synthetic construct
SEQUENCE: 20
PDGNST                                                       6

SEQ ID NO: 21          moltype = AA  length = 13
FEATURE                Location/Qualifiers
REGION                 1..13
                       note = Synthetic: ADX_4578_H08, FG loop
source                 1..13
                       mol_type = protein
                       organism = synthetic construct
SEQUENCE: 21
VEAYGKGYTR YTP                                               13

SEQ ID NO: 22          moltype = AA  length = 94
FEATURE                Location/Qualifiers
REGION                 1..94
                       note = Synthetic: ADX_4578_H08, full-length
source                 1..94
                       mol_type = protein
                       organism = synthetic construct
SEQUENCE: 22
VSDVPRDLEV VAATPTSLLI SWSGYDYGDS YYRITYGETG GNSPVQEFTV PDGSNTATIS  60
GLKPGVDYTI TVYAVEAYGK GYTRYTPISI NYRT                         94

SEQ ID NO: 23          moltype = AA  length = 103
FEATURE                Location/Qualifiers
REGION                 1..103
                       note = Synthetic: ADX_4578_H08, full-length w/N-terminal
                        leader and C-terminal tail
source                 1..103
                       mol_type = protein
                       organism = synthetic construct
SEQUENCE: 23
MGVSDVPRDL EVVAATPTSL LISWSGYDYG DSYYRITYGE TGGNSPVQEF TVPDGSNTAT  60
ISGLKPGVDY TITVYAVEAY GKGYTRYTPI SINYRTEIDK PSQ               103

SEQ ID NO: 24          moltype = AA  length = 104
FEATURE                Location/Qualifiers
REGION                 1..104
                       note = Synthetic: ADX_4578_H08, full-length with C-terminal
                        PmXn
VARIANT                1..104
                       note = In the C-terminal PmXn, up to 5 proline and up to 5
                        Xaa may or may not be present
VARIANT                100..104
                       note = Xaa can be any naturally occurring amino acid
source                 1..104
                       mol_type = protein
                       organism = synthetic construct
SEQUENCE: 24
VSDVPRDLEV VAATPTSLLI SWSGYDYGDS YYRITYGETG GNSPVQEFTV PDGSNTATIS  60
GLKPGVDYTI TVYAVEAYGK GYTRYTPISI NYRTPPPPPX XXXX              104

SEQ ID NO: 25          moltype = AA  length = 105
FEATURE                Location/Qualifiers
REGION                 1..105
                       note = Synthetic: ADX_4578_H08, full-length with C-terminal
                        PmCXn
VARIANT                1..105
                       note = In the C-terminal PmCXn, up to 5 proline and up to 5
                        Xaa may or may not be present
VARIANT                101..105
                       note = Xaa can be any naturally occurring amino acid
source                 1..105
```

```
                        mol_type = protein
                        organism = synthetic construct
SEQUENCE: 25
VSDVPRDLEV VAATPTSLLI SWSGYDYGDS YYRITYGETG GNSPVQEFTV PDGSNTATIS  60
GLKPGVDYTI TVYAVEAYGK GYTRYTPISI NYRTPPPPPC XXXXX                 105

SEQ ID NO: 26           moltype = AA  length = 96
FEATURE                 Location/Qualifiers
REGION                  1..96
                        note = Synthetic: ADX_4578_H08, full-length with C-terminal
                         PmCXn(m=1; n=0)
source                  1..96
                        mol_type = protein
                        organism = synthetic construct
SEQUENCE: 26
VSDVPRDLEV VAATPTSLLI SWSGYDYGDS YYRITYGETG GNSPVQEFTV PDGSNTATIS  60
GLKPGVDYTI TVYAVEAYGK GYTRYTPISI NYRTPC                           96

SEQ ID NO: 27           moltype = AA  length = 102
FEATURE                 Location/Qualifiers
REGION                  1..102
                        note = Synthetic: ADX_4578_H08, full-length with C-terminal
                         PmCXn(m=1; n=0) and His6 tag
source                  1..102
                        mol_type = protein
                        organism = synthetic construct
SEQUENCE: 27
VSDVPRDLEV VAATPTSLLI SWSGYDYGDS YYRITYGETG GNSPVQEFTV PDGSNTATIS  60
GLKPGVDYTI TVYAVEAYGK GYTRYTPISI NYRTPCHHHH HH                    102

SEQ ID NO: 28           moltype = AA  length = 111
FEATURE                 Location/Qualifiers
REGION                  1..111
                        note = Synthetic: ADX_4578_H08, full-length with C-terminal
                         PmCXn1CXn2
VARIANT                 1..111
                        note = In the C-terminal PmCXn1CXn2, up to 5 proline and up
                         to 5 Xaa (before and after the last Cys) may or may not be
                         present
VARIANT                 101..105
                        note = Xaa can be any naturally occurring amino acid
VARIANT                 107..111
                        note = Xaa can be any naturally occurring amino acid
source                  1..111
                        mol_type = protein
                        organism = synthetic construct
SEQUENCE: 28
VSDVPRDLEV VAATPTSLLI SWSGYDYGDS YYRITYGETG GNSPVQEFTV PDGSNTATIS  60
GLKPGVDYTI TVYAVEAYGK GYTRYTPISI NYRTPPPPPC XXXXXCXXXX X          111

SEQ ID NO: 29           moltype = AA  length = 102
FEATURE                 Location/Qualifiers
REGION                  1..102
                        note = Synthetic: ADX_4578_H08, full-length with C-terminal
                         PmCXn1CXn2 (m=1, n1=5, n2=0)
source                  1..102
                        mol_type = protein
                        organism = synthetic construct
SEQUENCE: 29
VSDVPRDLEV VAATPTSLLI SWSGYDYGDS YYRITYGETG GNSPVQEFTV PDGSNTATIS  60
GLKPGVDYTI TVYAVEAYGK GYTRYTPISI NYRTPCPPPP PC                    102

SEQ ID NO: 30           moltype = AA  length = 108
FEATURE                 Location/Qualifiers
REGION                  1..108
                        note = Synthetic: ADX_4578_H08, full-length with C-terminal
                         PmCXn1CXn2 (m=1, n1=5, n2=0) and His6 tag
source                  1..108
                        mol_type = protein
                        organism = synthetic construct
SEQUENCE: 30
VSDVPRDLEV VAATPTSLLI SWSGYDYGDS YYRITYGETG GNSPVQEFTV PDGSNTATIS  60
GLKPGVDYTI TVYAVEAYGK GYTRYTPISI NYRTPCPPPP PCHHHHHH              108

SEQ ID NO: 31           moltype = AA  length = 76
FEATURE                 Location/Qualifiers
REGION                  1..76
                        note = Synthetic: ADX_4578_B06, core
source                  1..76
```

```
                        mol_type = protein
                        organism = synthetic construct
SEQUENCE: 31
EVVAATPTSL LISWFPDRYV YYITYGETGG NSPVQEFTVE GHKQTAYISG LKPGVDYTIT  60
VYAAYISGLI SINYRT                                                  76

SEQ ID NO: 32           moltype = AA  length = 6
FEATURE                 Location/Qualifiers
REGION                  1..6
                        note = Synthetic: ADX_4578_B06, BC loop
source                  1..6
                        mol_type = protein
                        organism = synthetic construct
SEQUENCE: 32
FPDRYV                                                             6

SEQ ID NO: 33           moltype = AA  length = 6
FEATURE                 Location/Qualifiers
REGION                  1..6
                        note = Synthetic: ADX_4578_B06, DE loop
source                  1..6
                        mol_type = protein
                        organism = synthetic construct
SEQUENCE: 33
EGHKQT                                                             6

SEQ ID NO: 34           moltype = AA  length = 6
FEATURE                 Location/Qualifiers
REGION                  1..6
                        note = Synthetic: ADX_4578_B06, FG loop
source                  1..6
                        mol_type = protein
                        organism = synthetic construct
SEQUENCE: 34
AYISGL                                                             6

SEQ ID NO: 35           moltype = AA  length = 92
FEATURE                 Location/Qualifiers
REGION                  1..92
                        note = Synthetic: ADX_4578_B06, full-length
source                  1..92
                        mol_type = protein
                        organism = synthetic construct
SEQUENCE: 35
VSDVPRDLEV VAATPTSLLI SWFPDRYVYY ITYGETGGNS PVQEFTVEGH KQTAYISGLK  60
PGVDYTITVY AIYYYPDDFQ GYPQPISINY RT                                92

SEQ ID NO: 36           moltype = AA  length = 99
FEATURE                 Location/Qualifiers
REGION                  1..99
                        note = Synthetic: ADX_4578_B06, full-length w/N-terminal
                         leader and C-terminal tail
source                  1..99
                        mol_type = protein
                        organism = synthetic construct
SEQUENCE: 36
MGVSDVPRDL EVVAATPTSL LISWFPDRYV YYITYGETGG NSPVQEFTVE GHKQTAYISG  60
LKPGVDYTIT VYAIYYYPDD FQGYPQPISI NYRTEGSGS                         99

SEQ ID NO: 37           moltype = AA  length = 102
FEATURE                 Location/Qualifiers
REGION                  1..102
                        note = Synthetic: ADX_4578_B06, full-length with C-terminal
                         PmXn
VARIANT                 1..102
                        note = In the C-terminal PmXn, up to 5 proline and up to 5
                         Xaa may or may not be present
VARIANT                 98..102
                        note = Xaa can be any naturally occurring amino acid
source                  1..102
                        mol_type = protein
                        organism = synthetic construct
SEQUENCE: 37
VSDVPRDLEV VAATPTSLLI SWFPDRYVYY ITYGETGGNS PVQEFTVEGH KQTAYISGLK  60
PGVDYTITVY AIYYYPDDFQ GYPQPISINY RTPPPPPXXX XX                     102

SEQ ID NO: 38           moltype = AA  length = 103
FEATURE                 Location/Qualifiers
REGION                  1..103
```

```
                        note = Synthetic: ADX_4578_B06, full-length with C-terminal
                         PmCXn
VARIANT                 1..103
                        note = In the C-terminal PmCXn, up to 5 proline and up to 5
                         Xaa may or may not be present
VARIANT                 99..103
                        note = Xaa can be any naturally occurring amino acid
source                  1..103
                        mol_type = protein
                        organism = synthetic construct
SEQUENCE: 38
VSDVPRDLEV VAATPTSLLI SWFPDRYVYY ITYGETGGNS PVQEFTVEGH KQTAYISGLK  60
PGVDYTITVY AIYYYPDDFQ GYPQPISINY RTPPPPPCXX XXX                    103

SEQ ID NO: 39           moltype = AA  length = 94
FEATURE                 Location/Qualifiers
REGION                  1..94
                        note = Synthetic: ADX_4578_B06, full-length with C-terminal
                         PmCXn(m=1; n=0)
source                  1..94
                        mol_type = protein
                        organism = synthetic construct
SEQUENCE: 39
VSDVPRDLEV VAATPTSLLI SWFPDRYVYY ITYGETGGNS PVQEFTVEGH KQTAYISGLK  60
PGVDYTITVY AIYYYPDDFQ GYPQPISINY RTPC                              94

SEQ ID NO: 40           moltype = AA  length = 100
FEATURE                 Location/Qualifiers
REGION                  1..100
                        note = Synthetic: ADX_4578_B06, full-length with C-terminal
                         PmCXn(m=1; n=0) and His6 tag
source                  1..100
                        mol_type = protein
                        organism = synthetic construct
SEQUENCE: 40
VSDVPRDLEV VAATPTSLLI SWFPDRYVYY ITYGETGGNS PVQEFTVEGH KQTAYISGLK  60
PGVDYTITVY AIYYYPDDFQ GYPQPISINY RTPCHHHHHH                        100

SEQ ID NO: 41           moltype = AA  length = 109
FEATURE                 Location/Qualifiers
REGION                  1..109
                        note = Synthetic: ADX_4578_B06, full-length with C-terminal
                         PmCXn1CXn2
VARIANT                 1..109
                        note = In the C-terminal PmCXn1CXn2, up to 5 proline and up
                         to 5 Xaa (before and after the last Cys) may or may not be
                         present
VARIANT                 99..103
                        note = Xaa can be any naturally occurring amino acid
VARIANT                 105..109
                        note = Xaa can be any naturally occurring amino acid
source                  1..109
                        mol_type = protein
                        organism = synthetic construct
SEQUENCE: 41
VSDVPRDLEV VAATPTSLLI SWFPDRYVYY ITYGETGGNS PVQEFTVEGH KQTAYISGLK  60
PGVDYTITVY AIYYYPDDFQ GYPQPISINY RTPPPPPCXX XXXCXXXXX              109

SEQ ID NO: 42           moltype = AA  length = 100
FEATURE                 Location/Qualifiers
REGION                  1..100
                        note = Synthetic: ADX_4578_B06, full-length with C-terminal
                         PmCXn1CXn2 (m=1, n1=5, n2=0)
source                  1..100
                        mol_type = protein
                        organism = synthetic construct
SEQUENCE: 42
VSDVPRDLEV VAATPTSLLI SWFPDRYVYY ITYGETGGNS PVQEFTVEGH KQTAYISGLK  60
PGVDYTITVY AIYYYPDDFQ GYPQPISINY RTPCPPPPPC                        100

SEQ ID NO: 43           moltype = AA  length = 106
FEATURE                 Location/Qualifiers
REGION                  1..106
                        note = Synthetic: ADX_4578_B06, full-length with C-terminal
                         PmCXn1CXn2 (m=1, n1=5, n2=0) and His6 tag
source                  1..106
                        mol_type = protein
                        organism = synthetic construct
SEQUENCE: 43
```

-continued

```
VSDVPRDLEV VAATPTSLLI SWFPDRYVYY ITYGETGGNS PVQEFTVEGH KQTAYISGLK  60
PGVDYTITVY AIYYYPDDFQ GYPQPISINY RTPCPPPPPC HHHHHH                106

SEQ ID NO: 44          moltype = AA  length = 81
FEATURE                Location/Qualifiers
REGION                 1..81
                       note = Synthetic: ADX_4606_F06, core
source                 1..81
                       mol_type = protein
                       organism = synthetic construct
SEQUENCE: 44
EVVAATPTSL LISWNSGHSG QYYRITYGET GGNSPVQEFT VPRYGYTATI SGLKPGVDYT  60
ITVYAVAHSE ASAPISINYR T                                           81

SEQ ID NO: 45          moltype = AA  length = 8
FEATURE                Location/Qualifiers
REGION                 1..8
                       note = Synthetic: ADX_4606_F06, BC loop
source                 1..8
                       mol_type = protein
                       organism = synthetic construct
SEQUENCE: 45
NSGHSGQY                                                          8

SEQ ID NO: 46          moltype = AA  length = 6
FEATURE                Location/Qualifiers
REGION                 1..6
                       note = Synthetic: ADX_4606_F06, DE loop
source                 1..6
                       mol_type = protein
                       organism = synthetic construct
SEQUENCE: 46
PRYGYT                                                            6

SEQ ID NO: 47          moltype = AA  length = 9
FEATURE                Location/Qualifiers
REGION                 1..9
                       note = Synthetic: ADX_4606_F06, FG loop
source                 1..9
                       mol_type = protein
                       organism = synthetic construct
SEQUENCE: 47
VAHSEASAP                                                         9

SEQ ID NO: 48          moltype = AA  length = 89
FEATURE                Location/Qualifiers
REGION                 1..89
                       note = Synthetic: ADX_4606_F06, full-length
source                 1..89
                       mol_type = protein
                       organism = synthetic construct
SEQUENCE: 48
VSDVPRDLEV VAATPTSLLI SWNSGHSGQY YRITYGETGG NSPVQEFTVP RYGYTATISG  60
LKPGVDYTIT VYAVAHSEAS APISINYRT                                   89

SEQ ID NO: 49          moltype = AA  length = 98
FEATURE                Location/Qualifiers
REGION                 1..98
                       note = Synthetic: ADX_4606_F06, full-length w/N-terminal
                        leader and C-terminal tail
source                 1..98
                       mol_type = protein
                       organism = synthetic construct
SEQUENCE: 49
MGVSDVPRDL EVVAATPTSL LISWNSGHSG QYYRITYGET GGNSPVQEFT VPRYGYTATI  60
SGLKPGVDYT ITVYAVAHSE ASAPISINYR TEIDKPSQ                         98

SEQ ID NO: 50          moltype = AA  length = 99
FEATURE                Location/Qualifiers
REGION                 1..99
                       note = Synthetic: ADX_4606_F06, full-length with C-terminal
                        PmXn
VARIANT                1..99
                       note = In the C-terminal PmXn, up to 5 proline and up to 5
                        Xaa may or may not be present
VARIANT                95..99
                       note = Xaa can be any naturally occurring amino acid
source                 1..99
                       mol_type = protein
```

-continued

```
                        organism = synthetic construct
SEQUENCE: 50
VSDVPRDLEV VAATPTSLLI SWNSGHSGQY YRITYGETGG NSPVQEFTVP RYGYTATISG  60
LKPGVDYTIT VYAVAHSEAS APISINYRTP PPPPXXXXX                         99

SEQ ID NO: 51           moltype = AA  length = 100
FEATURE                 Location/Qualifiers
REGION                  1..100
                        note = Synthetic: ADX_4606_F06, full-length with C-terminal
                         PmCXn
VARIANT                 1..100
                        note = In the C-terminal PmCXn, up to 5 proline and up to 5
                         Xaa may or may not be present
VARIANT                 96..100
                        note = Xaa can be any naturally occurring amino acid
source                  1..100
                        mol_type = protein
                        organism = synthetic construct
SEQUENCE: 51
VSDVPRDLEV VAATPTSLLI SWNSGHSGQY YRITYGETGG NSPVQEFTVP RYGYTATISG  60
LKPGVDYTIT VYAVAHSEAS APISINYRTP PPPPCXXXXX                        100

SEQ ID NO: 52           moltype = AA  length = 91
FEATURE                 Location/Qualifiers
REGION                  1..91
                        note = Synthetic: ADX_4606_F06, full-length with C-terminal
                         PmCXn(m=1; n=0)
source                  1..91
                        mol_type = protein
                        organism = synthetic construct
SEQUENCE: 52
VSDVPRDLEV VAATPTSLLI SWNSGHSGQY YRITYGETGG NSPVQEFTVP RYGYTATISG  60
LKPGVDYTIT VYAVAHSEAS APISINYRTP C                                 91

SEQ ID NO: 53           moltype = AA  length = 97
FEATURE                 Location/Qualifiers
REGION                  1..97
                        note = Synthetic: ADX_4606_F06, full-length with C-terminal
                         PmCXn(m=1; n=0) and His6 tag
source                  1..97
                        mol_type = protein
                        organism = synthetic construct
SEQUENCE: 53
VSDVPRDLEV VAATPTSLLI SWNSGHSGQY YRITYGETGG NSPVQEFTVP RYGYTATISG  60
LKPGVDYTIT VYAVAHSEAS APISINYRTP CHHHHHH                           97

SEQ ID NO: 54           moltype = AA  length = 106
FEATURE                 Location/Qualifiers
REGION                  1..106
                        note = Synthetic: ADX_4606_F06, full-length with C-terminal
                         PmCXn1CXn2
VARIANT                 1..106
                        note = In the C-terminal PmCXn1CXn2, up to 5 proline and up
                         to 5 Xaa (before and after the last Cys) may or may not be
                         present
VARIANT                 96..100
                        note = Xaa can be any naturally occurring amino acid
VARIANT                 102..106
                        note = Xaa can be any naturally occurring amino acid
source                  1..106
                        mol_type = protein
                        organism = synthetic construct
SEQUENCE: 54
VSDVPRDLEV VAATPTSLLI SWNSGHSGQY YRITYGETGG NSPVQEFTVP RYGYTATISG  60
LKPGVDYTIT VYAVAHSEAS APISINYRTP PPPPCXXXXX CXXXXX                 106

SEQ ID NO: 55           moltype = AA  length = 97
FEATURE                 Location/Qualifiers
REGION                  1..97
                        note = Synthetic: ADX_4606_F06, full-length with C-terminal
                         PmCXn1CXn2 (m=1, n1=5, n2=0)
source                  1..97
                        mol_type = protein
                        organism = synthetic construct
SEQUENCE: 55
VSDVPRDLEV VAATPTSLLI SWNSGHSGQY YRITYGETGG NSPVQEFTVP RYGYTATISG  60
LKPGVDYTIT VYAVAHSEAS APISINYRTP CPPPPPC                           97

SEQ ID NO: 56           moltype = AA  length = 103
```

```
FEATURE                Location/Qualifiers
REGION                 1..103
                       note = Synthetic: ADX_4606_F06, full-length with C-terminal
                        PmCXn1CXn2 (m=1, n1=5, n2=0) and His6 tag
source                 1..103
                       mol_type = protein
                       organism = synthetic construct
SEQUENCE: 56
VSDVPRDLEV VAATPTSLLI SWNSGHSGQY YRITYGETGG NSPVQEFTVP RYGYTATISG  60
LKPGVDYTIT VYAVAHSEAS APISINYRTP CPPPPPCHHH HHH                    103

SEQ ID NO: 57          moltype = AA  length = 86
FEATURE                Location/Qualifiers
REGION                 1..86
                       note = Synthetic: ADX_5273_C01, core
source                 1..86
                       mol_type = protein
                       organism = synthetic construct
SEQUENCE: 57
EVVAATPTSL LISWSDPYEE ERYYRITYGE TGGNSPVQEF TVPAFHTTAT ISGLKPGVDY  60
TITVYAVTYK HKYAYYYPPI SINYRT                                       86

SEQ ID NO: 58          moltype = AA  length = 9
FEATURE                Location/Qualifiers
REGION                 1..9
                       note = Synthetic: ADX_5273_C01, BC loop
source                 1..9
                       mol_type = protein
                       organism = synthetic construct
SEQUENCE: 58
SDPYEEERY                                                          9

SEQ ID NO: 59          moltype = AA  length = 6
FEATURE                Location/Qualifiers
REGION                 1..6
                       note = Synthetic: ADX_5273_C01, DE loop
source                 1..6
                       mol_type = protein
                       organism = synthetic construct
SEQUENCE: 59
PAFHTT                                                             6

SEQ ID NO: 60          moltype = AA  length = 13
FEATURE                Location/Qualifiers
REGION                 1..13
                       note = Synthetic: ADX_5273_C01, FG loop
source                 1..13
                       mol_type = protein
                       organism = synthetic construct
SEQUENCE: 60
VTYKHKYAYY YPP                                                     13

SEQ ID NO: 61          moltype = AA  length = 94
FEATURE                Location/Qualifiers
REGION                 1..94
                       note = Synthetic: ADX_5273_C01, full-length
source                 1..94
                       mol_type = protein
                       organism = synthetic construct
SEQUENCE: 61
VSDVPRDLEV VAATPTSLLI SWSDPYEEER YYRITYGETG GNSPVQEFTV PAFHTTATIS  60
GLKPGVDYTI TVYAVTYKHK YAYYYPPISI NYRT                              94

SEQ ID NO: 62          moltype = AA  length = 103
FEATURE                Location/Qualifiers
REGION                 1..103
                       note = Synthetic: ADX_5273_C01, full-length w/N-terminal
                        leader and C-terminal tail
source                 1..103
                       mol_type = protein
                       organism = synthetic construct
SEQUENCE: 62
MGVSDVPRDL EVVAATPTSL LISWSDPYEE ERYYRITYGE TGGNSPVQEF TVPAFHTTAT  60
ISGLKPGVDY TITVYAVTYK HKYAYYYPPI SINYRTEIDK PSQ                    103

SEQ ID NO: 63          moltype = AA  length = 104
FEATURE                Location/Qualifiers
REGION                 1..104
                       note = Synthetic: ADX_5273_C01, full-length with C-terminal
```

```
                         PmXn
VARIANT                 1..104
                        note = In the C-terminal PmXn, up to 5 proline and up to 5
                         Xaa may or may not be present
VARIANT                 100..104
                        note = Xaa can be any naturally occurring amino acid
source                  1..104
                        mol_type = protein
                        organism = synthetic construct
SEQUENCE: 63
VSDVPRDLEV VAATPTSLLI SWSDPYEEER YYRITYGETG GNSPVQEFTV PAFHTTATIS  60
GLKPGVDYTI TVYAVTYKHK YAYYYPPISI NYRTPPPPPX XXXX                   104

SEQ ID NO: 64           moltype = AA  length = 105
FEATURE                 Location/Qualifiers
REGION                  1..105
                        note = Synthetic: ADX_5273_C01, full-length with C-terminal
                         PmCXn
VARIANT                 1..105
                        note = In the C-terminal PmCXn, up to 5 proline and up to 5
                         Xaa may or may not be present
VARIANT                 101..105
                        note = Xaa can be any naturally occurring amino acid
source                  1..105
                        mol_type = protein
                        organism = synthetic construct
SEQUENCE: 64
VSDVPRDLEV VAATPTSLLI SWSDPYEEER YYRITYGETG GNSPVQEFTV PAFHTTATIS  60
GLKPGVDYTI TVYAVTYKHK YAYYYPPISI NYRTPPPPPC XXXXX                  105

SEQ ID NO: 65           moltype = AA  length = 96
FEATURE                 Location/Qualifiers
REGION                  1..96
                        note = Synthetic: ADX_5273_C01, full-length with C-terminal
                         PmCXn(m=1; n=0)
source                  1..96
                        mol_type = protein
                        organism = synthetic construct
SEQUENCE: 65
VSDVPRDLEV VAATPTSLLI SWSDPYEEER YYRITYGETG GNSPVQEFTV PAFHTTATIS  60
GLKPGVDYTI TVYAVTYKHK YAYYYPPISI NYRTPC                            96

SEQ ID NO: 66           moltype = AA  length = 102
FEATURE                 Location/Qualifiers
REGION                  1..102
                        note = Synthetic: ADX_5273_C01, full-length with C-terminal
                         PmCXn(m=1; n=0) and His6 tag
source                  1..102
                        mol_type = protein
                        organism = synthetic construct
SEQUENCE: 66
VSDVPRDLEV VAATPTSLLI SWSDPYEEER YYRITYGETG GNSPVQEFTV PAFHTTATIS  60
GLKPGVDYTI TVYAVTYKHK YAYYYPPISI NYRTPCHHHH HH                     102

SEQ ID NO: 67           moltype = AA  length = 111
FEATURE                 Location/Qualifiers
REGION                  1..111
                        note = Synthetic: ADX_5273_C01, full-length with C-terminal
                         PmCXn1CXn2
VARIANT                 1..111
                        note = In the C-terminal PmCXn1CXn2, up to 5 proline and up
                         to 5 Xaa (before and after the last Cys) may or may not be
                         present
VARIANT                 101..105
                        note = Xaa can be any naturally occurring amino acid
VARIANT                 107..111
                        note = Xaa can be any naturally occurring amino acid
source                  1..111
                        mol_type = protein
                        organism = synthetic construct
SEQUENCE: 67
VSDVPRDLEV VAATPTSLLI SWSDPYEEER YYRITYGETG GNSPVQEFTV PAFHTTATIS  60
GLKPGVDYTI TVYAVTYKHK YAYYYPPISI NYRTPPPPPC XXXXXCXXXX X           111

SEQ ID NO: 68           moltype = AA  length = 102
FEATURE                 Location/Qualifiers
REGION                  1..102
                        note = Synthetic: ADX_5273_C01, full-length with C-terminal
                         PmCXn1CXn2 (m=1, n1=5, n2=0)
```

-continued

```
source                  1..102
                        mol_type = protein
                        organism = synthetic construct
SEQUENCE: 68
VSDVPRDLEV VAATPTSLLI SWSDPYEEER YYRITYGETG GNSPVQEFTV PAFHTTATIS  60
GLKPGVDYTI TVYAVTYKHK YAYYYPPISI NYRTPCPPPP PC                    102

SEQ ID NO: 69           moltype = AA  length = 108
FEATURE                 Location/Qualifiers
REGION                  1..108
                        note = Synthetic: ADX_5273_C01, full-length with C-terminal
                         PmCXn1CXn2 (m=1, n1=5, n2=0) and His6 tag
source                  1..108
                        mol_type = protein
                        organism = synthetic construct
SEQUENCE: 69
VSDVPRDLEV VAATPTSLLI SWSDPYEEER YYRITYGETG GNSPVQEFTV PAFHTTATIS  60
GLKPGVDYTI TVYAVTYKHK YAYYYPPISI NYRTPCPPPP PCHHHHHH              108

SEQ ID NO: 70           moltype = AA  length = 86
FEATURE                 Location/Qualifiers
REGION                  1..86
                        note = Synthetic: ADX_5273_D01, core
source                  1..86
                        mol_type = protein
                        organism = synthetic construct
SEQUENCE: 70
EVVAATPTSL LISWEPSYKD DRYYRITYGE TGGNSPVQEF TVPSFHQTAT ISGLKPGVDY  60
TITVYAVTYE PDEYYFYYPI SINYRT                                      86

SEQ ID NO: 71           moltype = AA  length = 9
FEATURE                 Location/Qualifiers
REGION                  1..9
                        note = Synthetic: ADX_5273_D01, BC loop
source                  1..9
                        mol_type = protein
                        organism = synthetic construct
SEQUENCE: 71
EPSYKDDRY                                                         9

SEQ ID NO: 72           moltype = AA  length = 6
FEATURE                 Location/Qualifiers
REGION                  1..6
                        note = Synthetic: ADX_5273_D01, DE loop
source                  1..6
                        mol_type = protein
                        organism = synthetic construct
SEQUENCE: 72
PSFHQT                                                            6

SEQ ID NO: 73           moltype = AA  length = 13
FEATURE                 Location/Qualifiers
REGION                  1..13
                        note = Synthetic: ADX_5273_D01, FG loop
source                  1..13
                        mol_type = protein
                        organism = synthetic construct
SEQUENCE: 73
VTYEPDEYYF YYP                                                    13

SEQ ID NO: 74           moltype = AA  length = 94
FEATURE                 Location/Qualifiers
REGION                  1..94
                        note = Synthetic: ADX_5273_D01, full-length
source                  1..94
                        mol_type = protein
                        organism = synthetic construct
SEQUENCE: 74
VSDVPRDLEV VAATPTSLLI SWEPSYKDDR YYRITYGETG GNSPVQEFTV PSFHQTATIS  60
GLKPGVDYTI TVYAVTYEPD EYYFYYPISI NYRT                             94

SEQ ID NO: 75           moltype = AA  length = 103
FEATURE                 Location/Qualifiers
REGION                  1..103
                        note = Synthetic: ADX_5273_D01, full-length w/N-terminal
                         leader and C-terminal tail
source                  1..103
                        mol_type = protein
                        organism = synthetic construct
```

```
SEQUENCE: 75
MGVSDVPRDL EVVAATPTSL LISWEPSYKD DRYYRITYGE TGGNSPVQEF TVPSFHQTAT  60
ISGLKPGVDY TITVYAVTYE PDEYYFYYPI SINYRTEIDK PSQ                   103

SEQ ID NO: 76          moltype = AA  length = 104
FEATURE                Location/Qualifiers
REGION                 1..104
                       note = Synthetic: ADX_5273_D01, full-length with C-terminal
                        PmXn
VARIANT                1..104
                       note = In the C-terminal PmXn, up to 5 proline and up to 5
                        Xaa may or may not be present
VARIANT                100..104
                       note = Xaa can be any naturally occurring amino acid
source                 1..104
                       mol_type = protein
                       organism = synthetic construct
SEQUENCE: 76
VSDVPRDLEV VAATPTSLLI SWEPSYKDDR YYRITYGETG GNSPVQEFTV PSFHQTATIS  60
GLKPGVDYTI TVYAVTYEPD EYYFYYPISI NYRTPPPPPX XXXX                  104

SEQ ID NO: 77          moltype = AA  length = 105
FEATURE                Location/Qualifiers
REGION                 1..105
                       note = Synthetic: ADX_5273_D01, full-length with C-terminal
                        PmCXn
VARIANT                1..105
                       note = In the C-terminal PmCXn, up to 5 proline and up to 5
                        Xaa may or may not be present
VARIANT                101..105
                       note = Xaa can be any naturally occurring amino acid
source                 1..105
                       mol_type = protein
                       organism = synthetic construct
SEQUENCE: 77
VSDVPRDLEV VAATPTSLLI SWEPSYKDDR YYRITYGETG GNSPVQEFTV PSFHQTATIS  60
GLKPGVDYTI TVYAVTYEPD EYYFYYPISI NYRTPPPPPC XXXXX                 105

SEQ ID NO: 78          moltype = AA  length = 96
FEATURE                Location/Qualifiers
REGION                 1..96
                       note = Synthetic: ADX_5273_D01, full-length with C-terminal
                        PmCXn(m=1; n=0)
source                 1..96
                       mol_type = protein
                       organism = synthetic construct
SEQUENCE: 78
VSDVPRDLEV VAATPTSLLI SWEPSYKDDR YYRITYGETG GNSPVQEFTV PSFHQTATIS  60
GLKPGVDYTI TVYAVTYEPD EYYFYYPISI NYRTPC                           96

SEQ ID NO: 79          moltype = AA  length = 102
FEATURE                Location/Qualifiers
REGION                 1..102
                       note = Synthetic: ADX_5273_D01, full-length with C-terminal
                        PmCXn(m=1; n=0) and His6 tag
source                 1..102
                       mol_type = protein
                       organism = synthetic construct
SEQUENCE: 79
VSDVPRDLEV VAATPTSLLI SWEPSYKDDR YYRITYGETG GNSPVQEFTV PSFHQTATIS  60
GLKPGVDYTI TVYAVTYEPD EYYFYYPISI NYRTPCHHHH HH                    102

SEQ ID NO: 80          moltype = AA  length = 111
FEATURE                Location/Qualifiers
REGION                 1..111
                       note = Synthetic: ADX_5273_D01, full-length with C-terminal
                        PmCXn1CXn2
VARIANT                1..111
                       note = In the C-terminal PmCXn1CXn2, up to 5 proline and up
                        to 5 Xaa (before and after the last Cys) may or may not be
                        present
VARIANT                101..105
                       note = Xaa can be any naturally occurring amino acid
VARIANT                107..111
                       note = Xaa can be any naturally occurring amino acid
source                 1..111
                       mol_type = protein
                       organism = synthetic construct
SEQUENCE: 80
```

-continued

```
VSDVPRDLEV VAATPTSLLI SWEPSYKDDR YYRITYGETG GNSPVQEFTV PSFHQTATIS  60
GLKPGVDYTI TVYAVTYEPD EYYFYYPISI NYRTPPPPPC XXXXXCXXXX X           111

SEQ ID NO: 81          moltype = AA  length = 102
FEATURE                Location/Qualifiers
REGION                 1..102
                       note = Synthetic: ADX_5273_D01, full-length with C-terminal
                        PmCXn1CXn2 (m=1, n1=5, n2=0)
source                 1..102
                       mol_type = protein
                       organism = synthetic construct
SEQUENCE: 81
VSDVPRDLEV VAATPTSLLI SWEPSYKDDR YYRITYGETG GNSPVQEFTV PSFHQTATIS  60
GLKPGVDYTI TVYAVTYEPD EYYFYYPISI NYRTPCPPPP PC                     102

SEQ ID NO: 82          moltype = AA  length = 108
FEATURE                Location/Qualifiers
REGION                 1..108
                       note = Synthetic: ADX_5273_D01, full-length with C-terminal
                        PmCXn1CXn2 (m=1, n1=5, n2=0) and His6 tag
source                 1..108
                       mol_type = protein
                       organism = synthetic construct
SEQUENCE: 82
VSDVPRDLEV VAATPTSLLI SWEPSYKDDR YYRITYGETG GNSPVQEFTV PSFHQTATIS  60
GLKPGVDYTI TVYAVTYEPD EYYFYYPISI NYRTPCPPPP PCHHHHHH               108

SEQ ID NO: 83          moltype = AA  length = 87
FEATURE                Location/Qualifiers
REGION                 1..87
                       note = Synthetic: ADX_5274_E01, core
source                 1..87
                       mol_type = protein
                       organism = synthetic construct
SEQUENCE: 83
EVVAATPTSL LISWSGDYHP HRYYRITYGE TGGNSPVQEF TVPGEHETAA TISGLKPGVD  60
YTITVYAVTY DGEKADKYPP ISINYRT                                      87

SEQ ID NO: 84          moltype = AA  length = 9
FEATURE                Location/Qualifiers
REGION                 1..9
                       note = Synthetic: ADX_5274_E01, BC loop
source                 1..9
                       mol_type = protein
                       organism = synthetic construct
SEQUENCE: 84
SGDYHPHRY                                                          9

SEQ ID NO: 85          moltype = AA  length = 6
FEATURE                Location/Qualifiers
REGION                 1..6
                       note = Synthetic: ADX_5274_E01, DE loop
source                 1..6
                       mol_type = protein
                       organism = synthetic construct
SEQUENCE: 85
PGEHET                                                             6

SEQ ID NO: 86          moltype = AA  length = 13
FEATURE                Location/Qualifiers
REGION                 1..13
                       note = Synthetic: ADX_5274_E01, FG loop
source                 1..13
                       mol_type = protein
                       organism = synthetic construct
SEQUENCE: 86
VTYDGEKADK YPP                                                     13

SEQ ID NO: 87          moltype = AA  length = 94
FEATURE                Location/Qualifiers
REGION                 1..94
                       note = Synthetic: ADX_5274_E01, full-length
source                 1..94
                       mol_type = protein
                       organism = synthetic construct
SEQUENCE: 87
VSDVPRDLEV VAATPTSLLI SWSGDYHPHR YYRITYGETG GNSPVQEFTV PGEHETATIS  60
GLKPGVDYTI TVYAVTYDGE KADKYPPISI NYRT                              94
```

-continued

```
SEQ ID NO: 88           moltype = AA  length = 103
FEATURE                 Location/Qualifiers
REGION                  1..103
                        note = Synthetic: ADX_5274_E01, full-length w/N-terminal
                         leader and C-terminal tail
source                  1..103
                        mol_type = protein
                        organism = synthetic construct
SEQUENCE: 88
MGVSDVPRDL EVVAATPTSL LISWSGDYHP HRYYRITYGE TGGNSPVQEF TVPGEHETAT  60
ISGLKPGVDY TITVYAVTYD GEKADKYPPI SINYRTEIDK PSQ                    103

SEQ ID NO: 89           moltype = AA  length = 104
FEATURE                 Location/Qualifiers
REGION                  1..104
                        note = Synthetic: ADX_5274_E01, full-length w/ C-terminal
                         PmXn
VARIANT                 1..104
                        note = In the C-terminal PmXn, up to 5 proline and up to 5
                         Xaa may or may not be present
VARIANT                 100..104
                        note = Xaa can be any naturally occurring amino acid
source                  1..104
                        mol_type = protein
                        organism = synthetic construct
SEQUENCE: 89
VSDVPRDLEV VAATPTSLLI SWSGDYHPHR YYRITYGETG GNSPVQEFTV PGEHETATIS  60
GLKPGVDYTI TVYAVTYDGE KADKYPPISI NYRTPPPPPX XXXX                   104

SEQ ID NO: 90           moltype = AA  length = 105
FEATURE                 Location/Qualifiers
REGION                  1..105
                        note = Synthetic: ADX_5274_E01, full-length with C-terminal
                         PmCXn
VARIANT                 1..105
                        note = In the C-terminal PmCXn, up to 5 proline and up to 5
                         Xaa may or may not be present
VARIANT                 101..105
                        note = Xaa can be any naturally occurring amino acid
source                  1..105
                        mol_type = protein
                        organism = synthetic construct
SEQUENCE: 90
VSDVPRDLEV VAATPTSLLI SWSGDYHPHR YYRITYGETG GNSPVQEFTV PGEHETATIS  60
GLKPGVDYTI TVYAVTYDGE KADKYPPISI NYRTPPPPPC XXXXX                  105

SEQ ID NO: 91           moltype = AA  length = 88
FEATURE                 Location/Qualifiers
REGION                  1..88
                        note = Synthetic: ADC_5274_E01, core with PmCXn C-terminal
                         modification (m=1; n=0); aka ADX_6561_A01 core
source                  1..88
                        mol_type = protein
                        organism = synthetic construct
SEQUENCE: 91
EVVAATPTSL LISWSGDYHP HRYYRITYGE TGGNSPVQEF TVPGEHETAT ISGLKPGVDY  60
TITVYAVTYD GEKADKYPPI SINYRTPC                                     88

SEQ ID NO: 92           moltype = AA  length = 96
FEATURE                 Location/Qualifiers
REGION                  1..96
                        note = Synthetic: ADX_5274_E01, full-length with C-terminal
                         PmCXn (m=1; n=0)]
source                  1..96
                        mol_type = protein
                        organism = synthetic construct
SEQUENCE: 92
VSDVPRDLEV VAATPTSLLI SWSGDYHPHR YYRITYGETG GNSPVQEFTV PGEHETATIS  60
GLKPGVDYTI TVYAVTYDGE KADKYPPISI NYRTPC                            96

SEQ ID NO: 93           moltype = AA  length = 102
FEATURE                 Location/Qualifiers
REGION                  1..102
                        note = Synthetic: ADX_5274_E01, full-length with C-terminal
                         PmCXn (m=1; n=0) and His6 tag
source                  1..102
                        mol_type = protein
                        organism = synthetic construct
SEQUENCE: 93
```

-continued

```
VSDVPRDLEV VAATPTSLLI SWSGDYHPHR YYRITYGETG GNSPVQEFTV PGEHETATIS  60
GLKPGVDYTI TVYAVTYDGE KADKYPPISI NYRTPCHHHH HH                    102

SEQ ID NO: 94          moltype = AA  length = 104
FEATURE                Location/Qualifiers
REGION                 1..104
                       note = Synthetic: ADX_5274_A01, full-length w/N-terminal
                        leader, C-terminal PmCXn (m=1; n=0) and His6 tag
source                 1..104
                       mol_type = protein
                       organism = synthetic construct
SEQUENCE: 94
MGVSDVPRDL EVVAATPTSL LISWSGDYHP HRYYRITYGE TGGNSPVQEF TVPGEHETAT  60
ISGLKPGVDY TITVYAVTYD GEKADKYPPI SINYRTPCHH HHHH                  104

SEQ ID NO: 95          moltype = AA  length = 111
FEATURE                Location/Qualifiers
REGION                 1..111
                       note = Synthetic: ADX_5274_E01, full-length with C-terminal
                        PmCXn1CXn2
VARIANT                1..111
                       note = In the C-terminal PmCXn1CXn2, up to 5 proline and up
                        to 5 Xaa (before and after the last Cys) may or may not be
                        present
VARIANT                101..105
                       note = Xaa can be any naturally occurring amino acid
VARIANT                107..111
                       note = Xaa can be any naturally occurring amino acid
source                 1..111
                       mol_type = protein
                       organism = synthetic construct
SEQUENCE: 95
VSDVPRDLEV VAATPTSLLI SWSGDYHPHR YYRITYGETG GNSPVQEFTV PGEHETATIS  60
GLKPGVDYTI TVYAVTYDGE KADKYPPISI NYRTPPPPPC XXXXXCXXXX X          111

SEQ ID NO: 96          moltype = AA  length = 102
FEATURE                Location/Qualifiers
REGION                 1..102
                       note = Synthetic: ADX_5274_E01, full-length with C-terminal
                        PmCXn1CXn2 (m=1; n1=5; n2=0)
source                 1..102
                       mol_type = protein
                       organism = synthetic construct
SEQUENCE: 96
VSDVPRDLEV VAATPTSLLI SWSGDYHPHR YYRITYGETG GNSPVQEFTV PGEHETATIS  60
GLKPGVDYTI TVYAVTYDGE KADKYPPISI NYRTPCPPPP PC                    102

SEQ ID NO: 97          moltype = AA  length = 108
FEATURE                Location/Qualifiers
REGION                 1..108
                       note = Synthetic: ADX_5274_E01, full-length with C-terminal
                        PmCXn1CXn2 (m=1; n1=5; n2=0) and His6 tag
source                 1..108
                       mol_type = protein
                       organism = synthetic construct
SEQUENCE: 97
VSDVPRDLEV VAATPTSLLI SWSGDYHPHR YYRITYGETG GNSPVQEFTV PGEHETATIS  60
GLKPGVDYTI TVYAVTYDGE KADKYPPISI NYRTPCPPPP PCHHHHHH              108

SEQ ID NO: 98          moltype = AA  length = 86
FEATURE                Location/Qualifiers
REGION                 1..86
                       note = Synthetic: ADX_6077_A01, core
source                 1..86
                       mol_type = protein
                       organism = synthetic construct
SEQUENCE: 98
EVVAATPTSL LISWSDDYHA HRYYRITYGE TGGNSPVQEF TVPGEHVTAT ISGLKPGVDY  60
TITVYAVTYD GEKAATDWSI SINYRT                                      86

SEQ ID NO: 99          moltype = AA  length = 9
FEATURE                Location/Qualifiers
REGION                 1..9
                       note = Synthetic: ADX_6077_F02, BC loop
source                 1..9
                       mol_type = protein
                       organism = synthetic construct
SEQUENCE: 99
SDDYHAHRY                                                         9
```

```
SEQ ID NO: 100         moltype = AA  length = 6
FEATURE                Location/Qualifiers
REGION                 1..6
                       note = Synthetic: ADX_6077_F02, DE loop
source                 1..6
                       mol_type = protein
                       organism = synthetic construct
SEQUENCE: 100
PGEHVT                                                    6

SEQ ID NO: 101         moltype = AA  length = 13
FEATURE                Location/Qualifiers
REGION                 1..13
                       note = Synthetic: ADX_6077_F02, FG loop
source                 1..13
                       mol_type = protein
                       organism = synthetic construct
SEQUENCE: 101
VTYDGEKAAT DWS                                            13

SEQ ID NO: 102         moltype = AA  length = 94
FEATURE                Location/Qualifiers
REGION                 1..94
                       note = Synthetic: ADX_6077_F02, full-length
source                 1..94
                       mol_type = protein
                       organism = synthetic construct
SEQUENCE: 102
VSDVPRDLEV VAATPTSLLI SWSDDYHAHR YYRITYGETG GNSPVQEFTV PGEHVTATIS  60
GLKPGVDYTI TVYAVTYDGE KAATDWSISI NYRT                     94

SEQ ID NO: 103         moltype = AA  length = 101
FEATURE                Location/Qualifiers
REGION                 1..101
                       note = Synthetic: ADX_6077_F02, full-length with C-terminal
                        tail
source                 1..101
                       mol_type = protein
                       organism = synthetic construct
SEQUENCE: 103
VSDVPRDLEV VAATPTSLLI SWSDDYHAHR YYRITYGETG GNSPVQEFTV PGEHVTATIS  60
GLKPGVDYTI TVYAVTYDGE KAATDWSISI NYRTEIEKPC Q             101

SEQ ID NO: 104         moltype = AA  length = 95
FEATURE                Location/Qualifiers
REGION                 1..95
                       note = Synthetic: ADX_6077_F02, full-length with N-terminal
                        leader (G)
source                 1..95
                       mol_type = protein
                       organism = synthetic construct
SEQUENCE: 104
GVSDVPRDLE VVAATPTSLL ISWSDDYHAH RYYRITYGET GGNSPVQEFT VPGEHVTATI  60
SGLKPGVDYT ITVYAVTYDG EKAATDWSIS INYRT                    95

SEQ ID NO: 105         moltype = AA  length = 96
FEATURE                Location/Qualifiers
REGION                 1..96
                       note = Synthetic: ADX_6077_F02, full-length with N-terminal
                        leader (MG)
source                 1..96
                       mol_type = protein
                       organism = synthetic construct
SEQUENCE: 105
MGVSDVPRDL EVVAATPTSL LISWSDDYHA HRYYRITYGE TGGNSPVQEF TVPGEHVTAT  60
ISGLKPGVDY TITVYAVTYD GEKAATDWSI SINYRT                   96

SEQ ID NO: 106         moltype = AA  length = 96
FEATURE                Location/Qualifiers
REGION                 1..96
                       note = Synthetic: ADX_6077_F02, core with C-terminal PmXn
VARIANT                1..96
                       note = In the C-terminal PmXn, up to 5 proline and up to 5
                        Xaa may or may not be present
VARIANT                92..96
                       note = Xaa can be any naturally occurring amino acid
source                 1..96
                       mol_type = protein
```

```
                         organism = synthetic construct
SEQUENCE: 106
EVVAATPTSL LISWSDDYHA HRYYRITYGE TGGNSPVQEF TVPGEHVTAT ISGLKPGVDY  60
TITVYAVTYD GEKAATDWSI SINYRTPPPP PXXXXX                            96

SEQ ID NO: 107           moltype = AA  length = 104
FEATURE                  Location/Qualifiers
REGION                   1..104
                         note = Synthetic: ADX_6077_F02, full-length with C-terminal
                          PmXn
VARIANT                  1..104
                         note = In the C-terminal PmXn, up to 5 proline and up to 5
                          Xaa may or may not be present
VARIANT                  100..104
                         note = Xaa can be any naturally occurring amino acid
source                   1..104
                         mol_type = protein
                         organism = synthetic construct
SEQUENCE: 107
VSDVPRDLEV VAATPTSLLI SWSDDYHAHR YYRITYGETG GNSPVQEFTV PGEHVTATIS  60
GLKPGVDYTI TVYAVTYDGE KAATDWSISI NYRTPPPPPX XXXX                   104

SEQ ID NO: 108           moltype = AA  length = 105
FEATURE                  Location/Qualifiers
REGION                   1..105
                         note = Synthetic: ADX_6077_F02, full-length with N-terminal
                          leader (G) and C-terminal PmXn
VARIANT                  1..105
                         note = In the C-terminal PmXn, up to 5 proline and up to 5
                          Xaa may or may not be present
VARIANT                  101..105
                         note = Xaa can be any naturally occurring amino acid
source                   1..105
                         mol_type = protein
                         organism = synthetic construct
SEQUENCE: 108
GVSDVPRDLE VVAATPTSLL ISWSDDYHAH RYYRITYGET GGNSPVQEFT VPGEHVTATI  60
SGLKPGVDYT ITVYAVTYDG EKAATDWSIS INYRTPPPPP XXXXX                  105

SEQ ID NO: 109           moltype = AA  length = 106
FEATURE                  Location/Qualifiers
REGION                   1..106
                         note = Synthetic: ADX_6077_F02, full-length with N-terminal
                          leader (MG) and C-terminal PmXn
VARIANT                  1..106
                         note = In the C-terminal PmXn, up to 5 proline and up to 5
                          Xaa may or may not be present
VARIANT                  102..106
                         note = Xaa can be any naturally occurring amino acid
source                   1..106
                         mol_type = protein
                         organism = synthetic construct
SEQUENCE: 109
MGVSDVPRDL EVVAATPTSL LISWSDDYHA HRYYRITYGE TGGNSPVQEF TVPGEHVTAT  60
ISGLKPGVDY TITVYAVTYD GEKAATDWSI SINYRTPPPP PXXXXX                 106

SEQ ID NO: 110           moltype = AA  length = 97
FEATURE                  Location/Qualifiers
REGION                   1..97
                         note = Synthetic: ADX_6077_F02, core with C-terminal PmCXn
VARIANT                  1..97
                         note = In the C-terminal PmCXn, up to 5 proline and up to 5
                          Xaa may or may not be present
VARIANT                  93..97
                         note = Xaa can be any naturally occurring amino acid
source                   1..97
                         mol_type = protein
                         organism = synthetic construct
SEQUENCE: 110
EVVAATPTSL LISWSDDYHA HRYYRITYGE TGGNSPVQEF TVPGEHVTAT ISGLKPGVDY  60
TITVYAVTYD GEKAATDWSI SINYRTPPPP PCXXXXX                           97

SEQ ID NO: 111           moltype = AA  length = 105
FEATURE                  Location/Qualifiers
REGION                   1..105
                         note = Synthetic: ADX_6077_F02, full-length with C-terminal
                          PmCXn
VARIANT                  1..105
                         note = In the C-terminal PmCXn, up to 5 proline and up to 5
```

```
                         Xaa may or may not be present
VARIANT                 101..105
                        note = Xaa can be any naturally occurring amino acid
source                  1..105
                        mol_type = protein
                        organism = synthetic construct
SEQUENCE: 111
VSDVPRDLEV VAATPTSLLI SWSDDYHAHR YYRITYGETG GNSPVQEFTV PGEHVTATIS  60
GLKPGVDYTI TVYAVTYDGE KAATDWSISI NYRTPPPPPC XXXXX                 105

SEQ ID NO: 112          moltype = AA  length = 106
FEATURE                 Location/Qualifiers
REGION                  1..106
                        note = Synthetic: ADX_6077_F02, full-length with N-terminal
                         leader (G) and C-terminal PmCXn
VARIANT                 1..106
                        note = In the C-terminal PmCXn, up to 5 proline and up to 5
                         Xaa may or may not be present
VARIANT                 102..106
                        note = Xaa can be any naturally occurring amino acid
source                  1..106
                        mol_type = protein
                        organism = synthetic construct
SEQUENCE: 112
GVSDVPRDLE VVAATPTSLL ISWSDDYHAH RYYRITYGET GGNSPVQEFT VPGEHVTATI  60
SGLKPGVDYT ITVYAVTYDG EKAATDWSIS INYRTPPPPP CXXXXX                106

SEQ ID NO: 113          moltype = AA  length = 107
FEATURE                 Location/Qualifiers
REGION                  1..107
                        note = Synthetic: ADX_6077_F02, full-length with N-terminal
                         leader (MG) and C-terminal PmCXn
VARIANT                 1..107
                        note = In the C-terminal PmCXn, up to 5 proline and up to 5
                         Xaa may or may not be present
VARIANT                 103..107
                        note = Xaa can be any naturally occurring amino acid
source                  1..107
                        mol_type = protein
                        organism = synthetic construct
SEQUENCE: 113
MGVSDVPRDL EVVAATPTSL LISWSDDYHA HRYYRITYGE TGGNSPVQEF TVPGEHVTAT  60
ISGLKPGVDY TITVYAVTYD GEKAATDWSI SINYRTPPPP PCXXXXX               107

SEQ ID NO: 114          moltype = AA  length = 88
FEATURE                 Location/Qualifiers
REGION                  1..88
                        note = Synthetic: ADX_6077_F02, core with C-terminal PmCXn
                         (m=1; n=0)
source                  1..88
                        mol_type = protein
                        organism = synthetic construct
SEQUENCE: 114
EVVAATPTSL LISWSDDYHA HRYYRITYGE TGGNSPVQEF TVPGEHVTAT ISGLKPGVDY  60
TITVYAVTYD GEKAATDWSI SINYRTPC                                    88

SEQ ID NO: 115          moltype = AA  length = 96
FEATURE                 Location/Qualifiers
REGION                  1..96
                        note = Synthetic: ADX_6077_F02, full-length with C-terminal
                         PmCXn (m=1; n=0)
source                  1..96
                        mol_type = protein
                        organism = synthetic construct
SEQUENCE: 115
VSDVPRDLEV VAATPTSLLI SWSDDYHAHR YYRITYGETG GNSPVQEFTV PGEHVTATIS  60
GLKPGVDYTI TVYAVTYDGE KAATDWSISI NYRTPC                           96

SEQ ID NO: 116          moltype = AA  length = 97
FEATURE                 Location/Qualifiers
REGION                  1..97
                        note = Synthetic: ADX_6007_F02, full-length w/ N-terminal
                         leader (G) and PmCXn C-terminal modification (m=1; n=0)
source                  1..97
                        mol_type = protein
                        organism = synthetic construct
SEQUENCE: 116
GVSDVPRDLE VVAATPTSLL ISWSDDYHAH RYYRITYGET GGNSPVQEFT VPGEHVTATI  60
SGLKPGVDYT ITVYAVTYDG EKAATDWSIS INYRTPC                          97
```

```
SEQ ID NO: 117         moltype = AA  length = 98
FEATURE                Location/Qualifiers
REGION                 1..98
                       note = Synthetic: ADX_6077_F02, full-length w/ N-terminal
                        eader (MG) and PmCXn C-terminal modification (m=1; n=0)
source                 1..98
                       mol_type = protein
                       organism = synthetic construct
SEQUENCE: 117
MGVSDVPRDL EVVAATPTSL LISWSDDYHA HRYYRITYGE TGGNSPVQEF TVPGEHVTAT  60
ISGLKPGVDY TITVYAVTYD GEKAATDWSI SINYRTPC                          98

SEQ ID NO: 118         moltype = AA  length = 104
FEATURE                Location/Qualifiers
REGION                 1..104
                       note = Synthetic: ADX_6077_F02, full-length w/ PmCXn
                        C-terminal modification, (m=1; n=0) and His6 tag
source                 1..104
                       mol_type = protein
                       organism = synthetic construct
SEQUENCE: 118
MGVSDVPRDL EVVAATPTSL LISWSDDYHA HRYYRITYGE TGGNSPVQEF TVPGEHVTAT  60
ISGLKPGVDY TITVYAVTYD GEKAATDWSI SINYRTPCHH HHHH                   104

SEQ ID NO: 119         moltype = AA  length = 103
FEATURE                Location/Qualifiers
REGION                 1..103
                       note = Synthetic: ADX_6077_F02, core with C-terminal
                        PmCXn1CXn2
VARIANT                1..103
                       note = In the C-terminal PmCXn1CXn2, up to 5 proline and up
                        to 5 Xaa (before and after the last Cys) may or may not be
                        present
VARIANT                93..97
                       note = Xaa can be any naturally occurring amino acid
VARIANT                99..103
                       note = Xaa can be any naturally occurring amino acid
source                 1..103
                       mol_type = protein
                       organism = synthetic construct
SEQUENCE: 119
EVVAATPTSL LISWSDDYHA HRYYRITYGE TGGNSPVQEF TVPGEHVTAT ISGLKPGVDY  60
TITVYAVTYD GEKAATDWSI SINYRTPPPP PCXXXXXCXX XXX                    103

SEQ ID NO: 120         moltype = AA  length = 111
FEATURE                Location/Qualifiers
REGION                 1..111
                       note = Synthetic: ADX_6077_F02, full-length with C-terminal
                        PmCXn1CXn2
VARIANT                1..111
                       note = In the C-terminal PmCXn1CXn2, up to 5 proline and up
                        to 5 Xaa (before and after the last Cys) may or may not be
                        present
VARIANT                101..105
                       note = Xaa can be any naturally occurring amino acid
VARIANT                107..111
                       note = Xaa can be any naturally occurring amino acid
source                 1..111
                       mol_type = protein
                       organism = synthetic construct
SEQUENCE: 120
VSDVPRDLEV VAATPTSLLI SWSDDYHAHR YYRITYGETG GNSPVQEFTV PGEHVTATIS  60
GLKPGVDYTI TVYAVTYDGE KAATDWSISI NYRTPPPPPC XXXXXCXXXX X           111

SEQ ID NO: 121         moltype = AA  length = 112
FEATURE                Location/Qualifiers
REGION                 1..112
                       note = Synthetic: ADX_6077_F02, full-length with N-terminal
                        leader (G), and C-terminal PmCXn1CXn2
VARIANT                1..112
                       note = In the C-terminal PmCXn1CXn2, up to 5 proline and up
                        to 5 Xaa (before and after the last Cys) may or may not be
                        present
VARIANT                102..106
                       note = Xaa can be any naturally occurring amino acid
VARIANT                108..112
                       note = Xaa can be any naturally occurring amino acid
source                 1..112
```

```
                         mol_type = protein
                         organism = synthetic construct
SEQUENCE: 121
GVSDVPRDLE VVAATPTSLL ISWSDDYHAH RYYRITYGET GGNSPVQEFT VPGEHVTATI  60
SGLKPGVDYT ITVYAVTYDG EKAATDWSIS INYRTPPPPP CXXXXXCXXX XX          112

SEQ ID NO: 122           moltype = AA  length = 113
FEATURE                  Location/Qualifiers
REGION                   1..113
                         note = Synthetic: ADX_6077_F02, full-length with N-terminal
                          leader (MG), and C-terminal PmCXn1CXn2
VARIANT                  1..113
                         note = In the C-terminal PmCXn1CXn2, up to 5 proline and up
                          to 5 Xaa (before and after the last Cys) may or may not be
                          present
VARIANT                  103..107
                         note = Xaa can be any naturally occurring amino acid
VARIANT                  109..113
                         note = Xaa can be any naturally occurring amino acid
source                   1..113
                         mol_type = protein
                         organism = synthetic construct
SEQUENCE: 122
MGVSDVPRDL EVVAATPTSL LISWSDDYHA HRYYRITYGE TGGNSPVQEF TVPGEHVTAT  60
ISGLKPGVDY TITVYAVTYD GEKAATDWSI SINYRTPPPP PCXXXXXCXX XXX         113

SEQ ID NO: 123           moltype = AA  length = 94
FEATURE                  Location/Qualifiers
REGION                   1..94
                         note = Synthetic: ADX_6077_F02, core with C-terminal
                          PmCXn1CXn2 (m=1; n1=5; n2=0)
source                   1..94
                         mol_type = protein
                         organism = synthetic construct
SEQUENCE: 123
EVVAATPTSL LISWSDDYHA HRYYRITYGE TGGNSPVQEF TVPGEHVTAT ISGLKPGVDY  60
TITVYAVTYD GEKAATDWSI SINYRTPCPP PPPC                              94

SEQ ID NO: 124           moltype = AA  length = 102
FEATURE                  Location/Qualifiers
REGION                   1..102
                         note = Synthetic: ADX_6077_F02, full-length with C-terminal
                          PmCXn1CXn2 (m=1; n1=5, n2=0)
source                   1..102
                         mol_type = protein
                         organism = synthetic construct
SEQUENCE: 124
VSDVPRDLEV VAATPTSLLI SWSDDYHAHR YYRITYGETG GNSPVQEFTV PGEHVTATIS  60
GLKPGVDYTI TVYAVTYDGE KAATDWSISI NYRTPCPPPP PC                     102

SEQ ID NO: 125           moltype = AA  length = 103
FEATURE                  Location/Qualifiers
REGION                   1..103
                         note = Synthetic: ADX_6077_F02, full-length with N-terminal
                          leader (G), and C-terminal PmCXn1CXn2 (m=1; n1=5, n2=0)
source                   1..103
                         mol_type = protein
                         organism = synthetic construct
SEQUENCE: 125
GVSDVPRDLE VVAATPTSLL ISWSDDYHAH RYYRITYGET GGNSPVQEFT VPGEHVTATI  60
SGLKPGVDYT ITVYAVTYDG EKAATDWSIS INYRTPCPPP PPC                    103

SEQ ID NO: 126           moltype = AA  length = 104
FEATURE                  Location/Qualifiers
REGION                   1..104
                         note = Synthetic: ADX_6077_F02, full-length w/N-terminal
                          leader (MG), and C-terminal PmCXn1CXn2 (m=1; n1=5, n2=0)
source                   1..104
                         mol_type = protein
                         organism = synthetic construct
SEQUENCE: 126
MGVSDVPRDL EVVAATPTSL LISWSDDYHA HRYYRITYGE TGGNSPVQEF TVPGEHVTAT  60
ISGLKPGVDY TITVYAVTYD GEKAATDWSI SINYRTPCPP PPPC                   104

SEQ ID NO: 127           moltype = AA  length = 110
FEATURE                  Location/Qualifiers
REGION                   1..110
                         note = Synthetic: ADX_6077_F02, full-length w/C-terminal
                          PmCXn1CXn2 (m=1; n1=5, n2=0)and His6 tag
```

-continued

```
source                  1..110
                        mol_type = protein
                        organism = synthetic construct
SEQUENCE: 127
MGVSDVPRDL EVVAATPTSL LISWSDDYHA HRYYRITYGE TGGNSPVQEF TVPGEHVTAT  60
ISGLKPGVDY TITVYAVTYD GEKAATDWSI SINYRTPCPP PPPCHHHHHH             110

SEQ ID NO: 128          moltype = AA  length = 86
FEATURE                 Location/Qualifiers
REGION                  1..86
                        note = Synthetic: ADX_6077_F02 DG-EG mutant, core,
source                  1..86
                        mol_type = protein
                        organism = synthetic construct
SEQUENCE: 128
EVVAATPTSL LISWSDDYHA HRYYRITYGE TGGNSPVQEF TVPGEHVTAT ISGLKPGVDY  60
TITVYAVTYE GEKAATDWSI SINYRT                                       86

SEQ ID NO: 129          moltype = AA  length = 13
FEATURE                 Location/Qualifiers
REGION                  1..13
                        note = Synthetic: ADX_6077_F02 DG-EG mutant, FG loop
source                  1..13
                        mol_type = protein
                        organism = synthetic construct
SEQUENCE: 129
VTYEGEKAAT DWS                                                     13

SEQ ID NO: 130          moltype = AA  length = 94
FEATURE                 Location/Qualifiers
REGION                  1..94
                        note = Synthetic: ADX_6077_F02 DG-EG mutant, full-length
source                  1..94
                        mol_type = protein
                        organism = synthetic construct
SEQUENCE: 130
VSDVPRDLEV VAATPTSLLI SWSDDYHAHR YYRITYGETG GNSPVQEFTV PGEHVTATIS  60
GLKPGVDYTI TVYAVTYEGE KAATDWSISI NYRT                              94

SEQ ID NO: 131          moltype = AA  length = 95
FEATURE                 Location/Qualifiers
REGION                  1..95
                        note = Synthetic: ADX_6077_F02 DG-EG mutant, full-length
                         with N-terminal leader (G)
source                  1..95
                        mol_type = protein
                        organism = synthetic construct
SEQUENCE: 131
GVSDVPRDLE VVAATPTSLL ISWSDDYHAH RYYRITYGET GGNSPVQEFT VPGEHVTATI  60
SGLKPGVDYT ITVYAVTYEG EKAATDWSIS INYRT                             95

SEQ ID NO: 132          moltype = AA  length = 96
FEATURE                 Location/Qualifiers
REGION                  1..96
                        note = Synthetic: ADX_6077_F02 DG-EG mutant, full-length
                         with N-terminal leader (MG)
source                  1..96
                        mol_type = protein
                        organism = synthetic construct
SEQUENCE: 132
MGVSDVPRDL EVVAATPTSL LISWSDDYHA HRYYRITYGE TGGNSPVQEF TVPGEHVTAT  60
ISGLKPGVDY TITVYAVTYE GEKAATDWSI SINYRT                            96

SEQ ID NO: 133          moltype = AA  length = 96
FEATURE                 Location/Qualifiers
REGION                  1..96
                        note = Synthetic: ADX_6077_F02 DG-EG mutant, core with
                         C-terminal PmXn
VARIANT                 1..96
                        note = In the C-terminal PmXn, up to 5 proline and up to 5
                         Xaa may or may not be present
VARIANT                 92..96
                        note = Xaa can be any naturally occurring amino acid
source                  1..96
                        mol_type = protein
                        organism = synthetic construct
SEQUENCE: 133
EVVAATPTSL LISWSDDYHA HRYYRITYGE TGGNSPVQEF TVPGEHVTAT ISGLKPGVDY  60
TITVYAVTYE GEKAATDWSI SINYRTPPPP PXXXXX                            96
```

```
SEQ ID NO: 134         moltype = AA  length = 104
FEATURE                Location/Qualifiers
REGION                 1..104
                       note = Synthetic: ADX_6077_F02 DG-EG mutant, full-length
                        with C-terminal PmXn
VARIANT                1..104
                       note = In the C-terminal PmXn, up to 5 proline and up to 5
                        Xaa may or may not be present
VARIANT                100..104
                       note = Xaa can be any naturally occurring amino acid
source                 1..104
                       mol_type = protein
                       organism = synthetic construct
SEQUENCE: 134
VSDVPRDLEV VAATPTSLLI SWSDDYHAHR YYRITYGETG GNSPVQEFTV PGEHVTATIS  60
GLKPGVDYTI TVYAVTYEGE KAATDWSISI NYRTPPPPPX XXXX                 104

SEQ ID NO: 135         moltype = AA  length = 105
FEATURE                Location/Qualifiers
REGION                 1..105
                       note = Synthetic: ADX_6077_F02 DG-EG mutant, full-length
                        with N-terminal leader (G) and C-terminal PmXn
VARIANT                1..105
                       note = In the C-terminal PmXn, up to 5 proline and up to 5
                        Xaa may or may not be present
VARIANT                101..105
                       note = Xaa can be any naturally occurring amino acid
source                 1..105
                       mol_type = protein
                       organism = synthetic construct
SEQUENCE: 135
GVSDVPRDLE VVAATPTSLL ISWSDDYHAH RYYRITYGET GGNSPVQEFT VPGEHVTATI  60
SGLKPGVDYT ITVYAVTYEG EKAATDWSIS INYRTPPPPP XXXXX                105

SEQ ID NO: 136         moltype = AA  length = 106
FEATURE                Location/Qualifiers
REGION                 1..106
                       note = Synthetic: ADX_6077_F02 DG-EG mutant, full-length
                        with N-terminal leader (MG) and C-terminal PmXn
VARIANT                1..106
                       note = In the C-terminal PmXn, up to 5 proline and up to 5
                        Xaa may or may not be present
VARIANT                102..106
                       note = Xaa can be any naturally occurring amino acid
source                 1..106
                       mol_type = protein
                       organism = synthetic construct
SEQUENCE: 136
MGVSDVPRDL EVVAATPTSL LISWSDDYHA HRYYRITYGE TGGNSPVQEF TVPGEHVTAT  60
ISGLKPGVDY TITVYAVTYE GEKAATDWSI SINYRTPPPP PXXXXX               106

SEQ ID NO: 137         moltype = AA  length = 97
FEATURE                Location/Qualifiers
REGION                 1..97
                       note = Synthetic: ADX_6077_F02 DG-EG mutant, core with
                        C-terminal PmCXn
VARIANT                1..97
                       note = In the C-terminal PmCXn, up to 5 proline and up to 5
                        Xaa may or may not be present
VARIANT                93..97
                       note = Xaa can be any naturally occurring amino acid
source                 1..97
                       mol_type = protein
                       organism = synthetic construct
SEQUENCE: 137
EVVAATPTSL LISWSDDYHA HRYYRITYGE TGGNSPVQEF TVPGEHVTAT ISGLKPGVDY  60
TITVYAVTYE GEKAATDWSI SINYRTPPPP PCXXXXX                         97

SEQ ID NO: 138         moltype = AA  length = 105
FEATURE                Location/Qualifiers
REGION                 1..105
                       note = Synthetic: ADX_6077_F02 DG-EG mutant, full-length
                        with C-terminal PmCXn
VARIANT                1..105
                       note = In the C-terminal PmCXn, up to 5 proline and up to 5
                        Xaa may or may not be present
VARIANT                101..105
                       note = Xaa can be any naturally occurring amino acid
```

```
source                  1..105
                        mol_type = protein
                        organism = synthetic construct
SEQUENCE: 138
VSDVPRDLEV VAATPTSLLI SWSDDYHAHR YYRITYGETG GNSPVQEFTV PGEHVTATIS  60
GLKPGVDYTI TVYAVTYEGE KAATDWSISI NYRTPPPPPC XXXXX                 105

SEQ ID NO: 139          moltype = AA  length = 106
FEATURE                 Location/Qualifiers
REGION                  1..106
                        note = Synthetic: ADX_6077_F02 DG-EG mutant, full-length
                         with N-terminal leader (G) and C-terminal PmCXn
VARIANT                 1..106
                        note = In the C-terminal PmCXn, up to 5 proline and up to 5
                         Xaa may or may not be present
VARIANT                 102..106
                        note = Xaa can be any naturally occurring amino acid
source                  1..106
                        mol_type = protein
                        organism = synthetic construct
SEQUENCE: 139
GVSDVPRDLE VVAATPTSLL ISWSDDYHAH RYYRITYGET GGNSPVQEFT VPGEHVTATI  60
SGLKPGVDYT ITVYAVTYEG EKAATDWSIS INYRTPPPPP CXXXXX                106

SEQ ID NO: 140          moltype = AA  length = 107
FEATURE                 Location/Qualifiers
REGION                  1..107
                        note = Synthetic: ADX_6077_F02 DG-EG mutant, full-length
                         with N-terminal leader (MG) and C-terminal PmCXn
VARIANT                 1..107
                        note = In the C-terminal PmCXn, up to 5 proline and up to 5
                         Xaa may or may not be present
VARIANT                 103..107
                        note = Xaa can be any naturally occurring amino acid
source                  1..107
                        mol_type = protein
                        organism = synthetic construct
SEQUENCE: 140
MGVSDVPRDL EVVAATPTSL LISWSDDYHA HRYYRITYGE TGGNSPVQEF TVPGEHVTAT  60
ISGLKPGVDY TITVYAVTYE GEKAATDWSI SINYRTPPPP PCXXXXX               107

SEQ ID NO: 141          moltype = AA  length = 88
FEATURE                 Location/Qualifiers
REGION                  1..88
                        note = Synthetic: ADX_6077_F02 DG-EG mutant, core with
                         C-terminal PmCXn (m=1; n=0)
source                  1..88
                        mol_type = protein
                        organism = synthetic construct
SEQUENCE: 141
EVVAATPTSL LISWSDDYHA HRYYRITYGE TGGNSPVQEF TVPGEHVTAT ISGLKPGVDY  60
TITVYAVTYE GEKAATDWSI SINYRTPC                                    88

SEQ ID NO: 142          moltype = AA  length = 96
FEATURE                 Location/Qualifiers
REGION                  1..96
                        note = Synthetic: ADX_6077_F02 DG-EG mutant, full-length
                         with C-terminal PmCXn(m=1; n=0)
source                  1..96
                        mol_type = protein
                        organism = synthetic construct
SEQUENCE: 142
VSDVPRDLEV VAATPTSLLI SWSDDYHAHR YYRITYGETG GNSPVQEFTV PGEHVTATIS  60
GLKPGVDYTI TVYAVTYEGE KAATDWSISI NYRTPC                           96

SEQ ID NO: 143          moltype = AA  length = 97
FEATURE                 Location/Qualifiers
REGION                  1..97
                        note = Synthetic: ADX_6077_F02 DG-EG mutant, full-length
                         w/ N-terminal leader (G) and PmCXn C-terminal modification
                         (m=1; n=0)
source                  1..97
                        mol_type = protein
                        organism = synthetic construct
SEQUENCE: 143
GVSDVPRDLE VVAATPTSLL ISWSDDYHAH RYYRITYGET GGNSPVQEFT VPGEHVTATI  60
SGLKPGVDYT ITVYAVTYEG EKAATDWSIS INYRTPC                          97

SEQ ID NO: 144          moltype = AA  length = 98
```

```
FEATURE                Location/Qualifiers
REGION                 1..98
                       note = Synthetic: ADX_6077_F02 DG-EG mutant, full-length
                        w/ N-terminal eader (MG) and PmCXn C-terminal modification
                        (m=1; n=0)
source                 1..98
                       mol_type = protein
                       organism = synthetic construct
SEQUENCE: 144
MGVSDVPRDL EVVAATPTSL LISWSDDYHA HRYYRITYGE TGGNSPVQEF TVPGEHVTAT  60
ISGLKPGVDY TITVYAVTYE GEKAATDWSI SINYRTPC                          98

SEQ ID NO: 145         moltype = AA  length = 102
FEATURE                Location/Qualifiers
REGION                 1..102
                       note = Synthetic: ADX_6077_F02 DG-EG mutant, full-length
                        with C-terminal PmCXn(m=1; n=0) and His6 tag
source                 1..102
                       mol_type = protein
                       organism = synthetic construct
SEQUENCE: 145
VSDVPRDLEV VAATPTSLLI SWSDDYHAHR YYRITYGETG GNSPVQEFTV PGEHVTATIS  60
GLKPGVDYTI TVYAVTYEGE KAATDWSISI NYRTPCHHHH HH                     102

SEQ ID NO: 146         moltype = AA  length = 103
FEATURE                Location/Qualifiers
REGION                 1..103
                       note = Synthetic: ADX_6077_F02 DG-EG mutant, core with
                        C-terminal PmCXn1CXn2
VARIANT                1..103
                       note = In the C-terminal PmCXn1CXn2, up to 5 proline and up
                        to 5 Xaa (before and after the last Cys) may or may not be
                        present
VARIANT                93..97
                       note = Xaa can be any naturally occurring amino acid
VARIANT                99..103
                       note = Xaa can be any naturally occurring amino acid
source                 1..103
                       mol_type = protein
                       organism = synthetic construct
SEQUENCE: 146
EVVAATPTSL LISWSDDYHA HRYYRITYGE TGGNSPVQEF TVPGEHVTAT ISGLKPGVDY  60
TITVYAVTYE GEKAATDWSI SINYRTPPPP PCXXXXXCXX XXX                    103

SEQ ID NO: 147         moltype = AA  length = 111
FEATURE                Location/Qualifiers
REGION                 1..111
                       note = Synthetic: ADX_6077_F02 DG-EG mutant, full-length
                        with C-terminal PmCXn1CXn2
VARIANT                1..111
                       note = In the C-terminal PmCXn1CXn2, up to 5 proline and up
                        to 5 Xaa (before and after the last Cys) may or may not be
                        present
VARIANT                101..105
                       note = Xaa can be any naturally occurring amino acid
VARIANT                107..111
                       note = Xaa can be any naturally occurring amino acid
source                 1..111
                       mol_type = protein
                       organism = synthetic construct
SEQUENCE: 147
VSDVPRDLEV VAATPTSLLI SWSDDYHAHR YYRITYGETG GNSPVQEFTV PGEHVTATIS  60
GLKPGVDYTI TVYAVTYEGE KAATDWSISI NYRTPPPPPC XXXXXCXXXX X           111

SEQ ID NO: 148         moltype = AA  length = 112
FEATURE                Location/Qualifiers
REGION                 1..112
                       note = Synthetic: ADX_6077_F02 DG-EG mutant, full-length
                        with N-terminal leader (G), and C-terminal PmCXn1CXn2
VARIANT                1..112
                       note = In the C-terminal PmCXn1CXn2, up to 5 proline and up
                        to 5 Xaa (before and after the last Cys) may or may not be
                        present
VARIANT                102..106
                       note = Xaa can be any naturally occurring amino acid
VARIANT                108..112
                       note = Xaa can be any naturally occurring amino acid
source                 1..112
                       mol_type = protein
```

```
                        organism = synthetic construct
SEQUENCE: 148
GVSDVPRDLE VVAATPTSLL ISWSDDYHAH RYYRITYGET GGNSPVQEFT VPGEHVTATI  60
SGLKPGVDYT ITVYAVTYEG EKAATDWSIS INYRTPPPPP CXXXXXCXXX XX          112

SEQ ID NO: 149          moltype = AA  length = 113
FEATURE                 Location/Qualifiers
REGION                  1..113
                        note = Synthetic: ADX_6077_F02 DG-EG mutant, full-length
                         with N-terminal leader (MG), and C-terminal PmCXn1CXn2
VARIANT                 1..113
                        note = In the C-terminal PmCXn1CXn2, up to 5 proline and up
                         to 5 Xaa (before and after the last Cys) may or may not be
                         present
VARIANT                 103..107
                        note = Xaa can be any naturally occurring amino acid
VARIANT                 109..113
                        note = Xaa can be any naturally occurring amino acid
source                  1..113
                        mol_type = protein
                        organism = synthetic construct
SEQUENCE: 149
MGVSDVPRDL EVVAATPTSL LISWSDDYHA HRYYRITYGE TGGNSPVQEF TVPGEHVTAT  60
ISGLKPGVDY TITVYAVTYE GEKAATDWSI SINYRTPPPP PCXXXXXCXX XXX         113

SEQ ID NO: 150          moltype = AA  length = 94
FEATURE                 Location/Qualifiers
REGION                  1..94
                        note = Synthetic: ADX_6077_F02 DG-EG mutant, core with
                         C-terminal PmCXn1CXn2 (m=1; n1=5; n2=0)
source                  1..94
                        mol_type = protein
                        organism = synthetic construct
SEQUENCE: 150
EVVAATPTSL LISWSDDYHA HRYYRITYGE TGGNSPVQEF TVPGEHVTAT ISGLKPGVDY  60
TITVYAVTYE GEKAATDWSI SINYRTPCPP PPPC                              94

SEQ ID NO: 151          moltype = AA  length = 102
FEATURE                 Location/Qualifiers
REGION                  1..102
                        note = Synthetic: ADX_6077_F02 DG-EG mutant, full-length
                         with C-terminal PmCXn1CXn2 (m=1; n1=5; n2=0)
source                  1..102
                        mol_type = protein
                        organism = synthetic construct
SEQUENCE: 151
VSDVPRDLEV VAATPTSLLI SWSDDYHAHR YYRITYGETG GNSPVQEFTV PGEHVTATIS  60
GLKPGVDYTI TVYAVTYEGE KAATDWSISI NYRTPCPPPP PC                     102

SEQ ID NO: 152          moltype = AA  length = 105
FEATURE                 Location/Qualifiers
REGION                  1..105
                        note = Synthetic: ADX_6077_F02 DG-EG mutant, full-length
                         with N-terminal leader (G), and C-terminal PmCXn1CXn2
                         (m=1; n1=5, n2=0)
source                  1..105
                        mol_type = protein
                        organism = synthetic construct
SEQUENCE: 152
GVSDVPRDLE VVAATPTSLL ISWSDDYHAH RYYRITYGET GGNSPVQEFT VPMGGEHVTA  60
TISGLKPGVD YTITVYAVTY EGEKAATDWS ISINYRTPCP PPPPC                  105

SEQ ID NO: 153          moltype = AA  length = 104
FEATURE                 Location/Qualifiers
REGION                  1..104
                        note = Synthetic: ADX_6077_F02 DG-EG mutant, full-length
                         with N-terminal leader (MG), and C-terminal PmCXn1CXn2
                         (m=1; n1=5, n2=0)
source                  1..104
                        mol_type = protein
                        organism = synthetic construct
SEQUENCE: 153
MGVSDVPRDL EVVAATPTSL LISWSDDYHA HRYYRITYGE TGGNSPVQEF TVPGEHVTAT  60
ISGLKPGVDY TITVYAVTYE GEKAATDWSI SINYRTPCPP PPPC                   104

SEQ ID NO: 154          moltype = AA  length = 108
FEATURE                 Location/Qualifiers
REGION                  1..108
                        note = Synthetic: ADX_6077_F02 DG-EG mutant, full-length
```

```
                        with C-terminal PmCXn1CXn2 (m=1; n1=5; n2=0), and His6 tag
source                 1..108
                       mol_type = protein
                       organism = synthetic construct
SEQUENCE: 154
VSDVPRDLEV VAATPTSLLI SWSDDYHAHR YYRITYGETG GNSPVQEFTV PGEHVTATIS  60
GLKPGVDYTI TVYAVTYEGE KAATDWSISI NYRTPCPPPP PCHHHHHH               108

SEQ ID NO: 155         moltype = AA  length = 86
FEATURE                Location/Qualifiers
REGION                 1..86
                       note = Synthetic: ADX_6077_F02 DG-SG mutant, core
source                 1..86
                       mol_type = protein
                       organism = synthetic construct
SEQUENCE: 155
EVVAATPTSL LISWSDDYHA HRYYRITYGE TGGNSPVQEF TVPGEHVTAT ISGLKPGVDY  60
TITVYAVTYS GEKAATDWSI SINYRT                                       86

SEQ ID NO: 156         moltype = AA  length = 13
FEATURE                Location/Qualifiers
REGION                 1..13
                       note = Synthetic: ADX_6077_F02 DG-SG mutant, FG loop
source                 1..13
                       mol_type = protein
                       organism = synthetic construct
SEQUENCE: 156
VTYSGEKAAT DWS                                                     13

SEQ ID NO: 157         moltype = AA  length = 94
FEATURE                Location/Qualifiers
REGION                 1..94
                       note = Synthetic: ADX_6077_F02 DG-SG mutant, full-length
source                 1..94
                       mol_type = protein
                       organism = synthetic construct
SEQUENCE: 157
VSDVPRDLEV VAATPTSLLI SWSDDYHAHR YYRITYGETG GNSPVQEFTV PGEHVTATIS  60
GLKPGVDYTI TVYAVTYSGE KAATDWSISI NYRT                              94

SEQ ID NO: 158         moltype = AA  length = 95
FEATURE                Location/Qualifiers
REGION                 1..95
                       note = Synthetic: ADX_6077_F02 DG-SG mutant, full-length
                        with N-terminal leader (G)
source                 1..95
                       mol_type = protein
                       organism = synthetic construct
SEQUENCE: 158
GVSDVPRDLE VVAATPTSLL ISWSDDYHAH RYYRITYGET GGNSPVQEFT VPGEHVTATI  60
SGLKPGVDYT ITVYAVTYSG EKAATDWSIS INYRT                             95

SEQ ID NO: 159         moltype = AA  length = 96
FEATURE                Location/Qualifiers
REGION                 1..96
                       note = Synthetic: ADX_6077_F02 DG-SG mutant, full-length
                        with N-terminal leader (MG)
source                 1..96
                       mol_type = protein
                       organism = synthetic construct
SEQUENCE: 159
MGVSDVPRDL EVVAATPTSL LISWSDDYHA HRYYRITYGE TGGNSPVQEF TVPGEHVTAT  60
ISGLKPGVDY TITVYAVTYS GEKAATDWSI SINYRT                            96

SEQ ID NO: 160         moltype = AA  length = 96
FEATURE                Location/Qualifiers
REGION                 1..96
                       note = Synthetic: ADX_6077_F02 DG-SG mutant, core with
                        C-terminal PmXn
VARIANT                1..96
                       note = In the C-terminal PmXn, up to 5 proline and up to 5
                        Xaa may or may not be present
VARIANT                92..96
                       note = Xaa can be any naturally occurring amino acid
source                 1..96
                       mol_type = protein
                       organism = synthetic construct
SEQUENCE: 160
EVVAATPTSL LISWSDDYHA HRYYRITYGE TGGNSPVQEF TVPGEHVTAT ISGLKPGVDY  60
```

-continued

```
TITVYAVTYS GEKAATDWSI SINYRTPPPP PXXXXX                        96

SEQ ID NO: 161          moltype = AA  length = 104
FEATURE                 Location/Qualifiers
REGION                  1..104
                        note = Synthetic: ADX_6077_F02 DG-SG mutant, full-length
                         with C-terminal PmXn
VARIANT                 1..104
                        note = In the C-terminal PmXn, up to 5 proline and up to 5
                         Xaa may or may not be present
VARIANT                 100..104
                        note = Xaa can be any naturally occurring amino acid
source                  1..104
                        mol_type = protein
                        organism = synthetic construct
SEQUENCE: 161
VSDVPRDLEV VAATPTSLLI SWSDDYHAHR YYRITYGETG GNSPVQEFTV PGEHVTATIS  60
GLKPGVDYTI TVYAVTYSGE KAATDWSISI NYRTPPPPPX XXXX                 104

SEQ ID NO: 162          moltype = AA  length = 105
FEATURE                 Location/Qualifiers
REGION                  1..105
                        note = Synthetic: ADX_6077_F02 DG-SG mutant, full-length
                         with N-terminal leader (G) and C-terminal PmXn
VARIANT                 1..105
                        note = In the C-terminal PmXn, up to 5 proline and up to 5
                         Xaa may or may not be present
VARIANT                 101..105
                        note = Xaa can be any naturally occurring amino acid
source                  1..105
                        mol_type = protein
                        organism = synthetic construct
SEQUENCE: 162
GVSDVPRDLE VVAATPTSLL ISWSDDYHAH RYYRITYGET GGNSPVQEFT VPGEHVTATI  60
SGLKPGVDYT ITVYAVTYSG EKAATDWSIS INYRTPPPPP XXXXX                105

SEQ ID NO: 163          moltype = AA  length = 106
FEATURE                 Location/Qualifiers
REGION                  1..106
                        note = Synthetic: ADX_6077_F02 DG-SG mutant, full-length
                         with N-terminal leader (MG) and C-terminal PmXn
VARIANT                 1..106
                        note = In the C-terminal PmXn, up to 5 proline and up to 5
                         Xaa may or may not be present
VARIANT                 102..106
                        note = Xaa can be any naturally occurring amino acid
source                  1..106
                        mol_type = protein
                        organism = synthetic construct
SEQUENCE: 163
MGVSDVPRDL EVVAATPTSL LISWSDDYHA HRYYRITYGE TGGNSPVQEF TVPGEHVTAT  60
ISGLKPGVDY TITVYAVTYS GEKAATDWSI SINYRTPPPP PXXXXX               106

SEQ ID NO: 164          moltype = AA  length = 97
FEATURE                 Location/Qualifiers
REGION                  1..97
                        note = Synthetic: ADX_6077_F02 DG-SG mutant, core with
                         C-terminal PmCXn
VARIANT                 1..97
                        note = In the C-terminal PmCXn, up to 5 proline and up to 5
                         Xaa may or may not be present
VARIANT                 93..97
                        note = Xaa can be any naturally occurring amino acid
source                  1..97
                        mol_type = protein
                        organism = synthetic construct
SEQUENCE: 164
EVVAATPTSL LISWSDDYHA HRYYRITYGE TGGNSPVQEF TVPGEHVTAT ISGLKPGVDY  60
TITVYAVTYS GEKAATDWSI SINYRTPPPP PCXXXXX                       97

SEQ ID NO: 165          moltype = AA  length = 105
FEATURE                 Location/Qualifiers
REGION                  1..105
                        note = Synthetic: ADX_6077_F02 DG-SG mutant, full-length
                         with C-terminal PmCXn
VARIANT                 1..105
                        note = In the C-terminal PmCXn, up to 5 proline and up to 5
                         Xaa may or may not be present
VARIANT                 101..105
```

-continued

```
                         note = Xaa can be any naturally occurring amino acid
source                   1..105
                         mol_type = protein
                         organism = synthetic construct
SEQUENCE: 165
VSDVPRDLEV VAATPTSLLI SWSDDYHAHR YYRITYGETG GNSPVQEFTV PGEHVTATIS  60
GLKPGVDYTI TVYAVTYSGE KAATDWSISI NYRTPPPPPC XXXXX                  105

SEQ ID NO: 166           moltype = AA  length = 106
FEATURE                  Location/Qualifiers
REGION                   1..106
                         note = Synthetic: ADX_6077_F02 DG-SG mutant, full-length
                          with N-terminal leader (G) and C-terminal PmCXn
VARIANT                  1..106
                         note = In the C-terminal PmCXn, up to 5 proline and up to 5
                          Xaa may or may not be present
VARIANT                  102..106
                         note = Xaa can be any naturally occurring amino acid
source                   1..106
                         mol_type = protein
                         organism = synthetic construct
SEQUENCE: 166
GVSDVPRDLE VVAATPTSLL ISWSDDYHAH RYYRITYGET GGNSPVQEFT VPGEHVTATI  60
SGLKPGVDYT ITVYAVTYSG EKAATDWSIS INYRTPPPPP CXXXXX                 106

SEQ ID NO: 167           moltype = AA  length = 107
FEATURE                  Location/Qualifiers
REGION                   1..107
                         note = Synthetic: ADX_6077_F02 DG-SG, full-length with
                          N-terminal leader (MG) and C-terminal PmCXn
VARIANT                  1..107
                         note = In the C-terminal PmCXn, up to 5 proline and up to 5
                          Xaa may or may not be present
VARIANT                  103..107
                         note = Xaa can be any naturally occurring amino acid
source                   1..107
                         mol_type = protein
                         organism = synthetic construct
SEQUENCE: 167
MGVSDVPRDL EVVAATPTSL LISWSDDYHA HRYYRITYGE TGGNSPVQEF TVPGEHVTAT  60
ISGLKPGVDY TITVYAVTYS GEKAATDWSI SINYRTPPPP PCXXXXX                107

SEQ ID NO: 168           moltype = AA  length = 88
FEATURE                  Location/Qualifiers
REGION                   1..88
                         note = Synthetic: ADX_6077_F02 DG-SG mutant, core with
                          C-terminal PmCXn (m=1; n=0)
source                   1..88
                         mol_type = protein
                         organism = synthetic construct
SEQUENCE: 168
EVVAATPTSL LISWSDDYHA HRYYRITYGE TGGNSPVQEF TVPGEHVTAT ISGLKPGVDY  60
TITVYAVTYS GEKAATDWSI SINYRTPC                                     88

SEQ ID NO: 169           moltype = AA  length = 96
FEATURE                  Location/Qualifiers
REGION                   1..96
                         note = Synthetic: ADX_6077_F02 DG-SG mutant, full-length
                          with C-terminal PmCXn(m=1; n=0)
source                   1..96
                         mol_type = protein
                         organism = synthetic construct
SEQUENCE: 169
VSDVPRDLEV VAATPTSLLI SWSDDYHAHR YYRITYGETG GNSPVQEFTV PGEHVTATIS  60
GLKPGVDYTI TVYAVTYSGE KAATDWSISI NYRTPC                            96

SEQ ID NO: 170           moltype = AA  length = 97
FEATURE                  Location/Qualifiers
REGION                   1..97
                         note = Synthetic: ADX_6077_F02 DG-SG mutant, full-length
                          w/ N-terminal leader and PmCXn(m=1; n=0)
source                   1..97
                         mol_type = protein
                         organism = synthetic construct
SEQUENCE: 170
GVSDVPRDLE VVAATPTSLL ISWSDDYHAH RYYRITYGET GGNSPVQEFT VPGEHVTATI  60
SGLKPGVDYT ITVYAVTYSG EKAATDWSIS INYRTPC                           97

SEQ ID NO: 171           moltype = AA  length = 98
```

```
FEATURE                Location/Qualifiers
REGION                 1..98
                       note = Synthetic: ADX_6077_F02 DG-SG mutant, full-length
                        w/ N-terminal eader (MG) and PmCXn C-terminal modification
                        (m=1; n=0)
source                 1..98
                       mol_type = protein
                       organism = synthetic construct
SEQUENCE: 171
MGVSDVPRDL EVVAATPTSL LISWSDDYHA HRYYRITYGE TGGNSPVQEF TVPGEHVTAT  60
ISGLKPGVDY TITVYAVTYS GEKAATDWSI SINYRTPC                          98

SEQ ID NO: 172         moltype = AA  length = 102
FEATURE                Location/Qualifiers
REGION                 1..102
                       note = Synthetic: ADX_6077_F02 DG-SG mutant, full-length
                        with C-terminal PmCXn(m=1; n=0) and His6 tag
source                 1..102
                       mol_type = protein
                       organism = synthetic construct
SEQUENCE: 172
VSDVPRDLEV VAATPTSLLI SWSDDYHAHR YYRITYGETG GNSPVQEFTV PGEHVTATIS  60
GLKPGVDYTI TVYAVTYSGE KAATDWSISI NYRTPCHHHH HH                     102

SEQ ID NO: 173         moltype = AA  length = 103
FEATURE                Location/Qualifiers
REGION                 1..103
                       note = Synthetic: ADX_6077_F02 DG-SG mutant, core with
                        C-terminal PmCXn1CXn2
VARIANT                1..103
                       note = In the C-terminal PmCXn1CXn2, up to 5 proline and up
                        to 5 Xaa (before and after the last Cys) may or may not be
                        present
VARIANT                93..97
                       note = Xaa can be any naturally occurring amino acid
VARIANT                99..103
                       note = Xaa can be any naturally occurring amino acid
source                 1..103
                       mol_type = protein
                       organism = synthetic construct
SEQUENCE: 173
EVVAATPTSL LISWSDDYHA HRYYRITYGE TGGNSPVQEF TVPGEHVTAT ISGLKPGVDY  60
TITVYAVTYS GEKAATDWSI SINYRTPPPP PCXXXXXCXX XXX                    103

SEQ ID NO: 174         moltype = AA  length = 111
FEATURE                Location/Qualifiers
REGION                 1..111
                       note = Synthetic: ADX_6077_F02 DG-SG mutant, full-length
                        with C-terminal PmCXn1CXn2
VARIANT                1..111
                       note = In the C-terminal PmCXn1CXn2, up to 5 proline and up
                        to 5 Xaa (before and after the last Cys) may or may not be
                        present
VARIANT                101..105
                       note = Xaa can be any naturally occurring amino acid
VARIANT                107..111
                       note = Xaa can be any naturally occurring amino acid
source                 1..111
                       mol_type = protein
                       organism = synthetic construct
SEQUENCE: 174
VSDVPRDLEV VAATPTSLLI SWSDDYHAHR YYRITYGETG GNSPVQEFTV PGEHVTATIS  60
GLKPGVDYTI TVYAVTYSGE KAATDWSISI NYRTPPPPPC XXXXXCXXXX X           111

SEQ ID NO: 175         moltype = AA  length = 112
FEATURE                Location/Qualifiers
REGION                 1..112
                       note = Synthetic: ADX_6077_F02 DG-SG mutant, full-length
                        with N-terminal leader (G), and C-terminal PmCXn1CXn2
VARIANT                1..112
                       note = In the C-terminal PmCXn1CXn2, up to 5 proline and up
                        to 5 Xaa (before and after the last Cys) may or may not be
                        present
VARIANT                102..106
                       note = Xaa can be any naturally occurring amino acid
VARIANT                108..112
                       note = Xaa can be any naturally occurring amino acid
source                 1..112
                       mol_type = protein
```

```
                         organism = synthetic construct
SEQUENCE: 175
GVSDVPRDLE VVAATPTSLL ISWSDDYHAH RYYRITYGET GGNSPVQEFT VPGEHVTATI  60
SGLKPGVDYT ITVYAVTYSG EKAATDWSIS INYRTPPPPP CXXXXXCXXX XX          112

SEQ ID NO: 176           moltype = AA  length = 113
FEATURE                  Location/Qualifiers
REGION                   1..113
                         note = Synthetic: ADX_6077_F02 DG-SG mutant, full-length
                          with N-terminal leader (MG), and C-terminal PmCXn1CXn2
VARIANT                  1..113
                         note = In the C-terminal PmCXn1CXn2, up to 5 proline and up
                          to 5 Xaa (before and after the last Cys) may or may not be
                          present
VARIANT                  103..107
                         note = Xaa can be any naturally occurring amino acid
VARIANT                  109..113
                         note = Xaa can be any naturally occurring amino acid
source                   1..113
                         mol_type = protein
                         organism = synthetic construct
SEQUENCE: 176
MGVSDVPRDL EVVAATPTSL LISWSDDYHA HRYYRITYGE TGGNSPVQEF TVPGEHVTAT  60
ISGLKPGVDY TITVYAVTYS GEKAATDWSI SINYRTPPPP PCXXXXXCXX XXX         113

SEQ ID NO: 177           moltype = AA  length = 94
FEATURE                  Location/Qualifiers
REGION                   1..94
                         note = Synthetic: ADX_6077_F02 DG-SG mutant, core with
                          C-terminal PmCXn1CXn2 (m=1; n1=5; n2=0)
source                   1..94
                         mol_type = protein
                         organism = synthetic construct
SEQUENCE: 177
EVVAATPTSL LISWSDDYHA HRYYRITYGE TGGNSPVQEF TVPGEHVTAT ISGLKPGVDY  60
TITVYAVTYS GEKAATDWSI SINYRTPCPP PPPC                              94

SEQ ID NO: 178           moltype = AA  length = 102
FEATURE                  Location/Qualifiers
REGION                   1..102
                         note = Synthetic: ADX_6077_F02 DG-SG mutant, full-length
                          with C-terminal PmCXn1CXn2 (m=1; n1=5; n2=0)
source                   1..102
                         mol_type = protein
                         organism = synthetic construct
SEQUENCE: 178
VSDVPRDLEV VAATPTSLLI SWSDDYHAHR YYRITYGETG GNSPVQEFTV PGEHVTATIS  60
GLKPGVDYTI TVYAVTYSGE KAATDWSISI NYRTPCPPPP PC                     102

SEQ ID NO: 179           moltype = AA  length = 103
FEATURE                  Location/Qualifiers
REGION                   1..103
                         note = Synthetic: ADX_6077_F02 DG-SG mutant, full-length
                          with N-terminal leader (G), and C-terminal PmCXn1CXn2
                          (m=1; n1=5, n2=0)
source                   1..103
                         mol_type = protein
                         organism = synthetic construct
SEQUENCE: 179
GVSDVPRDLE VVAATPTSLL ISWSDDYHAH RYYRITYGET GGNSPVQEFT VPGEHVTATI  60
SGLKPGVDYT ITVYAVTYSG EKAATDWSIS INYRTPCPPP PPC                    103

SEQ ID NO: 180           moltype = AA  length = 104
FEATURE                  Location/Qualifiers
REGION                   1..104
                         note = Synthetic: ADX_6077_F02 DG-SG mutant, full-length
                          with N-terminal leader (MG), and C-terminal PmCXn1CXn2
                          (m=1; n1=5, n2=0)
source                   1..104
                         mol_type = protein
                         organism = synthetic construct
SEQUENCE: 180
MGVSDVPRDL EVVAATPTSL LISWSDDYHA HRYYRITYGE TGGNSPVQEF TVPGEHVTAT  60
ISGLKPGVDY TITVYAVTYS GEKAATDWSI SINYRTPCPP PPPC                   104

SEQ ID NO: 181           moltype = AA  length = 108
FEATURE                  Location/Qualifiers
REGION                   1..108
                         note = Synthetic: ADX_6077_F02 DG-SG mutant, full-length
```

-continued

```
                         with C-terminal PmCXn1CXn2 (m=1; n1=5; n2=0), and His6 tag
source                  1..108
                        mol_type = protein
                        organism = synthetic construct
SEQUENCE: 181
VSDVPRDLEV VAATPTSLLI SWSDDYHAHR YYRITYGETG GNSPVQEFTV PGEHVTATIS  60
GLKPGVDYTI TVYAVTYSGE KAATDWSISI NYRTPCPPPP PCHHHHHH               108

SEQ ID NO: 182          moltype = AA  length = 86
FEATURE                 Location/Qualifiers
REGION                  1..86
                        note = Synthetic: ADX_6077_F02 DG-AG mutant, core
source                  1..86
                        mol_type = protein
                        organism = synthetic construct
SEQUENCE: 182
EVVAATPTSL LISWSDDYHA HRYYRITYGE TGGNSPVQEF TVPGEHVTAT ISGLKPGVDY  60
TITVYAVTYA GEKAATDWSI SINYRT                                       86

SEQ ID NO: 183          moltype = AA  length = 13
FEATURE                 Location/Qualifiers
REGION                  1..13
                        note = Synthetic: ADX_6077_F02 DG-AG mutant, FG loop
source                  1..13
                        mol_type = protein
                        organism = synthetic construct
SEQUENCE: 183
VTYAGEKAAT DWS                                                     13

SEQ ID NO: 184          moltype = AA  length = 94
FEATURE                 Location/Qualifiers
REGION                  1..94
                        note = Synthetic: ADX_6077_F02 DG-AG mutant, full-length
source                  1..94
                        mol_type = protein
                        organism = synthetic construct
SEQUENCE: 184
VSDVPRDLEV VAATPTSLLI SWSDDYHAHR YYRITYGETG GNSPVQEFTV PGEHVTATIS  60
GLKPGVDYTI TVYAVTYAGE KAATDWSISI NYRT                              94

SEQ ID NO: 185          moltype = AA  length = 95
FEATURE                 Location/Qualifiers
REGION                  1..95
                        note = Synthetic: ADX_6077_F02 DG-AG mutant, full-length
                         with N-terminal leader (G)
source                  1..95
                        mol_type = protein
                        organism = synthetic construct
SEQUENCE: 185
GVSDVPRDLE VVAATPTSLL ISWSDDYHAH RYYRITYGET GGNSPVQEFT VPGEHVTATI  60
SGLKPGVDYT ITVYAVTYAG EKAATDWSIS INYRT                             95

SEQ ID NO: 186          moltype = AA  length = 96
FEATURE                 Location/Qualifiers
REGION                  1..96
                        note = Synthetic: ADX_6077_F02 DG-AG mutant, full-length
                         with N-terminal leader (MG)
source                  1..96
                        mol_type = protein
                        organism = synthetic construct
SEQUENCE: 186
MGVSDVPRDL EVVAATPTSL LISWSDDYHA HRYYRITYGE TGGNSPVQEF TVPGEHVTAT  60
ISGLKPGVDY TITVYAVTYA GEKAATDWSI SINYRT                            96

SEQ ID NO: 187          moltype = AA  length = 97
FEATURE                 Location/Qualifiers
REGION                  1..97
                        note = Synthetic: ADX_6077_F02 DG-AG mutant, core with
                         C-terminal PmXn
VARIANT                 1..97
                        note = In the C-terminal PmXn, up to 5 proline and up to 5
                         Xaa may or may not be present
VARIANT                 93..97
                        note = Xaa can be any naturally occurring amino acid
source                  1..97
                        mol_type = protein
                        organism = synthetic construct
SEQUENCE: 187
LEVVAATPTS LLISWSDDYH AHRYYRITYG ETGGNSPVQE FTVPGEHVTA TISGLKPGVD  60
```

-continued

```
YTITVYAVTY AGEKAATDWS ISINYRTPPP PPXXXXX                        97

SEQ ID NO: 188          moltype = AA  length = 104
FEATURE                 Location/Qualifiers
REGION                  1..104
                        note = Synthetic: ADX_6077_F02 DG-AG mutant, full-length
                         with C-terminal PmXn
VARIANT                 1..104
                        note = In the C-terminal PmXn, up to 5 proline and up to 5
                         Xaa may or may not be present
VARIANT                 100..104
                        note = Xaa can be any naturally occurring amino acid
source                  1..104
                        mol_type = protein
                        organism = synthetic construct
SEQUENCE: 188
VSDVPRDLEV VAATPTSLLI SWSDDYHAHR YYRITYGETG GNSPVQEFTV PGEHVTATIS  60
GLKPGVDYTI TVYAVTYAGE KAATDWSISI NYRTPPPPPX XXXX                 104

SEQ ID NO: 189          moltype = AA  length = 105
FEATURE                 Location/Qualifiers
REGION                  1..105
                        note = Synthetic: ADX_6077_F02 DG-AG mutant, full-length
                         with N-terminal leader (G) and C-terminal PmXn
VARIANT                 1..105
                        note = In the C-terminal PmXn, up to 5 proline and up to 5
                         Xaa may or may not be present
VARIANT                 101..105
                        note = Xaa can be any naturally occurring amino acid
source                  1..105
                        mol_type = protein
                        organism = synthetic construct
SEQUENCE: 189
GVSDVPRDLE VVAATPTSLL ISWSDDYHAH RYYRITYGET GGNSPVQEFT VPGEHVTATI  60
SGLKPGVDYT ITVYAVTYAG EKAATDWSIS INYRTPPPPP XXXXX                105

SEQ ID NO: 190          moltype = AA  length = 106
FEATURE                 Location/Qualifiers
REGION                  1..106
                        note = Synthetic: ADX_6077_F02 DG-AG mutant, full-length
                         with N-terminal leader (MG) and C-terminal PmXn
VARIANT                 1..106
                        note = In the C-terminal PmXn, up to 5 proline and up to 5
                         Xaa may or may not be present
VARIANT                 102..106
                        note = Xaa can be any naturally occurring amino acid
source                  1..106
                        mol_type = protein
                        organism = synthetic construct
SEQUENCE: 190
MGVSDVPRDL EVVAATPTSL LISWSDDYHA HRYYRITYGE TGGNSPVQEF TVPGEHVTAT  60
ISGLKPGVDY TITVYAVTYA GEKAATDWSI SINYRTPPPP PXXXXX               106

SEQ ID NO: 191          moltype = AA  length = 97
FEATURE                 Location/Qualifiers
REGION                  1..97
                        note = Synthetic: ADX_6077_F02 DG-AG mutant, core with
                         C-terminal PmCXn
VARIANT                 1..97
                        note = In the C-terminal PmCXn, up to 5 proline and up to 5
                         Xaa may or may not be present
VARIANT                 93..97
                        note = Xaa can be any naturally occurring amino acid
source                  1..97
                        mol_type = protein
                        organism = synthetic construct
SEQUENCE: 191
EVVAATPTSL LISWSDDYHA HRYYRITYGE TGGNSPVQEF TVPGEHVTAT ISGLKPGVDY  60
TITVYAVTYA GEKAATDWSI SINYRTPPPP PCXXXXX                         97

SEQ ID NO: 192          moltype = AA  length = 105
FEATURE                 Location/Qualifiers
REGION                  1..105
                        note = Synthetic: ADX_6077_F02 DG-AG mutant, full-length
                         with C-terminal PmCXn
VARIANT                 1..105
                        note = In the C-terminal PmCXn, up to 5 proline and up to 5
                         Xaa may or may not be present
VARIANT                 101..105
```

-continued

```
                         note = Xaa can be any naturally occurring amino acid
source                   1..105
                         mol_type = protein
                         organism = synthetic construct
SEQUENCE: 192
VSDVPRDLEV VAATPTSLLI SWSDDYHAHR YYRITYGETG GNSPVQEFTV PGEHVTATIS  60
GLKPGVDYTI TVYAVTYAGE KAATDWSISI NYRTPPPPPC XXXXX                 105

SEQ ID NO: 193           moltype = AA  length = 106
FEATURE                  Location/Qualifiers
REGION                   1..106
                         note = Synthetic: ADX_6077_F02 DG-AG mutant, full-length
                          with N-terminal leader (G) and C-terminal PmCXn
VARIANT                  1..106
                         note = In the C-terminal PmCXn, up to 5 proline and up to 5
                          Xaa may or may not be present
VARIANT                  102..106
                         note = Xaa can be any naturally occurring amino acid
source                   1..106
                         mol_type = protein
                         organism = synthetic construct
SEQUENCE: 193
GVSDVPRDLE VVAATPTSLL ISWSDDYHAH RYYRITYGET GGNSPVQEFT VPGEHVTATI  60
SGLKPGVDYT ITVYAVTYAG EKAATDWSIS INYRTPPPPP CXXXXX                106

SEQ ID NO: 194           moltype = AA  length = 107
FEATURE                  Location/Qualifiers
REGION                   1..107
                         note = Synthetic: ADX_6077_F02 DG-AG mutant, full-length
                          with N-terminal leader (MG) and C-terminal PmCXn
VARIANT                  1..107
                         note = In the C-terminal PmCXn, up to 5 proline and up to 5
                          Xaa may or may not be present
VARIANT                  103..107
                         note = Xaa can be any naturally occurring amino acid
source                   1..107
                         mol_type = protein
                         organism = synthetic construct
SEQUENCE: 194
MGVSDVPRDL EVVAATPTSL LISWSDDYHA HRYYRITYGE TGGNSPVQEF TVPGEHVTAT  60
ISGLKPGVDY TITVYAVTYA GEKAATDWSI SINYRTPPPP PCXXXXX               107

SEQ ID NO: 195           moltype = AA  length = 88
FEATURE                  Location/Qualifiers
REGION                   1..88
                         note = Synthetic: ADX_6077_F02 DG-AG mutant, core with
                          C-terminal PmCXn (m=1; n=0)
source                   1..88
                         mol_type = protein
                         organism = synthetic construct
SEQUENCE: 195
EVVAATPTSL LISWSDDYHA HRYYRITYGE TGGNSPVQEF TVPGEHVTAT ISGLKPGVDY  60
TITVYAVTYA GEKAATDWSI SINYRTPC                                    88

SEQ ID NO: 196           moltype = AA  length = 96
FEATURE                  Location/Qualifiers
REGION                   1..96
                         note = Synthetic: ADX_6077_F02 DG-AG mutant, full-length
                          with C-terminal PmCXn(m=1; n=0)
source                   1..96
                         mol_type = protein
                         organism = synthetic construct
SEQUENCE: 196
VSDVPRDLEV VAATPTSLLI SWSDDYHAHR YYRITYGETG GNSPVQEFTV PGEHVTATIS  60
GLKPGVDYTI TVYAVTYAGE KAATDWSISI NYRTPC                           96

SEQ ID NO: 197           moltype = AA  length = 97
FEATURE                  Location/Qualifiers
REGION                   1..97
                         note = Synthetic: ADX_6077_F02 DG-AG mutant, full-length
                          w/ N-terminal leader (G) and PmCXn C-terminal modification
                          (m=1; n=0)
source                   1..97
                         mol_type = protein
                         organism = synthetic construct
SEQUENCE: 197
GVSDVPRDLE VVAATPTSLL ISWSDDYHAH RYYRITYGET GGNSPVQEFT VPGEHVTATI  60
SGLKPGVDYT ITVYAVTYAG EKAATDWSIS INYRTPC                          97
```

-continued

```
SEQ ID NO: 198         moltype = AA  length = 98
FEATURE                Location/Qualifiers
REGION                 1..98
                       note = Synthetic: ADX_6077_F02 DG-AG mutant, full-length
                        w/ N-terminal leader (MG) and PmCXn C-terminal
                        modification (m=1; n=0)
source                 1..98
                       mol_type = protein
                       organism = synthetic construct
SEQUENCE: 198
MGVSDVPRDL EVVAATPTSL LISWSDDYHA HRYYRITYGE TGGNSPVQEF TVPGEHVTAT  60
ISGLKPGVDY TITVYAVTYA GEKAATDWSI SINYRTPC                          98

SEQ ID NO: 199         moltype = AA  length = 102
FEATURE                Location/Qualifiers
REGION                 1..102
                       note = Synthetic: ADX_6077_F02 DG-AG mutant, full-length
                        with C-terminal PmCXn(m=1; n=0) and His6 tag
source                 1..102
                       mol_type = protein
                       organism = synthetic construct
SEQUENCE: 199
VSDVPRDLEV VAATPTSLLI SWSDDYHAHR YYRITYGETG GNSPVQEFTV PGEHVTATIS  60
GLKPGVDYTI TVYAVTYAGE KAATDWSISI NYRTPCHHHH HH                     102

SEQ ID NO: 200         moltype = AA  length = 103
FEATURE                Location/Qualifiers
REGION                 1..103
                       note = Synthetic: ADX_6077_F02 DG-AG mutant, core with
                        C-terminal PmCXn1CXn2
VARIANT                1..103
                       note = In the C-terminal PmCXn1CXn2, up to 5 proline and up
                        to 5 Xaa (before and after the last Cys) may or may not be
                        present
VARIANT                93..97
                       note = Xaa can be any naturally occurring amino acid
VARIANT                99..103
                       note = Xaa can be any naturally occurring amino acid
source                 1..103
                       mol_type = protein
                       organism = synthetic construct
SEQUENCE: 200
EVVAATPTSL LISWSDDYHA HRYYRITYGE TGGNSPVQEF TVPGEHVTAT ISGLKPGVDY  60
TITVYAVTYA GEKAATDWSI SINYRTPPPP PCXXXXXCXX XXX                    103

SEQ ID NO: 201         moltype = AA  length = 111
FEATURE                Location/Qualifiers
REGION                 1..111
                       note = Synthetic: ADX_6077_F02 DG-AG mutant, full-length
                        with C-terminal PmCXn1CXn2
VARIANT                1..111
                       note = In the C-terminal PmCXn1CXn2, up to 5 proline and up
                        to 5 Xaa (before and after the last Cys) may or may not be
                        present
VARIANT                101..105
                       note = Xaa can be any naturally occurring amino acid
VARIANT                107..111
                       note = Xaa can be any naturally occurring amino acid
source                 1..111
                       mol_type = protein
                       organism = synthetic construct
SEQUENCE: 201
VSDVPRDLEV VAATPTSLLI SWSDDYHAHR YYRITYGETG GNSPVQEFTV PGEHVTATIS  60
GLKPGVDYTI TVYAVTYAGE KAATDWSISI NYRTPPPPPC XXXXXCXXXX X           111

SEQ ID NO: 202         moltype = AA  length = 112
FEATURE                Location/Qualifiers
REGION                 1..112
                       note = Synthetic: ADX_6077_F02 DG-AG mutant, full-length
                        with N-terminal leader (G), and C-terminal PmCXn1CXn2
VARIANT                1..112
                       note = In the C-terminal PmCXn1CXn2, up to 5 proline and up
                        to 5 Xaa (before and after the last Cys) may or may not be
                        present
VARIANT                102..106
                       note = Xaa can be any naturally occurring amino acid
VARIANT                108..112
                       note = Xaa can be any naturally occurring amino acid
source                 1..112
```

```
                        mol_type = protein
                        organism = synthetic construct
SEQUENCE: 202
GVSDVPRDLE VVAATPTSLL ISWSDDYHAH RYYRITYGET GGNSPVQEFT VPGEHVTATI  60
SGLKPGVDYT ITVYAVTYAG EKAATDWSIS INYRTPPPPP CXXXXXCXXX XX          112

SEQ ID NO: 203          moltype = AA  length = 113
FEATURE                 Location/Qualifiers
REGION                  1..113
                        note = Synthetic: ADX_6077_F02 DG-AG mutant, full-length
                         with N-terminal leader (MG), and C-terminal PmCXn1CXn2
VARIANT                 1..113
                        note = In the C-terminal PmCXn1CXn2, up to 5 proline and up
                         to 5 Xaa (before and after the last Cys) may or may not be
                         present
VARIANT                 103..107
                        note = Xaa can be any naturally occurring amino acid
VARIANT                 109..113
                        note = Xaa can be any naturally occurring amino acid
source                  1..113
                        mol_type = protein
                        organism = synthetic construct
SEQUENCE: 203
MGVSDVPRDL EVVAATPTSL LISWSDDYHA HRYYRITYGE TGGNSPVQEF TVPGEHVTAT  60
ISGLKPGVDY TITVYAVTYA GEKAATDWSI SINYRTPPPP PCXXXXXCXX XXX         113

SEQ ID NO: 204          moltype = AA  length = 94
FEATURE                 Location/Qualifiers
REGION                  1..94
                        note = Synthetic: ADX_6077_F02 DG-AG mutant, core with
                         C-terminal PmCXn1CXn2 (m=1; n1=5; n2=0)
source                  1..94
                        mol_type = protein
                        organism = synthetic construct
SEQUENCE: 204
EVVAATPTSL LISWSDDYHA HRYYRITYGE TGGNSPVQEF TVPGEHVTAT ISGLKPGVDY  60
TITVYAVTYA GEKAATDWSI SINYRTPCPP PPPC                              94

SEQ ID NO: 205          moltype = AA  length = 102
FEATURE                 Location/Qualifiers
REGION                  1..102
                        note = Synthetic: ADX_6077_F02 DG-AG mutant, full-length
                         with C-terminal PmCXn1CXn2 (m=1; n1=5; n2=0)
source                  1..102
                        mol_type = protein
                        organism = synthetic construct
SEQUENCE: 205
VSDVPRDLEV VAATPTSLLI SWSDDYHAHR YYRITYGETG GNSPVQEFTV PGEHVTATIS  60
GLKPGVDYTI TVYAVTYAGE KAATDWSISI NYRTPCPPPP PC                     102

SEQ ID NO: 206          moltype = AA  length = 103
FEATURE                 Location/Qualifiers
REGION                  1..103
                        note = Synthetic: ADX_6077_F02 DG-AG mutant, full-length
                         with N-terminal leader (G), and C-terminal PmCXn1CXn2
                         (m=1; n1=5, n2=0)
source                  1..103
                        mol_type = protein
                        organism = synthetic construct
SEQUENCE: 206
GVSDVPRDLE VVAATPTSLL ISWSDDYHAH RYYRITYGET GGNSPVQEFT VPGEHVTATI  60
SGLKPGVDYT ITVYAVTYAG EKAATDWSIS INYRTPCPPP PPC                    103

SEQ ID NO: 207          moltype = AA  length = 104
FEATURE                 Location/Qualifiers
REGION                  1..104
                        note = Synthetic: ADX_6077_F02 DG-AG mutant, full-length
                         with N-terminal leader (MG), and C-terminal PmCXn1CXn2
                         (m=1; n1=5, n2=0)
source                  1..104
                        mol_type = protein
                        organism = synthetic construct
SEQUENCE: 207
MGVSDVPRDL EVVAATPTSL LISWSDDYHA HRYYRITYGE TGGNSPVQEF TVPGEHVTAT  60
ISGLKPGVDY TITVYAVTYA GEKAATDWSI SINYRTPCPP PPPC                   104

SEQ ID NO: 208          moltype = AA  length = 108
FEATURE                 Location/Qualifiers
REGION                  1..108
```

```
                        note = Synthetic: ADX_6077_F02 AG-AG mutant, full-length
                         with C-terminal PmCXn1CXn2 (m=1; n1=5; n2=0), and His6 tag
source                  1..108
                        mol_type = protein
                        organism = synthetic construct
SEQUENCE: 208
VSDVPRDLEV VAATPTSLLI SWSDDYHAHR YYRITYGETG GNSPVQEFTV PGEHVTATIS  60
GLKPGVDYTI TVYAVTYAGE KAATDWSISI NYRTPCPPPP PCHHHHHH               108

SEQ ID NO: 209          moltype = AA  length = 86
FEATURE                 Location/Qualifiers
REGION                  1..86
                        note = Synthetic: ADX_6077_F02 DG-GG mutant, core
source                  1..86
                        mol_type = protein
                        organism = synthetic construct
SEQUENCE: 209
EVVAATPTSL LISWSDDYHA HRYYRITYGE TGGNSPVQEF TVPGEHVTAT ISGLKPGVDY  60
TITVYAVTYG GEKAATDWSI SINYRT                                       86

SEQ ID NO: 210          moltype = AA  length = 12
FEATURE                 Location/Qualifiers
REGION                  1..12
                        note = Synthetic: ADX_6077_F02 DG-GG mutant, FG loop
source                  1..12
                        mol_type = protein
                        organism = synthetic construct
SEQUENCE: 210
TYGGEKAATD WS                                                      12

SEQ ID NO: 211          moltype = AA  length = 94
FEATURE                 Location/Qualifiers
REGION                  1..94
                        note = Synthetic: ADX_6077_F02 DG-GG mutant, full-length
source                  1..94
                        mol_type = protein
                        organism = synthetic construct
SEQUENCE: 211
VSDVPRDLEV VAATPTSLLI SWSDDYHAHR YYRITYGETG GNSPVQEFTV PGEHVTATIS  60
GLKPGVDYTI TVYAVTYGGE KAATDWSISI NYRT                              94

SEQ ID NO: 212          moltype = AA  length = 95
FEATURE                 Location/Qualifiers
REGION                  1..95
                        note = Synthetic: ADX_6077_F02 DG-GG mutant, full-length
                         with N-terminal leader (G)
source                  1..95
                        mol_type = protein
                        organism = synthetic construct
SEQUENCE: 212
GVSDVPRDLE VVAATPTSLL ISWSDDYHAH RYYRITYGET GGNSPVQEFT VPGEHVTATI  60
SGLKPGVDYT ITVYAVTYGG EKAATDWSIS INYRT                             95

SEQ ID NO: 213          moltype = AA  length = 96
FEATURE                 Location/Qualifiers
REGION                  1..96
                        note = Synthetic: ADX_6077_F02 DG-GG mutant, full-length
                         with N-terminal leader (MG)
source                  1..96
                        mol_type = protein
                        organism = synthetic construct
SEQUENCE: 213
MGVSDVPRDL EVVAATPTSL LISWSDDYHA HRYYRITYGE TGGNSPVQEF TVPGEHVTAT  60
ISGLKPGVDY TITVYAVTYG GEKAATDWSI SINYRT                            96

SEQ ID NO: 214          moltype = AA  length = 96
FEATURE                 Location/Qualifiers
REGION                  1..96
                        note = Synthetic: ADX_6077_F02 DG-GG mutant, core with
                         C-terminal PmXn
VARIANT                 1..96
                        note = In the C-terminal PmXn, up to 5 proline and up to 5
                         Xaa may or may not be present
VARIANT                 92..96
                        note = Xaa can be any naturally occurring amino acid
source                  1..96
                        mol_type = protein
                        organism = synthetic construct
SEQUENCE: 214
```

```
EVVAATPTSL LISWSDDYHA HRYYRITYGE TGGNSPVQEF TVPGEHVTAT ISGLKPGVDY  60
TITVYAVTYG GEKAATDWSI SINYRTPPPP PXXXXX                            96

SEQ ID NO: 215         moltype = AA  length = 104
FEATURE                Location/Qualifiers
REGION                 1..104
                       note = Synthetic: ADX_6077_F02 DG-GG mutant, full-length
                        with C-terminal PmXn
VARIANT                1..104
                       note = In the C-terminal PmXn, up to 5 proline and up to 5
                        Xaa may or may not be present
VARIANT                100..104
                       note = Xaa can be any naturally occurring amino acid
source                 1..104
                       mol_type = protein
                       organism = synthetic construct
SEQUENCE: 215
VSDVPRDLEV VAATPTSLLI SWSDDYHAHR YYRITYGETG GNSPVQEFTV PGEHVTATIS  60
GLKPGVDYTI TVYAVTYGGE KAATDWSISI NYRTPPPPPX XXXX                   104

SEQ ID NO: 216         moltype = AA  length = 105
FEATURE                Location/Qualifiers
REGION                 1..105
                       note = Synthetic: ADX_6077_F02 DG-GG mutant, full-length
                        with N-terminal leader (G) and C-terminal PmXn
VARIANT                1..105
                       note = In the C-terminal PmXn, up to 5 proline and up to 5
                        Xaa may or may not be present
VARIANT                101..105
                       note = Xaa can be any naturally occurring amino acid
source                 1..105
                       mol_type = protein
                       organism = synthetic construct
SEQUENCE: 216
GVSDVPRDLE VVAATPTSLL ISWSDDYHAH RYYRITYGET GGNSPVQEFT VPGEHVTATI  60
SGLKPGVDYT ITVYAVTYGG EKAATDWSIS INYRTPPPPP XXXXX                  105

SEQ ID NO: 217         moltype = AA  length = 106
FEATURE                Location/Qualifiers
REGION                 1..106
                       note = Synthetic: ADX_6077_F02 DG-GG mutant, full-length
                        with N-terminal leader (MG) and C-terminal PmXn
VARIANT                1..106
                       note = In the C-terminal PmXn, up to 5 proline and up to 5
                        Xaa may or may not be present
VARIANT                102..106
                       note = Xaa can be any naturally occurring amino acid
source                 1..106
                       mol_type = protein
                       organism = synthetic construct
SEQUENCE: 217
MGVSDVPRDL EVVAATPTSL LISWSDDYHA HRYYRITYGE TGGNSPVQEF TVPGEHVTAT  60
ISGLKPGVDY TITVYAVTYG GEKAATDWSI SINYRTPPPP PXXXXX                 106

SEQ ID NO: 218         moltype = AA  length = 97
FEATURE                Location/Qualifiers
REGION                 1..97
                       note = Synthetic: ADX_6077_F02 DG-GG mutant, core with
                        C-terminal PmCXn
VARIANT                1..97
                       note = In the C-terminal PmCXn, up to 5 proline and up to 5
                        Xaa may or may not be present
VARIANT                93..97
                       note = Xaa can be any naturally occurring amino acid
source                 1..97
                       mol_type = protein
                       organism = synthetic construct
SEQUENCE: 218
EVVAATPTSL LISWSDDYHA HRYYRITYGE TGGNSPVQEF TVPGEHVTAT ISGLKPGVDY  60
TITVYAVTYG GEKAATDWSI SINYRTPPPP PCXXXXX                           97

SEQ ID NO: 219         moltype = AA  length = 105
FEATURE                Location/Qualifiers
REGION                 1..105
                       note = Synthetic: ADX_6077_F02 DG-GG mutant, full-length
                        with C-terminal PmCXn
VARIANT                1..105
                       note = In the C-terminal PmCXn, up to 5 proline and up to 5
                        Xaa may or may not be present
```

```
VARIANT                101..105
                       note = Xaa can be any naturally occurring amino acid
source                 1..105
                       mol_type = protein
                       organism = synthetic construct
SEQUENCE: 219
VSDVPRDLEV VAATPTSLLI SWSDDYHAHR YYRITYGETG GNSPVQEFTV PGEHVTATIS  60
GLKPGVDYTI TVYAVTYGGE KAATDWSISI NYRTPPPPPC XXXXX                  105

SEQ ID NO: 220         moltype = AA  length = 106
FEATURE                Location/Qualifiers
REGION                 1..106
                       note = Synthetic: ADX_6077_F02 DG-GG mutant, full-length
                        with N-terminal leader (G) and C-terminal PmCXn
VARIANT                1..106
                       note = In the C-terminal PmCXn, up to 5 proline and up to 5
                        Xaa may or may not be present
VARIANT                102..106
                       note = Xaa can be any naturally occurring amino acid
source                 1..106
                       mol_type = protein
                       organism = synthetic construct
SEQUENCE: 220
MVSDVPRDLE VVAATPTSLL ISWSDDYHAH RYYRITYGET GGNSPVQEFT VPGEHVTATI  60
SGLKPGVDYT ITVYAVTYGG EKAATDWSIS INYRTPPPPP CXXXXX                 106

SEQ ID NO: 221         moltype = AA  length = 107
FEATURE                Location/Qualifiers
REGION                 1..107
                       note = Synthetic: ADX_6077_F02 DG-GG mutant, full-length
                        with N-terminal leader (MG) and C-terminal PmCXn
VARIANT                1..107
                       note = In the C-terminal PmCXn, up to 5 proline and up to 5
                        Xaa may or may not be present
VARIANT                103..107
                       note = Xaa can be any naturally occurring amino acid
source                 1..107
                       mol_type = protein
                       organism = synthetic construct
SEQUENCE: 221
MGVSDVPRDL EVVAATPTSL LISWSDDYHA HRYYRITYGE TGGNSPVQEF TVPGEHVTAT  60
ISGLKPGVDY TITVYAVTYG GEKAATDWSI SINYRTPPPP PCXXXXX                107

SEQ ID NO: 222         moltype = AA  length = 88
FEATURE                Location/Qualifiers
REGION                 1..88
                       note = Synthetic: ADX_6077_F02 DG-GG mutant, core with
                        C-terminal PmCXn (m=1; n=0)
source                 1..88
                       mol_type = protein
                       organism = synthetic construct
SEQUENCE: 222
EVVAATPTSL LISWSDDYHA HRYYRITYGE TGGNSPVQEF TVPGEHVTAT ISGLKPGVDY  60
TITVYAVTYG GEKAATDWSI SINYRTPC                                     88

SEQ ID NO: 223         moltype = AA  length = 96
FEATURE                Location/Qualifiers
REGION                 1..96
                       note = Synthetic: ADX_6077_F02 DG-GG mutant, full-length
                        with C-terminal PmCXn(m=1; n=0)
source                 1..96
                       mol_type = protein
                       organism = synthetic construct
SEQUENCE: 223
VSDVPRDLEV VAATPTSLLI SWSDDYHAHR YYRITYGETG GNSPVQEFTV PGEHVTATIS  60
GLKPGVDYTI TVYAVTYGGE KAATDWSISI NYRTPC                            96

SEQ ID NO: 224         moltype = AA  length = 97
FEATURE                Location/Qualifiers
REGION                 1..97
                       note = Synthetic: ADX_6077_F02 DG-GG mutant, full-length
                        with N-terminal leader (G) and C-terminal PmCXn(m=1; n=0)
source                 1..97
                       mol_type = protein
                       organism = synthetic construct
SEQUENCE: 224
GVSDVPRDLE VVAATPTSLL ISWSDDYHAH RYYRITYGET GGNSPVQEFT VPGEHVTATI  60
SGLKPGVDYT ITVYAVTYGG EKAATDWSIS INYRTPC                           97
```

-continued

```
SEQ ID NO: 225          moltype = AA  length = 98
FEATURE                 Location/Qualifiers
REGION                  1..98
                        note = Synthetic: ADX_6077_F02 DG-GG mutant, Full-length
                         with N-terminal leader (MG) and C-terminal PmCXn(m=1; n=0)
source                  1..98
                        mol_type = protein
                        organism = synthetic construct
SEQUENCE: 225
MGVSDVPRDL EVVAATPTSL LISWSDDYHA HRYYRITYGE TGGNSPVQEF TVPGEHVTAT  60
ISGLKPGVDY TITVYAVTYG GEKAATDWSI SINYRTPC                          98

SEQ ID NO: 226          moltype = AA  length = 102
FEATURE                 Location/Qualifiers
REGION                  1..102
                        note = Synthetic: ADX_6077_F02 DG-GG mutant, full-length
                         with C-terminal PmCXn(m=1; n=0) and His6 tag
source                  1..102
                        mol_type = protein
                        organism = synthetic construct
SEQUENCE: 226
VSDVPRDLEV VAATPTSLLI SWSDDYHAHR YYRITYGETG GNSPVQEFTV PGEHVTATIS  60
GLKPGVDYTI TVYAVTYGGE KAATDWSISI NYRTPCHHHH HH                     102

SEQ ID NO: 227          moltype = AA  length = 103
FEATURE                 Location/Qualifiers
REGION                  1..103
                        note = Synthetic: ADX_6077_F02 DG-GG mutant, core with
                         C-terminal PmCXn1CXn2
VARIANT                 1..103
                        note = In the C-terminal PmCXn1CXn2, up to 5 proline and up
                         to 5 Xaa (before and after the last Cys) may or may not be
                         present
VARIANT                 93..97
                        note = Xaa can be any naturally occurring amino acid
VARIANT                 99..103
                        note = Xaa can be any naturally occurring amino acid
source                  1..103
                        mol_type = protein
                        organism = synthetic construct
SEQUENCE: 227
EVVAATPTSL LISWSDDYHA HRYYRITYGE TGGNSPVQEF TVPGEHVTAT ISGLKPGVDY  60
TITVYAVTYG GEKAATDWSI SINYRTPPPP PCXXXXXCXX XXX                    103

SEQ ID NO: 228          moltype = AA  length = 111
FEATURE                 Location/Qualifiers
REGION                  1..111
                        note = Synthetic: ADX_6077_F02 DG-GG mutant, full-length
                         with C-terminal PmCXn1CXn2
VARIANT                 1..111
                        note = In the C-terminal PmCXn1CXn2, up to 5 proline and up
                         to 5 Xaa (before and after the last Cys) may or may not be
                         present
VARIANT                 101..105
                        note = Xaa can be any naturally occurring amino acid
VARIANT                 107..111
                        note = Xaa can be any naturally occurring amino acid
source                  1..111
                        mol_type = protein
                        organism = synthetic construct
SEQUENCE: 228
VSDVPRDLEV VAATPTSLLI SWSDDYHAHR YYRITYGETG GNSPVQEFTV PGEHVTATIS  60
GLKPGVDYTI TVYAVTYGGE KAATDWSISI NYRTPPPPPC XXXXXCXXXX X           111

SEQ ID NO: 229          moltype = AA  length = 112
FEATURE                 Location/Qualifiers
REGION                  1..112
                        note = Synthetic: ADX_6077_F02 DG-GG mutant, full-length
                         with N-terminal leader (G), and C-terminal PmCXn1CXn2
VARIANT                 1..112
                        note = In the C-terminal PmCXn1CXn2, up to 5 proline and up
                         to 5 Xaa (before and after the last Cys) may or may not be
                         present
VARIANT                 102..106
                        note = Xaa can be any naturally occurring amino acid
VARIANT                 108..112
                        note = Xaa can be any naturally occurring amino acid
source                  1..112
                        mol_type = protein
```

```
                        organism = synthetic construct
SEQUENCE: 229
GVSDVPRDLE VVAATPTSLL ISWSDDYHAH RYYRITYGET GGNSPVQEFT VPGEHVTATI  60
SGLKPGVDYT ITVYAVTYGG EKAATDWSIS INYRTPPPPP CXXXXXCXXX XX          112

SEQ ID NO: 230          moltype = AA  length = 113
FEATURE                 Location/Qualifiers
REGION                  1..113
                        note = Synthetic: ADX_6077_F02 DG-GG mutant, full-length
                         with N-terminal leader (MG), and C-terminal PmCXn1CXn2
VARIANT                 1..113
                        note = In the C-terminal PmCXn1CXn2, up to 5 proline and up
                         to 5 Xaa (before and after the last Cys) may or may not be
                         present
VARIANT                 103..107
                        note = Xaa can be any naturally occurring amino acid
VARIANT                 109..113
                        note = Xaa can be any naturally occurring amino acid
source                  1..113
                        mol_type = protein
                        organism = synthetic construct
SEQUENCE: 230
MGVSDVPRDL EVVAATPTSL LISWSDDYHA HRYYRITYGE TGGNSPVQEF TVPGEHVTAT  60
ISGLKPGVDY TITVYAVTYG GEKAATDWSI SINYRTPPPP PCXXXXXCXX XXX         113

SEQ ID NO: 231          moltype = AA  length = 94
FEATURE                 Location/Qualifiers
REGION                  1..94
                        note = Synthetic: ADX_6077_F02 DG-GG mutant, core with
                         C-terminal PmCXn1CXn2 (m=1; n1=5; n2=0)
source                  1..94
                        mol_type = protein
                        organism = synthetic construct
SEQUENCE: 231
EVVAATPTSL LISWSDDYHA HRYYRITYGE TGGNSPVQEF TVPGEHVTAT ISGLKPGVDY  60
TITVYAVTYG GEKAATDWSI SINYRTPCPP PPPC                              94

SEQ ID NO: 232          moltype = AA  length = 102
FEATURE                 Location/Qualifiers
REGION                  1..102
                        note = Synthetic: ADX_6077_F02 DG-GG mutant, full-length
                         with C-terminal PmCXn1CXn2 (m=1; n1=5; n2=0)
source                  1..102
                        mol_type = protein
                        organism = synthetic construct
SEQUENCE: 232
VSDVPRDLEV VAATPTSLLI SWSDDYHAHR YYRITYGETG GNSPVQEFTV PGEHVTATIS  60
GLKPGVDYTI TVYAVTYGGE KAATDWSISI NYRTPCPPPP PC                     102

SEQ ID NO: 233          moltype = AA  length = 103
FEATURE                 Location/Qualifiers
REGION                  1..103
                        note = Synthetic: ADX_6077_F02 DG-GG mutant, full-length
                         with N-terminal leader (G), and C-terminal PmCXn1CXn2
                         (m=1; n1=5, n2=0)
source                  1..103
                        mol_type = protein
                        organism = synthetic construct
SEQUENCE: 233
GVSDVPRDLE VVAATPTSLL ISWSDDYHAH RYYRITYGET GGNSPVQEFT VPGEHVTATI  60
SGLKPGVDYT ITVYAVTYGG EKAATDWSIS INYRTPCPPP PPC                    103

SEQ ID NO: 234          moltype = AA  length = 104
FEATURE                 Location/Qualifiers
REGION                  1..104
                        note = Synthetic: ADX_6077_F02 DG-GG mutant, full-length
                         with N-terminal leader (MG), and C-terminal PmCXn1CXn2
                         (m=1; n1=5, n2=0)
source                  1..104
                        mol_type = protein
                        organism = synthetic construct
SEQUENCE: 234
MGVSDVPRDL EVVAATPTSL LISWSDDYHA HRYYRITYGE TGGNSPVQEF TVPGEHVTAT  60
ISGLKPGVDY TITVYAVTYG GEKAATDWSI SINYRTPCPP PPPC                   104

SEQ ID NO: 235          moltype = AA  length = 108
FEATURE                 Location/Qualifiers
REGION                  1..108
                        note = Synthetic: ADX_6077_F02 DG-GG mutant, full-length
```

```
                         with C-terminal PmCXn1CXn2 (m=1; n1=5; n2=0), and His6 tag
source                  1..108
                        mol_type = protein
                        organism = synthetic construct
SEQUENCE: 235
VSDVPRDLEV VAATPTSLLI SWSDDYHAHR YYRITYGETG GNSPVQEFTV PGEHVTATIS  60
GLKPGVDYTI TVYAVTYGGE KAATDWSISI NYRTPCPPPP PCHHHHHH               108

SEQ ID NO: 236          moltype = AA  length = 86
FEATURE                 Location/Qualifiers
REGION                  1..86
                        note = Synthetic: ADX_6077_F02 DG-DS mutant, core
source                  1..86
                        mol_type = protein
                        organism = synthetic construct
SEQUENCE: 236
EVVAATPTSL LISWSDDYHA HRYYRITYGE TGGNSPVQEF TVPGEHVTAT ISGLKPGVDY  60
TITVYAVTYD SEKAATDWSI SINYRT                                       86

SEQ ID NO: 237          moltype = AA  length = 13
FEATURE                 Location/Qualifiers
REGION                  1..13
                        note = Synthetic: ADX_6077_F02 DG-DS mutant, FG loop
source                  1..13
                        mol_type = protein
                        organism = synthetic construct
SEQUENCE: 237
VTYDSEKAAT DWS                                                     13

SEQ ID NO: 238          moltype = AA  length = 94
FEATURE                 Location/Qualifiers
REGION                  1..94
                        note = Synthetic: ADX_6077_F02 DG-DS mutant, full-length
source                  1..94
                        mol_type = protein
                        organism = synthetic construct
SEQUENCE: 238
VSDVPRDLEV VAATPTSLLI SWSDDYHAHR YYRITYGETG GNSPVQEFTV PGEHVTATIS  60
GLKPGVDYTI TVYAVTYDSE KAATDWSISI NYRT                              94

SEQ ID NO: 239          moltype = AA  length = 95
FEATURE                 Location/Qualifiers
REGION                  1..95
                        note = Synthetic: ADX_6077_F02 DG-DS mutant, full-length
                         with N-terminal leader (G)
source                  1..95
                        mol_type = protein
                        organism = synthetic construct
SEQUENCE: 239
GVSDVPRDLE VVAATPTSLL ISWSDDYHAH RYYRITYGET GGNSPVQEFT VPGEHVTATI  60
SGLKPGVDYT ITVYAVTYDS EKAATDWSIS INYRT                             95

SEQ ID NO: 240          moltype = AA  length = 96
FEATURE                 Location/Qualifiers
REGION                  1..96
                        note = Synthetic: ADX_6077_F02 DG-DS mutant, full-length
                         with N-terminal leader (MG)
source                  1..96
                        mol_type = protein
                        organism = synthetic construct
SEQUENCE: 240
MGVSDVPRDL EVVAATPTSL LISWSDDYHA HRYYRITYGE TGGNSPVQEF TVPGEHVTAT  60
ISGLKPGVDY TITVYAVTYD SEKAATDWSI SINYRT                            96

SEQ ID NO: 241          moltype = AA  length = 96
FEATURE                 Location/Qualifiers
REGION                  1..96
                        note = Synthetic: ADX_6077_F02 DG-DS mutant, core with
                         C-terminal PmXn
VARIANT                 1..96
                        note = In the C-terminal PmXn, up to 5 proline and up to 5
                         Xaa may or may not be present
VARIANT                 92..96
                        note = Xaa can be any naturally occurring amino acid
source                  1..96
                        mol_type = protein
                        organism = synthetic construct
SEQUENCE: 241
EVVAATPTSL LISWSDDYHA HRYYRITYGE TGGNSPVQEF TVPGEHVTAT ISGLKPGVDY  60
```

```
TITVYAVTYD SEKAATDWSI SINYRTPPPP PXXXXX                        96

SEQ ID NO: 242          moltype = AA  length = 104
FEATURE                 Location/Qualifiers
REGION                  1..104
                        note = Synthetic: ADX_6077_F02 DG-DS mutant, full-length
                         with C-terminal PmXn
VARIANT                 1..104
                        note = In the C-terminal PmXn, up to 5 proline and up to 5
                         Xaa may or may not be present
VARIANT                 100..104
                        note = Xaa can be any naturally occurring amino acid
source                  1..104
                        mol_type = protein
                        organism = synthetic construct
SEQUENCE: 242
VSDVPRDLEV VAATPTSLLI SWSDDYHAHR YYRITYGETG GNSPVQEFTV PGEHVTATIS  60
GLKPGVDYTI TVYAVTYDSE KAATDWSISI NYRTPPPPPX XXXX                   104

SEQ ID NO: 243          moltype = AA  length = 105
FEATURE                 Location/Qualifiers
REGION                  1..105
                        note = Synthetic: ADX_6077_F02 DG-DS mutant, full-length
                         with N-terminal leader (G) and C-terminal PmXn
VARIANT                 1..105
                        note = In the C-terminal PmXn, up to 5 proline and up to 5
                         Xaa may or may not be present
VARIANT                 101..105
                        note = Xaa can be any naturally occurring amino acid
source                  1..105
                        mol_type = protein
                        organism = synthetic construct
SEQUENCE: 243
GVSDVPRDLE VVAATPTSLL ISWSDDYHAH RYYRITYGET GGNSPVQEFT VPGEHVTATI  60
SGLKPGVDYT ITVYAVTYDS EKAATDWSIS INYRTPPPPP XXXXX                  105

SEQ ID NO: 244          moltype = AA  length = 106
FEATURE                 Location/Qualifiers
REGION                  1..106
                        note = Synthetic: ADX_6077_F02 DG-DS mutant, full-length
                         with N-terminal leader (MG) and C-terminal PmXn
VARIANT                 1..106
                        note = In the C-terminal PmXn, up to 5 proline and up to 5
                         Xaa may or may not be present
VARIANT                 102..106
                        note = Xaa can be any naturally occurring amino acid
source                  1..106
                        mol_type = protein
                        organism = synthetic construct
SEQUENCE: 244
MGVSDVPRDL EVVAATPTSL LISWSDDYHA HRYYRITYGE TGGNSPVQEF TVPGEHVTAT  60
ISGLKPGVDY TITVYAVTYD SEKAATDWSI SINYRTPPPP PXXXXX                 106

SEQ ID NO: 245          moltype = AA  length = 97
FEATURE                 Location/Qualifiers
REGION                  1..97
                        note = Synthetic: ADX_6077_F02 DG-DS mutant, core with
                         C-terminal PmCXn
VARIANT                 1..97
                        note = In the C-terminal PmCXn, up to 5 proline and up to 5
                         Xaa may or may not be present
VARIANT                 93..97
                        note = Xaa can be any naturally occurring amino acid
source                  1..97
                        mol_type = protein
                        organism = synthetic construct
SEQUENCE: 245
EVVAATPTSL LISWSDDYHA HRYYRITYGE TGGNSPVQEF TVPGEHVTAT ISGLKPGVDY  60
TITVYAVTYD SEKAATDWSI SINYRTPPPP PCXXXXX                           97

SEQ ID NO: 246          moltype = AA  length = 105
FEATURE                 Location/Qualifiers
REGION                  1..105
                        note = Synthetic: ADX_6077_F02 DG-DS mutant, full-length
                         with C-terminal PmCXn
VARIANT                 1..105
                        note = In the C-terminal PmCXn, up to 5 proline and up to 5
                         Xaa may or may not be present
VARIANT                 101..105
```

-continued

```
                        note = Xaa can be any naturally occurring amino acid
source                  1..105
                        mol_type = protein
                        organism = synthetic construct
SEQUENCE: 246
VSDVPRDLEV VAATPTSLLI SWSDDYHAHR YYRITYGETG GNSPVQEFTV PGEHVTATIS  60
GLKPGVDYTI TVYAVTYDSE KAATDWSISI NYRTPPPPPC XXXXX                 105

SEQ ID NO: 247          moltype = AA  length = 106
FEATURE                 Location/Qualifiers
REGION                  1..106
                        note = Synthetic: ADX_6077_F02 DG-DS mutant, full-length
                         with N-terminal leader (G) and C-terminal PmCXn
VARIANT                 1..106
                        note = In the C-terminal PmCXn, up to 5 proline and up to 5
                         Xaa may or may not be present
VARIANT                 102..106
                        note = Xaa can be any naturally occurring amino acid
source                  1..106
                        mol_type = protein
                        organism = synthetic construct
SEQUENCE: 247
GVSDVPRDLE VVAATPTSLL ISWSDDYHAH RYYRITYGET GGNSPVQEFT VPGEHVTATI  60
SGLKPGVDYT ITVYAVTYDS EKAATDWSIS INYRTPPPPP CXXXXX                106

SEQ ID NO: 248          moltype = AA  length = 107
FEATURE                 Location/Qualifiers
REGION                  1..107
                        note = Synthetic: ADX_6077_F02 DG-DS mutant, full-length
                         with N-terminal leader (MG) and C-terminal PmCXn
VARIANT                 1..107
                        note = In the C-terminal PmCXn, up to 5 proline and up to 5
                         Xaa may or may not be present
VARIANT                 103..107
                        note = Xaa can be any naturally occurring amino acid
source                  1..107
                        mol_type = protein
                        organism = synthetic construct
SEQUENCE: 248
MGVSDVPRDL EVVAATPTSL LISWSDDYHA HRYYRITYGE TGGNSPVQEF TVPGEHVTAT  60
ISGLKPGVDY TITVYAVTYD SEKAATDWSI SINYRTPPPP PCXXXXX               107

SEQ ID NO: 249          moltype = AA  length = 88
FEATURE                 Location/Qualifiers
REGION                  1..88
                        note = Synthetic: ADX_6077_F02 DG-DS mutant, core with
                         C-terminal PmCXn (m=1; n=0)
source                  1..88
                        mol_type = protein
                        organism = synthetic construct
SEQUENCE: 249
EVVAATPTSL LISWSDDYHA HRYYRITYGE TGGNSPVQEF TVPGEHVTAT ISGLKPGVDY  60
TITVYAVTYD SEKAATDWSI SINYRTPC                                    88

SEQ ID NO: 250          moltype = AA  length = 96
FEATURE                 Location/Qualifiers
REGION                  1..96
                        note = Synthetic: ADX_6077_F02 DG-DS mutant, full-length
                         with C-terminal PmCXn(m=1; n=0)
source                  1..96
                        mol_type = protein
                        organism = synthetic construct
SEQUENCE: 250
VSDVPRDLEV VAATPTSLLI SWSDDYHAHR YYRITYGETG GNSPVQEFTV PGEHVTATIS  60
GLKPGVDYTI TVYAVTYDSE KAATDWSISI NYRTPC                           96

SEQ ID NO: 251          moltype = AA  length = 97
FEATURE                 Location/Qualifiers
REGION                  1..97
                        note = Synthetic: ADX_6077_F02 DG-DS mutant, full-length
                         w/ N-terminal leader (G) and PmCXn C-terminal modification
                         (m=1; n=0)
source                  1..97
                        mol_type = protein
                        organism = synthetic construct
SEQUENCE: 251
GVSDVPRDLE VVAATPTSLL ISWSDDYHAH RYYRITYGET GGNSPVQEFT VPGEHVTATI  60
SGLKPGVDYT ITVYAVTYDS EKAATDWSIS INYRTPC                          97
```

```
SEQ ID NO: 252          moltype = AA  length = 98
FEATURE                 Location/Qualifiers
REGION                  1..98
                        note = Synthetic: ADX_6077_F02 DG-DS mutant, full-length
                         w/ N-terminal eader (MG) and PmCXn C-terminal modification
                         (m=1; n=0)
source                  1..98
                        mol_type = protein
                        organism = synthetic construct
SEQUENCE: 252
MGVSDVPRDL EVVAATPTSL LISWSDDYHA HRYYRITYGE TGGNSPVQEF TVPGEHVTAT  60
ISGLKPGVDY TITVYAVTYD SEKAATDWSI SINYRTPC                          98

SEQ ID NO: 253          moltype = AA  length = 102
FEATURE                 Location/Qualifiers
REGION                  1..102
                        note = Synthetic: ADX_6077_F02 DG-DS mutant, full-length
                         with C-terminal PmCXn(m=1; n=0) and His6 tag
source                  1..102
                        mol_type = protein
                        organism = synthetic construct
SEQUENCE: 253
VSDVPRDLEV VAATPTSLLI SWSDDYHAHR YYRITYGETG GNSPVQEFTV PGEHVTATIS  60
GLKPGVDYTI TVYAVTYDSE KAATDWSISI NYRTPCHHHH HH                     102

SEQ ID NO: 254          moltype = AA  length = 103
FEATURE                 Location/Qualifiers
REGION                  1..103
                        note = Synthetic: ADX_6077_F02 DG-DS mutant, core with
                         C-terminal PmCXn1CXn2
VARIANT                 1..103
                        note = In the C-terminal PmCXn1CXn2, up to 5 proline and up
                         to 5 Xaa (before and after the last Cys) may or may not be
                         present
VARIANT                 93..97
                        note = Xaa can be any naturally occurring amino acid
VARIANT                 99..103
                        note = Xaa can be any naturally occurring amino acid
source                  1..103
                        mol_type = protein
                        organism = synthetic construct
SEQUENCE: 254
EVVAATPTSL LISWSDDYHA HRYYRITYGE TGGNSPVQEF TVPGEHVTAT ISGLKPGVDY  60
TITVYAVTYD SEKAATDWSI SINYRTPPPP PCXXXXXCXX XXX                    103

SEQ ID NO: 255          moltype = AA  length = 111
FEATURE                 Location/Qualifiers
REGION                  1..111
                        note = Synthetic: ADX_6077_F02 DG-DS mutant, full-length
                         with C-terminal PmCXn1CXn2
VARIANT                 1..111
                        note = In the C-terminal PmCXn1CXn2, up to 5 proline and up
                         to 5 Xaa (before and after the last Cys) may or may not be
                         present
VARIANT                 101..105
                        note = Xaa can be any naturally occurring amino acid
VARIANT                 107..111
                        note = Xaa can be any naturally occurring amino acid
source                  1..111
                        mol_type = protein
                        organism = synthetic construct
SEQUENCE: 255
VSDVPRDLEV VAATPTSLLI SWSDDYHAHR YYRITYGETG GNSPVQEFTV PGEHVTATIS  60
GLKPGVDYTI TVYAVTYDSE KAATDWSISI NYRTPPPPPC XXXXXCXXXX X           111

SEQ ID NO: 256          moltype = AA  length = 112
FEATURE                 Location/Qualifiers
REGION                  1..112
                        note = Synthetic: ADX_6077_F02 DG-DS mutant, full-length
                         with N-terminal leader (G), and C-terminal PmCXn1CXn2
VARIANT                 1..112
                        note = In the C-terminal PmCXn1CXn2, up to 5 proline and up
                         to 5 Xaa (before and after the last Cys) may or may not be
                         present
VARIANT                 102..106
                        note = Xaa can be any naturally occurring amino acid
VARIANT                 108..112
                        note = Xaa can be any naturally occurring amino acid
source                  1..112
```

```
                        mol_type = protein
                        organism = synthetic construct
SEQUENCE: 256
GVSDVPRDLE VVAATPTSLL ISWSDDYHAH RYYRITYGET GGNSPVQEFT VPGEHVTATI  60
SGLKPGVDYT ITVYAVTYDS EKAATDWSIS INYRTPPPPP CXXXXXCXXX XX         112

SEQ ID NO: 257          moltype = AA  length = 113
FEATURE                 Location/Qualifiers
REGION                  1..113
                        note = Synthetic: ADX_6077_F02 DG-DS mutant, full-length
                         with N-terminal leader (MG), and C-terminal PmCXn1CXn2
VARIANT                 1..113
                        note = In the C-terminal PmCXn1CXn2, up to 5 proline and up
                         to 5 Xaa (before and after the last Cys) may or may not be
                         present
VARIANT                 103..107
                        note = Xaa can be any naturally occurring amino acid
VARIANT                 109..113
                        note = Xaa can be any naturally occurring amino acid
source                  1..113
                        mol_type = protein
                        organism = synthetic construct
SEQUENCE: 257
MGVSDVPRDL EVVAATPTSL LISWSDDYHA HRYYRITYGE TGGNSPVQEF TVPGEHVTAT  60
ISGLKPGVDY TITVYAVTYD SEKAATDWSI SINYRTPPPP PCXXXXXCXX XXX        113

SEQ ID NO: 258          moltype = AA  length = 94
FEATURE                 Location/Qualifiers
REGION                  1..94
                        note = Synthetic: ADX_6077_F02 DG-DS mutant, core with
                         C-terminal PmCXn1CXn2 (m=1; n1=5; n2=0)
source                  1..94
                        mol_type = protein
                        organism = synthetic construct
SEQUENCE: 258
EVVAATPTSL LISWSDDYHA HRYYRITYGE TGGNSPVQEF TVPGEHVTAT ISGLKPGVDY  60
TITVYAVTYD SEKAATDWSI SINYRTPCPP PPPC                             94

SEQ ID NO: 259          moltype = AA  length = 102
FEATURE                 Location/Qualifiers
REGION                  1..102
                        note = Synthetic: ADX_6077_F02 DG-DS mutant, full-length
                         with C-terminal PmCXn1CXn2 (m=1; n1=5; n2=0)
source                  1..102
                        mol_type = protein
                        organism = synthetic construct
SEQUENCE: 259
VSDVPRDLEV VAATPTSLLI SWSDDYHAHR YYRITYGETG GNSPVQEFTV PGEHVTATIS  60
GLKPGVDYTI TVYAVTYDSE KAATDWSISI NYRTPCPPPP PC                    102

SEQ ID NO: 260          moltype = AA  length = 103
FEATURE                 Location/Qualifiers
REGION                  1..103
                        note = Synthetic: ADX_6077_F02 DG-DS mutant, full-length
                         with N-terminal leader (G), and C-terminal PmCXn1CXn2
                         (m=1; n1=5, n2=0)
source                  1..103
                        mol_type = protein
                        organism = synthetic construct
SEQUENCE: 260
GVSDVPRDLE VVAATPTSLL ISWSDDYHAH RYYRITYGET GGNSPVQEFT VPGEHVTATI  60
SGLKPGVDYT ITVYAVTYDS EKAATDWSIS INYRTPCPPP PPC                   103

SEQ ID NO: 261          moltype = AA  length = 104
FEATURE                 Location/Qualifiers
REGION                  1..104
                        note = Synthetic: ADX_6077_F02 DG-DS mutant, full-length
                         with N-terminal leader (MG), and C-terminal PmCXn1CXn2
                         (m=1; n1=5, n2=0)
source                  1..104
                        mol_type = protein
                        organism = synthetic construct
SEQUENCE: 261
MGVSDVPRDL EVVAATPTSL LISWSDDYHA HRYYRITYGE TGGNSPVQEF TVPGEHVTAT  60
ISGLKPGVDY TITVYAVTYD SEKAATDWSI SINYRTPCPP PPPC                  104

SEQ ID NO: 262          moltype = AA  length = 108
FEATURE                 Location/Qualifiers
REGION                  1..108
```

```
                         note = Synthetic: ADX_6077_F02 DG-DS mutant, full-length
                          with C-terminal PmCXn1CXn2 (m=1; n1=5; n2=0), and His6 tag
source                   1..108
                         mol_type = protein
                         organism = synthetic construct
SEQUENCE: 262
VSDVPRDLEV VAATPTSLLI SWSDDYHAHR YYRITYGETG GNSPVQEFTV PGEHVTATIS  60
GLKPGVDYTI TVYAVTYDSE KAATDWSISI NYRTPCPPPP PCHHHHHH              108

SEQ ID NO: 263           moltype = AA  length = 86
FEATURE                  Location/Qualifiers
REGION                   1..86
                         note = Synthetic: ADX_6077_F02 DG -DA mutant, core
source                   1..86
                         mol_type = protein
                         organism = synthetic construct
SEQUENCE: 263
EVVAATPTSL LISWSDDYHA HRYYRITYGE TGGNSPVQEF TVPGEHVTAT ISGLKPGVDY  60
TITVYAVTYD AEKAATDWSI SINYRT                                      86

SEQ ID NO: 264           moltype = AA  length = 13
FEATURE                  Location/Qualifiers
REGION                   1..13
                         note = Synthetic: ADX_6077_F02 DG -DA mutant, FG loop
source                   1..13
                         mol_type = protein
                         organism = synthetic construct
SEQUENCE: 264
VTYDAEKAAT DWS                                                    13

SEQ ID NO: 265           moltype = AA  length = 94
FEATURE                  Location/Qualifiers
REGION                   1..94
                         note = Synthetic: ADX_6077_F02 DG -DA mutant, full-length
source                   1..94
                         mol_type = protein
                         organism = synthetic construct
SEQUENCE: 265
VSDVPRDLEV VAATPTSLLI SWSDDYHAHR YYRITYGETG GNSPVQEFTV PGEHVTATIS  60
GLKPGVDYTI TVYAVTYDAE KAATDWSISI NYRT                             94

SEQ ID NO: 266           moltype = AA  length = 95
FEATURE                  Location/Qualifiers
REGION                   1..95
                         note = Synthetic: ADX_6077_F02 DG -DA mutant, full-length
                          with N-terminal leader (G)
source                   1..95
                         mol_type = protein
                         organism = synthetic construct
SEQUENCE: 266
GVSDVPRDLE VVAATPTSLL ISWSDDYHAH RYYRITYGET GGNSPVQEFT VPGEHVTATI  60
SGLKPGVDYT ITVYAVTYDA EKAATDWSIS INYRT                            95

SEQ ID NO: 267           moltype = AA  length = 96
FEATURE                  Location/Qualifiers
REGION                   1..96
                         note = Synthetic: ADX_6077_F02 DG -DA mutant, full-length
                          with N-terminal leader (MG)
source                   1..96
                         mol_type = protein
                         organism = synthetic construct
SEQUENCE: 267
MGVSDVPRDL EVVAATPTSL LISWSDDYHA HRYYRITYGE TGGNSPVQEF TVPGEHVTAT  60
ISGLKPGVDY TITVYAVTYD AEKAATDWSI SINYRT                           96

SEQ ID NO: 268           moltype = AA  length = 96
FEATURE                  Location/Qualifiers
REGION                   1..96
                         note = Synthetic: ADX_6077_F02 DG -DA mutant, core with
                          C-terminal PmXn
VARIANT                  1..96
                         note = In the C-terminal PmXn, up to 5 proline and up to 5
                          Xaa may or may not be present
VARIANT                  92..96
                         note = Xaa can be any naturally occurring amino acid
source                   1..96
                         mol_type = protein
                         organism = synthetic construct
SEQUENCE: 268
```

-continued

```
EVVAATPTSL LISWSDDYHA HRYYRITYGE TGGNSPVQEF TVPGEHVTAT ISGLKPGVDY  60
TITVYAVTYD AEKAATDWSI SINYRTPPPP PXXXXX                            96

SEQ ID NO: 269         moltype = AA  length = 104
FEATURE                Location/Qualifiers
REGION                 1..104
                       note = Synthetic: ADX_6077_F02, DG -DA mutant, full-length
                        with C-terminal PmXn
VARIANT                1..104
                       note = In the C-terminal PmXn, up to 5 proline and up to 5
                        Xaa may or may not be present
VARIANT                100..104
                       note = Xaa can be any naturally occurring amino acid
source                 1..104
                       mol_type = protein
                       organism = synthetic construct
SEQUENCE: 269
VSDVPRDLEV VAATPTSLLI SWSDDYHAHR YYRITYGETG GNSPVQEFTV PGEHVTATIS  60
GLKPGVDYTI TVYAVTYDAE KAATDWSISI NYRTPPPPPX XXXX                   104

SEQ ID NO: 270         moltype = AA  length = 105
FEATURE                Location/Qualifiers
REGION                 1..105
                       note = Synthetic: ADX_6077_F02 DG -DA mutant, full-length
                        with N-terminal leader (G) and C-terminal PmXn
VARIANT                1..105
                       note = In the C-terminal PmXn, up to 5 proline and up to 5
                        Xaa may or may not be present
VARIANT                101..105
                       note = Xaa can be any naturally occurring amino acid
source                 1..105
                       mol_type = protein
                       organism = synthetic construct
SEQUENCE: 270
GVSDVPRDLE VVAATPTSLL ISWSDDYHAH RYYRITYGET GGNSPVQEFT VPGEHVTATI  60
SGLKPGVDYT ITVYAVTYDA EKAATDWSIS INYRTPPPPP XXXXX                  105

SEQ ID NO: 271         moltype = AA  length = 106
FEATURE                Location/Qualifiers
REGION                 1..106
                       note = Synthetic: ADX_6077_F02 DG -DA mutant, full-length
                        with N-terminal leader (MG) and C-terminal PmXn
VARIANT                1..106
                       note = In the C-terminal PmXn, up to 5 proline and up to 5
                        Xaa may or may not be present
VARIANT                102..106
                       note = Xaa can be any naturally occurring amino acid
source                 1..106
                       mol_type = protein
                       organism = synthetic construct
SEQUENCE: 271
MGVSDVPRDL EVVAATPTSL LISWSDDYHA HRYYRITYGE TGGNSPVQEF TVPGEHVTAT  60
ISGLKPGVDY TITVYAVTYD AEKAATDWSI SINYRTPPPP PXXXXX                 106

SEQ ID NO: 272         moltype = AA  length = 97
FEATURE                Location/Qualifiers
REGION                 1..97
                       note = Synthetic: ADX_6077_F02 DG -DA mutant, core with
                        C-terminal PmCXn
VARIANT                1..97
                       note = In the C-terminal PmCXn, up to 5 proline and up to 5
                        Xaa may or may not be present
VARIANT                93..97
                       note = Xaa can be any naturally occurring amino acid
source                 1..97
                       mol_type = protein
                       organism = synthetic construct
SEQUENCE: 272
EVVAATPTSL LISWSDDYHA HRYYRITYGE TGGNSPVQEF TVPGEHVTAT ISGLKPGVDY  60
TITVYAVTYD AEKAATDWSI SINYRTPPPP PCXXXXX                           97

SEQ ID NO: 273         moltype = AA  length = 105
FEATURE                Location/Qualifiers
REGION                 1..105
                       note = Synthetic: ADX_6077_F02 DG -DA mutant, full-length
                        with C-terminal PmCXn
VARIANT                1..105
                       note = In the C-terminal PmCXn, up to 5 proline and up to 5
                        Xaa may or may not be present
```

```
VARIANT                 101..105
                        note = Xaa can be any naturally occurring amino acid
source                  1..105
                        mol_type = protein
                        organism = synthetic construct
SEQUENCE: 273
VSDVPRDLEV VAATPTSLLI SWSDDYHAHR YYRITYGETG GNSPVQEFTV PGEHVTATIS  60
GLKPGVDYTI TVYAVTYDAE KAATDWSISI NYRTPPPPPC XXXXX                  105

SEQ ID NO: 274          moltype = AA  length = 106
FEATURE                 Location/Qualifiers
REGION                  1..106
                        note = Synthetic: ADX_6077_F02 DG -DA mutant, full-length
                         with N-terminal leader (G) and C-terminal PmCXn
VARIANT                 1..106
                        note = In the C-terminal PmCXn, up to 5 proline and up to 5
                         Xaa may or may not be present
VARIANT                 102..106
                        note = Xaa can be any naturally occurring amino acid
source                  1..106
                        mol_type = protein
                        organism = synthetic construct
SEQUENCE: 274
GVSDVPRDLE VVAATPTSLL ISWSDDYHAH RYYRITYGET GGNSPVQEFT VPGEHVTATI  60
SGLKPGVDYT ITVYAVTYDA EKAATDWSIS INYRTPPPPP CXXXXX                 106

SEQ ID NO: 275          moltype = AA  length = 107
FEATURE                 Location/Qualifiers
REGION                  1..107
                        note = Synthetic: ADX_6077_F02 DG -DA mutant, full-length
                         with N-terminal leader (MG) and C-terminal PmCXn
VARIANT                 1..107
                        note = In the C-terminal PmCXn, up to 5 proline and up to 5
                         Xaa may or may not be present
VARIANT                 103..107
                        note = Xaa can be any naturally occurring amino acid
source                  1..107
                        mol_type = protein
                        organism = synthetic construct
SEQUENCE: 275
MGVSDVPRDL EVVAATPTSL LISWSDDYHA HRYYRITYGE TGGNSPVQEF TVPGEHVTAT  60
ISGLKPGVDY TITVYAVTYD AEKAATDWSI SINYRTPPPP PCXXXXX                107

SEQ ID NO: 276          moltype = AA  length = 88
FEATURE                 Location/Qualifiers
REGION                  1..88
                        note = Synthetic: ADX_6077_F02 DG -DA mutant, core with
                         C-terminal PmCXn (m=1; n=0)
source                  1..88
                        mol_type = protein
                        organism = synthetic construct
SEQUENCE: 276
EVVAATPTSL LISWSDDYHA HRYYRITYGE TGGNSPVQEF TVPGEHVTAT ISGLKPGVDY  60
TITVYAVTYD AEKAATDWSI SINYRTPC                                     88

SEQ ID NO: 277          moltype = AA  length = 96
FEATURE                 Location/Qualifiers
REGION                  1..96
                        note = Synthetic: ADX_6077_F02 DG -DA mutant, full-length
                         with C-terminal PmCXn(m=1; n=0)
source                  1..96
                        mol_type = protein
                        organism = synthetic construct
SEQUENCE: 277
VSDVPRDLEV VAATPTSLLI SWSDDYHAHR YYRITYGETG GNSPVQEFTV PGEHVTATIS  60
GLKPGVDYTI TVYAVTYDAE KAATDWSISI NYRTPC                            96

SEQ ID NO: 278          moltype = AA  length = 97
FEATURE                 Location/Qualifiers
REGION                  1..97
                        note = Synthetic: ADX_6077_F02 DG -DA mutant, full-length
                         w/ N-terminal leader and PmCXn C-terminal modification,
                         (m=1; n=0)
source                  1..97
                        mol_type = protein
                        organism = synthetic construct
SEQUENCE: 278
GVSDVPRDLE VVAATPTSLL ISWSDDYHAH RYYRITYGET GGNSPVQEFT VPGEHVTATI  60
SGLKPGVDYT ITVYAVTYDA EKAATDWSIS INYRTPC                           97
```

```
SEQ ID NO: 279          moltype = AA  length = 98
FEATURE                 Location/Qualifiers
REGION                  1..98
                        note = Synthetic: ADX_6077_F02 DG -DA mutant, full-length
                         w/ N-terminal eader (MG) and PmCXn C-terminal modification
                         (m=1; n=0)
source                  1..98
                        mol_type = protein
                        organism = synthetic construct
SEQUENCE: 279
MGVSDVPRDL EVVAATPTSL LISWSDDYHA HRYYRITYGE TGGNSPVQEF TVPGEHVTAT  60
ISGLKPGVDY TITVYAVTYD AEKAATDWSI SINYRTPC                          98

SEQ ID NO: 280          moltype = AA  length = 102
FEATURE                 Location/Qualifiers
REGION                  1..102
                        note = Synthetic: ADX_6077_F02 DG -DA mutant, full-length
                         with C-terminal PmCXn(m=1; n=0) and His6 tag
source                  1..102
                        mol_type = protein
                        organism = synthetic construct
SEQUENCE: 280
VSDVPRDLEV VAATPTSLLI SWSDDYHAHR YYRITYGETG GNSPVQEFTV PGEHVTATIS  60
GLKPGVDYTI TVYAVTYDAE KAATDWSISI NYRTPCHHHH HH                     102

SEQ ID NO: 281          moltype = AA  length = 103
FEATURE                 Location/Qualifiers
REGION                  1..103
                        note = Synthetic: ADX_6077_F02 DG -DA mutant, core with
                         C-terminal PmCXn1CXn2
VARIANT                 1..103
                        note = In the C-terminal PmCXn1CXn2, up to 5 proline and up
                         to 5 Xaa (before and after the last Cys) may or may not be
                         present
VARIANT                 93..97
                        note = Xaa can be any naturally occurring amino acid
VARIANT                 99..103
                        note = Xaa can be any naturally occurring amino acid
source                  1..103
                        mol_type = protein
                        organism = synthetic construct
SEQUENCE: 281
EVVAATPTSL LISWSDDYHA HRYYRITYGE TGGNSPVQEF TVPGEHVTAT ISGLKPGVDY  60
TITVYAVTYD AEKAATDWSI SINYRTPPPP PCXXXXXCXX XXX                    103

SEQ ID NO: 282          moltype = AA  length = 111
FEATURE                 Location/Qualifiers
REGION                  1..111
                        note = Synthetic: ADX_6077_F02 DG -DA mutant, full-length
                         with C-terminal PmCXn1CXn2
VARIANT                 1..111
                        note = In the C-terminal PmCXn1CXn2, up to 5 proline and up
                         to 5 Xaa (before and after the last Cys) may or may not be
                         present
VARIANT                 101..105
                        note = Xaa can be any naturally occurring amino acid
VARIANT                 107..111
                        note = Xaa can be any naturally occurring amino acid
source                  1..111
                        mol_type = protein
                        organism = synthetic construct
SEQUENCE: 282
VSDVPRDLEV VAATPTSLLI SWSDDYHAHR YYRITYGETG GNSPVQEFTV PGEHVTATIS  60
GLKPGVDYTI TVYAVTYDAE KAATDWSISI NYRTPPPPPC XXXXXCXXXX X           111

SEQ ID NO: 283          moltype = AA  length = 112
FEATURE                 Location/Qualifiers
REGION                  1..112
                        note = Synthetic: ADX_6077_F02 DG -DA mutant, full-length
                         with N-terminal leader (G), and C-terminal PmCXn1CXn2
VARIANT                 1..112
                        note = In the C-terminal PmCXn1CXn2, up to 5 proline and up
                         to 5 Xaa (before and after the last Cys) may or may not be
                         present
VARIANT                 102..106
                        note = Xaa can be any naturally occurring amino acid
VARIANT                 108..112
                        note = Xaa can be any naturally occurring amino acid
```

```
source                  1..112
                        mol_type = protein
                        organism = synthetic construct
SEQUENCE: 283
GVSDVPRDLE VVAATPTSLL ISWSDDYHAH RYYRITYGET GGNSPVQEFT VPGEHVTATI  60
SGLKPGVDYT ITVYAVTYDA EKAATDWSIS INYRTPPPPP CXXXXXCXXX XX          112

SEQ ID NO: 284          moltype = AA  length = 113
FEATURE                 Location/Qualifiers
REGION                  1..113
                        note = Synthetic: ADX_6077_F02 DG -DA mutant, full-length
                         with N-terminal leader (MG), and C-terminal PmCXn1CXn2
VARIANT                 1..113
                        note = In the C-terminal PmCXn1CXn2, up to 5 proline and up
                         to 5 Xaa (before and after the last Cys) may or may not be
                         present
VARIANT                 103..107
                        note = Xaa can be any naturally occurring amino acid
VARIANT                 109..113
                        note = Xaa can be any naturally occurring amino acid
source                  1..113
                        mol_type = protein
                        organism = synthetic construct
SEQUENCE: 284
MGVSDVPRDL EVVAATPTSL LISWSDDYHA HRYYRITYGE TGGNSPVQEF TVPGEHVTAT  60
ISGLKPGVDY TITVYAVTYD AEKAATDWSI SINYRTPPPP PCXXXXXCXX XXX         113

SEQ ID NO: 285          moltype = AA  length = 94
FEATURE                 Location/Qualifiers
REGION                  1..94
                        note = Synthetic: ADX_6077_F02 DG -DA mutant, core with
                         C-terminal PmCXn1CXn2 (m=1; n1=5; n2=0)
source                  1..94
                        mol_type = protein
                        organism = synthetic construct
SEQUENCE: 285
EVVAATPTSL LISWSDDYHA HRYYRITYGE TGGNSPVQEF TVPGEHVTAT ISGLKPGVDY  60
TITVYAVTYD AEKAATDWSI SINYRTPCPP PPPC                              94

SEQ ID NO: 286          moltype = AA  length = 102
FEATURE                 Location/Qualifiers
REGION                  1..102
                        note = Synthetic: ADX_6077_F02 DG -DAmutant, full-length
                         with C-terminal PmCXn1CXn2 (m=1; n1=5; n2=0)
source                  1..102
                        mol_type = protein
                        organism = synthetic construct
SEQUENCE: 286
VSDVPRDLEV VAATPTSLLI SWSDDYHAHR YYRITYGETG GNSPVQEFTV PGEHVTATIS  60
GLKPGVDYTI TVYAVTYDAE KAATDWSISI NYRTPCPPPP PC                     102

SEQ ID NO: 287          moltype = AA  length = 103
FEATURE                 Location/Qualifiers
REGION                  1..103
                        note = Synthetic: ADX_6077_F02 DG -DA mutant, full-length
                         with N-terminal leader (G), and C-terminal PmCXn1CXn2
                         (m=1; n1=5, n2=0)
source                  1..103
                        mol_type = protein
                        organism = synthetic construct
SEQUENCE: 287
GVSDVPRDLE VVAATPTSLL ISWSDDYHAH RYYRITYGET GGNSPVQEFT VPGEHVTATI  60
SGLKPGVDYT ITVYAVTYDA EKAATDWSIS INYRTPCPPP PPC                    103

SEQ ID NO: 288          moltype = AA  length = 104
FEATURE                 Location/Qualifiers
REGION                  1..104
                        note = Synthetic: ADX_6077_F02 DG -DA mutant, full-length
                         with N-terminal leader (MG), and C-terminal PmCXn1CXn2
                         (m=1; n1=5, n2=0)
source                  1..104
                        mol_type = protein
                        organism = synthetic construct
SEQUENCE: 288
MGVSDVPRDL EVVAATPTSL LISWSDDYHA HRYYRITYGE TGGNSPVQEF TVPGEHVTAT  60
ISGLKPGVDY TITVYAVTYD AEKAATDWSI SINYRTPCPP PPPC                   104

SEQ ID NO: 289          moltype = AA  length = 108
FEATURE                 Location/Qualifiers
```

```
REGION                  1..108
                        note = Synthetic: ADX_6077_F02 DG -DA mutant, full-length
                         with C-terminal PmCXn1CXn2 (m=1; n1=5; n2=0), and His6 tag
source                  1..108
                        mol_type = protein
                        organism = synthetic construct
SEQUENCE: 289
VSDVPRDLEV VAATPTSLLI SWSDDYHAHR YYRITYGETG GNSPVQEFTV PGEHVTATIS  60
GLKPGVDYTI TVYAVTYDAE KAATDWSISI NYRTPCPPPP PCHHHHHH              108

SEQ ID NO: 290          moltype = AA  length = 86
FEATURE                 Location/Qualifiers
REGION                  1..86
                        note = Synthetic: ADX_6077_F02 DG-DL mutant, core
source                  1..86
                        mol_type = protein
                        organism = synthetic construct
SEQUENCE: 290
EVVAATPTSL LISWSDDYHA HRYYRITYGE TGGNSPVQEF TVPGEHVTAT ISGLKPGVDY  60
TITVYAVTYD LEKAATDWSI SINYRT                                      86

SEQ ID NO: 291          moltype = AA  length = 13
FEATURE                 Location/Qualifiers
REGION                  1..13
                        note = Synthetic: ADX_6077_F02 DG-DL mutant, FG loop
source                  1..13
                        mol_type = protein
                        organism = synthetic construct
SEQUENCE: 291
VTYDLEKAAT DWS                                                    13

SEQ ID NO: 292          moltype = AA  length = 94
FEATURE                 Location/Qualifiers
REGION                  1..94
                        note = Synthetic: ADX_6077_F02 DG-DL mutant, full-length
source                  1..94
                        mol_type = protein
                        organism = synthetic construct
SEQUENCE: 292
VSDVPRDLEV VAATPTSLLI SWSDDYHAHR YYRITYGETG GNSPVQEFTV PGEHVTATIS  60
GLKPGVDYTI TVYAVTYDLE KAATDWSISI NYRT                             94

SEQ ID NO: 293          moltype = AA  length = 95
FEATURE                 Location/Qualifiers
REGION                  1..95
                        note = Synthetic: ADX_6077_F02 DG-DL mutant, full-length
                         with N-terminal leader (G)
source                  1..95
                        mol_type = protein
                        organism = synthetic construct
SEQUENCE: 293
GVSDVPRDLE VVAATPTSLL ISWSDDYHAH RYYRITYGET GGNSPVQEFT VPGEHVTATI  60
SGLKPGVDYT ITVYAVTYDL EKAATDWSIS INYRT                            95

SEQ ID NO: 294          moltype = AA  length = 96
FEATURE                 Location/Qualifiers
REGION                  1..96
                        note = Synthetic: ADX_6077_F02 DG-DL mutant, full-length
                         with N-terminal leader (MG)
source                  1..96
                        mol_type = protein
                        organism = synthetic construct
SEQUENCE: 294
MGVSDVPRDL EVVAATPTSL LISWSDDYHA HRYYRITYGE TGGNSPVQEF TVPGEHVTAT  60
ISGLKPGVDY TITVYAVTYD LEKAATDWSI SINYRT                           96

SEQ ID NO: 295          moltype = AA  length = 96
FEATURE                 Location/Qualifiers
REGION                  1..96
                        note = Synthetic: ADX_6077_F02 DG-DL mutant, core with
                         C-terminal PmXn
VARIANT                 1..96
                        note = In the C-terminal PmXn, up to 5 proline and up to 5
                         Xaa may or may not be present
VARIANT                 92..96
                        note = Xaa can be any naturally occurring amino acid
source                  1..96
                        mol_type = protein
                        organism = synthetic construct
```

```
SEQUENCE: 295
EVVAATPTSL LISWSDDYHA HRYYRITYGE TGGNSPVQEF TVPGEHVTAT ISGLKPGVDY  60
TITVYAVTYD LEKAATDWSI SINYRTPPPP PXXXXX                            96

SEQ ID NO: 296         moltype = AA  length = 104
FEATURE                Location/Qualifiers
REGION                 1..104
                       note = Synthetic: ADX_6077_F02 DG-DL mutant, full-length
                        with C-terminal PmXn
VARIANT                1..104
                       note = In the C-terminal PmXn, up to 5 proline and up to 5
                        Xaa may or may not be present
VARIANT                100..104
                       note = Xaa can be any naturally occurring amino acid
source                 1..104
                       mol_type = protein
                       organism = synthetic construct
SEQUENCE: 296
VSDVPRDLEV VAATPTSLLI SWSDDYHAHR YYRITYGETG GNSPVQEFTV PGEHVTATIS  60
GLKPGVDYTI TVYAVTYDLE KAATDWSISI NYRTPPPPPX XXXX                   104

SEQ ID NO: 297         moltype = AA  length = 105
FEATURE                Location/Qualifiers
REGION                 1..105
                       note = Synthetic: ADX_6077_F02 DG-DL mutant, full-length
                        with N-terminal leader (G) and C-terminal PmXn
VARIANT                1..105
                       note = In the C-terminal PmXn, up to 5 proline and up to 5
                        Xaa may or may not be present
VARIANT                101..105
                       note = Xaa can be any naturally occurring amino acid
source                 1..105
                       mol_type = protein
                       organism = synthetic construct
SEQUENCE: 297
MVSDVPRDLE VVAATPTSLL ISWSDDYHAH RYYRITYGET GGNSPVQEFT VPGEHVTATI  60
SGLKPGVDYT ITVYAVTYDL EKAATDWSIS INYRTPPPPP XXXXX                  105

SEQ ID NO: 298         moltype = AA  length = 106
FEATURE                Location/Qualifiers
REGION                 1..106
                       note = Synthetic: ADX_6077_F02 DG-DL mutant, full-length
                        with N-terminal leader (MG) and C-terminal PmXn
VARIANT                1..106
                       note = In the C-terminal PmXn, up to 5 proline and up to 5
                        Xaa may or may not be present
VARIANT                102..106
                       note = Xaa can be any naturally occurring amino acid
source                 1..106
                       mol_type = protein
                       organism = synthetic construct
SEQUENCE: 298
MGVSDVPRDL EVVAATPTSL LISWSDDYHA HRYYRITYGE TGGNSPVQEF TVPGEHVTAT  60
ISGLKPGVDY TITVYAVTYD LEKAATDWSI SINYRTPPPP PXXXXX                 106

SEQ ID NO: 299         moltype = AA  length = 97
FEATURE                Location/Qualifiers
REGION                 1..97
                       note = Synthetic: ADX_6077_F02 DG-DL mutant, core with
                        C-terminal PmCXn
VARIANT                1..97
                       note = In the C-terminal PmCXn, up to 5 proline and up to 5
                        Xaa may or may not be present
VARIANT                93..97
                       note = Xaa can be any naturally occurring amino acid
source                 1..97
                       mol_type = protein
                       organism = synthetic construct
SEQUENCE: 299
EVVAATPTSL LISWSDDYHA HRYYRITYGE TGGNSPVQEF TVPGEHVTAT ISGLKPGVDY  60
TITVYAVTYD LEKAATDWSI SINYRTPPPP PCXXXXX                           97

SEQ ID NO: 300         moltype = AA  length = 105
FEATURE                Location/Qualifiers
REGION                 1..105
                       note = Synthetic: ADX_6077_F02 DG-DL mutant, full-length
                        with C-terminal PmCXn
VARIANT                1..105
                       note = In the C-terminal PmCXn, up to 5 proline and up to 5
```

```
                         Xaa may or may not be present
VARIANT                 101..105
                        note = Xaa can be any naturally occurring amino acid
source                  1..105
                        mol_type = protein
                        organism = synthetic construct
SEQUENCE: 300
VSDVPRDLEV VAATPTSLLI SWSDDYHAHR YYRITYGETG GNSPVQEFTV PGEHVTATIS  60
GLKPGVDYTI TVYAVTYDLE KAATDWSISI NYRTPPPPPC XXXXX                 105

SEQ ID NO: 301          moltype = AA  length = 106
FEATURE                 Location/Qualifiers
REGION                  1..106
                        note = Synthetic: ADX_6077_F02 DG-DL mutant, full-length
                         with N-terminal leader (G) and C-terminal PmCXn
VARIANT                 1..106
                        note = In the C-terminal PmCXn, up to 5 proline and up to 5
                         Xaa may or may not be present
VARIANT                 102..106
                        note = Xaa can be any naturally occurring amino acid
source                  1..106
                        mol_type = protein
                        organism = synthetic construct
SEQUENCE: 301
MVSDVPRDLE VVAATPTSLL ISWSDDYHAH RYYRITYGET GGNSPVQEFT VPGEHVTATI  60
SGLKPGVDYT ITVYAVTYDL EKAATDWSIS INYRTPPPPP CXXXXX                106

SEQ ID NO: 302          moltype = AA  length = 107
FEATURE                 Location/Qualifiers
REGION                  1..107
                        note = Synthetic: ADX_6077_F02 DG-DL mutant, full-length
                         with N-terminal leader (MG) and C-terminal PmCXn
VARIANT                 1..107
                        note = In the C-terminal PmCXn, up to 5 proline and up to 5
                         Xaa may or may not be present
VARIANT                 103..107
                        note = Xaa can be any naturally occurring amino acid
source                  1..107
                        mol_type = protein
                        organism = synthetic construct
SEQUENCE: 302
MGVSDVPRDL EVVAATPTSL LISWSDDYHA HRYYRITYGE TGGNSPVQEF TVPGEHVTAT  60
ISGLKPGVDY TITVYAVTYD LEKAATDWSI SINYRTPPPP PCXXXXX               107

SEQ ID NO: 303          moltype = AA  length = 88
FEATURE                 Location/Qualifiers
REGION                  1..88
                        note = Synthetic: ADX_6077_F02 DG-DL mutant, core with
                         C-terminal PmCXn (m=1; n=0)
source                  1..88
                        mol_type = protein
                        organism = synthetic construct
SEQUENCE: 303
EVVAATPTSL LISWSDDYHA HRYYRITYGE TGGNSPVQEF TVPGEHVTAT ISGLKPGVDY  60
TITVYAVTYD LEKAATDWSI SINYRTPC                                    88

SEQ ID NO: 304          moltype = AA  length = 96
FEATURE                 Location/Qualifiers
REGION                  1..96
                        note = Synthetic: ADX_6077_F02 DG-DL mutant, full-length
                         with C-terminal PmCXn(m=1; n=0)
source                  1..96
                        mol_type = protein
                        organism = synthetic construct
SEQUENCE: 304
VSDVPRDLEV VAATPTSLLI SWSDDYHAHR YYRITYGETG GNSPVQEFTV PGEHVTATIS  60
GLKPGVDYTI TVYAVTYDLE KAATDWSISI NYRTPC                           96

SEQ ID NO: 305          moltype = AA  length = 97
FEATURE                 Location/Qualifiers
REGION                  1..97
                        note = Synthetic: ADX_6077_F02 DG-DL mutant, full-length
                         w/ N-terminal leader and PmCXn C-terminal modification,
                         (m=1; n=0)
source                  1..97
                        mol_type = protein
                        organism = synthetic construct
SEQUENCE: 305
GVSDVPRDLE VVAATPTSLL ISWSDDYHAH RYYRITYGET GGNSPVQEFT VPGEHVTATI  60
```

-continued

```
SGLKPGVDYT ITVYAVTYDL EKAATDWSIS INYRTPC                          97

SEQ ID NO: 306          moltype = AA  length = 98
FEATURE                 Location/Qualifiers
REGION                  1..98
                        note = Synthetic: ADX_6077_F02 DG-DL mutant, full-length
                         w/ N-terminal eader (MG) and PmCXn C-terminal modification
                         (m=1; n=0)
source                  1..98
                        mol_type = protein
                        organism = synthetic construct
SEQUENCE: 306
MGVSDVPRDL EVVAATPTSL LISWSDDYHA HRYYRITYGE TGGNSPVQEF TVPGEHVTAT  60
ISGLKPGVDY TITVYAVTYD LEKAATDWSI SINYRTPC                         98

SEQ ID NO: 307          moltype = AA  length = 102
FEATURE                 Location/Qualifiers
REGION                  1..102
                        note = Synthetic: ADX_6077_F02 DG-DL mutant, full-length
                         with C-terminal PmCXn(m=1; n=0) and His6 tag
source                  1..102
                        mol_type = protein
                        organism = synthetic construct
SEQUENCE: 307
VSDVPRDLEV VAATPTSLLI SWSDDYHAHR YYRITYGETG GNSPVQEFTV PGEHVTATIS  60
GLKPGVDYTI TVYAVTYDLE KAATDWSISI NYRTPCHHHH HH                    102

SEQ ID NO: 308          moltype = AA  length = 103
FEATURE                 Location/Qualifiers
REGION                  1..103
                        note = Synthetic: ADX_6077_F02 DG-DL mutant, core with
                         C-terminal PmCXn1CXn2
VARIANT                 1..103
                        note = In the C-terminal PmCXn1CXn2, up to 5 proline and up
                         to 5 Xaa (before and after the last Cys) may or may not be
                         present
VARIANT                 93..97
                        note = Xaa can be any naturally occurring amino acid
VARIANT                 99..103
                        note = Xaa can be any naturally occurring amino acid
source                  1..103
                        mol_type = protein
                        organism = synthetic construct
SEQUENCE: 308
EVVAATPTSL LISWSDDYHA HRYYRITYGE TGGNSPVQEF TVPGEHVTAT ISGLKPGVDY  60
TITVYAVTYD LEKAATDWSI SINYRTPPPP PCXXXXXCXX XXX                   103

SEQ ID NO: 309          moltype = AA  length = 111
FEATURE                 Location/Qualifiers
REGION                  1..111
                        note = Synthetic: ADX_6077_F02 DG-DL mutant, full-length
                         with C-terminal PmCXn1CXn2
VARIANT                 1..111
                        note = In the C-terminal PmCXn1CXn2, up to 5 proline and up
                         to 5 Xaa (before and after the last Cys) may or may not be
                         present
VARIANT                 101..105
                        note = Xaa can be any naturally occurring amino acid
VARIANT                 107..111
                        note = Xaa can be any naturally occurring amino acid
source                  1..111
                        mol_type = protein
                        organism = synthetic construct
SEQUENCE: 309
VSDVPRDLEV VAATPTSLLI SWSDDYHAHR YYRITYGETG GNSPVQEFTV PGEHVTATIS  60
GLKPGVDYTI TVYAVTYDLE KAATDWSISI NYRTPPPPPC XXXXXCXXXX X          111

SEQ ID NO: 310          moltype = AA  length = 112
FEATURE                 Location/Qualifiers
REGION                  1..112
                        note = Synthetic: ADX_6077_F02 DG-DL mutant, full-length
                         with N-terminal leader (G), and C-terminal PmCXn1CXn2
VARIANT                 1..112
                        note = In the C-terminal PmCXn1CXn2, up to 5 proline and up
                         to 5 Xaa (before and after the last Cys) may or may not be
                         present
VARIANT                 102..106
                        note = Xaa can be any naturally occurring amino acid
VARIANT                 108..112
```

```
                          note = Xaa can be any naturally occurring amino acid
source                    1..112
                          mol_type = protein
                          organism = synthetic construct
SEQUENCE: 310
GVSDVPRDLE VVAATPTSLL ISWSDDYHAH RYYRITYGET GGNSPVQEFT VPGEHVTATI  60
SGLKPGVDYT ITVYAVTYDL EKAATDWSIS INYRTPPPPP CXXXXXCXXX XX          112

SEQ ID NO: 311            moltype = AA  length = 113
FEATURE                   Location/Qualifiers
REGION                    1..113
                          note = Synthetic: ADX_6077_F02 DG-DL mutant, full-length
                           with N-terminal leader (MG), and C-terminal PmCXn1CXn2
VARIANT                   1..113
                          note = In the C-terminal PmCXn1CXn2, up to 5 proline and up
                           to 5 Xaa (before and after the last Cys) may or may not be
                           present
VARIANT                   103..107
                          note = Xaa can be any naturally occurring amino acid
VARIANT                   109..113
                          note = Xaa can be any naturally occurring amino acid
source                    1..113
                          mol_type = protein
                          organism = synthetic construct
SEQUENCE: 311
MGVSDVPRDL EVVAATPTSL LISWSDDYHA HRYYRITYGE TGGNSPVQEF TVPGEHVTAT  60
ISGLKPGVDY TITVYAVTYD LEKAATDWSI SINYRTPPPP PCXXXXXCXX XXX         113

SEQ ID NO: 312            moltype = AA  length = 94
FEATURE                   Location/Qualifiers
REGION                    1..94
                          note = Synthetic: ADX_6077_F02 DG-DL mutant, core with
                           C-terminal PmCXn1CXn2 (m=1; n1=5; n2=0)
source                    1..94
                          mol_type = protein
                          organism = synthetic construct
SEQUENCE: 312
EVVAATPTSL LISWSDDYHA HRYYRITYGE TGGNSPVQEF TVPGEHVTAT ISGLKPGVDY  60
TITVYAVTYD LEKAATDWSI SINYRTPCPP PPPC                              94

SEQ ID NO: 313            moltype = AA  length = 102
FEATURE                   Location/Qualifiers
REGION                    1..102
                          note = Synthetic: ADX_6077_F02 DG-DL mutant, full-length
                           with C-terminal PmCXn1CXn2 (m=1; n1=5; n2=0)
source                    1..102
                          mol_type = protein
                          organism = synthetic construct
SEQUENCE: 313
VSDVPRDLEV VAATPTSLLI SWSDDYHAHR YYRITYGETG GNSPVQEFTV PGEHVTATIS  60
GLKPGVDYTI TVYAVTYDLE KAATDWSISI NYRTPCPPPP PC                     102

SEQ ID NO: 314            moltype = AA  length = 103
FEATURE                   Location/Qualifiers
REGION                    1..103
                          note = Synthetic: ADX_6077_F02 DG-DL mutant, full-length
                           with N-terminal leader (G), and C-terminal PmCXn1CXn2
                           (m=1; n1=5, n2=0)
source                    1..103
                          mol_type = protein
                          organism = synthetic construct
SEQUENCE: 314
GVSDVPRDLE VVAATPTSLL ISWSDDYHAH RYYRITYGET GGNSPVQEFT VPGEHVTATI  60
SGLKPGVDYT ITVYAVTYDL EKAATDWSIS INYRTPCPPP PPC                    103

SEQ ID NO: 315            moltype = AA  length = 104
FEATURE                   Location/Qualifiers
REGION                    1..104
                          note = Synthetic: ADX_6077_F02 DG-DL mutant, full-length
                           with N-terminal leader (MG), and C-terminal PmCXn1CXn2
                           (m=1; n1=5, n2=0)
source                    1..104
                          mol_type = protein
                          organism = synthetic construct
SEQUENCE: 315
MGVSDVPRDL EVVAATPTSL LISWSDDYHA HRYYRITYGE TGGNSPVQEF TVPGEHVTAT  60
ISGLKPGVDY TITVYAVTYD LEKAATDWSI SINYRTPCPP PPPC                   104

SEQ ID NO: 316            moltype = AA  length = 108
```

-continued

```
FEATURE                Location/Qualifiers
REGION                 1..108
                       note = Synthetic: ADX_6077_F02 DG-DL mutant, full-length
                        with C-terminal PmCXn1CXn2 (m=1; n1=5; n2=0), and His6 tag
source                 1..108
                       mol_type = protein
                       organism = synthetic construct
SEQUENCE: 316
VSDVPRDLEV VAATPTSLLI SWSDDYHAHR YYRITYGETG GNSPVQEFTV PGEHVTATIS  60
GLKPGVDYTI TVYAVTYDLE KAATDWSISI NYRTPCPPPP PCHHHHHH               108

SEQ ID NO: 317         moltype = AA  length = 86
FEATURE                Location/Qualifiers
REGION                 1..86
                       note = Synthetic: ADX_6077_F02 DG-DV mutant, core
source                 1..86
                       mol_type = protein
                       organism = synthetic construct
SEQUENCE: 317
EVVAATPTSL LISWSDDYHA HRYYRITYGE TGGNSPVQEF TVPGEHVTAT ISGLKPGVDY  60
TITVYAVTYD VEKAATDWSI SINYRT                                       86

SEQ ID NO: 318         moltype = AA  length = 13
FEATURE                Location/Qualifiers
REGION                 1..13
                       note = Synthetic: ADX_6077_F02 DG-DV mutant, FG loop
source                 1..13
                       mol_type = protein
                       organism = synthetic construct
SEQUENCE: 318
VTYDVEKAAT DWS                                                     13

SEQ ID NO: 319         moltype = AA  length = 94
FEATURE                Location/Qualifiers
REGION                 1..94
                       note = Synthetic: ADX_6077_F02 DG-DV mutant, full-length
source                 1..94
                       mol_type = protein
                       organism = synthetic construct
SEQUENCE: 319
VSDVPRDLEV VAATPTSLLI SWSDDYHAHR YYRITYGETG GNSPVQEFTV PGEHVTATIS  60
GLKPGVDYTI TVYAVTYDVE KAATDWSISI NYRT                              94

SEQ ID NO: 320         moltype = AA  length = 95
FEATURE                Location/Qualifiers
REGION                 1..95
                       note = Synthetic: ADX_6077_F02 DG-DV mutant, full-length
                        with N-terminal leader (G)
source                 1..95
                       mol_type = protein
                       organism = synthetic construct
SEQUENCE: 320
GVSDVPRDLE VVAATPTSLL ISWSDDYHAH RYYRITYGET GGNSPVQEFT VPGEHVTATI  60
SGLKPGVDYT ITVYAVTYDV EKAATDWSIS INYRT                             95

SEQ ID NO: 321         moltype = AA  length = 96
FEATURE                Location/Qualifiers
REGION                 1..96
                       note = Synthetic: ADX_6077_F02 DG-DV mutant, full-length
                        with N-terminal leader (MG)
source                 1..96
                       mol_type = protein
                       organism = synthetic construct
SEQUENCE: 321
MGVSDVPRDL EVVAATPTSL LISWSDDYHA HRYYRITYGE TGGNSPVQEF TVPGEHVTAT  60
ISGLKPGVDY TITVYAVTYD VEKAATDWSI SINYRT                            96

SEQ ID NO: 322         moltype = AA  length = 96
FEATURE                Location/Qualifiers
REGION                 1..96
                       note = Synthetic: ADX_6077_F02 DG-DV mutant, core with
                        C-terminal PmXn
VARIANT                1..96
                       note = In the C-terminal PmXn, up to 5 proline and up to 5
                        Xaa may or may not be present
VARIANT                92..96
                       note = Xaa can be any naturally occurring amino acid
source                 1..96
                       mol_type = protein
```

```
                         organism = synthetic construct
SEQUENCE: 322
EVVAATPTSL LISWSDDYHA HRYYRITYGE TGGNSPVQEF TVPGEHVTAT ISGLKPGVDY  60
TITVYAVTYD VEKAATDWSI SINYRTPPPP PXXXXX                            96

SEQ ID NO: 323           moltype = AA  length = 104
FEATURE                  Location/Qualifiers
REGION                   1..104
                         note = Synthetic: ADX_6077_F02 DG-DV mutant, full-length
                          with C-terminal PmXn
VARIANT                  1..104
                         note = In the C-terminal PmXn, up to 5 proline and up to 5
                          Xaa may or may not be present
VARIANT                  100..104
                         note = Xaa can be any naturally occurring amino acid
source                   1..104
                         mol_type = protein
                         organism = synthetic construct
SEQUENCE: 323
VSDVPRDLEV VAATPTSLLI SWSDDYHAHR YYRITYGETG GNSPVQEFTV PGEHVTATIS  60
GLKPGVDYTI TVYAVTYDVE KAATDWSISI NYRTPPPPPX XXXX                   104

SEQ ID NO: 324           moltype = AA  length = 105
FEATURE                  Location/Qualifiers
REGION                   1..105
                         note = Synthetic: ADX_6077_F02 DG-DV mutant, full-length
                          with N-terminal leader (G) and C-terminal PmXn
VARIANT                  1..105
                         note = In the C-terminal PmXn, up to 5 proline and up to 5
                          Xaa may or may not be present
VARIANT                  101..105
                         note = Xaa can be any naturally occurring amino acid
source                   1..105
                         mol_type = protein
                         organism = synthetic construct
SEQUENCE: 324
GVSDVPRDLE VVAATPTSLL ISWSDDYHAH RYYRITYGET GGNSPVQEFT VPGEHVTATI  60
SGLKPGVDYT ITVYAVTYDV EKAATDWSIS INYRTPPPPP XXXXX                  105

SEQ ID NO: 325           moltype = AA  length = 106
FEATURE                  Location/Qualifiers
REGION                   1..106
                         note = Synthetic: ADX_6077_F02 DG-DV mutant, full-length
                          with N-terminal leader (MG) and C-terminal PmXn
VARIANT                  1..106
                         note = In the C-terminal PmXn, up to 5 proline and up to 5
                          Xaa may or may not be present
VARIANT                  102..106
                         note = Xaa can be any naturally occurring amino acid
source                   1..106
                         mol_type = protein
                         organism = synthetic construct
SEQUENCE: 325
MGVSDVPRDL EVVAATPTSL LISWSDDYHA HRYYRITYGE TGGNSPVQEF TVPGEHVTAT  60
ISGLKPGVDY TITVYAVTYD VEKAATDWSI SINYRTPPPP PXXXXX                 106

SEQ ID NO: 326           moltype = AA  length = 97
FEATURE                  Location/Qualifiers
REGION                   1..97
                         note = Synthetic: ADX_6077_F02 DG-DV mutant, core with
                          C-terminal PmCXn
VARIANT                  1..97
                         note = In the C-terminal PmCXn, up to 5 proline and up to 5
                          Xaa may or may not be present
VARIANT                  93..97
                         note = Xaa can be any naturally occurring amino acid
source                   1..97
                         mol_type = protein
                         organism = synthetic construct
SEQUENCE: 326
EVVAATPTSL LISWSDDYHA HRYYRITYGE TGGNSPVQEF TVPGEHVTAT ISGLKPGVDY  60
TITVYAVTYD VEKAATDWSI SINYRTPPPP PCXXXXX                           97

SEQ ID NO: 327           moltype = AA  length = 105
FEATURE                  Location/Qualifiers
REGION                   1..105
                         note = Synthetic: ADX_6077_F02 DG-DV mutant, full-length
                          with C-terminal PmCXn
VARIANT                  1..105
```

```
                        note = In the C-terminal PmCXn, up to 5 proline and up to 5
                         Xaa may or may not be present
VARIANT                 101..105
                        note = Xaa can be any naturally occurring amino acid
source                  1..105
                        mol_type = protein
                        organism = synthetic construct
SEQUENCE: 327
VSDVPRDLEV VAATPTSLLI SWSDDYHAHR YYRITYGETG GNSPVQEFTV PGEHVTATIS  60
GLKPGVDYTI TVYAVTYDVE KAATDWSISI NYRTPPPPPC XXXXX                 105

SEQ ID NO: 328          moltype = AA  length = 106
FEATURE                 Location/Qualifiers
REGION                  1..106
                        note = Synthetic: ADX_6077_F02 DG-DV mutant, full-length
                         with N-terminal leader (G) and C-terminal PmCXn
VARIANT                 1..106
                        note = In the C-terminal PmCXn, up to 5 proline and up to 5
                         Xaa may or may not be present
VARIANT                 102..106
                        note = Xaa can be any naturally occurring amino acid
source                  1..106
                        mol_type = protein
                        organism = synthetic construct
SEQUENCE: 328
GVSDVPRDLE VVAATPTSLL ISWSDDYHAH RYYRITYGET GGNSPVQEFT VPGEHVTATI  60
SGLKPGVDYT ITVYAVTYDV EKAATDWSIS INYRTPPPPP CXXXXX                106

SEQ ID NO: 329          moltype = AA  length = 107
FEATURE                 Location/Qualifiers
REGION                  1..107
                        note = Synthetic: ADX_6077_F02 DG-DV mutant, full-length
                         with N-terminal leader (MG) and C-terminal PmCXn
VARIANT                 1..107
                        note = In the C-terminal PmCXn, up to 5 proline and up to 5
                         Xaa may or may not be present
VARIANT                 103..107
                        note = Xaa can be any naturally occurring amino acid
source                  1..107
                        mol_type = protein
                        organism = synthetic construct
SEQUENCE: 329
MGVSDVPRDL EVVAATPTSL LISWSDDYHA HRYYRITYGE TGGNSPVQEF TVPGEHVTAT  60
ISGLKPGVDY TITVYAVTYD VEKAATDWSI SINYRTPPPP PCXXXXX               107

SEQ ID NO: 330          moltype = AA  length = 88
FEATURE                 Location/Qualifiers
REGION                  1..88
                        note = Synthetic: ADX_6077_F02 DG-DV mutant, core with
                         C-terminal PmCXn (m=1; n=0)
source                  1..88
                        mol_type = protein
                        organism = synthetic construct
SEQUENCE: 330
EVVAATPTSL LISWSDDYHA HRYYRITYGE TGGNSPVQEF TVPGEHVTAT ISGLKPGVDY  60
TITVYAVTYD VEKAATDWSI SINYRTPC                                    88

SEQ ID NO: 331          moltype = AA  length = 96
FEATURE                 Location/Qualifiers
REGION                  1..96
                        note = Synthetic: ADX_6077_F02 DG-DV mutant, full-length
                         with C-terminal PmCXn(m=1; n=0)
source                  1..96
                        mol_type = protein
                        organism = synthetic construct
SEQUENCE: 331
VSDVPRDLEV VAATPTSLLI SWSDDYHAHR YYRITYGETG GNSPVQEFTV PGEHVTATIS  60
GLKPGVDYTI TVYAVTYDVE KAATDWSISI NYRTPC                           96

SEQ ID NO: 332          moltype = AA  length = 97
FEATURE                 Location/Qualifiers
REGION                  1..97
                        note = Synthetic: ADX_6077_F02 DG-DV mutant, full-length
                         w/ N-terminal leader (G) and PmCXn C-terminal modification
                         (m=1; n=0)
source                  1..97
                        mol_type = protein
                        organism = synthetic construct
SEQUENCE: 332
```

-continued

```
GVSDVPRDLE VVAATPTSLL ISWSDDYHAH RYYRITYGET GGNSPVQEFT VPGEHVTATI  60
SGLKPGVDYT ITVYAVTYDV EKAATDWSIS INYRTPC                           97

SEQ ID NO: 333          moltype = AA  length = 98
FEATURE                 Location/Qualifiers
REGION                  1..98
                        note = Synthetic: ADX_6077_F02 DG-DV mutant, full-length
                         w/ N-terminal eader (MG) and PmCXn C-terminal modification
                         (m=1; n=0)
source                  1..98
                        mol_type = protein
                        organism = synthetic construct
SEQUENCE: 333
MGVSDVPRDL EVVAATPTSL LISWSDDYHA HRYYRITYGE TGGNSPVQEF TVPGEHVTAT  60
ISGLKPGVDY TITVYAVTYD VEKAATDWSI SINYRTPC                          98

SEQ ID NO: 334          moltype = AA  length = 102
FEATURE                 Location/Qualifiers
REGION                  1..102
                        note = Synthetic: ADX_6077_F02 DG-DV mutant, full-length
                         with C-terminal PmCXn(m=1; n=0) and His6 tag
source                  1..102
                        mol_type = protein
                        organism = synthetic construct
SEQUENCE: 334
VSDVPRDLEV VAATPTSLLI SWSDDYHAHR YYRITYGETG GNSPVQEFTV PGEHVTATIS  60
GLKPGVDYTI TVYAVTYDVE KAATDWSISI NYRTPCHHHH HH                     102

SEQ ID NO: 335          moltype = AA  length = 103
FEATURE                 Location/Qualifiers
REGION                  1..103
                        note = Synthetic: ADX_6077_F02 DG-DV mutant, core with
                         C-terminal PmCXn1CXn2
VARIANT                 1..103
                        note = In the C-terminal PmCXn1CXn2, up to 5 proline and up
                         to 5 Xaa (before and after the last Cys) may or may not be
                         present
VARIANT                 93..97
                        note = Xaa can be any naturally occurring amino acid
VARIANT                 99..103
                        note = Xaa can be any naturally occurring amino acid
source                  1..103
                        mol_type = protein
                        organism = synthetic construct
SEQUENCE: 335
EVVAATPTSL LISWSDDYHA HRYYRITYGE TGGNSPVQEF TVPGEHVTAT ISGLKPGVDY  60
TITVYAVTYD VEKAATDWSI SINYRTPPPP PCXXXXXCXX XXX                    103

SEQ ID NO: 336          moltype = AA  length = 111
FEATURE                 Location/Qualifiers
REGION                  1..111
                        note = Synthetic: ADX_6077_F02 DG-DV mutant, full-length
                         with C-terminal PmCXn1CXn2
VARIANT                 1..111
                        note = In the C-terminal PmCXn1CXn2, up to 5 proline and up
                         to 5 Xaa (before and after the last Cys) may or may not be
                         present
VARIANT                 101..105
                        note = Xaa can be any naturally occurring amino acid
VARIANT                 107..111
                        note = Xaa can be any naturally occurring amino acid
source                  1..111
                        mol_type = protein
                        organism = synthetic construct
SEQUENCE: 336
VSDVPRDLEV VAATPTSLLI SWSDDYHAHR YYRITYGETG GNSPVQEFTV PGEHVTATIS  60
GLKPGVDYTI TVYAVTYDVE KAATDWSISI NYRTPPPPPC XXXXXCXXXX X           111

SEQ ID NO: 337          moltype = AA  length = 112
FEATURE                 Location/Qualifiers
REGION                  1..112
                        note = Synthetic: ADX_6077_F02 DG-DV mutant, full-length
                         with N-terminal leader (G), and C-terminal PmCXn1CXn2
VARIANT                 1..112
                        note = In the C-terminal PmCXn1CXn2, up to 5 proline and up
                         to 5 Xaa (before and after the last Cys) may or may not be
                         present
VARIANT                 102..106
                        note = Xaa can be any naturally occurring amino acid
```

```
VARIANT                 108..112
                        note = Xaa can be any naturally occurring amino acid
source                  1..112
                        mol_type = protein
                        organism = synthetic construct
SEQUENCE: 337
GVSDVPRDLE VVAATPTSLL ISWSDDYHAH RYYRITYGET GGNSPVQEFT VPGEHVTATI  60
SGLKPGVDYT ITVYAVTYDV EKAATDWSIS INYRTPPPPP CXXXXXCXXX XX         112

SEQ ID NO: 338          moltype = AA  length = 113
FEATURE                 Location/Qualifiers
REGION                  1..113
                        note = Synthetic: ADX_6077_F02 DG-DV mutant, full-length
                         with N-terminal leader (MG), and C-terminal PmCXn1CXn2
VARIANT                 1..113
                        note = In the C-terminal PmCXn1CXn2, up to 5 proline and up
                         to 5 Xaa (before and after the last Cys) may or may not be
                         present
VARIANT                 103..107
                        note = Xaa can be any naturally occurring amino acid
VARIANT                 109..113
                        note = Xaa can be any naturally occurring amino acid
source                  1..113
                        mol_type = protein
                        organism = synthetic construct
SEQUENCE: 338
MGVSDVPRDL EVVAATPTSL LISWSDDYHA HRYYRITYGE TGGNSPVQEF TVPGEHVTAT  60
ISGLKPGVDY TITVYAVTYD VEKAATDWSI SINYRTPPPP PCXXXXXCXX XXX        113

SEQ ID NO: 339          moltype = AA  length = 94
FEATURE                 Location/Qualifiers
REGION                  1..94
                        note = Synthetic: ADX_6077_F02 DG-DV mutant, core with
                         C-terminal PmCXn1CXn2 (m=1; n1=5; n2=0)
source                  1..94
                        mol_type = protein
                        organism = synthetic construct
SEQUENCE: 339
EVVAATPTSL LISWSDDYHA HRYYRITYGE TGGNSPVQEF TVPGEHVTAT ISGLKPGVDY  60
TITVYAVTYD VEKAATDWSI SINYRTPCPP PPPC                             94

SEQ ID NO: 340          moltype = AA  length = 102
FEATURE                 Location/Qualifiers
REGION                  1..102
                        note = Synthetic: ADX_6077_F02 DG-DV mutant, full-length
                         with C-terminal PmCXn1CXn2 (m=1; n1=5; n2=0)
source                  1..102
                        mol_type = protein
                        organism = synthetic construct
SEQUENCE: 340
VSDVPRDLEV VAATPTSLLI SWSDDYHAHR YYRITYGETG GNSPVQEFTV PGEHVTATIS  60
GLKPGVDYTI TVYAVTYDVE KAATDWSISI NYRTPCPPPP PC                    102

SEQ ID NO: 341          moltype = AA  length = 103
FEATURE                 Location/Qualifiers
REGION                  1..103
                        note = Synthetic: ADX_6077_F02 DG-DV mutant, full-length
                         with N-terminal leader (G), and C-terminal PmCXn1CXn2
                         (m=1; n1=5, n2=0)
source                  1..103
                        mol_type = protein
                        organism = synthetic construct
SEQUENCE: 341
GVSDVPRDLE VVAATPTSLL ISWSDDYHAH RYYRITYGET GGNSPVQEFT VPGEHVTATI  60
SGLKPGVDYT ITVYAVTYDV EKAATDWSIS INYRTPCPPP PPC                   103

SEQ ID NO: 342          moltype = AA  length = 104
FEATURE                 Location/Qualifiers
REGION                  1..104
                        note = Synthetic: ADX_6077_F02 DG-DV mutant, full-length
                         with N-terminal leader (MG), and C-terminal PmCXn1CXn2
                         (m=1; n1=5, n2=0)
source                  1..104
                        mol_type = protein
                        organism = synthetic construct
SEQUENCE: 342
MGVSDVPRDL EVVAATPTSL LISWSDDYHA HRYYRITYGE TGGNSPVQEF TVPGEHVTAT  60
ISGLKPGVDY TITVYAVTYD VEKAATDWSI SINYRTPCPP PPPC                  104
```

```
SEQ ID NO: 343          moltype = AA  length = 108
FEATURE                 Location/Qualifiers
REGION                  1..108
                        note = Synthetic: ADX_6077_F02 DG-DV mutant, full-length
                         with C-terminal PmCXn1CXn2 (m=1; n1=5; n2=0), and His6 tag
source                  1..108
                        mol_type = protein
                        organism = synthetic construct
SEQUENCE: 343
VSDVPRDLEV VAATPTSLLI SWSDDYHAHR YYRITYGETG GNSPVQEFTV PGEHVTATIS  60
GLKPGVDYTI TVYAVTYDVE KAATDWSISI NYRTPCPPPP PCHHHHHH               108

SEQ ID NO: 344          moltype = AA  length = 580
FEATURE                 Location/Qualifiers
REGION                  1..580
                        note = Synthetic: Human GPC3
source                  1..580
                        mol_type = protein
                        organism = synthetic construct
SEQUENCE: 344
MAGTVRTACL VVAMLLSLDF PGQAQPPPPP PDATCHQVRS FFQRLQPGLK WVPETPVPGS  60
DLQVCLPKGP TCCSRKMEEK YQLTARLNME QLLQSASMEL KFLIIQNAAV FQEAFEIVVR  120
HAKNYTNAMF KNNYPSLTPQ AFEFVGEFFT DVSLYILGSD INVDDMVNEL FDSLFPVIYT  180
QLMNPGLPDS ALDINECLRG ARRDLKVFGN FPKLIMTQVS KSLQVTRIFL QALNLGIEVI  240
NTTDHLKFSK DCGRMLTRMW YCSYCQGLMM VKPCGGYCNV VMQGCMAGVV EIDKYWREYI  300
LSLEELVNGM YRIYDMENVL LGLFSTIHDS IQYVQKNAGK LTTTIGKLCA HSQQRQYRSA  360
YYPEDLFIDK KVLKVAHVEH EETLSSRRRE LIQKLKSFIS FYSALPGYIC SHSPVAENDT  420
LCWNGQELVE RYSQKAARNG MKNQFNLHEL KMKGPEPVVS QIIDKLKHIN QLLRTMSMPK  480
GRVLDKNLDE EGFESGDCGD DEDECIGGSG DGMIKVKNQL RFLAELAYDL DVDDAPGNSQ  540
QATPKDNEIS TFHNLGNVHS PLKLLTSMAI SVVCFFFLVH                        580

SEQ ID NO: 345          moltype = AA  length = 6
FEATURE                 Location/Qualifiers
REGION                  1..6
                        note = Synthetic: Human GPC3 Adnectin binding region 1
source                  1..6
                        mol_type = protein
                        organism = synthetic construct
SEQUENCE: 345
HQVSFF                                                             6

SEQ ID NO: 346          moltype = AA  length = 9
FEATURE                 Location/Qualifiers
REGION                  1..9
                        note = Synthetic: Human CPC3 Adnectin binding region 2
source                  1..9
                        mol_type = protein
                        organism = synthetic construct
SEQUENCE: 346
EQLLQSASM                                                          9

SEQ ID NO: 347          moltype = AA  length = 87
FEATURE                 Location/Qualifiers
REGION                  1..87
                        note = Synthetic: ADX_6093_A01 core, (non-binding control)
source                  1..87
                        mol_type = protein
                        organism = synthetic construct
SEQUENCE: 347
SEVVAATPTS LLISWDAPAV TVRYYRITYG ETGGNSPVQE FTVPGSKSTA TISGLKPGVD  60
YTITVYAVTG RGESPASSKP ISINYRT                                      87

SEQ ID NO: 348          moltype = AA  length = 104
FEATURE                 Location/Qualifiers
REGION                  1..104
                        note = Synthetic: ADX_6093_A01 full-length w/N-leader,
                         PmCXn C-terminal modification, (m=1; n=0), and His6 tag
source                  1..104
                        mol_type = protein
                        organism = synthetic construct
SEQUENCE: 348
MGVSDVPRDL EVVAATPTSL LISWDAPAVT VRYYRITYGE TGGNSPVQEF TVPGSKSTAT  60
ISGLKPGVDY TITVYAVTGR GESPASSKPI SINYRTPCHH HHHH                   104

SEQ ID NO: 349          moltype = AA  length = 97
FEATURE                 Location/Qualifiers
REGION                  1..97
                        note = Synthetic: ADX_6093_A01 full-length w/N-leader,
                         PmCXn C-terminal modification, (m=1; n=0)
```

-continued

```
source                1..97
                      mol_type = protein
                      organism = synthetic construct
SEQUENCE: 349
GVSDVPRDLE VVAATPTSLL ISWDAPAVTV RYYRITYGET GGNSPVQEFT VPGSKSTATI  60
SGLKPGVDYT ITVYAVTGRG ESPASSKPIS INYRTPC                           97

SEQ ID NO: 350        moltype = AA  length = 110
FEATURE               Location/Qualifiers
REGION                1..110
                      note = Synthetic: ADX_6093_A01 full-length w/N-leader,
                       PmCXn C-terminal modification, (m=1; n=7), and His6 tag
source                1..110
                      mol_type = protein
                      organism = synthetic construct
SEQUENCE: 350
MGVSDVPRDL EVVAATPTSL LISWDAPAVT VRYYRITYGE TGGNSPVQEF TVPGSKSTAT  60
ISGLKPGVDY TITVYAVTGR GESPASSKPI SINYRTPCPP PPPCHHHHHH             110

SEQ ID NO: 351        moltype = AA  length = 9
FEATURE               Location/Qualifiers
REGION                1..9
                      note = Synthetic: N-terminal leader
source                1..9
                      mol_type = protein
                      organism = synthetic construct
SEQUENCE: 351
MGVSDVPRD                                                          9

SEQ ID NO: 352        moltype = AA  length = 8
FEATURE               Location/Qualifiers
REGION                1..8
                      note = Synthetic: N-terminal leader
source                1..8
                      mol_type = protein
                      organism = synthetic construct
SEQUENCE: 352
GVSDVPRD                                                           8

SEQ ID NO: 353        moltype = AA  length = 11
FEATURE               Location/Qualifiers
REGION                1..11
                      note = Synthetic: N-terminal leader
VARIANT               1..5
                      note = Any one or all Xaa can either be present or absent;
                       if present, Xaa can be any naturally occurring amino acid
source                1..11
                      mol_type = protein
                      organism = synthetic construct
SEQUENCE: 353
XXXXXSDVPR D                                                       11

SEQ ID NO: 354        moltype = AA  length = 10
FEATURE               Location/Qualifiers
REGION                1..10
                      note = Synthetic: N-terminal leader
VARIANT               1..5
                      note = Any one or all Xaa can either be present or absent;
                       if present, Xaa can be any naturally occurring amino acid
source                1..10
                      mol_type = protein
                      organism = synthetic construct
SEQUENCE: 354
XXXXXDVPRD                                                         10

SEQ ID NO: 355        moltype = AA  length = 9
FEATURE               Location/Qualifiers
REGION                1..9
                      note = Synthetic: N-terminal leader
VARIANT               1..5
                      note = Any one or all Xaa can either be present or absent;
                       if present, Xaa can be any naturally occurring amino acid
source                1..9
                      mol_type = protein
                      organism = synthetic construct
SEQUENCE: 355
XXXXXVPRD                                                          9

SEQ ID NO: 356        moltype =   length =
```

```
SEQUENCE: 356
000

SEQ ID NO: 357          moltype =   length =
SEQUENCE: 357
000

SEQ ID NO: 358          moltype =   length =
SEQUENCE: 358
000

SEQ ID NO: 359          moltype = AA  length = 6
FEATURE                 Location/Qualifiers
REGION                  1..6
                        note = Synthetic: N-terminal leader
source                  1..6
                        mol_type = protein
                        organism = synthetic construct
SEQUENCE: 359
MASTSG                                                            6

SEQ ID NO: 360          moltype = AA  length = 4
FEATURE                 Location/Qualifiers
REGION                  1..4
                        note = Synthetic: C-terminal tail
source                  1..4
                        mol_type = protein
                        organism = synthetic construct
SEQUENCE: 360
EIEK                                                              4

SEQ ID NO: 361          moltype = AA  length = 5
FEATURE                 Location/Qualifiers
REGION                  1..5
                        note = Synthetic: C-terminal tail
source                  1..5
                        mol_type = protein
                        organism = synthetic construct
SEQUENCE: 361
EGSGC                                                             5

SEQ ID NO: 362          moltype = AA  length = 7
FEATURE                 Location/Qualifiers
REGION                  1..7
                        note = Synthetic: C-terminal tail
source                  1..7
                        mol_type = protein
                        organism = synthetic construct
SEQUENCE: 362
EIEKPCQ                                                           7

SEQ ID NO: 363          moltype = AA  length = 7
FEATURE                 Location/Qualifiers
REGION                  1..7
                        note = Synthetic: C-terminal tail
source                  1..7
                        mol_type = protein
                        organism = synthetic construct
SEQUENCE: 363
EIEKPSQ                                                           7

SEQ ID NO: 364          moltype = AA  length = 5
FEATURE                 Location/Qualifiers
REGION                  1..5
                        note = Synthetic: C-terminal tail
source                  1..5
                        mol_type = protein
                        organism = synthetic construct
SEQUENCE: 364
EIEKP                                                             5

SEQ ID NO: 365          moltype = AA  length = 6
FEATURE                 Location/Qualifiers
REGION                  1..6
                        note = Synthetic: C-terminal tail
source                  1..6
                        mol_type = protein
                        organism = synthetic construct
SEQUENCE: 365
```

```
EIEKPS                                                         6

SEQ ID NO: 366          moltype = AA  length = 6
FEATURE                 Location/Qualifiers
REGION                  1..6
                        note = Synthetic: C-terminal tail
source                  1..6
                        mol_type = protein
                        organism = synthetic construct
SEQUENCE: 366
EIEKPC                                                         6

SEQ ID NO: 367          moltype = AA  length = 4
FEATURE                 Location/Qualifiers
REGION                  1..4
                        note = Synthetic: C-terminal tail
source                  1..4
                        mol_type = protein
                        organism = synthetic construct
SEQUENCE: 367
EIDK                                                           4

SEQ ID NO: 368          moltype = AA  length = 7
FEATURE                 Location/Qualifiers
REGION                  1..7
                        note = Synthetic: C-terminal tail
source                  1..7
                        mol_type = protein
                        organism = synthetic construct
SEQUENCE: 368
EIDKPCQ                                                        7

SEQ ID NO: 369          moltype = AA  length = 7
FEATURE                 Location/Qualifiers
REGION                  1..7
                        note = Synthetic: C-terminal tail
source                  1..7
                        mol_type = protein
                        organism = synthetic construct
SEQUENCE: 369
EIDKPSQ                                                        7

SEQ ID NO: 370          moltype = AA  length = 6
FEATURE                 Location/Qualifiers
REGION                  1..6
                        note = Synthetic: 6X His tail
source                  1..6
                        mol_type = protein
                        organism = synthetic construct
SEQUENCE: 370
HHHHHH                                                         6

SEQ ID NO: 371          moltype = AA  length = 7
FEATURE                 Location/Qualifiers
REGION                  1..7
                        note = Synthetic: C-terminal tail
source                  1..7
                        mol_type = protein
                        organism = synthetic construct
SEQUENCE: 371
EIEPKSS                                                        7

SEQ ID NO: 372          moltype = AA  length = 6
FEATURE                 Location/Qualifiers
REGION                  1..6
                        note = Synthetic: C-terminal tail
source                  1..6
                        mol_type = protein
                        organism = synthetic construct
SEQUENCE: 372
EIDKPC                                                         6

SEQ ID NO: 373          moltype = AA  length = 5
FEATURE                 Location/Qualifiers
REGION                  1..5
                        note = Synthetic: C-terminal tail
source                  1..5
                        mol_type = protein
                        organism = synthetic construct
```

-continued

```
SEQUENCE: 373
EIDKP                                                       5

SEQ ID NO: 374        moltype = AA  length = 6
FEATURE               Location/Qualifiers
REGION                1..6
                      note = Synthetic: C-terminal tail
source                1..6
                      mol_type = protein
                      organism = synthetic construct
SEQUENCE: 374
EIDKPS                                                      6

SEQ ID NO: 375        moltype = AA  length = 9
FEATURE               Location/Qualifiers
REGION                1..9
                      note = Synthetic: C-terminal tail
source                1..9
                      mol_type = protein
                      organism = synthetic construct
SEQUENCE: 375
EIDKPSQLE                                                   9

SEQ ID NO: 376        moltype = AA  length = 12
FEATURE               Location/Qualifiers
REGION                1..12
                      note = Synthetic: C-terminal tail
source                1..12
                      mol_type = protein
                      organism = synthetic construct
SEQUENCE: 376
EIEDEDEDED ED                                               12

SEQ ID NO: 377        moltype = AA  length = 5
FEATURE               Location/Qualifiers
REGION                1..5
                      note = Synthetic: C-terminal tail
source                1..5
                      mol_type = protein
                      organism = synthetic construct
SEQUENCE: 377
EGSGS                                                       5

SEQ ID NO: 378        moltype = AA  length = 9
FEATURE               Location/Qualifiers
REGION                1..9
                      note = Synthetic: C-terminal tail
source                1..9
                      mol_type = protein
                      organism = synthetic construct
SEQUENCE: 378
EIDKPCQLE                                                   9

SEQ ID NO: 379        moltype = AA  length = 13
FEATURE               Location/Qualifiers
REGION                1..13
                      note = Synthetic: C-terminal tail
source                1..13
                      mol_type = protein
                      organism = synthetic construct
SEQUENCE: 379
EIDKPSQHHH HHH                                              13

SEQ ID NO: 380        moltype = AA  length = 10
FEATURE               Location/Qualifiers
REGION                1..10
                      note = Synthetic: C-terminal tail
source                1..10
                      mol_type = protein
                      organism = synthetic construct
SEQUENCE: 380
GSGCHHHHHH                                                  10

SEQ ID NO: 381        moltype = AA  length = 11
FEATURE               Location/Qualifiers
REGION                1..11
                      note = Synthetic: C-terminal tail
source                1..11
                      mol_type = protein
```

-continued

```
                        organism = synthetic construct
SEQUENCE: 381
EGSGCHHHHH H                                                    11

SEQ ID NO: 382          moltype = AA  length = 4
FEATURE                 Location/Qualifiers
REGION                  1..4
                        note = Synthetic: C-terminal tail
source                  1..4
                        mol_type = protein
                        organism = synthetic construct
SEQUENCE: 382
PIDK                                                            4

SEQ ID NO: 383          moltype = AA  length = 4
FEATURE                 Location/Qualifiers
REGION                  1..4
                        note = Synthetic: C-terminal tail
source                  1..4
                        mol_type = protein
                        organism = synthetic construct
SEQUENCE: 383
PIEK                                                            4

SEQ ID NO: 384          moltype = AA  length = 5
FEATURE                 Location/Qualifiers
REGION                  1..5
                        note = Synthetic: C-terminal tail
source                  1..5
                        mol_type = protein
                        organism = synthetic construct
SEQUENCE: 384
PIDKP                                                           5

SEQ ID NO: 385          moltype = AA  length = 5
FEATURE                 Location/Qualifiers
REGION                  1..5
                        note = Synthetic: C-terminal tail
source                  1..5
                        mol_type = protein
                        organism = synthetic construct
SEQUENCE: 385
PIEKP                                                           5

SEQ ID NO: 386          moltype = AA  length = 6
FEATURE                 Location/Qualifiers
REGION                  1..6
                        note = Synthetic: C-terminal tail
source                  1..6
                        mol_type = protein
                        organism = synthetic construct
SEQUENCE: 386
PIDKPS                                                          6

SEQ ID NO: 387          moltype = AA  length = 6
FEATURE                 Location/Qualifiers
REGION                  1..6
                        note = Synthetic: C-terminal tail
source                  1..6
                        mol_type = protein
                        organism = synthetic construct
SEQUENCE: 387
PIEKPS                                                          6

SEQ ID NO: 388          moltype = AA  length = 6
FEATURE                 Location/Qualifiers
REGION                  1..6
                        note = Synthetic: C-terminal tail
source                  1..6
                        mol_type = protein
                        organism = synthetic construct
SEQUENCE: 388
PIDKPC                                                          6

SEQ ID NO: 389          moltype = AA  length = 6
FEATURE                 Location/Qualifiers
REGION                  1..6
                        note = Synthetic: C-terminal tail
source                  1..6
```

```
                        mol_type = protein
                        organism = synthetic construct
SEQUENCE: 389
PIEKPC                                                                  6

SEQ ID NO: 390          moltype = AA  length = 7
FEATURE                 Location/Qualifiers
REGION                  1..7
                        note = Synthetic: C-terminal tail
source                  1..7
                        mol_type = protein
                        organism = synthetic construct
SEQUENCE: 390
PIDKPSQ                                                                 7

SEQ ID NO: 391          moltype = AA  length = 7
FEATURE                 Location/Qualifiers
REGION                  1..7
                        note = Synthetic: C-terminal tail
source                  1..7
                        mol_type = protein
                        organism = synthetic construct
SEQUENCE: 391
PIEKPSQ                                                                 7

SEQ ID NO: 392          moltype = AA  length = 7
FEATURE                 Location/Qualifiers
REGION                  1..7
                        note = Synthetic: C-terminal tail
source                  1..7
                        mol_type = protein
                        organism = synthetic construct
SEQUENCE: 392
PIDKPCQ                                                                 7

SEQ ID NO: 393          moltype = AA  length = 7
FEATURE                 Location/Qualifiers
REGION                  1..7
                        note = Synthetic: C-terminal tail
source                  1..7
                        mol_type = protein
                        organism = synthetic construct
SEQUENCE: 393
PIEKPCQ                                                                 7

SEQ ID NO: 394          moltype = AA  length = 7
FEATURE                 Location/Qualifiers
REGION                  1..7
                        note = Synthetic: C-terminal tail
source                  1..7
                        mol_type = protein
                        organism = synthetic construct
SEQUENCE: 394
PHHHHHH                                                                 7

SEQ ID NO: 395          moltype = AA  length = 8
FEATURE                 Location/Qualifiers
REGION                  1..8
                        note = Synthetic: C-terminal tail
source                  1..8
                        mol_type = protein
                        organism = synthetic construct
SEQUENCE: 395
PCHHHHHH                                                                8

SEQ ID NO: 396          moltype = AA  length = 4
FEATURE                 Location/Qualifiers
REGION                  1..4
                        note = Synthetic: C-terminal tail
source                  1..4
                        mol_type = protein
                        organism = synthetic construct
SEQUENCE: 396
PPID                                                                    4

SEQ ID NO: 397          moltype = AA  length = 4
FEATURE                 Location/Qualifiers
REGION                  1..4
                        note = Synthetic: C-terminal tail
```

```
source                  1..4
                        mol_type = protein
                        organism = synthetic construct
SEQUENCE: 397
PPIE                                                                        4

SEQ ID NO: 398          moltype = AA  length = 5
FEATURE                 Location/Qualifiers
REGION                  1..5
                        note = Synthetic: C-terminal tail
source                  1..5
                        mol_type = protein
                        organism = synthetic construct
SEQUENCE: 398
PPIDK                                                                       5

SEQ ID NO: 399          moltype = AA  length = 5
FEATURE                 Location/Qualifiers
REGION                  1..5
                        note = Synthetic: C-terminal tail
source                  1..5
                        mol_type = protein
                        organism = synthetic construct
SEQUENCE: 399
PPIEK                                                                       5

SEQ ID NO: 400          moltype = AA  length = 6
FEATURE                 Location/Qualifiers
REGION                  1..6
                        note = Synthetic: C-terminal tail
source                  1..6
                        mol_type = protein
                        organism = synthetic construct
SEQUENCE: 400
PPIDKP                                                                      6

SEQ ID NO: 401          moltype = AA  length = 6
FEATURE                 Location/Qualifiers
REGION                  1..6
                        note = Synthetic: C-terminal tail
source                  1..6
                        mol_type = protein
                        organism = synthetic construct
SEQUENCE: 401
PPIEKP                                                                      6

SEQ ID NO: 402          moltype = AA  length = 7
FEATURE                 Location/Qualifiers
REGION                  1..7
                        note = Synthetic: C-terminal tail
source                  1..7
                        mol_type = protein
                        organism = synthetic construct
SEQUENCE: 402
PPIDKPS                                                                     7

SEQ ID NO: 403          moltype = AA  length = 7
FEATURE                 Location/Qualifiers
REGION                  1..7
                        note = Synthetic: C-terminal tail
source                  1..7
                        mol_type = protein
                        organism = synthetic construct
SEQUENCE: 403
PPIEKPS                                                                     7

SEQ ID NO: 404          moltype = AA  length = 7
FEATURE                 Location/Qualifiers
REGION                  1..7
                        note = Synthetic: C-terminal tail
source                  1..7
                        mol_type = protein
                        organism = synthetic construct
SEQUENCE: 404
PPIDKPC                                                                     7

SEQ ID NO: 405          moltype = AA  length = 7
FEATURE                 Location/Qualifiers
REGION                  1..7
```

```
                        note = Synthetic: C-terminal tail
source                  1..7
                        mol_type = protein
                        organism = synthetic construct
SEQUENCE: 405
PPIEKPC                                                                    7

SEQ ID NO: 406          moltype = AA  length = 8
FEATURE                 Location/Qualifiers
REGION                  1..8
                        note = Synthetic: C-terminal tail
source                  1..8
                        mol_type = protein
                        organism = synthetic construct
SEQUENCE: 406
PPIDKPSQ                                                                   8

SEQ ID NO: 407          moltype = AA  length = 8
FEATURE                 Location/Qualifiers
REGION                  1..8
                        note = Synthetic: C-terminal tail
source                  1..8
                        mol_type = protein
                        organism = synthetic construct
SEQUENCE: 407
PPIEKPSQ                                                                   8

SEQ ID NO: 408          moltype = AA  length = 8
FEATURE                 Location/Qualifiers
REGION                  1..8
                        note = Synthetic: C-terminal tail
source                  1..8
                        mol_type = protein
                        organism = synthetic construct
SEQUENCE: 408
PPIDKPCQ                                                                   8

SEQ ID NO: 409          moltype = AA  length = 8
FEATURE                 Location/Qualifiers
REGION                  1..8
                        note = Synthetic: C-terminal tail
source                  1..8
                        mol_type = protein
                        organism = synthetic construct
SEQUENCE: 409
PPIEKPCQ                                                                   8

SEQ ID NO: 410          moltype = AA  length = 8
FEATURE                 Location/Qualifiers
REGION                  1..8
                        note = Synthetic: C-terminal tail
source                  1..8
                        mol_type = protein
                        organism = synthetic construct
SEQUENCE: 410
PPHHHHHH                                                                   8

SEQ ID NO: 411          moltype = AA  length = 9
FEATURE                 Location/Qualifiers
REGION                  1..9
                        note = Synthetic: C-terminal tail
source                  1..9
                        mol_type = protein
                        organism = synthetic construct
SEQUENCE: 411
PPCHHHHHH                                                                  9

SEQ ID NO: 412          moltype = AA  length = 4
FEATURE                 Location/Qualifiers
REGION                  1..4
                        note = Synthetic: C-terminal tail
source                  1..4
                        mol_type = protein
                        organism = synthetic construct
SEQUENCE: 412
PCGC                                                                       4

SEQ ID NO: 413          moltype = AA  length = 4
FEATURE                 Location/Qualifiers
```

```
REGION                  1..4
                        note = Synthetic: C-terminal tail
source                  1..4
                        mol_type = protein
                        organism = synthetic construct
SEQUENCE: 413
PCPC                                                                    4

SEQ ID NO: 414          moltype = AA  length = 6
FEATURE                 Location/Qualifiers
REGION                  1..6
                        note = Synthetic: C-terminal tail
source                  1..6
                        mol_type = protein
                        organism = synthetic construct
SEQUENCE: 414
PCGSGC                                                                  6

SEQ ID NO: 415          moltype = AA  length = 6
FEATURE                 Location/Qualifiers
REGION                  1..6
                        note = Synthetic: C-terminal tail
source                  1..6
                        mol_type = protein
                        organism = synthetic construct
SEQUENCE: 415
PCPPPC                                                                  6

SEQ ID NO: 416          moltype = AA  length = 8
FEATURE                 Location/Qualifiers
REGION                  1..8
                        note = Synthetic: C-terminal tail
source                  1..8
                        mol_type = protein
                        organism = synthetic construct
SEQUENCE: 416
PCPPPPPC                                                                8

SEQ ID NO: 417          moltype = AA  length = 8
FEATURE                 Location/Qualifiers
REGION                  1..8
                        note = Synthetic: C-terminal tail
source                  1..8
                        mol_type = protein
                        organism = synthetic construct
SEQUENCE: 417
PCGSGSGC                                                                8

SEQ ID NO: 418          moltype = AA  length = 9
FEATURE                 Location/Qualifiers
REGION                  1..9
                        note = Synthetic: C-terminal tail
source                  1..9
                        mol_type = protein
                        organism = synthetic construct
SEQUENCE: 418
PCCHHHHHH                                                               9

SEQ ID NO: 419          moltype = AA  length = 9
FEATURE                 Location/Qualifiers
REGION                  1..9
                        note = Synthetic: C-terminal tail
source                  1..9
                        mol_type = protein
                        organism = synthetic construct
SEQUENCE: 419
PCHHHHHHC                                                               9

SEQ ID NO: 420          moltype = AA  length = 10
FEATURE                 Location/Qualifiers
REGION                  1..10
                        note = Synthetic: C-terminal tail
source                  1..10
                        mol_type = protein
                        organism = synthetic construct
SEQUENCE: 420
PCGCHHHHHH                                                              10

SEQ ID NO: 421          moltype = AA  length = 10
```

-continued

```
FEATURE                Location/Qualifiers
REGION                 1..10
                       note = Synthetic: C-terminal tail
source                 1..10
                       mol_type = protein
                       organism = synthetic construct
SEQUENCE: 421
PCPCHHHHHH                                                    10

SEQ ID NO: 422         moltype = AA  length = 12
FEATURE                Location/Qualifiers
REGION                 1..12
                       note = Synthetic: C-terminal tail
source                 1..12
                       mol_type = protein
                       organism = synthetic construct
SEQUENCE: 422
PCGSGCHHHH HH                                                 12

SEQ ID NO: 423         moltype = AA  length = 12
FEATURE                Location/Qualifiers
REGION                 1..12
                       note = Synthetic: C-terminal tail
source                 1..12
                       mol_type = protein
                       organism = synthetic construct
SEQUENCE: 423
PCPPPCHHHH HH                                                 12

SEQ ID NO: 424         moltype = AA  length = 14
FEATURE                Location/Qualifiers
REGION                 1..14
                       note = Synthetic: C-terminal tail
source                 1..14
                       mol_type = protein
                       organism = synthetic construct
SEQUENCE: 424
PCPPPPPCHH HHHH                                               14

SEQ ID NO: 425         moltype = AA  length = 14
FEATURE                Location/Qualifiers
REGION                 1..14
                       note = Synthetic: C-terminal tail
source                 1..14
                       mol_type = protein
                       organism = synthetic construct
SEQUENCE: 425
PCGSGSGCHH HHHH                                               14

SEQ ID NO: 426         moltype = AA  length = 100
FEATURE                Location/Qualifiers
REGION                 1..100
                       note = Synthetic: Exemplary linker
VARIANT                1..100
                       note = At least one PSPEPPTPEP and up to ten PSPEPPTPEP may
                        be present
source                 1..100
                       mol_type = protein
                       organism = synthetic construct
SEQUENCE: 426
PSPEPPTPEP PSPEPPTPEP PSPEPPTPEP PSPEPPTPEP PSPEPPTPEP PSPEPPTPEP  60
PSPEPPTPEP PSPEPPTPEP PSPEPPTPEP PSPEPPTPEP                   100

SEQ ID NO: 427         moltype = AA  length = 61
FEATURE                Location/Qualifiers
REGION                 1..61
                       note = Synthetic: Exemplary linker
VARIANT                1..60
                       note = At least one EEEEDE and up to ten EEEEDE may be
                        present
source                 1..61
                       mol_type = protein
                       organism = synthetic construct
SEQUENCE: 427
EEEEDEEEEE DEEEEEDEEE EEDEEEEEDE EEEEDEEEEE DEEEEEDEEE EEDEEEEEDE  60
E                                                             61

SEQ ID NO: 428         moltype = AA  length = 18
FEATURE                Location/Qualifiers
```

-continued

```
REGION                1..18
                      note = Synthetic: Linker
source                1..18
                      mol_type = protein
                      organism = synthetic construct
SEQUENCE: 428
PSTPPTPSPS TPPTPSPS                                       18

SEQ ID NO: 429        moltype = AA  length = 14
FEATURE               Location/Qualifiers
REGION                1..14
                      note = Synthetic: Linker
source                1..14
                      mol_type = protein
                      organism = synthetic construct
SEQUENCE: 429
GSGSGSGSGS GSGS                                           14

SEQ ID NO: 430        moltype = AA  length = 13
FEATURE               Location/Qualifiers
REGION                1..13
                      note = Synthetic: Linker
source                1..13
                      mol_type = protein
                      organism = synthetic construct
SEQUENCE: 430
GGSGSGSGSG SGS                                            13

SEQ ID NO: 431        moltype = AA  length = 16
FEATURE               Location/Qualifiers
REGION                1..16
                      note = Synthetic: Linker
source                1..16
                      mol_type = protein
                      organism = synthetic construct
SEQUENCE: 431
GGSGSGSGSG SGSGSG                                         16

SEQ ID NO: 432        moltype = AA  length = 15
FEATURE               Location/Qualifiers
REGION                1..15
                      note = Synthetic: Linker
source                1..15
                      mol_type = protein
                      organism = synthetic construct
SEQUENCE: 432
GSEGSEGSEG SEGSE                                          15

SEQ ID NO: 433        moltype = AA  length = 8
FEATURE               Location/Qualifiers
REGION                1..8
                      note = Synthetic: Linker
source                1..8
                      mol_type = protein
                      organism = synthetic construct
SEQUENCE: 433
GGSEGGSE                                                  8

SEQ ID NO: 434        moltype = AA  length = 8
FEATURE               Location/Qualifiers
REGION                1..8
                      note = Synthetic: Linker
source                1..8
                      mol_type = protein
                      organism = synthetic construct
SEQUENCE: 434
GSGSGSGS                                                  8

SEQ ID NO: 435        moltype = AA  length = 35
FEATURE               Location/Qualifiers
REGION                1..35
                      note = Synthetic: Linker
source                1..35
                      mol_type = protein
                      organism = synthetic construct
SEQUENCE: 435
GGGGSGGGGS GGGGSGGGGS GGGGSGGGGS GGGGS                    35

SEQ ID NO: 436        moltype = AA  length = 25
```

-continued

```
FEATURE                Location/Qualifiers
REGION                 1..25
                       note = Synthetic: Linker
source                 1..25
                       mol_type = protein
                       organism = synthetic construct
SEQUENCE: 436
GGGGSGGGGS GGGGSGGGGS GGGGS                                         25

SEQ ID NO: 437         moltype = AA  length = 16
FEATURE                Location/Qualifiers
REGION                 1..16
                       note = Synthetic: Linker
source                 1..16
                       mol_type = protein
                       organism = synthetic construct
SEQUENCE: 437
GGGGSGGGGS GGGGSG                                                   16

SEQ ID NO: 438         moltype = AA  length = 7
FEATURE                Location/Qualifiers
REGION                 1..7
                       note = Synthetic: Linker
source                 1..7
                       mol_type = protein
                       organism = synthetic construct
SEQUENCE: 438
GPGPGPG                                                             7

SEQ ID NO: 439         moltype = AA  length = 11
FEATURE                Location/Qualifiers
REGION                 1..11
                       note = Synthetic: Linker
source                 1..11
                       mol_type = protein
                       organism = synthetic construct
SEQUENCE: 439
GPGPGPGPGP G                                                        11

SEQ ID NO: 440         moltype = AA  length = 6
FEATURE                Location/Qualifiers
REGION                 1..6
                       note = Synthetic: Linker
source                 1..6
                       mol_type = protein
                       organism = synthetic construct
SEQUENCE: 440
PAPAPA                                                              6

SEQ ID NO: 441         moltype = AA  length = 12
FEATURE                Location/Qualifiers
REGION                 1..12
                       note = Synthetic: Linker
source                 1..12
                       mol_type = protein
                       organism = synthetic construct
SEQUENCE: 441
PAPAPAPAPA PA                                                       12

SEQ ID NO: 442         moltype = AA  length = 18
FEATURE                Location/Qualifiers
REGION                 1..18
                       note = Synthetic: Linker
source                 1..18
                       mol_type = protein
                       organism = synthetic construct
SEQUENCE: 442
PAPAPAPAPA PAPAPAPA                                                 18

SEQ ID NO: 443         moltype = AA  length = 10
FEATURE                Location/Qualifiers
REGION                 1..10
                       note = Synthetic: Linker
source                 1..10
                       mol_type = protein
                       organism = synthetic construct
SEQUENCE: 443
PSPEPPTPEP                                                          10
```

```
SEQ ID NO: 444         moltype = AA  length = 20
FEATURE                Location/Qualifiers
REGION                 1..20
                       note = Synthetic: Linker
source                 1..20
                       mol_type = protein
                       organism = synthetic construct
SEQUENCE: 444
PSPEPPTPEP PSPEPPTPEP                                        20

SEQ ID NO: 445         moltype = AA  length = 30
FEATURE                Location/Qualifiers
REGION                 1..30
                       note = Synthetic: Linker
source                 1..30
                       mol_type = protein
                       organism = synthetic construct
SEQUENCE: 445
PSPEPPTPEP PSPEPPTPEP PSPEPPTPEP                             30

SEQ ID NO: 446         moltype = AA  length = 40
FEATURE                Location/Qualifiers
REGION                 1..40
                       note = Synthetic: Linker
source                 1..40
                       mol_type = protein
                       organism = synthetic construct
SEQUENCE: 446
PSPEPPTPEP PSPEPPTPEP PSPEPPTPEP PSPEPPTPEP                  40

SEQ ID NO: 447         moltype = AA  length = 6
FEATURE                Location/Qualifiers
REGION                 1..6
                       note = Synthetic: Linker
source                 1..6
                       mol_type = protein
                       organism = synthetic construct
SEQUENCE: 447
EEEEDE                                                       6

SEQ ID NO: 448         moltype = AA  length = 11
FEATURE                Location/Qualifiers
REGION                 1..11
                       note = Synthetic: Linker
source                 1..11
                       mol_type = protein
                       organism = synthetic construct
SEQUENCE: 448
EEEEDEEEED E                                                 11

SEQ ID NO: 449         moltype = AA  length = 21
FEATURE                Location/Qualifiers
REGION                 1..21
                       note = Synthetic: Linker
source                 1..21
                       mol_type = protein
                       organism = synthetic construct
SEQUENCE: 449
EEEEDEEEED EEEEDEEEED E                                      21

SEQ ID NO: 450         moltype = AA  length = 31
FEATURE                Location/Qualifiers
REGION                 1..31
                       note = Synthetic: Linker
source                 1..31
                       mol_type = protein
                       organism = synthetic construct
SEQUENCE: 450
EEEEDEEEED EEEEDEEEED EEEEDEEEED E                           31

SEQ ID NO: 451         moltype = AA  length = 23
FEATURE                Location/Qualifiers
REGION                 1..23
                       note = Synthetic: Linker
source                 1..23
                       mol_type = protein
                       organism = synthetic construct
SEQUENCE: 451
RGGEEKKKEK EKEEQEERET KTP                                    23
```

```
SEQ ID NO: 452          moltype = DNA  length = 297
FEATURE                 Location/Qualifiers
misc_feature            1..297
                        note = Synthetic: ADX_4578_F03 nucleotide sequence encoding
                         (SEQ ID NO: 10)
source                  1..297
                        mol_type = other DNA
                        organism = synthetic construct
SEQUENCE: 452
atgggagttt ctgatgtgcc gcgcgacttg gaagtggttg ccgccacccc caccagcctg  60
ctgatctctt ggcatccgcc gcatccgaac atcgtttctt accatatcta ctacggcgaa  120
acaggaggca atagccctgt ccaggagttc actgtggaag gttctaaatc tactgctaaa  180
atcagcggcc ttaaacctgg cgttgattat accatcactg tgtacgctgt tgctccggaa  240
atcgaaaaat actaccagat ttggattaat taccgcacag aaggcagcgg ttcctaa     297

SEQ ID NO: 453          moltype = DNA  length = 312
FEATURE                 Location/Qualifiers
misc_feature            1..312
                        note = Synthetic: ADX_4578_H08
source                  1..312
                        mol_type = other DNA
                        organism = synthetic construct
SEQUENCE: 453
atgggagttt ctgatgtgcc gcgcgacctg gaagtggttg ctgccacccc caccagcctg  60
ctgatcagct ggtctggtta cgactacggt gactcttatt accgcatcac ttacggcgaa  120
acaggaggca atagccctgt ccaggagttc actgtgcctg acggttctaa cacagctacc  180
atcagcggcc ttaaacctgg cgttgattat accatcactg tgtatgctgt cgaagcttac  240
ggtaaaggtt acactcgtta cactccaatt tccattaatt accgcacaga aattgacaaa  300
ccatcccagt aa                                                      312

SEQ ID NO: 454          moltype = DNA  length = 300
FEATURE                 Location/Qualifiers
misc_feature            1..300
                        note = Synthetic: ADX_4578_B06
source                  1..300
                        mol_type = other DNA
                        organism = synthetic construct
SEQUENCE: 454
atgggagttt ctgatgtgcc gcgcgacttg gaagtggttg ccgccacccc caccagcctg  60
ctgatctctt ggttcccgga ccgttacgtt tactacatca cttacggcga aacaggaggc  120
aatagccctg tccaggagtt cactgtggaa ggtcataaac agactgctta catcagcggc  180
cttaaacctg gcgttgatta taccatcact gtgtacgcta tctactacta cccggacgac  240
ttccagggtt acccgcagcc gatttctatt aattaccgca cagaaggcag cggttcctaa  300

SEQ ID NO: 455          moltype = DNA  length = 297
FEATURE                 Location/Qualifiers
misc_feature            1..297
                        note = Synthetic: ADX_4606_F06
source                  1..297
                        mol_type = other DNA
                        organism = synthetic construct
SEQUENCE: 455
atgggagttt ctgatgtgcc gcgcgacctg gaagtggttg ctgccacccc caccagcctg  60
ctgatcagct ggaactctgg tcattctggt cagtattacc gcatcactta cggcgaaaca  120
ggaggcaata gccctgtcca ggagttcact gtgcctcgtt acggttacac agctaccatc  180
agcggcctta aacctggcgt tgattatacc atcactgtgt atgctgtcgc tcattctgaa  240
gcttctgctc caatttccat taattaccgc acagaaattg acaaaccatc ccagtaa     297

SEQ ID NO: 456          moltype = DNA  length = 312
FEATURE                 Location/Qualifiers
misc_feature            1..312
                        note = Synthetic: ADX_5273_C01
source                  1..312
                        mol_type = other DNA
                        organism = synthetic construct
SEQUENCE: 456
atgggagttt ctgatgtgcc gcgcgacctg gaagtggttg ctgccacccc caccagcctg  60
ctgatcagct ggtctgaccc gtacgaagaa gaacgatatt accgcatcac ttacggcgaa  120
acaggaggca atagccctgt ccaggagttc actgtgcctg ctttccatac tacagctacc  180
atcagcggcc ttaaacctgg cgttgattat accatcactg tgtatgctgt cacttacaaa  240
cataaatacg cttactacta cccgccaatt tccattaatt accgcacaga aattgacaaa  300
ccatcccagt aa                                                      312

SEQ ID NO: 457          moltype = DNA  length = 312
FEATURE                 Location/Qualifiers
misc_feature            1..312
                        note = Synthetic: ADX_5273_D01
source                  1..312
```

```
                        mol_type = other DNA
                        organism = synthetic construct
SEQUENCE: 457
atgggagttt ctgatgtgcc gcgcgacctg gaagtggttg ctgccacccc caccagcctg  60
ctgatcagct gggaaccgtc ttacaaagac gaccgatatt accgcatcac ttacggcgaa  120
acaggaggca atagccctgt ccaggagttc actgtgcctt ctttccatca gacagctacc  180
atcagcggcc ttaaacctgg cgttgattat accatcactg tgtatgctgt cacttacgaa  240
ccggacgaat actacttcta ctacccaatt tccattaatt accgcacaga aattgacaaa  300
ccatcccagt aa                                                      312

SEQ ID NO: 458          moltype = DNA  length = 312
FEATURE                 Location/Qualifiers
misc_feature            1..312
                        note = Synthetic: ADX_5274_E01
source                  1..312
                        mol_type = other DNA
                        organism = synthetic construct
SEQUENCE: 458
atgggagttt ctgatgtgcc gcgcgacctg gaagtggttg ctgccacccc caccagcctg  60
ctgatcagct ggtctggtga ctaccatccg catcgatatt accgcatcac ttacggcgaa  120
acaggaggca atagccctgt ccaggagttc actgtgcctg gtgaacatga aacagctacc  180
atcagcggcc ttaaacctgg cgttgattat accatcactg tgtatgctgt cacttacgac  240
ggtgaaaaag ctgacaaata cccgccaatt tccattaatt accgcacaga aattgacaaa  300
ccatcccagt aa                                                      312

SEQ ID NO: 459          moltype = DNA  length = 315
FEATURE                 Location/Qualifiers
misc_feature            1..315
                        note = Synthetic: ADX_6077_F02
source                  1..315
                        mol_type = other DNA
                        organism = synthetic construct
SEQUENCE: 459
atgggagttt ctgatgtgcc gcgcgacctg gaagtggttg ctgccacccc caccagcctg  60
ctgatcagct ggtctgatga ctaccatgcg catcgatatt accgcatcac ttacggcgaa  120
acaggaggca atagccctgt ccaggagttc actgtgcctg gtgaacatgt gacagctacc  180
atcagcggcc ttaaacctgg cgttgattat accatcactg tgtatgctgt cacttacgac  240
ggtgaaaagg ctgccacaga ttggtcaatt tccattaatt accgcacacc gtgccaccat  300
caccaccacc actga                                                   315

SEQ ID NO: 460          moltype = DNA  length = 294
FEATURE                 Location/Qualifiers
misc_feature            1..294
                        note = Synthetic: ADX_6077_F02, w/o His-tag and including
                         leader sequence
source                  1..294
                        mol_type = other DNA
                        organism = synthetic construct
SEQUENCE: 460
ggtgttagtg atgttccgcg tgatctggaa gttgttgcag caacccgac cagcctgctg  60
attagctggt cagatgatta tcatgcccat cgttattatc gcattaccta tggtgaaacc  120
ggtggtaata gtccggttca agaattcacc gttccgggtg aacatgttac cgcaaccatt  180
agcggtctga aaccgggtgt tgattacacc attaccgttt atgcagttac ctacgatggt  240
gaaaaagcag caaccgattg gagcattagc attaactatc gtaccccgtg ttaa        294

SEQ ID NO: 461          moltype = DNA  length = 372
FEATURE                 Location/Qualifiers
misc_feature            1..372
                        note = Synthetic: ADX_6077_F02, w/ leader sequence and
                         PCPPPPPC
source                  1..372
                        mol_type = other DNA
                        organism = synthetic construct
SEQUENCE: 461
atgaaaaaaa tctggctggc actggcaggt ctggttctgg catttagcgc tagcgccggt  60
gttagtgatg ttccgcgtga tctggaagtt gttgcagcaa ccccgaccag cctgctgatt  120
agctggtcag atgattatca tgcccatcgt tattatcgca ttacctatgg tgaaaccggt  180
ggtaatagtc cggttcaaga attcaccgtt ccgggtgaac atgttaccgc aaccattagc  240
ggtctgaaac cgggtgttga ttacaccatt accgtttatg cagttaccta cgatggtgaa  300
aaagcagcaa ccgattggag cattagcatt aactatcgta ccccgtgtcc gccgccaccg  360
ccgtgttgat aa                                                      372

SEQ ID NO: 462          moltype = DNA  length = 333
FEATURE                 Location/Qualifiers
misc_feature            1..333
                        note = Synthetic: ADX_6077_F02, w/ leader sequence and
                         PCPPPPPCH6
source                  1..333
                        mol_type = other DNA
```

-continued

```
                        organism = synthetic construct
SEQUENCE: 462
atgggagttt ctgatgtgcc gcgcgacctg gaagtggttg ctgccacccc caccagcctg  60
ctgatcagct ggtctgatga ctaccatgcg catcgatatt accgcatcac ttacggcgaa  120
acaggaggca atagccctgt ccaggagttc actgtgcctg gtgaacatgt gacagctacc  180
atcagcggcc ttaaacctgg cgttgattat accatcactg tgtatgctgt cacttacgac  240
ggtgaaaagg ctgccacaga ttggtcaatt tccattaatt accgcacacc gtgcccgccg  300
ccaccgccgt gtcaccatca ccaccaccac tga                               333

SEQ ID NO: 463          moltype = AA  length = 94
FEATURE                 Location/Qualifiers
REGION                  1..94
                        note = Synthetic: ADX_6093_A01 full length
source                  1..94
                        mol_type = protein
                        organism = synthetic construct
SEQUENCE: 463
VSDVPRDLEV VAATPTSLLI SWDAPAVTVR YYRITYGETG GNSPVQEFTV PGSKSTATIS  60
GLKPGVDYTI TVYAVTGRGE SPASSKPISI NYRT                              94

SEQ ID NO: 464          moltype = AA  length = 20
FEATURE                 Location/Qualifiers
REGION                  1..20
                        note = Synthetic: linker
source                  1..20
                        mol_type = protein
                        organism = synthetic construct
SEQUENCE: 464
GSGSGSGSGS GSGSGSGSGS                                              20

SEQ ID NO: 465          moltype = AA  length = 25
FEATURE                 Location/Qualifiers
REGION                  1..25
                        note = Synthetic: linker
source                  1..25
                        mol_type = protein
                        organism = synthetic construct
SEQUENCE: 465
GGGGSGGGGS GGGGSGGGGS GGGGS                                        25

SEQ ID NO: 466          moltype = AA  length = 11
FEATURE                 Location/Qualifiers
REGION                  1..11
                        note = Synthetic: linker
source                  1..11
                        mol_type = protein
                        organism = synthetic construct
SEQUENCE: 466
GGGGSGGGGS G                                                       11

SEQ ID NO: 467          moltype = AA  length = 5
FEATURE                 Location/Qualifiers
REGION                  1..5
                        note = Synthetic: linker
source                  1..5
                        mol_type = protein
                        organism = synthetic construct
SEQUENCE: 467
PVGVV                                                              5
```

What is claimed is:

1. A method of producing a polypeptide comprising a tenth fibronectin type III ($^{10}$Fn3) domain comprising BC, DE and FG loops, wherein the polypeptide binds specifically to human glypican-3 (GPC3), and wherein (a) the BC, DE and FG loops comprise SEQ ID NOs: 6, 7 and 8, respectively;

(b) the BC, DE and FG loops comprise SEQ ID NOs: 19, 20 and 21, respectively;

(c) the BC, DE and FG loops comprise SEQ ID NOs: 32, 33 and 34, respectively;

(d) the BC, DE and FG loops comprise SEQ ID NOs: 45, 46 and 47, respectively;

(e) the BC, DE and FG loops comprise SEQ ID NOs: 58, 59 and 60, respectively;

(f) the BC, DE and FG loops comprise SEQ ID NOs: 71, 72 and 73, respectively;

(g) the BC, DE and FG loops comprise SEQ ID NOs: 84, 85 and 86, respectively;

(h) the BC, DE and FG loops comprise SEQ ID NOs: 99, 100 and 101, respectively;

(i) the BC, DE and FG loops comprise SEQ ID NOs: 99, 100 and 129, respectively;

(j) the BC, DE and FG loops comprise SEQ ID NOs: 99, 100 and 156, respectively;

(k) the BC, DE and FG loops comprise SEQ ID NOs: 99, 100 and 183, respectively;

(l) the BC, DE and FG loops comprise SEQ ID NOs: 99, 100 and 210, respectively;

(m) the BC, DE and FG loops comprise SEQ ID NOs: 99, 100 and 237, respectively;

(n) the BC, DE and FG loops comprise SEQ ID NOs: 99, 100 and 264, respectively;

(o) the BC, DE and FG loops comprise SEQ ID NOs: 99, 100 and 291, respectively; or (p) the BC, DE and FG loops comprise SEQ ID NOs: 99, 100 and 318, respectively, and the method comprising culturing a cell expressing a nucleic acid encoding the polypeptide under conditions suitable for expressing the polypeptide, and purifying the polypeptide.

2. The method of claim 1, wherein the nucleic acid encodes a polypeptide comprising an amino acid sequence at least 90% identical to the amino acid sequence of any one of SEQ ID NOs: 5, 9-18, 22-31, 35-44, 48-57, 61-70, 74-83, 87-98, 102-128, 130-155, 157-182, 184-209, 211-236, 238-263, 265-290, 292-317 or 319-343.

3. The method of claim 1, wherein the nucleic acid encodes a polypeptide comprising an amino acid sequence selected from the group consisting of SEQ ID NOs: 5, 9-18, 22-31, 35-44, 48-57, 61-70, 74-83, 87-98, 102-128, 130-155, 157-182, 184-209, 211-236, 238-263, 265-290, 292-317 and 319-343.

4. The method of claim 1, wherein the nucleic acid encodes a polypeptide further comprising a heterologous protein.

5. The method of claim 4, wherein the heterologous protein comprises a polypeptide selected from the group consisting of a $^{10}$Fn3 domain, an Fc, Fc fragment, transferrin, serum albumin, a serum albumin binding protein, and a serum immunoglobulin binding protein.

6. The method of claim 1, wherein the C-terminus of the $^{10}$Fn3 domain comprises a moiety consisting of the amino acid sequence $P_mX_n$, wherein P is proline, each X is independently any amino acid, m is an integer that is at least 1 and n is 0 or an integer that is at least 1.

* * * * *